(12) United States Patent
Gao et al.

(10) Patent No.: US 10,041,090 B2
(45) Date of Patent: Aug. 7, 2018

(54) METHOD OF DETECTING AND/OR IDENTIFYING ADENO-ASSOCIATED VIRUS (AAV) SEQUENCES AND ISOLATING NOVEL SEQUENCES IDENTIFIED THEREBY

(71) Applicant: The Trustees of the University of Pennsylvania, Philadelphia, PA (US)

(72) Inventors: Guangping Gao, Westborough, MA (US); James M. Wilson, Glen Mills, PA (US); Mauricio R. Alvira, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/956,934

(22) Filed: Dec. 2, 2015

(65) Prior Publication Data
US 2016/0097040 A1    Apr. 7, 2016

Related U.S. Application Data

(60) Continuation of application No. 13/633,971, filed on Oct. 3, 2012, now Pat. No. 9,790,472, which is a
(Continued)

(51) Int. Cl.
*A61K 39/23*    (2006.01)
*A01N 63/00*    (2006.01)
(Continued)

(52) U.S. Cl.
CPC ............ *C12N 15/86* (2013.01); *A61K 38/177* (2013.01); *A61K 38/4846* (2013.01); *C07K 14/005* (2013.01); *C12N 7/00* (2013.01); *C12Q 1/701* (2013.01); *C12Y 304/21022* (2013.01); *A61K 48/00* (2013.01); *C12N 2750/14121* (2013.01); *C12N 2750/14122* (2013.01);
(Continued)

(58) Field of Classification Search
None
See application file for complete search history.

(56) References Cited

U.S. PATENT DOCUMENTS 5,412,073 A    5/1995  Kalsheker
5,449,616 A    9/1995  Campbell
(Continued)

FOREIGN PATENT DOCUMENTS

CA    2406745 A1    1/2006
EP    1310571 A2    5/2003
(Continued)

OTHER PUBLICATIONS

Kay et al., "Therapeutic Serum Concentrations of Human Alpha-1-Antitrypsin After Adenoviral-Mediated Gene Transfer Into Mouse Hepatocytes," Hepatology 21:815-819 (1995).*
(Continued)

*Primary Examiner* — Janet L Andres
*Assistant Examiner* — M Franco G Salvoza
(74) *Attorney, Agent, or Firm* — Howson & Howson LLP; Colleen Schaller

(57) ABSTRACT

Adeno-associated virus rh.8 sequences, vectors containing same, and methods of use are provided.

31 Claims, 112 Drawing Sheets

Related U.S. Application Data division of application No. 12/962,793, filed on Dec. 8, 2010, now Pat. No. 8,524,446, which is a continuation of application No. 10/291,583, filed on Nov. 12, 2002.

(60) Provisional application No. 60/386,675, filed on Jun. 5, 2002, provisional application No. 60/377,066, filed on May 1, 2002, provisional application No. 60/341,117, filed on Dec. 17, 2001, provisional application No. 60/350,607, filed on Nov. 13, 2001.

(51) Int. Cl.

| | | |
|---|---|---|
| *C12N 15/00* | (2006.01) | |
| *C12N 15/86* | (2006.01) | |
| *C07K 14/005* | (2006.01) | |
| *C12N 7/00* | (2006.01) | |
| *C12Q 1/70* | (2006.01) | |
| *A61K 38/17* | (2006.01) | |
| *A61K 38/48* | (2006.01) | |
| *A61K 48/00* | (2006.01) | |

(52) U.S. Cl.
CPC ............ *C12N 2750/14143* (2013.01); *C12N 2750/14151* (2013.01); *C12N 2750/14152* (2013.01); *C12N 2750/14162* (2013.01); *C12N 2750/14171* (2013.01); *C12N 2830/008* (2013.01); *C12N 2830/48* (2013.01); *C12N 2830/85* (2013.01); *C12N 2830/90* (2013.01); *C12Q 2600/158* (2013.01)

(56) References Cited

U.S. PATENT DOCUMENTS

| | | |
|---|---|---|
| 5,871,982 A | 2/1999 | Wilson et al. |
| 5,866,552 A | 5/1999 | Chiorini et al. |
| 6,039,942 A | 3/2000 | Lassen |
| 6,156,303 A | 12/2000 | Russell et al. |
| 6,251,677 B1 | 6/2001 | Wilson et al. |
| 6,274,354 B1 | 8/2001 | Wilson et al. |
| 6,312,957 B1 | 11/2001 | Einerhand et al. |
| 6,365,394 B1 | 4/2002 | Gao et al. |
| 6,376,237 B1 | 4/2002 | Colosi |
| 6,387,368 B1 | 5/2002 | Wilson et al. |
| 6,399,385 B1 | 6/2002 | Croyle et al. |
| 6,428,988 B1 | 8/2002 | Wilson et al. |
| 6,468,524 B1 | 10/2002 | Chiorini et al. |
| 6,475,769 B1 | 11/2002 | Wilson et al. |
| 6,482,634 B1 | 11/2002 | Wilson et al. |
| 6,485,966 B2 | 11/2002 | Gao et al. |
| 6,632,670 B1 | 10/2003 | Wadsworth et al. |
| 6,759,237 B1 | 7/2004 | Wilson et al. |
| 6,821,512 B1 | 11/2004 | Gao et al. |
| 6,943,019 B2 | 9/2005 | Wilson |
| 6,953,690 B1 | 10/2005 | Gao et al. |
| 7,022,519 B2 | 4/2006 | Gao |
| 7,056,502 B2 | 6/2006 | Hildinger |
| 7,198,951 B2 | 4/2007 | Wilson et al. |
| 7,235,393 B2 | 6/2007 | Gao |
| 7,238,526 B2 | 7/2007 | Wilson |
| 7,282,199 B2 | 10/2007 | Gao |
| 7,790,449 B2 | 9/2010 | Gao |
| 8,906,675 B2 | 12/2014 | Gao et al. |
| 2001/0006955 A1 | 7/2001 | Wilson et al. |
| 2002/0037867 A1 | 3/2002 | Wilson et al. |
| 2002/0090717 A1 | 7/2002 | Gao et al. |
| 2003/0040101 A1 | 2/2003 | Wilson |
| 2003/0073232 A1 | 4/2003 | Wilson |
| 2003/0119191 A1 | 6/2003 | Gao |
| 2003/0138772 A1 | 7/2003 | Gao et al. |
| 2004/0002159 A1* | 1/2004 | Xiao ............... C12N 15/86 435/457 |
| 2004/0052764 A1 | 3/2004 | Hildinger |
| 2007/0036760 A1 | 2/2007 | Wilson |
| 2008/0075737 A1 | 3/2008 | Gao et al. |
| 2008/0075740 A1 | 3/2008 | Gao |
| 2009/0054823 A1 | 2/2009 | Bridges |
| 2009/0197338 A1 | 8/2009 | Vandenberghe |
| 2009/0227030 A1 | 9/2009 | Gao |
| 2009/0275107 A1 | 11/2009 | Lock |
| 2009/0280103 A1 | 11/2009 | Flueck |
| 2011/0053221 A1 | 3/2011 | Chen |
| 2011/0070210 A1 | 3/2011 | Andrijauskas |
| 2011/0151434 A1 | 6/2011 | Gao |
| 2011/0301226 A1 | 12/2011 | Mendell |
| 2013/0195801 A1 | 8/2013 | Gao |

FOREIGN PATENT DOCUMENTS

| | | |
|---|---|---|
| JP | 2003-235562 | 8/2003 |
| WO | WO-1996/000587 A1 | 1/1996 |
| WO | WO-1996/013598 A2 | 5/1996 |
| WO | WO-1998/009657 A2 | 3/1998 |
| WO | WO-1998/010086 A1 | 3/1998 |
| WO | WO-1998/010088 A1 | 3/1998 |
| WO | WO-1998/011244 | 3/1998 |
| WO | WO-1998/011244 A1 | 3/1998 |
| WO | WO-1999/014354 A1 | 3/1999 |
| WO | WO-1999/015677 A1 | 4/1999 |
| WO | WO-1999/015685 A1 | 4/1999 |
| WO | WO-1999/047691 A1 | 9/1999 |
| WO | WO-1999/061601 | 12/1999 |
| WO | WO-1999/061601 A2 | 12/1999 |
| WO | WO-2000/028061 | 5/2000 |
| WO | WO-2000/028061 A2 | 5/2000 |
| WO | WO-2000/075353 A1 | 12/2000 |
| WO | WO-2001/014539 A2 | 3/2001 |
| WO | WO-2001/023001 A2 | 4/2001 |
| WO | WO-2001/023597 A3 | 4/2001 |
| WO | WO-2001/040455 A2 | 6/2001 |
| WO | WO-2001/068888 A2 | 9/2001 |
| WO | WO-2001/070276 A2 | 9/2001 |
| WO | WO-2001/083692 A2 | 11/2001 |
| WO | WO-2002/018659 A2 | 3/2002 |
| WO | WO-2003/042397 A2 | 5/2003 |
| WO | WO-2003/052051 A2 | 6/2003 |
| WO | WO-2003/104392 A2 | 12/2003 |
| WO | WO-2013/078316 A1 | 5/2013 |
| WO | WO-2013/123503 A1 | 8/2013 |

OTHER PUBLICATIONS

Davidson, Beverly L., et al. "Recombinant adeno-associated virus type 2, 4, and 5 vectors: transduction of variant cell types and regions in the mammalian central nervous system." Proceedings of the National Academy of Sciences 97.7 (2000): 3428-3432.

Office Action dated Jul. 28, 2016 issued in related U.S. Appl. No. 13/633,971.

Office Action dated May 31, 2016 issued in corresponding Chinese Patent Application No. 201310326869.

Notice of Reasons for Rejection in Japanese Patent Application No. 2014-122390 dated Aug. 13, 2015.

Office Action issued in Canadian Patent Application No. 2,915,124, dated Aug. 15, 2016.

Allocca et al, Novel adeno-associated virus serotypes efficiently transduce murine photoreceptors, J Virol., Oct.;81(20):11372-80. (Epub Aug. 15, 2007).

Anissimov, M., "How many species of bacteria are there", accessed Sep. 23, 2011 from http://www.wisegeek.org/how-many-species-of-bacteria-are-there.htm (last modified Nov. 19, 2015).

Bantel-Schaal, Human adeno-associated virus type 5 is only distantly related to other known primate helper-dependent parvoviruses, Journal of Virology, vol. 73(2):939-947, (Feb. 1999).

Calcedo et al, Serologic Characterization of Human and Non-Human Primate AAVs, Abstract 102, Molecular Therapy, vol. 7(5): S41, (May 2003).

(56) References Cited

OTHER PUBLICATIONS

Cearley et al, A single injection of an adeno-associated virus vector into nuclei with divergent connections results in widespread vector distribution in the brain and global correction of a neurogenetic disease, vol. 27(37):9928-40, (Sep. 12, 2007).
Cearley et al, Transduction characteristics of adeno-associated virus vectors expressing cap serotypes 7, 8, 9, and Rh10 in the mouse brain, vol. 13(3):528-37. (Epub Jan. 18, 2006).
Chicoine et al, Vascular Delivery of rAAVrh74lMCK.GALGT2 to the Gastrocnemius Muscle of the Rhesus Macaque Stimulates the Expression of Dystrophin and Laminin α2 Surrogates, Molecular Therapy, vol. 22(4):713-24, (Apr. 2014).
Chiorini et al, Cloning and characterization of AAV5, Journal of Virology, vol. 73(2):1309-1319, (Feb. 1999).
De et al, High levels of persistent expression of alpha1-antitrypsin mediated by the nonhuman primate serotype rh.10 adeno-associated virus despite preexisting immunity to common human adeno-associated viruses, Mol Ther., vol. 13(1):67-76, (Epub Nov. 2, 2005).
De et al, Therapeutic Levels for #945; 1-Antitrypsin Following Intrapleural of a Non-Human Primate Serotype rh10 AAV Vector Expressing #945; 1-Antitrypsin, Abstract 338, 7th Annual Meeting of The American Society of Gene Therapy [Jun. 2-6, 2004] Minneapolis, Minnesota, p. 1, (e-published May 2, 2004).
Forslund et al, A broad range of human papillomavirus types detected with a general PCR method suitable for analysis of cutaneous tumors and normal skin, Journal of General Virology, vol. 80(9):2437-2443, XP002229850, (Sep. 1999).
Gao et al, Adeno-Associated Viruses Undergo Substantial Evolution in Primates During Natural Infections, PNAS, vol. 100(10):6081-6086, (May 13, 2003).
Gao et al, Autoimmune Anemia in Macaques Following Erythropoietin Gene Therapy, Abstract 341, 7th Annual Meeting of The American Society of Gene Therapy [Jun. 2-6, 2004] Minneapolis, Minnesota, p. 1 (e-published May 2, 2004).
Gao et al, Clades of Adeno-Associated Viruses are Widely Disseminated in human Tissues, Journal of Virology, vol. 78(12):6381-6388, (Jun. 2004).
Gao et al, Diversity of Latent AAV Genomes in Non-Human Primate and Human Tissues, Abstract 400, Molecular Therapy, vol. 7(5):S158, (May 2003).
Gao et al, Erythropoietin Gene Therapy leads to Autoimmune Anemia in Macaques, Blood, vol. 103(9):3300-3302, (May 2004).
Gao et al, Novel adeno-associated viruses from rhesus monkeys as vectors for human gene therapy, PNAS, vol. 99(18):11854-11859, (Sep. 2002).
Herzog et al, Stable gene transfer and expression of human blood coagulation factor IX after intramuscular injection of recombinant adeno-associated virus, Proc. Natl. Acad. Sci. USA, vol. 94:5804-5807, (May 1997).
Hicks et al, AAV-directed persistent expression of a gene encoding anti-nicotine antibody for smoking cessation, Science Translational Medicine, vol. 4(140):140ra87 (Jun. 27, 2012).
Hu et al, AAV-based neonatal gene therapy for hemophilia A: long-term correction and avoidance of immune responses in mice, vol. 19(12):1166-76. doi: 10.1038/gt.2011.200. (Epub Jan. 12, 2012).
Hu et al, RH10 provides superior transgene expression in mice when compared with natural AAV serotypes for neonatal gene therapy, vol. 12(9):766-78. doi: 10.1002/jgm.1496 (Sep. 2010).
Kelark et al, A common mechanism for cytoplasmic dynein-dependent microtubule binding shared among adeno-associated virus and adenovirus serotypes, vol. 80(15):7781-5. (Aug. 2006).
Kitajima et al, "Complete Prevention of Atherosclerosis in ApoE-Deficient Mice by Hepatic Human ApoE Gene Transfer with Adeno- Associated Virus Serotype 7 and 8" Arterioscler Thromb Vasc Biol, vol. 26:1852-1857, (Jun. 8, 2006).
Klein et al, AAV8, 9, Rh10, Rh43 vector gene transfer in the rat brain: effects of serotype, promoter and purification method, vol. 16(1):89-96. (Epub Oct. 23, 2007).

Kobinger et al, Pseudotyping HIV Vector with the Spike Envelope Protein of SARS-CoV for Studying Viral Tropism, Immunology and Gene Therapy Applications, Abstract 368, 7th Annual Meeting of The American Society of Gene Therapy [Jun. 2-6, 2004] Minneapolis, Minnesota, p. 1 (e-published May 2, 2004).
Lawlor et al, Efficient gene delivery and selective transduction of glial cells in the mammalian brain by AAV serotypes isolated from nonhuman primates, Mol Ther., vol. 17(10):1692-702. doi: 10.1038/mt.2009.170. (Epub Jul. 28, 2009).
Lebherz et al, Gene Therapy with Novel Adeno-Associated Virus Vectors Substantially Diminishes Atherosclerosis in a Murine Model of Familial Hypercholesterolemia, The Journal of Gene Medicine, vol. 6(6):663-672, (Jun. 2004).
Lebherz, C., et al., Novel AAV serotypes for improved ocular gene transfer, J. Gene Med, vol. 10(4):375-382, (Apr. 2008).
Limberis et al, A Novel AAV Vector for the Treatment of Cystic Fibrosis Airway Disease, Abstract 692, 7th Annual Meeting of The American Society of Gene Therapy [Jun. 2-6, 2004] Minneapolis, Minnesota, p. 1, (e-published May 2, 2004).
Lin, et al, "Vaccines Based on Novel Adeno-Associated Virus Vectors Elicit Aberrant CD8+ T-Cell Responses in Mice", J Virol, vol. 81(21):11840-11849, (Nov. 2007).
Lu et al, Analysis of Homologous Recombination Between Different AAV Genomes in In Vitro co-Infections, Abstract 38, Molecular Therapy, vol. 7(5):S15, (May 2003).
Maguire CA, et al, Directed evolution of adeno-associated virus for glioma cell transduction.J Neurooncol., vol. 96(3):337-47, (Epub Jul. 19, 2009).
Mao et al, Persistent suppression of ocular neovascularization with intravitreal administration of AAVrh.10 coding for bevacizumab, Human Gene Therapy, vol. 22(12):1525-35. doi: 10.1089/hum.2011.090. (Epub Oct. 27, 2011).
Monahan and Semulski, Adeno-Associated Virus Vectors for Gene Therapy: More Pros than Cons, Molecular Medicine Today, vol. 6(10:433-40, (Nov. 2000).
Mori et al, Two Novel Adeno-Associated Viruses from Cynomolgus Monkey: Pseudotyping Characterization of Capsid Protein, Virology, vol. 330(2):375-383, (Dec. 20, 2004).
Mountz et al, Monkey See, Monkey Do, Gene Therapy, vol. 10(3):194-196, (Feb. 2003).
Nathwani et al, Enhancing transduction of the liver by adeno-associated viral vectors, Gene Therapy, vol. 16(1):60-9. doi: 10.1038/gt.2008.137. (Epub Aug. 14, 2008).
Pacak et al, Long-term skeletal muscle protection after gene transfer in a mouse model of LGMD-2D, Molecular Therapy, vol. 15(10):1775-81, (Jul. 2007).
Piguet et al, Correction of brain oligodendrocytes by AAVrh.10 intracerebral gene therapy in metachromatic leukodystrophy mice, Human Gene Therapy, vol. 23(8):903-14. doi: 10.1089/hum.2012.015. (Epub Jul. 23, 2012).
Price et al, Targeted Gene Transfer to Lung Airway Epithelium Using Plasmid or Adenoviral Vectors Formulated with an Anti-Inflammatory Dexamathasone-Spermine conjugate, Abstract 498, 7th Annual Meeting of The American Society of Gene Therapy [Jun. 2-6, 2004] Minneapolis, Minnesota, p. 1, (e-published May 2, 2004).
Quesada, O., et al., Production, purification and preliminary x-ray crystallographic studies of adeno-associated virus serotype 7, Acta Crystallographica, vol. F(63):1073-1076, (Dec. 2007).
Rafi et al, Extended normal life after AAVrh10-mediated gene therapy in the mouse model of krabbe disease, Molecular Therapy, vol. 20(10:2031-42. doi: 10.1038/mt.2012.153. (Epub Jul. 31, 2012).
Research Genetics, Designer PCR (advertisement), Nucleic Acids Research, vol. 22(15):2882, (Aug. 11, 1994).
Rick et al, ASH education Book—Congenital Bleeding Disorders, Hematology/American Society of Hematology Educational Program, vol. 2003(1):559-574, (Jan. 1, 2003).
Rosenberg et al, AAVrh.10-mediated expression of an anti-cocaine antibody mediates persistent passive immunization that suppresses cocaine-induced behavior, Human Gene Therapy, vol. 23(5):451-9. doi: 10.1089/hum.2011.178. (May 2012).

(56) References Cited

OTHER PUBLICATIONS

Ruffing, M., et al., Assembly of viruslike particles by recombinant structural proteins of adeno-associated virus type 2 in insect cells, J Virol, , vol. 66(12):6922, (Dec. 1992).
Rutledge et al, Infectious clones and vectors derived from adeno-associated virus (AAV) serotypes other than AAV type 2, Journal of Virology, vol. 72(1)309-319, XP-002137089, (Jan. 1998).
Samaranch et al, "Strong Cortical and Spinal Cord Transduction after AAV7 and AAV9 Delivery into the Cerebrospinal Fluid of Nonhuman Primates", Hu Gene Therapy, vol. 24:526-53, (May 2013).
Sanmiguel et al, Real-time PCR as an Analytic Tool in Gene Therapy, Abstract 913, vol. 7(5):S352, (May 2003).
Skaricic et al, Genetic delivery of an anti-RSV antibody to protect against pulmonary infection with RSV, Jour. Virol., vol. 378(1):79-85. doi: 10.1016/j.virol.2008.04.016. (Epub Jun. 16, 2008).
Sommer and Tautz, Minimal homology requirement for PCR primers, Nucleic Acids Research, vol. 17(16):6749, (Aug. 25, 1989).
Sondhi et al, Enhanced survival of the LINCL mouse following CLN2 gene transfer using the rh.10 rhesus macaque-derived adeno-associated virus vector, Mol Ther., vol. 15(3):481-91. (Epub Dec. 19, 2006).
Sondhi et al, Long-term expression and safety of administration of AAVrh.10hCLN2 to the brain of rats and nonhuman primates for the treatment of late infantile neuronal ceroid lipofuscinosis, Human Gene Therapy, vol. 23(5):324-35. doi: 10.1089/hgtb.2012.120. (Epub Nov. 6, 2012).
Sondhi et al, Survival advantage of neonatal CNS gene transfer for late infantile neuronal ceroid lipofuscinosis, Jour Exp Neurol, vol. 213(1):18-27. doi: 10.1016/j.expneurol.2008.04.022. (Epub Apr. 30, 2008).
Tal, Adeno-associated virus-based vectors in gene therapy, Journal of Biomedical Science, vol. 7(4):279-291, (Jul. 2000).
Tobiasch, Discrimination between different types of human adeno-associated viruses clinical samples by PCR, Journal of Virology Methods, vol. 71(1):17-25, (Mar. 1998).
Vandenberghe et al, AAV Clades: Their Ability to Recombine and Cross Species-Barriers, Abstract 88, 7$^{th}$ Annual Meeting of The American Society of Gene Therapy [Jun. 2-6, 2004] Minneapolis, Minnesota, p. 1, (e-published May 2, 2004).
Vandenberghe et al, AAV9 Targets Cone Photoreceptors in the Nonhuman Primate Retina, PLoS One, vol. 8(1):e53463. doi: 10.1371/journal.pone.0053463. (Epub Jan. 30, 2013).
Vandenberghe et al, Structure-Function Relationship of the Novel Non-Human Primate Adeno-associated Viruses, Abstract 99, Molecular Therapy, vol. 7(5):S15, (May 2003).
Vandenberghe LH et al, Naturally occurring singleton residues in AAV capsid impact vector performance and illustrate structural constraints. Gene Ther., vol. 16(12):1416-28, (Dec. 2009).
Vincent M et al, Comparison of the efficacy of five adeno-associated virus vectors for transducing dorsal raphé nucleus cells in the mouse. J Neurosci Methods, vol. 30(235):189-92, (Epub Jul. 18, 2014).
Wang et al, Persistent expression of biologically active anti-HER2 antibody by AAVrh.10-mediated gene transfer, Cancer Gene Therapy, vol. 17(8):559-70. doi: 10.1038/cgt.2010.11. (Epub May 7, 2010).
Wang et al, Production of AAV Vectors with Different Serotypes, Abstract 906, Molecular Therapy, vol. 7(5):S350, (May 2003).
Wang et al, Systematic evaluation of AAV vectors for liver directed gene transfer in murine models, Mol Ther., vol. 18(1):118-25. doi: 10.1038/mt.2009.246. (Epub Oct. 27, 2009).
Wang et al, The pleiotropic effects of natural AAV infections on liver-directed gene transfer in macaques, Molecular Therapy, vol. 18(1):126-34, doi: 10.1038/mt.2009.245. (Epub Nov. 3, 2009).
Watanabe et al, AAVrh.10-mediated genetic delivery of bevacizumab to the pleura to provide local anti-VEGF to suppress growth of metastatic lung tumors. Gene Ther., vol. 17(8):1042-51. doi: 10.1038/gt.2010.87. (Epub Jul. 1, 2010).
Wikipedia.com, "Fungus", accessed Jun. 3, 2013 from https://en.wikipedia.org/wiki/Fungus (last modified Nov. 17, 2015).
Wikipedia.com, "List of sequenced bacterial genomes", accessed Jan. 24, 2014 from https://en.wikipedia.org/wiki/List_of_sequenced_bacterial_genomes (last modified Oct. 19, 2015).
Wikipedia.com, "Mammal", accessed Sep. 22, 2011 from https://en.wikipedia.org/wiki/Mammal (last modified Nov. 19, 2015).
Wikipedia.com, "Murinae", accessed Mar. 18, 2013 from https://en.wikipedia.org/wiki/Murinae (last modified Nov. 7, 2015).
Wikipedia.com, "Plant", accessed Mar. 8, 2013 from https://en.wikipedia.org/wiki.Plant (last modified Oct. 5, 2015).
Wikipedia.com, "Viruses", accessed Nov. 24, 2012 from https://en.wikipedia.org/wiki/Virus (last modified Nov. 1, 2015).
Xiao et al, Gene Therapy Vectors based on Adeno-Associated Virus Type 1, Journal of Virology, 73(5):3994-4003, (May 1999).
Xiao et al, Production of High-titer Recombinant Adeno-Associated Virus Vectors in the Absence of Helper Adenovirus, 72(3):2224-2232, (Mar. 1998).
Xie, Q., et al., Towards the atomic structure of the adeno-associated virus 2 capsid, Infectious Disease Review, from the VIIIth Parvbovirus Workshop, Mont Tremblant, Quebec, Canada, vol. 2(3):136, (Jun. 28-Jul. 20, 2000).
Xin et al, "Induction of Robust Immune Response Against Human Immunodeficiency Virus is Supported by the Inherent Tropism of Adeno-Associated Virus Type 5 for Dendritic Cells" J. Virol, vol. 80(24):11899-11910, (Dec. 2006).
Yang B, et al, Global CNS transduction of adult mice by intravenously delivered rAAVrh.8 and rAAVrh.10 and nonhuman primates by rAAVrh.10., Mol Ther., vol. 22(7):1299-309, (Epub Apr. 30, 2014).
Zhang, H., et al., Several rAAV vectors efficiently cross the blood-brain barrier and transduce neurons and astrocytes in the neonatal mouse central nervous system, Molecular Therapy, vol. 19(8):1440-1448, (Aug. 2011).
Zhou et al, Direct Rescue and Cloning of Infectious Novel AAV Genomes From Non-Human Primate Tissues, Abstract 907, Molecular Therapy, 7(5):S350, (May 2003).
Zhou et al, Evaluation of Novel Gene Transfer Vectors Derived from Infectious Molecular Clones of Primate AAVs, Abstract 90, 7$^{th}$ Annual Meeting of The American Society of Gene Therapy [Jun. 2-6, 2004] Minneapolis, Minnesota, p. 1, (e-published May 2, 2004).
Office Action issued in parent U.S. Appl. No. 10/291,583, dated Dec. 22, 2005.
Response to Office Action dated Dec. 22, 2005 issued in parent U.S. Appl. No. 10/291,583, dated May 15, 2006.
Office Action issued in parent U.S. Appl. No. 10/291,583, dated Feb. 16, 2007.
Response to Office Action dated Feb. 16, 2007 issued in parent U.S. Appl. No. 10/291,583, dated May 3, 2007.
Office Action issued in parent U.S. Appl. No. 10/291,583, dated Jun. 11, 2007.
Response to Office Action dated Jun. 11, 2007 issued in parent U.S. Appl. No. 10/291,583, dated Aug. 10, 2007.
Office Action dated Feb. 6, 2008 issued in parent U.S. Appl. No. 10/291,583, dated Feb. 6, 2008.
Response submitted Apr. 7, 2008 to Office Action dated Feb. 6, 2008 issued in parent U.S. Appl. No. 10/291,583, dated Apr. 7, 2008.
Office Action dated May 1, 2008 issued in parent U.S. Appl. No. 10/291,583, dated May 1, 2008.
Response submitted Sep. 29, 2008 to Office Action dated May 1, 2008 issued in parent U.S. Appl. No. 10/291,583, dated Sep. 29, 2008.
Office Action dated Apr. 15, 2009 issued in parent U.S. Appl. No. 10/291,583, dated Apr. 15, 2009.
Response submitted Jul. 15, 2009 to Office Action dated Apr. 15, 2009 issued in parent U.S. Appl. No. 10/291,583, dated Jul. 15, 2009.
Office Action dated Sep. 18, 2009 issued in parent U.S. Appl. No. 10/291,583, dated Sep. 18, 2009.
Response submitted Mar. 17, 2010 to Office Action dated Sep. 18, 2009 issued in parent U.S. Appl. No. 10/291,583, dated Mar. 17, 2010.

(56) References Cited

OTHER PUBLICATIONS

Office Action dated Jun. 8, 2010 issued in parent U.S. Appl. No. 10/291,583, dated Jun. 8, 2010.
Office Action issued in related U.S. Appl. No. 11/985,096, dated Dec. 12, 2011.
Response submitted to Office Action dated Dec. 12, 2011 issued in related U.S. Appl. No. 11/985,096, dated Jun. 12, 2012.
Office Action issued in related U.S. Appl. No. 11/985,096, dated Jul. 30, 2012.
Response to Office Action dated Jul. 30, 2012 issued in related U.S. Appl. No. 11/985,096, dated Jan. 30, 2013.
Advisory action issued in related U.S. Appl. No. 11/985,096, dated Mar. 1, 2013.
Response to Advisory action dated Mar. 1, 2013 issued in related U.S. Appl. No. 11/985,096, dated Mar. 18, 2013.
Office Action issued in related U.S. Appl. No. 11/985,096 and response dated Mar. 17, 2014, dated Sep. 18, 2013.
Office Action issued in related U.S. Appl. No. 11/985,096, dated Jun. 27, 2014.
Notice of Allowance and Interview Summary issued on related U.S. Appl. No. 11/985,096, dated Sep. 25, 2014.
Amendment after Notice of Allowance submitted in related U.S. Appl. No. 11/985,096, dated Oct. 14, 2014.
Amendment after Notice of Allowance submitted in related U.S. Appl. No. 11/985,096, dated Oct. 28, 2014.
Office Action issued in related U.S. Appl. No. 12/962,793, dated Dec. 19, 2011.
Response to Office Action dated Dec. 19, 2011 issued in related U.S. Appl. No. 12/962,793, dated Jun. 19, 2012.
Office Action issued in related U.S. Appl. No. 12/962,793, dated Aug. 30, 2012.
Response to Office Action dated Aug. 30, 2012 issued in related U.S. Appl. No. 12/962,793, dated Feb. 28, 2013.
Advisory Action issued in U.S. Appl. No. 12/962,793, dated Mar. 20, 2013.
Supplemental Amendment filed in U.S. Appl. No. 12/962,793, dated May 13, 2013.
Advisory Action dated issued in U.S. Appl. No. 12/962,793, dated May 24, 2013.
Notice of Allowance issued on U.S. Appl. No. 12/962,793, dated Jun. 11, 2013.
Amendment after Notice of Allowance filed in U.S. Appl. No. 12/962,793, dated Jul. 25, 2013.
Office Action issued on corresponding Chinese application No. 201310326978.2, dated Nov. 19, 2014.
Response to Office Action dated Nov. 19, 2014 issued in corresponding Chinese application No. 201310326978.2, dated Apr. 2, 2015.
Second Office Action issued on corresponding Chinese application No. 201310326978.2, dated Aug. 10, 2015.
Communication in corresponding EP Patent Application No. 10178940.2 including search report dated May 18, 2011, dated May 26, 2011.
Response to Communication dated May 26, 2011, dated Dec. 30, 2011, issued on corresponding EP Patent Application No. 10178940.2.
Communication in corresponding EP Patent Application No. 10178940.2 pursuant to Article 94(3) and Rule 71(1), invitation to amen claims, dated Feb. 3, 2012.
Response to Communication dated Feb. 3, 2012 issued on corresponding EP Patent Application No. 10178940.2, dated Jun. 13, 2012.
Communication under Rule 71(3) EPC—Intention to Grant issued on corresponding EP Patent Application No. 10178940.2, dated Nov. 5, 2012.
Amended claims filed in response to Communication from EPO dated Nov. 5, 2012 issued on corresponding EP Patent Application No. 10178940.2, dated Mar. 15, 2013.
Communication under Rule 71(3) EPC—Intention to Grant issued on corresponding EP Patent Application No. 10178940.2, dated May 2, 2013.
Response to Communication dated May 2, 2013 issued on corresponding EP Patent Application No. 10178940.2, dated Jul. 11, 2013.
Communication under Rule 71(3) EPC—Intention to Grant issued on corresponding EP Patent Application No. 10178940.2, dated Aug. 1, 2013.
Communication under Artile 91(1) EPC—Decision to Grant issued on corresponding EP Patent Application No. 10178940.2, dated Aug. 29, 2013.
Office Action issued in corresponding Japanese Patent Application No. 2009-102988, dated Oct. 4, 2011.
Final Office Action issued in corresponding Japanese Patent Application No. 2009-102988, dated Jun. 19, 2012.
Response to Office Action dated Jun. 19, 2012 issued in corresponding Japanese Patent Application No. 2009-102988, dated Sep. 12, 2012.
Decision to Grant issued in corresponding Japanese Patent Application No. 2009-102988, dated Nov. 14, 2012.
Office Action dated Dec. 31, 2014 issued in corresponding Chinese Patent Application No. 201310326869.
Office Action dated Sep. 24, 2015 issued in corresponding Chinese Patent Application No. 201310326869.
Office Action dated Jul. 9, 2014 issued in corresponding Australian Patent Application No. 2013202568.
Applicant's response dated Aug. 20, 2015 to Office Action dated Jul. 9, 2014 issued in corresponding Australian Patent Application No. 2013202568.
Inagaki et al., "Robust systemic transduction with AAV9 vectors in mice: efficient global cardiac gene transfer superior to that of AAV8", Mol Ther, vol. 14(1):45-53, Jul. 2006.
Srivastava et al., "Nucleotide sequence and organization of the adeno-associated virus 2 genome", J. Virol, vol. 45(2):555-564, Feb. 1983.
Office Action dated May 31, 2017 issued in corresponding Canadian Patent Application No. 2915124.
Applicant-Initiated Interview Summary filed in U.S. Appl. No. 13/633,971, dated Nov. 3, 2016.
Response to Office Action dated Jul. 28, 2016, filed in U.S. Appl. No. 13/633,971, dated Dec. 28, 2016.
Final Office Action, dated Feb. 22, 2017, issued on U.S. Appl. No. 13/633,971, with Response and Supplemental Response.
Notice of Allowance, dated Aug. 23, 2017, issued on U.S. Appl. No. 13/633,971.
Third Office Action issued on corresponding Chinese application No. 201310326978.2, dated Apr. 29, 2016.
Fourth Office Action issued on corresponding Chinese application No. 201310326978.2, dated Jan. 10, 2017.
Office Action dated Dec. 21, 2016 issued in corresponding Chinese Patent Application No. 201310326869.
Office Action issued in Canadian Patent Application No. 2,915,124, dated May 31, 2017.
Office Action issued in Israeli Patent Application No. 227866, dated Mar. 27, 2014.
Gao et al., "Novel adeno-associated viruses from rhesus monkeys as vectors for human gene therapy", PNAS, vol. 99(18):11854-11859, Sep. 2002.
GenBank entry AF513851, Sep. 2002.
GenBank entry AF513852, Sep. 2002.
Gao et al., "Biology of Adenovirus vectors with E1 and E4 deletions for liver-directed gene therapy", Journal of Viroloy, vol. 70(12):8934-8943, Dec. 1996.
Rutledge et al., "Infectious clones and vectors derived from Adeno-Associated Virus (AAV) serotypes other than AAV Type 2", Journal of Virology, vol. 72(1):309-319, Jan. 1998.
Xiao et al., "Gene therapy vectors based on Adeno-Associated Virus Type 1", Journal of Virology, vol. 73(5):3994-4003, May 1999.
Durigon et al., "Multiple primer pairs for polymerase chain reaction (PCR) amplification of human parvovirus B19 DNA", Journal of Virological Methods, vol. 44:155-165, Feb. 1993.

(56) References Cited

OTHER PUBLICATIONS

Hernandez et al., "Latent Adeno-associated virus infection elicits humoral but no cell-mediated immune responses in a nonhuman primate model", Journal of Virology, vol. 73(10):8549-8558, Oct. 1999.
Afione et al., "In vivo model of adeno-associated virus vector persistence and rescue", Journal of Virology, vol. 70(5):3235-3241, May 1996.
Schnell et al., "Activation of innate immunity in nonhuman primates following intraportal administration of adenoviral vectors", Molecular Therapy, vol. 3(5):708-722, May 2001.
Molecular Therapy, "Information for Authors", pp. 1-13.
Green et al., "Rhesus and pig-tailed macaque parvoviruses: identification of two new members of the erythrovirus genus in monkeys", Virology, vol. 269:105-112, Jan. 2000.
Brown et al., "Cloning and sequencing of the simial parvovirus genome", Virology, vol. 210:314-322, May 1995.
Zadori et al., "A viral phospholipase A2 is required for parvovirus infectivity", Developmental Cell, vol. 1:291-302, Aug. 2001.
Weitzman et al., "Adeno-associated virus (AAV) Rep proteins mediate complex formation between AAV DNA and its integration site in human DNA", PNAS, vol. 91:5808-5812, Jun. 1994.
Wang et al., "Enhancing Transgene Expression from Recombinant AAV8 Vectors in Different Tissues Using Woodchuck Hepatitis Virus Post-Transcriptional Regulatory Element", International Journal of Medical Sciences, vol. 13(4):286-291, Apr. 2016.
Charan et al., "Adeno-associated Virus Serotype 8 (AAV8) Delivery of Recombinant A20 to Skeletal Muscle Reduces Pathological Activation of Nuclear Factor (NF)-kB in Muscle of mdx Mice", Molecular Medicine, vol. 18:1527-1535, Nov. 2012.
Childers et al., "Gene Therapy Prolongs Survival and Restores Function in Murine and Canine Models of Myotubular Myopathy", Sci Transl Med, vol. 6(220):1-31, Jan. 2014.
Zhu et al., "Sustained Whole-Body Functional Rescue by Systemic Delivery of AAV8 Vectors in Heart Failure and Muscular Dystrophy Hamsters", Molecular Therapy, vol. 11(suppl 1):916, May 2005.
Lytle et al., "Effects of FVIII immunity on hepatocyte and hematopoietic stem cell-directed gene therapy of murine hemophilia A", Methods & Clinical Development, vol. 3:15056, Feb. 2016.
Gilkes et al., "Mucopolysaccharidosis IIIB confers enhanced neonatal intracranial transduction by AAV8 but not by 5, 9 or rh10", Gene Therapy, vol. 23:263-271, Jan. 2016.
Pignataro et al., "Adeno-Associated Viral Vectors Serotype 8 for Cell-Specific Delivery of Therapeutic Genes in the Central Nervous System", Frontiers in Neuroanatomy, vol. 11(2):1-13, Feb. 2017.
Black et al., "Adeno-associated virus 8-mediated gene therapy for choroideremia: preclinical studies in in vitro and in vivo models", The Journal of Gene Medicine, vol. 16:122-130, Jun. 2014.
Dai et al., "Long-term retinal cone rescue using a capsid mutant AAV8 vector in a mouse model of CNGA3-achromatopsia", PLOS One, vol. 12(11):e0188032, Nov. 2017.
Fischer et al., "Codon-Optimized RPGR Improves Stability and Efficacy of AAV8 Gene Therapy in Two Mouse Models of X-Linked Retinitis Pigmentosa", Molecular Therapy, vol. 25(8):1854-1865, May 2017.
ClinicalTrials.org, "AAV8 Vector Trials", Nov. 2017.
Mountz, "Monkey see, monkey do", vol. 10:194-196, Gene Therapy, vol. 10:194, Jan. 2003.
Statement of Opposition, dated Jun. 20, 2017, filed on related European Patent No. 1453547.
Proprietor's Response to the Opposition, dated Dec. 5, 2017, filed on related European Patent No. 1453547.
Summons to attend oral proceedings and Communication dated Mar. 29, 2018, issued in related European Patent No. 1453547.

\* cited by examiner

FIG. 1A

```
            1                                                                50
  42_2     ..........  ..........  ..........  ..........  ..........
  42_8     ..........  ..........  ..........  ..........  ..........
 42_15     ..........  ..........  ..........  ..........  ..........
 42_9b     ..........  ..........  ..........  ..........  ..........
 42_1b     ..........  ..........  ..........  ..........  ..........
 42_13     ..........  ..........  ..........  ..........  ..........
 42_3a     ..........  ..........  ..........  ..........  ..........
  42_4     ..........  ..........  ..........  ..........  ..........
 42_5a     ..........  ..........  ..........  ..........  ..........
 42_10     ..........  ..........  ..........  ..........  ..........
 42_3b     ..........  ..........  ..........  ..........  ..........
 42_11     ..........  ..........  ..........  ..........  ..........
 42_6b     ..........  ..........  ..........  ..........  ..........
  43_1     ..........  ..........  ..........  ..........  ..........
  43_5     ..........  ..........  ..........  ..........  ..........
 43_12     ..........  ..........  ..........  ..........  ..........
 43_20     ..........  ..........  ..........  ..........  ..........
 43_21     ..........  ..........  ..........  ..........  ..........
 43_23     ..........  ..........  ..........  ..........  ..........
 43_25     ..........  ..........  ..........  ..........  ..........
  44_1     ..........  ..........  ..........  ..........  ..........
  44_5     ..........  ..........  ..........  ..........  ..........
223_10     ..........  ..........  ..........  ..........  ..........
 223_2     ..........  ..........  ..........  ..........  ..........
 223_4     ..........  ..........  ..........  ..........  ..........
 223_5     ..........  ..........  ..........  ..........  ..........
 223_6     ..........  ..........  ..........  ..........  ..........
 223_7     ..........  ..........  ..........  ..........  ..........
  A3_4     ..........  ..........  ..........  ..........  ..........
  A3_5     ..........  ..........  ..........  ..........  ..........
  A3_7     ..........  ..........  ..........  ..........  ..........
  A3_3     ..........  ..........  ..........  ..........  ..........
 42_12     ..........  ..........  ..........  ..........  ..........
  AAV1     TTGCCCACTC  CCTCTCTGCG  CGCTCGCTCG  CTCGGTGGGG  CCTGCGGACC
  AAV2     TTGGCCACTC  CCTCTCTGCG  CGCTCGCTCG  CTCACTCAGG  CCGGGCGACC
  AAV3     TTGGCCACTC  CCTCTATGCG  CACTCGCTCG  CTCGGTGGGG  CCTGGCGACC
  AAV8     ..........  ..........  ..........  ..........  ..........
  AAV9     ..........  ..........  ..........  ..........  ..........
  AAV7     TTGGCCACTC  CCTCTATGCG  CGCTCGCTCG  CTCGGTGGGG  CCTGCGGACC
  44_2     ..........  ..........  ..........  ..........  ..........
```

FIG. 1B

```
                    51                                                              100
                                                                   Rep binding site
      42_2      ..........  ..........  ..........  ..........  ..........
      42_8      ..........  ..........  ..........  ..........  ..........
      42_15     ..........  ..........  ..........  ..........  ..........
      42_5b     ..........  ..........  ..........  ..........  ..........
      42_1b     ..........  ..........  ..........  ..........  ..........
      42_13     ..........  ..........  ..........  ..........  ..........
      42_3a     ..........  ..........  ..........  ..........  ..........
      42_4      ..........  ..........  ..........  ..........  ..........
      42_5a     ..........  ..........  ..........  ..........  ..........
      42_10     ..........  ..........  ..........  ..........  ..........
      42_3b     ..........  ..........  ..........  ..........  ..........
      42_11     ..........  ..........  ..........  ..........  ..........
      42_6b     ..........  ..........  ..........  ..........  ..........
      43_1      ..........  ..........  ..........  ..........  ..........
      43_5      ..........  ..........  ..........  ..........  ..........
      43_12     ..........  ..........  ..........  ..........  ..........
      43_20     ..........  ..........  ..........  ..........  ..........
      43_21     ..........  ..........  ..........  ..........  ..........
      43_23     ..........  ..........  ..........  ..........  ..........
      43_25     ..........  ..........  ..........  ..........  ..........
      44_1      ..........  ..........  ..........  ..........  ..........
      44_5      ..........  ..........  ..........  ..........  ..........
      223_10    ..........  ..........  ..........  ..........  ..........
      223_2     ..........  ..........  ..........  ..........  ..........
      223_4     ..........  ..........  ..........  ..........  ..........
      223_5     ..........  ..........  ..........  ..........  ..........
      223_6     ..........  ..........  ..........  ..........  ..........
      223_7     ..........  ..........  ..........  ..........  ..........
      A3_4      ..........  ..........  ..........  ..........  ..........
      A3_5      ..........  ..........  ..........  ..........  ..........
      A3_7      ..........  ..........  ..........  ..........  ..........
      A3_3      ..........  ..........  ..........  ..........  ..........
      42_12     ..........  ..........  ..........  ..........  ..........
      AAV1      AAAGGTCCGC  AGACGGCAGA  GCTCTGCTCT  GCCGGCCCCA  CCGAGCGAGC
      AAV2      AAAGGTCGCC  CGACGCCCGG  GCTTTGCCCG  GGCGGCCTCA  GTGAGCGAGC
      AAV3      AAAGGTCGCC  AGACGGACGT  GCTTTGCACG  TCCGGCCCCA  CCGAGCGAGC
      AAV8      ..........  ..........  ..........  ..........  ..........
      AAV9      ..........  ..........  ..........  ..........  ..........
      AAV7      AAAGGTCCGC  AGACGGCAGA  GCTCTGCTCT  GCCGGCCCCA  CCGAGCGAGC
      44_2      ..........  ..........  ..........  ..........  ..........
                                                         Rep binding site
```

FIG. 1C

```
Rep binding site                                                              150
       ←─────────────────────┐      TRS
    42_2      ..........     |..........    ..│.......    ..........    ..........
    42_8      ..........     |..........    ...........   ..........    ..........
    42_15     ..........      ..........    ...........   ..........    ..........
    42_5b     ..........      ..........    ...........   ..........    ..........
    42_1b     ..........      ..........    ...........   ..........    ..........
    42_13     ..........      ..........    ...........   ..........    ..........
    42_3a     ..........      ..........    ...........   ..........    ..........
    42_4      ..........      ..........    ...........   ..........    ..........
    42_5a     ..........      ..........    ...........   ..........    ..........
    42_10     ..........      ..........    ...........   ..........    ..........
    42_3b     ..........      ..........    ...........   ..........    ..........
    42_11     ..........      ..........    ...........   ..........    ..........
    42_6b     ..........      ..........    ...........   ..........    ..........
    43_1      ..........      ..........    ...........   ..........    ..........
    43_5      ..........      ..........    ...........   ..........    ..........
    43_12     ..........      ..........    ...........   ..........    ..........
    43_20     ..........      ..........    ...........   ..........    ..........
    43_21     ..........      ..........    ...........   ..........    ..........
    43_23     ..........      ..........    ...........   ..........    ..........
    43_25     ..........      ..........    ...........   ..........    ..........
    44_1      ..........      ..........    ...........   ..........    ..........
    44_5      ..........      ..........    ...........   ..........    ..........
   223_10     ..........      ..........    ...........   ..........    ..........
   223_2      ..........      ..........    ...........   ..........    ..........
   223_4      ..........      ..........    ...........   ..........    ..........
   223_5      ..........      ..........    ...........   ..........    ..........
   223_6      ..........      ..........    ...........   ..........    ..........
   223_7      ..........      ..........    ...........   ..........    ..........
    A3_4      ..........      ..........    ...........   ..........    ..........
    A3_5      ..........      ..........    ...........   ..........    ..........
    A3_7      ..........      ..........    ...........   ..........    ..........
    A3_3      ..........      ..........    ...........   ..........    ..........
    42_12     ..........      ..........    ...........   ..........    ..........
    AAV1      GAGCGCGCAG      AGAGGGAGTG    GGCAACTCCA    TCACTAGGGG    TAATCGCGAA
    AAV2      GAGCGCGCAG      AGAGGGAGTG    GCCAACTCCA    TCACTAGGGG    TTC.......
    AAV3      GAGTGCGCAT      AGAGGGAGTG    GCCAACTCCA    TCACTAGAGG    T.........
    AAV8      .......CAG      AGAGGGAGTG    GCCAACTCCA    TCACTAGGGG    TAG.CGCGAA
    AAV9      .......CAG      AGAGGGAGTG    GCCAACTCCA    TCACTAGGGG    TAATCGCGAA
    AAV7      GAGCGCGCAT      AGAGGGAGTG    GCCAACTCCA    TCACTAGGGG    TA.CCGCGAA
    44_2      ..........     |..........    ..│........   ..........    ..........
       ←─────────────────────┘      TRS
    Rep binding site
```

FIG. 1D

```
        151                                                                200
42_2    ..........  ..........  ..........  ..........  ..........
42_8    ..........  ..........  ..........  ..........  ..........
42_15   ..........  ..........  ..........  ..........  ..........
42_5b   ..........  ..........  ..........  ..........  ..........
42_1b   ..........  ..........  ..........  ..........  ..........
42_13   ..........  ..........  ..........  ..........  ..........
42_3a   ..........  ..........  ..........  ..........  ..........
42_4    ..........  ..........  ..........  ..........  ..........
42_5a   ..........  ..........  ..........  ..........  ..........
42_10   ..........  ..........  ..........  ..........  ..........
42_3b   ..........  ..........  ..........  ..........  ..........
42_11   ..........  ..........  ..........  ..........  ..........
42_6b   ..........  ..........  ..........  ..........  ..........
43_1    ..........  ..........  ..........  ..........  ..........
43_5    ..........  ..........  ..........  ..........  ..........
43_12   ..........  ..........  ..........  ..........  ..........
43_20   ..........  ..........  ..........  ..........  ..........
43_21   ..........  ..........  ..........  ..........  ..........
43_23   ..........  ..........  ..........  ..........  ..........
43_25   ..........  ..........  ..........  ..........  ..........
44_1    ..........  ..........  ..........  ..........  ..........
44_5    ..........  ..........  ..........  ..........  ..........
223_10  ..........  ..........  ..........  ..........  ..........
223_2   ..........  ..........  ..........  ..........  ..........
223_4   ..........  ..........  ..........  ..........  ..........
223_5   ..........  ..........  ..........  ..........  ..........
223_6   ..........  ..........  ..........  ..........  ..........
223_7   ..........  ..........  ..........  ..........  ..........
A3_4    ..........  ..........  ..........  ..........  ..........
A3_5    ..........  ..........  ..........  ..........  ..........
A3_7    ..........  ..........  ..........  ..........  ..........
A3_3    ..........  ..........  ..........  ..........  ..........
42_12   ..........  ..........  ..........  ..........  ..........
AAV1    GCGCCTCCCA  CGCTGCCGCG  TCAGCGCTGA  CGTAAATTAC  GTCATAGGGG
AAV2    .......CTG  GAGGGGTGGA  GTCGTGACGT  GAATTACGTC  ATAGGGTTAG
AAV3    .......ATG  GCAGTGACGT  AACGCGAAGC  GCGCGAAGCG  AGACCACGCC
AAV8    GCGCCTCCCA  CGCTGCCGCG  TCAGCGCTGA  CGTAAATTAC  GTCATAGGGG
AAV9    GCGCCTCCCA  CGCTGCCGCG  TCAGCGCTGA  CGTAGATTAC  GTCATAGGGG
AAV7    GCGCCTCCCA  CGCTGCCGCG  TCAGCGCTGA  CGTAAATCAC  GTCATAGGGG
44_2    ..........  ..........  ..........  ..........  ..........
```

FIG. 1H

```
            351                                                        400
    42_2    ..........  ..........  ..........  ..........  ..........
    42_8    ..........  ..........  ..........  ..........  ..........
   42_15    ..........  ..........  ..........  ..........  ..........
   42_5b    ..........  ..........  ..........  ..........  ..........
   42_1b    ..........  ..........  ..........  ..........  ..........
   42_13    ..........  ..........  ..........  ..........  ..........
   42_3a    ..........  ..........  ..........  ..........  ..........
    42_4    ..........  ..........  ..........  ..........  ..........
   42_5a    ..........  ..........  ..........  ..........  ..........
   42_10    ..........  ..........  ..........  ..........  ..........
   42_3b    ..........  ..........  ..........  ..........  ..........
   42_11    ..........  ..........  ..........  ..........  ..........
   42_6b    ..........  ..........  ..........  ..........  ..........
    43_1    ..........  ..........  ..........  ..........  ..........
    43_5    ..........  ..........  ..........  ..........  ..........
   43_12    ..........  ..........  ..........  ..........  ..........
   43_20    ..........  ..........  ..........  ..........  ..........
   43_21    ..........  ..........  ..........  ..........  ..........
   43_23    ..........  ..........  ..........  ..........  ..........
   43_25    ..........  ..........  ..........  ..........  ..........
    44_1    ..........  ..........  ..........  ..........  ..........
    44_5    ..........  ..........  ..........  ..........  ..........
  223_10    ..........  ..........  ..........  ..........  ..........
   223_2    ..........  ..........  ..........  ..........  ..........
   223_4    ..........  ..........  ..........  ..........  ..........
   223_5    ..........  ..........  ..........  ..........  ..........
   223_6    ..........  ..........  ..........  ..........  ..........
   223_7    ..........  ..........  ..........  ..........  ..........
    A3_4    ..........  ..........  ..........  ..........  ..........
    A3_5    ..........  ..........  ..........  ..........  ..........
    A3_7    ..........  ..........  ..........  ..........  ..........
    A3_3    ..........  ..........  ..........  ..........  ..........
   42_12    ..........  ..........  ..........  ..........  ..........
    AAV1    CGAGATCGTG  ATCAAGGTGC  CGAGCGACCT  GGACGAGCAC  CTGCCGGGCA
    AAV2    CGAGATTGTG  ATTAAGGTCC  CCAGCGACCT  TGACGGGCAT  CTGCCCGGCA
    AAV3    CGAGATTGTC  CTGAAGGTCC  CGAGTGACCT  GGACGAGCGC  CTGCCGGGCA
    AAV8    CGAGATCGTG  ATCAAGGTGC  CGAGCGACCT  GGACGAGCAC  CTGCCGGGCA
    AAV9    CGAGATTGTG  ATCAAGGTGC  CGAGCGACCT  GGACGAGCAC  CTGCCGGGCA
    AAV7    CGAGATCGTG  ATCAAGGTGC  CGAGCGACCT  GGACGAGCAC  CTGCCGGGCA
    44_2    ..........  ..........  ..........  ..........  ..........
```

FIG. 1I

```
        401                                                            450
 42_2   ..........  ..........  ..........  ..........  ..........
 42_8   ..........  ..........  ..........  ..........  ..........
 42_15  ..........  ..........  ..........  ..........  ..........
 42_5b  ..........  ..........  ..........  ..........  ..........
 42_1b  ..........  ..........  ..........  ..........  ..........
 42_13  ..........  ..........  ..........  ..........  ..........
 42_3a  ..........  ..........  ..........  ..........  ..........
 42_4   ..........  ..........  ..........  ..........  ..........
 42_5a  ..........  ..........  ..........  ..........  ..........
 42_10  ..........  ..........  ..........  ..........  ..........
 42_3b  ..........  ..........  ..........  ..........  ..........
 42_11  ..........  ..........  ..........  ..........  ..........
 42_6b  ..........  ..........  ..........  ..........  ..........
 43_1   ..........  ..........  ..........  ..........  ..........
 43_5   ..........  ..........  ..........  ..........  ..........
 43_12  ..........  ..........  ..........  ..........  ..........
 43_20  ..........  ..........  ..........  ..........  ..........
 43_21  ..........  ..........  ..........  ..........  ..........
 43_23  ..........  ..........  ..........  ..........  ..........
 43_25  ..........  ..........  ..........  ..........  ..........
 44_1   ..........  ..........  ..........  ..........  ..........
 44_5   ..........  ..........  ..........  ..........  ..........
223_10  ..........  ..........  ..........  ..........  ..........
223_2   ..........  ..........  ..........  ..........  ..........
223_4   ..........  ..........  ..........  ..........  ..........
223_5   ..........  ..........  ..........  ..........  ..........
223_6   ..........  ..........  ..........  ..........  ..........
223_7   ..........  ..........  ..........  ..........  ..........
 A3_4   ..........  ..........  ..........  ..........  ..........
 A3_5   ..........  ..........  ..........  ..........  ..........
 A3_7   ..........  ..........  ..........  ..........  ..........
 A3_3   ..........  ..........  ..........  ..........  ..........
 42_12  ..........  ..........  ..........  ..........  ..........
 AAV1   TTTCTGACTC  GTTTGTGAGC  TGGGTGGCCG  AGAAGGAATG  GGAGCTGCCC
 AAV2   TTTCTGACAG  CTTTGTGAAC  TGGGTGGCCG  AGAAGGAATG  GGAGTTGCCG
 AAV3   TTTCTAACTC  GTTTGTTAAC  TGGGTGGCCG  AGAAGGAATG  GGACGTGCCG
 AAV8   TTTCTCACTC  GTTTGTGAAC  TGGGTGGCCG  AGAAGGAATG  GGAGCTGCCC
 AAV9   TTTCTGACTC  TTTTGTGAAC  TGGGTGGCCG  AGAAGGAATG  GGAGCTGCCC
 AAV7   TTTCTGACTC  GTTTGTGAAC  TGGGTGGCCG  AGAAGGAATG  GGAGCTGCCC
 44_2   ..........  ..........  ..........  ..........  ..........
```

FIG. 1J

```
         451                                                    500
42_2     ..........  ..........  ..........  ..........  ..........
42_8     ..........  ..........  ..........  ..........  ..........
42_15    ..........  ..........  ..........  ..........  ..........
42_5b    ..........  ..........  ..........  ..........  ..........
42_1b    ..........  ..........  ..........  ..........  ..........
42_13    ..........  ..........  ..........  ..........  ..........
42_3a    ..........  ..........  ..........  ..........  ..........
42_4     ..........  ..........  ..........  ..........  ..........
42_5a    ..........  ..........  ..........  ..........  ..........
42_10    ..........  ..........  ..........  ..........  ..........
42_3b    ..........  ..........  ..........  ..........  ..........
42_11    ..........  ..........  ..........  ..........  ..........
42_6b    ..........  ..........  ..........  ..........  ..........
43_1     ..........  ..........  ..........  ..........  ..........
43_5     ..........  ..........  ..........  ..........  ..........
43_12    ..........  ..........  ..........  ..........  ..........
43_20    ..........  ..........  ..........  ..........  ..........
43_21    ..........  ..........  ..........  ..........  ..........
43_23    ..........  ..........  ..........  ..........  ..........
43_25    ..........  ..........  ..........  ..........  ..........
44_1     ..........  ..........  ..........  ..........  ..........
44_5     ..........  ..........  ..........  ..........  ..........
223_10   ..........  ..........  ..........  ..........  ..........
223_2    ..........  ..........  ..........  ..........  ..........
223_4    ..........  ..........  ..........  ..........  ..........
223_5    ..........  ..........  ..........  ..........  ..........
223_6    ..........  ..........  ..........  ..........  ..........
223_7    ..........  ..........  ..........  ..........  ..........
A3_4     ..........  ..........  ..........  ..........  ..........
A3_5     ..........  ..........  ..........  ..........  ..........
A3_7     ..........  ..........  ..........  ..........  ..........
A3_3     ..........  ..........  ..........  ..........  ..........
42_12    ..........  ..........  ..........  ..........  ..........
AAV1     CCGGATTCTG  ACATGGATCT  GAATCTGATT  GAGCAGGCAC  CCCTGACCGT
AAV2     CCAGATTCTG  ACATGGATCT  GAATCTGATT  GAGCAGGCAC  CCCTGACCGT
AAV3     CCGGATTCTG  ACATGGATCC  GAATCTGATT  GAGCAGGCAC  CCCTGACCGT
AAV8     CCGGATTCTG  ACATGGATCG  GAATCTGATC  GAGCAGGCAC  CCCTGACCGT
AAV9     CCGGATTCTG  ACATGGATCG  GAATCTGATC  GAGCAGGCAC  CCCTGACCGT
AAV7     CCGGATTCTG  ACATGGATCT  GAATCTGATC  GAGCAGGCAC  CCCTGACCGT
44_2     ..........  ..........  ..........  ..........  ..........
```

FIG. 1K

```
        501                                                        550
 42_2    ..........  ..........  ..........  ..........  ..........
 42_8    ..........  ..........  ..........  ..........  ..........
 42_15   ..........  ..........  ..........  ..........  ..........
 42_5b   ..........  ..........  ..........  ..........  ..........
 42_1b   ..........  ..........  ..........  ..........  ..........
 42_13   ..........  ..........  ..........  ..........  ..........
 42_3a   ..........  ..........  ..........  ..........  ..........
 42_4    ..........  ..........  ..........  ..........  ..........
 42_5a   ..........  ..........  ..........  ..........  ..........
 42_10   ..........  ..........  ..........  ..........  ..........
 42_3b   ..........  ..........  ..........  ..........  ..........
 42_11   ..........  ..........  ..........  ..........  ..........
 42_6b   ..........  ..........  ..........  ..........  ..........
 43_1    ..........  ..........  ..........  ..........  ..........
 43_5    ..........  ..........  ..........  ..........  ..........
 43_12   ..........  ..........  ..........  ..........  ..........
 43_20   ..........  ..........  ..........  ..........  ..........
 43_21   ..........  ..........  ..........  ..........  ..........
 43_23   ..........  ..........  ..........  ..........  ..........
 43_25   ..........  ..........  ..........  ..........  ..........
 44_1    ..........  ..........  ..........  ..........  ..........
 44_5    ..........  ..........  ..........  ..........  ..........
223_10   ..........  ..........  ..........  ..........  ..........
223_2    ..........  ..........  ..........  ..........  ..........
223_4    ..........  ..........  ..........  ..........  ..........
223_5    ..........  ..........  ..........  ..........  ..........
223_6    ..........  ..........  ..........  ..........  ..........
223_7    ..........  ..........  ..........  ..........  ..........
 A3_4    ..........  ..........  ..........  ..........  ..........
 A3_5    ..........  ..........  ..........  ..........  ..........
 A3_7    ..........  ..........  ..........  ..........  ..........
 A3_3    ..........  ..........  ..........  ..........  ..........
 42_12   ..........  ..........  ..........  ..........  ..........
 AAV1    GGCCGAGAAG  CTGCAGCGCG  ACTTCCTGGT  CCAATGGCGC  CGCGTGAGTA
 AAV2    GGCCGAGAAG  CTGCAGCGCG  ACTTTCTGAC  GGAATGGCGC  CGTGTGAGTA
 AAV3    GGCCGAAAAG  CTTCAGCGCG  AGTTCCTGGT  GGAGTGGCGC  CGCGTGAGTA
 AAV8    GGCCGAGAAG  CTGCAGCGCG  ACTTCCTGGT  CCAATGGCGC  CGCGTGAGTA
 AAV9    GGCCGAGAAG  CTGTAGCGCG  ACTTCCTGGT  CCAATGGCGC  CGCGTGAGTA
 AAV7    GGCCGAGAAG  CTGCAGCGCG  ACTTCCTGGT  CCAATGGCGC  CGCGTGAGTA
 44_2    ..........  ..........  ..........  ..........  ..........
```

FIG. 1L

```
         551                                                              600
  42_2   ..........  ..........  ..........  ..........  ..........
  42_8   ..........  ..........  ..........  ..........  ..........
 42_15   ..........  ..........  ..........  ..........  ..........
 42_5b   ..........  ..........  ..........  ..........  ..........
 42_1b   ..........  ..........  ..........  ..........  ..........
 42_13   ..........  ..........  ..........  ..........  ..........
 42_3a   ..........  ..........  ..........  ..........  ..........
  42_4   ..........  ..........  ..........  ..........  ..........
 42_5a   ..........  ..........  ..........  ..........  ..........
 42_10   ..........  ..........  ..........  ..........  ..........
 42_3b   ..........  ..........  ..........  ..........  ..........
 42_11   ..........  ..........  ..........  ..........  ..........
 42_6b   ..........  ..........  ..........  ..........  ..........
  43_1   ..........  ..........  ..........  ..........  ..........
  43_5   ..........  ..........  ..........  ..........  ..........
 43_12   ..........  ..........  ..........  ..........  ..........
 43_20   ..........  ..........  ..........  ..........  ..........
 43_21   ..........  ..........  ..........  ..........  ..........
 43_23   ..........  ..........  ..........  ..........  ..........
 43_25   ..........  ..........  ..........  ..........  ..........
  44_1   ..........  ..........  ..........  ..........  ..........
  44_5   ..........  ..........  ..........  ..........  ..........
 223_10  ..........  ..........  ..........  ..........  ..........
 223_2   ..........  ..........  ..........  ..........  ..........
 223_4   ..........  ..........  ..........  ..........  ..........
 223_5   ..........  ..........  ..........  ..........  ..........
 223_6   ..........  ..........  ..........  ..........  ..........
 223_7   ..........  ..........  ..........  ..........  ..........
  A3_4   ..........  ..........  ..........  ..........  ..........
  A3_5   ..........  ..........  ..........  ..........  ..........
  A3_7   ..........  ..........  ..........  ..........  ..........
  A3_3   ..........  ..........  ..........  ..........  ..........
 42_12   ..........  ..........  ..........  ..........  ..........
  AAV1   AGGCCCCGGA  GGCCCTCTTC  TTTGTTCAGT  TCGAGAAGGG  CGAGTCCTAC
  AAV2   AGGCCCCGGA  GGCCCTTTTC  TTTCTGCAAT  TTGAGAAGGG  AGAGAGCTAC
  AAV3   AGGCCCCGGA  GGCCCTCTTT  TTTGTCCAGT  TCGAAAAGGG  GGAGACCTAC
  AAV8   AGGCCCCGGA  GGCCCTCTTC  TTTGTTCAGT  TCGAGAAGGG  CGAGAGCTAC
  AAV9   AGGCCCCGGA  GGCCCTCTTC  TTTGTTCAGT  TCGAGAAGGG  CGAGAGCTAC
  AAV7   AGGCCCCGGA  GGCCCTGTTC  TTTGTTCAGT  TCGAGAAGGG  CGAGAGCTAC
  44_2   ..........  ..........  ..........  ..........  ..........
```

FIG. 1M

```
        601                                                           650
42_2    ..........  ..........  ..........  ..........  ..........
42_8    ..........  ..........  ..........  ..........  ..........
42_15   ..........  ..........  ..........  ..........  ..........
42_5b   ..........  ..........  ..........  ..........  ..........
42_1b   ..........  ..........  ..........  ..........  ..........
42_13   ..........  ..........  ..........  ..........  ..........
42_3a   ..........  ..........  ..........  ..........  ..........
42_4    ..........  ..........  ..........  ..........  ..........
42_5a   ..........  ..........  ..........  ..........  ..........
42_10   ..........  ..........  ..........  ..........  ..........
42_3b   ..........  ..........  ..........  ..........  ..........
42_11   ..........  ..........  ..........  ..........  ..........
42_6b   ..........  ..........  ..........  ..........  ..........
43_1    ..........  ..........  ..........  ..........  ..........
43_5    ..........  ..........  ..........  ..........  ..........
43_12   ..........  ..........  ..........  ..........  ..........
43_20   ..........  ..........  ..........  ..........  ..........
43_21   ..........  ..........  ..........  ..........  ..........
43_23   ..........  ..........  ..........  ..........  ..........
43_25   ..........  ..........  ..........  ..........  ..........
44_1    ..........  ..........  ..........  ..........  ..........
44_5    ..........  ..........  ..........  ..........  ..........
223_10  ..........  ..........  ..........  ..........  ..........
223_2   ..........  ..........  ..........  ..........  ..........
223_4   ..........  ..........  ..........  ..........  ..........
223_5   ..........  ..........  ..........  ..........  ..........
223_6   ..........  ..........  ..........  ..........  ..........
223_7   ..........  ..........  ..........  ..........  ..........
A3_4    ..........  ..........  ..........  ..........  ..........
A3_5    ..........  ..........  ..........  ..........  ..........
A3_7    ..........  ..........  ..........  ..........  ..........
A3_3    ..........  ..........  ..........  ..........  ..........
42_12   ..........  ..........  ..........  ..........  ..........
AAV1    TTCCACCTCC  ATATTCTGGT  GGAGACCACG  GGGGTCAAAT  CCATGGTGCT
AAV2    TTCCACATGC  ACGTGCTCGT  GGAAACCACC  GGGGTGAAAT  CCATGGTTTT
AAV3    TTCCACCTGC  ACGTGCTGAT  TGAGACCATC  GGGGTCAAAT  CCATGGTGGT
AAV8    TTTCACCTGC  ACGTTCTGGT  CGAGACCACG  GGGGTCAAGT  CCATGGTGCT
AAV9    TTTCACCTGC  ACGTTCTGGT  CGAGACCACG  GGGGTCAAGT  CCATGGTGCT
AAV7    TTCCACCTTC  ACGTTCTGGT  GGAGACCACG  GGGGTCAAGT  CCATGGTGCT
44_2    ..........  ..........  ..........  ..........  ..........
```

FIG. 1N

```
        651                                                              700
42_2     ..........  ..........  ..........  ..........  ..........
42_8     ..........  ..........  ..........  ..........  ..........
42_15    ..........  ..........  ..........  ..........  ..........
42_5b    ..........  ..........  ..........  ..........  ..........
42_1b    ..........  ..........  ..........  ..........  ..........
42_13    ..........  ..........  ..........  ..........  ..........
42_3a    ..........  ..........  ..........  ..........  ..........
42_4     ..........  ..........  ..........  ..........  ..........
42_5a    ..........  ..........  ..........  ..........  ..........
42_10    ..........  ..........  ..........  ..........  ..........
42_3b    ..........  ..........  ..........  ..........  ..........
42_11    ..........  ..........  ..........  ..........  ..........
42_6b    ..........  ..........  ..........  ..........  ..........
43_1     ..........  ..........  ..........  ..........  ..........
43_5     ..........  ..........  ..........  ..........  ..........
43_12    ..........  ..........  ..........  ..........  ..........
43_20    ..........  ..........  ..........  ..........  ..........
43_21    ..........  ..........  ..........  ..........  ..........
43_23    ..........  ..........  ..........  ..........  ..........
43_25    ..........  ..........  ..........  ..........  ..........
44_1     ..........  ..........  ..........  ..........  ..........
44_5     ..........  ..........  ..........  ..........  ..........
223_10   ..........  ..........  ..........  ..........  ..........
223_2    ..........  ..........  ..........  ..........  ..........
223_4    ..........  ..........  ..........  ..........  ..........
223_5    ..........  ..........  ..........  ..........  ..........
223_6    ..........  ..........  ..........  ..........  ..........
223_7    ..........  ..........  ..........  ..........  ..........
A3_4     ..........  ..........  ..........  ..........  ..........
A3_5     ..........  ..........  ..........  ..........  ..........
A3_7     ..........  ..........  ..........  ..........  ..........
A3_3     ..........  ..........  ..........  ..........  ..........
42_12    ..........  ..........  ..........  ..........  ..........
AAV1     GGGCCGCTTC  CTGAGTCAGA  TTAGGGACAA  GCT.GGTGCA  GACCATCTAC
AAV2     GGGACGTTTC  CTGAGTCAGA  TTCGCGAAAA  ACT..GATTC  AGAGAATTTA
AAV3     CGGCCGCTAC  GTGAGCCAGA  TTAAAGAGAA  GCT..GGTGA  CCCGCATCTA
AAV8     AGGCCGCTTC  CTGAGTCAGA  TTCGGGAAAA  GCTTGGTCCA  GACCATCTAC
AAV9     AGGCCGCTTC  CTGAGTCAGA  TTCGGGAGAA  GCT.GGTCCA  GACCATCTAC
AAV7     AGGCCGCTTC  CTGAGTCAGA  TTCGGGAGAA  GCT....G..  GTCCAGACCA
44_2     ..........  ..........  ..........  ..........  ..........
```

FIG. 10

```
              701                                                           750
     42_2     ..........    ..........    ..........    ..........    ..........
     42_8     ..........    ..........    ..........    ..........    ..........
     42_15    ..........    ..........    ..........    ..........    ..........
     42_5b    ..........    ..........    ..........    ..........    ..........
     42_1b    ..........    ..........    ..........    ..........    ..........
     42_13    ..........    ..........    ..........    ..........    ..........
     42_3a    ..........    ..........    ..........    ..........    ..........
     42_4     ..........    ..........    ..........    ..........    ..........
     42_5a    ..........    ..........    ..........    ..........    ..........
     42_10    ..........    ..........    ..........    ..........    ..........
     42_3b    ..........    ..........    ..........    ..........    ..........
     42_11    ..........    ..........    ..........    ..........    ..........
     42_6b    ..........    ..........    ..........    ..........    ..........
     43_1     ..........    ..........    ..........    ..........    ..........
     43_5     ..........    ..........    ..........    ..........    ..........
     43_12    ..........    ..........    ..........    ..........    ..........
     43_20    ..........    ..........    ..........    ..........    ..........
     43_21    ..........    ..........    ..........    ..........    ..........
     43_23    ..........    ..........    ..........    ..........    ..........
     43_25    ..........    ..........    ..........    ..........    ..........
     44_1     ..........    ..........    ..........    ..........    ..........
     44_5     ..........    ..........    ..........    ..........    ..........
    223_10    ..........    ..........    ..........    ..........    ..........
    223_2     ..........    ..........    ..........    ..........    ..........
    223_4     ..........    ..........    ..........    ..........    ..........
    223_5     ..........    ..........    ..........    ..........    ..........
    223_6     ..........    ..........    ..........    ..........    ..........
    223_7     ..........    ..........    ..........    ..........    ..........
     A3_4     ..........    ..........    ..........    ..........    ..........
     A3_5     ..........    ..........    ..........    ..........    ..........
     A3_7     ..........    ..........    ..........    ..........    ..........
     A3_3     ..........    ..........    ..........    ..........    ..........
     42_12    ..........    ..........    ..........    ..........    ..........
     AAV1     C.GCGGGATC    GAGCCG.ACC    CTGCCCAACT    GGTTCGCGGT    GACCAA.GAC
     AAV2     CCGCGGGATC    GAGCCG.ACT    TTGCCAAACT    GGTTCGCGGT    CACAAA...G
     AAV3     CCGCGGGGTC    GAGCCG.CAG    CTTCCGAACT    GGTTCGCGGT    GACCAA...A
     AAV8     CCGCGGGGTC    GAGCCCCACC    TTGCCCAACT    GGTTCGCGGT    GACCAAAGAC
     AAV9     C.GCGGGATC    GAGCCG.ACC    CTGCCCAACT    GGTTCGCGGT    GACCAA.GAC
     AAV7     TCTACCGCGG    GGTCGAGCCC    ACGCTGCCCA    ACTGGTTCGC    GGTGACCAAG
     44_2     ..........    ..........    ..........    ..........    ..........
```

FIG. 1P

```
         751                                                              800
  42_2   ..........  ..........  ..........  ..........  ..........
  42_8   ..........  ..........  ..........  ..........  ..........
  42_15  ..........  ..........  ..........  ..........  ..........
  42_5b  ..........  ..........  ..........  ..........  ..........
  42_1b  ..........  ..........  ..........  ..........  ..........
  42_13  ..........  ..........  ..........  ..........  ..........
  42_3a  ..........  ..........  ..........  ..........  ..........
  42_4   ..........  ..........  ..........  ..........  ..........
  42_5a  ..........  ..........  ..........  ..........  ..........
  42_10  ..........  ..........  ..........  ..........  ..........
  42_3b  ..........  ..........  ..........  ..........  ..........
  42_11  ..........  ..........  ..........  ..........  ..........
  42_6b  ..........  ..........  ..........  ..........  ..........
  43_1   ..........  ..........  ..........  ..........  ..........
  43_5   ..........  ..........  ..........  ..........  ..........
  43_12  ..........  ..........  ..........  ..........  ..........
  43_20  ..........  ..........  ..........  ..........  ..........
  43_21  ..........  ..........  ..........  ..........  ..........
  43_23  ..........  ..........  ..........  ..........  ..........
  43_25  ..........  ..........  ..........  ..........  ..........
  44_1   ..........  ..........  ..........  ..........  ..........
  44_5   ..........  ..........  ..........  ..........  ..........
 223_10  ..........  ..........  ..........  ..........  ..........
 223_2   ..........  ..........  ..........  ..........  ..........
 223_4   ..........  ..........  ..........  ..........  ..........
 223_5   ..........  ..........  ..........  ..........  ..........
 223_6   ..........  ..........  ..........  ..........  ..........
 223_7   ..........  ..........  ..........  ..........  ..........
  A3_4   ..........  ..........  ..........  ..........  ..........
  A3_5   ..........  ..........  ..........  ..........  ..........
  A3_7   ..........  ..........  ..........  ..........  ..........
  A3_3   ..........  ..........  ..........  ..........  ..........
  42_12  ..........  ..........  ..........  ..........  ..........
  AAV1   GCG.TAATGG  CGCCGGAGGG  GGG.AACAAG  GTGGTGGACG  AGTGCTACAT
  AAV2   ACCAGAAATG  GCGCCGGAGG  CGGGAACAAG  GTGGTGGATG  AGTGCTACAT
  AAV3   ACGCGAAATG  GCGCCGGGGG  CGGGAACAAG  GTGGTGGACG  ACTGCTACAT
  AAV8   GCGGTAATGG  CGCCGGCGGG  GGGGAACAAG  GTGGTGGACG  AGTGCTACAT
  AAV9   GCG.TAATGG  CGCCGGCGGG  GGG.AACAAG  GTGGTGGACG  AGTGCTACAT
  AAV7   ACGCGTAATG  GCGCCGGCGG  GGGGAACAAG  GTGGTGGACG  AGTGCTACAT
  44_2   ..........  ..........  ..........  ..........  ..........
```

FIG. 1Q

```
        801                                                       850
 42_2   ..........  ..........  ..........  ..........  ..........
 42_8   ..........  ..........  ..........  ..........  ..........
 42_15  ..........  ..........  ..........  ..........  ..........
 42_5b  ..........  ..........  ..........  ..........  ..........
 42_1b  ..........  ..........  ..........  ..........  ..........
 42_13  ..........  ..........  ..........  ..........  ..........
 42_3a  ..........  ..........  ..........  ..........  ..........
 42_4   ..........  ..........  ..........  ..........  ..........
 42_5a  ..........  ..........  ..........  ..........  ..........
 42_10  ..........  ..........  ..........  ..........  ..........
 42_3b  ..........  ..........  ..........  ..........  ..........
 42_11  ..........  ..........  ..........  ..........  ..........
 42_6b  ..........  ..........  ..........  ..........  ..........
 43_1   ..........  ..........  ..........  ..........  ..........
 43_5   ..........  ..........  ..........  ..........  ..........
 43_12  ..........  ..........  ..........  ..........  ..........
 43_20  ..........  ..........  ..........  ..........  ..........
 43_21  ..........  ..........  ..........  ..........  ..........
 43_23  ..........  ..........  ..........  ..........  ..........
 43_25  ..........  ..........  ..........  ..........  ..........
 44_1   ..........  ..........  ..........  ..........  ..........
 44_5   ..........  ..........  ..........  ..........  ..........
 223_10 ..........  ..........  ..........  ..........  ..........
 223_2  ..........  ..........  ..........  ..........  ..........
 223_4  ..........  ..........  ..........  ..........  ..........
 223_5  ..........  ..........  ..........  ..........  ..........
 223_6  ..........  ..........  ..........  ..........  ..........
 223_7  ..........  ..........  ..........  ..........  ..........
 A3_4   ..........  ..........  ..........  ..........  ..........
 A3_5   ..........  ..........  ..........  ..........  ..........
 A3_7   ..........  ..........  ..........  ..........  ..........
 A3_3   ..........  ..........  ..........  ..........  ..........
 42_12  ..........  ..........  ..........  ..........  ..........
 AAV1   CCCCAACTAC  CTCCTGCCCA  AGACTCAGCC  CGAGCTGCAG  TGGGCGTGGA
 AAV2   CCCCAATTAC  TTGCTCCCCA  AAACCCAGCC  TGAGCTCCAG  TGGGCGTGGA
 AAV3   CCCCAACTAC  CTGCTCCCCA  AGACCCAGCC  CGAGCTCCAG  TGGGCGTGGA
 AAV8   CCCCAACTAC  CTCCTGCCCA  AGACTCAGCC  CGAGCTGCAG  TGGGCGTGGA
 AAV9   CCCCAACTAC  CTCCTGCCCA  AGACTCAGCC  CGAGCTGCAG  TGGGCGTGGA
 AAV7   CCCCAACTAC  CTCCTGCCCA  AGACCCAGCC  CGAGCTGCAG  TGGGCGTGGA
 44_2   ..........  ..........  ..........  ..........  ..........
```

FIG. 1R

```
                              851                                                         900
                                    P19/TATA                        P19 RNA
        42_2      ..........   ..........   ..........   ..........   ..........
        42_8      ..........   ..........   ..........   ..........   ..........
        42_15     ..........   ..........   ..........   ..........   ..........
        42_5b     ..........   ..........   ..........   ..........   ..........
        42_1b     ..........   ..........   ..........   ..........   ..........
        42_13     ..........   ..........   ..........   ..........   ..........
        42_3a     ..........   ..........   ..........   ..........   ..........
        42_4      ..........   ..........   ..........   ..........   ..........
        42_5a     ..........   ..........   ..........   ..........   ..........
        42_10     ..........   ..........   ..........   ..........   ..........
        42_3b     ..........   ..........   ..........   ..........   ..........
        42_11     ..........   ..........   ..........   ..........   ..........
        42_6b     ..........   ..........   ..........   ..........   ..........
        43_1      ..........   ..........   ..........   ..........   ..........
        43_5      ..........   ..........   ..........   ..........   ..........
        43_12     ..........   ..........   ..........   ..........   ..........
        43_20     ..........   ..........   ..........   ..........   ..........
        43_21     ..........   ..........   ..........   ..........   ..........
        43_23     ..........   ..........   ..........   ..........   ..........
        43_25     ..........   ..........   ..........   ..........   ..........
        44_1      ..........   ..........   ..........   ..........   ..........
        44_5      ..........   ..........   ..........   ..........   ..........
        223_10    ..........   ..........   ..........   ..........   ..........
        223_2     ..........   ..........   ..........   ..........   ..........
        223_4     ..........   ..........   ..........   ..........   ..........
        223_5     ..........   ..........   ..........   ..........   ..........
        223_6     ..........   ..........   ..........   ..........   ..........
        223_7     ..........   ..........   ..........   ..........   ..........
        A3_4      ..........   ..........   ..........   ..........   ..........
        A3_5      ..........   ..........   ..........   ..........   ..........
        A3_7      ..........   ..........   ..........   ..........   ..........
        A3_3      ..........   ..........   ..........   ..........   ..........
        42_12     ..........   ..........   ..........   ..........   ..........
        AAV1      CTAACATGGA   GGAGTATATA   AGCGCCTGTT   TGAACCTGGC   CGAGCGCAAA
        AAV2      CTAATATGGA   ACAGTATTTA   AGCGCCTGTT   TGAATCTCAC   GGAGCGTAAA
        AAV3      CTAACATGGA   CCAGTATTTA   AGCGCCTGTT   TGAATCTCGC   GGAGCGTAAA
        AAV8      CTAACATGGA   GGAGTATATA   AGCGCGTGCT   TGAACCTGGC   CGAGCGCAAA
        AAV9      CTAACATGGA   GGAGTATATA   AGCGCGTGCT   TGAACCTGGC   CGAGCGCAAA
        AAV7      CTAACATGGA   GGAGTATATA   AGCGCGTGTT   TGAACCTGGC   CGAACGCAAA
        44_2      ..........   ..........   ..........   ..........   ..........
                                   P19/TATA                       P19 RNA
```

FIG. 1S

```
          901                                                          950
   42_2   ..........  ..........  ..........  ..........  ..........
   42_8   ..........  ..........  ..........  ..........  ..........
  42_15   ..........  ..........  ..........  ..........  ..........
  42_5b   ..........  ..........  ..........  ..........  ..........
  42_1b   ..........  ..........  ..........  ..........  ..........
  42_13   ..........  ..........  ..........  ..........  ..........
  42_3a   ..........  ..........  ..........  ..........  ..........
   42_4   ..........  ..........  ..........  ..........  ..........
  42_5a   ..........  ..........  ..........  ..........  ..........
  42_10   ..........  ..........  ..........  ..........  ..........
  42_3b   ..........  ..........  ..........  ..........  ..........
  42_11   ..........  ..........  ..........  ..........  ..........
  42_6b   ..........  ..........  ..........  ..........  ..........
   43_1   ..........  ..........  ..........  ..........  ..........
   43_5   ..........  ..........  ..........  ..........  ..........
  43_12   ..........  ..........  ..........  ..........  ..........
  43_20   ..........  ..........  ..........  ..........  ..........
  43_21   ..........  ..........  ..........  ..........  ..........
  43_23   ..........  ..........  ..........  ..........  ..........
  43_25   ..........  ..........  ..........  ..........  ..........
   44_1   ..........  ..........  ..........  ..........  ..........
   44_5   ..........  ..........  ..........  ..........  ..........
 223_10   ..........  ..........  ..........  ..........  ..........
  223_2   ..........  ..........  ..........  ..........  ..........
  223_4   ..........  ..........  ..........  ..........  ..........
  223_5   ..........  ..........  ..........  ..........  ..........
  223_6   ..........  ..........  ..........  ..........  ..........
  223_7   ..........  ..........  ..........  ..........  ..........
   A3_4   ..........  ..........  ..........  ..........  ..........
   A3_5   ..........  ..........  ..........  ..........  ..........
   A3_7   ..........  ..........  ..........  ..........  ..........
   A3_3   ..........  ..........  ..........  ..........  ..........
  42_12   ..........  ..........  ..........  ..........  ..........
   AAV1   CGGCTCGTGG  CGCAGCACCT  GACCCACGTC  AGCCAGACCC  AGGAGCAGAA
   AAV2   CGGTTGGTGG  CGCAGCATCT  GACGCACGTG  TCGCAGACGC  AGGAGCAGAA
   AAV3   CGGCTGGTGG  CGCAGCATCT  GACGCACGTG  TCGCAGACGC  AGGAGCAGAA
   AAV8   CGGCTCGTGG  CGCAGCACCT  GACCCACGTC  AGCCAGACGC  AGGAGCAGAA
   AAV9   CGGCTCGTGG  CGCAGCACCT  GACCCACGTC  AGCCAGACGC  AGGAGCAGAA
   AAV7   CGGCTCGTGG  CGCAGCACCT  GACCCACGTC  AGCCAGACGC  AGGAGCAGAA
   44_2   ..........  ..........  ..........  ..........  ..........
```

FIG. 1T

```
           951                                                          1000
 42_2      ..........  ..........  ..........  ..........  ..........
 42_8      ..........  ..........  ..........  ..........  ..........
 42_15     ..........  ..........  ..........  ..........  ..........
 42_5b     ..........  ..........  ..........  ..........  ..........
 42_1b     ..........  ..........  ..........  ..........  ..........
 42_13     ..........  ..........  ..........  ..........  ..........
 42_3a     ..........  ..........  ..........  ..........  ..........
 42_4      ..........  ..........  ..........  ..........  ..........
 42_5a     ..........  ..........  ..........  ..........  ..........
 42_10     ..........  ..........  ..........  ..........  ..........
 42_3b     ..........  ..........  ..........  ..........  ..........
 42_11     ..........  ..........  ..........  ..........  ..........
 42_6b     ..........  ..........  ..........  ..........  ..........
 43_1      ..........  ..........  ..........  ..........  ..........
 43_5      ..........  ..........  ..........  ..........  ..........
 43_12     ..........  ..........  ..........  ..........  ..........
 43_20     ..........  ..........  ..........  ..........  ..........
 43_21     ..........  ..........  ..........  ..........  ..........
 43_23     ..........  ..........  ..........  ..........  ..........
 43_25     ..........  ..........  ..........  ..........  ..........
 44_1      ..........  ..........  ..........  ..........  ..........
 44_5      ..........  ..........  ..........  ..........  ..........
223_10     ..........  ..........  ..........  ..........  ..........
223_2      ..........  ..........  ..........  ..........  ..........
223_4      ..........  ..........  ..........  ..........  ..........
223_5      ..........  ..........  ..........  ..........  ..........
223_6      ..........  ..........  ..........  ..........  ..........
223_7      ..........  ..........  ..........  ..........  ..........
 A3_4      ..........  ..........  ..........  ..........  ..........
 A3_5      ..........  ..........  ..........  ..........  ..........
 A3_7      ..........  ..........  ..........  ..........  ..........
 A3_3      ..........  ..........  ..........  ..........  ..........
 42_12     ..........  ..........  ..........  ..........  ..........
 AAV1      CAAGGAGAAT  CTGAACCCCA  ATTCTGACGC  GCCTGTCATC  CGGTCAAAAA
 AAV2      CAAAGAGAAT  CAGAATCCCA  ATTCTGATGC  GCCGGTGATC  AGATCAAAAA
 AAV3      CAAAGAGAAT  CAGAACCCCA  ATTCTGACGC  GCCGGTCATC  AGGTCAAAAA
 AAV8      CAAGGAGAAT  CTGAACCCCA  ATTCTGACGC  GCCCGTGATC  AGGTCAAAAA
 AAV9      CAAGGAGAAT  CTGAACCCCA  ATTCTGACGC  GCCCGTGATC  AGGTCAAAAA
 AAV7      CAAGGAGAAT  CTGAACCCCA  ATTCTGACGC  GCCCGTGATC  AGGTCAAAAA
 44_2      ..........  ..........  ..........  ..........  ..........
```

FIG. 1U 1001                                                                                                  1050

```
                    Rep52/40 start codon
 42_2       .......... .....↓.↓... .......... .......... ..........
 42_8       .......... .......... .......... .......... ..........
 42_15      .......... .......... .......... .......... ..........
 42_5b      .......... .......... .......... .......... ..........
 42_1b      .......... .......... .......... .......... ..........
 42_13      .......... .......... .......... .......... ..........
 42_3a      .......... .......... .......... .......... ..........
 42_4       .......... .......... .......... .......... ..........
 42_5a      .......... .......... .......... .......... ..........
 42_10      .......... .......... .......... .......... ..........
 42_3b      .......... .......... .......... .......... ..........
 42_11      .......... .......... .......... .......... ..........
 42_6b      .......... .......... .......... .......... ..........
 43_1       .......... .......... .......... .......... ..........
 43_5       .......... .......... .......... .......... ..........
 43_12      .......... .......... .......... .......... ..........
 43_20      .......... .......... .......... .......... ..........
 43_21      .......... .......... .......... .......... ..........
 43_23      .......... .......... .......... .......... ..........
 43_25      .......... .......... .......... .......... ..........
 44_1       .......... .......... .......... .......... ..........
 44_5       .......... .......... .......... .......... ..........
223_10      .......... .......... .......... .......... ..........
223_2       .......... .......... .......... .......... ..........
223_4       .......... .......... .......... .......... ..........
223_5       .......... .......... .......... .......... ..........
223_6       .......... .......... .......... .......... ..........
223_7       .......... .......... .......... .......... ..........
 A3_4       .......... .......... .......... .......... ..........
 A3_5       .......... .......... .......... .......... ..........
 A3_7       .......... .......... .......... .......... ..........
 A3_3       .......... .......... .......... .......... ..........
 42_12      .......... .......... .......... .......... ..........
 AAV1       CCTCCGCGCG CTACATGGAG CTGGTCGGGT GGCTGGTGGA CCGGGGCATC
 AAV2       CTTCAGCCAG GTACATGGAG CTGGTCGGGT GGCTCGTGGA CAAGGGGATT
 AAV3       CCTCAGCCAG GTACATGGAG CTGGTCGGGT GGCTGGTGGA CCGCGGGATC
 AAV8       CCTCCGCGCG CTATATGGAG CTGGTCGGGT GGCTGGTGGA CCGGGGCATC
 AAV9       CCTCCGCGCG CTACATGGAG CTGGTCGGGT GGCTGGTGGA CCGGGGCATC
 AAV7       CCTCCGCGCG CTACATGGAG CTGGTCGGGT GGCTGGTGGA CCGGGGCATC
 44_2       .......... ...↑↑.... .......... .......... ..........
                         Rep 52/40 start
```

FIG. 1V

```
          1051                                                              1100
 42_2     ..........  ..........  ..........  ..........  ..........
 42_8     ..........  ..........  ..........  ..........  ..........
 42_15    ..........  ..........  ..........  ..........  ..........
 42_5b    ..........  ..........  ..........  ..........  ..........
 42_1b    ..........  ..........  ..........  ..........  ..........
 42_13    ..........  ..........  ..........  ..........  ..........
 42_3a    ..........  ..........  ..........  ..........  ..........
 42_4     ..........  ..........  ..........  ..........  ..........
 42_5a    ..........  ..........  ..........  ..........  ..........
 42_10    ..........  ..........  ..........  ..........  ..........
 42_3b    ..........  ..........  ..........  ..........  ..........
 42_11    ..........  ..........  ..........  ..........  ..........
 42_6b    ..........  ..........  ..........  ..........  ..........
 43_1     ..........  ..........  ..........  ..........  ..........
 43_5     ..........  ..........  ..........  ..........  ..........
 43_12    ..........  ..........  ..........  ..........  ..........
 43_20    ..........  ..........  ..........  ..........  ..........
 43_21    ..........  ..........  ..........  ..........  ..........
 43_23    ..........  ..........  ..........  ..........  ..........
 43_25    ..........  ..........  ..........  ..........  ..........
 44_1     ..........  ..........  ..........  ..........  ..........
 44_5     ..........  ..........  ..........  ..........  ..........
223_10    ..........  ..........  ..........  ..........  ..........
223_2     ..........  ..........  ..........  ..........  ..........
223_4     ..........  ..........  ..........  ..........  ..........
223_5     ..........  ..........  ..........  ..........  ..........
223_6     ..........  ..........  ..........  ..........  ..........
223_7     ..........  ..........  ..........  ..........  ..........
 A3_4     ..........  ..........  ..........  ..........  ..........
 A3_5     ..........  ..........  ..........  ..........  ..........
 A3_7     ..........  ..........  ..........  ..........  ..........
 A3_3     ..........  ..........  ..........  ..........  ..........
 42_12    ..........  ..........  ..........  ..........  ..........
 AAV1     ACCTCCGAGA  AGCAGTGGAT  CCAGGAGGAC  CAGGCCTCGT  ACATCTCCTT
 AAV2     ACCTCGGAGA  AGCAGTGGAT  CCAGGAGGAC  CAGGCCTCAT  ACATCTCCTT
 AAV3     ACGTCAGAAA  AGCAATGGAT  TCAGGAGGAC  CAGGCCTCGT  ACATCTCCTT
 AAV6     ACCTCCGAGA  AGCAGTGGAT  CCAGGAGGAC  CAGGCCTCGT  ACATCTCCTT
 AAV9     ACCTCCGAGA  AGCAGTGGAT  CCAGGAGGAC  CAGGCCTCGT  ACATCTCCTT
 AAV7     ACCTCCGAGA  AGCAGTGGAT  CCAGGAGGAC  CAGGCCTCGT  ACATCTCCTT
 44_2     ..........  ..........  ..........  ..........  ..........
```

FIG. 1W

```
      1101                                                      1150
42_2   ..........  ..........  ..........  ..........  ..........
42_8   ..........  ..........  ..........  ..........  ..........
42_15  ..........  ..........  ..........  ..........  ..........
42_5b  ..........  ..........  ..........  ..........  ..........
42_1b  ..........  ..........  ..........  ..........  ..........
42_13  ..........  ..........  ..........  ..........  ..........
42_3a  ..........  ..........  ..........  ..........  ..........
42_4   ..........  ..........  ..........  ..........  ..........
42_5a  ..........  ..........  ..........  ..........  ..........
42_10  ..........  ..........  ..........  ..........  ..........
42_3b  ..........  ..........  ..........  ..........  ..........
42_11  ..........  ..........  ..........  ..........  ..........
42_6b  ..........  ..........  ..........  ..........  ..........
43_1   ..........  ..........  ..........  ..........  ..........
43_5   ..........  ..........  ..........  ..........  ..........
43_12  ..........  ..........  ..........  ..........  ..........
43_20  ..........  ..........  ..........  ..........  ..........
43_21  ..........  ..........  ..........  ..........  ..........
43_23  ..........  ..........  ..........  ..........  ..........
43_25  ..........  ..........  ..........  ..........  ..........
44_1   ..........  ..........  ..........  ..........  ..........
44_5   ..........  ..........  ..........  ..........  ..........
223_10 ..........  ..........  ..........  ..........  ..........
223_2  ..........  ..........  ..........  ..........  ..........
223_4  ..........  ..........  ..........  ..........  ..........
223_5  ..........  ..........  ..........  ..........  ..........
223_6  ..........  ..........  ..........  ..........  ..........
223_7  ..........  ..........  ..........  ..........  ..........
A3_4   ..........  ..........  ..........  ..........  ..........
A3_5   ..........  ..........  ..........  ..........  ..........
A3_7   ..........  ..........  ..........  ..........  ..........
A3_3   ..........  ..........  ..........  ..........  ..........
42_12  ..........  ..........  ..........  ..........  ..........
AAV1   CAACGCCGCT  TCCAACTCGC  GGTCCCAGAT  CAAGGCCGCT  CTGGACAATG
AAV2   CAATGCGGCC  TCCAACTCGC  GGTCCCAAAT  CAAGGCTGCC  TTGGACAATG
AAV3   CAACGCCGCC  TCCAACTCGC  GGTCCCAGAT  CAAGGCCGCG  CTGGACAATG
AAV8   CAACGCCGCC  TCCAACTCGC  GGTCCCAGAT  CAAGGCCGCG  CTGGACAATG
AAV9   CAACGCCGCC  TCCAACTCGC  GGTCCCAGAT  CAAGGCCGCG  CTGGACAATG
AAV7   CAACGCCGCC  TCCAACTCGC  GGTCCCAGAT  CAAGGCCGCG  CTGGACAATG
44_2   ..........  ..........  ..........  ..........  ..........
```

FIG. 1X

```
        1151                                                        1200
 42_2   ..........  ..........  ..........  ..........  ..........
 42_8   ..........  ..........  ..........  ..........  ..........
 42_15  ..........  ..........  ..........  ..........  ..........
 42_5b  ..........  ..........  ..........  ..........  ..........
 42_1b  ..........  ..........  ..........  ..........  ..........
 42_13  ..........  ..........  ..........  ..........  ..........
 42_3a  ..........  ..........  ..........  ..........  ..........
 42_4   ..........  ..........  ..........  ..........  ..........
 42_5a  ..........  ..........  ..........  ..........  ..........
 42_10  ..........  ..........  ..........  ..........  ..........
 42_3b  ..........  ..........  ..........  ..........  ..........
 42_11  ..........  ..........  ..........  ..........  ..........
 42_6b  ..........  ..........  ..........  ..........  ..........
 43_1   ..........  ..........  ..........  ..........  ..........
 43_5   ..........  ..........  ..........  ..........  ..........
 43_12  ..........  ..........  ..........  ..........  ..........
 43_20  ..........  ..........  ..........  ..........  ..........
 43_21  ..........  ..........  ..........  ..........  ..........
 43_23  ..........  ..........  ..........  ..........  ..........
 43_25  ..........  ..........  ..........  ..........  ..........
 44_1   ..........  ..........  ..........  ..........  ..........
 44_5   ..........  ..........  ..........  ..........  ..........
223_10  ..........  ..........  ..........  ..........  ..........
223_2   ..........  ..........  ..........  ..........  ..........
223_4   ..........  ..........  ..........  ..........  ..........
223_5   ..........  ..........  ..........  ..........  ..........
223_6   ..........  ..........  ..........  ..........  ..........
223_7   ..........  ..........  ..........  ..........  ..........
 A3_4   ..........  ..........  ..........  ..........  ..........
 A3_5   ..........  ..........  ..........  ..........  ..........
 A3_7   ..........  ..........  ..........  ..........  ..........
 A3_3   ..........  ..........  ..........  ..........  ..........
 42_12  ..........  ..........  ..........  ..........  ..........
 AAV1   CCGGCAAGAT  CATGGCGCTG  ACCAAATCCG  CGCCCGACTA  CCTGGTAGGC
 AAV2   CGGGAAAGAT  TATGAGCCTG  ACTAAAACCG  CCCCCGACTA  CCTGGTGGGC
 AAV3   CCTCCAAGAT  CATGAGCCTG  ACAAAGACGG  CTCCGGACTA  CCTGGTGGGC
 AAV8   CCGGCAAGAT  CATGGCGCTG  ACCAAATCCG  CGCCCGACTA  CCTGGTGGGG
 AAV9   CCGGCAAGAT  CATGGCGCTG  ACCAAATCCG  CGCCCGACTA  CCTGGTAGGC
 AAV7   CCGGCAAGAT  CATGGCGCTG  ACCAAATCCG  CGCCCGACTA  CCTGGTGGGG
 44_2   ..........  ..........  ..........  ..........  ..........
```

FIG 1Y

```
             1201                                                      1250
    42_2     ..........  ..........  ..........  ..........  ..........
    42_8     ..........  ..........  ..........  ..........  ..........
   42_15     ..........  ..........  ..........  ..........  ..........
   42_5b     ..........  ..........  ..........  ..........  ..........
   42_1b     ..........  ..........  ..........  ..........  ..........
   42_13     ..........  ..........  ..........  ..........  ..........
   42_3a     ..........  ..........  ..........  ..........  ..........
    42_4     ..........  ..........  ..........  ..........  ..........
   42_5a     ..........  ..........  ..........  ..........  ..........
   42_10     ..........  ..........  ..........  ..........  ..........
   42_3b     ..........  ..........  ..........  ..........  ..........
   42_11     ..........  ..........  ..........  ..........  ..........
   42_6b     ..........  ..........  ........GA  ATTCGCCCTT  TCTACGGCTG
    43_1     ..........  ..........  ..........  ..........  ..........
    43_5     ..........  ..........  ..........  ..........  ..........
   43_12     ..........  ..........  ..........  ..........  ..........
   43_20     ..........  ..........  ..........  ..........  ..........
   43_21     ..........  ..........  ..........  ..........  ..........
   43_23     ..........  ..........  ..........  ..........  ..........
   43_25     ..........  ..........  ..........  ..........  ..........
    44_1     ..........  ..........  ..........  ..........  ..........
    44_5     ..........  ..........  ..........  ..........  ..........
  223_10     ..........  ..........  ..........  ..........  ..........
   223_2     ..........  ..........  ..........  ..........  ..........
   223_4     ..........  ..........  ..........  ..........  ..........
   223_5     ..........  ..........  ..........  ..........  ..........
   223_6     ..........  ..........  ..........  ..........  ..........
   223_7     ..........  ..........  ..........  ..........  ..........
    A3_4     ..........  ..........  ..........  ..........  ..........
    A3_5     ..........  ..........  ..........  ..........  ..........
    A3_7     ..........  ..........  ..........  ..........  ..........
    A3_3     ..........  ..........  ..........  ..........  ..........
   42_12     ..........  ..........  ..........  ..........  ..........
    AAV1     CCCGCTCCGC  CCGCGGACAT  TAAAACCAAC  CGCATCTACC  GCATCCTGGA
    AAV2     CAGCAGCCCG  TGGAGGACAT  TTCCAGCAAT  CGGATTTATA  AAATTTTGGA
    AAV3     AGCAACCCGC  CGGAGGACAT  TACCAAAAAT  CGGATCTACC  AAATCCTGGA
    AAV8     CCCTCGCTGC  CCGCGGACAT  TACCCAGAAC  CGCATCTACC  GCATCCTCGC
    AAV9     CCTTCACTTC  CGGTGGACAT  TACGCAGAAC  CGCATCTACC  GCATCCTGCA
    AAV7     CCCTCGCTGC  CCGCGGACAT  TAAAACCAAC  CGCATCTACC  GCATCCTGGA
    44_2     ..........  ..........  ..........  ..........  ..........
```

FIG. 1Z

```
        1251                                                    1300
42_2    ..........  ..........  ..........  ..........  ..........
42_8    ..........  ..........  ..........  ..........  ..........
42_15   ..........  ..........  ..........  ..........  ..........
42_5b   ..........  ..........  ..........  ..........  ..........
42_1b   ..........  ..........  ..........  ..........  ..........
42_13   ..........  ..........  ..........  ..........  ..........
42_3a   ..........  ..........  ..........  ..........  ..........
42_4    ..........  ..........  ..........  ..........  ..........
42_5a   ..........  ..........  ..........  ..........  ..........
42_10   ..........  ..........  ..........  ..........  ..........
42_3b   ..........  ..........  ..........  ..........  ..........
42_11   ..........  ..........  ..........  ..........  ..........
42_6b   CGTCAACTGG  ACCAATGAGA  ACTTTCCCTT  CAACGATTGC  GTCGACAAGA
43_1    ..........  ..........  ..........  ..........  ..........
43_5    ..........  ..........  ..........  ..........  ..........
43_12   ..........  ..........  ..........  ..........  ..........
43_20   ..........  ..........  ..........  ..........  ..........
43_21   ..........  ..........  ..........  ..........  ..........
43_23   ..........  ..........  ..........  ..........  ..........
43_25   ..........  ..........  ..........  ..........  ..........
44_1    ..........  ..........  ..........  ..........  ..........
44_5    ..........  ..........  ..........  ..........  ..........
223_10  ..........  ..........  ..........  ..........  ..........
223_2   ..........  ..........  ..........  ..........  ..........
223_4   ..........  ..........  ..........  ..........  ..........
223_5   ..........  ..........  ..........  ..........  ..........
223_6   ..........  ..........  ..........  ..........  ..........
223_7   ..........  ..........  ..........  ..........  ..........
A3_4    ..........  ..........  ..........  ..........  ..........
A3_5    ..........  ..........  ..........  ..........  ..........
A3_7    ..........  ..........  ..........  ..........  ..........
A3_3    ..........  ..........  ..........  ..........  ..........
42_12   ..........  ..........  ..........  ..........  ..........
AAV1    GCTGAACGGC  TACGAACCTG  CCTACGCCGG  CTCCGTCTTT  CTCGGCTGGG
AAV2    ACTAAACGGG  TACGATCCCC  AATATGCGGC  TTCCGTCTTT  CTGGGATGGG
AAV3    GCTGAACGGG  TACGATCCGC  AGTACGCGGC  CTCCGTCTTC  CTGGGCTGGG
AAV8    TCTCAACGGC  TACGACCCTG  CCTACGCCGG  CTCCGTCTTT  CTCGGCTGGG
AAV9    GCTCAACGGC  TACGACCCTG  CCTACGCCGG  CTCCGTCTTT  CTCGGCTGGG
AAV7    GCTGAACGGG  TACGATCCTG  CCTACGCCGG  CTCCGTCTTT  CTCGGCTGGG
44_2    ..........  ..........  ..........  ..........  ..........
```

FIG. 1AA

```
           1301                                                              1350
    42_2   ..........  ..........  ..........  ..........  ..........
    42_8   ..........  ..........  ..........  ..........  ..........
   42_15   ..........  ..........  ..........  ..........  ..........
   42_5b   ..........  ..........  ..........  ..........  ..........
   42_1b   ..........  ..........  ..........  ..........  ..........
   42_13   ..........  ..........  ..........  ..........  ..........
   42_3a   ..........  ..........  ..........  ..........  ..........
    42_4   ..........  ..........  ..........  ..........  ..........
   42_5a   ..........  ..........  ..........  ..........  ..........
   42_10   ..........  ..........  ..........  ..........  ..........
   42_3b   ..........  ..........  ..........  ..........  ..........
   42_11   ..........  ..........  ..........  ..........  ..........
   42_6b   TGGTGATCTG  GTGGGAGGAG  GGCAAGATGA  CGGCCAAGGT  CGTGGAGTCC
    43_1   ..........  ..........  ..........  ..........  ..........
    43_5   ..........  ..........  ..........  ..........  ..........
   43_12   ..........  ..........  ..........  ..........  ..........
   43_20   ..........  ..........  ..........  ..........  ..........
   43_21   ..........  ..........  ..........  ..........  ..........
   43_23   ..........  ..........  ..........  ..........  ..........
   43_25   ..........  ..........  ..........  ..........  ..........
    44_1   ..........  ..........  ..........  ..........  ..........
    44_5   ..........  ..........  ..........  ..........  ..........
  223_10   ..........  ..........  ..........  ..........  ..........
   223_2   ..........  ..........  ..........  ..........  ..........
   223_4   ..........  ..........  ..........  ..........  ..........
   223_5   ..........  ..........  ..........  ..........  ..........
   223_6   ..........  ..........  ..........  ..........  ..........
   223_7   ..........  ..........  ..........  ..........  ..........
    A3_4   ..........  ..........  ..........  ..........  ..........
    A3_5   ..........  ..........  ..........  ..........  ..........
    A3_7   ..........  ..........  ..........  ..........  ..........
    A3_3   ..........  ..........  ..........  ..........  ..........
   42_12   ..........  ..........  ..........  ..........  ..........
    AAV1   CCCAGAAAAG  GTTCGGGAAG  CGCAACACCA  TCTGGCTGTT  TGGGCCGGCC
    AAV2   CCACGAAAAA  GTTCGGCAAG  AGGAACACCA  TCTGGCTGTT  TGGGCCTGCA
    AAV3   CGCAAAAGAA  GTTCGGGAAG  AGGAACACCA  TCTGGCTCTT  TGGGCCGGCC
    AAV8   CTCAGAAAAA  GTTCGGGAAA  CGCAACACCA  TCTGGCTGTT  TGGACCCGCC
    AAV9   CACAAAAGAA  GTTCGGGAAA  CGCAACACCA  TCTGGCTGTT  TGGGCCGGCC
    AAV7   CCCAGAAAAA  GTTCGGGAAG  CGCAACACCA  TCTGGCTGTT  TGGGCCCGCC
    44_2   ..........  ..........  ..........  ..........  ..........
```

42_2   ..........  ..........  ..........  .......GAA  TTCGCCCTTT
    42_8   ..........  ..........  ..........  .......GAA  TTCGCCCTTT
   42_15   ..........  ..........  ..........  .......GAA  TTCGCCCTTT
   42_5b   ..........  ..........  ..........  .......GAA  TTCGCCCTTT
   42_1b   ..........  ..........  ..........  ..........  ..........
   42_13   ..........  ..........  ..........  .......GAA  TTCGCCCTTT
   42_3a   ..........  ..........  ..........  .......GAA  TTCGCCCTTT
    42_4   ..........  ..........  ..........  ..........  ..........
   42_5a   ..........  ..........  ..........  ........GA  ATTCGCCCTT
   42_10   ..........  ..........  ..........  ..........  ..........
   42_3b   ..........  ..........  ..........  ..........  ..........
   42_11   ..........  ..........  ..........  .......GAA  TTCGCCCTTT
   42_6b   GCCAAGGCCA  TTCTCGGCGG  CAGCAAGGTG  CGCGTGGACC  AAAAGTGCAA
    43_1   ..........  ..........  ..........  .......GAA  TTCGCCCTTT
    43_5   ..........  ..........  ..........  .......GAA  TTCGCCCTTT
   43_12   ..........  ..........  ..........  .......GAA  TTCGCCCTT.
   43_20   ..........  ..........  ..........  .......GAA  TTCGCCCTTT
   43_21   ..........  ..........  ..........  .......GAA  TTCGCCCTT.
   43_23   ..........  ..........  ..........  .......GAA  TTCGCCCTT.
   43_25   ..........  ..........  ..........  .......GAA  TTCGCCCTTT
    44_1   ..........  ..........  ..........  .......GAA  TTCGCCCTTT
    44_5   ..........  ..........  ..........  .......GAA  TTCGCCCTTT
  223_10   ..........  ..........  ..........  ..........  ..........
   223_2   ..........  ..........  ..........  ..........  ..........
   223_4   ..........  ..........  ..........  ..........  ..........
   223_5   ..........  ..........  ..........  ..........  ..........
   223_6   ..........  ..........  ..........  ..........  ..........
   223_7   ..........  ..........  ..........  ..........  ..........
    A3_4   ..........  ..........  ..........  ........GA  ATTCGCCCTT
    A3_5   ..........  ..........  ..........  ........GA  ATTCGCCCTT
    A3_7   ..........  ..........  ..........  .......A    GCGGCCGCGA  ATTCGCCCTT
    A3_3   ..........  ..........  ..........  ........GA  ATTCGCCCTT
   42_12   ..........  ..........  ..........  .......GAA  TTCGCCCTTT
    AAV1   ACCACGGGCA  AGACCAACAT  CGCGGAAGCC  ATCGCCCACG  CCGTGCCCTT
    AAV2   ACTACCGGGA  AGACCAACAT  CGCGGAGGCC  ATAGCCCACA  CTGTGCCCTT
    AAV3   ACGACGGGTA  AAACCAACAT  CGCGGAAGCC  ATCGCCCACG  CCGTGCCCTT
    AAV8   ACCACCGGCA  AGACCAACAT  TGCGGAAGCC  ATCGCCCACG  CCGTGCCCTT
    AAV9   ACCACGGGAA  AGACCAACAT  CGCAGAAGCC  ATTGCCCACG  CCGTGCCCTT
    AAV7   ACCACCGGCA  AGACCAACAT  TGCGGAAGCC  ATCGCCCACG  CCGTGCCCTT
    44_2   ..........  ..........  ..........  ........GA  ATTCGCCCTT
```

FIG. 1AC

```
           1401                                                          1450
  42_2    .CTACGGCTG CGTCAACTGG ACCAATGAGA ACTTTCCCTT CAACGATTGC
  42_8    .CTACGGCTG CGTCAACTGG ACCAATGAGA ACTTTCCCTT CAACGATTGC
  42_15   .CTACGGCTG CGTCAACTGG ACCAATGAGA ACTTTCCCTT CAACGATTGC
  42_5b   .CTACGGCTG CGTCAACTGG ACCAATGAGA ACTTTCCCTT CAACGATTGC
  42_1b   .......... .......... .......... .......... ..........
  42_13   .CTACGGCTG CGTCAACTGG ACCAATGAGA ACTTTCCCTT CAACGATTGC
  42_3a   .CTACGGCTG CGTCAACTGG ACCAATGAGA ACTTTCCCTT CAACGATTGC
  42_4    .......... .......... .......... .......... ..........
  42_5a   .CTACGGCTG CGTCAACTGG ACCAATGAGA ACTTTCCCTT CAACGATTGC
  42_10   .......... .......... .......... .......... ..........
  42_3b   .......... .......... .......... .......... ..........
  42_11   .CTACGGCTG CGTCAACTGG ACCAATGAGA ACTTTCCCTT CAACGATTGC
  42_6b   .GTCTTCCGC CCAGATCGAT CCCACCCCCG TGATCGTCAC TTCCAACACC
  43_1    .CTACGGCTG CATCAACTGG ACCAATGAGA ACTTTCCCTT CAACGATTGC
  43_5    .CTACGGCTG CGTCAACTGG ACCAATGAGA ACTTTCCCTT CAACGATTGC
  43_12   .....GGCTG CGTCAACTGG ACCAATGAGA ACTTTCCCTT CAACGATTGC
  43_20   .CTACGGCTG CGTCAACTGG ACCAATGAGA ACTTTCCCTT CAACGATTGC
  43_21   .....GGCTG CGTCAACTGG ACCAATGAGA ACTTTCCCTT CAACGATTGC
  43_23   .CTACGGCTG CGTCAACTGG ACCAATGAGA ACTTTCCCTT CAACGATTGC
  43_25   .CTACGGCTG CGTCAACTGG ACCAATGAGA ACTTTCCCTT CAACGATTGC
  44_1    .CTACGGCTG CGTCAACTGG ACCAATGAGA ACTTTCCCTT CAACGATTGC
  44_5    .CTACGGCTG CGTCAACTGG ACCAATGAGA ACTTTCCCTT CAACGATTGC
 223_10   .......... .......... .......... .......... ..........
 223_2    .......... .......... .......... .......... ..........
 223_4    .......... .......... .......... .......... ..........
 223_5    .......... .......... .......... .......... ..........
 223_6    .......... .......... .......... .......... ..........
 223_7    .......... .......... .......... .......... ..........
  A3_4    TCTACGGCTG CGTCAACTGG ACCAATGAAA ACTTTCCCTT CAACGATTGC
  A3_5    TCTACGGCTG CGTCAACTGG ACCAATGAAA ACTTTCCCTT CAACGATTGC
  A3_7    TCTACGGCTG CGTCAACTGG ACCAATGAAA ACTTTCCCTT CAACGATTGC
  A3_3    TCTACGGCTG CGTCAACTGG ACCAATGAAA ACTTTCCCTT CAACGATTGC
  42_12   .CTACGGCTG CGTCAACTGG ACCAATGAGA ACTTTCCCTT CAACGATTGC
  AAV1    .CTACGGCTG CGTCAACTGG ACCAATGAGA ACTTTCCCTT CAATGATTGC
  AAV2    .CTACGGGTG CGTAAACTGG ACCAATGAGA ACTTTCCCTT CAACGACTGT
  AAV3    .CTACGGCTG CGTAAACTGG ACCAATGAGA ACTTTCCCTT CAACGATTGC
  AAV8    .CTACGGCTG CGTCAACTGG ACCAATGAGA ACTTTCCCTT CAATGATTGC
  AAV9    .CTACGGCTG CGTCAACTGG ACCAATGAGA ACTTTCCCTT CAACGATTGC
  AAV7    .CTACGGCTG CGTCAACTGG ACCAATGAGA ACTTTCCCTT CAACGATTGC
  44_2    TCTACGGCTG CGTCAACTGG ACCAATGAGA ACTTTCCCTT CAACGATTGC
```

FIG. 1AD

```
       1451                                                              1500
 42_2   GTCGACAAGA TGGTGATCTG GTGGGAGGAG GGCAAGATGA CGGCCAAGGT
 42_8   GTCGACAAGA TGGTGATCTG GTGGGAGGAG GGCAAGATGA CGGCCAAGGT
 42_15  GTCGACAAGA TGGTGATCTG GTGGGAGGAG GGCAAGATGA CGGCCAAGGT
 42_5b  GTCGACAAGA TGGTGATCTG GTGGGAGGAG GGCAAGATGA CGGCCAAGGT
 42_1b  .......... .......... .......... .......... ..........
 42_13  GTCGACAAGA TGGTGATCTG GTGGGAGGAG GGCAAGATGA CGGCCAAGGT
 42_3a  GTCGACAAGA TGGTGATCTG GTGGGAGGAG GGCAAGATGA CGGCCAAGGT
 42_4   .......... .......... .......... .......... ..........
 42_5a  GTCGACAAGA TGGTGATCTG GTGGGAGGAG GGCAAGATGA CGGCCAAGGT
 42_10  .......... .......... .......... .......... ..........
 42_3b  .......... .......... .......... .......... ..........
 42_11  GTCGACAAGA TGGTGATCTG GTGGGAGGAG GGCAAGATGA CGGCCAAGGT
 42_6b  AACATGTGCG CCCTGATTGA CGGCAACAGC ACCACCTTCG AGCACCAGCA
 43_1   GTCGACAAGA TGGTGATCTG GTGGGAGGAG GGCAAGATGA CGGCCAAGGT
 43_5   GTCGACAAGA TGGTGATCTG GTGGGAGGAG GGCAAGATGA CGGCCAAGGT
 43_12  GTCGACAAGA TGGTGATCTG GTGGGAGGAG GGCAAGATGA CGGCCAAGGT
 43_20  GTCGACAAGA TGGTGATCTG GTGGGAGGAG GGCAAGATGA CGGCCAAGGT
 43_21  GTCGACAAGA TGGTGATCTG GTGGGAGGAC GGCAAGATGA CGGCCAAGGT
 43_23  GTCGACAAGA TGGTGATCTG GTGGGAGGAG GGCAAGATGA CGGCCAAGGT
 43_25  GTCGACAAGA TGGTGATCTG GTGGGAGGAG GGCAAGATGA CGGCCAAGGT
 44_1   GTCGACAAGA TGTTGATCTG GTGGGAGGAG GGCAAGATGA CGGCCAAGGT
 44_5   GTCGACAAGA TGGTGATCTG GTGGGAGGAG GGCAAGATGA CGGCCAAGGT
 223_10 .......... .......... .......... .......... ..........
 223_2  .......... .......... .......... .......... ..........
 223_4  .......... .......... .......... .......... ..........
 223_5  .......... .......... .......... .......... ..........
 223_6  .......... .......... .......... .......... ..........
 223_7  .......... .......... .......... .......... ..........
 A3_4   GTCGACAAGA TGGTGATCTG GTGGGAGGAG GGAAAGATGA CCGCCAAGGT
 A3_5   GTCGACAAGA TGGTGATCTG GTGGGAGGAG GGAAAGATGA CCGCCAAGGT
 A3_7   GTCGACAAGA TGGTGATCTG GTGGGAGGAG GGAAAGATGA CCGCCAAGGT
 A3_3   GTCGACAAGA TGGTGATCTG GTGGGAGGAG GGAAAGATGA CCGCCAAGGT
 42_12  GTCGACAAGA TGGTGATCTG GTGGGAGGAG GGCAAGATGA CGGCCAAGGT
 AAV1   GTCGACAAGA TGGTGATCTG GTGGGAGGAG GGCAAGATGA CGGCCAAGGT
 AAV2   GTCGACAAGA TGGTGATCTG GTGGGAGGAG GGAAGATGA CCGCCAAGGT
 AAV3   GTCGACAAGA TGGTGATCTG GTGGGAGGAG GGCAAGATGA CGGCCAAGGT
 AAV8   GTCGACAAGA TGGTGATCTG GTGGGAGGAG GGCAAGATGA CGGCCAAGGT
 AAV9   GTCGACAAGA TGGTGATCTG GTGGGAGGAG GGCAAGATGA CGGCCAAGGT
 AAV7   GTCGACAAGA TGGTGATCTG GTGGGAGGAG GGCAAGATGA CGGCCAAGGT
 44_2   GTCGACAAGA TGGTGATCTG GTGGGAGGAG GGCAAGATGA CGGCCAAGGT
```

FIG. 1AE

```
         1501                                                              1550
  42_2   CGTGGAGTCC GCCAAGGCCA TTCTCGGCGG CAGCAAGGTG CGCGTGGACC
  42_8   CGTGGAGTCC GCCAAGGCCA TTCTCGGCGG CAGCAAGGTG CGCGTGGACC
 42_15   CGTGGAGTCC GCCAAGGCCA TTCTCGGCGG CAGCAAGGTG CGCGTGGACC
 42_5b   CGTGGAGTCC GCCAAGGCCA TTCTCGGCGG CAGCAAGGTG CGCGTGGACC
 42_1b   .......... .......... .......... .......... ..........
 42_13   CGTGGAGTCC GCCAAGGCCA TTCTCGGCGG CAGCAAGGTG CGCGTGGACC
 42_3a   CGTGGAGTCC GCCAAGGCCA TTCTCGGCGG CAGCAAGGTG CGCGTGGACC
  42_4   .......... .......... .......... .......... ..........
 42_5a   CGTGGAGTCC GCCAAGGCCA TTCTCGGCGG CAGCAAGGTG CGCGTGGACC
 42_10   .......... .......... .......... .......... ..........
 42_3b   .......... .......... .......... .......... ..........
 42_11   CGTGGAGTCC GCCAAGGCCA TTCTCGGCGG CAGCAAGGTG CGCGTGGACC
 42_6b   GCCGTTGCAG GACCGGATGT TCAAATTTGA ACTCACCCGC CGTCTGGAGC
  43_1   CGTGGAGTCC GCCAAGGCCA TTCTCGGCGG CAGCAAGGTG CGCGTGGACC
  43_5   CGTGGAGTCC GCCAAGGCCA TTCTCGGCGG CAGCAAGGTG CGCGTGGACC
 43_12   CGTGGAGTCC GCCAAGGCCA TTCTCGGCGG CAGCAAGGTG CGCGTGGACC
 43_20   CGTGGAGTCC GCCAAGGCCA TTCTCGGCGG CAGCAAGGTG CGTGTGGACC
 43_21   CGTGGAGTCC GCCAAGGCCA TTCTCGGCGG CAGCAAGGTG CGTGTGGACC
 43_23   CGTGGAGTCC GCCAAGGCCA TTCTCGGCGG CAGCAAGGTG CGTGTGGACC
 43_25   CGTGGAGTCC GCCAAGGCCA TTCTCGGCGG CAGCAAGGTG CGTGTGGACC
  44_1   CGTGGAGTCC GCCAAGGCCA TTCTCGGCGG CAGCAAAGTG CGCGTGGACC
  44_5   CGTGGAGTCC GCCAAGGCCA TTCTCGGCGG CAGCAAAGTG CGCGTGGACC
 223_10  .......... .......... .......... .......... ..........
 223_2   .......... .......... .......... .......... ..........
 223_4   .......... .......... .......... .......... ..........
 223_5   .......... .......... .......... .......... ..........
 223_6   .......... .......... .......... .......... ..........
 223_7   .......... .......... .......... .......... ..........
  A3_4   CGTGGAATCT GCCAAAGCCA TTCTGGGTGG AAGCAAGGTT CGTGTGGACC
  A3_5   CGTGGAATCT GCCAAAGCCA TTCTGGGTGG AAGCAAGGTT CGTGTGGACC
  A3_7   CGTGGAATCT GCCAAAGCCA TTCTGGGTGG AAGCAAGGTT CGTGTGGACC
  A3_3   CGTGGAATCT GCCAAAGCCA TTCTGGGTGG AGGCAAGGTT CGTGTGGACC
 42_12   CGTGGAGTCC GCCAAGGCCA TTCTCGGCGG CAGCAAGGTG CGCGTGGACC
  AAV1   CGTGGAGTCC GCCAAGGCCA TTCTCGGCGG CAGCAAGGTG CGCGTGGACC
  AAV2   CGTGGAGTCG GCCAAAGCCA TTCTCGGAGG AAGCAAGGTG CGCGTGGACC
  AAV3   CGTGGAGAGC GCCAAGGCCA TTCTGGGCGG AAGCAAGGTG CGCGTGGACC
  AAV8   CGTGGAGTCC GCCAAGGCCA TTCTCGGCGG CAGCAAGGTG CGCGTGGACC
  AAV9   CGTGGAGTCC GCCAAGGCCA TTCTCGGCGG CAGCAAGGTG CGCGTGGACC
  AAV7   CGTGGAGTCC GCCAAGGCCA TTCTCGGCGG CAGCAAGGTG CGCGTGGACC
  44_2   CGTGGAGTCC GCCAAGGCCA TTCTCGGCGG CAGCAAAGTG CGCGTGGACC
```

FIG. 1AF

```
         1551                                                          1600
 42_2    AAAAGTGCAA GTCTTCCGCC CAGATCGATC CCACCCCCGT GATCGTCACT
 42_8    AAAAGTGCAA GTCTTCCGCC CAGATCGATC CCACCCCCGT GATCGTCACT
 42_15   AAAAGTGCAA GTCGTCCGCC CAGATCGACC CCACCCCCGT GATCGTCACC
 42_5b   AAAAGTGCAA GTCGTCCGCC CAGATCGACC CCACCCCCGT GATCGTCACC
 42_1b   .......... .......... .......... .......... ..........
 42_13   AAAAGTGCAA GTCGTCCGCC CAGATCGATC CCACCCCCGT GATCGTCACT
 42_3a   AAAAGTGCAA GTCGTCCGCC CAGATCGATC CCACCCCCGT GATCGTCACT
 42_4    .......... .......... .......... .......... ..........
 42_5a   AAAAGTGCAA GTCGTCCGCC CAGATCGACC CCACCCCCGT GATCGTCACC
 42_10   .......... .......... .......... .......... ..........
 42_3b   .......... .......... .......... .......... ..........
 42_11   AAAAGTGCAA GTCTTCCGCC CAGATCGATC CCACCCCCGT GATCGTCACT
 42_6b   ATGACTTTGG CAAGGTGACA AAGCAGGAAG TCAAAGAGTT CTTCCGCTGG
 43_1    AAAAGTGCAA GTCGTCCGCC CAGATCGACC CCACCCCCGT GATCGTCACC
 43_5    AAAAGTGCAA GTCGTCCGCC CAGATCGACC CCACCCCCGT GATCGTCACC
 43_12   AAAAGTGCAA GTCGTCCGCC CAGATCGACC CCACCCCCGT GATCGTCACC
 43_20   AAAAGTGCAA GTCTTCCGCC CAGATCGATC CCACCCCCGT GATCGTCACC
 43_21   AAAAGTGCAA GTCTTCCGCC CAGATCGATC CCACCCCCGT GATCGTCACC
 43_23   AAAAGTGCAA GTCTTCCGCC CAGATCGATC CCACCCCCGT GATCGTCACC
 43_25   AAAAGTGCAA GTCTTCCGCC CAGATCGATC CCACCCCCGT GATCGTCACC
 44_1    AAAAGTGCAA GCCGTCCGCC CAGATCGACC CCACCCCCGT GATCGTCACC
 44_5    AAAAGTGCAA GTCGTCCGCC CAGATCGACC CCACCCCCGT GATCGTCACC
 223_10  .......... .......... .......... .......... ..........
 223_2   .......... .......... .......... .......... ..........
 223_4   .......... .......... .......... .......... ..........
 223_5   .......... .......... .......... .......... ..........
 223_6   .......... .......... .......... .......... ..........
 223_7   .......... .......... .......... .......... ..........
 A3_4    AGAAATGCAA GTCTTCGGCC CAGATCGACC CGACTCCGGT GATTGTCACC
 A3_5    AGAAATGCAA GTCTTCGGCC CAGATCGACC CGACTCCGGT GATTGTCACC
 A3_7    AGAAATGCAG GTCTTCGGCC CAGATCGACC CGACTCCGGT GATTGTCACC
 A3_3    AGAAATGCAA GTCTTCGGCC CAGATCGACC CGACTCCGGT GATTGTCACC
 42_12   AAAAGTGCAA GTCGTCCGCC CAGATCGACC CCACCCCCGT GATCGTCACC
 AAV1    AAAAGTGCAA GTCGTCCGCC CAGATCGACC CCACCCCCGT GATCGTCACC
 AAV2    AGAAATGCAA GTCCTCGGCC CAGATAGACC CGACTCCCGT GATCGTCACC
 AAV3    AAAAGTGCAA GTCATCGGCC CAGATCGAAC CCACTCCCGT GATCGTCACC
 AAV8    AAAAGTGCAA GTCGTCCGCC CAGATCGACC CCACCCCCGT GATCGTCACC
 AAV9    AAAAGTGCAA GTCGTCCGCC CAGATCGACC CCACTCCCGT GATCGTCACC
 AAV7    AAAAGTGCAA GTCGTCCGCC CAGATCGACC CCACCCCCGT GATCGTCACC
 44_2    AAAAGTGCAA GTCGTCCGCC CAGATCGACC CCACCCCCGT GATCGTCACC
```

FIG. 1AG

```
          1601                                                      1650
   42_2   TCCAACACCA ACATGTGCGC TGTGATTGAC GGGAACAGCA CCACCTTCGA
   42_8   TCCAACACCA ACATGTGCGC CGTGATTGAC GGGAACAGCA CCACCTTCGA
  42_15   TCCAACACCA ACATGTGCGC CGTGATTGAC GGGAACAGCA CCACCTTCGA
  42_5b   TCCAACACCA ACATGTGCGC CGTGATTGAC GGGAACAGCA CCACCTTCGA
  42_1b   .......... .......... .......... .......... ..........
  42_13   TCCAACACCA ACATGTGCGC CGTGATTGAC GGGAACAGCA CCACCTTCGA
  42_3a   TCCAACACCA ACATGTGCGC CGTGATTGAC GGGAACAGCA CCACCTTCGA
   42_4   .......... .......... .......... .......... ..........
  42_5a   TCCAACACCA ACATGTGCGC CGTGATTGAC GGGAACAGCA CCACCTTCGA
  42_10   .......... .......... .......... .......... ..........
  42_3b   .......... .......... .......... .......... ..........
  42_11   TCCAACACCA ACATGTGCGC CGTGATTGAC GGGAACAGCA CCACCTTCGA
  42_6b   GCGCAGGATC ACGTGACCGA GGTGGCGCAT GAGTTCTACG TCAGAAAGGG
   43_1   TCCAACACCA ACATGTGCGC CGTGATTGAC GGGAACAGCA CCACCTTCGA
   43_5   TCCAACACCA ACATGTGCGC CGTGATTGAC GGGAACAGCA CCACCTTCGA
  43_12   TCCAACACCA ACATGTGCGC CGTGATTGAC GGGAACAGCA CCACCTTCGA
  43_20   TCCAACACCA ACATGTGCGC CGTGATTGAC GGGAACAGCG CCACCTTCGA
  43_21   TCCAACACCA ACATGTGCGC CGTGATTGAC GGGAACAGCA CCACCTTCGA
  43_23   TCCAACACCA ACATGTGCGC CGTGATTGAC GGGAACAGCA CCACCTTCGA
  43_25   TCCAACACCA ACATGTGCGC CGTGATTGAC GGGAACAGCA CCACCTTCGA
   44_1   TCCAACACCA ACATGTGCGC CGTGATTGAC GGGAACAGCA CCACCTTCGA
   44_5   TCCAACACCA ACATGTGCGC CGTGATTGAC GGGAACAGCA CCACCTTCGA
 223_10   .......... .......... .......... .......... ..........
  223_2   .......... .......... .......... .......... ..........
  223_4   .......... .......... .......... .......... ..........
  223_5   .......... .......... .......... .......... ..........
  223_6   .......... .......... .......... .......... ..........
  223_7   .......... .......... .......... .......... ..........
   A3_4   TCTAACACCA ACATGTGCGC CGTGATTGAC GGAAACTCGA CCACCTTCGA
   A3_5   TCTAACACCA ACATGTGCGC CGTGATTGAC GGAAACTCGA CCACCTTCGA
   A3_7   TCTAACACCA ACATGTGCGC CGTGATTGAC GGAAACTCGA CCACCTTCGA
   A3_3   TCTAACACCA ACATGTGCGC CGTGATTGAC GGAAACTCGA CCACCTTCGA
  42_12   TCCAACACCA ACATGTGCGC CGTGATTGAC GGGAACAGCA CCACCTTCGA
   AAV1   TCCAACACCA ACATGTGCGC CGTGATTGAC GGGAACAGCA CCACCTTCGA
   AAV2   TCCAACACCA ACATGTGCGC CGTGATTGAC GGGAACTCAA CGACCTTCGA
   AAV3   TCCAACACCA ACATGTGCGC CGTGATTGAC GGGAACAGCA CCACCTTCGA
   AAV8   TCCAACACCA ACATGTGCGC CGTGATTGAC GGGAACAGCA CCACCTTCGA
   AAV9   TCCAACACCA ACATGTGCGC CGTGATTGAC GGGAACAGCA CCACCTTCGA
   AAV7   TCCAACACCA ACATGTGCGC CGTGATTGAC GGGAACAGCA CCACCTTCGA
   44_2   TCCAACACCA ACATGTGCGC CGTGATTGAC GGGAACAGCA CCACCTTCGA
```

FIG. 1AH

```
         1651                                                              1700
  42_2   GCACCAGCAG CCGTTACAAG ACCGGATGTT CAAATTTGAA CTCACCCGCC
  42_8   GCACCAGCAG CCGTTACAAG ACCGGATGTT CAAATTTGAA CTCACCCGCC
 42_15   GCACCAGCAG CCGTTGCAGG ACCGGATGTT CAAATTTGAA CTCACCCGCC
 42_5b   GCACCAGCAG CCGTTACAAG ACCGGATGTT CAAATTTGAA CTCACCCGCC
 42_1b   .......... .......... .......... .......... ..........
 42_13   GCACCAGCAG CCGTTACAAG ACCGGATGTT CAAATTTGAA CTCACCCGCC
 42_3a   GCACCAGCAG CCGTTACAAG ACCGGATGTT CAAATTTGAA CTCACCCGCC
  42_4   .......... .......... .......... .......... ..........
 42_5a   GCACCAGCAG CCGTTGCAGG ACCGGATGTT CAAATTTGAA CTCACCCGCC
 42_10   .......... .......... .......... .......... ..........
 42_3b   .......... .......... .......... .......... ..........
 42_11   GCACCAGCAG CCGTTACAAG ACCGGATGTT CAAATTTGAA CTCACCCGCC
 42_6b   TGGAGCCAAC AAGAGACCCG CCCCCGATGA CGCGGATAAA AGCGAGCCCA
  43_1   GCACCAGCAG CCGTTGCAGG ACCGGATGTT CAAGTTCGAA CTCACCCGCC
  43_5   GCACCAGCAG CCGTTGCAGG ACCGGATGTT CAAGTTCGAA CTCACCCGCC
 43_12   GCACCAGCAG CCGTTGCAGG ACCGGATGTT CAAGTTCGAA CTCACCCGCC
 43_20   GCACCAGCAG CCGTTGCAGG ACCGGATGTT CAAATTTGAA CTCACCCGCC
 43_21   GCACCAGCAG CCGTTGCAGG ACCGGATGTT CAAATTTGAA CTCACCCGCC
 43_23   GCACCAGCAG CCGTTGCAGG ACCGGATGTT CAAATTTGAA CTCACCCGCC
 43_25   GCACCAGCAG CCGTTGCAGG ACCGGATGTT CAAATTTGAA CTCACCCGCC
  44_1   GCACCAGCAG CCGTTGCGGG ACCGGATGTT CAAGTTTGAA CTCACCCGCC
  44_5   GCACCAGCAG CCGTTGCAGG ACCGGATGTT CAAGTTTGAA CTCACCCGCC
 223_10  .......... .......... .......... .......... ..........
 223_2   .......... .......... .......... .......... ..........
 223_4   .......... .......... .......... .......... ..........
 223_5   .......... .......... .......... .......... ..........
 223_6   .......... .......... .......... .......... ..........
 223_7   .......... .......... .......... .......... ..........
  A3_4   GCACCAGCAG CCGTTGCAAG ACCGGATGTT CAAATTTGAA CTTACCCGCC
  A3_5   GCACCAGCAG CCGTTGCAAG ACCGGATGTT CAAATTTGAA CTTACCCGCC
  A3_7   GCACCAGCAG CCGTTGCAAG ACCGGATGTT CAAATTTGAA CTTACCCGCC
  A3_3   GCACCAGCAG CCGTTGCAAG ACCGGATGTT CAAATTTGAA CTTACCCGCC
 42_12   GCACCAGCAG CCGTTACAAG ACCGGATGTT CAAATTTGAA CTCACCCGCC
  AAV1   GCACCAGCAG CCGTTGCAGG ACCGGATGTT CAAATTTGAA CTCACCCGCC
  AAV2   ACACCAGCAG CCGTTGCAAG ACCGGATGTT CAAATTTGAA CTCACCCGCC
  AAV3   GCATCAGCAG CCGCTGCAGG ACCGGATGTT TGAATTTGAA CTTACCCGCC
  AAV8   GCACCAGCAG CCTCTCCAGG ACCGGATGTT TAAGTTCGAA CTCACCCGCC
  AAV9   GCACCAGCAG CCTCTCCAGG ACCGGATGTT TAAGTTCGAA CTCACCCGCC
  AAV7   GCACCAGCAG CCGTTGCAGG ACCGGATGTT CAAATTTGAA CTCACCCGCC
  44_2   GCACCAGCAG CCGTTGCAGG ACCGGATGTT CAAGTTTGAA CTCACCCGCC
```

FIG. 1AI

```
         1701                                                          1750
 42_2    GTCTGGAGCA CGACTTTGGC AAGGTGACAA AGCAGGAAGT CAAAGAGTTC
 42_8    GTCTGGAGCA CGACTTTGGC AAGGTGACAA AGCAGGAAGT CAAAGAGTTC
 42_15   GTCTGGAGCA TGACTTTGGC AAGGTGACAA AGCAGGAAGT CAAAGAGTTC
 42_5b   GTCTGGAGCA CGACTTTCGC AAGGTGACAA AGCAGGAAGT CAAAGAGTTC
 42_1b   .......... .......... .......... .......... ..........
 42_13   GTCTGGAGCA TGACTTTGGC AAGGTGACAA AGCAGGAAGT CAAAGAGTTC
 42_3a   GTCTGGAGCA TGACTTTGGC AAGGTGACAA AGCAGGAAGT CAAAGAGTTC
 42_4    .......... .......... .......... .......... ..........
 42_5a   GTCTGGAGCA TGACTTTGGC AAGGCGACAA AGCAGGAAGT CAAAGAGTTC
 42_10   .......... .......... .......... .......... ..........
 42_3b   .......... .......... .......... .......... ..........
 42_11   GTCTGGAGCA CGACTTTGGC AAGGTGACAA AGCAGGAAGT CAAAGAGTTC
 42_6b   AGCGGGCCTG CCCCTCAGTC GCGGATCCAT CGACGTCAGA CGCGGAAGGA
 43_1    GTCTGGAGCA CGACTTTGGC AAGGTGACCA AGCAGGAAGT CAAAGAGTTC
 43_5    GTCTGGAGCA CGACTTTGGC AAGGTGACCA AGCAGGAAGT CAAAGAGTTC
 43_12   GTCTGGAGCA CGACTTTGGC AAGGTGACCA AGCAGGAAGT CAAAGAGTTC
 43_20   GTCTGGAGCA TGACTTTGGC AAGGTGACGA AGCAGGAAGT CAAAGAGTTC
 43_21   GTCTGGAGCA TGACTTTGGC AAGGTGACGA AGCAGGAAGT CAAAGAGTTC
 43_23   GTCTGGAGCA TGACTTTGGC AAGGTGACGA AGCAGGAAGT CAAAGAGTTC
 43_25   GTCTGGAGCA TGACTTTGGC AAGGTGACGA AGCAGGAAGT CAAAGCGTTC
 44_1    GTCTGGAGCA CGACTTTGGC AAGGTGACAA AGCAGCAACT CAGAGAGTTC
 44_5    GTCTGGAGCA CGACTTTGGC AAGGTGACAA AGCAGGAAGT CAGAGAGTTC
223_10   .......... .......... .......... .......... ..........
223_2    .......... .......... .......... .......... ..........
223_4    .......... .......... .......... .......... ..........
223_5    .......... .......... .......... .......... ..........
223_6    .......... .......... .......... .......... ..........
223_7    .......... .......... .......... .......... ..........
 A3_4    GTTTGGATCA TGACTTTGGG AAGGTCACCA AGCAGGAAGT CAAAGACTTT
 A3_5    GTTTGGATCA TGACTTTGGG AAGGTCACCA AGCAGGAAGT CAAAGACTTT
 A3_7    GTTTGGATCA TGACTTTGGG AAGGTCACCA AGCAGGAAGT CAAAGACTTT
 A3_3    GTTTGGATCA TGACTTTGGG AAGGTCACCA AGCAGGAAGT CAAAGACTTT
 42_12   GTCTGGAGCA CGACTTTGGC AAGGTGACAA AGCAGGAAGT CAAAGAGTTC
 AAV1    GTCTGGAGCA TGACTTTGGC AAGGTGACAA AGCAGGAAGT CAAAGAGTTC
 AAV2    GTCTGGATCA TGACTTTGGG AAGGTCACCA AGCAGGAAGT CAAAGACTTT
 AAV3    GTTTGGACCA TGACTTTGGG AAGGTCACCA AACAGGAAGT AAAGGACTTT
 AAV8    GTCTGGAGCA CGACTTTGGC AAGGTGACAA AGCAGGAAGT CAAAGACTTC
 AAV9    GTCTGGAGCA CGACTTTGGC AAGGTGACAA AGCAGGAAGT CAAAGAGTTC
 AAV7    GTCTGGAGCA CGACTTTGGC AAGGTGACGA AGCAGGAAGT CAAAGAGTTC
 44_2    GTCTGGAGCA CGACTTTGGC AAGGTGACAA AGCAGGAAGT CAGAGAGTTC
```

FIG. 1AJ

```
        1751                                                          1800
 42_2   TTCCGCTGGG CGCAGGATCA CGTGACCGAG GTGGCGCATG AGTTCTACGT
 42_8   TTCCGCTGGG CGCAGGATCA CGTGACCGAG GTGGCGCATG AGTTCTACGT
 42_15  TTCCGCTGGG CGCAGGATCA CGTGACCGAG GTGGCGCATG AGTTCTACGT
 42_5b  TTCCGCTGGG CGCAGGATCA CGTGACCGAG GTGGCGCATG AGTTCTACGT
 42_1b  .......... .......... .......... .......... ..........
 42_13  TTCCGCTGGG CGCAGGATCA CGTGACCGAG GTGGCGCATG AGTTCTACGT
 42_3a  TTCCGCTGGG CGCAGGATCA CGTGACCGAG GTGGCGCATG AGTTCTACGT
 42_4   .......... .......... .......... .......... ..........
 42_5a  TTCCGCTGGG CGCAGGATCA CGTGACCGAG GTGGCGCATG AGTTCTACGT
 42_10  .......... .......... .......... .......... ..........
 42_3b  .......... .......... .......... .......... ..........
 42_11  TTCCGCTGGG CGCAGGATCA CGTGACCGAG GTGGCGCATG AGTTCTACGT
 42_6b  GCTCCGGTGG ACTTTGCCGA CACGTACCAA AACAAATGTT CTCGTCACGC
 43_1   TTCCGCTGGG CGCAGGATCA CGTGACCGAG GTGGCGCATG AGTTCTACGT
 43_5   TTCCGCTGGG CGCAGGATCA CGTGACCGAG GTGGCGCATG AGTTCTACGT
 43_12  TTCCGCTGGG CGCAGGATCA CGTGACCGAG GTGGCGCATG AGTTCTACGT
 43_20  TTCCGCTGGG CGCAGGATCA CGTGACCGAG GTGGCGCATG AGTTCCACGT
 43_21  TTCCGCTGGG CGCAGGATCA CGTGACCGAG GTGGCGCATG AGTTCCACGT
 43_23  TTCCGCTGGG CGCAGGATCA CGTGACCGAG GTGGCGCATG AGTTCCACGT
 43_25  TTCCGCTGGG CGCAGGATCA CGTGACCGAG GTGGCGCATG AGTTCCACGT
 44_1   TTCCGCTGGG CGCAGGATCA CGTGACCGAG GTGGCGCACG AGTTCTACGT
 44_5   TTCCGCTGGG CGCAGGATCA CGTGACCGAG GTGGCGCACG AGTTCTACGT
223_10  .......... .......... .......... .......... ..........
223_2   .......... .......... .......... .......... ..........
223_4   .......... .......... .......... .......... ..........
223_5   .......... .......... .......... .......... ..........
223_6   .......... .......... .......... .......... ..........
223_7   .......... .......... .......... .......... ..........
 A3_4   TTCCGGTGGG CTCAAGATCA CGTGACTGAG GTGGAGCATG AGTTCTACGT
 A3_5   TTCCGGTGGG CTCAAGATCA CGTGACTGAG GTGGAGCATG AGTTCTACGT
 A3_7   TTCCGGTGGG CTCAAGATCA CGTGACTGAG GTGGAGCATG AGTTCTACGT
 A3_3   TTCCGGTGGG CTCAAGATCA CGTGACTGAG GTGGAGCATG AGTTCTACGT
 42_12  TTCCGCTGGG CGCAGGATCA CGTGACCGAG GTGGCGCATG AGTTCTACGT
 AAV1   TTCCGCTGGG CGCAGGATCA CGTGACCGAG GTGGCGCATG AGTTCTACGT
 AAV2   TTCCGGTGGG CAAAGGATCA CGTGGTTGAG GTGGAGCATG AATTCTACGT
 AAV3   TTCCGGTGGG CTTCCGATCA CGTGACTGAC GTGGCTCATG AGTTCTACGT
 AAV8   TTCCGCTGGG CCAGTGATCA CGTGACCGAG GTGGCGCATG AGTTTTACGT
 AAV9   TTCCGCTGGG CCAGTGATCA CGTGACCGAG GTGGCGCATG AGTTTTACGT
 AAV7   TTCCGCTGGG CCAGTGATCA CGTGACCGAG GTGGCGCATG AGTTCTACGT
 44_2   TTCCGCTGGG CGCAGGATCA CGTGACCGAG GTGGCGCACG AGTTCTACGT
```

FIG. 1AK

```
       1801                                                    1850
                                                          P40/TATA
 42_2   CAGAAAGGGT  GGAGCCAACA  AGAGACCCGC  CCCCGATGAC  GCGGATAAAA
 42_8   CAGAAAGGGT  GGAGCCAACA  AGAGACCCGC  CCCCGATGAC  GCGGATAAAA
 42_15  CAGAAAGGGT  GGAGCCAACA  AGAGACCCGC  CCCCGATGAC  GCGGATAAAA
 42_5b  CAGAAAGGGT  GGAGCCAACA  AGAGACCCGC  CCCCGATGAC  GCGGATAAAA
 42_1b  ..........  ..........  ..........  ..........  ..........
 42_13  CAGAAAGGGT  GGAGCCAACA  AGAGACCCGC  CCCCGATGAC  GCGGATAAAA
 42_3a  CAGAAAGGGT  GGAGCCAACA  AGAGACCCGC  CCCCGATGAC  GCGGATAAAA
 42_4   ..........  ..........  ..........  ..........  ..........
 42_5a  CAGAAAGGGT  GGAGCCAACA  AGAGACCCGC  CCCCGATGAC  GCGGATAAAA
 42_10  ..........  ..........  ..........  ..........  ..........
 42_3b  ..........  ..........  ..........  ..........  ..........
 42_11  CAGAAAGGGT  GGAGCCAACA  AGAGACCCGC  CCCCGATGAC  GCGGATAAAA
 42_6b  GGGCATAGCC  CTGACGTAAA  TCACGTCATA  GGGGAGTGGT  CCTGTATTAG
 43_1   CAGAAAGGGC  GGAGCCAGCA  AAAGACCCGC  CCCCGATGAC  GCGGATATAA
 43_5   CAGAAAGGGC  GGAGCCAGCA  AAAGACCCGC  CCCCGATGAC  GCGGATATAA
 43_12  CAGAAAGGGC  GGAGCCAGCA  AAAGACCCGC  CCCCGATGAC  GCGGATATAA
 43_20  CAGAAAGGGT  GGAGCCAACA  AGAGACCCGC  CCCCGATGAC  GCGGATATAA
 43_21  CAGAAAGGGT  GGAGCCAACA  AGAGACCCGC  CCCCGATGAC  GCGGATATAA
 43_23  CAGAAAGGGT  GGCGCCAACA  AGAGACCCGC  CCCCGATGAC  GCGGATATAA
 43_25  CAGAAAGGGT  GGAGCCAACA  AGAGACCCGC  CCCCGATGAC  GCGGATATAA
 44_1   CAGAAAGGGT  GGAGCCAACA  AGAGACCCGC  CCCCGATGAC  GCGGATAAAA
 44_5   CAGAAAGGGT  GGAGCCAACA  AGAGACCCGC  CCCCGATGAC  GCGGATAAAA
223_10  ..........  ..........  ..........  ..........  ..........
223_2   ..........  ..........  ..........  ..........  ..........
223_4   ..........  ..........  ..........  ..........  ..........
223_5   ..........  ..........  ..........  ..........  ..........
223_6   ..........  ..........  ..........  ..........  ..........
223_7   ..........  ..........  ..........  ..........  ..........
 A3_4   CAAAAAGGGT  GGAGCCAAGA  AAAGGCCCGC  CCCCGATGAT  GTATATATAA
 A3_5   CAAAAAGGGT  GGAGCCAAGA  AAAGGCCCGC  CCCCGATGAT  GTATATATAA
 A3_7   CAAAAAGGGT  GGAGCCAAGA  AAAGGCCCGC  CCCCGATGAT  GTATATATAA
 A3_3   CAAAAAGGGT  GGAGCCAAGA  AAAGGCCCGC  CCCCGATGAT  GTATATATAA
 42_12  CAGAAAGGGT  GGAGCCAACA  AGAGACCCGC  CCCCGATGAC  GCGGATAAAA
 AAV1   CAGAAAGGGT  GGAGCCAACA  AAAGACCCGC  CCCCGATGAC  GCGGATAAAA
 AAV2   CAAAAAGGGT  GGAGCCAAGA  AAAGACCCGC  CCCCAGTGAC  GCAGATATAA
 AAV3   CAGAAAGGGT  GGAGCTAAGA  AACGCCCCGC  CTCCAATGAC  GCGGATGTAA
 AAV8   CAGAAAGGGC  GGAGCCAGCA  AAAGACCCGC  CCCCGATGAC  GCGGATAAAA
 AAV9   CAGAAAGGGC  GGAGCCAGCA  AAAGACCCGC  CCCCGATGAC  GCGGATAAAA
 AAV7   CAGAAAGGGC  GGAGCCAGCA  AAAGACCCGC  CCCCGATCAC  GCGGATATAA
 44_2   CAGAAAGGGT  GGAGCCAACA  AGAGACCCGC  CCCCGATGAC  GCGGATAAAA
                                                          P40/TATA
```

FIG. 1AL

```
        1851                                                              1900
                                              P40 RNA
  42_2   GCGAGCCCAA GCGGGCCTGC CCCTCAGTCG CGGATCCATC GACGTCAGAC
  42_8   GCGAGCCCAA GCGGGCCTGC CCCTCAGTCG CGGATCCATC GACGTCAGAC
 42_15   GCGAGCCCAA GCGGGCCTGC CCCTCAGTCG CGGATCCATC GACGTCAGAC
 42_5b   GCGAGCCCAA GCGGGCCTGC CCCTCAGTCG CGGATCCATC GACGTCAGAC
 42_1b   .......... .......... .......... .......... ..........
 42_13   GCGAGCCCAA GCGGGCCTGC CCCTCAGTCG CGGATCCATC GACGTCAGAC
 42_3a   GCGAGCCCAA GCGGGCCTGC CCCTCAGTCG CGGATCCATC GACGTCAGAC
  42_4   .......... .......... .......... .......... ..........
 42_5a   GCGAGCCCAA GCGGGCCCGC CCCTCAGTCG CGGATCCATC GACGTCAGAC
 42_10   .......... .......... .......... .......... ..........
 42_3b   .......... .......... .......... .......... ..........
 42_11   GCGAGCCCAA GCGGGCCTGC CCCTCAGTCG CGGATCCATC GACGTCAGAC
 42_6b   CTGTCACGTG AGTGCTTTTG CGACATTTTG C..ATCCATC GACGTCAGAC
  43_1   GCGAGCCCAA GCGGGCCTGC CCCTCAGTCG CGGATCCATC GACGTCAGAC
  43_5   GCGAGCCCAA GCGGGCCTGC CCCTCAGTCG CGGATCCATC GACGTCAGAC
 43_12   GCGAGCCCAA GCGGGCCTGC CCCTCAGTCG CGGATCCATC GACGTCAGAC
 43_20   GCGAGCCCAA GCGGGCCTGC CCCTCAGTCG CGGATCCATC GACGTCAGAC
 43_21   GCGAGCCCAA GCGGGCCTGC CCCTCAGTCG CGGATCCATC GACGTCAGAC
 43_23   GCGAGCCCAA GCGGGCCTGC CCCTCAGTCG CGGATCCATC GACGTCAGAC
 43_25   GCGAGCCCAA GCGGGCCTGC CCCTCAGTCG CGGATCCATC GACGTCAGAC
  44_1   GCGAGCCCAA GCGGGCCTGC CCCTCAGTCG CGGATCCATC GACGTCAGAC
  44_5   GCGAGCCCAA GCGGGCCTGC CCCTCAGTCG CGGATCCATC GACGTCAGAC
 223_10  .......... .......... .......... .......... ..........
 223_2   .......... .......... .......... .......... ..........
 223_4   .......... .......... .......... .......... ..........
 223_5   .......... .......... .......... .......... ..........
 223_6   .......... .......... .......... .......... ..........
 223_7   .......... .......... .......... .......... ..........
  A3_4   ATGAGCCCAA GCGGGCGCGC GAGTCAGTTG CGCAGCCATC GACGTCAGAC
  A3_5   ATGAGCCCAA GCGGGCGCGC GAGTCAGTTG CGCAGCCATC GACGTCAGAC
  A3_7   ATGAGCCCAA GCGGGCGCGC GAGTCAGTTG CGCAGCCATC GACGTCAGAC
  A3_3   ATGAGCCCAA GCGGGCGCGC GAGTCAGTTG CGCAGCCATC GACGTCAGAC
 42_12   GCGAGCCCAA GCGGGCCTGC CCCTCAGTCG CGGATCCATC GACGTCAGAC
  AAV1   GCGAGCCCAA GCGGGCCTGC CCCTCAGTCG CGGATCCATC GACGTCAGAC
  AAV2   GTGAGCCCAA ACGGGTGCGC GAGTCAGTTG CGCAGCCATC GACGTCAGAC
  AAV3   GCGAGCCAAA ACGGGAGTGC ACGTCACTTG CGCAGCCGAC AACGTCAGAC
  AAV8   GCGAGCCCAA GCGGGCCTGC CCCTCAGTCG CGGATCCATC GACGTCAGAC
  AAV9   GCGAGCCCAA GCGGGCCTGC CCCTCAGTCG CGGATCCATC GACGTCAGAC
  AAV7   GCGAGCCCAA GCGGGCCTGC CCCTCAGTCG CGGATCCATC GACGTCAGAC
  44_2   GCGAGCCCAA GCGGGCCTGC CCCTCAGTCG CGGATCCATC GACGTCAGAC

P40 RNA
```

FIG. 1AM

```
         1901                                                      1950
 42_2    GCGGAAGGAG  CTCCGGTGGA  CTTTGCCGAC  AGGTACCAAA  ACAAATGTTC
 42_8    GCGGAAGGAG  CTCCGGTGGA  CTTTGCCGAC  AGGTACCAAA  ACAAATGTTC
 42_15   GCGGAAGGAG  CTCCGGTGGA  CTTTGCCGAC  AGGTACCAAA  ACAAATGTTC
 42_5b   GCGGAAGGAG  CTCCGGTGGA  CTTTGCCGAC  AGGTACCAAA  ACAAATGTTC
 42_1b   ..........  ..........  ..........  ..........  ..........
 42_13   GCGGAAGGAG  CTCCGGTGGA  CTTTGCCGAC  AGGTACCAAA  ACAAATGTTC
 42_3a   GCGGAAGGAG  CTCCGGTGGA  CTTTGCCGAC  AGGTACCAAA  ACAAATGTTC
 42_4    ..........  ..........  ..........  ..........  ..........
 42_5a   GCGGAAGGAG  CTCCGGTGGA  CTTTGCCGAC  AGGTACCAAA  ACAAATGTTC
 42_10   ..........  ..........  ..........  ..........  ..........
 42_3b   ..........  ..........  ..........  ..........  ..........
 42_11   GCGGAAGGAG  CTCCGGTGGA  CTTTGCCGAC  AGGTACCAAA  ACAAATGTTC
 42_6b   GCGGAAGGAG  CTCCGGTGGA  CTTTGCCGAC  AGGTACCAAA  ACAAGTGTTC
 43_1    GCGGAAGGAG  CTCCGGTGGA  CTTTGCCGAC  AGGTACCAAA  ACAAATGTTC
 43_5    GCGGAAGGAG  CTCCGGTGGA  CTTTGCCGAC  AGGTACCAAA  ACAAATGTTC
 43_12   GCGGAAGGAG  CTCCGGTGGA  CTTTGCCGAC  AGGTACCAAA  ACAAATGTTC
 43_20   GCGGAAGGAG  CTCCGGTGGA  CTTTGCCGAC  AGGTACCAAA  ACAAATGTTC
 43_21   GCGGAAGGAG  CTCCGGTGGA  CTTTGCCGAC  AGGTACCAAA  ACAAATGTTC
 43_23   GCGGAAGGAG  CTCCGGTGGA  CTTTGCCGAC  AGGTACCAAA  ACAAATGTTC
 43_25   GCGGAAGGAG  CTCCGGTGGA  CTTTGCCGAC  AGGTACCAAA  ACAAATGTTC
 44_1    GCGGAAGGAG  CTCCGGTGGA  CTTTGCCGAC  AGGTACCAAA  ACAAATGTTC
 44_5    GCGGAAGGAG  CTCCGGTGGA  CTTTGCCGAC  AGGTACCAAA  ACAAATGTTC
223_10   ..........  ..........  ..........  ..........  ..........
223_2    ..........  ..........  ..........  ..........  ..........
223_4    ..........  ..........  ..........  ..........  ..........
223_5    ..........  ..........  ..........  ..........  ..........
223_6    ..........  ..........  ..........  ..........  ..........
223_7    ..........  ..........  ..........  ..........  ..........
 A3_4    GCGGA...AG  CTTCGATAAA  CTACGCGGGC  AGGTACCAAA  ACAAATGTTC
 A3_5    GCGGA...AG  CTTCGATAAA  CTACGCGGAC  AGGTACCAAA  ACAAATGTTC
 A3_7    GCGGA...AG  CTTCGATAAA  CTACGCGGAC  AGGTACCAAA  ACAAATGTTC
 A3_3    GCGGA...AG  CTTCGATAAA  CTACGCGGAC  AGGTACCAAA  ACAAATGTTC
 42_12   GCGGAAGGAG  CTCCGGTGGA  CTTTGCCGAC  AGGTACCAAA  ACAAATGTTC
 AAV1    GCGGAAGGAG  CTCCGGTGGA  CTTTGCCGAC  AGGTACCAAA  ACAAATGTTC
 AAV2    GCGGA...AG  CTTCGATCAA  CTACGCAGAC  AGGTACCAAA  ACAAATGTTC
 AAV3    GCGGA...AG  CACCGGCGGA  CTACGCGGAC  AGGTACCAAA  ACAAATGTTC
 AAV8    GCGGAAGGAG  CTCCGGTGGA  CTTTGCCGAC  AGGTACCAAA  ACAAATGTTC
 AAV9    GCGGAAGGAG  CTCCGGTGGA  CTTTGCCGAC  AGGTACCAAA  ACAAATGTTC
 AAV7    GCGGAAGGAG  CTCCGGTGGA  CTTTGCCGAC  AGGTACCAAA  ACAAATGTTC
 44_2    GCGGAAGGAG  CTCCGGTGGA  CTTTGCCGAC  AGGTACCAAA  ACAAATGTTC
```

FIG. 1AN

```
          1951                                                              2000
  42_2    TCGTCACGCG GGCATGCTTC AGATGCTGTT TCCCTG.CAA GACATGCGAG
  42_8    TCGTCACGCG GGCATGCTTC AGATGCTGTT TCCCTG.CAA GACATGCGAG
  42_15   TCGTCACGCG GGCATGCTTC AGATGCTGTT TCCCTG.CAA GACATGCGAG
  42_5b   TCGTCACGCG GGCATGCTTC AGATGCTGTT TCCCTG.CAA GACATGCGAG
  42_1b   .......... ..........  ....GAATTC GCCCTT....  .GGCTGCGTC
  42_13   TCGTCACGCG GGCATGCTTC AGATGCTGTT TCCCTG.CAA GACATGCGAG
  42_3a   TCGTCACGCG GGCATGCTTC AGATGCTGCT TCCCTG.CAA GACATGCGAG
  42_4    .......... ..........  ....GAATTC GCCCTTTCTA CGGCTGCGTC
  42_5a   TCGTCACGCG GGCATGCTTC AGATGCTGTT TCCCTG.CAA AACATGCGAG
  42_10   .......... ..........  ....GAATTC GCCCTTTCTA CGGCTGCGTC
  42_3b   .......... ..........  ....GAATTC GCCCTTTCTA CGGCTGCGTC
  42_11   TCGTCACGCG GGCATGCTTC AGATGCTGTT TCCCTG.CAA GACATGCGAG
  42_6b   TCGTCACGCG GGCATGCTTC AGATGCTGTT TCCCTG.CAA GACATGCGAG
  43_1    TCGTCACGCG GGCATGCTTC AGATGCTGTT TCCCTG.CAA AACGTGCGAG
  43_5    TCGTCACGCG GGCATGCTTC AGACGCTGTT TCCCTG.CAA AACGTGCGAG
  43_12   TCGTCACGCG GGCATGCTCC AGATGCTGTT TCCCTG.CAA AACGTGCGAG
  43_20   TCGTCACGCG GGCATGCTTC AGATGCTGTT TCCCTG.CAA GACATGCGAG
  43_21   TCGTCACGCG GGCATGCTTC AGATGCTGTT TCCCTG.CAA GACATGCGAG
  43_23   TCGTCACGCG GGCATGCTTC AGATGCTGTT TCCCTG.CAA GACATGCGAG
  43_25   TCGTCACGCG GGCATGCTTC AGATGCTGTT TCCCTG.CAA GACATGCGAG
  44_1    TCGTCACGCG GGCATGCTTC AGATGCTGTT TCCCTG.CAA AACATGCGAG
  44_5    TCGTCACGCG GGCATGCTTC AGATGCTGTT TCCCTG.CAA AACATGCGAG
  223_10  .......... ..........  .......... .......... ..........
  223_2   .......... ..........  .......... .......... ..........
  223_4   .......... ..........  .......... .......... ..........
  223_5   .......... ..........  .......... .......... ..........
  223_6   .......... ..........  .......... .......... ..........
  223_7   .......... ..........  .......... .......... ..........
  A3_4    TCGTCACGTG GGCATGAATC TGATGCTGTT TCCCTG.TCG ACAATGCGAA
  A3_5    TCGTCACGTG GGCATGAATC TGATGCTGTT TCCCTG.TCG ACAATGCGAA
  A3_7    TCGTCACGTG GGCATGAATC TGATGCTGTT TCCCTG.TCG ACAATGCGAA
  A3_3    TCGTCACGTG GGCATGAATC TGATGCTGTT TCCCTG.TCG ACAATGCGAA
  42_12   TCGTCACGCG GGCATGCTTC AGATGCTGTT TCCCTG.CAA GACATGCGAG
  AAV1    TCGTCACGCG GGCATGCTTC AGATGCTGTT TCCCTG.CAA GACATGCGAG
  AAV2    TCGTCACGTG GGCATGAATC TGATGCTGTT TCCCTG.CAG ACAATGCGAG
  AAV3    TCGTCACGTG GGCATGAATC TGATGCTTTT TCCCTG.TAA AACATGCGAG
  AAV8    TCGTCACGCG GGCATGCTTC AGATGCTGTT TCCCTG.CAA AACGTGCGAG
  AAV9    TCGTCACGCG GGCATGCTTC AGATGCTGCT TCCCTG.CAA AACGTGCGAG
  AAV7    TCGTCACGCG GGCATGATTC AGATGCTGTT TCCCTG.CAA AACGTGCGAG
  44_2    TCGTCACGCG GGCATGCTTC AGATGCTGTT TCCCTG.CAA AACATGCGAG
```

FIG. 1AO

```
             2001                                                                    2050
   42_2    AGAATGAATC  AGAATTTCAA  CATTTGCTTC  ACGCACGGGA  CCAGAGACTG
   42_8    AGAATGAATC  AGAATTTCAA  CATTTGCTTC  ACGCACGGGA  CCAGAGACTG
   42_15   AGAATGAATC  AGAATTTCAA  CATTTGCTTC  ACGCGCGGGA  CCAGAGACTG
   42_5b   AGAATGAATC  AGAATTTCAA  CATTTGCTTC  ACGCACGGGA  CCAGAGACTG
   42_1b   A.ACTGGACC  A..ATGAGAA  CTTTCCCTTC  A........A  CGATTGCGTC
   42_13   AGAATGAATC  AGAATTTCAA  CATTTGCTTC  ACGCACGGGA  CCAGAGACTG
   42_3a   AGAATGAATC  AGAATTTCAG  CATTTGCTTC  ACGCACGGGA  CCAGAGACTG
   42_4    A.ACTGGACC  A..ATGAGAA  CTTTCCCTTC  A........A  CGATTGCGTC
   42_5a   AGAATGAATC  AGAATTTCAA  CATTTGCTTC  ACGCACGGGA  CCAGAGACTG
   42_10   A.ACTGGACC  A..ATGAGAA  CTTTCCCTTC  A........A  CGATTGCGTC
   42_3b   A.ACTAGACC  A..ATGAGAA  CTTTCCCTTC  A........A  CGATTGCGTC
   42_11   AGAATGAATC  AGAATTTCAA  CATTTGCTTC  ACGCACGGGA  CCGGAGACTG
   42_6b   AGAATGAATC  AGAATTTCAA  CATTTGCTTC  ACGCACGGGA  CCAGAGACTG
   43_1    AAAATGAATC  AGAATTTCAA  CATTTGCTTC  ACGCACGGGG  TCAGAGACTG
   43_5    AGAATGAATC  AGAATTTCAA  CATTTGCTTC  ACGCACGCGG  TCAGAGACTG
   43_12   AGAATGAATC  AGAATTTCAA  CATTTGCTTC  ACGCACGGGG  TCAGAGACTG
   43_20   AGAATGAATC  AGAATTTCAA  CATTTGCTTC  ACGCACGGGA  CCAGAGACTG
   43_21   AGAATGAATC  AGAATTTCAA  CATTTGCTTC  ACGCACGGGA  CCAGAGACTG
   43_23   AGAATGAATC  AGAATTTCAA  CATTTGCTTC  ACGCACGGGA  CCAGAGACTG
   43_25   AGAATGAATC  AGAATTTCAA  CATTTGCTTC  ACGCACGGGA  CCAGAGACTG
   44_1    AGAATGAATC  AGAATTTCAA  CATTTGCTTC  ACGCACGGGA  CCAGAGACTG
   44_5    AGAATGAATC  AGAATTTCAA  CATTTGCTTC  ACGCACGGGA  CCAGAGACTG
  223_10   ..........  ..........  ..........  ..........  ..........
  223_2    ..........  ..........  ..........  ..........  ..........
  223_4    ..........  ..........  ..........  ..........  ..........
  223_5    ..........  ..........  ..........  ..........  ..........
  223_6    ..........  ..........  ..........  ..........  ..........
  223_7    ..........  ..........  ..........  ..........  ..........
   A3_4    AGAATGAATC  AGAATTCAAA  TATCTGCTTC  ACACACGGGC  AAAAAGACTG
   A3_5    AGAATGAATC  AGAATTCAAA  TATCTGCTTC  ACACACGGGC  AAAAAGACTG
   A3_7    AGAATGAATC  AGAATTCAAA  TATCTGCTTC  ACACACGGGC  AAAAAGACTG
   A3_3    AGAATGAATC  AGAATTCAAA  TATCTGCTTC  ACACACGGGC  AAAAAGACTG
   42_12   AGAATGAATC  AGAATTTCAA  CATTTGCTTC  ACGCACGGGA  CCAGAGACTG
   AAV1    AGAATGAATC  AGAATTTCAA  CATTTGCTTC  ACGCACGGGA  CGAGAGACTG
   AAV2    AGAATGAATC  AGAATTCAAA  TATCTGCTTC  ACTCACGGAC  AGAAAGACTG
   AAV3    AGAATGAATC  AAATTTCCAA  TGTCTGTTTT  ACGCATGGTC  AAAGAGACTG
   AAV8    AGAATGAATC  AGAATTTCAA  CATTTGCTTC  ACACACGGGG  TCAGAGACTG
   AAV9    AGAATGAATC  AGAATTTCAA  CATTTGCTTC  ACACACGGGG  TCAGAGACTG
   AAV7    AGAATGAATC  AGAATTTCAA  CATTTGCTTC  ACACACGGGG  TCAGAGACTG
   44_2    AGAATGAATC  AGAATTTCAA  CATTTGCTTC  ACGCACGGGA  CCAGAGACTG
```

FIG. 1AP

```
         2051                                              2100
 42_2    TTCAGAATGT TTCCCCGGCG TGTCAGAATC TCAACC.... ..GGTCGTCA

42_8    TTCAGAATGT TTCCCCGGCG TGTCAGAATC TCAACC.... ..GGTCGTCA
 42_15   TTCAGAATGT TTCCCCGGCG TGTCAGAATC TCAACC.... ..GGTCGTCA
 42_5b   TTCAGAATGT TTCCCCGGCG TGTCAGAATC TCAACC.... ..GGTCGTCA
 42_1b   GACAAGATGG TGATCTGGTG GG..AGGAGG GCAAGA.... ..TGACGGCC
 42_13   TTCAGAATGT TTCCCCGGCG TGTCAGAATC TCAACC.... ..GGTCGTCA
 42_3a   TTCAGAATGT TTCCCCGGCG TGTCAGAATC TCAACC.... ..GGTCGTCA
 42_4    GACAAGATGG TGATCTGGTG GG..AGGAGG GCAAGA.... ..TGACGGCC
 42_5a   TTCAGAATGT TTCCCCGGCG TGTCAGAATC TCAACC.... ..GGTCGTCA
 42_10   GACAAGATGG TGATCTGGTG GG..AGGAGG GCAAGA.... ..TGACGGCC
 42_3b   GACAAGATGG TGATCTGGTG GG..AGGAGG GCAAGA.... ..TGACGGCC
 42_11   TTCAGAATGT TTCCCCGGCG TGTCAGAATC TCAACC.... ..GGTCGTCA
 42_6b   TTCAGAATGT TTCCCCGGCG TGTCAGAATC TCAACC.... ..GGTCGTCA
 43_1    CTCAGAATGT TTCCCCGGTG CATCAGAATC TCAACC.... ..GGTCGTCA
 43_5    CTCAGAATGT TTCCCCGGTG CATCAGAATC TCAACC.... ..GGTCGTCA
 43_12   CTCAGAATGT TTCCCCGGTG CATCAGAATC TCAACC.... ..GGTCGTCA
 43_20   TTCAGAATGT TTCCCCGGCG TGTCAGAATC TCAACC.... ..GGTCGTCA
 43_21   TTCAGAATGT TTCCCCGGCG TGTCAGAATC TCAACC.... ..GGTCGTCA
 43_23   TTCAGAATGT TTCCCCGGCG TGTCAGAATC TCAACC.... ..GGTCGTCA
 43_25   TTCAGAATGT TTCCCCGGCG TGTCAGAATC TCAACC.... ..GGTCGTCA
 44_1    TTCAGAATGT TTCCCCGGCG TGTCAGAATC TCAACC.... ..GGTCGTCA
 44_5    TTCAGAATGT TTCCCCGGCG TGTCAGAATC TCAACC.... ..GGTTGTCA
223_10   .......... .......... .......... .......... ..........
223_2    .......... .......... .......... .......... ..........
223_4    .......... .......... .......... .......... ..........
223_5    .......... .......... .......... .......... ..........
223_6    .......... .......... .......... .......... ..........
223_7    .......... .......... .......... .......... ..........
 A3_4    TTTGGAATGC TTTCCCG... TGTCAGAATC TCAACCCGTT TCTGTCGTCA
 A3_5    TTTGGAATGC TTTCCCG... TGTCAGAATC TCAACCCGTT CCTGTCGTCA
 A3_7    TTTGGAATGC TTTCCCG... TGTCAGAATC TCAACCCGTT TCTGTCGTCA
 A3_3    TTTGGAATGC TTTCCCG... TGTCAGAATC TCAACCCGTT TCTGTCGTCA
 42_12   TTCAGAATGT TTCCCCGGCG TGTCAGAATC TCAACC.... ..GGTCGTCA
 AAV1    TTCAGAGTGC TTCCCCGGCG TGTCAGAATC TCAACC.... ..GGTCGTCA
 AAV2    TTTAGAGTGC TTTCCCG... TGTCAGAATC TCAACCCGTT TCTGTCGTCA
 AAV3    TGGGAATGC  TTCCCTGGAA TGTCAGAATC TCAACCCGTT TCTGTCGTCA
 AAV8    CTCAGAGTGT TTCCCCGGCG TGTCAGAATC TCAACC.... ..GGTCGTCA
 AAV9    CTCAGAGTGT TTCCCCGGCG TGTCAGAATC TCAACC.... ..GGTCGTCA
 AAV7    TTTAGAGTGT TTCCCCGGCG TGTCAGAATC TCAACC.... ..GGTCGTCA
 44_2    TTCAGAATGT TTCCCCGGCG TGTCAGAATC TCAACC.... ..GGTCGTCA
```

FIG. 1AQ

```
           2101                                                   2150
   42_2    GAAAGAGGAC GTATCGGAAA CTCTGTGCCA TTCATCATCT GCTGGGG.CG
   42_8    GAAAGAGGAC GTATCGGAAA CTCTGTGCCA TTCATCATCT GCTAGGG.CG
  42_15    GAAAGAGGAC GTATCGGAAA CTCTGTGCCA TTCATCATCT GCTGGGG.CG
  42_5b    GAAAGAGGAC GTATCGGAAA CTCTGTGCCA TTCATCATCT GCTGGGG.CG
  42_1b    .AAGGTCGTG GAGTCCGCCA AG...GCCA TTCATCATCT GCTGGGG.CG
  42_13    GAAAGAGGAC GTATCGGAAA CTCTGTGCCA TTCATCATCT GCTGGGG.CG
  42_3a    GAAAGAGGAC GTATCGGAAA CTCTGTGCCA TTCATCATCT GCTGGGG.CG
   42_4    .AAGGTCGTG GAGTCCGCCA AG...GCCA TTCATCATCT GCTGGGG.CG
  42_5a    GAAAGAGGAC GTATCGGAAA CTCTGTGCCA TTCATCATCT GCTGGGG.CG
  42_10    AA...GGTC GTGAAGTCCG CCAAG.GCCA TTCATCATCT GCTGGGG.CG
  42_3b    AA...GGTC GTGGAGTCCG CCAAG.GCCA TTCATCATCT GCTGGGG.CG
  42_11    GAAAGAGGAC GTATCGGAAA CTCTGTGCCA TTCATCATCT GCTGGGG.CG
  42_6b    GAAAGAGGAC GTATCGGAAA CTCTGTGCCA TTCATCATCT GCTGGGG.CG
   43_1    GAAAAAAAAC GTATCAGAAA CTGTGTGCCA TTCATCATCT GCTGGGG.CG
   43_5    GAAAAAAAAC GTATCAGAAA CTGTGTGCCA TTCATCATCT GCTGGGG.CG
  43_12    GAAAAAAAAC GTATCAGAAA CTGTGTGCCA TTCATCATCT GCTGGGG.CG
  43_20    GAAAGAGGAC GTATCGGAAA CTCTGTGCGA TTCATCATCT GCTGGGG.CG
  43_21    GAAAGAGGAC GTATCGGAAA CTCTGTGCGA TTCATCATCT GCTGGGG.CG
  43_23    GAAAGAGGAC GTATCGGAAA CTCTGTGCCA TTCATCATCT GCTGGGG.CG
  43_25    GAAAGAGGAC GTATCGGAAA CTCTGTGCGA TTCATCATCT GCTGGGG.CG
   44_1    GAAAAAGAC GTATCGGAAA CTCTGTGCGA TTCATCATCT GCTGGGG.CG
   44_5    GAAAAAGAC GTATCGGAAA CTCTGTGCGA TTCATCATCT GCTGGGG.CG
 223_10    .......... .......... .......... .......... ..........
  223_2    .......... .......... .......... .......... ..........
  223_4    .......... .......... .......... .......... ..........
  223_5    .......... .......... .......... .......... ..........
  223_6    .......... .......... .......... .......... ..........
  223_7    .......... .......... .......... .......... ..........
   A3_4    GAAAAACG.. .TATCAGAAA CTTTGTTACA TTCATCATAT CATGGGA.AA
   A3_5    GAAAAACG.. .TATCAGAAA CTTTGTTACA TTCATCATAT CATGGGA.AA
   A3_7    GAAAAACG.. .TATCAGAAA CTTTGTTACA TTCATCATAT CATGGGA.AA
   A3_3    GAAAAACG.. .TATCAGAAA CTTTGTTACA TTCATCATAT CATGGGA.AA
  42_12    GAAAGAGGAC GTATCGGAAA CTCTGTGCCA TTCATCATCT GCTGGGG.CG
   AAV1    GAAAGAGGAC GTATCGGAAA CTCTGTGCCA TTCATCATCT GCTGGGG.CG
   AAV2    AAAAGGCG.. .TATCAGAAA CTGTGCTACA TTCATCATAT CATGGGA.AA
   AAV3    AAAAGAAGAC TTATCAGAAA CTGTGTCCAA TTCATCATAT CCTGGGA.AG
   AAV8    GAAAGAGGAC GTATCGGAAA CTCTGTGCGA TTCATCATCT GCTGGGG.CG
   AAV9    GAAAGAGGAC GTATCGGAAA CTCTGTGCGA TTCATCATCT GCTGGGG.CG
   AAV7    GAAAAAGAC GTATCGGAAA CTCTGCGCGA TTCATCATCT GCTGGGG.CG
   44_2    GAAAAAGAC GTATCGGAAA CTCTGTGCGA TTCATCATCT GCTGGGGGCG
```

FIG. 1AR

```
       2151                                                           2200
 42_2   GGCTCCCGAG ATTGCTTGCT CGGCCTGCGA TCTGGTCAAC GTGGACCTGG
 42_8   GGCTCCCGAG ATTGCTTGCT CGGCCTGCGA TCTGGTCAAC GTGGACCTGG
 42_15  GGCTCCCGAG ATTGCTTGCT CGGCCTGCGA TCTGGTCAAC GTGGACCTGG
 42_5b  GGCTCCCGAG ATTGCTTGCT CGGCCTGCGA TCTGGTCAAC GTGGACCTGG
 42_1b  GGCTCCCGAG ATTGCTTGCT CGGCCTGCGA TCTGGTCAAC GTGGACCTGG
 42_13  GGCTCCCGAG ATTGCTTGCT CGGCCTGCGA TCTGGTCAAC GTGGACCTGG
 42_3a  GGCTCCCGAG ATTGCTTGCT CGGCCTGCGA TCTGGTCAAC GTGGACCTGG
 42_4   GGCTCCCGAG ATTGCTTGCT CGGCCTGCGA TCTGGTCAAC GTGGACCTGG
 42_5a  GGCTCCCGAG ATTGCTTGCT CGGCCTGCGA TCTGGTCAAC GTGGACCTGG
 42_10  GGCTCCCGAG ATTGCTTGCT CGGCCTGCGA TCTGGTCAAC GTGGACCTGG
 42_3b  GGCTCCCGAG ATTGCTTGCT CGGCCTGCGA TCTGGTCAAC GTGGACCTGG
 42_11  GGCTCCCGAG ATTGCTTGCT CGGCCTGCGA TCTGGTCAAC GTGGACCTGG
 42_6b  GGCTCCCGAG ATTGCTTGCT CGGCCTGCGA TCTGGTCAAC GTGGACCTGG
 43_1   GGCACCCGAG ATTGCTTGCT CGGCCTGCGA TCTGGTCAAC GTGGACCTGG
 43_5   GGCACCCGAG ATTGCTTGCT CGGCCTGCGA TCTGGTCAAC GTGGACCTGG
 43_12  GGCACCCGAG ATTGCTTGCT CGGCCTGCGA TCTGGTCAAC GTGGACCTGG
 43_20  GGCTCCCGAG ATTGCTTGCT CGGCCTGCGA TCTGGTCAAC GTGGACCTGG
 43_21  GGCTCCCGAG ATTGCTTGCT CGGCCTGCGA TCTGGTCAAC GTGGACCTGG
 43_23  GGCTCCCGAG ATTGCTTGCT CGGCCTGCGA TCTGGTCAAC GTGGACCTGG
 43_25  GGCTCCCGAG ATTGCTTGCT CGGCCTGCGA TCTGGTCAAC GTGGACCTGG
 44_1   GGCACCCGAG ATTGCTTGCT CGGCCTGCGA TCTGGTCAAC GTGGACCTAG
 44_5   GGCACCCGAG ATTGCTTGCT CGGCCTGCGA TCTGGTCAAC GTGGACCTAG
223_10  .......... .......... .......... .......... ..........
223_2   .......... .......... .......... .......... ..........
223_4   .......... .......... .......... .......... ..........
223_5   .......... .......... .......... .......... ..........
223_6   .......... .......... .......... .......... ..........
223_7   .......... .......... .......... .......... ..........
 A3_4   AGAACCAGAC ...GCCTGCA CTGCCTGCGA CCTGGTAAAT GTGGACTTGG
 A3_5   AGTACCAGAC ...GCCTGCA CTGCCTGCGA CCTGGTAAAT GTGGACTTGG
 A3_7   AGTACCAGAC ...GCCTGCA CTGCCTGCGA CCTGGTAAAT GTGGACTTGG
 A3_3   AGTACCAGAC ...GCCTGCA CTGCCTGCGA CCTGGTAAAT GTGGACTTGG
 42_12  GGCTCCCGAG ATTGCTTGCT CGGCCTGCGA TCTGGTCAAC GTGGACCTGG
 AAV1   GGCTCCCGAG ATTGCTTGCT CGGCCTGCGA TCTGGTCAAC GTGGACCTGG
 AAV2   GGTGCCAGAC ...GCTTGCA CTGCCTGCGA TCTGGTCAAT GTGGATTTGG
 AAV3   GGCACCCGAG ATTGCCTGTT CGGCCTGCGA TTTGGCCAAT GTGGACTTGG
 AAV8   GGCTCCCGAG ATTGCTTGCT CGGCCTGCGA TCTGGTCAAC GTGGACCTGG
 AAV9   GGCTCCCGAG ATTGCTTGCT CGGCCTGCGA TCTGGTCAAC GTGGACCTGG
 AAV7   GGCGCCCGAG ATTGCTTGCT CGGCCTGCGA CCTGGTCAAC GTGGACCTGG
 44_2   GGCACCCGAG ATTGCTTGCT CGGCCTGCGA TCTGGTCAAC GTGGACCTAG
```

FIG. 1AS

```
       2201                                                                              2250
                                          Rep 78 stop           vp1 start
   42_2    ATGACCGTGT TTCTGAGCAA TAAATGACTT AAACCAGGTA TGGCTGCCGA
   42_8    ATGACTGTGT TTCTGAGCAA TAAATGACTT AAACCAGGTA TGGCTGCCGA
   42_15   ATGACTGTGT TTCTGAGCAA TAAATGACTT AAACCAGGTA TGGCTGCCGA
   42_5b   ATGACTGTGT TTCTGAGCAA TAAATGACTT AAACCAGGTA TGGCTGCCGA
   42_1b   ATGACTGTGT TTCTGAGCAA TAAATGACTT AAACCAGGTA TGGCTGCCGA
   42_13   ATGACTGTGT TTCTGAGCAA TAAATGACTT AAACCAGGTA TGGCTGCCGA
   42_3a   ATGACTGTGT TTCTGAGCAA TAAATGACTT AAACCAGGTA TGGCTGCCGA
   42_4    ATGACTGTGT TTCTGAGCAA TAAATGACTT AAACCAGGTA TGGCTGCCGA
   42_5a   ATGACTGTGT TTCTGAGCAA TAAATGACTT AAACCAGGTA TGGCTGCCGA
   42_10   ATGACTGTGT TTCTGAGCAA TAAATGACTT AAACCAGGTA TGGCTGCCGA
   42_3b   ATGACTGTGT TTCTGAGCAA TAAATGACTT AAACCAGGTA TGGCTGCCGA
   42_11   ATGACTGTGT TTCTGAGCAA TAAATGACTT AAACCAGGTA TGGCTGCCGA
   42_6b   ATGACTGTGT TTCTGAGCAA TAAATGACTT AAACCAGGTA TGGCTGCCGA
   43_1    ACGACTGTGT TTCTGAGCAA TAAATGACTT AAACCAGGTA TGGCTGCCGA
   43_5    ACGACTGTGT TTCTGAGCAA TAAATGACTT AAACCAGGTA TGGCTGCCGA
   43_12   ACGACTGTGT TTCTGAGCAA TAAATGACTT AAACCAGGTA TGGCTGCCGA
   43_20   ATGACTGTGT TTCTGAGCAA TAAATGACTT AAACCAGGTA TGGCTGCCGA
   43_21   ATGACTGTGT TTCTGAGCAA TAAATGACTT AAACCAGGTA TGGCTGCCGA
   43_23   ATGACTGTGT TTCTGAGCAA TAAATGACTT AAACCAGGTA TGGCTGCCGA
   43_25   ATGACTGTGT TTCTGAGCAA TAAATGACTT AAACCAGGTA TGGCTGCCGA
   44_1    ATGACTGTGT TTCTGAGCAA TAAATGACTT AAACCAGGTA TGGCTGCCGA
   44_5    ATGACTGTGT TTCTGAGCAA TAAATGACTT AAACCAGGTA TGGCTGCCGA
  223_10   .......... .......... .......... .......... ..........
  223_2    .......... .......... .......... .......... ..........
  223_4    .......... .......... .......... .......... ..........
  223_5    .......... .......... .......... .......... ..........
  223_6    .......... .......... .......... .......... ..........
  223_7    .......... .......... .......... .......... ..........
   A3_4    ATGACTGTAT TTCTGAGCAA TAAATGACTT AAATCAGGTA TGGCTGCTGA
   A3_5    ATGACTGTAT TTCTGAGCAA TAAATGACTT AAATCAGGTA TGGCTGCTGA
   A3_7    ATGACTGTAT TTCTGAGCAA TAAATGACTT AAATCAGGTA TGGCTGCTGA
   A3_3    ATGACTGTAT TTCTGAGCAA TAAATGACTT AAATCAGGTA TGGCTGCTGA
   42_12   ATGACTGTGT TTCTGAGCAA TAAATGACTT AAACCAGGTA TGGCTGCCGA
   AAV1    ATGACTGTGT TTCTGAGCAA TAAATGACTT AAACCAGGTA TGGCTGCCGA
   AAV2    ATGACTGCAT CTTTGAACAA TAAATGATTT AAATCAGGTA TGGCTGCCGA
   AAV3    ATGACTGTGT TTCTGAGCAA TAAATGACTT AAACCAGGTA TGGCTGCTGA
   AAV8    ATGACTGTGT TTCTGAGCAA TAAATGACTT AAACCAGGTA TGGCTGCCGA
   AAV9    ATGACTGTGT TTCTGAGCAA TAAATGACTT AAACCAGGTA TGGCTGCCGA
   AAV7    ACGACTGCGT TTCTGAGCAA TAAATGACTT AAACCAGGTA TGGCTGCCGA
   44_2    ATGACTGTGT TTCTGAGCAA TAAATGACTT AAACCAGGTA TGGCTGCCGA
                                          Rep78 stop           vp1 start
```

FIG. 1AT

```
        2251                                                    2300
                                                  Rep68 stop
   42_2  TGGTTATCTT CCAGATTGGC TCGAGGACAA CCTCTCTGAG GGCATTCGCG
   42_8  TGGTTATCTT CCAGATTGGC TCGAGGACAA CCTCTCTGAG GGCATTCGCG
  42_15  TGGTTATCTT CCAGATTGGC TCGAGGACAA CCTCTCTGAG GGCATTCGCG
  42_5b  TGGTTATCTT CCAGATTGGC TCGAGGACAA CCTCTCTGAG GGCATTCGCG
  42_1b  TGGTTATCTT CCAGATTGGC TCGAGGACAA CCTCTCTGAG GGCATTCGCG
  42_13  TGGTTATCTT CCAGATTGGC TCGAGGACAA CCTCTCTGAG GGCATTCGCG
  42_3a  TGGTCATCTT CCAGATTGGC TCGAGGACAA CCTCTCTGAG GGCATTCGCG
   42_4  TGGTTATCTT CCAGATTGGC TCGAGGACAA CCTCTCTGAG GGCATTCGCG
  42_5a  TGGTTATCTT CCAGATTGGC TCGAGGACAA CCTCTCTGAG GGCATTCGCG
  42_10  TGGTTATCTT CCAGATTGGC TCGAGGACAA CCTCTCTGAG GGCATTCGCG
  42_3b  TGGTTATCTT CCAGATTGGC TCGAGGACAA CCTCTCTGAG GGCATTCGCG
  42_11  TGGTTATCTT CCAGATTGGC TCGAGGACAA CCTCTCTGAG GGCATTCGCG
  42_6b  TGGTTATCTT CCAGATTGGC TCGAGGACAA CCTCTCTGAG GGCATTCGCG
   43_1  TGGTTATCTT CCAGATTGGC TTGAGGACAA CCTCTCTGAG GGCATTCGCG
   43_5  TGGTTATCTT CCAGATTGGC TTGAGGACAA CCTCTCTGAG GGCATTCGCG
  43_12  TGGTTATCTT CCAGATTGGC TTGAGGACAA CCTCTCTGAG GGCATTCGCG
  43_20  TGGTTATCTT CCAGATTGGC TCGAGGACAA CCTCTCTGAG GGCATTCGCG
  43_21  TGGTTATCTT CCAGATTGGC TCGAGGACAA CCTCTCTGAG GGCATTCGCG
  43_23  TGGTTATCTT CCAGATTGGC TCGAGGACAA CCTCTCTGAG GGCATTCGCG
  43_25  TGGTTATCTT CCAGATTGGC TCGAGGACAA CCTCTCTGAG GGCATTCGCG
   44_1  TGGTTATCTT CCAGATTGGC TCGAGGACAA CCTCTCTGAG GGCATTCGCG
   44_5  TGGTTATCTT CCAGATTGGC TCGAGGACAA CCTCTCTGAG GGCATTCGCG
 223_10  .......... .......... .......... .......... ..........
  223_2  .......... .......... .......... .......... ..........
  223_4  .......... .......... .......... .......... ..........
  223_5  .......... .......... .......... .......... ..........
  223_6  .......... .......... .......... .......... ..........
  223_7  .......... .......... .......... .......... ..........
   A3_4  CGGTTATCTT CCAGATTGGC TCGAGGACAC TCTCTCTGAA GGAATCAGAC
   A3_5  CGGTTATCTT CCAGATTGGC TCGAGGACAC TCTCTCTGAA GGAATCAGAC
   A3_7  CGGTTATCTT CCAGATTGGC TCGAGGACAC TCTCTCTGAA GGAATCAGAC
   A3_3  CGGTTATCTT CCAGATTGGC TCGAGGACAC TCTCTCTGAA GGAATCAGAC
  42_12  TGGTTATCTT CCAGATTGGC TCGAGGACAA CCTCTCTGAG GGCATCCGCG
   AAV1  TGGTTATCTT CCAGATTGGC TCGAGGACAA CCTCTCTGAG GGCATTCGCG
   AAV2  TGGTTATCTT CCAGATTGGC TCGAGGACAC TCTCTCTGAA GGAATAAGAC
   AAV3  CGGTTATCTT CCAGATTGGC TCGAGGACAA CCTTTCTGAA GGCATTCGTG
   AAV8  TGGTTATCTT CCAGATTGGC TCGAGGACAA CCTCTCTGAG GGCATTCGCG
   AAV9  TGGTTATCTT CCAGATTGGC TCGAGGACAA CCTCTCTGAG GGCATTCGCG
   AAV7  TGGTTATCTT CCAGATTGGC TCGAGGACAA CCTCTCTGAG GGCATTCGCG
   44_2  TGGTTATCTT CCAGATTGGC TCGAGGACAA CCTCTCTGAG GGCATTCGCG
                                                  Rep 68 stop
```

FIG. 1AU

```
           2301                                                               2350
  42_2    AGTGGTGGGA CTTGAAACCT GGAGCCCCGA AACCCAAAGC CAACCAGCAA

42_8    AGTGGTGGGA CTTGAAACCT GGAGCCCCGA AACCCAAAGC CAACCAGCAA
  42_15   AGTGGTGGGA CTTGAAACCT GGAGCCCCGA AACCCAAAGC CAACCAGCAA
  42_5b   AGTGGTGGGA CTTGAAACCT GGAGCCCCGA AACCCAAAGC CAACCAGCAA
  42_1b   AGTGGTGGGA CTTGAGACCT GGAGCCCCGA AACCCAAAGC CAACCAGCAA
  42_13   AGTGGTGGGA CTTGAAACCT GGAGCCCCGA AACCCAAAGC CAACCAGCAA
  42_3a   AGTGGTGGGA CTTGAAACCT GGAGCCCCGA AACCCAAAGC CAACCAGCAA
  42_4    AGTGGTGGGA CTTGAAACCT GGAGCCCCGA AACCCAAAGC CAACCAGCAA
  42_5a   AGTGGTGGGA CTTGAAACCT GGAGCCCCGA AACCCAAAGC CAACCAGCAA
  42_10   AGTGGTGGGA CTTGAAACCT GGAGCCCCGA AACCCAAAGC CAACCAGCAA
  42_3b   AGTGGTGGGA CTTGAAACCT GGAGCCCCGA AACCCAAAGC CAACCAGCAA
  42_11   AGTGGTGGGA CTTGAAACCT GGAGCCCCGA AACCCAAAGC CAACCAGCAA
  42_6b   AGTGGTGGGA CTTGAAACCT GGAGCCCCGA AACCCAAAGC CAACCAGCAA
  43_1    AGTGGTGGGA CCTGAAACCT GGAGCCCCGA AACCCAAAGC CAACCAGCAA
  43_5    AGTGGTGGGA CCTGAAACCT GGAGCCCCGA AACCCAAAGC CAACCAGCAA
  43_12   AGTGGTGGGA CCTGAAACCT GGAGCCCCGA AACCCAAAGC CAACCAGCAA
  43_20   AGTGGTGGGA CTTGAAACCT GGAGCCCCGA AACCCAAAGC CAACCAGCAA
  43_21   AGTGGTGGGA CTTGAAACCT GGAGCCCCGA AACCCAAAGC CAACCAGCAA
  43_23   AGTGGTGGGA CTTGAAACCT GGAGCCCCGA AACCCAAAGC CAACCAGCAA
  43_25   AGTGGTGGGA CTTGAAACCT GGAGCCCCGA AACCCAAAGC CAACCAGCAA
  44_1    AGTGGTGGGA CTTGAAACCT GGAGCCCCGA AACCCAAAGC CAACCAGCAA
  44_5    AGTGGTGGGA CTTGAAACCT GGAGCCCCGA AACCCAAAGC CAACCAGCAA
 223_10   .......... .......... .......... .......... ..........
 223_2    .......... .......... .......... .......... ..........
 223_4    .......... .......... .......... .......... ..........
 223_5    .......... .......... .......... .......... ..........
 223_6    .......... .......... .......... .......... ..........
 223_7    .......... .......... .......... .......... ..........
  A3_4    AGTGGTGGAA GCTCAAACCT GGCCCACCAC CGCCGAAACC TAACCAACAA
  A3_5    AGTGGTGGAA GCTCAAACCT GGCCCACCAC CGCCGAAACC TAACCAACAA
  A3_7    AGTGGTGGAA GCTCAAACCT GGCCCACCAC CGCCGAAACC TAACCAACAA
  A3_3    AGTGGTGGAA GCTCAAACCT GGCCCACCAC CGCCGAAACC TAACCAACAA
  42_12   AGTGGTGGGA CTTGAAACCT GGAGCCCCGA AACCCAAAGC CAACCAGCAA
  AAV1    AGTGGTGGGA CTTGAAACCT GGAGCCCCGA AGCCCAAAGC CAACCAGCAA
  AAV2    AGTGGTGGAA GCTCAAACCT GGCCCACCAC CACCAAAGCC CGCAGAGCGG
  AAV3    AGTGGTGGGC TCTGAAACCT GGAGTCCCTC AACCCAAAGC GAACCAACAA
  AAV8    AGTGGTGGCC GCTGAAACCT GGAGCCCCGA AGCCCAAAGC CAACCAGCAA
  AAV9    AGTGGTGGGC GCTGAAACCT GGAGCCCCGA AGCCCAAAGC CAACCAGCAA
  AAV7    AGTGGTGGGA CCTGAAACCT GGAGCCCCGA AACCCAAAGC CAACCAGCAA
  44_2    AGTGGTGGGA CTTGAAACCT GGAGCCCCGA AACCCAAAGC CAACCAGCAA
```

FIG. 1AV

```
          2351                                                    2400
 42_2    AAGCAGGACG  ACGGCCGGGG  TCTGGTGCTT  CCTGGCTACA  AGTACCTCGG
 42_8    AAGCAGGACG  ACGGCCGGGG  TCTGGTGCTT  CCTGGCTACA  AGTACCTCGG
 42_15   AAGCAGGACG  ACGGCCGGGG  TCTGGTGCTT  CCTGGCTACA  AGTACCTCGG
 42_5b   AAGCAGGACG  ACGGCCGGGG  TCTGGTGCTT  CCTGGCTACA  AGTACCTCGG
 42_1b   AAGCAGGACG  ACGGCCGGGG  TCTGGTGCTT  CCTGGCTACA  AGTACCTCGG
 42_13   AAGCAGGACG  ACGGCCGGGG  TCTGGTGCTT  CCTGGCTACA  AGTACCTCGG
 42_3a   AAGCAGGACG  ACGGCCGGGG  TCTGGTGCTT  CCTGGCTACA  AGTACCTCGG
 42_4    AAGCAGGACG  ACGGCCGGGG  TCTGGTGCTT  CCTGGCTACA  AGTACCTCGG
 42_5a   AAGCAGGACG  ACGGCCGGGG  TCTGGTGCTT  CCTGGCTACA  AGTACCTCGG
 42_10   AAGCAGGACG  ACGGCCGGGG  TCTGGTGCTT  CCTGGCTACA  AGTACCTCGG
 42_3b   AAGCAGGACG  ACGGCCGGGG  TCTGGTGCTT  CCTGGCTACA  AGTACCTCGG
 42_11   AAGCAGGACG  ACGGCCGGGG  TCTGGTGCTT  CCTGGCTACA  AGTACCTCGG
 42_6b   AAGCAGGACG  ACGGCCGGGG  TCTGGTGCTT  CCTGGCTACA  AGTACCTCGG
 43_1    AAGCAGGACG  ACGGCCGGGG  TCTGGTGCTT  CCTGGCTACA  AGTACCTCGG
 43_5    AAGCAGGACG  ACGGCCGGGG  TCTGGTGCTT  CCTGGCTACA  AGTACCTCGG
 43_12   AAGCAGGACG  ACGGCCGGGG  TCTGGTGCTT  CCTGGCTACA  AGTACCTCGG
 43_20   AAGCAGGACG  ACGGCCGGGG  TCTGGTGCTT  CCTGGCTACA  AGTACCTCGG
 43_21   AAGCAGGACG  ACGGCCGGGG  TCTGGTGCTT  CCTGGCTACA  AGTACCTCGG
 43_23   AAGCAGGACG  ACGGCCGGGG  TCTGGTGCTT  CCTGGCTACA  AGTACCTCGG
 43_25   AAGCAGGACG  ACGGCCGGGG  TCTGGTGCTT  CCTGGCTACA  AGTACCTCGG
 44_1    AAGCAGGACG  ACGGCCGGGG  TCTGGTGCTT  CCTGGCTACA  AGTACCTCGG
 44_5    AAGCAGGACG  ACGGCCGGGG  TCTGGTGCTT  CCTGGCTACA  AGTACCTCGG
223_10   ..........  ..........  ..........  ..........  ..........
223_2    ..........  ..........  ..........  ..........  ..........
223_4    ..........  ..........  ..........  ..........  ..........
223_5    ..........  ..........  ..........  ..........  ..........
223_6    ..........  ..........  ..........  ..........  ..........
223_7    ..........  ..........  ..........  ..........  ..........
 A3_4    CACCGGGACG  ACAGTAGGGG  TCTTGTGCTT  CCTGGGTACA  AGTACCTCGG
 A3_5    CACCGGGACG  ACAGTAGGGG  TCTTGTGCTT  CCTGGGTACA  AGTACCTCGG
 A3_7    CACCGGGACG  ACAGTAGGGG  TCTTGTGCTT  CCTGGGTACA  AGTACCTCGG
 A3_3    CACCGGGACG  ACAGTAGGGG  TCTTGTGCTT  CCTGGGTACA  AGTACCTCGG
 42_12   AAGCAGGACG  ACGGCCGGGG  TCTGGTGCTT  CCTGGCTACA  AGTACCTCGG
 AAV1    AAGCAGGACG  ACGGCCGGGG  TCTGGTGCTT  CCTGGCTACA  AGTACCTCGG
 AAV2    CATAAGGACG  ACAGCAGGGG  TCTTGTGCTT  CCTGGGTACA  AGTACCTCGG
 AAV3    CACCAGGACA  ACCGTCGGGG  TCTTGTGCTT  CCGGGTTACA  AATACCTCGG
 AAV8    AAGCAGGACG  ACGGCCGGGG  TCTGGTGCTT  CCTGGCTACA  AGTACCTCGG
 AAV9    AAGCAGGACG  ACGGCCGGGG  TCTGGTGCTT  CCTGGCTACA  AGTACCTCGG
 AAV7    AAGCAGGACA  ACGGCCGGGG  TCTGGTGCTT  CCTGGCTACA  AGTACCTCGG
 44_2    AAGCAGGACG  ACGGCCGGGG  TCTGGTGCTT  CCTGGCTACA  AGTACCTCGG
```

FIG. 1AW

```
        2401                                                              2450
42_2    ACCCTTCAAC  GGACTCGACA  AGGGAGAGCC  GGTCAACGAG  GCAGACGCCG
42_8    ACCCTTCAAC  GGACTCGACA  AGGGGGAGCC  CGTCAACGCG  GCGGACGCAG
42_15   ACCCTTCAAC  GGACTCGACA  AGGGGGAGCC  CGTCAACGCG  GCGGACGCAG
42_5b   ACCCTTCAAC  GGACTCGACA  AGGGAGAGCC  GGTCAACGAG  GCAGACGCCG
42_1b   ACCCTTCAAC  GGACTCGACA  AGGGAGAGCC  GGTCAACGAG  GCAGACGCCG
42_13   ACCCTTCAAC  GGACTCGACA  AGGGGGAGCC  CGTCAACGCG  GCGGACGCAG
42_3a   ACCCTTCAAC  GGACTCGACA  AGGGGGAGCC  CGTCAACGCG  GCGGACGCAG
42_4    ACCCTTCAAC  GGACTCGACA  AGGGAGAGCC  GGTCAACGAG  GCAGACGCCG
42_5a   ACCCTTCAAC  GGACTCGACA  AGGGAGAGCC  GGTCAACGAG  GCAGACGCCG
42_10   ACCCTTCAAC  GGACTCGACA  AGGGAGAGCC  GGTCAACGAG  GCAGACGCCG
42_3b   ACCCTTCAAC  GGACTCGACA  AGGGAGAGCC  GGTCAACGAG  GCAGACGCCG
42_11   ACCCTTCAAC  GGACTCGACA  AGGGAGAGCC  GGTCAACGCG  GCGGACGCAG
42_6b   ACCCTTCAAC  GGACTCGACA  AGGGAGAGCC  GGTCAACGAG  GCAGACGCCG
43_1    ACCCTTCAAC  GGACTCGACA  AGGGGGAGCC  CGTCAACGCG  GCGGACGCAG
43_5    ACCCTTCAAC  GGACTCGACA  AGGGGGAGCC  CGTCAACGCG  GCGGACGCAG
43_12   ACCCTTCAAC  GGACTCGACA  AGGGGGAGCC  CGTCAACGCG  GCGGACGCAG
43_20   ACCCTTCAAC  GGACTCGACA  AGGGCGAGCC  CGTCAACGCG  GCGGACGCAG
43_21   ACCCTTCAAC  GGACTCGACA  AGGGGGAGCC  CGTCAACGCG  GCGGACGCAG
43_23   ACCCTTCAAC  GGACTCGACA  AGGGGGAGCC  CGTCAACGCG  GCGGACGCAG
43_25   ACCCTTCAAC  GGACTCGACA  AGGGGGAGCC  CGTCAACGCG  GCGGACGCAG
44_1    ACCCTTCAAC  GGACTCGACA  AGGGGGAGCC  CGTCAACGCG  GCGGACGCAG
44_5    ACCCTTCAAC  GGACTCGACA  AGGGGGAGCC  CGTCAACGCG  GCGGACGCAG
223_10  ..........  ..........  ..........  ..........  ..........
223_2   ..........  ..........  ..........  ..........  ..........
223_4   ..........  ..........  ..........  ..........  ..........
223_5   ..........  ..........  ..........  ..........  ..........
223_6   ..........  ..........  ..........  ..........  ..........
223_7   ..........  ..........  ..........  ..........  ..........
A3_4    ACCCTTCAAC  GGACTCGACA  AAGGAGAGCC  GGTCAACGAG  GCAGACGCCG
A3_5    ACCCTTCAAC  GGACTCGACA  AAGGAGAGCC  GGTCAACGAG  GCAGACGCCG
A3_7    ACCCTTCAAC  GGACTCGACA  AAGGAGAGCC  GGTCAACGAG  GCAGACGCCG
A3_3    ACCCTTCAAC  GGACTCGACA  AAGGAGAGCC  GGTCAACGAG  GCAGACGCCG
42_12   ACCCTTCAAC  GGACTCGACA  AGGGAGAGCC  GGTCAACGAG  GCAGACGCCG
AAV1    ACCCTTCAAC  GGACTCGACA  AGGGGGAGCC  CGTCAACGCG  GCGGACGCAG
AAV2    ACCCTTCAAC  GGACTCGACA  AGGGAGAGCC  GGTCAACGAG  GCAGACGCCG
AAV3    ACCCGGTAAC  GGACTCGACA  AAGGAGAGCC  GGTCAACGAG  GCGGACGCGG
AAV8    ACCCTTCAAC  GGACTCGACA  AGGGGGAGCC  CGTCAACGCG  GCGGACGCAG
AAV9    ACCCTTCAAC  GGACTCGACA  AGGGGGAGCC  CGTCAACGCG  GCGGACGCAG
AAV7    ACCCTTCAAC  GGACTCGACA  AGGGGGAGCC  CGTCAACGCG  GCGGACGCAG
44_2    ACCCTTCAAC  GGACTCGACA  AGGGGGAGCC  CGTCAACGCG  GCGGACGCAG
```

FIG. 1AX

```
            2451                                                    2500
   42_2   CGGCCCTCGA GCACG.ACAA GGCCTACGAC AAGCAGCTCG AGCAGGGGGA
   42_8   CGGCCCTCGA GCACG.ACAA GGCCTACGAC CAGCAGCTCA AAGCGGGTGA
  42_15   CGGCCCTCGA GCACG.ACAA GGCCTACGAC CAGCAGCTCA AAGCGGGTGA
  42_5b   CGGCCCTCGA GCACG.ACAA GGCCTACGAC AAGCAGCTCG AGCAGGGGGA
  42_1b   CGGCCCTCGA GCACG.ACAA GGCCTACGAC AAGCAGCTCG AGCAGGGGGA
  42_13   CGGCCCTCGA GCACG.ACAA GGCCTACGAC CAGCAGCTCA AAGCGGGTGA
  42_3a   CGGCCCTCGA GCACG.ACAA GGCCTACGAC CAGCAGCTCA AAGCGGGTGA
   42_4   CGGCCCTCGA GCACG.ACAA GGCCTACGAC AAGCAGCTCG AGCAGGGGGA
  42_5a   CGGCCCTCGA GCACG.ACAA GGCCTACGAC AAGCAGCTCG AGCAGGGGGA
  42_10   CGGCCCTCGA GCACG.ACAA GGCCTACGAC AAGCAGCTCG AGCAGGGGGA
  42_3b   CGGCCCTCGA GCACG.ACAA GGCCTACGAC AAGCAGCTCG AGCAGGGGGA
  42_11   CGGCCCTCGA GCACG.ACAA GGCCTACGAC CAGCAGCTCA AAGCGGGTGA
  42_6b   CGGCCCTCGA GCACG.ACAA GGCCTACGAC AAGCAGCTCG AGCAGGGGGA
   43_1   CGGCCCTCGA GCACG.ACAA GGCCTACGAC CAGCAGCTCA AAGCGGGTGA
   43_5   CGGCCCTCGA GCACG.ACAA GGCCTACGAC CAGCAGCTCA AAGCGGGTGA
  43_12   CGGCCCTCGA GCACG.ACAA GGCCTACGAC CAGCAGCTCA AAGCGGGTGA
  43_20   CGGCCCTCGA GCACG.ACAA AGCCTACGAC CAGCAGCTCA AAGCGGGTGA
  43_21   CGGCCCTCGA GCACG.ACAA AGCCTACGAC CAGCAGCTCA AAGCGGGTGA
  43_23   CGGCCCTCGA GCACG.ACAA AGCCTACGAC CAGCAGCTCA AAGCGGGTGA
  43_25   CGGCCCTCGA GCACG.ACAA AGCCTACGAC CAGCAGCTCA AAGCGGGTGA
   44_1   CGGCCCTCGA GCACG.ACAA GGCCTACGAC CAGCAGCTCA AAGCGGGTGA
   44_5   CGGCCCTCGA GCACG.ACAA GGCCTACGAC CAGCAGCTCA AAGCGGGTGA
 223_10   .......... .......CAA GGCCTACGAC CAGCAGCTCA AAGCGGGTGA
  223_2   .......... .......CAA GGCCTACGAC CAGCAGCTCA AAGCGGGTGA
  223_4   .......... .......CAA GGCCTACGAC CAGCAGCTCA AAGCGGGTGA
  223_5   .......... .......CAA GGCCTACGAC CAGCAGCTCA AAGCGGGTGA
  223_6   .......... .......CAA GGCCTACGAC CAGCAGCTCA AAGCGGGTGA
  223_7   .......... .......CAA GGCCTACGAC CAGCAGCTCA AAGCGGGTGA
   A3_4   CGGCCCTCGA GCACG.ACAA AGCCTACGAC CACCAGCTCA AGCAAGGGGA
   A3_5   CGGCCCTCGA GCACG.ACAA AGCCTACGAC CACCAGCTCA AGCAAGGGGA
   A3_7   CGGCCCTCGA GCACG.ACAA AGCCTACGAC CACCAGCTCA AGCAAGGGGA
   A3_3   CGGCCCTCGA GCACG.ACAA AGCCTACGAC CACCAGCTCA AGCAAGGGGA
  42_12   CGGCCCTCGA GCACG.ACAA GGCCTACGAC AAGCAGCTCG AGCAGGGGGA
   AAV1   CGGCCCTCGA GCACG.ACAA GGCCTACGAC CAGCAGCTCA AAGCGGGTGA
   AAV2   CGGCCCTCGA GCACGTACAA AGCCTACGAC CGGCAGCTCG ACAGCGGAGA
   AAV3   CAGCCCTCGA ACACG.ACAA AGCTTACGAC CAGCAGCTCA AGGCCGGTGA
   AAV8   CGGCCCTCGA GCACG.ACAA GGCCTACGAC CAGCAGCTGC AGGCGGGTGA
   AAV9   CGGCCCTCGA GCACG.GCAA GGCCTACGAC CAGCAGCTGC AGGCGGGTGA
   AAV7   CGGCCCTCGA GCACG.ACAA GGCCTACGAC CAGCAGCTCA AAGCGGGTGA
   44_2   CGGCCCTCGA GCACG.ACAA GGCCTACGAC CAGCAGCTCA AAGCGGGTGA
```

FIG. 1AY

```
          2501                                                    2550
 42_2     CAACCCGTAC CTCAAGTACA ACCACGCCGA CGCCGAGTTT CAGGAGCGTC
 42_8     CAATCCGTAC CTGCGGTATA ACCACGCCGA CGCCGAGTTT CAGGAGCGTC
 42_15    CAATCCGTAC CTGCGGTATA ACCACGCCGA CGCCGAGTTT CAGGAGCGTC
 42_5b    CAACCCGTAC CTCAAGTACA ACCACGCCGA CGCCGAGTTT CAGGAGCGTC
 42_1b    CAACCCGTAC CTCAAGTACA ACCACGCCGA CGCCGAGTTT CAGGAGCGTC
 42_13    CAATCCGTAC CTGCGGTATA ACCACGCCGA CGCCGAGTTT CAGGAGCGTC
 42_3a    CAATCCGTAC CTGCGGTATA ACCACGCCGA CGCCGAGTTT CAGGAGCGTC
 42_4     CAACCCGTAC CTCAAGTACA ACCACGCCGA CGCCGAGTTT CAGGAGCGTC
 42_5a    CAACCCGTAC CTCAAGTACA ACCACGCCGA CGCCGAGTTT CAGGAGCGTC
 42_10    CAACCCGTAC CTCAAGTACA ACCACGCCGA CGCCGAGTTT CAGGAGCGTC
 42_3b    CAACCCGTAC CTCAAGTACA ACCACGCCGA CGCCGAGTTT CAGGAGCGTC
 42_11    CAATCCGTAC CTGCGGTATA ACCACGCCGA CGCCGAGTTT CAGGAGCGTC
 42_6b    CAACCCGTAC CTCAAGTACA ACCACGCCGA CGCCGAGTTT CAGGAGCGTC
 43_1     CAATCCGTAC CTGCGGTATA ACCACGCCGA CGCCGAGTTT CAGGAGCGTC
 43_5     CAATCCGTAC CTGCGGTATA ACCACGCCGA CGCCGAGTTT CAGGAGCGTC
 43_12    CAATCCGTAC CTGCGGTATA ACCACGCCGA CGCCGAGTTT CAGGAGCGTC
 43_20    CAATCCGTAC CTGCGGTATA ATCACGCCGA CGCCGAGTTT CAGGAGCGTC
 43_21    CAATCCGTAC CTGCGGTATA ATCACGCCGA CGCCGAGTTT CAGGAGCGTC
 43_23    CAATCCGTAC CTGCGGTATA ATCACGCCGA CGCCGAGTTT CAGGAGCGTC
 43_25    CAATCCGTAC CTGCGGTATA ATCACGCCGA CGCCGAGTTT CAGGAGCGTC
 44_1     CAATCCGTAC CTGCGGTATA ACCACGCCGA CGCCGAGTTT CAGGAGCGTC
 44_5     CAATCCGTAC CTGCGGTATA ACCACGCCGA CGCCGAGTTT CAGGAGCGTC
 223_10   CAATCCGTAC CTGCGGTATA ACCACGCCGA CGCCGAGTTT CAGGAGCGTC
 223_2    CAATCCGTAC CTGCGGTATA ACCACGCCGA CGCCGAGTTT CAGGAGTCTC
 223_4    CAATCCGTAC CTGCGGTATA ACCACGCCGA CGCCGAGTTT CAGGAGCGTC
 223_5    CAATCCGTAC CTGCGGTATA ACCACGCCGA CGCCGAGTTT CAGGAGCGTC
 223_6    CAATCCGTAC CTGCGGTATA ACCACGCCGA CGCCGAGTTT CAGGAGCGTC
 223_7    CAATCCGTAC CTGCGGTATA ACCACGCCGA CGCCGAGTTT CAGGAGCGTC
 A3_4     CAACCCGTAC CTCAAATACA ACCACGCGGA CGCTGAATTT CAGGAGCGTC
 A3_5     CAACCCGTAC CTCAAATACA ACCACGCGGA CGCTGAATTT CAGGAGCGTC
 A3_7     CAACCCGTAC CTCAAATACA ACCACGCGGA CGCTGAATTT CAGGAGCGTC
 A3_3     CAACCCGTAC CTCAAATACA ACCACGCGGA CGCTGAATTT CAGGAGCGTC
 42_12    CAACCCGTAC CTCAAGTACA ACCACGCCGA CGCCGAGTTT CAGGAGCGTC
 AAV1     CAATCCGTAC CTGCGGTATA ACCACGCCGA CGCCGAGTTT CAGGAGCGTC
 AAV2     CAACCCGTAC CTCAAGTACA ACCACGCCGA CGCGGAGTTT CAGGAGCGCC
 AAV3     CAACCCGTAC CTCAAGTACA ACCACGCCGA CGCCGAGTTT CAGGAGCGTC
 AAV8     CAATCCGTAC CTGCGGTATA ACCACGCCGA CGCCGAGTTT CAGGAGCGTC
 AAV9     CAATCCGTAC CTGCGGTATA ACCACGCCGA CGCCGAGTTT CAGGAGCGTC
 AAV7     CAATCCGTAC CTGCGGTATA ACCACGCCGA CGCCGAGTTT CAGGAGCGTC
 44_2     CAATCCGTAC CTGCGGTATA ACCACGCCGA CGCCGAGTTT CAGGAGCGTC
```

FIG. 1AZ

```
         2551                                                        2600
  42_2   TTCAAGAAGA TACGTCTTTT GGGGGCAACC TCGGGCGAGC AGTCTTCCAG
  42_8   TGCAAGAAGA TACGTCTTTT GGGGGCAACC TCGGGCGAGC AGTCTTCCAG
  42_15  TGCAAGAAGA TACGTCTTTT GGGGGCAACC TCGGGCGAGC AGTCTTCCAG
  42_5b  TTCAAGAAGA TACGTCTTTT GGGGGCAACC TCGGGCGAGC AGTCTTCCAG
  42_1b  TTCAAGAAGA TACGTCTTTT GGGGGCAACC TCGGGCGAGC AGTCTTCCAG
  42_13  TTCAAGAAGA TACGTCTTTT GGGGGCAACC TCGGGCGAGC AGTCTTCCAG
  42_3a  TTCAAGAAGA TACGTCTTTT GGGGGCAACC TCGGGCGAGC AGTCTTCCAG
  42_4   TTCAAGAAGA TACGTCTTTT GGGGGCAACC TCGGGCGAGC AGTCTTCCAG
  42_5a  TTCAAGAAGA TACGTCTTTT GGGGGCAACC TCGGGCGAGC AGTCTTCCGG
  42_10  TTCAAGAAGA TACGTCTTTT GGGGGCAACC TCGGGCGAGC AGTCTTCCAG
  42_3b  TTCAAGAAGA TACGTCTTTT GGGGGCAACC TCGGGCGAGC AGTCTTCCAG
  42_11  TTCAAGAAGA TACGTCTTTT GGGGGCAACC TCGGGCGAGC AGTCTTCCAG
  42_6b  TTCAAGAAGA TACGTCTTTT GGGGGCAACC TCGGGCGAGC AGTCTTCCAG
  43_1   TGCAAGAAGA TACGTCTTTT GGGGGCAACC TCGGGCGAGC AGTCTTCCAG
  43_5   TGCAAGAAGA TACGTCTTTT GGGGGCAACC TCGGGCGAGC AGTCTTCCAG
  43_12  TGCAAGAAGA TACGTCTTTT GGGGGCAACC TCGGGCGAGC AGTCTTCCAG
  43_20  TGCAAGAAGA TACGTCTTTT GGGGGCAACC TCGGGCGAGC AGTCTTCCAG
  43_21  TGCAAGAAGA TACGTCTTTT GGGGGCAACC TCGGGCGAGC AGTCTTCCAG
  43_23  TGCAAGAAGA TACGTCCTTT GGGGGCAACC TCGGGCGAGC AGTCTTCCAG
  43_25  TGCAAGAAGA TACGTCTTTT GGGGGCAACC TCGGGCGAGC AGTCTTCCAG
  44_1   TGCAAGAAGA TACGTCTTTT GGGGGCAACC TCGGGCGAGC AGTCTTCCAG
  44_5   TGCAAGAAGA TACGTCTTTT GGGGGCAACC TCGGGCGAGC AGTCTTCCAG
  223_10 TTCAAGAAGA TACGTCTTTT GGGGGCAACC TCGGGCGAGC AGTCTTCCAG
  223_2  TTCAAGAAGA TACGTCTTTT GGGGGCAACC TCGGGCGAGC AGTCTTCCAG
  223_4  TTCAAGAAGA TACGTCTTTT GGGGGCAACC TCGGGCGAGC AGTCTTCCAG
  223_5  TTCAAGAAGA TACGTCTTTT GGGGGCAACC TCGGGCGAGC AGTCTTCCAG
  223_6  TTCAAGAAGA TACGTCTTTT GGGGGCAACC TCGGGCGAGC AGTCTTCCAG
  223_7  TTCAAGAAGA TACGTCTTTT GGGGGCAACC TCGGGCGAGC AGTCTTCCAG
  A3_4   TTCAAGAAGA TACGTCTTTC GGGGGCAACC TCGGGCGAGC AGTCTTCCAG
  A3_5   TTCAAGAAGA TACGTCTTTC GGGGGCAACC TCGGGCGAGC AGTCTTCCAG
  A3_7   TTCAAGAAGA TACGTCTTTC GGGGGCAACC TCGGGCGAGC AGTCTTCCAG
  A3_3   TTCAAGAAGA TACGTCTTTC GGGGGCAACC TCGGGCGAGC AGTCTTCCAG
  42_12  TTCAAGAAGA TACGTCTTTT GGGGGCAACC TCGGGCGAGC AGTCTTCCAG
  AAV1   TGCAAGAAGA TACGTCTTTT GGGGGCAACC TCGGGCGAGC AGTCTTCCAG
  AAV2   TTAAAGAAGA TACGTCTTTT GGGGGCAACC TCGGACGAGC AGTCTTCCAG
  AAV3   TTCAAGAAGA TACGTCTTTT GGGGGCAACC TTGGCAGAGC AGTCTTCCAG
  AAV8   TGCAAGAAGA TACGTCTTTT GGGGGCAACC TCGGGCGAGC AGTCTTCCAG
  AAV9   TGCAAGAAGA TACGTCTTTT GGGGGCAACC TCGGGCGAGC AGTCTTCCAG
  AAV7   TGCAAGAAGA TACGTCATTT GGGGGCAACC TCGGGCGAGC AGTCTTCCAG
  44_2   TGCAAGAAGA TACGTCTTTT GGGGGCAACC TCGGGCGAGC AGTCTTCCAG
```

FIG. 1AAA

```
          2601                                                    2650
 42_2    GCCAAGAAGC GGGTTCTCGA ACCTCTCGGT CTGGTTGAGG AAGGCGCTAA
 42_8    GCCAAGAAGC GGGTTCTCGA ACCTCTCGGT CTGGTTGAGG AAGGCGCTAA
 42_15   GCCAAGAAGC GGGTTCTCGA ACCTCTCGGT CTGGTTGAGG AAGGCGCTAA
 42_5b   GCCAAGAAGC GGGTTCTCGA ACCTCTCGGT CTGGTTGAGG AAGGCGCTAA
 42_1b   GCCAAGAAGC GGGTTCTCGA ACCTCTCGGT CTGGTTGAGG AAGGCGCTAA
 42_13   GCCAAGAAGC GGGTTCTCGA ACCTCTCGGT CTGGTTGAGG AAGGCGCTAA
 42_3a   GCCAAGAAGC GGGTTCTCGA ACCTCTCGGT CTGGTTGAGG AAGGCGCTAA
 42_4    GCCAAGAAGC GGGTTCTCGA ACCTCTCGGT CTGGTTGAGG AAGGCGCTAA
 42_5a   GCCAAGAAGC GGGTTCTCGA ACCTCTCGGT CTGGTTGAGG AAGGCGCTAA
 42_10   GCCAAGAAGC GGGTTCTCGA ACCTCTCGGT CTGGTTGAGG AAGGCGCTAA
 42_3b   GCCAAGAAGC GGGTTCTCGA ACCTCTCGGT CTGGTTGAGG AAGGCGCTAA
 42_11   GCCAAGAAGC GGGTTCTCGA ACCTCTCGGT CTGGTTGAGG AAGGCGCTAA
 42_6b   GCCAAGAAGC GGGTTCTCGA ACCTCTCGGT CTGGTTGAGG AAGGCGCTAA
 43_1    GCCAAGAAGC GGGTTCTCGA ACCTCTCGGT CTGGTTGAGG AAGGCGCTAA
 43_5    GCCAAGAAGC GGGTTCTCGA ACCTCTCGGT CTGGTTGAGG AAGGCGCTAA
 43_12   GCCAAGAAGC GGGTTCTCGA ACCTCTCGGT CTGGTTGAGG AAGGCGCTAA
 43_20   GCCAAGAAGC GGGTTCTCGA ACCTCTCGGT CTGGTTGAGG AAGGCGCTAA
 43_21   GCCAAGAAGC GGGTTCTCGA ACCTCTCGGT CTGGTTGAGG AAGGCGCTAA
 43_23   GCCAAGAAGC GGGTTCTCGA ACCTCTCGGT CTGGTTGAGG AAGGCGCTAA
 43_25   GCCAAGAAGC GGGTTCTCGA ACCTCTCGGT CTGGTTGAGG AAGGCGCTAA
 44_1    GCCAAGAAGC GGGTTCTCGA ACCTCTCGGT CTGGTTGAGG AAGGCGCTAA
 44_5    GCCAAGAAGC GGGTTCTCGA ACCTCTCGGT CTGGTTGAGG AAGGCGCTAA
 223_10  GCCAAAAAGC GGGTTCTCGA ACCTCTTGGT CTGGTTGAGA CGCCAGCTAA
 223_2   GCCAAAAAGC GGGTTCTCGA ACCTCTTGGT CTGGTTGAGA CGCCAGCTAA
 223_4   GCCAAAAAGC GGGTTCTCGA ACCTCTTGGT CTGGTTGAGA CGCCAGCTAA
 223_5   GCCAAAAAGC GGGTTCTCGA ACCTCTTGGT CTGGTTGAGA CGCCAGCTAA
 223_6   GCCAAAAAGC GGGTTCTCGA ACCTCTTGGT CTGGTTGAGA CGCCAGCTAA
 223_7   GCCAAAAAGC GGGTTCTCGA ACCTCTTGGT CTGGTTGAGA CGCCAGCTAA
 A3_4    GCCAAAAAGA GGGTACTCGA GCCTCTTGGT CTGGTTGAGG AAGCTGTTAA
 A3_5    GCCAAAAAGA GGGTACTCGA GCCTCTTGGT CTGGTTGAGG AAGCTGTTAA
 A3_7    GCCAAAAAGA GGGTACTCGA GCCTCTTGGT CTGGTTGAGG AAGCTGTTAA
 A3_3    GCCAAAAAGA GGGTACTCGA GCCTCTTGGT CTGGTTGAGG AAGCTGTTAA
 42_12   GCCAAGAAGC GGGTTCTCGA ACCTCTCGGT CTGGTTGAGG AAGGCGCTAA
 AAV1    GCCAAGAAGC GGGTTCTCGA ACCTCTCGGT CTGGTTGAGG AAGGCGCTAA
 AAV2    GCGAAAAAGA GGGTTCTTGA ACCTCTGGGC CTGGTTGAGG AACCTGTTAA
 AAV3    GCCAAAAAGA GGATCCTTGA GCCTCTTGGT CTGGTTGAGG AAGCAGCTAA
 AAV8    GCCAAGAAGC GGGTTCTCGA ACCTCTCGGT CTGGTTGAGG AAGGCGCTAA
 AAV9    GCCAAGAAGC GGGTTCTCGA ACCTCTCGGT CTGGTTGAGG AAGGCGCTAA
 AAV7    GCCAAGAAGC GGGTTCTCGA ACCTCTCGGT CTGGTTGAGG AAGGCGCTAA
 44_2    GCCAAGAAGC GGGTTCTCGA ACCTCTCGGT CTGGTTGAGG AAGGCGCTAA
```

FIG. 1AAB

```
                    2651                                                              2700
           vp2 start
    42_2   GACGGCTCCT GGAAAGAAGA GACCCATAGA ...ATCCCCC  ..........
    42_8   GACGGCTCCT GGAAAGAAGA GACCGGTAGA GCCATCACCC CAGCGTTCTC
    42_15  GACGGCTCCT GGAAAGAAGA GACCGGTAGA GCCATCACCC CAGCGTTCTC
    42_5b  GACGGCTCCT GGAAAGAAGA GACCGGTAGA GCCATCACCC CAGCGTTCTC
    42_1b  GACGGCTCCT GGAAAGAAGA GACCCATAGA ...ATCCCCC  ..........
    42_13  GACGGCTCCT GGAAAGAAGA GACCCATAGA ...ATCCCCC  ..........
    42_3a  GACGGCTCCT GGAAAGAAGA GACCCATAGA ...ATCCCCC  ..........
    42_4   GACGGCTCCT GGAAAGAAGA GACCCATAGA ...ATCCCCC  ..........
    42_5a  GACGGCTCCT GGAAAGAAGA GACCCATAGA ...ATCCCCC  ..........
    42_10  GACGGCTCCT GGAAAGAAGA GACCCATAGA ...ATCCCCC  ..........
    42_3b  GACGGCTCCT GGAAAGAAGA GACCCATAGA ...ATCCCCC  ..........
    42_11  GACGGCTCCT GGAAAGAAGA GACCCATAGA ...ATCCCCC  ..........
    42_6b  GACGGCTCCT GGAAAGAAGA GACCGGTAGA GCCATCACCC CAGCGTTCTC
    43_1   GACGGCTCCT GGAAAGAAGA GACCGGTAGA GCCATCACCT CAGCGTTCCC
    43_5   GACGGCTCCT GGAAAGAAGA GACCGGTAGA GCCATCACCT CAGCGTTCCC
    43_12  GACGGCTCCT GGAAAGAAGA GACCGGTAGA GCCATCACCT CAGCGTTCCC
    43_20  GACGGCTCCT GGAAAGAAGA GACTGGTAGA GCAGTCGCCA CAAGAG...C
    43_21  GACGGCTCCT GGAAAGAAGA GACCGGTAGA GCAGTCGCCA CAAGAG...C
    43_23  GACGGCTCCT GGAAAGAAGA GACCGGTAGA GCAGTCGCCA CAAGAG...C
    43_25  GACGGCTCCT GGAAAGAAGA GACCGGTAGA GCAGTCGCCA CAAGAG...C
    44_1   GACGGCTCCT GGAAAGAAGA GACCGGTAGA GCCATCACCC CAGCGTTCTC
    44_5   GACGGCTCCT GGAAAGAAGA GACCGGTAGA GCCATCACCC CAGCGTTCTC
    223_10 GACGGCACCT GGAAAGAAGC GACCGGTAGA CTCGCCA...  ..........
    223_2  GACGGCACCT GGAAAGAAGC GACCGGTAGA CTCGCCA...  ..........
    223_4  GACGGCACCT GGAAAGAAGC GACCGGTAGA CTCGCCA...  ..........
    223_5  GACGGCACCT GGAAAGAAGC GACCGGTAGA CTCGCCA...  ..........
    223_6  GACGGCACCT GGAAAGAAGC GACCGGTAGA CTCGCCA...  ..........
    223_7  GACGGCACCT GGAAAGAAGC GACCGGTAGA CTCGCCA...  ..........
    A3_4   GACGGCTCCT GGAAAAAAGA GACCTATAGA GCAGTCTCCT GCAGAA...C
    A3_5   GACGGCTCCT GGAAAAAAGA GACCTATAGA GCAGTCTCCT GCAGAA...C
    A3_7   GACGGCTCCT GGAAAAAAGA GACCTATAGA GCAGTCTCCT GCAGAA...C
    A3_3   GACGGCTCCT GGAAAAAAGA GACCTATAGA GCAGTCTCCT GCAGAA...C
    42_12  GACGGCTCCT GGAAAGAAGA GACCGGTAGA GCCATCACCC CAGCGTTCTC
    AAV1   GACGGCTCCT GGAAAGAAAC GTCCGGTAGA GCAGTCGCCA CAAGAG...C
    AAV2   GACGGCTCCG GGAAAAAAGA GGCCGGTAGA GCACTCTCCT GTGGAG...C
    AAV3   AACGGCTCCT GGAAAGAAGG GGGCTGTAGA TCAGTCTCCT CAGGAA...C
    AAV8   GACGGCTCCT GGAAAGAAGA GACCGGTAGA GCCATCACCC CAGCGTTCTC
    AAV9   GACGGCTCCT GGAAAGAAGA GACCGGTAGA GCCATCACCC CAGCGTTCTC
    AAV7   GACGGCTCCT GCAAAGAAGA GACCGGTAGA GCCGTCACCT CAGCGTTCCC
    44_2   GACGGCTCCT GGAAAGAAGA GACCGGTAGA GCCATCACCC CAGCGTTCTC
           vp2 start
```

FIG. 1AAC

```
            2701                                                    2750
   42_2   ..GACTCCTC CACGGGCATC GGCAAGAAAG GCCAGCAGCC CGCTAAAAAG
   42_8   CAGACTCCTC TACGGGCATC GGCAAGACAG GCCAGCAGCC CGCGAAAAAG
   42_15  CAGACTCCTC TACGGGCATC GGCAAGACAG GCCAGCAGCC CGCGAAAAAG
   42_5b  CAGACTCCTC TACGGGCATC GGCAAGACAG GCCAGCAGCC CGCGAAAAAG
   42_1b  ..GACTCCTC CACGGGCATC GGCAAGAAAG GCCAGCAGCC CGCTAAAAAG
   42_13  ..GACTCCTC CACGGGCATC GGCAAGAAAG GCCAGCAGCC CGCTAAAAAG
   42_3a  ..GACTCCTC CACGGGCATC GGCAAGAAAG GCCAGCAGCC CGCTAAAAAG
   42_4   ..GACTCCTC CACGGGCATC GGCAAGAAAG GCCAGCAGCC CGCTAAAAAG
   42_5a  ..GACTCCTC CACGGGCATC GGCAAGAAAG GCCAGCAGCC CGCTAAAAAG
   42_10  ..GACTCCTC CACGGGCATC GGCAGGAAAG GCCAGCAGCC CGCTAAAAAG
   42_3b  ..GACTCCTC CACGGGCATC GGCAAGAAAG GCCAGCAGCC CGCTAAAAAG
   42_11  ..GACTCCTC CACGGGCATC GGCAAGAAAG GCCAGCAGCC CGCTAAAAAG
   42_6b  CAGACTCCTC TACGGGCATC GGCAAGACAG GCCAGCAGCC CGCGAAAAAG
   43_1   CCGACTCCTC CACGGGCATC GGCAAGAAAG GCCACCAGCC CGCGAGAAAG
   43_5   CCGACTCCTC CACGGGCATC GGCAAGAAAG GCCACCAGCC CGCGAGAAAG
   43_12  CCGACTCCTC CACGGGCATC GGCAAGAAAG GCCACCAGCC CGCGAGAAAG
   43_20  CAGACTCCTC CTCGGGCATC GGCAAGACAG GCCAGCAGCC CGCTAAAAAG
   43_21  CAGACTCCTC CTCGGGCATC GGCAAGACAG GCCAGCAGCC CGCTAAAAAG
   43_23  CAGACTCCTC CTCGGGCATC GGCAAGACAG GCCAGCAGCC CGCTAAAAAG
   43_25  CAGACTCCTC CTCGGGCATC GGCAAGACAG GCCAGCAGCC CGCTAAAAAG
   44_1   CAGACTCCTC TACGGGCATC GGCAAGAAAG GCCAGCAGCC CGCGAAAAAG
   44_5   CAGACTCCTC TACGGGCATC GGCAAGAAAG GCCAGCAGCC CGCGAAAAAG
   223_10 ..GACTCCAC CTCGGGCATC GGCAAGAAAG GCCAGCAGCC CGCGAAAAAG
   223_2  ..GACTCCAC CTCGGGCATC GGCAAGAAAG GCCAGCAGCC CGCGAAAAAG
   223_4  ..GACTCCAC CTCGGGCATC GGCAAGAAAG GCCAGCAGCC CGCGAAAAAG
   223_5  ..GACTCCAC CTCGGGCATC GGCAAGAAAG GCCAGCAGCC CGCGAAAAAG
   223_6  ..GACTCCAC CTCGGGCATC GGCAAGAAAG GCCAGCAGCC CGCGAAAAAG
   223_7  ..GACTCCAC CTCGGGCATC GGCAAGAAAG GCCAGCAGCC CGCGAAAAAG
   A3_4   CGGACTCTTC CTCGGGCATC GGCGAATCAG GCCAGCAGCC CGCTAAGAAA
   A3_5   CGGACTCTTC CTCGGGCATC GGCAAATCAG GCCAGCAGCC CGCTAAGAAA
   A3_7   CGGACTCTTC CTCGGGCATC GGCAAATCAG GCCAGCAGCC CGCTAAGAAA
   A3_3   CGGACTCTTC CTCGGGCATC GGCAAATCAG GCCAGCAGCC CGCTAAGAAA
   42_12  CAGACTCCTC TACGGGCATC GGCAAGACAG GCCAGCAGCC CGCGAAAAAG
   AAV1   CAGACTCCTC CTCGGGCATC GGCAAGACAG GCCAGCAGCC CGCTAAAAAG
   AAV2   CAGACTCCTC CTCGGGAACC GGAAAGGCGG GCCAGCAGCC TGCAAGAAAA
   AAV3   CGGACTCATC ATCTGGTGTT GGCAAATCGG GCAAACAGCC TGCCAGAAAA
   AAV8   CAGACTCCTC TACGGGCATC GGCAAGAAAG GCCAACAGCC CGCCAGAAAA
   AAV9   CAGACTCCTC TACGGGCATC GGCAAGAAAG GCCAACAGCC CGCCAGAAAA
   AAV7   CCGACTCCTC CACGGGCATC GGCAAGAAAG GCCAACAGCC CGCCAGAAAG
   44_2   CAGACTCCTC TACGGGCATC GGCAAGAAAG GCCAGCAGCC CGCGAAAAAG
```

FIG. 1AAD

```
        2751                                                        2800
 42_2   AAGCTCAACT TTGGGCAGAC TGGCGACTCA GAGTCAGTGC CCGACCCCCA
 42_8   AGACTCAACT TTGGGCAGAC TGGCGACTCA GAGTCAGTGC CCGACCCTCA
 42_15  AGACTCAACT TTGGGCAGAC TGGCGACTCA GAGTCAGTGC CCGACCCTCA
 42_5b  AGACTCAACT TTGGGCAGAC TGGCGACTCA GAGTCAGTGC CCGACCCTCA
 42_1b  AGACTCAACT TTGGGCAGAC TGGCGACTCA GAGTCAGTGC CCGACCCTCA
 42_13  AAGCTCAACT TTGGGCAGAC TGGCGACTCA GAGTCAGTGC CCGACCCTCA
 42_3a  AAGCTCAACT TTGGGCAGAC TGGCGACTCA GAGTCAGTGC CCGACCCTCA
 42_4   AAGCTCAACT TTGGGCAGAC TGGCGACTCA GAGTCAGTGC CCGACCCTCA
 42_5a  AAGCTCAACT TTGGGCAGAC TGGCGACTCA GAGTCAGTGC CCGACCCCCA
 42_10  AAGCTCAACT TTGGGCAGAC TGGCGACTCA GAGTCAGTGC CCGACCCTCA
 42_3b  AAGCTCAACT TTGGGCAGAC TGGCGACTCA GAGTCAGTGC CCGACCCTCA
 42_11  AAGCTCAACT TTGGGCAGAC TGGCGACTCA GAGTCAGTGC CCGACCCTCA
 42_6b  AGACTCAACT TTGGGCAGAC TGGCGACTCA GAGTCAGTGC CCGACCCTCA
 43_1   AGACTGAACT TTGGGCAGAC TGGCGACTCG GAGTCAGTCC CCGACCCTCA
 43_5   AGACTGAACT TTGGGCAGAC TGGCGACTCG GAGTCAGTCC CCGACCCTCA
 43_12  AGACTGAACT TTGGGCAGAC TGGCGACTCG GAGTCAGTCC CCGACCCTCA
 43_20  AGACTCAATT TTGGTCAGAC TGGCGACTCA GAGTCAGTCC CCGACCCACA
 43_21  AGACTCAATT TTGGTCAGAC TGGCGACTCA GAGTCAGTCC CCGACCCACA
 43_23  AGACTCAATT TTGGTCAGAC TGGCGACTCA GAGTCAGTCC CCGACCCACA
 43_25  AGACTCAATT TTGGTCAGAC TGGCGACTCA GAGTCAGTCC CCGACCCACA
 44_1   AGACTCAACT TTGGGCAGAC TGGCGACTCA GAGTCAGTGC CCGACCCTCA
 44_5   AGACTCAACT TTGGGCAGAC TGGCGACTCA GAGTCAGTGC CCGACCCTCA
 223_10 AGACTCAACT TTGGGCAGAC TGGCGACTCA GAGTCAGTCC CCGACCCTCA
 223_2  AGACTCAACT TTGGGCAGAC TGGCGACTCA GAGTCAGTCC CCGACCCTCA
 223_4  AGACTCAACT TTGGGCAGAC TGGCGACTCA GAGCCAGTCC CCGACCCTCA
 223_5  AGACTCAACT TTGGGCAGAC TGGCGACTCA GAGCCAGTCC CCGACCCTCA
 223_6  AGACTCAACT TTGGGCAGAC TGGCGACTCA GAGTCAGTCC CCGACCCTCA
 223_7  AGACTCAACT TTGGGCAGAC TGGCGACTCA GAGTCAGTCC CCGACCCTCA
 A3_4   AGACTCAATT TTGGTCAGAC TGGCGACACA GAGTCAGTCC CAGACCCTCA
 A3_5   AGACTCAATT TTGGTCAGAC TGGCGACACA GAGTCAGTCC CAGACCCTCA
 A3_7   AGACTCAATT TTGGTCAGAC TGGCGACACA GAGTCAGTCC CAGACCCTCA
 A3_3   AGACTCAATT TTGGTCAGAC TGGCGACACA GAGTCAGTCC CAGGCCCTCA
 42_12  AGACTCAACT TTGGGCAGAC TGGCGACTCA GAGTCAGTGC CCGACCCTCA
 AAV1   AGACTCAATT TTGGTCAGAC TGGCGACTCA GAGTCAGTCC CCGATCCACA
 AAV2   AGATTGAATT TTGGTCAGAC TGGAGACGCA GACTCAGTAC CTGACCCCCA
 AAV3   AGACTAAATT TCGGTCAGAC TGGAGACTCA GAGTCAGTCC CAGACCCTCA
 AAV8   AGACTCAATT TTGGTCAGAC TGGCGACTCA GAGTCAGTTC CAGACCCTCA
 AAV9   AGACTCAATT TTGGTCAGAC TGGCGACTCA GAGTCAGTTC CAGACCCTCA
 AAV7   AGACTCAATT TCGGTCAGAC TGGCGACTCA GAGTCAGTCC CCGACCCTCA
 44_2   AGACTCAACT TTGGGCAGAC TGGCGACTCA GAGTCAGTGC CCGACCCTCA
```

FIG. 1AAE

```
       2901                                                    2950
                                                              vp3 start
  42_2   ACCTCTCGGA GAACCTCCCG CCGCGCCCTC AGGTCTGGGA TCTGGTACAA
  42_8   ACCAATCGGA GAACCCCCCG CAGGCCCCTC TGGTCTGGGA TCTGGTACAA
  42_15  ACCAATCGGA GAACCCCCCG CAGGCCCCTC TGGTCTGGGA TCTGGTACAA
  42_5b  ACCAATCGGA GAACCCCCCG CAGGCCCCTC TGGTCTGGGA TCTGGTACAA
  42_1b  ACCAATCGGA GAACCCCCCG CAGGCCCCTC TGGTCTGGGA TCTGGCACAA
  42_13  ACCAATCGGA GAACCCCCCG CAGGCCCCTC TGGTCTGGGA TCTGGTACAA
  42_3a  ACCAATCGGA GAACCCCCCG CAGGCCCCTC TGGTCTGGGA TCTGGTACAA
  42_4   ACCAATCGGA GAACCCCCCG CAGGCCCCTC TGGTCTGGGA TCTGGTACAA
  42_5a  ACCTCTCGGA GAACCTCCCG CCGCGCCCTC AGGTCTGGGA TCTGGTACAA
  42_10  ACCAATCGGA GAACCCCCCG CAGGCCCCTC TGGTCTGGGA TCTGGTACAA
  42_3b  ACCAATCGGA GAACCCCCCG CAGGCCCCTC TGGTCTGGGA TCTGGTACAA
  42_11  ACCAATCGGA GAACCCCCCG CAGGCCCCTC TGGTCTGGGA TCTGGTACAA
  42_6b  ACCAATCGGA GAACCCCCCG CAGGCCCCTC TGGTCTGGGA TCTGGTACAA
  43_1   ACCAATCGGA GAACCACCAG CAGGCCCCTC TGGTCTGGGA TCTGGTACAA
  43_5   ACCAATCGGA GAACCACCAG CAGGCCCCTC TGGTCTGGGA TCTGGTACAA
  43_12  ACCAATCGGA GAACCACCAG CAGGCCCCTC TGGTCTGGGA TCTGGTACAA
  43_20  ACCTCTCGGA GAACCTCCAG CAGCCCCCTC AGGTCTGGGA CCTAATACAA
  43_21  ACCTCTCGGA GAACCTCCAG CAGCCCCCTC AGGTCTGGGA CCTAATACAA
  43_23  ACCTCTCGGA GAACCTCCAG CAGCCCCCTC AGGTCTGGGA CCTAATACAA
  43_25  ACCTCTCGGA GAACCTCCAG CAGCCCCCTC AGGTCTGGGA CCTAATACAA
  44_1   ACCAATCGGA GAACCCCCCG CAGGCCCCTC TGGTCTGGGA TCTGGTACAA
  44_5   ACCAATCGGA GAACCCCCCG CAGGCCCCTC TGGTCTGGGA TCTGGTACAA
  223_10 ACCAATCGGA GAACCACCAG CAGGCCCCTC TGGTCTGGGA TCTGGTACAA
  223_2  ACCAATCGGA GAACCACCAG CAGGCCCCTC TGGTCTGGGA TCTGGTACAA
  223_4  ACCAATCGGA GAACCACCAG CAGGCCCCTC TGGTCTGGGA TCTGGTACAA
  223_5  ACCAATCGGA GAACCACCAG CAGGCCCCTC TGGTCTGGGA TCTGGTACAA
  223_6  ACCAATCGGA GAACCACCAG CAGGCCCCTC TGGTCTGGGA TCTGGTACAA
  223_7  ACCAATCGGA GAACCACCAG CAGGCCCCTC TGGTCTGGGA TCTGGTACAA
  A3_4   ACCAATCGGA GAACCCCCCG CAGCCCCCTC TGGTGTGGGA TCTAATACAA
  A3_5   ACCAATCGGA GAACCCCCCG CAGCCCCCTC TGGTGTGGGA TCTAATACAA
  A3_7   ACCAATCGGA GAACCCCCCG CAGCCCCCTC TGGTGTGGGA TCTAATACAA
  A3_3   ACCAATCGGA GAACCCCCCG CAGCCCCCTC TGGTGTGGGA TCTAATACAA
  42_12  ACCAATCGGA GAACCCCCCG CAGGCCCCTC TGGTCTGGGA TCTGGTACAA
  AAV1   ACCTCTCGGA GAACCTCCAG CAACCCCCGC TGCTGTGGGA CCTACTACAA
  AAV2   GCCTCTCGGA CAGCCACCAG CAGCCCCCTC TGGTCTGGGA ACTAATACGA
  AAV3   ACCTCTCGGA GAACCACCAG CAGCCCCCAC AAGTTTGGGA TCTAATACAA
  AAV8   ACCTCTCGGA GAACCTCCAG CAGCGCCCTC TGGTGTGGGA CCTAATACAA
  AAV9   ACCTCTCGGA GAACCTCCAG CAGCGCCCTC TGGTGTGGGA CCTAATACAA
  AAV7   ACCTCTCGGA GAACCTCCAG CAGCGCCCTC TAGTGTGGGA TCTGGTACAG
  44_2   ACCAATCGGA GAACCCCCCG CAGCCCCCTC TGGTCTGGGA TCTGGTACAA
                                                              vp3 start
```

FIG. 1AAF

```
         2851                                                        2900
         vp3 start codon
 42_2    TGGCTGCAGG CGGTGGCGCA CCAATGGCAG ACAATAACGA AGGCGCCGAC
 42_8    TGGCTGCAGG CGGTGGCGCT CCAATGGCAG ACAATAACGA AGGCGCCGAC
 42_15   TGGCTGCAGG CGGTGGCGCT CCAATGGCAG ACAATAACGA AGGCGCCGAC
 42_5b   TGGCTGCAGG CGGTGGCGCT CCAATGGCAG ACAATAACGA AGGCGCCGAC
 42_1b   TGGCTGCAGG CGGTGGCGCT CCAATGGCAG ACAATAACGA AGGCGCCGAC
 42_13   TGGCTGCAGG CGGTGGCGCT CCAATGGCAG ACAATAACGA AGGCGCCGAC
 42_3a   TGGCTGCAGG CGGTGGCGCT CCAATGGCAG ACAATAACGA AGGCGCCGAC
 42_4    TGGCTGCAGG CGGTGGCGCT CCAATGGCAG ACAATAACGA AGGCGCCGAC
 42_5a   TGGCTGCAGG CGGTGGCGCA CCAATGGCAG ACAATAACGA AGGCGCCGAC
 42_10   TGGCTGCAGG CGGTGGCGCT CCAATGGCAG ACAATAACGA AGGCGCCGAC
 42_3b   TGGCTGCAGG CGGTGGCGCT CCAATGGCAG ACAATAACGA AGGCGCCGAC
 42_11   TGGCTGCAGG CGGTGGCGCT CCAATGGCAG ACAATAACGA AGGCGCCGAC
 42_6b   TGGCTGCAGG CGGTGGCGCT CCAATGGCAG ACAATAACGA AGGCGCCGAC
 43_1    TGGCTGCAGG CGGTGGCGCT CCAATGGCAG ACAATAACGA AGGCGCCGAC
 43_5    TGGCTGCAGG CGGTGGCGCT CCAATGGCAG ACAATAACGA AGGCGCCGAC
 43_12   TGGCTGCAGG CGGTGGCGCT CCAATGGCAG ACAATAACGA AGGCGCCGAC
 43_20   TGGCTTCAGG CGGTGGCGCT CCAATGGCAG ACAATAACGA AGGCGCCGAC
 43_21   TGGCTTCAGG CGGTGGCGCT CCAATGGCAG ACAATAACGA AGGCGCCGAC
 43_23   TGGCTTCAGG CGGTGGCGCT CCAATGGCAG ACAATAACGA AGGCGCCGAC
 43_25   TGGCTTCAGG CGGTGGCGCT CCAATGGCAG ACAATAACGA AGGCGCCGAC
 44_1    TGGCTGCAGG CGGTGGCGCT CCAATGGCAG ACAATAACGA AGGCGCCGAC
 44_5    TGGCTGCAGG CGGTGGCGCT CCAATGGCAG ACAATAACGA AGGCGCCGAC
 223_10  TGGCTGCAGG CGGTGGCGCA CCAATGGCTG ACAATAACGA GGGCGCCGAC
 223_2   TGGTTGCAGG CGGTGGCGCA CCAATGGCTG ACAATAACGA GGGCGCCGAC
 223_4   TGGCTGCAGG CGGTGGCGCA CCAATGGCTG ACAATAACGA GGGCGCCGAC
 223_5   TGGCTGCAGG CGGTGGCGCA CCAATGGCTG ACAATAACGA GGGCGCCGAC
 223_6   TGGCTGCAGG CGGTGGCGCA CCAATGGCTG ACAATAGCGA GGGCGCCGAC
 223_7   TGGCTGCAGG CGGTGGCGCA CCAATGGCTG ACAATAACGA GGGCGCCGAC
 A3_4    TGGCTTCAGG CGGTGGGGCA CCAATGGCAG ACGATAACGA AGGCGCCGAC
 A3_5    TGGCTTCAGG CGGTGGGGCA CCAATGGCAG ACAATAACGA AGGCGCCGAC
 A3_7    TGGCTTCAGG CGGTGGGGCA CCAATGGCAG ACAATAACGA AGGCGCCGAC
 A3_3    TGGCTTCAGG CGGTGGGGCA CCAATGGCAG ACAATAACGA AGGCGCCGAC
 42_12   TGGCTGCAGG CGGTGGCGCT CCAATGGCAG ACAATAACGA AGGCGCCGAC
 AAV1    TGGCTTCAGG CGGTGGCGCA CCAATGGCAG ACAATAACGA AGGCGCCGAC
 AAV2    TGGCTACAGG CAGTGGCGCA CCAATGGCAG ACAATAACGA GGGCGCCGAC
 AAV3    TGGCTTCAGG CGGTGGCGCA CCAATGGCAG ACAATAACGA GGGTGCCGAT
 AAV8    TGGCTGCAGG CGGTGGCGCA CCAATGGCAG ACAATAACGA AGGCGCCGAC
 AAV9    TGGCTGCAGG CGGTGGCGCA CCAATGGCAG ACAATAACGA AGGCGCCGAC
 AAV7    TGGCTGCAGG CGGTGGCGCA CCAATGGCAG ACAATAACGA AGGTGCCGAC
 44_2    TGGCTGCAGG CGGTGGCGCT CCAATGGCAG ACAATAACGA AGGCGCCGAC
         vp3 start codon (cont'd)
```

FIG. 1AAG

```
         2901                                              2950
  42_2   GGAGTGGGTA ATGCCTCCGG AAATTGGCAT TGCGATTCCA CATGGCTGGG
  42_8   GGAGTGGGTA GTTCCTCAGG AAATTGGCAT TGCGATTCCA CATGGCTGGG
 42_15   GGAGTGGGTA GTTCCTCAGG AAATTGGCAT TGCGATTCCA CATGGCTGGG
 42_5b   GGAGTGGGTA GTTCCTCAGG AAATTGGCAT TGCGATTCCA CATGGCTGGG
 42_1b   GGAGTGGGTA GTTCCTCAGG AAATTGGCAT TGCGATTCCA CATGGCTGGG
 42_13   GGAGTGGGTA GTTCCTCAGG AAATTGGCAT TGCGATTCCA CATGGCTGGG
 42_3a   GGAGTGGGTA GTTCCTCAGG AAATTGGCAT TGCGATTCCA CATAGCTGGG
  42_4   GGAGTGGGTA ATGCCTCCGG AAATTGGCAT TGCGATTCCA CATGGCTGGG
 42_5a   GGAGTGGGTA ATGCCTCCGG AAATTGGCAT TGCGATTCCA CATGGCTGGG
 42_10   GGAGTGGGTA ATGCCTCCGG AAATTGGCAT TGCGATTCCA CATGGCTGGG
 42_3b   GGAGTGGGTA ATGCCTCCGG AAATTGGCAT TGCGATTCCA CATGGCTGGG
 42_11   GGAGTGGGTA ATGCCTCCGG AAATTGGCAT TGCGATTCCA CATGGCTGGG
 42_6b   GGAGTGGGTA GTTCCTCAGG AAATTGGCAT TGCGATTCCA CATGGCTGGG
  43_1   GGAGTGGGTA GTTCCTCAGG AAATTGGCAT TGCGATTCCA CATGGCTGGG
  43_5   GGAGTGGGTA GTTCCTCAGG AAATTGGCAT TGCGATTCCA CATGGCTGGG
 43_12   GGAGTGGGTA GTTCCTCAGG AAATTGGCAT TGCGATTCCA CATGGCTGGG
 43_20   GGAGTGGGTA ATTCCTCGGG AAATTGGCAT TGCGATTCCA CATGGCTGGG
 43_21   GGAGTGGGTA ATTCCTCGGG AAATTGGCAT TGCGATTCCA CATGGCTGGG
 43_23   GGAGTGGGTA ATTCCTCGGG AAATTGGCAT TGCGATTCCA CATGGCTGGG
 43_25   GGAGTGGGTA ATTCCTCGGG AAATTGGCAT TGCGATTCCA CATGGCTGGG
  44_1   GGAGTGGGTA GTTCCTCAGG AAATTGGCAT TGCGATTCCA CATGGCTGGG
  44_5   GGAGTGGGTA GTTCCTCAGG AAATTGGCAT TGCGATTCCA CATGGCTGGG
 223_10  GGAGTGGGTA ATGCCTCAGG AAATTGGCAT TGCGATTCCA CATGGCTGGG
 223_2   GGAGTGGGTA ATGCCTCAGG AAATTGGCAT TGCGATTCCA CATGGCTGGG
 223_4   GGAGTGGGTA ATGCCTCAGG AAATTGGCAT TGCGATTCCA CACGGCTGGG
 223_5   GGAGTGGGTA ATGCCTCAGG AAATTGGCAT TGCGATTCCA CACGGCTGGG
 223_6   GGAGTGGGTA ATGCCTCAGG AAATTGGCAT TGCGATTCCA CATGGCTGGG
 223_7   GGAGTGGGTA ATGCCTCAGG AAATTGGCAT TGCGATTCCA CATGGCTGGG
   A3_4  GGAGTGGGTA ATTCCTCGGG AAATTGGCAT TGCGATTCCA CATGGATGGG
   A3_5  GGAGTGGGTA ATTCCTCGGG AAATTGGCAT TGCGATTCCA CATGGATGGG
   A3_7  GGAGTGGGTA ATTCCTCGGG AAATTGGCAT TGCGATTCCA CATGGATGGG
   A3_3  GGAGTGGGTA ATTCCTCGGG AAATTGGCAT TGCGATTCCA CATGGATGGG
  42_12  GGAGTGGGTA GTTCCTCAGG AAATTGGCAT TGCGATTCCA CATGGCTGGG
   AAV1  GGAGTGGGTA ATGCCTCAGG AAATTGGCAT TGCGATTCCA CATGGCTGGG
   AAV2  GGAGTGGGTA ATTCCTCCGG AAATTGGCAT TGCGATTCCA CATGGATGGG
   AAV3  GGAGTGGGTA ATTCCTCAGG AAATTGGCAT TGCGATTCCC AATGGCTGGG
   AAV8  GGAGTGGGTA GTTCCTCGGG AAATTGGCAT TGCGATTCCA CATGGCTGGG
   AAV9  GGAGTGGGTA ATTCCTCGGG AAATTGGCAT TGCGATTCCA CATGGCTGGG
   AAV7  GGAGTGGGTA ATGCCTCAGG AAATTGGCAT TGCGATTCCA CATGGCTGGG
  AAV10         GGTA ATTCCTCCGG AAATTGGCAT TGCGATTCCA CATGGCTGGG
  AAV11         GGTA ATTCCTCCGG AAATTGGCAT TGCGATTCCA CATGGCTGGG
  AAV12         GGTA ATTCCTCCGG AAATTGGCAT TGCGATTCCA CATGGCTGGG
   44_2  GGAGTGGGTA GTTCCTCAGG AAATTGGCAT TGCGATTCCA CATGGCTGGG
```

FIG. 1AAH

```
          2951                                                    3000
   42_2   CGACAGAGTC ATCACCACCA GCACCCGCAC CTGGGCCCTG CCCACCTACA
   42_8   CGACAGAGTC ATCACCACCA GCACCCGAAC CTGGGCCCTC CCCACCTACA
  42_15   CGACAGAGTC ATCACCACCA GCACCCGAAC CTGGGCCCTC CCCACCTACA
  42_5b   CGACAGAGTC ATCACCACCA GCACCCGAAC CTGGGCCCTC CCCACCTACA
  42_1b   CGACAGAGTC ATCACCACCA GCACCCGAAC CTGGGCCCTC CCCACCTACA
  42_13   CGACAGAGTC ATCACCACCA GCACCCGAAC CTGGGCCCTC CCCACCTACA
  42_3a   CGACAGAGTC ATCACCACCA GCACCCGAAC CTGGGCCCTC CCCACCTACA
   42_4   CGACAGAGTC ATCACCACCA GCACCCGCAC CTGGGCCCTG CCCACCTACA
  42_5a   CGACAGAGTC ATCACCACCA GCACCCGCAC CTGGGCCCTG CCCACCTACA
  42_10   CGACAGAGTC ATCACCACCA GCACCCGCAC CTGGGCCCTG CCCACCTACA
  42_3b   CGACAGAGTC ATCACCACCA GCACCCGCAC CTGGGCCCTG CCCACCTACA
  42_11   CGACAGAGTC ATCACCACCA GCACCCGCAC CTGGGCCCTG CCCACCTACA
  42_6b   CGACAGAGTC ATCACCACCA GCACCCGAAC CTGGGCCCTC CCCACCTACA
   43_1   CGACAGAGTC ATCACCACCA GCACCCGAAC CTGGGCCCTG CCCACCTACA
   43_5   CGACAGAGTC ATCACCACCA GCACCCGAAC CTGGGCCCTG CCCACCTACA
  43_12   CGACAGAGTC ATCACCACCA GCACCCGAAC CTGGGCCCTG CCCACCTACA
  43_20   GGACAGAGTC ATCACCACCA GCACCCGAAC CTGGGCCCTG CCCACCTACA
  43_21   GGACAGAGTC ATCACCACCA GCACCCGAAC CTGGGCCCTG CCCACCTACA
  43_23   GGACAGAGTC ATCACCACCA GCACCCGAAC CTGGGCCCTG CCCACCTACA
  43_25   GGACAGAGTC ATCACCACCA GCACCCGAAC CTGGGCCCTG CCCACCTACA
   44_1   CGACAGAGTC ATCACCACCA GCACCCGAAC CTGGGCCCTC CCCACCTACA
   44_5   CGACAGAGTC ATCACCACCA GCACCCGAAC CTGGGCCCTC CCCACCTACA
 223_10   CGACAGAGTC ATCACCACCA GCACCCGAAC CTGGGCCCTG CCCACCTACA
  223_2   CGACAGAGTC ATCACCACCA GCACCCGAAC CTGGGCCCTG CCCACCTACA
  223_4   CGACAGAGTC ATCACCACCA GCACCCGAAC CTGGGCCCTG CCCACCTACA
  223_5   CGACAGAGTC ATCACCACCA GCACCCGAAC CTGGGCCCTG CCCACCTACA
  223_6   CGACAGAGTC ATCACCACCA GCACCCGAAC CTGGGCCCTG CCCACCTACA
  223_7   CGACAGAGTC ATCACCACCA GCACCCGAAC CTGGGCCCTG CCCACCTACA
   A3_4   CGACAGAGTT ATCACCACCA GCACAAGAAC CTGGGCCCTC CCCACCTACA
   A3_5   CGACAGAGTT ATCACCACCA GCACAAGAAC CTGGGCCCTC CCCACCTACA
   A3_7   CGACAGAGTT ATCACCACCA GCACAAGAAC CTGGGCCCTC CCCACCTACA
   A3_3   CGACAGAGTT ATCACCACCA GCACAAGAAC CTGGGCCCTC CCCACCTACA
  42_12   CGACAGAGTC ATCACCACCA GCACCCGAAC CTGGGCCCTC CCCACCTACA
   AAV1   CGACAGAGTC ATCACCACCA GCACCCGCAC CTGGGCCTTG CCCACCTACA
   AAV2   CGACAGAGTC ATCACCACCA GCACCCGAAC CTGGGCCCTG CCCACCTACA
   AAV3   CGACAGAGTC ATCACCACCA GCACCAGAAC CTGGGCCCTG CCCACTTACA
   AAV8   CGACAGAGTC ATCACCACCA GCACCCGAAC CTGGGCCCTG CCCACCTACA
   AAV9   GGACAGAGTC ATCACCACCA GCACCCGAAC CTGGGCATTG CCCACCTACA
   AAV7   CGACAGAGTC ATTACCACCA GCACCCGAAC CTGGGCCCTG CCCACCTACA
  AAV10   CGACAGAGTC ATCACCACCA GCACCCGAAC CTGGGTCCTG CCCACCTACA
  AAV11   CGACAGAGTC ATCACCACCA GCACCCGAAC CTGGGCCCTG CCAACCTACA
  AAV12   CGACCGAGTC ATTACCACCA GCACCCGGAC TTGGGCCCTG CCCACCTACA
   44_2   CGACAGAGTC ATCACCACCA GCACCCGAAC CTGGGCCCTC CCCACCTACA
```

FIG. 1AAI

```
            3001                                              3050
   42_2    ACAACCACCT CTACAAGCAG ATATCAA..G TCAGAGCGGG GCT....ACC
   42_8    ACAACCACCT CTACAAGCAA ATCTCCAACG GGACATCGGG AGGAAGCACC
   42_15   ACAACCACCT CTACAAGCAA ATCTCCAACG GGACATCGGG AGGAAGCACC
   42_5b   ACAACCACCT CTACAAGCAA ATCTCCAACG GGACATCGGG AGGAAGCACC
   42_1b   ACAACCACCT CTACAAGCAA ATCTCCAACG GGACATCGGG AGGAAGCACC
   42_13   ACAACCACCT CTACAAGCAA ATCTCCAACG GGACATCGGG AGGAAGCACC
   42_3a   ACAACCACCT CTACAAGCAA ATCTCCAACG GGACATCGGG AGGAAGCACC
   42_4    ACAACCACCT CTACAAGCAG ATATCAA... .GTCAGAGCG GGGC..TACC
   42_5a   ACAACCACCT CTACAAGCAG ATATCAA... .GTCAGAGCG GGGC..TACC
   42_10   ACAACCACCT CTACAAGCAG ATATCAA..G TCAGAGCGGG GCTA....CC
   42_3b   ACAACCACCT CTACAAGCAG ATATCAA..G TCAGAGCGGG GCTA....CC
   42_11   ACAACCACCT CTACAAGCAG ATATCAA..G TCAGAGCGGG GCTA....CC
   42_6b   ACAACCACCT CTACAAGCAA ATCTCCAACG GGACATCGGG AGGAAGCACC
   43_1    ACAACCATCT CTACAAGCAA ATCTCCAACG GGACATCGGG AGGAAGCACT
   43_5    ACAACCATCT CTACAAGCAA ATCTCCAACG GGACATCGGG AGGAAGCACT
   43_12   ACAACCATCT CTACAAGCAA ATCTCCAACG GGACATCGGG AGGAAGCACT
   43_20   ACAACCACCT CTACAAGCAA ATCTCCAACG GCACCTCGGG AGGAAGCACC
   43_21   ACAACCACCT CTACAAGCAA ATCTCCAACG GCACCTCGGG AGGAAGCACC
   43_23   ACAACCACCT CTACAAGCAA ATCTCCAACG GCACCTCGGG AGGAAGCACC
   43_25   ACAACCACCT CTACAAGCAA ATCTCCAACG GCACCTCGGG AGGAAGCACC
   44_1    ACAACCACCT CTACAAGCAA ATCTCCAACG GGACTTCGGG AGGAAGCACC
   44_5    ACAACCACCT CTACAAGCAA ATCTCCAACG GGACTTCGGG AGGAAGCACC
  223_10   ACAACCACCT CTACAAGCAA ATCTCCAGTC AGTCAGCAGG GAG...CACC
  223_2    ACAACCACCT CTACAAGCAA ATCTCCAGTC AGTCAGCAGG GAG...CACC
  223_4    ACAACCACCT CTACAAGCAA ATCTCCAGTC AGTCAGCAGG GAG...CACC
  223_5    ACAACCACCT CTACAAGCAA ATCTCCAGTC AGTCAGCAGG GAG...CACC
  223_6    ACAACCACCT CTACAAGCAA ATCTCCAGTC AGTCAGCAGG GAG...CACC
  223_7    ACAACCACCT CTACAAGCAA ATCTCCAGTC AGTCAGCAGG GAG...CACC
   A3_4    ATAATCACCT CTACAAGCAA ATCTCCA... GCGAATCGGG AGC...CACC
   A3_5    ATAATCACCT CTACAAGCAA ATCTCCA... GCGAATCGGG AGC...CACC
   A3_7    ATAATCGCCT CTACAAGCAA ATCTCCA... GCGAATCGGG AGC...CACC
   A3_3    ATAATCACCT CTACAAGCAA ATCTCCA... GCGAATCGGG AGC...CACC
   42_12   ACAACCACCT CTACAAGCAA ATCTCCAACG GGACATCGGG AGGAAGCACC
   AAV1    ATAACCACCT CTACAAGCAA ATCTCCAGTG CTTCAACGGG .GG..CCAGC
   AAV2    ACAACCACCT CTACAAACAA ATTTCCA... GCCAATCAGG AGC...CTCG
   AAV3    ACAACCATCT CTACAAGCAA ATCTCCA... GCCAATCAGG AGC...TTCA
   AAV8    ACAACCACCT CTACAAGCAA ATCTCCAACG GCACATCGGG AGGAGCCACC
   AAV9    ACAACCACCT CTACAAGCAA ATCTCCAATG GAACATCGGG AGGAAGCACC
   AAV7    ACAACCACCT CTACAAGCAA ATCTCCAGTG AAACTGCAGG TAG...TACC
   AAV10   ACAACCACAT CTACAAGCAA ATCTCCAGCG AGACAGGAGC CACCAACGAC
   AAV11   ACAACCACCT CTACAAACAA ATCTCCAGCG CTTCAACGGG GGCCAGCAAC
   AAV12   ACAACCACCT CTACAAGCAA ATCTCCAGCC AATCGGGTGC CACCAACGAC
   44_2    ACAACCACCT CTACAAGCAA ATCTCCAACG GGACTTCGGG AGGAAGCACC
```

FIG. 1AAJ

```
            3051                                                        3100
    42_2    AACGACAACC  ACTTCTTCGG  CTACAGCACC  CCCTGGGGCT  ATTTTGACTT
    42_8    AACGACAACA  CCTACTTCGG  CTACAGCACC  CCCTGGGGGT  ATTTTGACTT
    42_15   AACGACAACA  CCTACTTCGG  CTACAGCACC  CCCTGGGGGT  ATTTTGACTT
    42_5b   AACGACAACA  CCTACTTCGG  CTACAGCACC  CCCTGGGGGT  ATTTTGACTT
    42_1b   AACGACAACA  CCTACTTCGG  CTACAGCACC  CCCTGGGGGT  ATTTTGACTT
    42_13   AACGACAACA  CCTACTTCGG  CTACAGCACC  CCCTGGGGGT  ATTTTGACTT
    42_3a   AACGACAACA  CCTACTTCGG  CTACAGCACC  CCCTGGGGGT  ATTTTGACTT
    42_4    AACGACAACC  ACTTCTTCGG  CTACAGCACC  CCCTGGGGCT  ATTTTGACTT
    42_5a   AACGACAACC  ACTTCTTCGG  CTACAGCACC  CCCTGGGGCT  ATTTTGACTT
    42_10   AACGACAACC  ACTTCTTCGG  CTACAGCACC  CCCTGGGGCT  ATTTTGACTT
    42_3b   AACGACAACC  ACTTCTTCGG  CTACAGCACC  CCCTGGGGCT  ATTTTGACTT
    42_11   AACGACAACC  ACTTCTTCGG  CTACAGCACC  CCCTGGGGCT  ATTTTGACTT
    42_6b   AACGACAACA  CCTACTTCGG  CTACAGCACC  CCCTGGGGGT  ATTTTGACTT
    43_1    AACGACAACA  CCTACTTTGG  CTACAGCACC  CCCTGGGGGT  ATTTTGACTT
    43_5    AACGACAACA  CCTACTTTGG  CTACAGCACC  CCCTGGGGGT  ATTTTGACTT
    43_12   AACGACAACA  CCTACTTTGG  CTACAGCACC  CCCTGGGGGT  ATTTTGACTT
    43_20   AACGACAACA  CCTATTTTGG  CTACAGCACC  CCCTGGGGGT  ATTTTGACTT
    43_21   AACGACAACA  CCTATTTTGG  CTACAGCACC  CCCTGGGGGT  ATTTTGACTT
    43_23   AACGACAACA  CCTATTTTGG  CTACAGCACC  CCCTGGGGGT  ATTTTGACTT
    43_25   AACGACAACA  CCTATTTTGG  CTACAGCACC  CCCTGGGGGT  ATTTTGACTT
    44_1    AACGACAACA  CCTACTTCGG  CTACAGCACC  CCCTGGGGGT  ATTTTGACTT
    44_5    AACGACAACA  CCTACTTCGG  CTACAGCACC  CCCTGGGGGT  ATTTTGACTT
   223_10   AACGATAACG  TCTATTTCGG  CTACAGCACC  CCCTGGGGGT  ATTTTGACTT
   223_2    AACGATAACG  TCTATTTCGG  CTACAGCACC  CCCTGGGGGT  ATTTTGACTT
   223_4    AACGATAACG  TCTATTTCGG  CTACAGCACC  CCCTGGGGGT  ATTTTGACTT
   223_5    AACGATAACG  TCTATTTCGG  CTACAGCACC  CCCTGGGGGT  ATTTTGACTT
   223_6    AACGATAACG  TCTATTTCGG  CTACAGCACC  CCCTGGGGGT  ATTTTGACTT
   223_7    AACGATAACG  TCTATTTCGG  CTACAGCACC  CCCTGGGGGT  ATTTTGACTT
    A3_4    AACGACAACC  ACTACTTCGG  CTACAGCACC  CCCTGGGGGT  ATTTTGACTT
    A3_5    AACGACAACC  ACTACTTCGG  CTACAGCACC  CCCTGGGGGT  ATTTTGACTT
    A3_7    AACGACAACC  ACTACTTCGG  CTACAGCACC  CCCTGGGGGT  ATTTTGACTT
    A3_3    AACGACAACC  ACTACTTCGG  CTACAGCACC  CCCTGGGGGT  ATTTTGACTT
    42_12   AACGACAACA  CCTACTTCGG  CTACAGCACC  CCCTGGGGGT  ATTTTGACTT
    AAV1    AACGACAACC  ACTACTTCGG  CTACAGCACC  CCCTGGGGGT  ATTTTGATTT
    AAV2    AACGACAATC  ACTACTTTGG  CTACAGCACC  CCTTGGGGGT  ATTTTGACTT
    AAV3    AACGACAACC  ACTACTTTGG  CTACAGCACC  CCTTGGGGGT  ATTTTGACTT
    AAV8    AACGACAACA  CCTACTTCGG  CTACAGCACC  CCCTGGGGGT  ATTTTGACTT
    AAV9    AACGACAACA  CCTACTTTGG  CTACAGCACC  CCCTGGGGGT  ATTTTGACTT
    AAV7    AACGACAACA  CCTACTTCGG  CTACAGCACC  CCCTGGGGGT  ATTTTGACTT
    AAV10   AACCACTACT  TCGGCTACAG  C......ACC  CCCTGGGGGT  ATTTTGACTT
    AAV11   ...GACAACC  ACTACTTTGG  CTACAGCACC  CCCTGGGGGT  ATTTTGACTT
    AAV12   AACCACTACT  TCGGCTA...  ...CAGCACC  CCTTGGGGGT  ATTTTGATTT
    44_2    AACGACAACA  CCTACTTCGG  CTACAGCACC  CCCTGGGGGT  ATTTTGACTT
```

FIG. 1AAK

```
          3101                                                    3150
   42_2   TAACAGATTC CACTGCCACT TCTCACCACG TGACTGGCAG CGACTCATCA
   42_8   TAACAGATTC CACTGCCACT TCTCACCACG TGACTGGCAG CGACTCATCA
  42_15   TAACAGATTC CACTGCCACT TCTCACCACG TGACTGGCAG CGACTCATCA
  42_5b   TAACAGATTC CACTGCCACT TCTCACCACG TGACTGGCAG CGACTCATCA
  42_1b   TAACAGATTC CACTGCCACT TCTCACCACG TGACTGGCAG CGACTCATCA
  42_13   TAACAGATTC CACTGCCACT TCTCACCACG TGACTGGCAG CGACTCATCA
  42_3a   TAACAGATTC CACTGCCACT TCTCACCACG TGACTGGCAG CGACTCATCA
   42_4   CAACAGATTC CACTGCCACT TCTCATCACG TGACTGGCAG CGACTCATCA
  42_5a   CAACAGATTC CACTGCCACT TCTCACCACG TGACTGGCAG CGACTCATCA
  42_10   CAACAGATTC CACTGCCACT TCTCACCACG TGACTGGCAG CGACTCATCA
  42_3b   CAACAGATTC CACTGCCACT TCTCACCACG TGACTGGCAG CGACTCATCA
  42_11   CAACAGATTC CACTGCCACT TCTCACCACG TGACTGGCAG CGACTCATCA
  42_6b   TAACAGATTC CACTGCCACT TCTCACCACG TGACTGGCAG CGACTCATCA
   43_1   CAACAGATTC CACTGCCACT TCTCACCACG TGACTGGCAG CGACTCATCA
   43_5   CAACAGATTC CACTGCCACT TCTCACCACG TGACTGGCAG CGACTCATCA
  43_12   CAACAGATTC CACTGCCACT TCTCACCACG TGACTGGCAG CGACTCATCA
  43_20   CAACAGATTC CACTGTCACT TTTCACCACG TGACTGGCAA CGACTCATCA
  43_21   CAACAGATTC CACTGTCACT TTTCACCACG TGACTGGCAA CGACTCATCA
  43_23   CAACAGATTC CACTGTCACT TTTCACCACG TGACTGGCAA CGACTCATCA
  43_25   CAACAGATTC CACTGTCACT TTTCACCACG TGACTGGCAA CGACTCATCA
   44_1   TAACAGATTC CACTGCCACT TCTCACCACG TGACTGGCAG CGACTCATCA
   44_5   TAACAGATTC CACTGCCACT TCTCACCACG TGACTGGCAG CGACTCATCA
 223_10   CAACAGATTC CATTGCCACT TCTCACCACG TGACTGGCAG CGACTTATCA
  223_2   CAACAGATTC CATTGCCACT TCTCACCACG TGACTGGCAG CGACTTATCA
  223_4   CAACAGATTC CATTGCCACT TCTCACCACG TGACTGGCAG CGACTTATCA
  223_5   CAACAGATTC CATTGCCACT TCTCACCACG TGACTGGCAG CGACTTATCA
  223_6   CAACAGATTC CATTGCCACT TCTCACCACG TGACTGGCAG CGACTTATCA
  223_7   CAACAGATTC CATTGCCACT TCTCACCACG TGACTGGCAG CGACTTATCA
   A3_4   TAACAGATTC CACTGTCACT TCTCACCACG TGACTGGCAG CGACTCATCA
   A3_5   TAACAGATTC CACTGTCACT TCTCACCACG TGACTGGCAG CGACTCATCA
   A3_7   TAACAGATTC CACTGTCACT TCTCACCACG TGACTGGCAG CGACTCATCA
   A3_3   TAACAGATTC CACTGTCACT TCTCACCACG TGACTGGCAG CGACTCATCA
  42_12   TAACAGATTC CACTGCCACT TCTCACCACG TGACTGGCAG CGACTCATCA
   AAV1   CAACAGATTC CACTGCCACT TTTCACCACG TGACTGGCAG CGACTCATCA
   AAV2   CAACAGATTC CACTGCCACT TTTCACCACG TGACTGGCAA AGACTCATCA
   AAV3   TAACAGATTC CACTGCCACT TCTCACCACG TGACTGGCAG CGACTCATTA
   AAV8   TAACAGATTC CACTGCCACT TTTCACCACG TGACTGGCAG CGACTCATCA
   AAV9   CAACAGATTC CACTGCCACT TCTCACCACG TGACTGGCAG CGACTCATCA
   AAV7   TAACAGATTC CACTGCCACT TCTCACCACG TGACTGGCAG CGACTCATCA
  AAV10   TAACAGATTC CACTGCCACT TTTCACCACG TGACTGGCAG CGACTCATCA
  AAV11   TAACAGATTC CACTGCCACT TCTCACCACG TGACTGGCAG CGACTCATCA
  AAV12   CAACAGATTC CACTGCCATT TCTCACCACG TGACTGGCAG CGACTCATCA
   44_2   TAACAGATTC CACTGCCACT TCTCACCACG TGACTGGCAG CGACTCATCA
```

FIG. 1AAL

```
          3151                                                    3200
  42_2    ACAACAACTG GGGATTCCGG CCCAGAAAGC TGCGGTTCAA GTTGTTCAAC
  42_8    ACAACAACTG GGGATTCCGG CCCAAGAGAC TCAACTTCAA GCTCTTCAAC
  42_15   ACAACAACTG GGGATTCCGG CCCAAGAGAC TCAACTTCAA GCTCTTCAAC
  42_5b   ACAACAACTG GGGATTCCGG CCCAAGAGAC TCAACTTCAA GCTCTTCAAC
  42_1b   ACAACAACTG GGGATTCCGG CCCAAGAGAC TCAACTTCAA GCTCTTCAAC
  42_13   ACAACAACTG GGGATTCCGG CCCAAGAGAC TCAACTTCAA GCTCTTCAAC
  42_3a   ACAACAGCTG GGGATTCCGG CCCAAGAGAC TCAACTTCAA GCTCTTCAAC
  42_4    ACAACAACTG GGGATTCCGG CCCAAGAGAC TCAACTTCAA GCTCTTCAAC
  42_5a   ACAACAACCG GGGATTCCGG CCCAGAAAGC TGCGGTTCAA GTTGTTCAAC
  42_10   ACAACAACTG GGGATTCCGG CCCAGAAAGC TGCGGTTCAA GTTGTTCAAC
  42_3b   ACAACAACTG GGGATTCCGG CCCAGAAAGC TGCGGTTCAA GTTGTTCAAC
  42_11   ACAACAACTG GGGATTCCGG CCCAGAAAGC TGCGGTTCAA GTTGTTCAAC
  42_6b   ACAACAACTG GGGATTCCGG CCCAGAAAGC TGCGGTTCAA GTTGTTCAAC
  43_1    ACAATAACTG GGGATTCCGG CCCAAGAGAC TCAACTTCAA GCTCTTCAAC
  43_5    ACAATAACTG GGGATTCCGG CCCAAGAGAC TCAACTTCAA GCTCTTCAAC
  43_12   ACAATAACTG GGGATTCCGG CCCAAGAGAC TCAACTTCAA GCTCTTCAAC
  43_20   ACAACAATTG GGGATTCCGG CCCAAAAGAC TCAACTTCAA GCTGTTCAAC
  43_21   ACAACAATTG GGGATTCCGG CCCAAAAGAC TCAACTTCAA GCTGTTCAAC
  43_23   ACAACAATTG GGGATTCCGG CCCAAAAGAC TCAACTTCAA GCTGTTCAAC
  43_25   ACAACAATTG GGGATTCCGG CCCAAAAGAC TCAACTTCAA GCTGTTCAAC
  44_1    ACAACAACTG GGGATTCCGG CCCAAGAGAC TCAACTTCAA GCTCTTCAAC
  44_5    ACAACAACTG GGGATTCCGG CCCAAGAGAC CCAACTTCAA GCTCTTCAAC
  223_10  ACAACAACTG GGGATTCCGG CCCAAGAAGC TCAACTTCAA GCTCTTCAAC
  223_2   ACAACAACTG GGGATTCCGG CCCAAGAAGC TCAACTTCAA GCTCTTCAAC
  223_4   ACAACAACTG GGGATTCCGG CCCAAGAAGC TCAACTTCAA GCTCTTCAAC
  223_5   ACAACAACTG GGGATTCCGG CCCAAGAAGC TCAACTTCAA GCTCTTCAAC
  223_6   ACAACAACTG GGGATTCCGG CCCAAGAAGC TCAACTTCAA GCTCTTCAAC
  223_7   ACAACAACTG GGGATTCCGG CCCAAGAAGC TCAACTTCAA GCTCTTCAAC
  A3_4    ACAACAACTG GGGATTTAGA CCCAAGAAAC TCAATTTCAA GCTCTTCAAC
  A3_5    ATAACAACTG GGGATTTAGA CCCAAGAAAC TCAATTTCAA GCTCTTCAAC
  A3_7    ACAACAACTG GGGATTTAGA CCCAAGAAAC TCAATTTCAA GCTCTTCAAC
  A3_3    ACAACAACTG GGGATTTAGA CCCAAGAAAC TCAATTTCAA GCTCTTCAAC
  42_12   ACAACAACTG GGGATTCCGG CCCAAGAGAC TCAACTTCAA GCTCTTCAAC
  AAV1    ACAACAATTG GGGATTCCGG CCCAAGAGAC TCAACTTCAA ACTCTTCAAC
  AAV2    ACAACAACTG GGGATTCCGA CCCAAGAGAC TCAACTTCAA GCTCTTTAAC
  AAV3    ACAACAACTG GGGATTCCGG CCCAAGAAAC TCAGCTTCAA GCTCTTCAAC
  AAV8    ACAACAACTG GGGATTCCGG CCCAAGAGAC TCAGCTTCAA GCTCTTCAAC
  AAV9    ACAACAACTG GGGATTCCGG CCAAAGAGAC TCAACTTCAA GCTGTTCAAC
  AAV7    ACAACAACTG GGGATTCCGG CCCAAGAAGC TGCGGTTCAA GCTCTTCAAC
  AAV10   ACAACAACTG GGGATTC
  AAV11   ACAACAACTG GGGATTC
  AAV12   ACAACAACTG GGGATTC
  44_2    ACAACAACTG GGGATTCCGG CCCAAGAGAC TCAACTTCAA GCTCTTCAAC
```

FIG. 1AAM

|        | 3201       |            |            |            | 3250       |
|--------|------------|------------|------------|------------|------------|
| 42_2   | ATCCAGGTCA | AGGAGGTCAC | GACGAACGAC | GGCGTTACGA | CCATCGCTAA |
| 42_8   | ATCCAGGTCA | AGGAGGTCAC | GCAGAATGAA | GGCACCAAGA | CCATCGCCAA |
| 42_15  | ATCCAGGTCA | AGGAGGTCAC | GCAGAATGAA | GGCACCAAGA | CCATCGCCAA |
| 42_5b  | ATCCAGGTCA | AGGAGGTCAC | GCAGAATGAA | GGCACCAAGA | CCATCGCCAA |
| 42_1b  | ATCCAGGTCA | AGGAGGTCAC | GCAGAATGAA | GGCACCAAGA | CCATCGCCAA |
| 42_13  | ATCCAGGTCA | AGGAGGTCAC | GCAGAATGAA | GGCACCAAGA | CCATCGCCAA |
| 42_3a  | ATCCAGGTCA | AGGAGGTCAC | GCAGAATGAA | GGCACCAAGA | CCATCGCCAA |
| 42_4   | ATCCAGGTCA | AGGAGGTCAC | GCAGAATGAA | GGCACCAAGA | CCATCGCCAA |
| 42_5a  | ATCCAGGTCA | AGGAGGTCAC | GACGAACGAC | GGCGTTACGA | CCATCGCTAA |
| 42_10  | ATCCAGGTCA | AGGAGGTCAC | GACGAACGAC | GGCGTTACGA | CCATCGCCAA |
| 42_3b  | ATCCAGGTCA | AGGAGGTCAC | GACGAACGAC | GGCGTTACGA | CCATCGCTAA |
| 42_11  | ATCCAGGTCA | AGGAGGTCAC | GACGAACGAC | GGCGTTACGA | CCATCGCTAA |
| 42_6b  | ATCCAGGTCA | AGGAGGTCAC | GACGGACGAC | GGCGTTACGA | CCATCGCTAA |
| 43_1   | ATCCAGGTCA | AGGAGGTCAC | GCAGAATGAA | GGCACCAAGA | CCATCGCCAA |
| 43_5   | ATCCAGGTCA | AGGAGGTCAC | GCAGAATGAA | GGCACCAAGA | CCATCGCCAA |
| 43_12  | ATCCAGGTCA | AGGAGGTCAC | GCAGAATGAA | GGCACCAAGA | CCATCGCCAA |
| 43_20  | ATCCAGGTCA | AGGAAGTCAC | GACGAACGAA | GGCACCAAGA | CCATCGCCAA |
| 43_21  | ATCCAGGTCA | AGGAAGTCAC | GACGAACGAA | GGCACCAAGA | CCATCGCCAA |
| 43_23  | ATCCAGGTCA | AGGAAGTCAC | GACGAACGAA | GGCACCAAGA | CCATCGCCAA |
| 43_25  | ATCCAGGTCA | AGGAAGTCAC | GACGAACGAA | GGCACCAAGA | CCATCGCCAA |
| 44_1   | ATCCAGGTCA | AGGAGGTCAC | GCAGAATGAA | GGCACCAAGA | CCATCGCCAA |
| 44_5   | ATCCAGGTCA | AGGAGGTCAC | GCAGAATGAA | GGCACCAAGA | CCATCGCCAA |
| 223_10 | ATCCAGGTCA | AGGAGGTCAC | GACGAATGAC | GGTGTCACAA | CCATCGCTAA |
| 223_2  | ATCCAGGTCA | AGGAGGTCAC | GACGAATGAC | GGTGTCACAA | CCATCGCTAA |
| 223_4  | ATCCAGGTCA | AGGAGGTCAC | GACGAATGAC | GGCGTCACAA | CCATCGCTAA |
| 223_5  | ATCCAGGTCA | AGGAGGTCAC | GACGAATGAC | GGCGTCACAA | CCATCGCTAA |
| 223_6  | ATCCAGGTCA | AGGAGGTCAC | GACGAATGAC | GGTGTCACAA | CCATCGCTAA |
| 223_7  | ATCCAGGTCA | AGGAGGTCAC | GACGAATGAC | GGCGTCACAA | CCATCGCTAA |
| A3_4   | ATCCAAGTCA | AGGAGGTCAC | GCAGAATGAT | GGAACCACGA | CCATCGCCAA |
| A3_5   | ATCCAAGTCA | AGGAGGTCAC | GCAGAATGAT | GGAACCACGA | CCATCGCCAA |
| A3_7   | ATCCAAGTCA | AGGAGGTCAC | GCAGAATGAT | GGAACCACGA | CCATCGCCAA |
| A3_3   | ATCCAAGTCA | AGGAGGTCAC | GCAGAATGAT | GGAACCACGA | CCATCGCCAA |
| 42_12  | ATCCAGGTCA | AGGAGGTCAC | GCAGAATGAA | GGCACCAAGA | CCATCGCCAA |
| AAV1   | ATCCAAGTCA | AGGAGGTCAC | GACGAATGAT | GGCGTCACAA | CCATCGCTAA |
| AAV2   | ATTCAAGTCA | AAGAGGTCAC | GCAGAATGAC | GGTACGACGA | CGATTGCCAA |
| AAV3   | ATCCAAGTTA | GAGGGGTCAC | GCAGAACGAT | GGCACGACGA | CTATTGCCAA |
| AAV8   | ATCCAGGTCA | AGGAGGTCAC | GCAGAATGAA | GGCACCAAGA | CCATCGCCAA |
| AAV9   | ATCCAGGTCA | AGGAGGTTAC | GACGAACGAA | GGCACCAAGA | CCATCGCCAA |
| AAV7   | ATCCAGGTCA | AGGAGGTCAC | GACGAATGAC | GGCGTTACGA | CCATCGCTAA |
| 44_2   | ATCCAGGTCA | AGGAGGTCAC | GCAGAATGAA | GGCACCAAGA | CCATCGCCAA |

FIG. 1AAN

```
        3251                                                    3300
 42_2   TAACCTTACC AGCACGATTC AGGTCTTCTC GGACTCGGAG TACCAACTGC
 42_8   TAACCTTACC AGCACGATTC AGGTCTTTAC GGACTCGGAA TACCAGCTCC
 42_15  TAACCTTACC AGCACGATTC AGGTCTTTAC GGACTCGGAA TACCAGCTCC
 42_5b  TAACCTTACC AGCACGATTC AGGTCTTTAC GGACTCGGAA TACCAGCTCC
 42_1b  TAACCTTACC AGCACGATTC AGGTCTTTAC GGACTCGGAA TACCAGCTCC
 42_13  TAACCTTACC ACCACGATTC AGGTCTTTAC GGACTCGGAA TACCAGCTCC
 42_3a  TAACCTTACC AGCACGATTC AGGTCTTTAC GGACTCGGAA TACCAGCTCC
 42_4   TAACCTTACC AGCACGATTC AGGTCTTTAC GGACTCGGAA TACCGGCTCC
 42_5a  TAACCTTACC AGCACGATTC AGGTCTTCTC GGACTCGGAG TACCAACTGC
 42_10  TAACCTTACC AGCACGATTC AGGTCTTCTC GGACTCGGAG TACCAACTGC
 42_3b  TAACCTTACC AGCACGATTC AGGTCTTCTC GGACTCGGAG TACCAACTGC
 42_11  TAACCTTACC AGCACGATTC AGGTCTTCTC GGACTCGGAG TACCAACTGC
 42_6b  TAACCTTACC AGCACGATTC AGGTCTTCTC GGACTCGGAG TACCAACTGC
 43_1   TAACCTTACC AGCACGATTC AGGTGTTTAC GGACTCGGAA TACCAGCTCC
 43_5   TAACCTTACC AGCACGATTC AGGTGTTTAC GGACTCGGAA TACCAGCTCC
 43_12  TAACCTTACC AGCACGATTC AGGTGTTTAC GGACTCGGAA TACCAGCTCC
 43_20  TAATCTCACC AGCACCGTGC AGGTCTTTAC GGACTCGGAG TACCAGTTAC
 43_21  TAATCTCACC AGCACCGTGC GGGTCTTTAC GGACTCGGAG TACCAGTTAC
 43_23  TAATCTCACC AGCACCGTGC AGGTCTTTAC GGACTTGGAG TACCAGTTAC
 43_25  TAATCTCACC AGCACCGTGC AGGTCTTTAC GGACTCGGAG TACCAGTTAC
 44_1   TAACCTTACC AGCACGATTC AGGTCTTTAC GGACTCGGAA TACCAGCTCC
 44_5   TAACCTTACC AGCACGATTC AGGTCTTTAC GGACTCGGAA TACCAGCTCC
223_10  TAACCTTACC AGCACGGTTC AGGTCTTTTC GGACTCGGAA TATCAACTGC
223_2   TAACCTTACC AGCACGGTTC AGGTCTTTTC GGACTCGGAA TATCAACTGC
223_4   TAACCTTACC AGCACGGTTC AGGTCTTTTC GGACTCGGAA TATCAACTGC
223_5   TAACCTTACC AGCACGGTTC AGGTCTTTTC GGACTCGGAA TATCAACTGC
223_6   TAACCTTACC AGCACGGTTC AGGTCTTTTC GGACTCGGAA TATCAACTGC
223_7   TAACCTTACC AGCACGGTTC AGGTCTTTTC GGACCCGGAA TATCAACTGC
 A3_4   TAACCTTACC AGCACGGTGC AGGTCTTCAC AGACTCTGAG TACCAGCTGC
 A3_5   TAACCTTACC AGCACGGTGC AGGTCTTCAC AGACTCTGAG TACCAGCTGC
 A3_7   TAACCTTACC AGCACGGTGC AGGTCTTCAC AGACTCTGAG TACCAGCTGC
 A3_3   TAACCTTACC AGCGCGGTGC AGGTCTTCAC AGACTCTGAG TACCAGCTGC
 42_12  TAACCTTACC AGCACGATTC AGGTCTTTAC GGACTCGGAA TACCAGCTCC
 AAV1   TAACCTTACC AGCACGGTTC AAGTCTTCTC GGACTCGGAG TACCAGCTTC
 AAV2   TAACCTTACC AGCACGGTTC AGGTGTTTAC TGACTCGGAG TACCAGCTCC
 AAV3   TAACCTTACC AGCACGGTTC AACTGTTTAC GGACTCGGAG TATCAGCTCC
 AAV8   TAACCTCACC AGCACCATCC AGGTGTTTAC GGACTCGGAG TACCAGCTGC
 AAV9   TAACCTTACC AGCACGTCC  AGGTCTTTAC GGACTCGGAG TACCAGCTAC
 AAV7   TAACCTTACC AGCACGATTC AGGTATTCTC GGACTCGGAA TACCAGCTGC
 44_2   TAACCTTACC AGCACGATTC AGGTCTTTAC GGACTCGGAA TACCAGCTCC
```

FIG. 1AAO

```
            3301                                                        3350
   42_2     CGTACGTCCT  CGGCTCTGCG  CACCAGGGCT  GCCTCCCTCC  GTTCCCTGCG
   42_8     CGTACGTCCT  CGGCTCTGCG  CACCAGGGCT  GCCTGCCTCC  GTTCCCGGCG
   42_15    CGTACGTCCT  CGGCTCTGCG  CACCAGGGCT  GCCCGCCTCC  GTTCCCGGCG
   42_5b    CGTACGTCCT  CGGCTCTGCG  CACCAGGGCT  GCCTGCCTCC  GTTCCCGGCG
   42_1b    CGTACGTCCT  CGGCTCTGCG  CACCAGGGCT  GCCTGCCTCC  GTTCCCGGCG
   42_13    CGTACGTCCT  CGGCTCTGCG  CACCAGGGCT  GCCTGCCTCC  GTTCCCGGCG
   42_3a    CGTACGTCCT  CGGCTCTGCG  CACCAGGGCT  GCCTGCCTCC  GTTCCCGGCG
   42_4     CGTACGTCCT  CGGCTCTGCG  CACCAGGGCT  GCCTGCCTCC  GTTCCCGGCG
   42_5a    CGTACGTCCT  CGGCTCTGCG  CACCAGGGCT  GCCTCCCTCC  GTTCCCTGCG
   42_10    CGTACGTCCT  CGGCTCTGCG  CACCAGGGCT  GCCTCCCTCC  GTTCCCTGCG
   42_3b    CGTACGTCCT  CGGCTCTGCG  CACCAGGGCT  GCCTCCCTCC  GTTCCCTGCG
   42_1     CGTACGTCCT  CGGCTCTGCG  CACCAGGGCT  GCCTCCCTCC  GTTCCCTGCG
   42_6b    CGTACGTCCT  CGGCTCTGCG  CACCAGGGCT  GCCTCCCTCC  GTTCCCTGCG
   43_1     CGTACGTCCC  CGGCTCTGCG  CACCAGGGCT  GCCTCCCTCC  GTTCCCGGCG
   43_5     CGTACGTCCT  CGGCTCTGCG  CACCAGGGCT  GCCTCCCTCC  GTTCCCGGCG
   43_12    CGTACGTCCT  CGGCTCTGCG  CACCAGGGCT  GCCTCCCTCC  GTTCCCGGCG
   43_20    CGTACGTGCT  AGGATCCGCT  CACCAGGGAT  GTCTGCCTCC  GTTCCCGGCG
   43_21    CGTACGTGCT  AGGATCCGCT  CACCAGGGAT  GTCTGCCTCC  GTTCCCGGCG
   43_23    CGTACGTGCT  AGGATCCGCT  CACCAGGGAT  GTCTGCCTCC  GTTCCCGGCG
   43_25    CGTACGTGCT  AGGATCCGCT  CACCAGGGAT  GTCTGCCTCC  GTTCCCGGCG
   44_1     CGTACGTCCT  CGGCTCTGCG  CACCAGGGCT  GCCTGCCTCC  GTTCCCGGCG
   44_5     CGTACGTCCT  CGGCTCTGCG  CACCAGGGCT  GCCTGCCTCC  GTTCCCGGCG
   223_10   CGTACGTCCT  CGGCTCCGCG  CACCAGGGCT  GCCTGCCTCC  GTTCCCGGCA
   223_2    CGTACGTCCT  CGGCTCCGCG  CACCAGGGCT  GCCTGCCTCC  GTTCCCGGCA
   223_4    CGTACGTCCT  CGGCTCCGCG  CACCAGGGCT  GCCTGCCTCC  GTTCCCGGCA
   223_5    CGTACGTCCT  CGGCTCCGCG  CACCAGGGCT  GCCTGCCTCC  GTTCCCGGCA
   223_6    CGTACGTCCT  CGGCTCCGCG  CACCAGGGCT  GCCTGCCTCC  GTTCCCGGCA
   223_7    CGTACGTCCT  CGGCTCCGCG  CACCAGGGCT  GCCTGCCTCC  GTTCCCGGCA
   A3_4     CCTACGTCCT  CGGTTCGGCT  CACCAGGGCT  GCCTTCCGCC  GTTCCCAGCA
   A3_5     CCTACGTCCT  CGGTTCGGCT  CACCAGGGCT  GCCTTCCGCC  GTTCCCAGCA
   A3_7     CCTACGTCCT  CGGTTCGGCT  CACCAGGGCT  GCCTTCCGCC  GTTCCCAGCA
   A3_3     CCTACGTCCT  CGGTTCGGCT  CACCAGGGCT  GCCTTCCGCC  GTTCCCAGCA
   42_12    CGTACGTCCT  CGGCTCTGCG  CACCAGGGCT  GCCTGCCTCC  GTTCCCGGCG
   AAV1     CGTACGTCCT  CGGCTCTGCG  CACCAGGGCT  GCCTCCCTCC  GTTCCCGGCG
   AAV2     CGTACGTCCT  CGGCTCGGCG  CATCAAGGAT  GCCTCCCGCC  GTTCCCAGCA
   AAV3     CGTACGTGCT  CGGGTCGGCG  CACCAAGGCT  GTCTCCCGCC  GTTCCAGCG
   AAV8     CGTACGTTCT  CGGCTCTGCC  CACCAGGGCT  GCCTGCCTCC  GTTCCCGGCG
   AAV9     CGTACGTCCT  AGGCTCTGCC  CACCAAGGAT  GCCTGCCACC  GTTCCTGCA
   AAV7     CGTACGTCCT  CGGCTCTGCG  CACCAGGGCT  GCCTGCCTCC  GTTCCCGGCG
   44_2     CGTACGTCCT  CGGCTCTGCG  CACCAGGGCT  GCCTGCCTCC  GTTCCCGGCG
```

FIG. 1AAP

```
            3351                                                        3400
   42_2   GACGTGTTCA TGATTCCTCA GTACGGATAT CTGACTCTAA ACAACGGCAG
   42_8   GACGTCTTCA TGATTCCTCA GTACGGGTAC CTGACTCTGA ACAACGGCAG
  42_15   GACGTCTTCA TGATTCCTCA GTACGGGTAC CTGACTCTGA ACAACGGCAG
  42_5b   GACGTCTTCA TGATTCCTCA GTACGGGTAC CTGACTCTGA ACAACGGCAG
  42_1b   GACGTCTTCA TGATTCCTCA GTACGGGTAC CTGACTCTGA ACAACGGCAG
  42_13   GACGTCTTCA TGATTCCTCA GTACGGGTAC CTGACTCTGA ACAACGGCAG
  42_3a   GACGTCTTCA TGATTCCTCA GTACGGGTAC CTGACTCTGA ACAACGGCAG
   42_4   GACGTCTTCA TGATTCCTCA GTACGGGTAC CTGACTCTGA ACAACGGCAG
  42_5a   GACGTGTTCA TGATTCCTCA GTACGGATAT CTGACTCTAA ACAACGGCAG
  42_10   GACGTGTTCA TGATTCCTCA GTACGGATAT CTGACTCTAA ACAACGGCAG
  42_3b   GACGTGTTCA TGATTCCTCA GTACGGATAT CTGACTCTAA ACAACGGCAG
   42_1   GACGTGTTCA TGATTCCTCA GTACGGATAT CTGACTCTAA ACAACGGCAG
  42_6b   GACGTGTTCA TGATTCCTCA GTACGGATAT CTGACTCTAA ACAACGGCAG
   43_1   GACGTCTTCA TGATTCCTCA GTACGGGTAT CTGACCCTAA ACAATGGCAG
   43_5   GACGTCTTCA TGATTCCTCA GTACGGGTAT CTGACCCTAA ACAATGGCAG
  43_12   GACGTCTTCA TGATTCCTCA GTACGGGTAT CTGACCCTAA ACAATGGCAG
  43_20   GACGTCTTCA CGGTTCCTCA GTACGGCTAT TTAACTTTAA ACAATGGAAG
  43_21   GACGTCTTCA TGGTTCCTCA GTACGGCTAT TTAACTTTAA ACAATGGAAG
  43_23   GACGTCTTCA TGGTTCCTCA GTACGGCTAT TTAACTTTAA ACAATGGAAG
  43_25   GACGTCTTCA TGGTTCCTCA GTACGGCTAT TTAACTTTAA ACAATGGAAG
   44_1   GACGTCTTCA TGATTCCTCA GTACGGGTAC CTGACTCTGA ACAATGGCAG
   44_5   GACGTCTTCA TGATTCCTCA GTACGGGTAC CTGACTCTGA ACAATGGCAG
  223_10  GACGTGTTCA TGATTCCGCA GTACGGATAC CTGACTCTGA ACAATGGCAG
  223_2   GACGTGTTCA TGATTCCGCA GTACGGATAC CTGACTCTGA ACAATGGCAG
  223_4   GACGTGTTCA TGATTCCGCA GTACGGATAC CTGACTCTGA ACAATGGCAG
  223_5   GACGTGTTCA TGATTCCGCA GTACGGATAC CTGACTCTGA ACAATGGCAG
  223_6   GACGTGTTCA TGATTCCGCA GTACGGATAC CTGACTCTGA ACAATGGCAG
  223_7   GACGTGTTCA TGATTCCGCA GTACGGATAC CTGACTCTGA ACAATGGCAG
   A3_4   GACGTCTTCA TGATTCCTCA GTACGGCTAC TTGACTCTGA ACAATGGCAG
   A3_5   GACGTCTTCA TGATTCCTCA GTACGGCTAC TTGACTCTGA ACAATGGCAG
   A3_7   GACGTCTTCA TGATTCCTCA GTACGGCTAC TTGACTCTGA ACAATGGCAG
   A3_3   GACGTCTTCA TGATTCCTCA GTACGGCTAC TTGACTCTGA ACAATGGCAG
  42_12   GACGTCTTCA TGATTCCTCA GTACGGGTAC CTGACTCTGA ACAACGGCAG
   AAV1   GACGTGTTCA TGATTCCGCA ATACGGCTAC CTGACGCTCA ACAATGGCAG
   AAV2   GACGTCTTCA TGGTGCCACA GTATGGATAC CTCACCCTGA ACAACGGGAG
   AAV3   GACGTCTTCA TGGTCCCTCA GTATGGATAC CTCACCCTGA ACAACGGAAG
   AAV8   GACGTGTTCA TGATTCCCCA GTACGGCTAC CTAACACTCA ACAACGGTAG
   AAV9   GACGTCTTCA TGGTTCCTCA GTACGGCTAC CTGACGCTCA ACAATGGAAG
   AAV7   GACGTCTTCA TGATTCCTCA GTACGGCTAC CTGACTCTCA ACAATGGCAG
   44_2   GACGTCTTCA TGATTCCTCA GTACGGGTAC CTGACTCTGA ACAATGGCAG
```

FIG. 1AAQ

```
        3401                                                    3450
 42_2   TCAGTCTGTG  GGACGTTCCT  CCTTCTACTG  CCTGGAGTAC  TTTCCTTCTC
 42_8   TCAGGCCGTG  GGCCGTTCCT  CCTTCTACTG  CCTGGAGTAC  TTTCCTTCTC
 42_15  TCAGGCCGTG  GGCCGTTCCT  CCTTCTACTG  CCTGGAGTAC  TTTCCTTCTC
 42_5b  TCAGGCCGTG  GGCCGTTCCT  CCTTCTACTG  CCTGGAGTAC  TTTCCTTCTC
 42_1b  TCAGGCCGTG  GGCCGTTCCT  CCTTCTACTG  CCTGGAGTAC  TTTCCTTCTC
 42_13  TCAGGCCGTG  GGCCGTTCCT  CCTTCTACTG  CCTGGAGTAC  TTTCCTTCTC
 42_3a  TCAGGCCGTG  GGCCGTTCCT  CCTTCTACTG  CCTGGAGTAC  TTTCCTTCTC
 42_4   TCAGGCCGTG  GGCCGTTCCT  CCTTCTACTG  CCTGGAGTAC  TTTCCTTCTC
 42_5a  TCAGTCTGTG  GGACGTTCCT  CCTTCTACTG  CCTGGAGTAC  TTTCCTTCTC
 42_10  TCAGTCTGTG  GGACGTTCCT  CCTTCTACTG  CCTGGAGTAC  TTTCCTTCTC
 42_3b  TCAGTCTGTG  GGACGTTCCT  CCTTCTACTG  CCTGGAGTAC  TTTCCTTCTC
 42_11  TCAGTCTGTG  GGACGTTCCT  CCTTCTACTG  CCTGGAGTAC  TTTCCTTCTC
 42_6b  TCAGTCTGTG  GGACGTTCCT  CCTTCTACTG  CCTGGAGTAC  TTTCCTTCTC
 43_1   TCAGGCTGTG  GGCCGTTCCT  CCTTCTACTG  CCTGGAATAC  TTCCCTTCTC
 43_5   TCAGGCTGTG  GGCCGTTCCT  CCTTCTACTG  CCTGGAATAC  TTCCCTTCTC
 43_12  TCAGGCTGTG  GGCCGTTCCT  CCTTCTACTG  CCTGGAATAC  TTCCCTTCTC
 43_20  CCAAGCCCTG  GGACGTTCCT  CCTTCTACTG  TCTGGAGTAT  TTCCCATCGC
 43_21  CCAAGCCCTG  GGACGTTCCT  CCTTCTACTG  TCTGGAGTAT  TTCCCATCGC
 43_23  CCAAGCCCTG  GGACGTTCCT  CCTTCTACTG  TCTGGAGTAT  TTCCCATCGC
 43_25  CCAAGCCCTG  GGACGTTCCT  CCTTCTACTG  TCTGGAGTAT  TTCCCATCGC
 44_1   TCAGGCCGTG  GGCCGTTCCT  CCTTCTACTG  CCTGGAGTAC  TTTCCTTCTC
 44_5   TCAGGCCGTG  GGCCGTTCCT  CCTTCTACTG  CCTGGAGTAC  TTTCCTTCTC
 223_10 CCAATCGGTA  GGCCGTTCCT  CCTTCTACTG  CCTGGAGTAC  TTTCCTTCTC
 223_2  CCAATCGGTA  GGCCGTTCCT  CCTTCTACTG  CCTGGAGTAC  TTTCCTTCTC
 223_4  CCAATCGGTA  GGCCGTTCCT  CCTTCTACTG  CCTGGAGTAC  TTTCCTTCTC
 223_5  CCAATCGGTA  GGCCGTTCCT  CCTTCTACTG  CCTGGAGTAC  TTTCCTTCTC
 223_6  CCAATCGGTA  GGCCGTTCCT  CCTTCTACTG  CCTGGAGTAC  TTTCCTTCTC
 223_7  CCAATCGGTA  GGCCGTTCCT  CCTTCTACTG  CCTGGAGTAC  TTTCCTTCTC
 A3_4   CCAAGCGGTA  GGACGTTCTT  CATTCTACTG  TCTAGAGTAT  TTTCCCTCTC
 A3_5   CCAAGCGGTA  GGACGTTCTT  CATTCTACTG  TCTAGAGTAT  TTTCCCTCTC
 A3_7   CCAAGCGGTA  GGACGTTCTT  CATTCTACTG  TCTAGAGTAT  TTTCCCTCTC
 A3_3   CCAAGCGGTA  GGACGTTCTT  CATTCTACTG  TCTAGAGTAT  TTTCCCTCTC
 42_12  TCAGGCCGTG  GGCCGTTCCT  CCTTCTACTG  CCTGGAGTAC  TTTCCTTCTC
 AAV1   CCAAGCCGTG  GGACGTTCAT  CCTTTTACTG  CCTGGAATAT  TTCCCTTCTC
 AAV2   TCAGGCAGTA  GGACGCTCTT  CATTTACTG   CCTGGAGTAC  TTTCCTTCTC
 AAV3   TCAAGCGGTG  GGACGCTCAT  CCTTTTACTG  CCTGGAGTAC  TTCCCTTCGC
 AAV8   TCAGGCCGTG  GGACGCTCCT  CCTTCTACTG  CCTGGAATAC  TTTCCTTCGC
 AAV9   TCAAGCGTTA  GGACGTTCTT  CTTTCTACTG  TCTGGAATAC  TTCCCTTCTC
 AAV7   TCAGTCTGTG  GGACGTTCCT  CCTTCTACTG  CCTGGAGTAC  TTCCCCTCTC
 44_2   TCAGGCCGTG  GGCCGTTCCT  CCTTCTACTG  CCTGGAGTAC  TTTCCTTCTC
```

FIG. 1AAR

```
          3451                                                            3500
   42_2   AGATGCTGAG AACGGGCAAT AACTTTGAAT TCAGCTACAC CTTTGAGGAA
   42_8   AAATGCTGAG AACGGGCAAC AACTTTGAGT TCAGCTACCA GTTTGAGGAC
   42_15  AAATGCGGAG AACGGGCAAC AACTTTGAGT TCAGCTACCA GTTTGAGGAC
   42_5b  AAATGCTGAG AACGGGCAAC AACTTTGAGT TCAGCTACCA GTTTGAGGAC
   42_1b  AAATGCTGAG AACGGGCAAC AACTTTGAGT TCAGCTACCA GTTTGAGGAC
   42_13  AAATGCTGAG AACGGGCAAC AACTTTGAGT TCAGCTACCA GTTTGAGGAC
   42_3a  AAATGCTGAG AACGGGCAAC AACTTTGAGT TCAGCTACCA GTTTGAGGAC
   42_4   AAATGCTGAG AACGGGCAAC AACTTTGAGT TCAGCTACCA GTTTGAGGAC
   42_5a  AGATGCTGAG AACGGGCAAT AACTTTGAAT TCAGCTACCA GTTTGAGGAC
   42_10  AGATGCTGAG AACGGGCAAT AACTTTGAAT TCAGCTACAC CTTTGAGGAA
   42_3b  AGATGCTGAG AACGGGCAAT AACTTTGAAT TCAGCTACAC CTTTGAGGAA
   42_11  AGATGCTGAG AACGGGCAAT AACTTTGAAT TCAGCTACAC CTTTGAGGAA
   42_6b  AGATGCTGAG AACGGGCAAT AACTTTGAAT TCAGCTACAC CTTTGAGGAA
   43_1   AAATGCTGAG GACGGGCAAC AACTTTGAAT TCAGCTACAC CTTCGAGGAC
   43_5   AAATGCTGAG GACGGGCAAC AACTTTGAAT TCAGCTACAC CTTCGAGGAC
   43_12  AAATGCTGAG GACGGGCAAC AACTTTGAAT TCAGCTACAC CTTCGAGGAC
   43_20  AGATGCTGAG AACCGGCAAC AACTTTCAGT TCAGCTACAC CTTCGAGGAC
   43_21  AGATGCTGAG AACCGGCAAC AACTTTCAGT TCAGCTACAC CTTCGAGGAC
   43_23  AGATGCCGAG AACCGGCAAC AACTTTCAGT TCAGCTACAC CTTCGAGGAC
   43_25  AGATGCTGAG AACCGGCAAC AACTTTCAGT TCAGCTACAC CTTCGAGGAC
   44_1   AAATGCTGAG AACGGGCAAC AACTTTGAGT TCAGCTACCA GTTTGAGGAC
   44_5   AAATGCTGAG AACGGGCAAC AACTTTGAGT TCAGCTACCA GTTTGAGGAC
  223_10  AGATGCTGAG AACGGGCAAC AACTTCACCT TTAGCTACAC CTTCGAGGAC
  223_2   AGATGCTGAG AACGGGCAAC AACTTCACCT TTAGCTACAC CTTCGAGGAC
  223_4   AGATGCTGAG AACGGGCAAC AACTTCACCT TTAGCTACAC CTTCGAGGAC
  223_5   AGATGCTGAG AACGGGCAAC AACTTCACCT TTAGCTACAC CTTCGAGGAC
  223_6   AGATGCTGAG AACGGGCAAC AACTTCACCT TTAGCTACAC CTTCGAGGAC
  223_7   AGATGCTGAG AACGGGCAAC AACTTCACCT TTAGCTACAC CTTCGAGGAC
   A3_4   AGATGCTGAG GACGGGAAAC AACTTCACCT TCAGCTACAC TTTTGAAGAC
   A3_5   AGATGCTGAG GACGGGAAAC AACTTCACCT TCAGCTACAC TTTTGAAGAC
   A3_7   AGATGCTGAG GACGGGAAAC AACTTCACCT TCAGCTACAC TTTTGAAGAC
   A3_3   AGATGCTGAG GACGGGAAAC AACTTCACCT TCAGCTACAC TTTTGAAGAC
   42_12  AAATGCTGAG AACGGGCAAC AACTTTGAGT TCAGCTACCA GTTTGAGGAC
   AAV1   AGATGCTGAG AACGGGCAAC AACTTTACCT TCAGCTACAC CTTTCAGCAA
   AAV2   AGATGCTGCG TACCGGAAAC AACTTTACCT TCAGCTACAC TTTTGAGGAC
   AAV3   AGATGCTAAG GACTGGAAAT AACTTCCAAT TCAGCTATAC CTTCGAGGAT
   AAV8   AGATGCTGAG AACCGGCAAC AACTTCCAGT TTACTTACAC CTTCGAGGAC
   AAV9   AGATGCTGAG AACCGGCAAC AACTTTCAGT TCAGCTACAC TTTCGAGGAC
   AAV7   AGATGCTGAG AACGGGCAAC AACTTTGAGT TCAGCTACAG CTTCGAGGAC
   44_2   AAATGCTGAG AACGGGCAAC AACTTTGAGT TCAGCTACCA GTTTGAGGAC
```

FIG. 1AAS

```
          3501                                                    3550
  42_2    GTGCCTTTCC ACAGCAGCTA TGCGCACAGC CAGAGCCTGG ACCGGCTGAT
  42_8    GTGCCTTTTC ACAGCAGCTA CGCGCACAGC CAAAGCCTGG ACCGGCTGAT
  42_15   GTGCCTTTTC ACAGCAGCTA CGCGCATAGC CAAAGCCTGG ACCGGCTGAT
  42_5b   GTGCCTTTTC ACAGCAGCTA CGCGCACAGC CAAAGCCTGG ACCGGCTGAT
  42_1b   GTGCCTTTTC ACAGCAGCTA TGCGCACAGC CAAAGCCTGG ACCGGCTGAT
  42_13   GTGCCTTTTC ACAGCAGCTA TGCGCACAGC CAAAGCCTGG ACCGGCTGAT
  42_3a   GTGCCTTTTC ACAGCAGCTA CGCGCACAGC CAAAGCCTGG ACCGGCTGAT
  42_4    GTGCCTTTTC ACAGCAGCTA CGCGCACAGC CAAAGCCTGG ACCGGCTGAT
  42_5a   GTGCCCTTTC ACAGCAGCTA CGCGCACAGC CAAAGCCTGG ACCGGCTGAT
  42_10   GTGCCTTTCC ACAGCAGCTA TGCGCACAGC CAGAGCCTGG ACCGGCTGAT
  42_3b   GTGCCTTTCC ACAGCAGCTA TGCGCACAGC CAGAGCCTGG ACCGGCTGAT
  42_11   GTGCCTTTCC ACAGCAGCTA TGCGCACAGC CAGAGCCTGG ACCGGCTGAT
  42_6b   GTGCCTTTCC ACAGCAGCTA TGCGCATAGC CAGAGCCTGG ACCGGCTGAT
  43_1    GTGCCTTTCC ACAGCAGCTA CGCGCACAGC CAGAGCCTGG ACCGGCTGAT
  43_5    GTGCCTTTCC ACAGCAGCTA CGCGCACAGC CAGAGCCTGG ACCGGCTGAT
  43_12   GTGCCTTTCC ACAGCAGCTA CGCGCACAGC CAGAGCCTGG ACCGGCTGAT
  43_20   GTGCCTTTCC ACAGCAGCTA CGCGCACAGC CAGAGCCTGG ACAGGCTGAT
  43_21   GTGCCTTTCC ACAGCAGCTA CGCGCACAGC CAGAGCCTGG ACAGGCTGAT
  43_23   GTGCCTTTCC ACAGCAGCTA CGCGCACAGC CAGAGCCTGG ACAGGCTGAT
  43_25   GTGCCTTTCC ACAGCAGCTA CGCGCACAGC CAGAGCCTGG ACAGGCTGAT
  44_1    GTGCCTTTTC ACAGCAGCTA CGCGCACAGC CAAAGCCTGG ACCGGCTGAT
  44_5    GTGCCTTTTC ACAGCAGCTA CGCGCACAGC CAAAGCCTGG ACCGGCTGAT
  223_10  GTGCCTTTCC ACAGCAGCTA CGCGCACAGC CAGAGTCTGG ACCGGCTGAT
  223_2   GTGCCTTTCC ACAGCAGCTA CGCGCACAGC CAGAGTCTGG ACCGGCTGAT
  223_4   GTGCCTTTCC ACAGCAGCTA CGCGCACAGC CAGAGTCTGG GCCGGCTGAT
  223_5   GTGCCTTTCC ACAGCAGCTA CGCGCACAGC CAGAGTCTGG GCCGGCTGAT
  223_6   GTGCCTTTCC ACAGCAGCTA CGCGCACAGC CAGAGTCTGG ACCGGCTGAT
  223_7   GTGCCTTTCC ACAGCAGCTA CGCGCACAGC CAGAGTCTGG ACCGGCTGAT
  A3_4    GTGCCTTTCC ACAGCAGCTA CGCGCACAGC CAGAGTCTGG ATCGGCTGAT
  A3_5    GTGCCTTTCC ACAGCAGCTA CGCGCACAGC CAGAGTCTGG ATCGGCTGAT
  A3_7    GTGCCTTTCC ACAGCAGCTA CGCGCACAGC CAGAGTCTGG ATCGGCTGAT
  A3_3    GTGCCTTTCC ACAGCAGCTA CGCGCACAGC CAGAGTCTGG ATCGGCTGAT
  42_12   GTGCCTTTTC ACAGCAGCTA CGCGCACAGC CAAAGCCTGG ACCGGCTGAC
  AAV1    GTGCCTTTCC ACAGCAGCTA CGCGCACAGC CAGAGCCTGG ACCGGCTGAT
  AAV2    GTTCCTTTCC ACAGCAGCTA CGCTCACAGC CAGAGTCTGG ACCGTCTCAT
  AAV3    GTACCTTTTC ACAGCAGCTA CGCTCACAGC CAGAGTTTGG ATCGCTTGAT
  AAV8    GTGCCTTTCC ACAGCAGCTA CGCCCACAGC CAGAGCTTGG ACCGGCTGAT
  AAV9    GTGCCTTTCC ACAGCAGCTA CGCACACAGC CAGAGTCTAG ATCGACTGAT
  AAV7    GTGCCTTTCC ACAGCAGCTA CGCACACAGC CAGAGCCTGG ACCGGCTGAT
  44_2    GTGCCTTTTC ACAGCAGCTA CGCGCACAGC CAAAGCCTGG ACCGGCTGAT
```

FIG. 1AAT

```
         3551                                                          3600
 42_2    GAATCCCCTC ATCGACCAGT ACCTGTACTA CCTGGCCCGG ACCCAGAGCA
 42_8    GAACCCCCTC ATCGACCAGT ACCTGTACTA CCTGTCTCGG ACTCAGTCCA
 42_15   GAACCCCCTC ATCGACCAGT ACCTGTACTA CCTGTCTCGG ACTCAGTCCA
 42_5b   GAACCCCCTC ATCGACCAGT ACCTGTACTA CCTGTCTCGG ACTCAGTCCA
 42_1b   GAACCCCCTC ATCGACCAGT ACCTGTACTA CCTGTCTCGG ACTCAGTCCA
 42_13   GAACCCCCTC ATCGACCAGT ACCTGTACTA CCTGTCTCGG ACTCAGTCCA
 42_3a   GAACCCCCTC ATCGACCAGT ACCTGTACTA CCTGTCTCGG ACTCAGTCCA
 42_4    GAACCCCCTC ATCGACCAGT ACCTGTACTA CCTGTCTCGG ACTCAGTCCA
 42_5a   GAACCCCCTC ATCGACCAGT ACCTGTACTA CCTGTCTCGG ACTCAGTCCA
 42_10   GAATCCCCTC ATCGACCAGT ACCTGTACTA CCTGGCCCGG ACCCAGAGCA
 42_3b   GAATCCCCTC ATCGACCAGT ACCTGTACTA CCTGGCCCGG ACCCAGAGCA
 42_11   GAATCCCCTC ATCGACCAGT ACCTGTACTA CCTGGCCCGG ACCCAGAGCA
 42_6b   GAATCCCCTC ATCGACCAGT ACCTGTACTA CCTGGCCCGG ACCCAGAGCA
 43_1    GAACCCTCTC ATCGACCAGT ACCTGTATTA CTTATCCAGA ACTCAGTCCA
 43_5    GAACCCTCTC ATCGACCAGT ACCTGTATTA CTTATCCAGA ACTCAGTCCA
 43_12   GAACCCTCTC ATCGACCAGT ACCTGTATTA CTTATCCAGA ACTCAGTCCA
 43_20   GAATCCCCTC ATCGACCAGT ACCTGTACTA CCTGGTCAGA ACGCAAACGA
 43_21   GAATCCCCTC ATCGACCAGT ACCTGTACTA CCTGGTCAGA ACGCAAACGA
 43_23   GAATCCCCTC ATCGACCAGT ACCTGTACTA CCTGGTCAGA ACGCAAACGA
 43_25   GAATCCCCTC ATCGACCAGT ACCTGTACTA CCTGGTCAGA ACGCAAACGA
 44_1    GAACCCCCTC ATCGACCAGT ACCTGTACTA CCTGTCTCGG ACTCAGTCCA
 44_5    GAACCCCCTC ATCGACCAGT ACCTGTACTA CCTGTCTCGG ACTCAGTCCA
 223_10  GAATCCCCTC ATCGACCAGT ACCTGTACTA CTTGGCCAGA ACACAGAGCA
 223_2   GAATCCCCTC ATCGACCAGT ACCTGTACTA CTTGGCCAGA ACACAGAGCA
 223_4   GAATCCCCTC ATCGACCAGT ACCTGTACTA CTTGGCCAGA ACACAGAGCA
 223_5   GAATCCCCTC ATCGACCAGT ACCTGTACTA CTTGGCCAGA ACACAGAGCA
 223_6   GAATCCCCTC ATCGACCAGT ACCTGTACTA CTTGGCCAGA ACACAGAGCA
 223_7   GAATCCCCTC ATCGACCAGT ACCTGTACTA CTTGGCCAGA ACACAGAGCA
 A3_4    GAATCCTCTC ATTGACCAGT ACCTGTATTA CCTGAGCAAA ACTCAGGGTA
 A3_5    GAATCCTCTC ATTGACCAGT ACCTGTATTA CCTGAGCAAA ACTCAGGGTA
 A3_7    GAATCCTCTC ATTGACCAGT ACCTGTATTA CCTGAGCAAA ACTCAGGGTA
 A3_3    GAATCCTCTC ATTGACCAGT ACCTGTATTA CCTGAGCAAA ACTCAGGGTA
 42_12   GAACCCCCTC ATCGACCAGT ACCTGTACTA CCTGGCCCGG ACCCAGAGCA
 AAV1    GAATCCTCTC ATCGACCAAT ACCTGTATTA CCTGAACAGA ACTCAAA.AT
 AAV2    GAATCCTCTC ATCGACCAGT ACCTGTATTA CTTGAGCAGA ACAAACACTC
 AAV3    GAATCCTCTT ATTGATCAGT ATCTGTACTA CCTGAACAGA ACGCAAGGAA
 AAV8    GAATCCTCTG ATTGACCAGT ACCTGTACTA CTTGTCTCGG ACTCAAACAA
 AAV9    GAACCCCCTC ATCGACCAGT ACCTATACTA CCTGGTCAGA ACACAGACAA
 AAV7    GAATCCCCTC ATCGACCAGT ACTTGTACTA CCTGGCCAGA ACACAGAGTA
 44_2    GAACCCCCTC ATCGACCAGT ACCTGTACTA CCTGTCTCGG ACTCAGTCCA
```

FIG. 1AAU

```
         3601                                                    3650
  42_2   CTACGG...GG TCCACAAGGG AGCTGCA.GT TCCA...... TCAGGCTGGG
  42_8   CGGGA...GG  TACCGCAGGA ACTCAGCAGT TGCTATTTTC TCAGGCCGGG
  42_15  CGGGA...GG  TACCGCAGGA ACTCAGCAGT TGCTATTTTC TCAGGCCGGG
  42_5b  CGGGA...GG  TACCGCAGGA ACTCAGCAGT TGCTATTTTC TCAGGCCGGG
  42_1b  CGGGA...GG  TACCGCAGGA ACTCAGCAGT TGCTATTTTC TCAGGCCGGG
  42_13  CGGGA...GG  TACCGCAGGA ACTCAGCAGT TGCTATTTTC TCAGGCCGGG
  42_3a  CGGGA...GG  TACCGCAGGA ACTCAGCAGT TGCTATTTTC TCAGGCCGGG
  42_4   CGGGA...GG  TACCGCAGGA ACTCAGCAGT TGCTATTTTC TCAGGCCGGG
  42_5a  CGGGA...GG  TACCGCAGGA ACTCAGCAGT TGCTATTTTC TCAGGCCGGG
  42_10  CTACG...GG  GTCCACAAGG GAGCTGCAGT TCCA...... TCAGGCTGGG
  42_3b  CTACG...GG  GTCCACAAGG GAGCTGCAGT TCCA...... TCAGGCTGGG
  42_11  CTACG...GG  GTCCACAAGG GAGCTGCAGT TCCA...... TCAGGCTGGG
  42_6b  CTACG...GG  GTCCACAAGG GAGCTGCAGT TCCA...... TCAGGCTGGG
  43_1   CAGGA...GG  AACTCAAGGT ACTCAGCAAT TGTTATTTTC TCAAGCCGGG
  43_5   CAGGA...GG  AACTCAAGGT ACTCAGCAAT TGTTATTTTC TCAAGCCGGG
  43_12  CAGGA...GG  AACTCAAGGT ACTCAGCAAT TGTTATTTTC TCAAGCCGGG
  43_20  CT......GG  AACTGGAGGG ACGCAGACTC TGGCATTCAG CCAAGCGGGT
  43_21  CT......GG  AACTGGAGGG ACGCAGACTC TGGCATTCAG CCAAGCGGGT
  43_23  CT......GG  AACTGGAGGG ACGCAGACTC TGGCATTCAG CCAAGCGGGT
  43_25  CT......GG  AACTGGAGGG ACGCAGACTC TGGCATTCAG CCAAGCGGGT
  44_1   CGGGA...GG  TACCGCAGGA ACTCAGCAGT TGCTATTTTC TCAGGCCGGG
  44_5   CGGGA...GG  TACCGCAGGA ACTCAGCAGT TGCTATTTTC TCAGGCCGGG
 223_10  ACGCAGGAGG  TACTGCTGGC AATCGGGAAC TGCAGTTTTA TCAGGGCGGA
 223_2   ACGCAGGAGG  TACTGCTGGC AATCGGGAAC TGCAGTTTTA TCAGGGCGGA
 223_4   ACGCAGGAGG  TACTGCTGGC AATCGGGAAC TGCAGTTTTA TCAGGGCGGA
 223_5   ACGCAGGAGG  TACTGCTGGC AATCGGGAAC TGCAGTTTTA TCAGGGCGGA
 223_6   ACGCAGGAGG  TACTGCTGGC AATCGGGAAC TGCAGTTTTA TCAGGGCGGA
 223_7   ACGCAGGAGG  TACTGCTGGC AATCGGGAAC TGCAGTTTTA TCAGGGCGGA
  A3_4   CAAG...TGG  AACAACGCAG CAATCGAGAC TGCAGTTCAG CCAAGCTGGG
  A3_5   CAAG...TGG  AACAACGCAG CAATCGAGAC TGCAGTTCAA CCAAGCTGGG
  A3_7   CAAG...TGG  AACAACGCAG CAATCGAGAC TGCAGTTCAG CCAAGCTGGG
  A3_3   CAAG...TGG  AACAACGCAG CAATCGAGAC TGCAGTTCAG CCAAGCTGGG
  42_12  CTACG...GG  GTCCACAAGG GGGCTGCAGT TCCA...... TCAGGCTGGG
  AAV1   CAGTCC..GG  AAGTGCCCAA AACAAGGACT TGCTGTTTAG CCGTGGGTCT
  AAV2   CAAG...TGG  AACCACCACG CAGTCAAGGC TTCAGTTTTC TCAGGCCGGA
  AAV3   CAACCTCTGG  AACAACCAAC CAATCACGGC TGCTTTTTAG CCAGGCTGGG
  AAV8   CAGGAG..GC  .ACGGCAAAT ACGCAGACTC TGGGCTTCAG CCAAGGTGGG
  AAV9   CTGGA.....  .ACTGGGGGA ACTCAAACTT TGGCATTCAG CCAAGCAGGC
  AAV7   ACCCAGGAGG  CACAGCTGGC AATCGGGAAC TGCAGTTTTA CCAGGGCGGG
  44_2   CGGGA...GG  TACCGCAGGA ACTCAGCAGT TGCTATTTTC TCAGGCCGGG
```

FIG. 1AAV

```
         3651                                                      3700
  42_2   CCCAACACCA TGGCCGAGCA ATCAAAGAAC TGGCTGCCCG GACCCTGTTA
  42_8   CCTAATAACA TGTCGGCTCA GGCCAAAAAC TGGCTACCCG GGCCCTGCTA
 42_15   CCTAATAACA TGTCGGCTCA GGCCAAAAAC TGGCTACCCG GGCCCTGCTA
 42_5b   CCTAATAACA TGTCGGCTCA GGCCAAAAAC TGGCTACCCG GGCCCTGCTA
 42_1b   CCTAATAACA TGTCGGCTCA GGCCAAAAAC TGGCTACCCG GGCCCTGCTA
 42_13   CCTAATAACA TGTCGGCTCA GGCCAAAAAC TGGCTACCCG GGCCCTGCTA
 42_3a   CCTAATAACA TGTCGGCTCA GGCCAAAAAC TGGCTACCCG GGCCCTGCTA
  42_4   CCTAATAACA TGTCGGCTCA GGCCAAAAAC TGGCTACCCG GGCCCTGCTA
 42_5a   CCTAATAACA TGTCGGCTCA GGCCAAAAAC TGGCTACCCG GGCCCTGCTA
 42_10   CCCAACACCA TGGCCGAGCA ATCAAAGAAC TGGCTGCCCG GACCCTGTTA
 42_3b   CCCAACACCA TGGCCGAGCA ATCAAAGAAC TGGCTGCCCG GACCCTGTTA
 42_11   CCCAACACCA TGGCCGAGCA ATCAAAGAAC TGGCTGCCCG GACCCTGTTA
 42_6b   CCCAACACCA TGGCCGAGCA ATCAAAGAAC TGGCTGCCCG GACCCTGTTA
  43_1   CCCGCAAACA TGTCGGCTCA GGCCAAGAAC TGGCTACCTG GACCGTGTTA
  43_5   CCCGCAAACA TGTCGGCTCA GGCCAAGAAC TGGCTACCTG GACCGTGTTA
 43_12   CCCGCAAACA TGTCGGCTCA GGCCAAGAAC TGGCTACCTG GACCGTGTTA
 43_20   CCTAGCTCAA TGGCCAACCA GGCTAGAAAT TGGGTGCCCG GACCTTGCTA
 43_21   CCTAGCTCAA TGGCCAACCA GGCTAGAAAT TGGGTGCCCG GACCTTGCTA
 43_23   CCTAGCTCAA TGGCCAACCA GGCTAGAAAT TGGGTGCCCG GACCTTGCTA
 43_25   CCTAGCTCAA TGGCCAACCA GGCTAGAAAT TGGGTGCCCG GACCTTGCTA
  44_1   CCTAATAACA TGTCGGCTCA GGCCAAAAAC TGGCTACCCG GGCCCTGCTA
  44_5   CCTAATAACA TGTCGGCTCA GGCCAAAAAC TGGCTACCCG GGCCCTGCTA
 223_10  CCTACCACCA TGGCCGAACA AGCAAAGAAC TGGCTGCCCG GACCTTGCTT
 223_2   CCTACCACCA TGGCCGAACA AGCAAAGAAC TGGCTGCCCG GACCTTGCTT
 223_4   CCTACCACCA TGGCCGAACA AGCAAAGAAC TGGCTGCCCG GACCTTGCTT
 223_5   CCTACCACCA TGGCCGAACA AGCAAAGAAC TGGCTGCCCG GACCTTGCTT
 223_6   CCTACCACCA TGGCCGAACA AGCAAAGAAC TGGCTGCCCG GACCTTGCTT
 223_7   CCTACCACCA TGGCCGAACA AGCAAAGAAC TGGCTGCCCG GACCTTGCTT
  A3_4   CCTAGCTCCA TGGCTCAGCA GGCCAAAAAC TGGCTACCGG GACCCAGCTA
  A3_5   CCTAGCTCCA TGGCTCAGCA GGCCAAAAAC TGGCTACCGG GACCCAGCTA
  A3_7   CCTAGCTCCA TGGCTCAGCA GGCCAAAAAC TGGCTACCGG GACCCAGCTA
  A3_3   CCTAGCTCCA TGGCTCAGCA GGCCAAAAAC TGGCTACCGG GACCCAGCTA
 42_12   CCCAACACCA TGGCCGAGCA ATCAAAGAAC TGGCTGCCCG GACCCTGTTA
  AAV1   CCAGCTGGCA TGTCTGTTCA GCCCAAAAAC TGGCTACCTG GACCCTGTTA
  AAV2   GCGAGTGACA TTCGGGACCA GTCTAGGAAC TGGCTTCCTG GACCCTGTTA
  AAV3   CCTCAGTCTA TGTCTTTGCA GGCCAGAAAT TGGCTACCTG GGCCCTGCTA
  AAV8   CCTAATACAA TGGCCAATCA GGCAAAGAAC TGGCTGCCAG GACCCTGTTA
  AAV9   CCTAGCTCAA TGGCCAATCA GGCTAGAAAC TGGGTACCCG GGCCTTGCTA
  AAV7   CCTTCAACTA TGGCCGAACA AGCCAAGAAT TGGTTACCTG GACCTTGCTT
  44_2   CCTAATAACA TGTCGGCTCA GGCCAAAAAC TGGCTACCCG GGCCCTGCTA
```

FIG. 1AAW

```
         3701                                                    3750
  42_2   TCGGCAGCAG AGACTGTCAA AAAACATAGA CAGCAACAAC AACAGTAACT
  42_8   CCGGCAGCAA CGCGTCTCCA CGACACTGTC GCAAAATAAC AACAGCAACT
  42_15  CCGGCAGCAA CGCGTCTCCA CGACACTGTC GCAAAATAAC AACAGCAACT
  42_5b  CCGGCAGCAA CGCGTCTCCA CGACACTGTC GCAAAATAAC AACAGCAACT
  42_1b  CCGGCAGCAA CGCGTCTCCA CGACAGTGTC GCAAAATAAC AACAGCAACT
  42_13  CCGGCAGCAA CGCGTCTCCA CGACAGTGTC GCAAAATAAC AACAGCAACT
  42_3a  CCGGCAGCAA CGCGTCTCCA CGACACTGTC GCAAAATAAC AACAGCAACT
  42_4   CCGGCAGCAA CGCGTCTCCA CGACACTGTC GCAAAATAAC AACAGCAACT
  42_5a  CCGGCAGCAA CGCGTCTCCA CGACACTGTC GCAAAATAAC AACAGCAACT
  42_10  TCGGCAGCAG AGACTGTCAA AAAACATAGA CAGCAACAAC AACAGTAACT
  42_3b  TCGGCAGCAG AGACTGTCAA AAAACATAGA CAGCAACAAC ACCAGTAACT
  42_11  TCGGCGGCAG AGACTGTCAA AAGACATAGA CAGCAACAAC AACAGTAACT
  42_6b  TCGGCAGCAG AGACTGTCAA AAAACATAGA CAGCAACAAC AACAGTAACT
  43_1   CCGTCAGCAA CGAGTTTCCA CGACACTGTC GCAAAACAAC AACAGCAATT
  43_5   CCGTCAGCAA CGAGTTTCCA CGACACTGTC GCAAAACAAC AACAGCAATT
  43_12  CCGTCAGCAA CGAGTTTCCA CGACACTGTC GCAAAACAAC AACAGCAATT
  43_20  CCGGCAGCAG CGCGTCTCCA CGACAACCAA CCAGAACAAC AACAGCAACT
  43_21  CCGGCAGCAG CGCGTCTCCA CGACAACCAA CCAGAGCAAC AACAGCAACT
  43_23  CCGGCAGCAG CGCGTCTCCA CGACAACCAA CCAGAACAAC AACAGCAACT
  43_25  CCGGCAGCAG CGCGTCTCCA CGACAACCAA CCAGAACAAC AACAGCAACT
  44_1   CCGGCAGCAA CGCGTCTCCA CGACACTGTC GCAAAATAAC AACAGCAACT
  44_5   CCGGCAGCAA CGCGTCTCCA CGACACTGTC GCAAAATAAC AACAGCAACT
 223_10  CCGGCAACAG AGAGTATCCA AGACGCTGGA TCAAAATAAC AACAGCAACT
 223_2   CCGGCAACAG AGAGTATCCA AGACGCTGGA TCAAAATAAC AACAGCAACT
 223_4   CCGGCAACAG AGAGTATCCA AGACGCTGGA TCAAAATAAC AACAGCAACT
 223_5   CCGGCAACAG AGAGTATCCA AGACGCTGGA TCAAAATAAC AACAGCAACT
 223_6   CCGGCAACAG AGAGTATCCA AGACGCTGGA TCAAAATAAC AACAGCAACT
 223_7   CCGGCAACAG AGAGTATCCA AGACGCTGGA TCAAAATAAC AACAGCAACT
  A3_4   CCGACAGCAG CGAATGTCTA AGACGGCTAA TGACAACAAC AACAGTGAAT
  A3_5   CCGACAGCAG CGAATGTCTA AGACGGCTAA TGACAACAAC AACAGTGAAT
  A3_7   CCGACAGCAG CGAATGTCTA AGACGGCTAA TGACAACAAC AACAGTGAAT
  A3_3   CCGACAGCAG CGAATGTCTA AGACGGCTAA TGACAACAAC AACAGTGAAT
  42_12  TCGGCAGCAG AGACTGTCAA AAAACATAGA CAGCAACAAC AACAGTAACT
  AAV1   TCGGCAGCAG CGCGTTTCTA AAACAAAAAC AGACAACAAC AACAGCAATT
  AAV2   CCGCCAGCAG CGAGTATCAA AGACATCTGC GGATAACAAC AACAGTGAAT
  AAV3   CCGGCAACAG AGACTTTCAA AGACTGCTAA CGACAACAAC AACAGTAACT
  AAV8   CCGCCAACAA CGCGTCTCAA CGACAACCGG GCAAAACAAC AATAGCAACT
  AAV9   CCGTCAGCAG CGCGTCTCCA CAACCACCAA CCAAAATAAC AACAGCAACT
  AAV7   CCGGCAACAA AGAGTCTCCA AAACGCTGGA TCAAAACAAC AACAGCAACT
  44_2   CCGGCAGCAA CGCGTCTCCA CGACACTGTC GCAAAATAAC AACAGCAACT
```

FIG. 1AAX

```
         3751                                                        3800
  42_2   TTGCCTGGAC CGGGGCCACT AAATACCATC TGAATGGTAG AAATTCATTA
  42_8   TTGCTTGGAC CGGTGCCACC AAGTATCATC TGAATGGCAG AGACTCTCTG
 42_15   TTGCTTGGAC CGGTGCCACC AAGTATCATC TGAATGGCAG AGACTCTCTG
 42_5b   TTGCTTGGAC CGGTGCCACC AAGTATCATC TGAATGGCAG AGACTCTCTG
 42_1b   TTGCTTGGAC CGGTGCCACC AAGTATCATC TGAATGGCAG AGACTCTCTG
 42_13   TTGCTTGGAC CGGTGCCACC AAGTATCATC TGAATGGCAG AGACTCTCTG
 42_3a   TTGCTTGGAC CGGTGCCACC AAGTATCATC TGAATGGCAG AGACTCTCTG
  42_4   TTGCTTGGAC CGGTGCCACC AAGTATCATC TGAATGGCAG AGACTCTCTG
 42_5a   TTGCTTGGAC CGGTGCCACC AAGTATCATC TGAATGGCAG AGACTCTCTG
 42_10   TTGCCTGGAC CGGGGCCACT AAATACCATC TGAATGGTAG AAATTCATTA
 42_3b   TTGCCTGGAC CGGGGCCACT AAATACCATC TGAATGGTAG AAATTCATTA
 42_11   TTGCCTGGAC CGGGGCCACT AAATACCATC TGAATGGTAG AAATTCATTA
 42_6b   TTGCCTGGAC CGGGGCCACT AAATACCATC TGAATGGTAG AAATTCATTA
  43_1   TTGCTTGGAC CGGTGCCACC AAGTATCACC TGAATGGCAG AGACTCCCTG
  43_5   TTGCTTGGAC CGGTGCCACC AAGTATCACC TGAATGGCAG AGACTCCCTG
 43_12   TTGCTTGGAC CGGTGCCACC AAGTATCACC TGAATGGCAG AGACTCCCTG
 43_20   TTGCCTGGAC GGGAGCTGCC AAGTTTAAGC TGAACGGCCG AGACTCTCTA
 43_21   TTGCCTGGAC GGGAGCTGCC AAGTTTAAGC TGAACGGCCG AGACTCTCTA
 43_23   TTGCCTGGAC GGGAGCTGCC AAGTTTAAGC TGAACGGCCG AGACTCTCTA
 43_25   TTGCCTGGAC GGGAGCTGCC AAGTTTAAGC TGAACGGCCG AGACTCTCTA
  44_1   TTGCCTGGAC CGGTGCCACC AAGTATCATC TGAATGGCAG AGACTCTCTG
  44_5   TTGCCTGGAC CGGTGCCACC AAGTATCATC TGAATGGCAG AGACTCTCTG
 223_10  TTGCCTGGAC TGGTGCCACA AAATACCATT TAAATGNAAG AAATTCATTG
 223_2   TTGCCTGGAC TGGTGCCACA AAATACCATT TAAATGGAAG AAATTCATTG
 223_4   TTGCCTGGAC TGGTGCCACA AAATACCATT TAAATGGAAG AAATTCATTG
 223_5   TTGCCTGGAC TGGTGCCACA AAATACCATT TAAATGGAAG AAATTCATTG
 223_6   TTGCCTGGAC TGGTGCCACA AAATACCATT TAAATGGAAG AAATTCATTG
 223_7   TTGCCTGGAC TGGTGCCACA AAATACCATT TAAATGGAAG AAATTCATTG
  A3_4   TTGCTTGGAC TGCAGCCACC AAATATTACC TGAATGGAAG AAATTCTCTG
  A3_5   TTGCTTGGAC TGCAGCCACC AAATATTACC CGAATGGAAG AAATTCTCTG
  A3_7   TTGCTTGGAC TGCAGCCACC AAATATTACC TGAATGGAAG AAATTCTCTG
  A3_3   TTGCTTGGAC TGCAGCCACC AAATATTACC TGAATGGAAG AAATTCTCTG
 42_12   TTGCCTGGAC CGGGGCCACT AAATACCATC TGAATGGTAG AAATTCATTA
  AAV1   TTACCTGGAC TGGTGCTTCA AAATATAACC TCAATGGGCG TGAATCCATC
  AAV2   ACTCGTGGAC TGGAGCTACC AAGTACCACC TCAATGGCAG AGACTCTCTG
  AAV3   TTCCTTGGAC AGCGGCCAGC AAATATCATC TCAATGGCCG CGACTCGCTG
  AAV8   TTGCCTGGAC TGCTGGGACC AAATACCATC TGAATGGAAG AAATTCATTG
  AAV9   TTGCGTGGAC GGGAGCTGCT AAATTCAAGC TGAACGGGAG AGACTCGCTA
  AAV7   TTGCTTGGAC TGGTGCCACC AAATATCACC TGAACGGCAG AAACTCGTTG
  44_2   TTGCCTGGAC CGGTGCCACC AAGTATCATC TGAATGGCAG AGACTCTCTG
```

FIG. 1AAY

```
          3801                                                        3850
  42_2    ACCAACCCGG  GCGTAGCCAT  GGCCACCAAC  AAGGACGACG  AGGACCAGTT
  42_8    GTAAATCCCG  GTGTCGCTAT  GGCAACGCAC  AAGGACGACG  AAGAGCGATT
  42_15   GTAAATCCCG  GTGTCGCTAT  GGCAACGCAC  AAGGACGACG  AAGAGCGATT
  42_5b   GTAAATCCCG  GTGTCGCTAT  GGCAACGCAC  AAGGACGACG  AAGAGCGATT
  42_1b   GTAAATCCCG  GTGTCGCTAT  GGCAACGCAC  AAGGGCGACG  AAGAGCGATT
  42_13   GTAAATCCCG  GTGTCGCTAT  GGCAACGCAC  AAGGGCGACG  AAGAGCGATT
  42_3a   GTAAATCCCG  GTGTCGCTAT  GGCAACGCAC  AAGGACGACG  AAGAGCGATT
  42_4    GTAAATCCCG  GTGTCGCTAT  GGCAACGCAC  AAGGACGACG  AAGAGCGATT
  42_5a   GTAAATCCCG  GTGTCGCTAT  GGCAACGCAC  AAGGACGACG  AAGAGCGATT
  42_10   ACCAACCCGG  GCGTAGCCAT  GGCCACCAAC  AAGGACGACG  AGGACCAGTT
  42_3b   ACCAACCCGG  GCGTAGCCAT  GGCCACCAAC  AAGGACGACG  AGGACCAGTT
  42_11   ACCAACCCGG  GCGTAGCCAT  GGCCACCAAC  AAGGACGACG  AGGACCAGTT
  42_6b   ACCAACCCGG  GCGTAGCCAT  GGCCACCAAC  AAGGACGACG  AGGACCAGTT
  43_1    GTTAATCCCG  GCGTTGCCAT  GGCTACCCAC  AAGGACGACG  AGGAGCGCTT
  43_5    GTTAATCCCG  GCGTTGCCAT  GGCTACCCAC  AAGGACGACG  AGGAGCGCTT
  43_12   GTTAATCCCG  GCGTTGCCAT  GGCTACCCAC  AAGGACGACG  AGGAGCGCTT
  43_20   ATGAATCCGG  GCGTGGCAAT  GGCTTCCCAC  AAGGATGACG  ACGACCGCTT
  43_21   ATGAATCCGG  GCGTGGCAAT  GGCTTCCCAC  AAGGATGACG  ACGACCGCTT
  43_23   ATGAATCCGG  GCGTGGCAAT  GGCTTCCCAC  AAGGATGACG  ACGACCGCTT
  43_25   ATGAATCCGG  GCGTGGCAAT  GGCTTCCCAC  AAGGATGACG  ACGACCGCTT
  44_1    GTAAATCCCG  GTGTCGCTAT  GGCAACCCAC  AAGGACGACG  AAGAGCGATT
  44_5    GTAAATCCCG  GTGTCGCTAT  GGCAACCCAC  AAGGACGACG  AAGAGCGATT
  223_10  GTTAATCCCG  GTGTCGCCAT  GGCAACCCAC  AAGGACGACG  AGGAACGCTT
  223_2   GTTAATCCCG  GTGTCGCCAT  GGCAACCCAC  AAGGACGACG  AGGAACGCTT
  223_4   GTTAATCCCG  GTGTCGCCAT  GGCAACCCAC  AAGGACGACG  AGGAACGCTT
  223_5   GTTAATCCCG  GTGTCGCCAT  GGCAACCCAC  AAGGACGACG  AGGAACGCTT
  223_6   GTTAATCCCG  GTGTCGCCAT  GGCAACCCAC  AAGGACGACG  AGGAACGCTT
  223_7   GTTAATCCCG  GTGTCGCCAT  GGCAACCCAC  AAGGACGACG  AGGAACGCTT
  A3_4    GTCAATCCCG  GGCCCCCAAT  GGCCAGTCAC  AAGGACGATG  AGGAAAAGTA
  A3_5    GTCAATCCCG  GGCCCCCAAT  GGCCAGTCAC  AAGGACGATG  AGGAAAAGTA
  A3_7    GTCAATCCCG  GGCCCCCAAT  GGCCAGTCAC  AAGGACGATG  AGGAAAAGTA
  A3_3    GTCAATCCCG  GGCCCCCAGT  GGCCAGTCAC  AAGGACGATG  AGGAAAAGTA
  42_12   ACCAACCCGG  GCGTAGCCAT  GGCCACCAAC  AAGGACGACG  AGGACCAGTT
  AAV1    ATCAACCCTG  GCACTGCTAT  GGCCTCACAC  AAAGACGACG  AAGACAAGTT
  AAV2    GTGAATCC..  GGCC....AT  GGCAAGCCAC  AAGGACGATG  AAGAAAAGTT
  AAV3    GTGAATCCAG  GACCAGCTAT  GGCCAGTCAC  AAGGACGATG  AAGAAAAATT
  AAV8    GCTAATCCTG  GCATCGCTAT  GGCAACACAC  AAAGACGACG  AGGAGCGTTT
  AAV9    ATGAATCCTG  GCGTGGCTAT  GGCATCGCAC  AAAGACGACG  AGGACCGCTT
  AAV7    GTTAATCCCG  GCGTCGCCAT  GGCAACTCAC  AAGGACGACG  AGGACCGCTT
  44_2    GTAAATCCCG  GTGTCGCTAT  GGCAACCCAC  AAGGACGACG  AAGAGCGATT
```

FIG. 1AAZ

```
          3851                                                              3900
  42_2    CTTTCCCATC  AACGGAGTGC  TGGTTTTTGG  CGAAACGGGG  GCTGCCAACA
  42_8    TTTTCCATCC  AGCGGAGTCT  TGATGTTTGG  GAAACAGGGA  GCTGGAAA..
  42_15   TTTTCCATCC  AGCGGAGTCT  TGATGTTTGG  GAAACAGGGA  GCTGGAAA..
  42_5b   TTTTCCATCC  AGCGGAGTCT  TGATGTTTGG  GAAACAGGGA  GCTGGAAA..
  42_1b   TTTTCCATCC  AGCGGAGTCT  TGATGTTTGG  GAAACAGGGA  GCTGGAAA..
  42_13   TTTTCCATCC  AGCGGAGTCT  TGATGTTTGG  GAAACAGGGA  GCTGGAAA..
  42_3a   TTTTCCATCC  AGCGGAGTCT  TGATGTTTGG  GAAACAGGGA  GCTGGAAA..
  42_4    TTTTCCATCC  AGCGGAGTCT  TGATGTTTGG  GAAACAGGGA  GCTGGAAA..
  42_5a   TTTTCCATCC  AGCGGAGTCT  TGATGTTTGG  GAAACAGGGA  GCTGGAAA..
  42_10   CTTTCCCATC  AACGGAGTGC  TGGTTTTTGG  CAAAACGGGG  GCTGCCAACA
  42_3b   CTTTCCCATC  AACGGAGTGC  TGGTTTTTGG  CAAAACGGGG  GCTGCCAACA
  42_11   CTTTCCCATC  AACGGAGTGC  TGGTTTTTGG  CAAAACGGGG  GCTGCCAACA
  42_6b   CTTTCCCATC  AACGGAGTGC  TGGTTTTTGG  CAAAACGGGG  GCTGCCAACA
  43_1    CTTCCCGTCA  AGCGGAGTTC  TAATGTTTGG  CAAGCAGGGG  GCTGGAAA..
  43_5    CTTCCCGTCA  AGCGGAGTTC  TAATGTTTGG  CAAGCAGGGG  GCTGGAAA..
  43_12   CTTCCCGTCA  AGCGGAGTTC  TAATGTTTGG  CAAGCAGGGG  GCTGGAAA..
  43_20   CTTCCCTTCG  AGCGGGGTCC  TGATTTTTGG  CAAGCAAGGA  GCCGGGAA..
  43_21   CTTCCCTTCG  AGCGGGGTCC  TGATTTTTGG  CAAGCAAGGA  GCCGGGAA..
  43_23   CTTCCCTTCG  AGCGGGGTCC  TGATTTTTGG  CAAGCAAGGA  GCCGGGAA..
  43_25   CTTCCCTTCG  AGCGGGGTCC  TGATTTTTGG  CAAGCAAGGA  GCCGGGAA..
  44_1    TTTTCCGTCC  AGCGGAGTCT  TAATGTTTGG  GAAACAGGGA  GCTGGAAA..
  44_5    TTTTCCGTCC  AGCGGAGTCT  TAATGTTTGG  GAAACAGGGA  GCTGGAAA..
  223_10  CTTCCCTTCG  AGCGGAGTTC  TAATTTTTGG  CAAAACTGGA  GCAGCTAATA
  223_2   CTCCCCTTCG  AGCGGAGTTC  TAATTTTTGG  CAAAACTGGA  GCAGCTAATA
  223_4   CTTCCCTTCG  AGCGGAGTTC  TAATTTTTGG  CAAAACTGGA  GCAGCTAATA
  223_5   CTTCCCTTCG  AGCGGAGTTC  TAATTTTTGG  CAAAACTGGA  GCAGCTAATA
  223_6   CTTCCCTTCG  AGCGGAGTTC  TAATTTTTGG  CAAAACTGGA  GCAGCTAATA
  223_7   CTTCCCTTCG  AGCGGAGTTC  TAATTTTTGG  CAAAACTGGA  GCAGCTAATA
  A3_4    TTTCCCCATG  CACGGAAATC  TCATCTTTGG  AAAACAAGGC  ACAGGAAC..
  A3_5    TTTCCCCATG  CACGGAAATC  TCATCTTTGG  AAAACAAGGC  ACAGGAAC..
  A3_7    TTTCCCCATG  CACGGAAATC  TCATCTTTGG  AAAACAAGGC  ACAGGAAC..
  A3_3    TTTCCCCATG  CACGGAAATC  TCATCTTTGG  AAAACAAGGC  ACAGGAAC..
  42_12   CTTCCCCATC  AACGGAGTGC  TGGTTTTTGG  CAAAACGGGG  GCTGCCAACA
  AAV1    CTTTCCCATG  AGCGCTGTCA  TGATTTTTGG  AAAACAGAGC  GCCGGAGC..
  AAV2    TTTTCCTCAG  AGCGGGGTTC  TCATCTTTGG  GAAGCAAGGC  TCAGAGAA..
  AAV3    TTTCCCTATG  CACGGCAATC  TAATATTTGG  CAAAGAACGG  ACAACGGC..
  AAV8    TTTTCCCAGT  AACGGATCC   TGATTTTTGG  CAAACAAAAT  GCTGCCAG..
  AAV9    CTTTCCATCA  AGTGGCGTTC  TCATATTTGG  CAAGCAAGGA  GCCGGGAA..
  AAV7    TTTCCCATCC  AGCGGAGTCC  TGATTTTTGG  AAAAACTGGA  GCAACTAACA
  44_2    TTTTCCGTCC  AGCGGAGTCT  TAATGTTTGG  GAAACAGGGA  GCTGGAAA..
```

FIG. 1AAAA

```
        3901                                                          3950
 42_2   AGACAACGCT GGAA......  AACGTGCTAA TGACCAGCGA GGAGGAGATC
 42_8   AGACAACG.T GGACTATAGC AGCGTTATGC TAACCAGTGA GGAAGAAATC
 42_15  AGACAACG.T GGACTATAGC AGCGTTATGC TAACCAGTGA GGAAGAAATC
 42_5b  AGACAACG.T GGACTATAGC AGCGTTATGC TAACCAGTGA GGAAGAAATC
 42_1b  AGACAACG.T AGACTATAGC AGCGTTATGC TAACCAGTGA GGAAGAAATC
 42_13  AGACAACG.T GGACTATAGC AGCGTTATGC TAACCAGTGA GGAAGAAATC
 42_3a  AGACAACG.T GGACTATAGC AGCGTTATGC TAACCAGTGA GGAAGAAATC
 42_4   AGACAACG.T GGACTATAGC AGCGTTATGC TAACCAGTGA GGAAGAAATC
 42_5a  AGACAACG.T GGACTATAGC AGCGTTATGC TAACCAGTGA GGAAGAAATC
 42_10  AGACAACGCT GGAA......  AACGTGCTAA TGACCAGCGA GGAGGAGATC
 42_3b  AGACAACGCT GGAA......  AACGTGCTAA TGACCAGCGA GGAGGAGATC
 42_11  AGACAACGCT GGAA......  AACGTGCTAA TGACCAGCGA GGAGGAGATC
 42_6b  AGACAACGCT GGAA......  AACGTGCTAA TGACCAGCGA GGAGGAGATC
 43_1   AGACAATG.T GGACTACAGC AGCGTGATGC TCACCAGCGA AGAAGAAATT
 43_5   AGACAATG.T GGACTACAGC AGCGTGATGC TCACCAGCGA AGAAGAAATT
 43_12  AGACAATG.T GGACTACAGC AGCGTGATGC TCACCAGCGA AGAAGAAATT
 43_20  CGATGGAG.T GGATTACAGC CAAGTGCTGA TTACAGATGA GGAAGAAATC
 43_21  CGATGGAG.T GGATTACAGC CAAGTGCTGA TTACAGATGA GGAAGAAATC
 43_23  CGATGGAG.T GGATTACAGC CAAGTGCTGA TTACAGATGA GGAAGAAATC
 43_25  CGATGGAG.T GGATTACAGC CAAGTGCTGA TTACAGATGA GGAAGAAATC
 44_1   AGACAACG.T GGACTATAGC AGCGTTATGC TAACCAGTGA GGAAGAAATT
 44_5   AGACAACG.T GGACTATAGC AGCGTTATGC TAACCAGTGA GGAAGAAATT
223_10  AAACTACATT AGAA......  AACGTGCTCA TGACAAATGA AGAAGAAATT
223_2   AAACTACATT AGAA......  AACGTGCTCA TGACAAATGA AGAAGAAATT
223_4   AAACTACATT AGAA......  AACGTGCTCA TGACAAATGA AGAAGAAATT
223_5   AAACTACATT AGAA......  AACGTGCTCA TGACAAATGA AGAAGAAATT
223_6   AAACTACATT AGAA......  AACGTGCTCA TGACAAATGA AGAAGAAATT
223_7   AAACTACATT AGAA......  AACGTGCTCA TGACAAATGA AGAAGAAATT
 A3_4   TACCAATG.T GGACATTGAA TCAGTGCTTA TTACAGACGA AGAAGAAATC
 A3_5   TACCAATG.T GGACATTGAA TCAGTGCTTA TTACAGACGA AGAAGAAATC
 A3_7   TACCAATG.T GGACATTGAA TCAGTGCTTA TTACAGACGA AGAAGAAATC
 A3_3   TACCAATG.T GGACATTGAA TCAGTGCTTA TTACAGACGA AGAAGAAATC
 42_12  AGACAACGCT GGAA......  AACGTGCTAA TGACCAGCGA GGAGGAGATC
 AAV1   TTCAAACA.C TGCATTGGAC AATGTCATGA TTACAGACGA AGAGGAAATT
 AAV2   AACAAATG.T GAACATTGAA AAGGTCATGA TTACAGACGA AGAGGAAATC
 AAV3   AAGTAACG.C AGAATTAGAT AATGTAATGA TTACGGATGA AGAACAGATT
 AAV8   AGACAATG.C GGATTACAGC GATGTCATGC TCACCAGCGA GGAAGAAATC
 AAV9   CGATGGAG.T CGACTACAGC CAGGTGCTGA TTACAGATGA GGAAGAAATT
 AAV7   AAACTACATT GGAA......  AATGTGTTAA TGACAAATGA AGAAGAAATT
 44_2   AGACAACG.T GGACTATAGC AGCGTTATGC TAACCAGTGA GGAAGAAATT
```

FIG. 1AAAB

|        | 3951       |            |            |            | 4000       |
|--------|------------|------------|------------|------------|------------|
| 42_2   | AAAACCACCA | ATCCCGTGGC | TACAGAAGAA | TACGGTGTGG | TCTCCAGCAA |
| 42_8   | AAAACCACCA | ACCCAGTGGC | CACAGAACAG | TACGGCGTGG | TGGCCGATAA |
| 42_15  | AAAACCACCA | ACCCAGTGGC | CACAGAACAG | TACGGCGTGG | TGGCCGATAA |
| 42_5b  | AAAACCACCA | ACCCAGTGGC | CACAGAACAG | TACGGCGTGG | TGGCCGATAA |
| 42_1b  | AAAACCACCA | ACCCAGTGGC | CACAGAACAG | TACGGCGTGG | TGGCCGATAA |
| 42_13  | AAAACCACCA | ACCCAGTGGC | CACAGAACAG | TACGGCGTGG | TGGCCGATAA |
| 42_3a  | AAAACCACCA | ACCCAGTGGC | CACAGAACAG | TACGGCGTGG | TGGCCGATAA |
| 42_4   | AAAACCACCA | ACCCAGTGGC | CACAGAACAG | TACGGCGTGG | TGGCCGATAA |
| 42_5a  | AAAACCACCA | ACCCAGTGGC | CACAGAACAG | TACGGCGTGG | TGGCCGATAA |
| 42_10  | AAAACCACCA | ATCCCGTGGC | TACAGAAGAA | TACGGTGTGG | TCTCCAGCAA |
| 42_3b  | AAAACCACCA | ATCCCGTGGC | TACAGAACAG | TACGGTGTGG | TCTCCAGCAA |
| 42_11  | AAAACCACCA | ATCCCGTGGC | TACAGAAGAA | TACGGTGTGG | TCTCCAGCAA |
| 42_6b  | AAAACCACCA | ATCCCGTGGC | TACAGAAGAA | TACGGTGTGG | TCTCCAGCAA |
| 43_1   | AAAACTACTA | ACCCAGTGGC | TACAGAGCAG | TATGGTGTGG | TGGCAGACAA |
| 43_5   | AAAACTACTA | ACCCAGTGGC | TACAGAGCAG | TATGGTGTGG | TGGCAGACAA |
| 43_12  | AAAACTACTA | ACCCAGTGGC | TACAGAGCAG | TATGGTGTGG | TGGCAGACAA |
| 43_20  | AAGGCTACCA | ACCCCGTGGC | CACAGAAGAA | TATGGAGCAG | TGGCCATCAA |
| 43_21  | AAGGCTACCA | ACCCCGTGGC | CACAGAAGAA | TATGGAGCAG | TGGCCATCAA |
| 43_23  | AAGGCTACCA | ACCCCGTGGC | CACAGAAGAA | TATGGAGCAG | TGGCCATCAA |
| 43_25  | AAGGCTACCA | ACCCCGTGGC | CACAGAAGAA | TATGCAGCAG | TGGCCATCAA |
| 44_1   | AAAACCACCA | ACCCAGTGGC | CACGGAACAG | TACGGCGTGG | TGGCCGATAA |
| 44_5   | AAAACCACCA | ACCCAGTGGC | CACAGAACAG | TACGGCGTGG | TGGCCGATAA |
| 223_10 | CGTCCTACCA | ACCCGGTAGC | TACCGAGGAA | TACGGGATTG | TAAGCAGCAA |
| 223_2  | CGTCCTACCA | ACCCGGTAGC | TACCGAGGAA | TACGGGATTG | TAAGCAGCAA |
| 223_4  | CGTCCTACCA | ACCCGGTAGC | TACCGAGGAA | TACGGGATTG | TAAGCAGCAA |
| 223_5  | CGTCCTACCA | ACCCGGTAGC | TACCGAGGAA | TACGGGATTG | TAAGCAGCAA |
| 223_6  | CGTCCTACCA | ACCCGGTAGC | TACCGAGGAA | TACGGGATTG | TAAGCAGCAA |
| 223_7  | CGTCCTACCA | ACCCGGTAGC | TACCGAGGAA | TACGGGATTG | TAAGCAGCAA |
| A3_4   | AGAACAACTA | ATCCTGTGGC | TACAGAACAA | TACGGACAGG | TTGCCACCAA |
| A3_5   | AGAACGACTA | ATCCTGTGGC | TACAGAACAA | TACGGACAGG | TTGCCACCAA |
| A3_7   | AGAACAACTA | ATCCTGTGGC | TACAGAACAA | TACGGACAGG | TTGCCACCAA |
| A3_3   | AGAACAACTA | ATCCTGTGGC | TACAGAACAA | TACGGACAGG | TTGCCACCAA |
| 42_12  | AAAACCACCA | ATCCCGTGGC | TACAGAAGAA | TACGGTGTGG | TCTCCAGCAA |
| AAV1   | AAAGCCACTA | ACCCTGTGGC | CACCGAAAGA | TTTGGGACCG | TGGCAGTCAA |
| AAV2   | GGAACAACCA | ATCCCGTGGC | TACGGAGCAG | TATGGTTCTG | TATCTACCAA |
| AAV3   | CGTACCACCA | ATCCTGTGGC | AACAGAGCAG | TATGGAACTG | TGGCAAATAA |
| AAV8   | AAAACCACTA | ACCCTGTGGC | TACAGAGGAA | TACGGTATCG | TGGCAGATAA |
| AAV9   | AAAGCCACCA | ACCCTGTAGC | CACAGAGGAA | TACGGAGCAG | TGGCCATCAA |
| AAV7   | CGTCCTACTA | ATCCTGTAGC | CACGGAAGAA | TACGGGATAG | TCAGCAGCAA |
| 44_2   | AAAACCACCA | ACCCAGTGGC | CACAGAACAG | TACGGCGTGG | TGGCCGATAA |

FIG. 1AAAC

```
          4001                                                    4050
  42_2    CCTGCAATCG TCTACGGCCG GACCCCAGAC ACAGACTGTC AACAGCCAGG
  42_8    CCTGCAACAG CAAAACGCCG CTCCTATTGT AGGGGCCGTC AACAGTCAAG
  42_15   CCTGCAACAG CAAAACGCCG CTCCTATTGT AGGGGCCGTC AACAGTCAAG
  42_5b   CCTGCAACAG CAAAACGCCG CTCCTATTGT AGGGGCCGTC AACAGTCAAG
  42_1b   CCTGCAACAG CAAAACGCCG CTCCTATTGT AGGGGCCGTC AACAGTCAAG
  42_13   CCTGCAACAG CAAAACGCCG CTCCTATTGT AGGGGCCGTC AACAGTCAAG
  42_3a   CCTGCAACAG CAAAACGCCG CTCCTATTGT AGGGGCCGTC AACAGTCAAG
  42_4    CCTGCAACAG CAAAACGCCG CTCCTATTGT AGGGGCCGTC AACAGTCAAG
  42_5a   CCTGCAACAG CAAAACGCCG CTCCTATTGT AGGGGCCGTC AACAGTCAAG
  42_10   CCTGCAATCG TCTACGGCCG GACCCCAGAC ACAGACTGTC AACAGCCAGG
  42_3b   CCTGCAATCG TCTACGGCCG GACCCCAGAC ACAGACTGTC AACAGCCAGG
  42_11   CCTGCAATCG TCTACGGCCG GACCCCAGAC ACAGACTGTC AACAGCCAGG
  42_6b   CCTGCAATCG TCTACGGCCG GACCCCAGAC ACAGACTGTC AACAGCCAGG
  43_1    CCTGCAGCAG ACCAACGGAG CTCCCATTGT GGGAACTGTC AACAGCCAGG
  43_5    CCTGCAGCAG ACCAACGGAG CTCCCATTGT GGGAACTGTC AACAGCCAGG
  43_12   CCTGCAGCAG ACCAACGGAG CTCCCATTGT GGGAACTGTC AACAGCCAGG
  43_20   CAACCAGGCC GCCAATACGC AGGCGCAGAC CGGACTCGTG CACAACCAGG
  43_21   CAACCAGGCC GCCAATACGC AGGCGCAGAC CGGACTCGTG CACAACCAGG
  43_23   CAACCAGGCC GCCAATACGC AGGCGCAGAC CGGACTCGTG CACAACCAGG
  43_25   CAACCAGGCC GCCAATACGC AGGCGCAGAC CGGACTCGTG CACAACCAGG
  44_1    CCTGCAACAG CAAAACGCCG CTCCTATTGT AGGGGCCGTC AACAGTCAAG
  44_5    CCTGCAACAG CAAAACGCCG CTCCTATTGT AGGGGCCGTC AACAGTCAAG
  223_10  CTTGCAGGCG GCTAGCACCG CAGCCCAGAC ACAAGTTGTT AACAACCAGG
  223_2   CTTGCAGGCG GCTAGCACCG CAGCCCAGAC ACAAGTTGTT AACAACCAGG
  223_4   CTTGCAGGCG GCTAGCACCG CAGCCCAGAC ACAAGTTGTT AACAACCAGG
  223_5   CTTGCAGGCG GCTAGCACCG CAGCCCAGAC ACAAGTTGTT AACAACCAGG
  223_6   CTTGCAGGCG GCTAGCACCG CAGCCCAGAC ACAAGTTGTT AACAACCAGG
  223_7   CTTGCAGGCG GCTAGCACCG CAGCCCAGAC ACAAGTTGTT AACAACCAGG
  A3_4    CCATCAGAGT CAGGACACCA CAGCTTCCTA TGGAAGTGTG GACAGCCAGG
  A3_5    CCGTCAGAGT CAGAACACCA CAGCTTCCTA TGGAAGTGTG GACAGCCAGG
  A3_7    CCATCAGAGT CAGAACACCA CAGCTTCCTA TGGAAGTGTG GACAGCCAGG
  A3_3    CCATCAGAGT CAGAACACCA CAGCTTCCTA TGGAAGTGTG GACAGCCAGG
  42_12   CCTGCAATCG TCTACGGCCG GACCCCAGAC ACAGACTGTC AACAGCCAGG
  AAV1    TTTCCAGAGC AGCAGCACAG ACCCTGCGAC GGAGATGTG  CATGCTATGG
  AAV2    CCTCCAGAGA GGCAACAGAC AAGCAGCTAC CGCAGATGTC AACACACAAG
  AAV3    CTTGCAGAGC TCAAATACAG CTCCCACGAC TGGAACTGTC AATCATCAGG
  AAV8    CTTGCAGCAG CAAAACACGG CTCCTCAAAT TGGAACTGTC AACAGCCAGG
  AAV9    CAACCAGGCC GCTAACACGC AGGCGCAAAC TGGACTTGTG CATAACCAGG
  AAV7    CTTACAAGCG GCTAATACTG CAGCCCAGAC ACAAGTTGTC AACAACCAGG
  44_2    CCTGCAACAG CAAAACGCCG CTCCTATTGT AGGGGCCGTC AACAGTCAAG
```

FIG. 1AAAD

```
           4051                                                          4100
  42_2    GGGCTCTGCC  CGGCATGGTC  TGGCAGAACC  GGGACGTGTA  CCTGCAGGGT
  42_8    GAGCCTTACC  TGGCATGGTC  TGGCAGAACC  GGGACGTGTA  CCTGCAGGGT
  42_15   GAGCCTTACC  TGGCATGGTC  TGGCAGAACC  GGGACGTGTA  CCTGCAGGGT
  42_5b   GAGCCTTACC  TGGCATGGTC  TGGCAGAACC  GGGACGTGTA  CCTGCAGGGT
  42_1b   GAGCCTTACC  TGGCATGGTC  TGGCAGAACC  GGGACGTGTA  CCTGCAGGGT
  42_13   GAGCCTTACC  TGGCATGGTC  TGGCAGAACC  GGGACGTGTA  CCTGCAGGGT
  42_3a   GAGCCTTACC  TGGCATGGTC  TGGCAGAACC  GGGACGTGTA  CCTGCAGGGT
  42_4    GAGCCTTACC  TGGCATGGTC  TGGCAGAACC  GGGACGTGTA  CCTGCAGGGT
  42_5a   GAGCCTTACC  TGGCATGGCC  TGGCAGAACC  GGGACGTGTA  CCTGCAGGGT
  42_10   GGGCTCTGCC  CGGCATGGTC  TGGCAGAACC  GGGACGTGTA  CCTGCAGGGT
  42_3b   GGGCTCTGCC  CGGCATGGTC  TGGCAGAACC  GGGACGTGTA  CCTGCAGGGT
  42_11   GGGCTCTGCC  CGGCATGGTC  TGGCAGAACC  GGGACGTGTA  CCTGCAGGGT
  42_6b   GGGCTCTGCC  CGGCATGGTC  TGGCAGAACC  GGGACGTGTA  CCTGCAGGGT
  43_1    GGGCCTTACC  TGGTATGGTC  TGGCAAAACC  GGGACGTGTA  CCTGCAGGGC
  43_5    GGGCCTTACC  TGGTATGGTC  TGGCAAAACC  GGGACGTGTA  CCTGCAGGGC
  43_12   GGGCCTTACC  TGGTATGGTC  TGGCAAAACC  GGGACGTGTA  CCTGCAGGGC
  43_20   GGGTGATTCC  CGGCATGGTG  TGGCAGAATA  GAGACGTGTA  CCTGCAGGGT
  43_21   GGGTGATTCC  CGGCATGGTG  TGGCAGAATA  GAGACGTGTA  CCTGCAGGGT
  43_23   GGGTGATTCC  CGGCATGGTG  TGGCAGAATA  GAGACGTGTA  CCTGCAGGGT
  43_25   GGGTGATTCC  CGGCATGGTG  TGGCAGAATA  GAGACGTGTA  CCTGCAGGGT
  44_1    GAGCCTTACC  TGGCATGGTC  TGGCAGAACC  GGGACGTGTA  CCTGCAGGGT
  44_5    GAGCCTTACC  TGGCATGGTC  TGGCAGAACC  GGGACGTGTA  CCTGCAGGGT
  223_10  GAGCCTTACC  TGGCATGGTC  TGGCAGAACC  GGGACGTGTA  CCTGCAAGGT
  223_2   GAGCCTTACC  TGGCATGGTC  TGGCAGAACC  GGGACGTGTA  CCTGCAAGGT
  223_4   GAGCCTTACC  TGGCATGGTC  TGGCAGAACC  GGGACGTGTA  CCTGCAAGGT
  223_5   GAGCCTTACC  TGGCATGGTC  TGGCAGAACC  GGGACGTGTA  CCTGCAAGGT
  223_6   GAGCCTTACC  TGGCATGGTC  TGGCAGAACC  GGGACGTGTA  CCTGCAAGGT
  223_7   GAGCCTTACC  TGGCATGGTC  TGGCAGAACC  GGGACGTGTA  CCTGCAAGGT
  A3_4    GAATCTTACC  TGGAATGGTG  TGGCAGGACC  GCGATGTCTA  TCTTCAAGGT
  A3_5    GAATCTTACC  TGGAATGGTG  TGGCAGGACC  GCGATGTCTA  TCTTCAAGGT
  A3_7    GAATCTTACC  TGGAATGGTG  TGGCAGGACC  GCGATGTCTA  TCTTCAAGGT
  A3_3    GAATCTTACC  TGGAATGGTG  TGGCAGGACC  GCGATGTCTA  TCTTCAAGGT
  42_12   GGGCTCTGCC  CGGCATGGTC  TGGCAGAACC  GGGACGTGTA  CCTGCAGGGT
  AAV1    GAGCATTACC  TGGCATGGTG  TGGCAAGATA  GAGACGTGTA  CCTGCAGGCT
  AAV2    GCGTTCTTCC  AGGCATGGTC  TGGCAGGACA  GAGATGTGTA  CCTTCAGGGG
  AAV3    GGGCCTTACC  TGGCATGGTG  TGGCAAGATC  GTGACGTGTA  CCTTCAAGGA
  AAV6    GGGCCTTACC  CGGTATGGTC  TGGCAGAACC  GGGACGTGTA  CCTGCAGGGT
  AAV9    GAGTTATTCC  TGGTATGGTC  TGGCAGAACC  GGGACGTGTA  CCTGCAGGGC
  AAV7    GAGCCTTACC  TGGCATGGTC  TGGCAGAACC  GGGACGTGTA  CCTGCAGGGT
  44_2    GAGCCTTACC  TGGCATGGTC  TGGCAGAACC  GGGACGTGTA  CCTGCAGGGT
```

FIG. 1AAAE

```
          4101                                                    4150
42_2     CCC.ATCTGG  GCCAAAATTC  CTCACACGGA  CGGCAACTTT  CACCCGTCTC
42_8     CCT.ATCTGG  GCCAAGATTC  CTCACACGGA  CGGCAACTTT  CATCCTTCGC
42_15    CCT.ATCTGG  GCCAAGATTC  CTCACACGGA  CGGCAACTTT  CATCCTTCGC
42_5b    CCT.ATCTGG  GCCAAGATTC  CTCACACGGA  CGGCAACTTT  CATCCTTCGC
42_1b    CCT.ATCTGG  GCCAAGATTC  CTCACACGGA  CGGCAACTTT  CATCCTTCGC
42_13    CCT.ATCTGG  GCCAAGATTC  CTCACACGGA  CGGCAACTTT  CATCCTTCGC
42_3a    CCT.ATCTGG  GCCAAGATTC  CTCACACGGA  CGGCAACTTT  CATCCTTCGC
42_4     CCT.ATCTGG  GCCAAGATTC  CTCACACGGA  CGGCAACTTT  CATCCTTCGC
42_5a    CCT.ATCTGG  GCCAAGATTC  CTCACACGGA  CGGCAACTTT  CATCCTTCGC
42_10    CCC.ATCTGG  GCCAAAATTC  CTCACACGGA  CGGCAACTTT  CACCCGTCTC
42_3b    CCC.ATCTGG  GCCAAAATTC  CTCACACGGA  CGGCAACTTT  CACCCGTCTC
42_11    CCC.ATCTGG  GCCAAAATTC  CTCACACGGA  CGGCAACTTT  CACCCGTCTC
42_6b    CCC.ATCTGG  GCCAAAATTC  CTCACACGGA  CGGCAACTTT  CACCCGTCTC
43_1     CCC.ATCTGG  GCCAAAATTC  CTCACACGGA  CGGCAACTTT  CATCCTTCGC
43_5     CCC.ATCTGG  GCCAAAATTC  CTCACACGGA  CGGCAACTTT  CATCCTTCGC
43_12    CCC.ATCTGG  GCCAAAATTC  CTCACACGGA  CGGCAACTTT  CATCCTTCGC
43_20    CCC.ATCTGG  GCCAAAATTC  CTCACACGGA  CGGCAACTTT  CACCCGTCTC
43_21    CCC.ATCTGG  GCCAAAATTC  CTCACACGGA  CGGCAACTTT  CACCCGTCTC
43_23    CCC.ATCTGG  GCCAAAATTC  CTCACACGGA  CGGCAACTTT  CACCCGTCTC
43_25    CCC.ATCTGG  GCCAAAATTC  CTCACACGGA  CGGCAACTTT  CACCCGTCTC
44_1     CCT.ATCTGG  GCCAAGATTC  CTCACACGGA  CGGAAACTTT  CATCCCTCGC
44_5     CCT.ATCTGG  GCCAAGATTC  CTCACACGGA  CGGAAACTTT  CATCCCTCGC
223_10   CCC.ATTTGG  GCCAAGATTC  CTCACACGGA  CGGCAACTTT  CACCCGTCTC
223_2    CCC.ATTTGG  GCCAAGATTC  CTCACACGGA  CGGCAACTTT  CACCCGTCTC
223_4    CCC.ATTTGG  GCCAAGATTC  CTCACACGGA  CGGCAACTTT  CACCCGTCTC
223_5    CCC.ATTTGG  GCCAAGATTC  CTCACACGGA  CGGCAACTTT  CACCCGTCTC
223_6    CCC.ATTTGG  GCCAAGATTC  CTCACACGGA  CGGCAACTTT  CACCCGTCTC
223_7    CCC.ATTTGG  GCCAAGATTC  CTCACACGGA  CGGCAACTTT  CACCCGTCTC
A3_4     CCC.ATTTGG  GCCAAAACTC  CTCACACGGA  CGGACACTTT  CATCCTTCTC
A3_5     CCC.ATTTGG  GCCAAAACTC  CTCACACGGA  CGGACACTTT  CATCCTTCTC
A3_7     CCC.ATTTGG  GCCAAAACTC  CTCACACGGA  CGGACACTTT  CATCCTTCTC
A3_3     CCC.ATTTGG  GCCAAAACTC  CTCACACGGA  CGGACACTTT  CATCCTTCTC
42_12    CCC.ATCTGG  GCCAAAATTC  CTCACACGGA  CGGCAACTTT  CACCCGTCTC
AAV1     CCC.ATTTGG  GCCAAAATTC  CTCACACAGA  TGGACACTTT  CACCCGTCTC
AAV2     CCC.ATCTGG  GCAAAGATTC  CACACACGGA  CGGACATTTT  CACCCCTCTC
AAV3     CCT.ATCTGG  GCAAAGATTC  CTCACACGGA  TGGACACTTT  CATCCTTCTC
AAV8     CCC.ATCTGG  GCCAAGATTC  CTCACACGGA  CGGCAACTTC  CACCCGTCTC
AAV9     CCCTATTTGG  GCTAAAATAC  CTCACACAGA  TGGCAACTTT  CACCCGTCTC
AAV7     CCC.ATCTGG  GCCAAGATTC  CTCACACGGA  TGGCAACTTT  CACCCGTCTC
44_2     CCT.ATCTGG  GCCAAGATTC  CTCACACGGA  CGGAAACTTT  CATCCCTCGC
```

FIG. 1AAAF

```
           4151                                                    4200
  42_2     CCCTGATGGG  CGGATTTGGA  CTCAAACACC  CGCCTCCTCA  AATTCTCATC
  42_8     CGCTGATGGG  AGGCTTTGGA  CTGAAACACC  CGCCTCCTCA  GATCCTGATT
  42_15    CGCTGATGGG  AGGCTTTGGA  CTGAAACACC  CGCCTCCTCA  GATCCTGATT
  42_5b    CGCTGATGGG  AGGCTTTGGA  CTGAAACACC  CGCCTCCTCA  GATCCTGATT
  42_1b    CGCTGATGGG  AGGCTTTGGA  CTGAAACACC  CGCCTCCTCA  GATCCTGATT
  42_13    CGCTGATGGG  AGGCTTTGGA  CTGAAACACC  CGCCTCCTCA  GATCCTGATT
  42_3a    CGCTGATGGG  AGGCTTTGGA  CTGAAACACC  CGCCTCCTCA  GATCCTGATT
  42_4     CGCTGATGGG  AGGCTTTGGA  CTGAAACACC  CGCCTCCTCA  GATCCTGATT
  42_5a    CGCTGATGGG  AGGCTTTGGA  CTGAAACACC  CGCCTCCTCA  GATCCTGATT
  42_10    CCCTGATGGG  CGGATTTGGA  CTCAAACACC  CGCCTCCTCA  AATTCTCATC
  42_3b    CCCTGATGGG  CGGATTTGGA  CTCAAACACC  CGCCTCCTCA  AATTCTCATC
  42_11    CCCTGATGGG  CGGATTTGGA  CTCAAACACC  CGCCTCCTCA  AATTCTCATC
  42_6b    CCCTGATGGA  CGGATTTGGA  CTCAAACACC  CGCCTCCTCA  AATTCTCATC
  43_1     CGCTGATGGG  AGGCTTTGGA  CTGAAACACC  CGCCTCCTCA  GATCCTGGTG
  43_5     CGCTGATGGG  AGGCTTTGGA  CTGAAACACC  CGCCTCCTCA  GATCCTGGTG
  43_12    CGCTGATGGG  AGGCTTTGGA  CTGAAACACC  CGCCTCCTCA  GATCCTGGTG
  43_20    CCCTGATGGG  CGGCTTTGGA  CTGAAGCACC  CGCCTCCTCA  AATTCTCATC
  43_21    CCCTGATGGG  CGGCTTTGGA  CTGAAGCACC  CGCCTCCTCA  AATTCTCATC
  43_23    CCCTGATGGG  CGCCTTTGGA  CTGAAGCACC  CGCCTCCTCA  AATTCTCATC
  43_25    CCCTGATGGG  CGCCTTTGGA  CTGAAGCACC  CGCCTCCTCA  AATTCTCATC
  44_1     CGCTGATGGG  AGGCTTTGGA  CTGAAACACC  CGCCTCCTCA  GATCCTGATT
  44_5     CGCTGATGGG  AGGCTTTGGA  CTGAAACACC  CGCCTCCTCA  GATCCTGATT
  223_10   CTCTAATGGG  TGGCTTTGGA  CTGAAACACC  CGCCTCCCCA  GATCCTGATC
  223_2    CTCTAATGGG  TGGCTTTGGA  CTGAAACACC  CGCCTCCCCA  GATCCTGATC
  223_4    CTCTAATGGG  TGGCTTTGGA  CTGAAACACC  CGCCTCCCCA  GATCCTGATC
  223_5    CTCTAATGGG  TGGCTTTGGA  CTGAAACACC  CGCCTCCCCA  GATCCTGATC
  223_6    CTCTAATGGG  TGGCTTTGGA  CTGAAACACC  CGCCTCCCCA  GATCCTGATC
  223_7    CTCTAATGGG  TGGCTTTGGA  CTGAAACACC  CGCCTCCCCA  GATCCTGATC
  A3_4     CGCTCATGGG  AGGCTTTGGA  CTGAAACACC  CTCCTCCCCA  GATCCTGATC
  A3_5     CGCTCATGGG  AGGCTTTGGA  CTGAAACACC  CTCCTCCCCA  GATCCTGATC
  A3_7     CGCTCATGGG  AGGCTTTGGA  CTGAAACACC  CTCCTCCCCA  GATCCTGATC
  A3_3     CGCTCATGGG  AGGCTTTGGA  CTGAAACACC  CTCCTCCCCA  GATCCTGATC
  42_12    CCCTGATGGG  CGGATTTGGA  CTCAAACACC  CGCCTCCTCA  AATTCTCATC
  AAV1     CTCTTATGGG  CGGCTTTGGA  CTCAAGAACC  CGCCTCCTCA  GATCCTCATC
  AAV2     CCCTCATGGG  TGGATTCGGA  CTTAAACACC  CTCCTCCACA  GATTCTCATC
  AAV3     CTCTGATGGG  AGGCTTTGGA  CTGAAACATC  CGCCTCCTCA  AATCATGATC
  AAV8     CGCTGATGGG  CGGCTTTGGC  CTGAAACATC  CTCCGCCTCA  GATCCTGATC
  AAV9     CTCTGATGGG  TGGATTTGGA  CTGAAACACC  CACCTCCACA  GATTCTAATT
  AAV7     CTTTGATGGG  CGGCTTTGGA  CTTAAACATC  CGCCTCCTCA  GATCCTGATC
  44_2     CGCTGATGGG  AGGCTTTGGA  CTGAAACACC  CGCCTCCTCA  GATCCTGATT
```

FIG. 1AAAG

```
             4201                                                    4250
   42_2    AAAAACACCC CGGTACCTGC TAATCCTCCA GAGGTGTTTA CTCCTGCCAA
   42_8    AAGAATACAC CTGTTCCCGC GGATCCTCCA ACTACCTTCA GTCAAGCCAA
   42_15   AAGAATACAC CTGTTCCCGC GGATCCTCCA ACTACCTTCA GTCAAGCCAA
   42_5b   AAGAATACAC CTGTTCCCGC GGATCCTCCA ACTACCTTCA GTCAAGCCAA
   42_1b   AAGAATACAC CTGTTCCCGC GGATCCTCCA ACTACCTTCA GTCAAGCCAA
   42_13   AAGAATACAC CTGTTCCCGC GGATCCTCCA ACTACCTTCA GTCAAGCCAA
   42_3a   AAGAATACAC CTGTTCCCGC GGATCCTCCA ACTACCTTCA GTCAAGCCAA
   42_4    AAGAATACAC CTGTTCCCGC GGATCCTCCA ACTACCTTCA GTCAAGCCAA
   42_5a   AAGAATACAC CTGTTCCCGC GGATCCTCCA ACTACCTTCA GTCAAGCCAA
   42_10   AAAAACACCC CGGTACCTGC TAATCCTCCA GAGGTGTTTA CTCCTGCCAA
   42_3b   AAAAACACCC CGGTACCTGC TAATCCTCCA GAGGTGTTTA CTCCTGCCAA
   42_11   AAAAACACCC CGGTACCTGC TAATCCTCCA GAGGTGTTTA CTCCTGCCAA
   42_6b   AAAAACACCC CGGTACCTGC TAATCCTCCA GAGGTGTTTA CTCCTGCCAA
   43_1    AAAAACACTC CTGTTCCTGC GGATCCTCCG ACCACCTTCA GCCAGGCCAA
   43_5    AAAAACACTC CTGTTCCTGC GGATCCTCCG ACCACCTTCA GCCAGGCCAA
   43_12   AAAAACACTC CTGTTCCTGC GGATCCTCCG ACCACCTTCA GCCAGGCCAA
   43_20   AAGAACACAC CGGTTCCAGC GGACCCGCCG CTTACCTTCA ACCAGGCCAA
   43_21   AAGAACACAC CGGTTCCAGC GGACCCGCCG CTTACCTTCA ACCAGGCCAA
   43_23   AAGAACACAC CGGTTCCAGC GGACCCGCCG CTTACCTTCA ACCAGGCCAA
   43_25   AAGAACACAC CGGTTCCAGC GGACCCGCCG CTTACCTTCA ACCAGGCCAA
   44_1    AAGAATACAC CTGTTCCCGC GGATCCTCCA ACTACCTTCA GTCAAGCTAA
   44_5    AAGAATACAC CTGTTCCCGC GGATCCTCCA ACTACCTTCA GTCAAGCTAA
  223_10   AAAAACACAC CGGTACCTGC TAATCCTCCA GAAGTGTTTA CTCCTGCCAA
  223_2    AAAAACACGC CGGTACCTGC TAATCCTCCA GAAGTGTTTA CTCCTGCCAA
  223_4    AAAAACACAC CGGTACCTGC TAATCCTCCA GAAGTGTTTA CTCCTGCCAA
  223_5    AAAAACACAC CGGTACCTGC TAATCCTCCA GAAGTGTTTA CTCCTGCCAA
  223_6    AAAAACACAC CGGTACCTGC TAATCCTCCA GAAGTGTTTA CTCCTGCCAA
  223_7    AAAAACACAC CGGTACCTGC TAATCCTCCA GAAGTGTTTA CTCCTGCCAA
   A3_4    AAAAACACAC CTGTGCCAGC GAATCCCGCG ACCACTTTCA CTCCTGGAAA
   A3_5    AAAAACACAC CTGTGCCAGC GAATCCCGCG ACCACTTTCA CTCCTGGAAA
   A3_7    AAAAACACAC CTGTGCCAGC GAATCCCGCG ACCACTTTCA CTCCTGGAAA
   A3_3    AAAAACACAC CTGTGCCAGC GAATCCCGCG ACCACTTTCA CTCCTGGAAA
   42_12   A...A..... .......... .......... .......... ..........
   AAV1    AAAAACACGC CTGTTCCTGC GAATCCTCCG GCGGAGTTTT CAGCTACAAA
   AAV2    AAGAACACCC CGGTACCTGC GAATCCTTCG ACCACCTTCA GTGCGGCAAA
   AAV3    AAAAATACTC CGGTACCGGC AAATCCTCCG ACGACTTTCA GCCCGGCCAA
   AAV8    AAGAACACGC CTGTACCTGC GGATCCTCCG ACCACCTTCA ACCAGTCAAA
   AAV9    AAAAATACAC CAGTGCCGGC AGATCCTCCT CTTACCTTCA ATCAAGCCAA
   AAV7    AAGAACACTC CCGTTCCCGC TAATCCTCCG GAGGTGTTTA CTCCTGCCAA
   44_2    AAGAATACAC CTGTTCCCGC GGATCCTCCA ACTACCTTCA GTCAAGCTAA
```

FIG. 1AAAH

```
           4251                                                              4300
  42_2     GTTTGCCTCA  TTTATCACGC  AGTACAGCAC  CGGCCA.GGT  CAGCGTGGAG
  42_8     GCTGGCGTCG  TTCATCACGC  AGTACAGCAC  CGGACA.GGT  CAGCGTGGAA
  42_15    GCTGGCGTCG  TTCATCACGC  AGTACAGCAC  CGGACA.GGT  CAGCGTGGAA
  42_5b    GCTGGCGTCG  TTCATCACGC  AGTACAGCAC  CGGACA.GGT  CAGCGTGGAA
  42_1b    GCTGGCGTCG  TTCATCACGC  AGTACAGCAC  CGGACA.GGT  CAGCGTGGAA
  42_13    GCTGGCGTCG  TTCATCACGC  AGTACAGCAC  CGGACA.GGT  CAGCGTGGAA
  42_3a    GCTGGCGTCG  TTCATCACGC  AGTACAGCAC  CGGACA.GGT  CAGCGTGGAA
  42_4     GCCGGCGTCG  TTCATCACGC  AGTACAGCAC  CGGACA.GGT  CAGCGTGGAA
  42_5a    GCTGGCGTCG  TTCATCACGC  AGTACAGCAC  CGGACA.GGT  CAGCGTGGAA
  42_10    GTTTGCCTCA  TTTATCACGC  AGTACAGCAC  CGGCCA.GGT  CAGCGTGGAG
  42_3b    GTTTGCCTCA  TTTATCACGC  AGTACAGCAC  CGGCCA.GGT  CAGCGTGGAG
  42_11    GTTTGCCTCA  TTTATCACGC  AGTACAGCAC  CGGCCA.GGT  CAGCGTGGAG
  42_6b    GTTTGCCTCA  TTTATCACGC  AGTACAGCAC  CGGCCA.GGT  CAGCGTGGAG
  43_1     GCTGGCTTCT  TTTATCACGC  AGTACAGCAC  CGGACA.GGT  CAGCGTGGAA
  43_5     GCTGGCTTCT  TTTATCACGC  AGTACAGCAC  CGGACA.GGT  CAGCGTGGAA
  43_12    GCTGGCTTCT  TTTATCACGC  AGTACAGCAC  CGGACA.GGT  CAGCGTGGAA
  43_20    GCTGAACTCT  TTCATCACGC  AGTACAGCAC  CGGACA.GGT  CAGCGTGGAA
  43_21    GCTGAACTCT  TTCATCACGC  AGTACAGCAC  CGGACA.GGT  CAGCGTGGAA
  43_23    GCTGAACTCT  TTCATCACGC  AGTACAGCAC  CGGACA.GGT  CAGCGTGGAA
  43_25    GCTGAACTCT  TTCATCACGC  AGTACAGCAC  CGGACA.GGT  CAGCGTGGAA
  44_1     GCTGGCGTCG  TTCATCACGC  AGTACAGCAC  CGGACA.GGT  CAGCGTGGAA
  44_5     GCTGGCGTCG  TTCATCACGC  AGTACAGCAC  CGGACA.GGT  CAGCGTGGAA
 223_10    GTTTGCTTCC  TTCATCACGC  AGTACAGCAC  CGGGCA.AGT  CAGCGTTGAG
 223_2     GTTTGCTTCC  TTCATCACGC  AGTACAGCAC  CGGGCA.AGT  CAGCGTTGAG
 223_4     GTTTGCTTCC  TTCATCACGC  AGTACAGCAC  CGGGCA.AGT  CAGCGTTGAG
 223_5     GTTTGCTTCC  TTCATCACGC  AGTACAGCAC  CGGGCA.AGT  CAGCGTTGAG
 223_6     GCTTGCTTCC  TTCATCACGC  AGTACAGCAC  CGGGCA.AGT  CAGCGTTGAG
 223_7     GATTGCTTCC  TTCATCACGC  AGTACAGCAC  CGGGCA.AGT  CAGCGTTGAG
  A3_4     GTTTGCTTCG  TTCATTACCC  AGTATTCCAC  CGGACA.GGT  CAGCGTGGAA
  A3_5     GTTTGCTTCG  TTCATTACCC  AGTATTCCAC  CGGACA.GGT  CAGCGTGGAA
  A3_7     GTTTGCTTCG  TTCATTACCC  AGTATTCCAC  CGGACA.GGT  CAGCGTGGAA
  A3_3     GTTTGCTTCG  TTCATTACCC  AGTATTCCAC  CGGACA.GGT  CAGCGTGGAA
  42_12    ..........  ..........  ..........  ..........  ..........
  AAV1     GTTTGCTTCA  TTCATCACCC  AATACTCCAC  AGGACA.AGT  GAGTGTGGAA
  AAV2     GTTTGCTTCC  TTCATCACAC  AGTACTCCAC  GGCACACGGT  CAGCGTGGAG
  AAV3     GTTTGCTTCA  TTTATCACTC  AGTACTCCAC  TGGACA.GGT  CAGCGTGGAA
  AAV8     GCTGAACTCT  TTCATCACGC  AATACAGCAC  CGGACA.GGT  CAGCGTGGAA
  AAV9     GCTGAACTCT  TTCATCACGC  AGTACAGCAC  GGGACA.AGT  CAGCGTGGAA
  AAV7     GTTTGCTTCG  TTCATCACAC  AGTACAGCAC  CGGACA.AGT  CAGCGTGGAA
  44_2     GCTGGCGTCG  TTCATCACGC  AGTACAGCAC  CGGACA.GGT  CAGCGTGGAA
```

FIG. 1AAAI

```
           4301                                                                    4350
  42_2     ATCGAGTGGG  AACTGCAGAA  AGAAAACAGC  AAACGCTGGA  ATCCAGAGAT
  42_8     ATTGAATGGG  AGCTGCAGAA  AGAGAACAGC  AAGCGCTGGA  ACCCAGAGAT
  42_15    ATTGAATGGG  AGCTGCAGAA  AGAGAACAGC  AAGCGCTGGA  ACCCAGAGAT
  42_5b    ATTGAATGGG  AGCTGCAGAA  AGAGAACAGC  AAGCGCTGGA  ACCCAGAGAT
  42_1b    ATTGAATGGG  AGCTGCAGAA  AGAGAACAGC  AAGCGCTGGA  ACCCAGAGAT
  42_13    ATTGAATGGG  AGCTGCAGAA  AGAGAACAGC  AAGCGCTGGA  ACCCAGAGAT
  42_3a    ATTGAATGGG  AGCTGCAGAA  AGAGAACAGC  AAGCGCTGGA  ACCCAGAGAT
  42_4     ATTGAATGGG  AGCTGCAGAA  AGAGAACAGC  AAGCGCTGGA  ACCCAGAGAT
  42_5a    ATTGAATGGG  AGCTGCAGAA  AGAGAACAGC  AAGCGCTGGA  ACCCAGAGAT
  42_10    ATCGAGTGGG  AACTGCAGAA  AGAAAACAGC  AAACGCTGGA  ATCCAGAGAT
  42_3b    ATCGAGTGGG  AACTGCAGAA  AGAAAACAGC  AAACGCTGGA  ATCCAGAGAT
  42_11    ATCGAGTGGG  AACTGCAGAA  AGAGAACAGC  AAACGCTGGA  ATCCAGAGAT
  42_6b    ATCGAGTGGG  AACTGCAGAA  AGAAAACAGC  AAACGCTGGA  ATCCAGAGAT
  43_1     ATCGAATGGG  AGCTGCAGAA  AGAAAACAGC  AAGCGCTGGA  ACCCAGAGAT
  43_5     ATCGAATGGG  AGCTGCAGAA  AGAAAACAGC  AAGCGCTGGA  ACCCAGAGAT
  43_12    ATCGAATGGG  AGCTGCAGAA  AGAAAACAGC  AAGCGCTGGA  ACCCAGAGAT
  43_20    ATCGAGTGGG  AGCTGCAGAA  AGAAAACAGC  AAACGCTGGA  ATCCAGAGAT
  43_21    ATCGAGTGGG  AGCTGCAGAA  AGAAAACAGC  AAACGCTGGA  ATCCAGAGAT
  43_23    ATCGAGTGGG  AGCTGCAGAA  AGAAAACAGC  AAACGCTGGA  ATCCAGAGAT
  43_25    ATCGAGTGGG  AGCTGCAGAA  AGAAAACAGC  AAACGCTGGA  ATCCAGAGAT
  44_1     ATTGAATGGG  AGCTGCAGAA  AGAAAACAGC  AAACGCTGGA  ACCCAGAGAT
  44_5     ATTGAATGGG  AGCTGCAGAA  AGAAAACAGC  AAACGCTGGA  ACCCAGAGAT
  223_10   ATCGAGTGGG  AGCTGCAGAA  AGAGAACAGC  AAGCGCTGGA  ACCCAGAGAT
  223_2    ATCGAGTGGG  AGCTGCAGAA  AGAGAACAGC  AAGCGCTGGA  ACCCAGAGAT
  223_4    ATCGAATGGG  AGCTGCAGAA  AGAGAACAGC  AAGCGCTGGA  ACCCAGAGAT
  223_5    ATCGAATGGG  AGCTGCAGAA  AGAGAACAGC  AAGCGCTGGA  ACCCAGAGAT
  223_6    ATCGAGTGGG  AGCTGCAGAA  AGAGAACAGC  AAGCGCTGGA  ACCCAGAGAT
  223_7    ATCGAGTGGG  AGCTGCAGAA  AGAGAACAGC  AAGCGCTGGA  ACCCAGAGAT
  A3_4     ATAGAGTGGG  AGCTGCAGAA  AGAAAACAGC  AAACGCTGGA  ACCCAGAAAT
  A3_5     ATAGAGTGGG  AGCTGCAGAA  AGAAAACAGC  AAACGCTGGA  ACCCGGAAAT
  A3_7     ATAGAGTGGG  AGCTGCAGAA  AGAAAACAGC  AAACGCTGGA  ACCCAGAAAT
  A3_3     ATAGAGTGGG  AGCTGCAGAA  AGAAAACAGC  AAACGCTGGA  ACCCAGAAAT
  42_12    ..........  ..........  ..........  ..........  ..........
  AAV1     ATTGAATGGG  AGCTGCAGAA  AGAAAACAGC  AAGCGCTGGA  ATCCCGAAGT
  AAV2     ATCGAGTGGG  AGCTGCAGAA  GGAAAACAGC  AAACGCTGGA  ATCCCGAAAT
  AAV3     ATTGAGTGGG  AGCTACAGAA  AGAAAACAGC  AAACGTTGGA  ATCCAGAGAT
  AAV8     ATTGAATGGG  AGCTGCAGAA  GGAAAACAGC  AAGCGCTGGA  ACCCGAGAT
  AAV9     ATCGAGTGGG  AGCTGCAGAA  AGAAAACAGC  AAGCGCTGGA  ATCCAGAGAT
  AAV7     ATCGAGTGGG  AGCTGCAGAA  GGAAAACAGC  AAGCGCTGGA  ACCCGGAGAT
  44_2     ATTGAATGGG  AGCTGCAGAA  AGAAAACAGC  AAACGCTGGA  ACCCAGAGAT
```

FIG. 1AAAJ

```
         4351                                                    4400
  42_2   TCAGTACACC TCAAATTATG CCAAGTCTAA TAAT.GTGGA ATTTGCTGTC
  42_8   TCAGTATACT TCCAACTACT ACAAATCTAC AAAT.GTGGA CTTTGCTGTC
  42_15  TCAGTATACT TCCAACTACT ACAAATCTAC AAAT.GTGGA CTTTGCTGTC
  42_5b  TCAGTATACT TCCAACTACT ACAAATCTAC AAAT.GTGGA CTTTGCTGTC
  42_1b  TCAGTATACT TCCAACTACT ACAAATCTAC AAAT.GTGGA CTTTGCTGTC
  42_13  TCAGTATACT TCCAACTACT ACAAATCTAC AAAT.GTGGA CTTTGCTGTC
  42_3a  TCAGTATACT TCCAACTACT ACAAATCTAC AAAT.GTGGA CTTTGCTGTC
  42_4   TCAGTATACT TCCAACTACT ACAAATCTAC AAAT.GTGGA CTTTGCTGTC
  42_5a  TCAGTATACT TCCAACTACT ACAAATCTAC AAAT.GTGGA CTTTGCTGTC
  42_10  TCAGTACACC TCAAATTATG CCAAGTCTAA TAAT.GTGGA ATTTGCTGTC
  42_3b  TCAGTACACC TCAAATTATG CCAAGTCTAA TAAT.GTGGA ATTTGCTGTC
  42_11  TCAGTACACC TCAAATTATG CCAAGTCTAA TAAT.GTGGA ATTTGCTGTC
  42_6b  TCAGTACACC TCAAATTATG CCAAGTCTAA TAAT.GTGGA ATTTGCTGTC
  43_1   TCAGTATACT TCCAACTACT ACAAATCTAC AAAT.GTGGA CTTTGCTGTC
  43_5   TCAGTATACT TCCAACTACT ACAAATCTAC AAAT.GTGGA CTTTGCTGTC
  43_12  TCAGTATACT TCCAACTACT ACAAATCTAC AAAT.GTGGA CTTTGCTGTC
  43_20  TCAATACACT TCCAACTACT ACAAATCTAC AAAT.GTGGA CTTTGCTGTC
  43_21  TCAATACACT TCCAACTACT ACAAATCTAC AAAT.GTGGA CTTTGCTGTC
  43_23  TCAATACACT TCCAACTACT ACAAATCTAC AAAT.GTGGA CTTTGCTGTC
  43_25  TCAATACACT TCCAACTACT ACAAATCTAC AAAT.GTGGA CTTTGCTGTC
  44_1   TCAATACACT TCCAACTACT ACAAATCTAC AAAT.GTGGA CTTCGCTGTT
  44_5   TCAATACACT TCCAACTACT ACAAATCTAC AAAT.GTGGA CTTTGCTGTT
  223_10 TCAGTACACC TCCAACTTTG ACAAACAGAC TGGA.GTGGA CTTTGCTGTT
  223_2  TCAGTACACC TCCAACTTTG ACAAACAGAC TGGA.GTGGA CTTTGCTGTT
  223_4  TCAGTACACC TCCAACTTTG ACAAACAGAC TGGA.GTGGA CTTTGCTGTT
  223_5  TCAGTACACC TCCAACTTTG ACAAACAGAC TGGA.GTGGA CTTTGCTGTT
  223_6  TCAGTACACC TCCAACTTTG ACAAACAGAC TGGA.GTGGA CTTTGCTGTT
  223_7  TCAGTACACC TCCAACTTTG ACAAACAGAC TGGA.GTGGA CTTTGCTGTT
  A3_4   TCAGTACACC TCCAACTACA ACAAGTCGGT GAAT.GTGGA GTTTACCGTG
  A3_5   TCAGTACACC TCCAACTACA ACAAGTCGGT GAAT.GTGGA GTTTACCGTG
  A3_7   TCAGTACACC TCCAACTACA ACAAGTCGGT GAAT.GTGGA GTTTACCGTG
  A3_3   TCAGTACACC TCCAACTACA ACAAGTCGGT GAAT.GTGGA GTTTACCGTG
  42_12  ...GTATACT TCCAACTACT ACAAATCTAC AAAT.GTGGA CTTTGCTGTC
  AAV1   GCAGTACACA TCCAATTATG CAAAATCTGC CAAC.GTTGA TTTTACTGTG
  AAV2   TCAGTACACT TCCAACTACA ACAAGTCTGT TAATCGTGGA CTT.ACCGTG
  AAV3   TCAGTACACT TCCAACTACA ACAAGTCTGT TAAT.GTGGA CTTACTGTA
  AAV8   CCAGTACACC TCCAACTACT ACAAATCTAC AAGT.GTGGA CTTTGCTGTT
  AAV9   CCAGTATACT TCAAACTACT ACAAATCTAC AAAT.GTGGA CTTTGCTGTC
  AAV7   TCAGTACACC TCCAACTTTG AAAGCAGAC  TGGT.GTGGA CTTTGCCGTT
  44_2   TCAATACACT TCCAACTACT ACAAATCTAC AAAT.GTGGA CTTTGCTGTT
```

FIG. 1AAAK

```
          4401                                                        4450
42_2      AACAACGAAG  GGGTTTATAC  TGAGCCTCGC  CCCATTGGCA  CCCGTTACCT
42_8      AATACTGAGG  GTACTTATTC  AGAGCCTCGC  CCCATTGGCA  CCCGTTACCT
42_15     AATACTGAGG  GTACTTATTC  AGAGCCTCGC  CCCATTGGCA  CCCGTTACCT
42_5b     AATACTGAGG  GTACTTATTC  AGAGCCTCGC  CCCATTGGCA  CCCGTTACCT
42_1b     AATACTGAGG  GTACTTATTC  AGAGCCTCGC  CCCATTGGCA  CCCGTTACCT
42_13     AATACTGAGG  GTACTTATTC  AGAGCCTCGC  CCCATTGGCA  CCCGTTACCT
42_3a     AATACTGAGG  GTACTTATTC  AGAGCCTCGC  CCCATTGGCA  CCCGTTACCT
42_4      AATACTGAGG  GTACTTATTC  AGAGCCTCGC  CCCATTGGCA  CCCGTTACCT
42_5a     AATACTGAGG  GTACTTATTC  AGAGCCTCGC  CCCATTGGCA  CCCGTTACCT
42_10     AACAACGAAG  GGGTTTATAC  TGAGCCTCGC  CCCATTGGCA  CCCGTTACCT
42_3b     AACAACGAAG  GGGTTTATAC  TGAGCCTCGC  CCCATTGGCA  CCCGTTACCT
42_11     AACAACGAAG  GGGTTTATAC  TGAGCCTCGC  CCCATTGGCA  CCCGTTACCT
42_6b     AACAACGAAG  GGGTTTATAC  TGAGCCTCGC  CCCATTGGCA  CCCGTTACCT
43_1      AATACTGAGG  GTACTTATTC  AGAGCCTCGC  CCCATTGGCA  CTCGTTATCT
43_5      AATACCGAGG  GTACTTATTC  AGAGCCTCGC  CCCATTGGCA  CTCGTTATCT
43_12     AATACTGAGG  GTACTTATTC  AGAGCCTCGC  CCCATTGGCA  CTCGTTATCT
43_20     AACACGGAAG  GAGTTTATAG  CGAGCCTCGC  CCCATTGGCA  CCCGTTACCT
43_21     AACACGGAAG  GAGTTTATAG  CGAGCCTCGC  CCCATTGGCA  CCCGTTACCT
43_23     AACACGGAAG  GAGTTTATAG  CGAGCCTCGC  CCCATTGGCA  CCCGTTACCT
43_25     AACACGGAGG  GGGTTTATAG  CGAGCCTCGC  CCCATTGGCA  CCCGTTACCT
44_1      AACACAGATG  GCACTTATTC  TGAGCCTCGC  CCCATTGGCA  CCCGTTACCT
44_5      AACACAGATG  GCACTTATTC  TGAGCCTCGC  CCCATTGGCA  CCCGTTACCT
223_10    GACAGCCAGG  GTGTTTACTC  TGAGCCT...  ..........  ..........
223_2     GACAGCCAGG  GTGTTTACTC  TGAGCCT...  ..........  ..........
223_4     GACAGCCAGG  GTGTTTACTC  TGAGCCT...  ..........  ..........
223_5     GACAGCCAGG  GTGTTTACTC  TGAGCCT...  ..........  ..........
223_6     GACAGCCAGG  GTGTTTACTC  TGAGCCT...  ..........  ..........
223_7     GACAGCCAGG  GTGTTTACTC  TGAGCCT...  ..........  ..........
A3_4      GACGCAAACG  GTGTTTATTC  TGAACCCCGC  CCTATTGGCA  CTCGTTACCT
A3_5      GACGCAAACG  GTGTTTATTC  TGAACCCCGC  CCTATTGGCA  CTCGTTACCT
A3_7      GACGCAAACG  GTGTTTATTC  TGAACCCCGC  CCTATTGGCA  CTCGTTACCT
A3_3      GACGCAAACG  GTGTTTATTC  TGAACCCCGC  CCTATTGGCA  CTCGTTACCT
42_12     AATACTGAGG  GTACTTATTC  AGAGCCTCGC  CCCATTGGCA  CCCGTTACCT
AAV1      GACAACAATG  GACTTATAC   TGAGCCTCGC  CCCATTGGCA  CCCGTTACCT
AAV2      GATACTAATG  GCGTGTATTC  AGAGCCTCGC  CCCATTGGCA  CCAGATACCT
AAV3      GACACTAATG  GTGTTTATAG  TGAACCTCGC  CCTATTGGAA  CCCGGTATCT
AAV8      AATACAGAAG  GCGTGTACTC  TGAACCCCGC  CCCATTGGCA  CCCGTTACCT
AAV9      AATACCGAAG  GTGTTACTC   TGAGCCTCGC  CCCATTGGTA  CTCGTTACCT
AAV7      GACAGCCAGG  GTGTTTACTC  TGAGCCTCGC  CCTATTGGCA  CTCGTTACCT
44_2      AACACAGATG  GCACTTATTC  TGAGCCTCGC  CCCATCGGCA  CCCGTTACCT
```

FIG. 1AAAL

|        | 4451       |            |            |            | 4500       |
|        | VP1-3 stop |            | Poly A signal |         |            |
| 42_2   | CACCCGTAAC | CTGTAATTGC | CTGTTAATCA | ATAAACCGGT | TAATTCGTTT |
| 42_8   | CACCCGTAAC | CTGTAATTGC | CTGTTAATCA | ATAAACCGGC | TAATTCGTTT |
| 42_15  | CACCCGTAAC | CTGTAATTGC | CTGTTAATCA | ATAAACCGGT | TAATTCGTTT |
| 42_5b  | CACCCGTAAC | CTGTAATTGC | CTGTTAATCA | ATAAACCGGT | TAATTCGTTT |
| 42_1b  | CACCCGTAAC | CTGTAATTGC | CTGTTAATCA | ATAAACCGGT | TGATTCGTTT |
| 42_13  | CACCCGTAGC | CTGTAATTGC | CTGTTAATCA | ATAAACCGGT | TGATTCGTTT |
| 42_3a  | CACCCGTAAC | CTGTAATTGC | CTGTTAATCA | ATAAACCGGT | TAATTCGTTT |
| 42_4   | CACCCGTAAC | CTGTAATTGC | CTGTTAATCA | ATAAACCGGT | TAATTCGTTT |
| 42_5a  | CACCCGTAAC | CTGTAATTGC | CTGTTAATCA | ATAAACCGGT | TAATTCGTTT |
| 42_10  | CACCCGTAAC | CTGTAATTGC | CTGTTAATCA | ATAAACCGGT | TAATTCGTTT |
| 42_3b  | CACCCGTAAC | CTGTAATTGC | CTGTTAATCA | ATAAACCGGT | TAATTCGTTT |
| 42_11  | CACCCGTAAC | CTGTAATTAC | TTGTTAATCA | ATAAACCGGT | TGATTCGTTT |
| 42_6b  | CACCCGTAAC | CTGTAATTGC | CTGTTAATCA | ATAAACCGGT | TAATTCGTTT |
| 43_1   | CACCCGTAAT | CTGTAATTGC | TTGTTAATCA | ATAAACCGGT | .......... |
| 43_5   | CACCCGTAAT | CTGTAATTGC | TTGTTAATCA | ATAAACCGGT | TAATTCGTTT |
| 43_12  | CACCCGTAAT | CTGTAATTGC | TTGTTAATCA | ATAAACCGGT | TAATTCGTTT |
| 43_20  | CACCCGCAAC | CTGTAATTAC | ATGTTAATCA | ATAAACCGGT | TAATTCGTTT |
| 43_21  | CACCCGCAAC | CTGTAATTAC | ATGTTAATCA | ATAAACCGGT | TAATTCGTTT |
| 43_23  | CACCCGCAAC | CTGTAATTAC | ATGTTAATCA | ATAAACCGGT | TAATTCGTTT |
| 43_25  | CACCCGCAAC | CTGTAATTAC | ATGTTAATCA | ATAAACCGGT | TAATTCGTTT |
| 44_1   | CACCCGTAAT | CTGTAATTGC | TCGTTAATCA | ATAAACCGGT | TGATTCGTTT |
| 44_5   | CACCCGTAAT | CTGTAATTGC | TTGTTAATCA | ATAAACCGGT | TGATTCGTTT |
| 223_10 | .......... | .......... | .......... | .......... | .......... |
| 223_2  | .......... | .......... | .......... | .......... | .......... |
| 223_4  | .......... | .......... | .......... | .......... | .......... |
| 223_5  | .......... | .......... | .......... | .......... | .......... |
| 223_6  | .......... | .......... | .......... | .......... | .......... |
| 223_7  | .......... | .......... | .......... | .......... | .......... |
| A3_4   | TACCCGGAAC | TTGTAATTTC | CTGTTAATGA | ATAAACCGAT | TTATGCGTTT |
| A3_5   | TACCCGGAAC | TTGTAATTTC | CTGTTAATGA | ATAAACCGAT | TTATGCGTTT |
| A3_7   | TACCCGGAAC | TTGTAATTTC | CTGTTAATGA | ATAAACCGAT | TTATGCGTTT |
| A3_3   | TACCCGGAAC | TTGTAATTTC | CTGTTAATGA | ATAAGCCGAT | TTATGCGTTT |
| 42_12  | CACCCGTAAC | CTGTAATTGC | CTGTTAATCA | ATAAACCGGT | TAATTCGTTT |
| AAV1   | TACCCGTCCC | CTGTAATTAC | GTGTTAATCA | ATAAACCGGT | TGATTCGTTT |
| AAV2   | GACTCGTAAT | CTGTAATTGC | TTGTTAATCA | ATAAACCGTT | TAATTCGTTT |
| AAV3   | CACACGAAAC | TTGTGAATCC | TGGTTAATCA | ATAAACCGTT | TAATTCGTTT |
| AAV8   | CACCCGTAAT | CTGTAATTGC | CTGTTAATCA | ATAAACCGGT | TGATTCGTTT |
| AAV9   | CACCCGTAAT | TTGTAATTGC | CTGTTAATCA | ATAAACCGGT | TAATTCGTTT |
| AAV7   | CACCCGTAAT | CTGTAATTGC | ATGTTAATCA | ATAAACCGGT | TGATTCGTTT |
| 44_2   | CACCCGTAAT | CTGTAATTGC | TTGTTAATCA | ATAAACCGGT | TGATTCGTTT |
|        | vp1-3 stop |            | PolyA signal |          |            |

FIG. 1AAAM

```
            4501                                           4550
  42_2    CAGTTGAACT TTGGTCTC.T GCGAAGGGCG AATTC..... ..........
  42_8    CAGTTGAACT TTGGTCTC.T GCGAAGGGCG AATTC..... ..........
  42_15   CAGTTGAACT TTGGTCTC.T GCGAAGGGCG AATTC..... ..........
  42_5b   CAGTTGAACT TTGGTCTC.T GCGAAGGGCG AATTCGTTTA AACCTGCAGG
  42_1b   CAGTTGAACT TTGGTCTC.. ...AAGGGCG AATTC..... ..........
  42_13   CAGTTGAACT TTGGTCTC.T GCGAAGGGCG AATTC..... ..........
  42_3a   CAGTTGAACT TTGGTCTC.T GCGAAGGGCG AATTC..... ..........
  42_4    CAGTTGAACT TTGGTCTC.T GCGAAGGGCG AATTC..... ..........
  42_5a   CAGTTGAACT TTGGTCTC.T GCGAAGGGCG AATTC..... ..........
  42_10   CAGTTGAACT TTGGTC.... ...AAGGGCG AATTC..... ..........
  42_3b   CAGTTGAACT TTGGTCTC.T GCGAAGGGCG AATTC..... ..........
  42_11   CAGTTGAACT TTGGTCTC.T GCGAAGGGCG AATTC..... ..........
  42_6b   CAGTTGAACT TTGGTCTC.T GCGAAGGGCG AATTC..... ..........
  43_1    .......... .......... .......... .......... ..........
  43_5    CAGTTGAACT TTGGTCTC.T GCGAAGGGCG AATTCGTTTA AACCTGCAGG
  43_12   CAGTTGAACT TTGGTCTC.T GCGAAGGGCG AATTC..... ..........
  43_20   CAGTTGAACT TTGGTCTC.T GCGAAGGGCG AATTC..... ..........
  43_21   CAGTTGAACT TTGGTCTC.T GCGAAGGGCG AATTC..... ..........
  43_23   CAGTTGAACT TTGGTCTC.T GCGAAGGGCG AATTC..... ..........
  43_25   CAGTTGAACT TTGGTCTC.T GCGAAGGGCG AATTC..... ..........
  44_1    CAGTTGAACT TTGGTCTC.T GCGAAGGGCG AATTC..... ..........
  44_5    CAGTTGAACT TTGGTCTC.T GCGAAGGGCG AATTC..... ..........
  223_10  .......... .......... .......... .......... ..........
  223_2   .......... .......... .......... .......... ..........
  223_4   .......... .......... .......... .......... ..........
  223_5   .......... .......... .......... .......... ..........
  223_6   .......... .......... .......... .......... ..........
  223_7   .......... .......... .......... .......... ..........
  A3_4    CAGTTGAACT TTGGTCTC.T GCGAAGGGCG AATTCGC.GG CCGCTA....
  A3_5    CAGTTGAACT TTGGTCTC.T GCGAAGGGCG AATTC..... ..........
  A3_7    CAGTTGAACT TTGGTCTC.T GCGAAGGGCG AATTC..... ..........
  A3_3    CAGTTGAACT TTGGTCTC.T GCGAAGGGCG AATTCGT.TT AAACCT....
  42_12   CAGTTGAACT TTGGTCTC.T GCGAAGGGCG AATTC..... ..........
  AAV1    CAGTTGAACT TTGGTCTCCT GTCCTTCTTA TCTTATCGGT TACCATGGTT
  AAV2    CAGTTGAACT TTGGTCTC.T GCGTATTTCT ..TTCTT.AT CTAGTTTCCA
  AAV3    CAGTTGAACT TTGGCTCT.T GTGCACTTCT TTATCTTTAT CTTGTTTCCA
  AAV8    CAGTTGAACT TTGGTCTC.T GCG....... .......... ..........
  AAV9    CAGTTGAACT TTGGTCTC.T GCG....... .......... ..........
  AAV7    CAGTTGAACT TTGGTCTCCT GTGCTTCTTA TCTTATCGGT TTCCATAGCA
  44_2    CAGTTGAACT TTGGTCTC.T GCGAAGGGCG AATTC..... ..........
```

FIG. 1AAAN

```
          4551                                                              4600
  42_2    ..........  ..........  ..........  ..........  ..........
  42_8    ..........  ..........  ..........  ..........  ..........
  42_15   ..........  ..........  ..........  ..........  ..........
  42_5b   ACTAGTCCCT  TTAGTGAGGG  TTAATTCTGA  G.........  ..........
  42_1b   ..........  ..........  ..........  ..........  ..........
  42_13   ..........  ..........  ..........  ..........  ..........
  42_3a   ..........  ..........  ..........  ..........  ..........
  42_4    ..........  ..........  ..........  ..........  ..........
  42_5a   ..........  ..........  ..........  ..........  ..........
  42_10   ..........  ..........  ..........  ..........  ..........
  42_3b   ..........  ..........  ..........  ..........  ..........
  42_11   ..........  ..........  ..........  ..........  ..........
  42_6b   ..........  ..........  ..........  ..........  ..........
  43_1    ..........  ..........  ..........  ..........  ..........
  43_5    AC........  ..........  ..........  ..........  ..........
  43_12   ..........  ..........  ..........  ..........  ..........
  43_20   ..........  ..........  ..........  ..........  ..........
  43_21   ..........  ..........  ..........  ..........  ..........
  43_23   ..........  ..........  ..........  ..........  ..........
  43_25   ..........  ..........  ..........  ..........  ..........
  44_1    ..........  ..........  ..........  ..........  ..........
  44_5    ..........  ..........  ..........  ..........  ..........
 223_10   ..........  ..........  ..........  ..........  ..........
 223_2    ..........  ..........  ..........  ..........  ..........
 223_4    ..........  ..........  ..........  ..........  ..........
 223_5    ..........  ..........  ..........  ..........  ..........
 223_6    ..........  ..........  ..........  ..........  ..........
 223_7    ..........  ..........  ..........  ..........  ..........
  A3_4    ..........  ..........  ..........  ..........  ..........
  A3_5    ..........  ..........  ..........  ..........  ..........
  A3_7    ..........  ..........  ..........  ..........  ..........
  A3_3    ..........  ..........  ..........  ..........  ..........
  42_12   ..........  ..........  ..........  ..........  ..........
  AAV1    ATAGCTTACA  CATTAACTGC  TTGGTTGCGC  T.........  ..........
  AAV2    TGGCTAC...  GTAGATAAGT  AGC.......  ..........  ..........
  AAV3    TGGCTACTGC  GTAGATAAGC  AGCGGCCTGC  GGCGCTTGCG  CTTCGCGGTT
  AAV8    ..........  ..........  ..........  ..........  ..........
  AAV9    ..........  ..........  ..........  ..........  ..........
  AAV7    ACTGGTTACA  CATTAACTGC  TTGGGTGCGC  TTCACGATAA  GAACACTGAC
  44_2    ..........  ..........  ..........  ..........  ..........
```

FIG. 1AAAO

```
        4601                                              4650
42_2    ..........  ..........  ..........  ..........  ..........
42_9    ..........  ..........  ..........  ..........  ..........
42_15   ..........  ..........  ..........  ..........  ..........
42_5b   ....CTTGGC  GTAATCATGG  GTCATAG...  ..........  ..........
42_1b   ..........  ..........  ..........  ..........  ..........
42_13   ..........  ..........  ..........  ..........  ..........
42_3a   ..........  ..........  ..........  ..........  ..........
42_4    ..........  ..........  ..........  ..........  ..........
42_5a   ..........  ..........  ..........  ..........  ..........
42_10   ..........  ..........  ..........  ..........  ..........
42_3b   ..........  ..........  ..........  ..........  ..........
42_11   ..........  ..........  ..........  ..........  ..........
42_6b   ..........  ..........  ..........  ..........  ..........
43_1    ..........  ..........  ..........  ..........  ..........
43_5    ..........  ..........  ..........  ..........  ..........
43_12   ..........  ..........  ..........  ..........  ..........
43_20   ..........  ..........  ..........  ..........  ..........
43_21   ..........  ..........  ..........  ..........  ..........
43_23   ..........  ..........  ..........  ..........  ..........
43_25   ..........  ..........  ..........  ..........  ..........
44_1    ..........  ..........  ..........  ..........  ..........
44_5    ..........  ..........  ..........  ..........  ..........
223_10  ..........  ..........  ..........  ..........  ..........
223_2   ..........  ..........  ..........  ..........  ..........
223_4   ..........  ..........  ..........  ..........  ..........
223_5   ..........  ..........  ..........  ..........  ..........
223_6   ..........  ..........  ..........  ..........  ..........
223_7   ..........  ..........  ..........  ..........  ..........
A3_4    ..........  ..........  ..........  ..........  ..........
A3_5    ..........  ..........  ..........  ..........  ..........
A3_7    ..........  ..........  ..........  ..........  ..........
A3_3    ..........  ..........  ..........  ..........  ..........
42_12   ..........  ..........  ..........  ..........  ..........
AAV1    ....TCGCGA  TAAAAGACTT  ACGTCATCGG  GTTACCCCTA  GTGATGGAGT
AAV2    ....ATGGCG  GGTTAATCAT  TAACTACAAG  GA.ACCCCTA  GTGATGGAGT
AAV3    TACAACTGCT  GGTTAATATT  TAACTCTCGC  CATACCTCTA  GTGATGGAGT
AAV8    ..........  ..........  ..........  ..........  ..........
AAV9    ..........  ..........  ..........  ..........  ..........
AAV7    ..........  ..........  ..GTCACCGC  GGTACCCCTA  GTGATGGAGT
44_2    ..........  ..........  ..........  ..........  ..........
```

FIG. 1AAAP

```
           4651                                                              4700
   42_2    ..........  ..........  ..........  ..........  ..........
   42_8    ..........  ..........  ..........  ..........  ..........
   42_15   ..........  ..........  ..........  ..........  ..........
   42_5b   ..........  ..........  ..........  ..........  ..........
   42_1b   ..........  ..........  ..........  ..........  ..........
   42_13   ..........  ..........  ..........  ..........  ..........
   42_3a   ..........  ..........  ..........  ..........  ..........
   42_4    ..........  ..........  ..........  ..........  ..........
   42_5a   ..........  ..........  ..........  ..........  ..........
   42_10   ..........  ..........  ..........  ..........  ..........
   42_3b   ..........  ..........  ..........  ..........  ..........
   42_11   ..........  ..........  ..........  ..........  ..........
   42_6b   ..........  ..........  ..........  ..........  ..........
   43_1    ..........  ..........  ..........  ..........  ..........
   43_5    ..........  ..........  ..........  ..........  ..........
   43_12   ..........  ..........  ..........  ..........  ..........
   43_20   ..........  ..........  ..........  ..........  ..........
   43_21   ..........  ..........  ..........  ..........  ..........
   43_23   ..........  ..........  ..........  ..........  ..........
   43_25   ..........  ..........  ..........  ..........  ..........
   44_1    ..........  ..........  ..........  ..........  ..........
   44_5    ..........  ..........  ..........  ..........  ..........
   223_10  ..........  ..........  ..........  ..........  ..........
   223_2   ..........  ..........  ..........  ..........  ..........
   223_4   ..........  ..........  ..........  ..........  ..........
   223_5   ..........  ..........  ..........  ..........  ..........
   223_6   ..........  ..........  ..........  ..........  ..........
   223_7   ..........  ..........  ..........  ..........  ..........
   A3_4    ..........  ..........  ..........  ..........  ..........
   A3_5    ..........  ..........  ..........  ..........  ..........
   A3_7    ..........  ..........  ..........  ..........  ..........
   A3_3    ..........  ..........  ..........  ..........  ..........
   42_12   ..........  ..........  ..........  ..........  ..........
   AAV1    TGCCCACTCC  CTCTCTGCGC  GCTCGCTCGC  TCGGTGGGGC  CTGCGGACCA
   AAV2    TGGCCACTCC  CTCTCTGCGC  GCTCGCTCGC  TCACTGAGGC  CGGGCGACCA
   AAV3    TGGCCACTCC  CTCTATGCGC  ACTCGCTCGC  TCGGTGGGGC  CTGGCGACCA
   AAV8    ..........  ..........  ..........  ..........  ..........
   AAV9    ..........  ..........  ..........  ..........  ..........
   AAV7    TGGCCACTCC  CTCTATGCGC  GCTCGCTCGC  TCGGTGGGGC  CTGCGGACCA
   44_2    ..........  ..........  ..........  ..........  ..........
```

FIG. 1AAAQ

```
         4701                                                                        4750
  42_2   ..........  ..........  ..........  ..........  ..........
  42_8   ..........  ..........  ..........  ..........  ..........
 42_15   ..........  ..........  ..........  ..........  ..........
 42_5b   ..........  ..........  ..........  ..........  ..........
 42_1b   ..........  ..........  ..........  ..........  ..........
 42_13   ..........  ..........  ..........  ..........  ..........
 42_3a   ..........  ..........  ..........  ..........  ..........
  42_4   ..........  ..........  ..........  ..........  ..........
 42_5a   ..........  ..........  ..........  ..........  ..........
 42_10   ..........  ..........  ..........  ..........  ..........
 42_3b   ..........  ..........  ..........  ..........  ..........
 42_11   ..........  ..........  ..........  ..........  ..........
 42_6b   ..........  ..........  ..........  ..........  ..........
  43_1   ..........  ..........  ..........  ..........  ..........
  43_5   ..........  ..........  ..........  ..........  ..........
 43_12   ..........  ..........  ..........  ..........  ..........
 43_20   ..........  ..........  ..........  ..........  ..........
 43_21   ..........  ..........  ..........  ..........  ..........
 43_23   ..........  ..........  ..........  ..........  ..........
 43_25   ..........  ..........  ..........  ..........  ..........
  44_1   ..........  ..........  ..........  ..........  ..........
  44_5   ..........  ..........  ..........  ..........  ..........
 223_10  ..........  ..........  ..........  ..........  ..........
 223_2   ..........  ..........  ..........  ..........  ..........
 223_4   ..........  ..........  ..........  ..........  ..........
 223_5   ..........  ..........  ..........  ..........  ..........
 223_6   ..........  ..........  ..........  ..........  ..........
 223_7   ..........  ..........  ..........  ..........  ..........
  A3_4   ..........  ..........  ..........  ..........  ..........
  A3_5   ..........  ..........  ..........  ..........  ..........
  A3_7   ..........  ..........  ..........  ..........  ..........
  A3_3   ..........  ..........  ..........  ..........  ..........
 42_12   ..........  ..........  ..........  ..........  ..........
  AAV1   AAGGTCCGCA  GACGGCAGAG  CTCTGCTCTG  CCGGCCCCAC  CGAGCGAGCG
  AAV2   AAGGTCGCCC  GACGCCCGGG  CTTTGCCCGG  GCGGCCTCAG  TGAGCGAGCG
  AAV3   AAGGTCGCCA  GACGGACGTG  CTTTGCACGT  CCGGCCCCAC  CGAGCGAGCG
  AAV8   ..........  ..........  ..........  ..........  ..........
  AAV9   ..........  ..........  ..........  ..........  ..........
  AAV7   AAGGTCCGCA  GACGGCAGAG  CTCTGCTCTG  CCGGCCCCAC  CGAGCGAGCG
  44_2   ..........  ..........  ..........  ..........  ..........
```

FIG. 1AAAR

```
                4751                           4774
      42_2      ..........    ..........    ....
      42_8      ..........    ..........    ....
      42_15     ..........    ..........    ....
      42_5b     ..........    ..........    ....
      42_1b     ..........    ..........    ....
      42_13     ..........    ..........    ....
      42_3a     ..........    ..........    ....
      42_4      ..........    ..........    ....
      42_5a     ..........    ..........    ....
      42_10     ..........    ..........    ....
      42_3b     ..........    ..........    ....
      42_11     ..........    ..........    ....
      42_6b     ..........    ..........    ....
      43_1      ..........    ..........    ....
      43_5      ..........    ..........    ....
      43_12     ..........    ..........    ....
      43_20     ..........    ..........    ....
      43_21     ..........    ..........    ....
      43_23     ..........    ..........    ....
      43_25     ..........    ..........    ....
      44_1      ..........    ..........    ....
      44_5      ..........    ..........    ....
      223_10    ..........    ..........    ....
      223_2     ..........    ..........    ....
      223_4     ..........    ..........    ....
      223_5     ..........    ..........    ....
      223_6     ..........    ..........    ....
      223_7     ..........    ..........    ....
      A3_4      ..........    ..........    ....
      A3_5      ..........    ..........    ....
      A3_7      ..........    ..........    ....
      A3_3      ..........    ..........    ....
      42_12     ..........    ..........    ....
      AAV1      AGCGCGCAGA    GAGGGAGTGG    GCAA
      AAV2      AGCGCGCAGA    GAGGGAGTGG    CCAA
      AAV3      AGTGCGCATA    GAGGGAGTGG    CCAA
      AAV8      ..........    ..........    ....
      AAV9      ..........    ..........    ....
      AAV7      AGCGCGCATA    GAGGGAGTGG    CCAA
      44_2      ..........    ..........    ....
```

```
                          10        20        30        40        50        60
                     ....|....|....|....|....|....|....|....|....|....|....|....|
    C1\VP1           MAADGYLPDWLEDNLSEGIREWWDLKPGAPKPKANQQKQDDGRGLVLPGYKYLGPFNGLD
    C2\VP1           MAADGYLPDWLEDNLSEGIREWWDLKPGAPKLKANQQKQDDGRGLVLPGYKYLGPFHGLD
    C5\VP1@2         MAADGYLPDWLEDNLSEGIREWWDLKPGAPKPKANQQKQDDGRGLVLPGYEYLGPFNGLD
    AAV4\VP1         -MTDGYLPDWLEDNLSEGVREWWALQPGAPKPKANQQHQDNARGLVLPGYKYLGPGNGLD
    AAV1             MAADGYLPDWLEDNLSEGIREWWDLKPGAPKPKANQQKQDDGRGLVLPGYKYLGPFNGLD
    AAV6\VP1         MAADGYLPDWLEDNLSEGIREWWDLKPGAPKPKANQQKQDDGRGLVLPGYKYLGPFNGLD
    A3_3             MAADGYLPDWLEDTLSEGIRQWWKLKPGPPPPKPNQQHRDDSRGLVLPGYKYLGPFNGLD
    A3_7             MAADGYLPDWLEDTLSEGIRQWWKLKPGPPPPKPNQQHRDDSRGLVLPGYKYLGPFNGLD
    A3_4             MAADGYLPDWLEDTLSEGIRQWWKLKPGPPPPKPNQQHRDDSRGLVLPGYKYLGPFNGLD
    A3_5             MAADGYLPDWLEDTLSEGIRQWWKLKPGPPPPKPNQQHRDDSRGLVLPGYKYLGPFNGLD
    AAV2             MAADGYLPDWLEDTLSEGIRQWWKLKPGPPPPKPAERHKDDSRGLVLPGYKYLGPFNGLD
    AAV3             MAADGYLPDWLEDNLSEGIREWWALKPGVPQPKANQQHQDNRRGLVLPGYKYLGPGNGLD
    13.3b\VP1        MAADGYLPDWLEDNLSEGIREWWDLKPGAPKPKANQQKQDNGRGLVLPGYKYLGPFNGLD
    AAV7             MAADGYLPDWLEDNLSEGIREWWDLKPGAPKPKANQQKQDNGRGLVLPGYKYLGPFNGLD
    223_4            ------------------------------------------------------------
    223_5            ------------------------------------------------------------
    223_10           ------------------------------------------------------------
    223_2            ------------------------------------------------------------
    223_7            ------------------------------------------------------------
    223_6            ------------------------------------------------------------
    44_1             MAADGYLPDWLEDNLSEGIREWWDLKPGAPKPKANQQKQDDGRGLVLPGYKYLGPFNGLD
    44_5             MAADGYLPDWLEDNLSEGIREWWDLKPGAPKPKANQQKQDDGRGLVLPGYKYLGPFNGLD
    44_2             MAADGYLPDWLEDNLSEGIREWWDLKPGAPKPKANQQKQDDGRGLVLPGYKYLGPFNGLD
    29.3\VP1         MAADGYLPDWLEDNLSEGIREWWALKPGAPKPKANQQKQDDGRGLVLPGYKYLGPFNGLD
    29.5\VP1         MAADGYLPDWLEDNLSEGIREWWALKPGAPKPKANQQKQDDGRGLVLPGYKYLGPFNGLD
    42_15            MAADGYLPDWLEDNLSEGIREWWDLKPGAPKPKANQQKQDDGRGLVLPGYKYLGPFNGLD
    42_8             MAADGYLPDWLEDNLSEGIREWWDLKPGAPKPKANQQKQDDGRGLVLPGYKYLGPFNGLD
    42_13            MAADGYLPDWLEDNLSEGIREWWDLKPGAPKPKANQQKQDDGRGLVLPGYKYLGPFNGLD
    42_3A            MAADGHLPDWLEDNLSEGIREWWDLKPGAPKPKANQQKQDDGRGLVLPGYKYLGPFNGLD
    42_4             MAADGYLPDWLEDNLSEGIREWWDLKPGAPKPKANQQKQDDGRGLVLPGYKYLGPFNGLD
    42_5A            MAADGYLPDWLEDNLSEGIREWWDLKPGAPKPKANQQKQDDGRGLVLPGYKYLGPFNGLD
    42_1B            MAADGYLPDWLEDNLSEGIREWWDLRPGAPKPKANQQKQDDGRGLVLPGYKYLGPFNGLD
    42_5B            MAADGYLPDWLEDNLSEGIREWWDLKPGAPKPKANQQKQDDGRGLVLPGYKYLGPFNGLD
    43_1             MAADGYLPDWLEDNLSEGIREWWDLKPGAPKPKANQQKQDDGRGLVLPGYKYLGPFNGLD
    43_12            MAADGYLPDWLEDNLSEGIREWWDLKPGAPKPKANQQKQDDGRGLVLPGYKYLGPFNGLD
    43_5             MAADGYLPDWLEDNLSEGIREWWDLKPGAPKPKANQQKQDDGRGLVLPGYKYLGPFNGLD
    AAV8             MAADGYLPDWLEDNLSEGIREWWALKPGAPKPKANQQKQDDGRGLVLPGYKYLGPFNGLD
    43_21            MAADGYLPDWLEDNLSEGIREWWDLKPGAPKPKANQQKQDDGRGLVLPGYKYLGPFNGLD
    43_25            MAADGYLPDWLEDNLSEGIREWWDLKPGAPKPKANQQKQDDGRGLVLPGYKYLGPFNGLD
    43_23            MAADGYLPDWLEDNLSEGIREWWDLKPGAPKPKANQQKQDDGRGLVLPGYKYLGPFNGLD
    43_20            MAADGYLPDWLEDNLSEGIREWWDLKPGAPKPKANQQKQDDGRGLVLPGYKYLGPFNGLD
    AAV_9            MAADGYLPDWLEDNLSEGIREWWDLKPGAPKPKANQQKQDDGRGLVLPGYKYLGPFNGLD
    24.1             MAADGYLPDWLEDNLSEGIREWWDLKPGAPKPKANQQKQDDGRGLVLPGYKYLRPFNGLD
    42.2REAL         MAADGYLPDWLEDNLSEGIREWWDLKPGAPKPKANQQKQDDGRGLVLPGYKYLGPFNGLD
    7.2\VP1          MAADGYLPDWLEGNLSEGIREWWDLKPGAPKPKANQQKQDDGRGLVLPGYRYLGPFNGLD
    27.3\VP1         MAADGYLPDWLEDNLSEGIREWWDLKPGAPKPKANQQKQDDGRGLVLPGYKYLGPFNGLD
    16.3\VP1         MAADGYLPDWLEDNLSEGIREWWDLKPGAPKPKANQQKQDDGRGLVLPGYKYLGPFNGLD
    42_10            MAADGYLPDWLEDNLSEGIREWWDLKPGAPKPKANQQKQDDGRGLVLPGYKYLGPFNGLD
    42_3B            MAADGYLPDWLEDNLSEGIREWWDLKPGAPKPKANQQKQDDGRGLVLPGYKYLGPFNGLD
    42_11            MAADGYLPDWLEDNLSEGIREWWDLKPGAPKPKANQQKQDDGRGLVLPGYKYLGPFNGLD
    F1\VP1           MAADGYLPDWLEDNLSEGIREWWDLKPGAPKPKANQQKQDDGRGLVLPGYKYLGPFNGLD
    F5\VP1@3         MAADGYLPDWLEDNLSEGIREWWDLKPGAPKPKANQQKQDDGRGLVLPGYKYLGPFNGLD
    F3\VP1           MAADGYLPDWLEDNLSEGIREWWDLKPGAPKPKANQQKQDDGRGLVLPGYKYLGPFNGLD
    42_6B            MAADGYLPDWLEDNLSEGIREWWDLKPGAPKPKANQQKQDDGRGLVLPGYKYLGPFNGLD
    42_12            MAADGYLPDWLEDNLSEGIREWWDLKPGAPKPKANQQKQDDGRGLVLPGYKYLGPFNGLD
    AAV5\CAP         MSFVDHPPDWLEE-VGEGLREFLGLEAGPPKPKPNQQHQDQARGLVLPGYNYLGPGNGLD
```

FIG. 2A

```
                          70        80        90       100       110       120
                  ....|....|....|....|....|....|....|....|....|....|....|....|
     C1\VP1       KGEPVNAADAAALEHDKAYDQQLKAGDNPYLRYNHADAEFQERLQEDTSFGGNLGRAVFQ
     C2\VP1       KGEPVNAADAAALEHDKAYDQQLKAGDNPYLRYNHADAEFQERLQEDTSFGGNLGRAVFQ
     C5\VP1@2     KGEPVNAADAAALEHDKAYDQQLKAGDNPYLRYNHADAEFQERLQEDTSFGGNLGRAVFQ
     AAV4\VP1     KGEPVNAADAAALEHDKAYDQQLKAGDNPYLKYNHADAEFQQRLQGDTSFGGNLGRAVFQ
     AAV1         KGEPVNAADAAALEHDKAYDQQLKAGDNPYLRYNHADAEFQERLQEDTSFGGNLGRAVFQ
     AAV6\VP1     KGEPVNAADAAALEHDKAYDQQLKAGDNPYLRYNHADAEFQERLQEDTSFGGNLGRAVFQ
     A3_3         KGEPVNEADAAALEHDKAYDHQLKQGDNPYLKYNHADAEFQERLQEDTSFGGNLGRAVFQ
     A3_7         KGEPVNEADAAALEHDKAYDHQLKQGDNPYLKYNHADAEFQERLQEDTSFGGNLGRAVFQ
     A3_4         KGEPVNEADAAALEHDKAYDHQLKQGDNPYLKYNHADAEFQERLQEDTSFGGNLGRAVFQ
     A3_5         KGEPVNEADAAALEHDKAYDHQLKQGDNPYLKYNHADAEFQERLQEDTSFGGNLGRAVFQ
     AAV2         KGEPVNEADAAALEHDKAYDRQLDSGDNPYLKYNHADAEFQERLKEDTSFGGNLGRAVFQ
     AAV3         KGEPVNEADAAALEHDKAYDQQLKAGDNPYLKYNHADAEFQERLQEDTSFGGNLGRAVFQ
     13.3b\VP1    KGEPVNAADAAALEHDKAYDQQLNAGDNPYLRYNHADAEFQERLQEDTSFGGNLGRAVFQ
     AAV7         KGEPVNAADAAALEHDKAYDQQLKAGDNPYLRYNHADAEFQERLQEDTSFGGNLGRAVFQ
     223_4        ------------------KAYDQQLKAGDNPYLRYNHADAEFQERLQEDTSFGGNLGRAVFQ
     223_5        ------------------KAYDQQLKAGDNPYLRYNHADAEFQERLQEDTSFGGNLGRAVFQ
     223_10       ------------------KAYDQQLKAGDNPYLRYNHADAEFQERLQEDTSFGGNLGRAVFQ
     223_2        ------------------KAYDQQLKAGDNPYLRYNHADAEFQECLQEDTSFGGNLGRAVFQ
     223_7        ------------------KAYDQQLKAGDNPYLRYNHADAEFQERLQEDTSFGGNLGRAVFQ
     223_6        ------------------KAYDQQLKAGDNPYLRYNHADAEFQERLQEDTSFGGNLGRAVFQ
     44_1         KGEPVNAADAAALEHDKAYDQQLKAGDNPYLRYNHADAEFQERLQEDTSFGGNLGRAVFQ
     44_5         KGEPVNAADAAALEHDKAYDQQLKAGDNPYLRYNHADAEFQERLQEDTSFGGNLGRAVFQ
     44_2         KGEPVNAADAAALEHDKAYDQQLKAGDNPYLRYNHADAEFQERLQEDTSFGGNLGRAVFQ
     29.3\VP1     KGEPVNAADAAALEHDKAYDQQLKAGDNPYLRYNHADAEFQERLQEDTSFGGNLGRAVFQ
     29.5\VP1     KGEPVNAADAAALEHDKAYDQQLKAGDNPYLRYNHADAEFQERLQEDTSFGGNLGRAVFQ
     42_15        KGEPVNAADAAALEHDKAYDQQLKAGDNPYLRYNHADAEFQERLQEDTSFGGNLGRAVFQ
     42_8         KGEPVNAADAAALEHDKAYDQQLKAGDNPYLRYNHADAEFQERLQEDTSFGGNLGRAVFQ
     42_13        KGEPVNAADAAALEHDKAYDQQLKAGDNPYLRYNHADAEFQERLQEDTSFGGNLGRAVFQ
     42_3A        KGEPVNAADAAALEHDKAYDQQLKAGDNPYLRYNHADAEFQERLQEDTSFGGNLGRAVFQ
     42_4         KGEPVNEADAAALEHDKAYDKQLEQGDNPYLKYNHADAEFQERLQEDTSFGGNLGRAVFQ
     42_5A        KGEPVNEADAAALEHDKAYDKQLEQGDNPYLKYNHADAEFQERLQEDTSFGGNLGRAVFR
     42_1B        KGEPVNEADAAALEHDKAYDKQLEQGDNPYLKYNHADAEFQERLQEDTSFGGNLGRAVFQ
     42_5B        KGEPVNEADAAALEHDKAYDKQLEQGDNPYLKYNHADAEFQERLQEDTSFGGNLGRAVFQ
     43_1         KGEPVNAADAAALEHDKAYDQQLKAGDNPYLRYNHADAEFQERLQEDTSFGGNLGRAVFQ
     43_12        KGEPVNAADAAALEHDKAYDQQLKAGDNPYLRYNHADAEFQERLQEDTSFGGNLGRAVFQ
     43_5         KGEPVNAADAAALEHDKAYDQQLKAGDNPYLRYNHADAEFQERLQEDTSFGGNLGRAVFQ
     AAV8         KGEPVNAADAAALEHDKAYDQQLQAGDNPYLRYNHADAEFQERLQEDTSFGGNLGRAVFQ
     43_21        KGEPVNAADAAALEHDKAYDQQLKAGDNPYLRYNHADAEFQERLQEDTSFGGNLGRAVFQ
     43_25        KGEPVNAADAAALEHDKAYDQQLKAGDNPYLRYNHADAEFQERLQEDTSFGGNLGRAVFQ
     43_23        KGEPVNAADAAALEHDKAYDQQLKAGDNPYLRYNHADAEFQERLQEDTSFGGNLGRAVFQ
     43_20        KGEPVNAADAAALEHDKAYDQQLKAGDNPYLRYNHADAEFQERLQEDTSFGGNLGRAVFQ
     AAV_9        KGEPVNAADAAALEHDKAYDQQLKAGDNPYLRYNHADAEFQERLQEDTSFGGNLGRAVFQ
     24.1         KGEPVNEADAAALEHDKAYDKQLEQGDNPYLKYNHADAEFQERLQEDTSFGGNLGRAVFQ
     42.2REAL     KGEPVNEADAAALEHDKAYDKQLEQGDNPYLKYNHADAEFQERLQEDTSFGGNLGRAVFQ
     7.2\VP1      KGEPVNEADAAALEHDKAYDKQLEQGDNPYLKYNHADAEFQERLQEDTSFGGNLGRAVFQ
     27.3\VP1     KGEPVNEADAAALEHDKAYDKQLEQGDNPYLKYNHADAEFQERLQEDTSFGGNLGRAVFQ
     16.3\VP1     KGEPVNEADAAALEHDKAYDKQLEQGDNPYLKYNHADAEFQERLQEDTSFGGNLGRAVFQ
     42_10        KGEPVNEADAAALEHDKAYDKQLEQGDNPYLKYNHADAEFQERLQEDTSFGGNLGRAVFQ
     42_3B        KGEPVNEADAAALEHDKAYDKQLEQGDNPYLKYNHADAEFQERLQEDTSFGGNLGRAVFQ
     42_11        KGEPVNAADAAALEHDKAYDQQLKAGDNPYLRYNHADAEFQERLQEDTSFGGNLGRAVFQ
     F1\VP1       KGEPVNAADAAALEHDKAYDQQLKAGDNPYLRYNHADAEFQERLQEDTSFGGNLGRAVFQ
     F5\VP1@3     KGEPVNAADAAALEHDKAYDQQLKAGDNPYLRYNHADAEFQERLQEDTSFGGNLGRAVFQ
     F3\VP1       KGEPVNAADAAALEHDKAYDQQLKAGDNPYLRYNHADAEFQERLQEDTSFGGNLGRAVFQ
     42_6B        KGEPVNEADAAALEHDKAYDKQLEQGDNPYLKYNHADAEFQERLQEDTSFGGNLGRAVFQ
     42_12        KGEPVNEADAAALEHDKAYDKQLEQGDNPYLKYNHADAEFQERLQEDTSFGGNLGRAVFQ
     AAV5\CAP     RGEPVNRADEVAREHDISYNEQLEAGDNPYLKYNHADAEFQEKLADDTSFGGNLGKAVFQ
```

FIG. 2B

```
                      130        140        150        160        170        180
              ....|....|....|....|....|....|....|....|....|....|....|....|
C1\VP1        AKKRVLEPLGLVEEGAKTAPGKKRP-LESPQ-EPDSSSGIGKKGKQPAKKRLNFEEDTGA
C2\VP1        AKKRVLEPLGLVEEGAKTAPGKKRP-LESPQ-EPDSSSGIGKKGKQPAKKRLNFEEDTGA
C5\VP1@2      AKKRVLEPLGLVEEGAKTAPGKKRP-LESPQ-EPDSSSGIGKKGKQPAKKRLNFEEDTGA
AAV4\VP1      AKKRVLEPLGLVEQAGETAPGKKRPLIESPQ-QPDSSTGIGKKGKQPAKKKLVFEDETGA
AAV1          AKKRVLEPLGLVEEGAKTAPGKKRPVEQSPQ-EPDSSSGIGKTGQQPAKKRLNFGQTGDS
AAV6\VP1      AKKRVLEPFGLVEEGAKTAPGKKRPVEQSPQ-EPDSSSGIGKTGQQPAKKRLNFGQTGDS
A3_3          AKKRVLEPLGLVEEAVKTAPGKKRPIEQSPA-EPDSSSGIGKSGQQPAKKRLNFGQTGDT
A3_7          AKKRVLEPLGLVEEAVKTAPGKKRPIEQSPA-EPDSSSGIGKSGQQPAKKRLNFGQTGDT
A3_4          AKKRVLEPLGLVEEAVKTAPGKKRPIEQSPA-EPDSSSGIGESGQQPAKKRLNFGQTGDT
A3_5          AKKRVLEPLGLVEEAVKTAPGKKRPIEQSPA-EPDSSSGIGKSGQQPAKKRLNFGQTGDT
AAV2          AKKRVLEPLGLVEEPVKTAPGKKRPVEHSPV-EPDSSSGTGKAGQQPARKRLNFGQTGDA
AAV3          AKKRILEPLGLVEEAAKTAPGKKGAVDQSPQ-EPDSSSGVGKSGKQPARKRLNFGQTGDS
13.3b\VP1     AKKRVLEPLGLVEEGAKTAPAKKRPVEPSPQRSPDSSTGIGKKGQQPARKRLNFGQTGDS
AAV7          AKKRVLEPLGLVEEGAKTAPAKKRPVEPSPQRSPDSSTGIGKKGQQPARKRLNFGQTGDS
223_4         AKKRVLEPLGLVETPAKTAPGKKRPVD-----SPDSTSGIGKKGQQPAKKRLNFGQTGDS
223_5         AKKRVLEPLGLVETPAKTAPGKKRPVD-----SPDSTSGIGKKGQQPAKKRLNFGQTGDS
223_10        AKKRVLEPLGLVETPAKTAPGKKRPVD-----SPDSTSGIGKKGQQPAKKRLNFGQTGDS
223_2         AKKRVLEPLGLVETPAKTAPGKKRPVD-----SPDSTSGIGKKGQQPAKKRLNFGQTGDS
223_7         AKKRVLEPLGLVETPAKTAPGKKRPVD-----SPDSTSGIGKKGQQPAKKRLNFGQTGDS
223_6         AKKRVLEPLGLVETPAKTAPGKKRPVD-----SPDSTSGIGKKGQQPAKKRLNFGQTGDS
44_1          AKKRVLEPLGLVEEGAKTAPGKKRPVEPSPQRSPDSSTGIGKKGQQPAKKRLNFGQTGDS
44_5          AKKRVLEPLGLVEEGAKTAPGKKRPVEPSPQRSPDSSTGIGKKGQQPAKKRLNFGQTGDS
44_2          AKKRVLEPLGLVEEGAKTAPGKKRPVEPSPQRSPDSSTGIGKKGQQPAKKRLNFGQTGDS
29.3\VP1      AKKRVLEPLGLVEEGAKTAPGKKRPVEPSPQRSPDSTTGIGKKGQQPAKKRLNFGQTGDS
29.5\VP1      AKKRVLEPLGLVEEGAKTAPGKKRPVEPSPQRSPDSSTGIGKKGQQPAKKRLNFGQTGDS
42_15         AKKRVLEPLGLVEEGAKTAPGKKRPVEPSPQRSPDSSTGIGKTGQQPAKKRLNFGQTGDS
42_8          AKKRVLEPLGLVEEGAKTAPGKKRPVEPSPQRSPDSSTGIGKTGQQPAKKRLNFGQTGDS
42_13         AKKRVLEPLGLVEEGAKTAPGKKRPIE-----SPDSSTGIGKKGQQPAKKKLNFGQTGDS
42_3A         AKKRVLEPLGLVEEGAKTAPGKKRPIE-----SPDSSTGIGKKGQQPAKKKLNFGQTGDS
42_4          AKKRVLEPLGLVEEGAKTAPGKKRPIE-----SPDSSTGIGKKGQQPAKKKLNFGQTGDS
42_5A         AKKRVLEPLGLVEEGAKTAPGKKRPIE-----SPDSSTGIGKKGQQPAKKKLNFGQTGDS
42_1B         AKKRVLEPLGLVEEGAKTAPGKKRPIE-----SPDSSTGIGKKGQQPAKKRLNFGQTGDS
42_5B         AKKRVLEPLGLVEEGAKTAPGKKRPVEPSPQRSPDSSTGIGKTGQQPAKKRLNFGQTGDS
43_1          AKKRVLEPLGLVEEGAKTAPGKKRPVEPSPQRSPDSSTGIGKKGHQPARKRLNFGQTGDS
43_12         AKKRVLEPLGLVEEGAKTAPGKKRPVEPSPQRSPDSSTGIGKKGHQPARKRLNFGQTGDS
43_5          AKKRVLEPLGLVEEGAKTAPGKKRPVEPSPQRSPDSSTGIGKKGHQPARKRLNFGQTGDS
AAV8          AKKRVLEPLGLVEEGAKTAPGKKRPVEPSPQRSPDSSTGIGKKGQQPARKRLNFGQTGDS
43_21         AKKRVLEPLGLVEEGAKTAPGKKRPVEQSPQ-EPDSSSGIGKTGQQPAKKRLNFGQTGDS
43_25         AKKRVLEPLGLVEEGAKTAPGKKRPVEQSPQ-EPDSSSGIGKTGQQPAKKRLNFGQTGDS
43_23         AKKRVLEPLGLVEEGAKTAPGKKRPVEQSPQ-EPDSSSGIGKTGQQPAKKRLNFGQTGDS
43_20         AKKRVLEPLGLVEEGAKTAPGKKRLVEQSPQ-EPDSSSGIGKTGQQPAKKRLNFGQTGDS
AAV_9         AKKRVLEPLGLVEEGAKTAPGKKRPVEQSPQ-EPDSSSGIGKSGQQPAKKRLNFGQTGDS
24.1          AKKRVLEPLGLVEEVAKTAPGKKRPIE-----SPDSSTGIGKKGQQPAKKKLNFGQTGDS
42.2REAL      AKKRVLEPLGLVEEGAKTAPGKKRPIE-----SPDSSTGIGKKGQQPAKKKLNFGQTGDS
7.2\VP1       AKKRVLEPLGLVEEGAKTAPGKKRPIE-----SPDSSTGIGKNGQPPAKKKLNFGQTGDS
27.3\VP1      AKKRVLEPLGLVEEGAKTASGKKRPIE-----SPDSSTGIGKKGQQPAKKKLNFGQTGDS
16.3\VP1      AKKRVLEPLGLVEEGAKTAPGKKRPIE-----SPDSSTGIGKKGQQPAKKKLNFGQTGDS
42_10         AKKRVLEPLGLVEEGAKTAPGKKRPIE-----SPDSSTGIGRKGQQPAKKKLNFGQTGDS
42_3B         AKKRVLEPLGLVEEGAKTAPGKKRPIE-----SPDSSTGIGKKGQQPAKKKLNFGQTGDS
42_11         AKKRVLEPLGLVEEGAKTAPGKKRPIE-----SPDSSTGIGKKGQQPAKKKLNFGQTGDS
F1\VP1        AKKRVLEPLGLVEEGAKTAPGKKRPID-----SPDSSTGIGKKGQQPAKKKLNFGQTGDS
F5\VP1@3      AKKRVLEPLGLVEEGAKTAPGKKRPID-----SPDSSTGIGKKGQQPAKKKLNFGQTGDS
F3\VP1        AKKRVLEPLGLVEEGAKTAPGKKRPIG-----SPDSSTGIGKKGQQPAKKKLNFGQTGDS
42_6B         AKKRVLEPLGLVEEGAKTAPGKKRPVEPSPQRSPDSSTGIGKTGQQPAKKRLNFGQTGDS
42_12         AKKRVLEPLGLVEEGAKTAPGKKRPVEPSPQRSPDSSTGIGKTGQQPAKKRLNFGQTGDS
AAV5\CAP      AKKRVLEPFGLVEEGAKTAPTGKR---------IDDHFPKRKKARTEEDSKP--STSSDA
```

FIG. 2C

```
                   190       200       210       220       230       240
              ....|....|....|....|....|....|....|....|....|....|....|....|
C1\VP1        GDGP----PEGSDTSAMS--SDIEMRAAPGGNAVDAGQGSDGVGNASGDWHCDSTWSEGK
C2\VP1        GDGP----PEGSDTSAMS--SDIEMRAAPGGNAVDAGQGSDGVGNASGDWHCDSTWSEGK
C5\VP1@2      GDGP----PEGSDTSAMS--SDIEMRAAPGGNAVDAGQGSDGVGNASGDWHCDSTWSEGK
AAV4\VP1      GDGP----PEGSTSGAMS--DDSEMRAAAGGAAVEGGQGADGVGNASGDWHCDSTWSEGH
AAV1          ESVPD-PQPLGEPPATPAAVGPTTMASGGGAPMADNNEGADGVGNASGNWHCDSTWLGDR
AAV6\VP1      ESVPD-PQPLGEPPATPAAVGPTTMASGGGAPMADNNEGADGVGNASGNWHCDSTWLGDR
A3_3          ESVPG-PQPIGEPPAAPSGVGSNTMASGGGAPMADNNEGADGVGNSSGNWHCDSTWMGDR
A3_7          ESVPD-PQPIGEPPAAPSGVGSNTMASGGGAPMADNNEGADGVGNSSGNWHCDSTWMGDR
A3_4          ESVPD-PQPIGEPPAAPSGVGSNTMASGGGAPMADDNEGADGVGNSSGNWHCDSTWMGDR
A3_5          ESVPD-PQPIGEPPAAPSGVGSNTMASGGGAPMADNNEGADGVGNSSGNWHCDSTWMGDR
AAV2          DSVPD-PQPLGQPPAAPSGLGTNTMATGSGAPMADNNEGADGVGNSSGNWHCDSTWMGDR
AAV3          ESVPD-PQPLGEPPAAPTSLGSNTMASGGGAPMADNNEGADGVGNSSGNWHCDSQWLGDR
13.3b\VP1     ESVPD-PQPLGEPPAAPSSVGSGTVAAGGGAPMADNNEGADGVGNASGNWHCDSTWLGDR
AAV7          ESVPD-PQPLGEPPAAPSSVGSGTVAAGGGAPMADNNEGADGVGNASGNWHCDSTWLGDR
223_4         EPVPD-PQPIGEPPAGPSGLGSGTMAAGGGAPMADNNEGADGVGNASGNWHCDSTRLGDR
223_5         EPVPD-PQPIGEPPAGPSGLGSGTMAAGGGAPMADNNEGADGVGNASGNWHCDSTRLGDR
223_10        ESVPD-PQPIGEPPAGPSGLGSGTMAAGGGAPMADNNEGADGVGNASGNWHCDSTWLGDR
223_2         ESVPD-PQPIGEPPAGPSGLGSGTMVAGGGAPMADNNEGADGVGNASGNWHCDSTWLGDR
223_7         ESVPD-PQPIGEPPAGPSGLGSGTMAAGGGAPMADNNEGADGVGNASGNWHCDSTWLGDR
223_6         ESVPD-PQPIGEPPAGPSGLGSGTMAAGGGAPMADNSEGADGVGNASGNWHCDSTWLGDR
44_1          ESVPD-PQPIGEPPAGPSGLGSGTMAAGGGAPMADNNEGADGVGSSSGNWHCDSTWLGDR
44_5          ESVPD-PQPIGEPPAGPSGLGSGTMAAGGGAPMADNNEGADGVGSSSGNWHCDSTWLGDR
44_2          ESVPD-PQPIGEPPAGPSGLGSGTMAAGGGAPMADNNEGADGVGSSSGNWHCDSTWLGDR
29.3\VP1      ESVPD-PQPIGEPPAGPSGLGSGTMAAGGGAPMADNNEGADGVGSSSGNWHCDSTWLGDR
29.5\VP1      ESVPD-PQPIGEPPAGPSGLGSGTMAAGGGAPMADNNEGADGVGSSSGNWHCDSTWLGDG
42_15         ESVPD-PQPIGEPPAGPSGLGSGTMAAGGGAPMADNNEGADGVGSSSGNWHCDSTWLGDR
42_8          ESVPD-PQPIGEPPAGPSGLGSGTMAAGGGAPMADNNEGADGVGSSSGNWHCDSTWLGDR
42_13         ESVPD-PQPIGEPPAGPSGLGSGTMAAGGGAPMADNNEGADGVGSSSGNWHCDSTWLGDR
42_3A         ESVPD-PQPIGEPPAGPSGLGSGTMAAGGGAPMADNNEGADGVGSSSGNWHCDSTWLGDR
42_4          ESVPD-PQPIGEPPAGPSGLGSGTMAAGGGAPMADNNEGADGVGNASGNWHCDSTWLGDR
42_5A         ESVPD-PQPLGEPPAAPSGLGSGTMAAGGGAPMADNNEGADGVGNASGNWHCDSTWLGDR
42_1B         ESVPD-PQPIGEPPAGPSGLGSGTMAAGGGAPMADNNEGADGVGSSSGNWHCDSTWLGDR
42_5B         ESVPD-PQPIGEPPAGPSGLGSGTMAAGGGAPMADNNEGADGVGSSSGNWHCDSTWLGDR
43_1          ESVPD-PQPIGEPPAGPSGLGSGTMAAGGGAPMADNNEGADGVGSSSGNWHCDSTWLGDR
43_12         ESVPD-PQPIGEPPAGPSGLGSGTMAAGGGAPMADNNEGADGVGSSSGNWHCDSTWLGDR
43_5          ESVPD-PQPIGEPPAGPSGLGSGTMAAGGGAPMADNNEGADGVGSSSGNWHCDSTWLGDR
AAV8          ESVPD-PQPLGEPPAAPSGVGPNTMAAGGGAPMADNNEGADGVGSSSGNWHCDSTWLGDR
43_21         ESVPD-PQPLGEPPAAPSGLGPNTMASGGGAPMADNNEGADGVGNSSGNWHCDSTWLGDR
43_25         ESVPD-PQPLGEPPAAPSGLGPNTMASGGGAPMADNNEGADGVGNSSGNWHCDSTWLGDR
43_23         ESVPD-PQPLGEPPAAPSGLGPNTMASGGGAPMADNNEGADGVGNSSGNWHCDSTWLGDR
43_20         ESVPD-PQPLGEPPAAPSGLGPNTMASGGGAPMADNNEGADGVGNSSGNWHCDSTWLGDR
AAV_9         ESVPD-PQPLGEPPEAPSGLGPNTMASGGGAPMADNNEGADGVGNSSGNWHCDSTWLGDR
24.1          ESVPD-PQPLGEPPAAPSGLGSGTMAAGGGAPMADNNEGADGVGNASGNWHCDSTWLGDR
42.2REAL      ESVPD-PQPLGEPPAAPSGLGSGTMAAGGGAPMADNNEGADGVGNASGNWHCDSTWLGDR
7.2\VP1       ESVPD-PQPLGEPPAAPSGLGSGTMAAGGGAPMADNNEGADGVGNASGNWHCDSTWLGDR
27.3\VP1      ESVPD-PQPLGEPPAAPSGLGSGTMAAGGGAPMADNNEGADGVGNASGNWHCDSTWLGDR
16.3\VP1      ESVPD-PQPLGEPPAAPSGLGSGTMAAGGGAPMADNNEGADGVGNASGNWHCDSTWLGDR
42_10         ESVPD-PQPIGEPPAGPSGLGSGTMAAGGGAPMADNNEGADGVGNASGNWHCDSTWLGDR
42_3B         ESVPD-PQPIGEPPAGPSGLGSGTMAAGGGAPMADNNEGADGVGNASGNWHCDSTWLGDR
42_11         ESVPD-PQPIGEPPAGPSGLGSGTMAAGGGAPMADNNEGADGVGNASGNWHCDSTWLGDR
F1\VP1        ESVPD-PQPLGEPPAAPSSVGSGTMAAGGGAPMADNNEGADGVGNASGNWHCDSTWLGDR
F5\VP1@3      ESVPD-PQPLGEPPAAPSSVGSGTMAAGGGAPTADNNEGADGVGNASGNWHCDSTWLGDR
F3\VP1        ESVPD-PQPLGEPPAAPSSVGSGTMAAGGGAPMADNNEGADGVGNASGNWHCDSTWLGDR
42_6B         ESVPD-PQPIGEPPAGPSGLGSGTMAAGGGAPMADNNEGADGVGSSSGNWHCDSTWLGDR
42_12         ESVPD-PQPIGEPPAGPSGLGSGTMAAGGGAPMADNNEGADGVGSSSGNWHCDSTWLGDR
AAV5\CAP      EAGPSGSQQLQIPAQPASSLGADTMSAGGGGPLGDNNQGADGVGNASGDWHCDSTWMGDR
```

FIG. 2D

```
                    250       260       270       280       290       300
              ....|....|....|....|....|....|....|....|....|....|....|....|
C1\VP1        VTTTSTRTWVLPTYNNHLYLRLG-----TTSNSNTYNGFSTPWGYFDFNRFHCHFSPRDW
C2\VP1        VTTTSTRTWVLPTYNNHLYLRLG-----TTSNSNTYNGFSTPWGYFDFNRFHCHFSPRDW
C5\VP1@2      VTTTSTRTWVLPTYNNHLYLRLG-----TTSNSNTYNGFSTPWGYFDFNRFHCHFSPRDW
AAV4\VP1      VTTTSTRTWVLPTYNNHLYLRLG-----ESLQSNTYNGFSTPWGYFDFNRFHCHFSPRDW
AAV1          VITTSTRTWALPTYNNHLYKQIS-SASTGASNDNHYFGYSTPWGYFDFNRFHCHFSPRDW
AAV6\VP1      VITTSTRTWALPTYNNHLYKQIS-SASTGASNDNHYFGYSTPWGYFDFNRFHCHFSPRDW
A3_3          VITTSTRTWALPTYNNHLYKQIS---SESGATNDNHYFGYSTPWGYFDFNRFHCHFSPRDW
A3_7          VITTSTRTWALPTYNNRLYKQIS---SESGATNDNHYFGYSTPWGYFDFNRFHCHFSPRDW
A3_4          VITTSTRTWALPTYNNHLYKQIS---SESGATNDNHYFGYSTPWGYFDFNRFHCHFSPRDW
A3_5          VITTSTRTWALPTYNNHLYKQIS---SESGATNDNHYFGYSTPWGYFDFNRFHCHFSPRDW
AAV2          VITTSTRTWALPTYNNHLYKQIS---SQSGASNDNHYFGYSTPWGYFDFNRFHCHFSPRDW
AAV3          VITTSTRTWALPTYNNHLYKQIS---SQSGASNDNHYFGYSTPWGYFDFNRFHCHFSPRDW
13.3b\VP1     VITTSTRTWALPTYNNHLYEQIS-SETAGSTNDNTYFGYSTPWGYFDFNRFHCHFSPRDW
AAV7          VITTSTRTWALPTYNNHLYKQIS-SETAGSTNDNTYFGYSTPWGYFDFNRFHCHFSPRDW
223_4         VITTSTRTWALPTYNNHLYKQIS-SQSAGSTNDNVYFGYSTPWGYFDFNRFHCHFSPRDW
223_5         VITTSTRTWALPTYNNHLYKQIS-SQSAGSTNDNVYFGYSTPWGYFDFNRFHCHFSPRDW
223_10        VITTSTRTWALPTYNNHLYKQIS-SQSAGSTNDNVYFGYSTPWGYFDFNRFHCHFSPRDW
223_2         VITTSTRTWALPTYNNHLYKQIS-SQSAGSTNDNVYFGYSTPWGYFDFNRFHCHFSPRDW
223_7         VITTSTRTWALPTYNNHLYKQIS-SQSAGSTNDNVYFGYSTPWGYFDFNRFHCHFSPRDW
223_6         VITTSTRTWALPTYNNHLYKQIS-SQSAGSTNDNVYFGYSTPWGYFDFNRFHCHFSPRDW
44_1          VITTSTRTWALPTYNNHLYKQISNGTSGGSTNDNTYFGYSTPWGYFDFNRFHCHFSPRDW
44_5          VITTSTRTWALPTYNNHLYKQISNGTSGGSTNDNTYFGYSTPWGYFDFNRFHCHFSPRDW
44_2          VITTSTRTWALPTYNNHLYKQISNGTSGGSTNDNTYFGYSTPWGYFDFNRFHCHFSPRDW
29.3\VP1      VITTSTRTWALPTYNNHLYKQISNGTSGGSTNDNTYFGYSTPWGYFDFNRFHCHFSPRDW
29.5\VP1      VITTSTRTWALPTYNNHLYKQISNGTSGGSTNDNTYFGYSTPWGYFDFNRFHCHFSPRDW
42_15         VITTSTRTWALPTYNNHLYKQISNGTSGGSTNDNTYFGYSTPWGYFDFNRFHCHFSPRDW
42_8          VITTSTRTWALPTYNNHLYKQISNGTSGGSTNDNTYFGYSTPWGYFDFNRFHCHFSPRDW
42_13         VITTSTRTWALPTYNNHLYKQISNGTSGGSTNDNTYFGYSTPWGYFDFNRFHCHFSPRDW
42_3A         VITTSTRTWALPTYNNHLYKQISNGTSGGSTNDNTYFGYSTPWGYFDFNRFHCHFSPRDW
42_4          VITTSTRTWALPTYNNHLYKQIS---SQSGATNDNHFFGYSTPWGYFDFNRFHCHFSSRDW
42_5A         VITTSTRTWALPTYNNHLYKQIS---SQSGATNDNHFFGYSTPWGYFDFNRFHCHFSPRDW
42_1B         VITTSTRTWALPTYNNHLYKQISNGTSGGSTNDNTYFGYSTPWGYFDFNRFHCHFSPRDW
42_5B         VITTSTRTWALPTYNNHLYKQISNGTSGGSTNDNTYFGYSTPWGYFDFNRFHCHFSPRDW
43_1          VITTSTRTWALPTYNNHLYKQISNGTSGGSTNDNTYFGYSTPWGYFDFNRFHCHFSPRDW
43_12         VITTSTRTWALPTYNNHLYKQISNGTSGGSTNDNTYFGYSTPWGYFDFNRFHCHFSPRDW
43_5          VITTSTRTWALPTYNNHLYKQISNGTSGGSTNDNTYFGYSTPWGYFDFNRFHCHFSPRDW
AAV8          VITTSTRTWALPTYNNHLYKQISNGTSGGATNDNTYFGYSTPWGYFDFNRFHCHFSPRDW
43_21         VITTSTRTWALPTYNNHLYKQISNGTSGGSTNDNTYFGYSTPWGYFDFNRFHCHFSPRDW
43_25         VITTSTRTWALPTYNNHLYKQISNGTSGGSTNDNTYFGYSTPWGYFDFNRFHCHFSPRDW
43_23         VITTSTRTWALPTYNNHLYKQISNGTSGGSTNDNTYFGYSTPWGYFDFNRFHCHFSPRDW
43_20         VITTSTRTWALPTYNNHLYKQISNGTSGGSTNDNTYFGYSTPWGYFDFNRFHCHFSPRDW
AAV_9         VITTSTRTWALPTYNNHLYKQISNGTSGGSTNDNTYFGYSTPWGYFDFNRFHCHFSPRDW
24.1          VITTSTRTWALPTYNNHLYKQIS-SQS-GATNDNHFFSYSTPWGYFDFNRFHCHFSPRDW
42.2REAL      VITTSTRTWALPTYNNHLYKQIS-SQS-GATNDNHFFGYSTPWGYFDFNRFHCHFSPRDW
7.2\VP1       VITTSTRTWALPTYNNHLYKQIS-SQS-GATNDNHFFGYSTPWGYFDFNRFHCHFSPRDW
27.3\VP1      VITTSTRTWALPTYNNHLYKQIS-SQS-GATNDNHFFGYSTPWGYFDFNRFHCHFSPRDW
16.3\VP1      VITTSTRTWALPTYNNHLYKQIS-SQS-GATNDNHFFGYSTPWGYFDFNRFHCHFSPRDW
42_10         VITTSTRTWALPTYNNHLYKQIS-SQS-GATNDNHFFGYSTPWGYFDFNRFHCHFSPRDW
42_3B         VITTSTRTWALPTYNNHLYKQIS-SQS-GATNDNHFFGYSTPWGYFDFNRFHCHFSPRDW
42_11         VITTSTRTWALPTYNNHLYKQIS-SQS-GATNDNHFFGYSTPWGYFDFNRFHCHFSPRDW
F1\VP1        VITTSTRTWALPTYNNHLYKQIS-SSSSGATNDNHYFGYSTPWGYFDFNRFHCHFSPRDW
F5\VP1@3      VITTSTRTWALPTYNNHLYKQIS-SSSSGATNDNHYFGYSTPWGYFDFNRFHCHFSPRDW
F3\VP1        VITTSTRTWALPTYNNHLYKQIS-SSSSGATNDNHYFGYSTPWGYFDFNRFHCHFSPRDW
42_6B         VITTSTRTWALPTYNNHLYKQISNGTSGGSTNDNTYFGYSTPWGYFDFNRFHCHFSPRDW
42_12         VITTSTRTWALPTYNNHLYKQISNGTSGGSTNDNTYFGYSTPWGYFDFNRFHCHFSPRDW
AAV5\CAP      VVTKSTRTWVLPSYNNHQYREIK-SGSVDGSNANAYFGYSTPWGYFDFNRFHSHWSPRDW
```

FIG. 2E

```
                         310       320       330       340       350       360
                    ....|....|....|....|....|....|....|....|....|....|....|....|
C1\VP1              QRLINNNWGLRPKAMRVKIFNIQVKEVTTSNGETTVANNLTSTVQIFADSSYELPYVMDA
C2\VP1              QRLINNNWGLRPKAMRVKIFNIQVKEVTTSNGETTVANNLTSTVQIFADSSYELPYVMDA
C5\VP1@2            QRLINNNWGLRPKAMRVKIFNIQVKEVTTSNGETTVANNLTSTVQIFADSSYELPYVMDA
AAV4\VP1            QRLINNNWGMRPKAMRVKIFNIQVKEVTTSNGETTVANNLTSTVQIFADSSYELPYVMDA
AAV1                QRLINNNWGFRPKRLNFKLFNIQVKEVTTNDGVTTIANNLTSTVQVFSDSEYQLPYVLGS
AAV6\VP1            QRLINNNWGFRPKRLNFKLFNIQVKEVTTNDGVTTIANNLTSTVQVFSDSEYQLPYVLGS
A3_3                QRLINNNWGFRPKKLNFKLFNIQVKEVTQNDGTTTIANNLTSAVQVFTDSEYQLPYVLGS
A3_7                QRLINNNWGFRPKKLNFKLFNIQVKEVTQNDGTTTIANNLTSTVQVFTDSEYQLPYVLGS
A3_4                QRLINNNWGFRPKKKLNFKLFNIQVKEVTQNDGTTTIANNLTSTVQVFTDSEYQLPYVLGS
A3_5                QRLINNNWGFRPKKLNFKLFNIQVKEVTQNDGTTTIANNLTSTVQVFTDSEYQLPYVLGS
AAV2                QRLINNNWGFRPKRLNFKLFNIQVKEVTQNDGTTTIANNLTSTVQVFTDSEYQLPYVLGS
AAV3                QRLINNNWGFRPKKLSFKLFNIQVRGVTQNDGTTTIANNLTSTVQVFTDSEYQLPYVLGS
13.3b\VP1           QRLINNNWGFRPKKLRFKLFNIQVKEVTTNDGVTTIANNLTSTIQVFSDSEYQLPYVLGS
AAV7                QRLINNNWGFRPKKLRFKLFNIQVKEVTTNDGVTTIANNLTSTIQVFSDSEYQLPYVLGS
223_4               QRLINNNWGFRPKKLNFKLFNIQVKEVTTNDGVTTIANNLTSTVQVFSDSEYQLPYVLGS
223_5               QRLINNNWGFRPKKLNFKLFNIQVKEVTTNDGVTTIANNLTSTVQVFSDSEYQLPYVLGS
223_10              QRLINNNWGFRPKKLNFKLFNIQVKEVTTNDGVTTIANNLTSTVQVFSDSEYQLPYVLGS
223_2               QRLINNNWGFRPKKLNFKLFNIQVKEVTTNDGVTTIANNLTSTVQVFSDSEYQLPYVLGS
223_7               QRLINNNWGFRPKKLNFKLFNIQVKEVTTNDGVTTIANNLTSTVQVFSDPEYQLPYVLGS
223_6               QRLINNNWGFRPKKLNFKLFNIQVKEVTTNDGVTTIANNLTSTVQVFSDSEYQLPYVLGS
44_1                QRLINNNWGFRPKRLNFKLFNIQVKEVTQNEGTKTIANNLTSTIQVFTDSEYQLPYVLGS
44_5                QRLINNNWGFRPKRPNFKLFNIQVKEVTQNEGTKTIANNLTSTIQVFTDSEYQLPYVLGS
44_2                QRLINNNWGFRPKRLNFKLFNIQVKEVTQNEGTKTIANNLTSTIQVFTDSEYQLPYVLGS
29.3\VP1            QRLINNNWGFRPKRLNFKLFNIQVKEVTQNEGTKTIANNLTSTIQVFTDSEYQLPYVLGS
29.5\VP1            QRLINNNWGFRPKSLNFKLFNIQVKEVTQNEGTKTIANNLTSTIQVFTDSEYQLPYVLGS
42_15               QRLINNNWGFRPKRLNFKLFNIQVKEVTQNEGTKTIANNLTSTIQVFTDSEYQLPYVLGS
42_8                QRLINNNWGFRPKRLNFKLFNIQVKEVTQNEGTKTIANNLTSTIQVFTDSEYQLPYVLGS
42_13               QRLINNNWGFRPKRLNFKLFNIQVKEVTQNEGTKTIANNLTSTIQVFTDSEYQLPYVLGS
42_3A               QRLINNSWGFRPKRLNFKLFNIQVKEVTQNEGTKTIANNLTSTIQVFTDSEYQLPYVLGS
42_4                QRLINNNWGFRPKRLNFKLFNIQVKEVTQNEGTKTIANNLTSTIQVFTDSEYRLPYVLGS
42_5A               QRLINNNRGFRPRKLRFKLFNIQVKEVTTNDGVTTIANNLTSTIQVFSDSEYQLPYVLGS
42_1B               QRLINNNWGFRPKRLNFKLFNIQVKEVTQNEGTKTIANNLTSTIQVFTDSEYQLPYVLGS
42_5B               QRLINNNWGFRPKRLNFKLFNIQVKEVTQNEGTKTIANNLTSTIQVFTDSEYQLPYVLGS
43_1                QRLINNNWGFRPKRLNFKLFNIQVKEVTQNEGTKTIANNLTSTIQVFTDSEYQLPYVPGS
43_12               QRLINNNWGFRPKRLNFKLFNIQVKEVTQNEGTKTIANNLTSTIQVFTDSEYQLPYVLGS
43_5                QRLINNNWGFRPKRLNFKLFNIQVKEVTQNEGTKTIANNLTSTIQVFTDSEYQLPYVLGS
AAV8                QRLINNNWGFRPKRLSFKLFNIQVKEVTQNEGTKTIANNLTSTIQVFTDSEYQLPYVLGS
43_21               QRLINNNWGFRPKRLNFKLFNIQVKEVTTNEGTKTIANNLTSTVRVFTDSEYQLPYVLGS
43_25               QRLINNNWGFRPKRLNFKLFNIQVKEVTTNEGTKTIANNLTSTVQVFTDSEYQLPYVLGS
43_23               QRLINNNWGFRPKRLNFKLFNIQVKEVTTNEGTKTIANNLTSTVQVFTDLEYQLPYVLGS
43_20               QRLINNNWGFRPKRLNFKLFNIQVKEVTTNEGTKTIANNLTSTVQVFTDSEYQLPYVLGS
AAV_9               QRLINNNWGFRPKRLNFKLFNIQVKEVTTNEGTKTIANNLTSTVQVFTDSEYQLPYVLGS
24.1                QRLINNNWGFRPRKLRFKLFNIQVKEVTTNDGVTTIANNLTSTIQVFSDSEYQLPYVLGS
42.2REAL            QRLINNNWGFRPRKLRFKLFNIQVKEVTTNDGVTTIANNLTSTIQVFSDSEYQLPYVLGS
7.2\VP1             QRLINNNWGFRPRKLRFKLFNIQVKEVTTNDGVTTIANNLTSTIQVFSDSEYQLPYVLGS
27.3\VP1            QRLINNNWGFRPRKLRFKLFNIQVKEVTTNDGVTTIANNLTSTIQVFSDSEYQLPYVLGS
16.3\VP1            QRLINNNWGFRPRKLRFKLFNIQVKEVTTNDGVTTIANNLTSTIQVFSDSEYQLPYVLGS
42_10               QRLINNNWGFRPRKLRFKLFNIQVKEVTTNDGVTTIANNLTSTIQVFSDSEYQLPYVLGS
42_3B               QRLINNNWGFRPRKLRFKLFNIQVKEVTTNDGVTTIANNLTSTIQVFSDSEYQLPYVLGS
42_11               QRLINNNWGFRPRKLRFKLFNIQVKEVTTNDGVTTIANNLTSTIQVFSDSEYQLPYVLGS
F1\VP1              QRLINNNWGFRPKKLRFKLFNIQVKEVTTNDGVTTIANNLTSTVQVFSDSEYQLPYVLGS
F5\VP1@3            QRLINNNWGFRPKKLRFKLFNIQVKEVTTNDGVTTIANNLTSTVQVFSDSEYQLPYVLGS
F3\VP1              QRLINNNWGFRPKKLRFKLLNIQVKEVTTNDGVTTIANNLTSTVQVFSDSEYQLPYVLGS
42_6B               QRLINNNWGFRPRKLRFKLFNIQVKEVTTDDGVTTIANNLTSTIQVFSDSEYQLPYVLGS
42_12               QRLINNNWGFRPKRLNFKLFNIQVKEVTQNEGTKTIANNLTSTIQVFTDSEYQLPYVLGS
AAV5\CAP            QRLINNYWGFRPRSLRVKIFNIQVKEVTVQDSTTTIANNLTSTVQVFTDDDYQLPYVVGN
```

FIG. 2F

```
                        370       380       390       400       410       420
                        ....|....|....|....|....|....|....|....|....|....|....|....|
C1\VP1        GQEGSLSPFPNDVFMVPQYGYCGIVTG-ENQNQTDRNAFYCLEYFPSQMLRTGNNFEMAY
C2\VP1        GQEGSLPPFPNDVFMVPQYGYCGIVTG-ENQNQTDRNAFYCLEYFPSQMLRTGNNFEMAY
C5\VP1@2      GQEGSLPPFPNDVFMVPQYGYCGIVTG-ENQNQTDRNAFYCLEYFPSQMLRTGNNFETAY
AAV4\VP1      GQEGSLPPFPNDVFMVPQYGYCGLVTGNTSQQQTDRNAFYCLEYFPSQMLRTGNNFEITY
AAV1          AHQGCLPPFPADVFMIPQYGYLTLNNG---SQAVGRSSFYCLEYFPSQMLRTGNNFTFSY
AAV6\VP1      AHQGCLPPFPADVFMIPQYGYLTLNNG---SQAVGRSSFYCLEYFPSQMLRTGNNFTFSY
A3_3          AHQGCLPPFPADVFMIPQYGYLTLNNG---SQAVGRSSFYCLEYFPSQMLRTGNNFTFSY
A3_7          AHQGCLPPFPADVFMIPQYGYLTLNNG---SQAVGRSSFYCLEYFPSQMLRTGNNFTFSY
A3_4          AHQGCLPPFPADVFMIPQYGYLTLNNG---SQAVGRSSFYCLEYFPSQMLRTGNNFTFSY
A3_5          AHQGCLPPFPADVFMIPQYGYLTLNNG---SQAVGRSSFYCLEYFPSQMLRTGNNFTFSY
AAV2          AHQGCLPPFPADVFMVPQYGYLTLNNG---SQAVGRSSFYCLEYFPSQMLRTGNNFTFSY
AAV3          AHQGCLPPFPADVFMVPQYGYLTLNNG---SQAVGRSSFYCLEYFPSQMLRTGNNFQFSY
13.3b\VP1     AHQGCLPPFPADVFMIPQYGYLTLNNG---SQSVGRSSFYCLEYFPSQMLRTGNNFEFSY
AAV7          AHQGCLPPFPADVFMIPQYGYLTLNNG---SQSVGRSSFYCLEYFPSQMLRTGNNFEFSY
223_4         AHQGCLPPFPADVFMIPQYGYLTLNNG---SQSVGRSSFYCLEYFPSQMLRTGNNFTFSY
223_5         AHQGCLPPFPADVFMIPQYGYLTLNNG---SQSVGRSSFYCLEYFPSQMLRTGNNFTFSY
223_10        AHQGCLPPFPADVFMIPQYGYLTLNNG---SQSVGRSSFYCLEYFPSQMLRTGNNFTFSY
223_2         AHQGCLPPFPADVFMIPQYGYLTLNNG---SQSVGRSSFYCLEYFPSQMLRTGNNFTFSY
223_7         AHQGCLPPFPADVFMIPQYGYLTLNNG---SQSVGRSSFYCLEYFPSQMLRTGNNFTFSY
223_6         AHQGCLPPFPADVFMIPQYGYLTLNNG---SQSVGRSSFYCLEYFPSQMLRTGNNFTFSY
44_1          AHQGCLPPFPADVFMIPQYGYLTLNNG---SQAVGRSSFYCLEYFPSQMLRTGNNFEFSY
44_5          AHQGCLPPFPADVFMIPQYGYLTLNNG---SQAVGRSSFYCLEYFPSQMLRTGNNFEFSY
44_2          AHQGCLPPFPADVFMIPQYGYLTLNNG---SQAVGRSSFYCLEYFPSQMLRTGNNFEFSY
29.3\VP1      ARQGCLPPFPADVFMIPQYGYLTLNNG---SQAVGRSSFYCLEYFPSQMLRTGNNFEFSY
29.5\VP1      AHQGCLPPFPADVFMIPQYGYLTLNNG---SQAVGRSSFYCLEYFPSQMLRTGNNFEFSY
42_15         AHQGCPPPFPADVFMIPQYGYLTLNNG---SQAVGRSSFYCLEYFPSQMRRTGNNFEFSY
42_8          AHQGCLPPFPADVFMIPQYGYLTLNNG---SQAVGRSSFYCLEYFPSQMLRTGNNFEFSY
42_13         AHQGCLPPFPADVFMIPQYGYLTLNNG---SQAVGRSSFYCLEYFPSQMLRTGNNFEFSY
42_3A         AHQGCLPPFPADVFMIPQYGYLTLNNG---SQAVGRSSFYCLEYFPSQMLRTGNNFEFSY
42_4          AHQGCLPPFPADVFMIPQYGYLTLNNG---SQAVGRSSFYCLEYFPSQMLRTGNNFEFSY
42_5A         AHQGCLPPFPADVFMIPQYGYLTLNNG---SQSVGRSSFYCLEYFPSQMLRTGNNFEFSY
42_1B         AHQGCLPPFPADVFMIPQYGYLTLNNG---SQAVGRSSFYCLEYFPSQMLRTGNNFEFSY
42_5B         AHQGCLPPFPADVFMIPQYGYLTLNNG---SQAVGRSSFYCLEYFPSQMLRTGNNFEFSY
43_1          AHQGCLPPFPADVFMIPQYGYLTLNNG---SQAVGRSSFYCLEYFPSQMLRTGNNFEFSY
43_12         AHQGCLPPFPADVFMIPQYGYLTLNNG---SQAVGRSSFYCLEYFPSQMLRTGNNFEFSY
43_5          AHQGCLPPFPADVFMIPQYGYLTLNNG---SQAVGRSSFYCLEYFPSQMLRTGNNFEFSY
AAV8          AHQGCLPPFPADVFMIPQYGYLTLNNG---SQAVGRSSFYCLEYFPSQMLRTGNNFQFTY
43_21         AHQGCLPPFPADVFMVPQYGYLTLNNG---SQALGRSSFYCLEYFPSQMLRTGNNFQFSY
43_25         AHQGCLPPFPADVFMVPQYGYLTLNNG---SQALGRSSFYCLEYFPSQMLRTGNNFQFSY
43_23         AHQGCLPPFPADVFMVPQYGYLTLNNG---SQALGRSSFYCLEYFPSQMPRTGNNFQFSY
43_20         AHQGCLPPFPADVFTVPQYGYLTLNNG---SQALGRSSFYCLEYFPSQMLRTGNNFQFSY
AAV_9         AHQGCLPPFPADVFMVPQYGYLTLNNG---SQALGRSSFYCLEYFPSQMLRTGNNFQFSY
24.1          AHQGCLPPFPADVFMIPQYGYLTLNNG---SQSVGRSSFYCLEYFPSQMLRTGNNFEFSY
42.2REAL      AHQGCLPPFPADVFMIPQYGYLTLNNG---SQSVGRSSFYCLEYFPSQMLRTGNNFEFSY
7.2\VP1       AHQGCLPPFPADVFMIPQYGYLTLNNG---SQSVGRSSFYCLEYFPSQMLRTGDNFEFSY
27.3\VP1      AHQGCLPPFPADVFMIPQYGYLTLNNG---SQSVGRSSFCCLEYFPSQMLRTGNNFEFSY
16.3\VP1      AHQGCLPPFPADVFMIPQYGYLTLNNG---SQSMGRSSFYCLEYFPSQMLRTGNNFEFSY
42_10         AHQGCLPPFPADVFMIPQYGYLTLNNG---SQSVGRSSFYCLEYFPSQMLRTGNNFEFSY
42_3B         AHQGCLPPFPADVFMIPQYGYLTLNNG---SQSVGRSSFYCLEYFPSQMLRTGNNFEFSY
42_11         AHQGCLPPFPADVFMIPQYGYLTLNNG---SQSVGRSSFYCLEYFPSQMLRTGNNFEFSY
F1\VP1        AHQGCLPPFPADVFMIPQYGYLTLNNG---SQSVGRSSFYCLEYFPSQMLRTGNNFEFSY
F5\VP1@3      AHQGCLPPFPADVFMIPQYGYLTLNNG---SQSVGRSSFYCLEYFPSQMLRTGNNFEFSY
F3\VP1        AHQGCLPPFPADVFMIPQYGYLTLDNG---SQSVGRSSFYCLEYFPSQMLRTGNNFEFSY
42_6B         AHQGCLPPFPADVFMIPQYGYLTLNNG---SQSVGRSSFYCLEYFPSQMLRTGNNFEFSY
42_12         AHQGCLPPFPADVFMIPQYGYLTLNNG---SQAVGRSSFYCLEYFPSQMLRTGNNFEFSY
AAV5\CAP      GTEGCLPAFPPQVFTLPQYGYATLNRD-NTENPTERSSFFCLEYFPSKMLRTGNNFEFTY
```

FIG. 2G

```
                        430       440       450       460       470       480
                 ....|....|....|....|....|....|....|....|....|....|....|....|
C1\VP1           NFGKVPFHSMYAYSQSPDRLMNPLLDQYLWHLQSTTSGETLNQGNAATTFGKIRSGDFAF
C2\VP1           NFEKVPFHSMYAHSQSLDRLMNPLLDQYLWHLQSTTSGETLNQGNAATTFGKIRSGDFAF
C5\VP1@2         NFEKVPFHSMYAHSQSLDGLMNPLLDQYLWHLQSTTSGETLNQGNAATTFGKIRSGDFAF
AAV4\VP1         SFEKVPFHSMYAHSQSLDRLMNPLIDQYLWGLQSTTTGTTLNAGTATTNFTKLRPTNFSN
AAV1             TFEEVPFHSSYAHSQSLDRLMNPLIDQYLYYLNRTQNQSG-SAQNKDLLFSRGSPAGMSV
AAV6\VP1         TFEDVPFHSSYAHSQSLDRLMNPLIDQYLYYLNRTQNQSG-SAQNKDLLFSRGSPAGMSV
A3_3             TFEDVPFHSSYAHSQSLDRLMNPLIDQYLYYLSKTQ-GTSGTTQQSRLQFSQAGPSSMAQ
A3_7             TFEDVPFHSSYAHSQSLDRLMNPLIDQYLYYLSKTQ-GTSGTTQQSRLQFSQAGPSSMAQ
A3_4             TFEDVPFHSSYAHSQSLDRLMNPLIDQYLYYLSKTQ-GTSGTTQQSRLQFSQAGPSSMAQ
A3_5             TFEDVPFHSSYAHSQSLDRLMNPLIDQYLYYLSKTQ-GTSGTTQQSRLQFNQAGPSSMAQ
AAV2             TFEDVPFHSSYAHSQSLDRLMNPLIDQYLYYLSRTN-TPSGTTTQSRLQFSQAGASDIRD
AAV3             TFEDVPFHSSYAHSQSLDRLMNPLIDQYLYYLNRTQGTTSGTTNQSRLLFSQAGPQSMSL
13.3b\VP1        SFEDVPFHSSYAHSQSLDRLMNPLIDQYLYYLARTQSDPGGTAGNRELQFYQGGPSTMAE
AAV7             SFEDVPFHSSYAHSQSLDRLMNPLIDQYLYYLARTQSNPGGTAGNRELQFYQGGPSTMAE
223_4            TFEDVPFHSSYAHSQSLGRLMNPLIDQYLYYLARTQSNAGGTAGNRELQFYQGGPTTMAE
223_5            TFEDVPFHSSYAHSQSLGRLMNPLIDQYLYYLARTQSNAGGTAGNRELQFYQGGPTTMAE
223_10           TFEDVPFHSSYAHSQSLGRLMNPLIDQYLYYLARTQSNAGGTAGNRELQFYQGGPTTMAE
223_2            TFEDVPFHSSYAHSQSLGRLMNPLIDQYLYYLARTQSNAGGTAGNRELQFYQGGPTTMAE
223_7            TFEDVPFHSSYAHSQSLGRLMNPLIDQYLYYLARTQSNAGGTAGNRELQFYQGGPTTMAE
223_6            TFEDVPFHSSYAHSQSLGRLMNPLIDQYLYYLARTQSNAGGTAGNRELQFYQGGPTTMAE
44_1             QFEDVPFHSSYAHSQSLDRLMNPLIDQYLYYLSRTQSTGG-TAGTQQLLFSQAGPNNMSA
44_5             QFEDVPFHSSYAHSQSLDRLMNPLIDQYLYYLSRTQSTGG-TAGTQQLLFSQAGPNNMSA
44_2             QFEDVPFHSSYAHSQSLDRLMNPLIDQYLYYLSRTQSTGG-TAGTQQLLFSQAGPNNMSA
29.3\VP1         QFEDVPFHSSYAHSQSLDRLMNPLIDQYLYYLSRTQSTGG-TAGTQQLLFSQAGPNNMSA
29.5\VP1         QFEDVPFHSSYAHSQSLDRLMNPLIDQYLYYLSRTQSTGG-TAGTQQLLFSQAGPNNMSA
42_15            QFEDVPFHSSYAHSQSLDRLMNPLIDQYLYYLSRTQSTGG-TAGTQQLLFSQAGPNNMSA
42_8             QFEDVPFHSSYAHSQSLDRLMNPLIDQYLYYLSRTQSTGG-TAGTQQLLFSQAGPNNMSA
42_13            QFEDVPFHSSYAHSQSLDRLMNPLIDQYLYYLSRTQSTGG-TAGTQQLLFSQAGPNNMSA
42_3A            QFEDVPFHSSYAHSQSLDRLMNPLIDQYLYYLSRTQSTGG-TAGTQQLLFSQAGPNNMSA
42_4             QFEDVPFHSSYAHSQSLDRLMNPLIDQYLYYLSRTQSTGG-TAGTQQLLFSQAGPNNMSA
42_5A            QFEDVPFHSSYAHSQSLDRLMNPLIDQYLYYLSRTQSTGG-TAGTQQLLFSQAGPNNMSA
42_1B            QFEDVPFHSSYAHSQSLDRLMNPLIDQYLYYLSRTQSTGG-TAGTQQLLFSQAGPNNMSA
42_5B            QFEDVPFHSSYAHSQSLDRLMNPLIDQYLYYLSRTQSTGG-TAGTQQLLFSQAGPNNMSA
43_1             TFEDVPFHSSYAHSQSLDRLMNPLIDQYLYYLSRTQSTGG-TQGTQQLLFSQAGPANMSA
43_12            TFEDVPFHSSYAHSQSLDRLMNPLIDQYLYYLSRTQSTGG-TQGTQQLLFSQAGPANMSA
43_5             TFEDVPFHSSYAHSQSLDRLMNPLIDQYLYYLSRTQSTGG-TQGTQQLLFSQAGPANMSA
AAV8             TFEDVPFHSSYAHSQSLDRLMNPLIDQYLYYLSRTQTTGG-TANTQTLGFSQGGPNTMAN
43_21            TFEDVPFHSSYAHSQSLDRLMNPLIDQYLYYLVRTQTTG--TGGTQTLAFSQAGPSSMAN
43_25            TFEDVPFHSSYAHSQSLDRLMNPLIDQYLYYLVRTQTTG--TGGTQTLAFSQAGPSSMAN
43_23            TFEDVPFHSSYAHSQSLDRLMNPLIDQYLYYLVRTQTTG--TGGTQTLAFSQAGPSSMAN
43_20            TFEDVPFHSSYAHSQSLDRLMNPLIDQYLYYLVRTQTTG---TGGTQTLAFSQAGPSSMAN
AAV_9            TFEDVPFHSSYAHSQSLDRLMNPLIDQYLYYLVRTQTTG--TGGTQTLAFSQAGPSSMAN
24.1             TFEEVPFHSSYVHSQSLDRLMNPLIDQYLYYLARTQST---TGSTRELQFHQAGPNTMAE
42.2REAL         TFEEVPFHSSYAHSQSLDRLMNPLIDQYLYYLARTQST---TGSTRELQFHQAGPNTMAE
7.2\VP1          TFEEVPFHSSYAHSQSLDRLMNPLIDQYLYYLARTQST---TGSTRELQFHQAGPNTMAE
27.3\VP1         TFEEVPFHSSYAHSQSLDRLMNPLIDQYLYYLARTQST---TGSTRELQFHQAGPNTVAE
16.3\VP1         TFEEVPFHSSYAHSQSLDRLMNPLIDQYLYYLARTQST---TGSTRELQFHQAGPNTMAE
42_10            TFEEVPFHSSYAHSQSLDRLMNPLIDQYLYYLARTQST---TGSTRELQFHQAGPNTMAE
42_3B            TFEEVPFHSSYAHSQSLDRLMNPLIDQYLYYLARTQST---TGSTRELQFHQAGPNTMAE
42_11            TFEEVPFHSSYAHSQSLDRLMNPLIDQYLYYLARTQST---TGSTRELQFHQAGPNTMAE
F1\VP1           SFEDVPFHSSYAHSQSLDRLMNPLIDQYLYYLARTQST---TGSTRELQFHQAGPNTMAE
F5\VP1@3         SFEDVPFHSSYAHSQSLDRLMNPLIDQYLYYLARTQST---TGSTRELQFHQAGPNTMAE
F3\VP1           SFEDVPFHSSYAHSQSLDRLMNPLIDQYLYYLARTQST---TGSTRELQFHQAGPNTMAE
42_6B            TFEEVPFHSSYAHSQSLDRLMNPLIDQYLYYLARTQST---TGSTRELQFHQAGPNTMAE
42_12            QFEDVPFHSSYAHSQSLDRLTNPLIDQYLYYLARTQST---TGSTRGLQFHQAGPNTMAE
AAV5\CAP         NFEEVPFHSSFAPSQNLFKLANPLVDQYLRFVSTNNTGG-------VQFNKNLAGRYAN
```

FIG. 2H

```
                   490       500       510       520       530       540
            ....|....|....|....|....|....|....|....|....|....|....|....|
C1\VP1      YRKNWLPGPCVKQQRLSKTASQNYKIPASGGNALLKYDTHYTLNNRWSNIAPGPPMATAG
C2\VP1      YRKNWLPGPCVKQQRFSKTASQNYKIPASGGNALLKYDTHYTLNNRWSNIAPGPPMATAG
C5\VP1@2    YRKNWLPGPCVKQQRFSKTASQNYKIPASGGNALLKYDTHYTLNNRWSNIAPGPPMATAG
AAV4\VP1    FKKNWLPGPSIKQQGFSKTANQNYKIPATGSDSLIKYETHSTLDGRWSALTPGPPMATAG
AAV1        QPKNWLPGPCYRQQRVSKTKTDN-----NNSNFTWTGASKYNLNGRESIINPGTAMASHK
AAV6\VP1    QPKNWLPGPCYRQQRVSKTKTDN-----NNSNFTWTGASKYNLNGRESIINPGTAMASHK
A3_3        QAKNWLPGPSYRQQRMSKTANDN-----NNSEFAWTAATKYYLNGRNSLVNPGPPVASHK
A3_7        QAKNWLPGPSYRQQRMSKTANDN-----NNSEFAWTAATKYYLNGRNSLVNPGPPMASHK
A3_4        QAKNWLPGPSYRQQRMSKTANDN-----NNSEFAWTAATKYYLNGRNSLVNPGPPMASHK
A3_5        QAKNWLPGPSYRQQRMSKTANDN-----NNSEFAWTAATKYYPNGRNSLVNPGPPMASHK
AAV2        QSRNWLPGPCYRQQRVSKTSADN-----NNSEYSWTGATKYHLNGRDSLVNPGPAMASHK
AAV3        QARNWLPGPCYRQQRLSKTANDN-----NNSNFPWTAASKYHLNGRDSLVNPGPAMASHK
13.3b\VP1   QAKNWLPGPCFRQQRVSKTLDQN-----NNSNFAWTGATKYHLNGRNSLVNPGVAMATHK
AAV7        QAKNWLPGPCFRQQRVSKTLDQN-----NNSNFAWTGATKYHLNGRNSLVNPGVAMATHK
223_4       QAKNWLPGPCFRQQRVSKTLDQN-----NNSNFAWTGATKYHLNGRNSLVNPGVAMATHK
223_5       QAKNWLPGPCFRQQRVSKTLDQN-----NNSNFAWTGATKYHLNGRNSLVNPGVAMATHK
223_10      QAKNWLPGPCFRQQRVSKTLDQN-----NNSNFAWTGATKYHLNXRNSLVNPGVAMATHK
223_2       QAKNWLPGPCFRQQRVSKTLDQN-----NNSNFAWTGATKYHLNGRNSLVNPGVAMATHK
223_7       QAKNWLPGPCFRQQRVSKTLDQN-----NNSNFAWTGATKYHLNGRNSLVNPGVAMATHK
223_6       QAKNWLPGPCFRQQRVSKTLDQN-----NNSNFAWTGATKYHLNGRNSLVNPGVAMATHK
44_1        QAKNWLPGPCYRQQRVSTTLSQN-----NNSNFAWTGATKYHLNGRDSLVNPGVAMATHK
44_5        QAKNWLPGPCYRQQRVSTTLSQN-----NNSNFAWTGATKYHLNGRDSLVNPGVAMATHK
44_2        QAKNWLPGPCYRQQRVSTTLSQN-----NNSNFAWTGATKYHLNGRDSLVNPGVAMATHK
29.3\VP1    QAKNWLPGPCYRQQRVSTTLSQN-----NNSNFAWTGATKYHLNGRDSLVNPGVAMATHK
29.5\VP1    QAKNWLPGPCYRQQRVSTTLSQN-----DNSNFAWTGATKYHLNGRDSLVNPGVAMATHK
42_15       QAKNWLPGPCYRQQRVSTTLSQN-----NNSNFAWTGATKYHLNGRDSLVNPGVAMATHK
42_8        QAKNWLPGPCYRQQRVSTTLSQN-----NNSNFAWTGATKYHLNGRDSLVNPGVAMATHK
42_13       QAKNWLPGPCYRQQRVSTTVSQN-----NNSNFAWTGATKYHLNGRDSLVNPGVAMATHK
42_3A       QAKNWLPGPCYRQQRVSTTLSQN-----NNSNFAWTGATKYHLNGRDSLVNPGVAMATHK
42_4        QAKNWLPGPCYRQQRVSTTLSQN-----NNSNFAWTGATKYHLNGRDSLVNPGVAMATHK
42_5A       QAKNWLPGPCYRQQRVSTTLSQN-----NNSNFAWTGATKYHLNGRDSLVNPGVAMATHK
42_1B       QAKNWLPGPCYRQQRVSTTVSQN-----NNSNFAWTGATKYHLNGRDSLVNPGVAMATHK
42_5B       QAKNWLPGPCYRQQRVSTTLSQN-----NNSNFAWTGATKYHLNGRDSLVNPGVAMATHK
43_1        QAKNWLPGPCYRQQRVSTTLSQN-----NNSNFAWTGATKYHLNGRDSLVNPGVAMATHK
43_12       QAKNWLPGPCYRQQRVSTTLSQN-----NNSNFAWTGATKYHLNGRDSLVNPGVAMATHK
43_5        QAKNWLPGPCYRQQRVSTTLSQN-----NNSNFAWTGATKYHLNGRDSLVNPGVAMATHK
AAV8        QAKNWLPGPCYRQQRVSTTTGQN-----NNSNFAWTAGTKYHLNGRNSLANPGIAMATHK
43_21       QARNWVPGPCYRQQRVSTTTNQS-----NNSNFAWTGAAKFKLNGRDSLMNPGVAMASHK
43_25       QARNWVPGPCYRQQRVSTTTNQN-----NNSNFAWTGAAKFKLNGRDSLMNPGVAMASHK
43_23       QARNWVPGPCYRQQRVSTTTNQN-----NNSNFAWTGAAKFKLNGRDSLMNPGVAMASHK
43_20       QARNWVPGPCYRQQRVSTTTNQN-----NNSNFAWTGAAKFKLNGRDSLMNPGVAMASHK
AAV9        QARNWVPGPCYRQQRVSTTTNQN-----NNSNFAWTGAAKFKLNGRDSLMNPGVAMASHK
24.1        QSKNWLPGPCYRQQRLSKNIDSN-----NNSNFAWTGATKYHLNGRNSLTNPGVAMATNK
42.2REAL    QSKNWLPGPCYRQQRLSKNIDSN-----NNSNFAWTGATKYHLNGRNSLTNPGVAMATNK
7.2\VP1     QSKNWLPGPCYRQQRLSKNIDSN-----NNSNFAWTGATKYHLNGRNSLTNPGVAMATNK
27.3\VP1    QSKNWLPGPCYRQQRLSKNIDSN-----NNSNFAWTGATKYHLNGRNSLTNPGVAMATNK
16.3\VP1    QSKNWLPGPCYRQQRLSKNIDSN-----NNSNFAWTGATKYHLNGRNSLTNPGVAMATNK
42_10       QSKNWLPGPCYRQQRLSKNIDSN-----NNSNFAWTGATKYNLNGRNSLTNPGVAMATNK
42_3B       QSKNWLPGPCYRQQRLSKNIDSN-----NTSNFAWTGATKYHLNGRNSLTNPGVAMATNK
42_11       QSKNWLPGPCYRQQRLSKDIDSN-----NNSNFAWTGATKYHLNGRNSLTNPGVAMATNK
F1\VP1      QSKNWLPGPCYRQQGLSKNLDFN-----NNSNFAWTAATKYHLNGRNSLTNPGIPMATNK
F5\VP1@3    QSKNWLPGPCYRQQRLSKNLDFN-----NNSNFAWTAATKYHLNGRNSLTNPGIPMATNK
F3\VP1      QSKNWLPGPCYRQQRLSKNLDFN-----NNSNFAWTAATKYHLNGRNSLTNPGIPMATNK
42_6B       QSKNWLPGPCYRQQRLSKNIDSN-----NNSNFAWTGATKYHLNGRNSLTNPGVAMATNK
42_12       QSKNWLPGPCYRQQRLSKNIDSN-----NNSNFAWTGATKYHLNGRNSLTNPGVAMATNK
AAV5\CAP    TYKNWFPGPMGRTQGWNLGSGVN-----RASVSAFATTNRMELEGASYQVPPQPNGMTNN
```

FIG. 2I

```
                       550       560       570       580       590       600
                ....|....|....|....|....|....|....|....|....|....|....|....|
C1\VP1          PSDGDFS-NAQLIFPGPS--VTGNTTTSAN-NLLFTSEEEIAATNPRDTDMFGQIADNNQ
C2\VP1          PSDGDFS-NAQLIFPGPS--VTGNTTTSAN-NLLFTSEGEIAATNPRDTDMFGQIADNNQ
C5\VP1@2        PSDGDFS-NAQLIFPGPS--VTGNTTTSAN-NLLFTSEEEIAATNPRDTDMFGQIADNNQ
AAV4\VP1        PADSKFS-NSQLIFAGPK--QNGNTATVPG-TLIFTSEEELAATNATDTDMWGNLPGGDQ
AAV1            DDEDKFFPMSGVMIFGKE--SAGASNTALD-NVMITDEEEIKATNPVATERFGTVAVNFQ
AAV6\VP1        DDKDKFFPMSGVMIFGKE--SAGASNTALD-NVMITDEEEIKATNPVATERFGTVAVNLQ
A3_3            DDEEKYFPMHGNLIFGKQ---GTGTTNVDIE-SVLITDEEEIRTTNPVATEQYGQVATNHQ
A3_7            DDEEKYFPMHGNLIFGKQ---GTGTTNVDIE-SVLITDEEEIRTTNPVATEQYGQVATNHQ
A3_4            DDEEKYFPMHGNLIFGKQ---GTGTTNVDIE-SVLITDEEEIRTTNPVATEQYGQVATNHQ
A3_5            DDEEKYFPMHGNLIFGKQ---GTGTTNVDIE-SVLITDEEEIRTTNPVATEQYGQVATNRQ
AAV2            DDEEKFFPQSGVLIFGKQ---GSEKTNVDIE-KVMITDEEEIRTTNPVATEQYGSVSTNLQ
AAV3            DDEEKFFPMHGNLIFGKE--GTTASNAELD-NVMITDEEEIRTTNPVATEQYGTVANNLQ
13.3b\VP1       DDEDRFFPSSGVLIFGKT--GATN-KTTLE-NVLMTNEEEIRPTNPVATEEYGIVSSNLQ
AAV7            DDEDRFFPSSGVLIFGKT--GATN-KTTLE-NVLMTNEEEIRPTNPVATEEYGIVSSNLQ
223_4           DDEERFFPSSGVLIFGKT---GAAN-KTTLE-NVLMTNEEEIRPTNPVATEEYGIVSSNLQ
223_5           DDEERFFPSSGVLIFGKT---GAAN-KTTLE-NVLMTNEEEIRPTNPVATEEYGIVSSNLQ
223_10          DDEERFFPSSGVLIFGKT---GAAN-KTTLE-NVLMTNEEEIRPTNPVATEEYGIVSSNLQ
223_2           DDEERFSPSSGVLIFGKT---GAAN-KTTLE-NVLMTNEEEIRPTNPVATEEYGIVSSNLQ
223_7           DDEERFFPSSGVLIFGKT---GAAN-KTTLE-NVLMTNEEEIRPTNPVATEEYGIVSSNLQ
223_6           DDEERFFPSSGVLIFGKT---GAAN-KTTLE-NVLMTNEEEIRPTNPVATEEYGIVSSNLQ
44_1            DDEERFFPSSGVLMFGKQ--GAGKDNVDYS-SVMLTSEEEIKTTNPVATEQYGVVADNLQ
44_5            DDEERFFPSSGVLMFGKQ--GAGKDNVDYS-SVMLTSEEEIKTTNPVATEQYGVVADNLQ
44_2            DDEERFFPSSGVLMFGKQ--GAGKDNVDYS-SVMLTSEEEIKTTNPVATEQYGVVADNLQ
29.3\VP1        DDEERFFPSSGVLMFGKQ--GAGKGNVDYS-SVMLTSEEEIKTTNPVATEQYGVVADNLQ
29.5\VP1        DDEERFFPSSGVLMFGKQ--GAGKDNVDYS-SVMLTSEEEIKTTNPVATEQYGVVADNLQ
42_15           DDEERFFPSSGVLMFGKQ---GAGKDNVDYS-SVMLTSEEEIKTTNPVATEQYGVVADNLQ
42_8            DDEERFFPSSGVLMFGKQ--GAGKDNVDYS-SVMLTSEEEIKTTNPVATEQYGVVADNLQ
42_13           GDEERFFPSSGVLMFGKQ---GAGKDNVDYS-SVMLTSEEEIKTTNPVATEQYGVVADNLQ
42_3A           DDEERFFPSSGVLMFGKQ--GAGKDNVDYS-SVMLTSEEEIKTTNPVATEQYGVVADNLQ
42_4            DDEERFFPSSGVLMFGKQ--GAGKDNVDYS-SVMLTSEEEIKTTNPVATEQYGVVADNLQ
42_5A           DDEERFFPSSGVLMFGKQ--GAGKDNVDYS-SVMLTSEEEIKTTNPVATEQYGVVADNLQ
42_1B           GDEERFFPSSGVLMFGKQ---GAGKDNVDYS-SVMLTSEEEIKTTNPVATEQYGVVADNLQ
42_5B           DDEERFFPSSGVLMFGKQ--GAGKDNVDYS-SVMLTSEEEIKTTNPVATEQYGVVADNLQ
43_1            DDEERFFPSSGVLMFGKQ--GAGKDNVDYS-SVMLTSEEEIKTTNPVATEQYGVVADNLQ
43_12           DDEERFFPSSGVLMFGKQ--GAGKDNVDYS-SVMLTSEEEIKTTNPVATEQYGVVADNLQ
43_5            DDEERFFPSSGVLMFGKQ--GAGKDNVDYS-SVMLTSEEEIKTTNPVATEQYGVVADNLQ
AAV8            DDEERFFPSNGILIFGKQ---NAARDNADYS-DVMLTSEEEIKTTNPVATEEYGIVADNLQ
43_21           DDDDRFFPSSGVLIFGKQ---GAGNDGVDYS-QVLITDEEEIKATNPVATEEYGAVAINNQ
43_25           DDDDRFFPSSGVLIFGKQ---GAGNDGVDYS-QVLITDEEEIKATNPVATEEYGAVAINNQ
43_23           DDDDRFFPSSGVLIFGKQ---GAGNDGVDYS-QVLITDEEEIKATNPVATEEYGAVAINNQ
43_20           DDDDRFFPSSGVLIFGKQ---GAGNDGVDYS-QVLITDEEEIKATNPVATEEYGAVAINNQ
AAV_9           DDEDRFFPSSGVLIFGKQ---GAGNDGVDYS-QVLITDEEEIKATNPVATEEYGAVAINNQ
24.1            DDEDQFFPINGVLVFGKT--GAAN-KTTLE-NVLMTSEEEIKTTNPVATEEYGVVSSNLQ
42.2REAL        DDEDQFFPINGVLVFGET--GAAN-KTTLE-NVLMTSEEEIKTTNPVATEEYGVVSSNLQ
7.2\VP1         DDEDQFFPINGVLVFGKT--GAAN-KTTLE-NVLMTSEEEIKTTNPVATEEYGVVSSNLQ
27.3\VP1        DDEDQFLPINGVLVFGKT--GAAN-KTTLE-NVLMTSEEEIKTTNPVATEEYGVVSSNLQ
16.3\VP1        DDEGQFFPINGVLVFGKT--GAAN-KTTLE-NVLMTSEGEIKTTNPVATEEYGVVSSNLQ
42_10           DDEDQFFPINGVLVFGKT--GAAN-KTTLE-NVLMTSEEEIKTTNPVATEEYGVVSSNLQ
42_3B           DDEDQFFPINGVLVFGKT--GAAN-KTTLE-NVLMTSEEEIKTTNPVATEQYGVVSSNLQ
42_11           DDEDQFFPINGVLVFGKT--GAAN-KTTLE-NVLMTSEEEIKTTNPVATEEYGVVSSNLQ
F1\VP1          DDEDQFFPINGVLVFGKT--GAAN-KTTLE-NVLMTSEEEIKTTNPVATEEYGVVSSNLQ
F5\VP1@3        DDEDQFFPINGVLVFGKT--GAAN-KTTLE-NVLMTSEEEIKTTNPVATEEYGVVSSNLQ
F3\VP1          DDEDQFFPINGVLVFGKT--GAAN-KTTLE-NVLMTSEEEIKTTNPVATEEYGVVSSNLQ
42_6B           DDEDQFFPINGVLVFGKT--GAAN-KTTLE-NVLMTSEEEIKTTNPVATEEYGVVSSNLQ
42_12           DDEDQFFPINGVLVFGKT--GAAN-KTTLE-NVLMTSEEEIKTTNPVATEEYGVVSSNLQ
AAV5\CAP        LQGSNTYALENTMIFNSQPANPGTTATYLEGNMLITSESETQPVNRVAYNVGGQMATNNQ
```

FIG. 2J

```
                      610       620       630       640       650       660
                 ....|....|....|....|....|....|....|....|....|....|....|....|
C1\VP1           NATTAPITGNVTAMGVLPGMVWQNRDIYYQGPIWAKIPHADGHFHPSPLIGGFGLKHPPP
C2\VP1           NATTAPITGNVTAMGVLPGMVWQNRDIYYQGPIWAKIPHADGHFHPSPLIGGFGLKHPPP
C5\VP1@2         NATTAPITGNVTAMGVLPGMVWQNRDIYYQGPIWAKIPHADGHFHPSPLIGGFGLKHPPP
AAV4\VP1         SNSNLPTVDRLTALGAVPGMVWQNRDIYYQGPIWAKIPHTDGHFHPSPLIGGFGLKHPPP
AAV1             SSSTDPATGDVHAMGALPGMVWQDRDVYLQGPIWAKIPHTDGHFHPSPLMGGFGLKNPPP
AAV6\VP1         SSSTDPATGDVHVMGALPGMVWQDRDVYLQGPIWAKIPHTDGHFHPSPLMGGFGLKHPPP
A3_3             SQNTTASYGSVDSQGILPGMVWQDRDVYLQGPIWAKTPHTDGHFHPSPLMGGFGLKHPPP
A3_7             SQNTTASYGSVDSQGILPGMVWQDRDVYLQGPIWAKTPHTDGHFHPSPLMGGFGLKHPPP
A3_4             SQDTTASYGSVDSQGILPGMVWQDRDVYLQGPIWAKTPHTDGHFHPSPLMGGFGLKHPPP
A3_5             SQNTTASYGSVDSQGILPGMVWQDRDVYLQGPIWAKTPHTDGHFHPSPLMGGFGLKHPPP
AAV2             RGNRQAATADVNTQGVLPGMVWQDRDVYLQGPIWAKIPHTDGHFHPSPLMGGFGLKHPPP
AAV3             SSNTAPTTGTVNHQGALPGMVWQDRDVYLQGPIWAKIPHTDGHFHPSPLMGGFGLKHPPP
13.3b\VP1        AANTAAQTQVVNNQGALPGMVWQNRDVYLQGPIWAKIPHTDGNFHPSPLMGGFGLKHPPP
AAV7             AANTAAQTQVVNNQGALPGMVWQNRDVYLQGPIWAKIPHTDGNFHPSPLMGGFGLKHPPP
223_4            AASTAAQTQVVNNQGALPGMVWQNRDVYLQGPIWAKIPHTDGNFHPSPLMGGFGLKHPPP
223_5            AASTAAQTQVVNNQGALPGMVWQNRDVYLQGPIWAKIPHTDGNFHPSPLMGGFGLKHPPP
223_10           AASTAAQTQVVNNQGALPGMVWQNRDVYLQGPIWAKIPHTDGNFHPSPLMGGFGLKHPPP
223_2            AASTAAQTQVVNNQGALPGMVWQNRDVYLQGPIWAKIPHTDGNFHPSPLMGGFGLKHPPP
223_7            AASTAAQTQVVNNQGALPGMVWQNRDVYLQGPIWAKIPHTDGNFHPSPLMGGFGLKHPPP
223_6            AASTAAQTQVVNNQGALPGMVWQNRDVYLQGPIWAKIPHTDGNFHPSPLMGGFGLKHPPP
44_1             QQNAAPIVGAVNSQGALPGMVWQNRDVYLQGPIWAKIPHTDGNFHPSPLMGGFGLKHPPP
44_5             QQNAAPIVGAVNSQGALPGMVWQNRDVYLQGPIWAKIPHTDGNFHPSPLMGGFGLKHPPP
44_2             QQNAAPIVGAVNSQGALPGMVWQNRDVYLQGPIWAKIPHTDGNFHPSPLMGGFGLKHPPP
29.3\VP1         QQNAAPIVGAVNSQGALPGMVWQNRDVYLQGPIWAKIPHTDGNFHPSPLMGGFGLKHPPP
29.5\VP1         QQNAAPIVGAVNSQGALPGMVWQNRDVYLQGPIWAKIPHTDGNFHPSPLMGGFGLKHPPP
42_15            QQNAAPIVGAVNSQGALPGMVWQNRDVYLQGPIWAKIPHTDGNFHPSPLMGGFGLKHPPP
42_8             QQNAAPIVGAVNSQGALPGMVWQNRDVYLQGPIWAKIPHTDGNFHPSPLMGGFGLKHPPP
42_13            QQNAAPIVGAVNSQGALPGMVWQNRDVYLQGPIWAKIPHTDGNFHPSPLMGGFGLKHPPP
42_3A            QQNAAPIVGAVNSQGALPGMVWQNRDVYLQGPIWAKIPHTDGNFHPSPLMGGFGLKHPPP
42_4             QQNAAPIVGAVNSQGALPGMVWQNRDVYLQGPIWAKIPHTDGNFHPSPLMGGFGLKHPPP
42_5A            QQNAAPIVGAVNSQGALPGMAWQNRDVYLQGPIWAKIPHTDGNFHPSPLMGGFGLKHPPP
42_1B            QQNAAPIVGAVNSQGALPGMVWQNRDVYLQGPIWAKIPHTDGNFHPSPLMGGFGLKHPPP
42_5B            QQNAAPIVGAVNSQGALPGMVWQNRDVYLQGPIWAKIPHTDGNFHPSPLMGGFGLKHPPP
43_1             QTNGAPIVGTVNSQGALPGMVWQNRDVYLQGPIWAKIPHTDGNFHPSPLMGGFGLKHPPP
43_12            QTNGAPIVGTVNSQGALPGMVWQNRDVYLQGPIWAKIPHTDGNFHPSPLMGGFGLKHPPP
43_5             QTNGAPIVGTVNSQGALPGMVWQNRDVYLQGPIWAKIPHTDGNFHPSPLMGGFGLKHPPP
AAV8             QQNTAPQIGTVNSQGALPGMVWQNRDVYLQGPIWAKIPHTDGNFHPSPLMGGFGLKHPPP
43_21            AANTQAQTGLVHNQGVIPGMVWQNRDVYLQGPIWAKIPHTDGNFHPSPLMGGFGLKHPPP
43_25            AANTQAQTGLVHNQGVIPGMVWQNRDVYLQGPIWAKIPHTDGNFHPSPLMGGFGLKHPPP
43_23            AANTQAQTGLVHNQGVIPGMVWQNRDVYLQGPIWAKIPHTDGNFHPSPLMGGFGLKHPPP
43_20            AANTQAQTGLVHNQGVIPGMVWQNRDVYLQGPIWAKIPHTDGNFHPSPLMGGFGLKHPPP
AAV_9            AANTQAQTGLVHNQGVIPGMVWQNRDVYLQGPIWAKIPHTDGNFHPSPLMGGFGLKHPPP
24.1             SSTAGPQTQTVNSQGALPGMVWQNRDVCLQGPIWAKIPHTDGNFHPSPLMGGFGLKHPPP
42.2REAL         SSTAGPQTQTVNSQGALPGMVWQNRDVYLQGPIWAKIPHTDGNFHPSPLMGGFGLKHPPP
7.2\VP1          SSTAGPQTQTVNSQGALPGMVWQNRDVYLQGPIWAKIPHTDGNFHPSPLMGGFGLKHPPP
27.3\VP1         SSTAGPRTQTVNSQGALPGMVWQNRDVYLQGPIWAEIPHTDGNFHPSPLMGGFGLKHPPP
16.3\VP1         SSTAGPQTQTVNSQGALPGMVWQNRDVYLQGPIWAKIPHTDGNFHPSPLMGGFGLKHPPP
42_10            SSTAGPQTQTVNSQGALPGMVWQNRDVYLQGPIWAKIPHTDGNFHPSPLMGGFGLKHPPP
42_3B            SSTAGPQTQTVNSQGALPGMVWQNRDVYLQGPIWAKIPHTDGNFHPSPLMGGFGLKHPPP
42_11            SSTAGPQTQTVNSQGALPGMVWQNRDVYLQGPIWAKIPHTDGNFHPSPLMGGFGLKHPPP
F1\VP1           PSTAGPQSQTINSQGALPGMVWQNRDVYLQGPIWAKIPHTDGNFHPSPLMGGFGLKHPPP
F5\VP1@3         SSTAGPQSQTINSQGALPGMVWQNRDVYLQGPIWAKIPHTDGNFHPSPLMGGFGLKEHPPP
F3\VP1           SSTAGPQSQTINSQGALPGMVWQNRDVYLQGPIWAKIPHTDGNFHPSPLMGGFGLKHPPP
42_6B            SSTAGPQTQTVNSQGALPGMVWQNRDVYLQGPIWAKIPHTDGNFHPSPLMDGFGLKHPPP
42_12            SSTAGPQTQTVNSQGALPGMVWQNRDVYLQGPIWAKIPHTDGNFHPSPLMGGFGLKHPPP
AAV5\CAP         SSTTAPATGTYNLQEIVPGSVWMERDVYLQGPIWAKIPETGAHFHPSPAMGGFGLKHPPP
```

FIG. 2K

```
                        670       680       690       700       710       720
                 ....|....|....|....|....|....|....|....|....|....|....|....|
C1\VP1           QIFIKNTPVPANPATTFTAARVDSFITQYSTGQVAVQIEWEIEKERSKRWNPEVQFTSNY
C2\VP1           QIFIKNTPVPANPATTFTAARVDSFITQYSTGQVAVQIEWEIEKERSKRRNPEVQFTSNY
C5\VP1@2         QIFIKNTPVPAYPATTFTAARVDSFITQYSTGQVAVQIEWEIEKERSKRWNPEVQFTSNC
AAV4\VP1         QIFIKNTPVPANPATTFSSTPVNSFITQYSTGQVSVQIDWEIQKERSKRWNPEVQFTSNY
AAV1             QILIKNTPVPANPPAEFSATKFASFITQYSTGQVSVEIEWELQKENSKRWNPEVQYTSNY
AAV6\VP1         QILIKNTPVPANPPAEFSATKFASFITQYSTGQVSVEIEWELQKENSKRWNPEVQYTSNY
A3_3             QILIKNTPVPANPATTFTPGKFASFITQYSTGQVSVEIEWELQKENSKRWNPEIQYTSNY
A3_7             QILIKNTPVPANPATTFTPGKFASFITQYSTGQVSVEIEWELQKENSKRWNPEIQYTSNY
A3_4             QILIKNTPVPANPATTFTPGKFASFITQYSTGQVSVEIEWELQKENSKRWNPEIQYTSNY
A3_5             QILIKNTPVPANPATTFTPGKFASFITQYSTGQVSVEIEWELQKENSKRWNPEIQYTSNY
AAV2             QILIKNTPVPANPSTTFSAAKFASFITQYSTGQVSVEIEWELQKENSKRWNPEIQYTSNY
AAV3             QIMIKNTPVPANPPTTFSPAKFASFITQYSTGQVSVEIEWELQKENSKRWNPEIQYTSNY
13.3b\VP1        QILIKNTPVPANPPEVFTPAKFASFITQYSTGQVSVEIEWELQKENSKRWDPEIQYTSNF
AAV7             QILIKNTPVPANPPEVFTPAKFASFITQYSTGQVSVEIEWELQKENSKRWNPEIQYTSNF
223_4            QILIKNTPVPANPPEVFTPAKFASFITQYSTGQVSVEIEWELQKENSKRWNPEIQYTSNF
223_5            QILIKNTPVPANPPEVFTPAKFASFITQYSTGQVSVEIEWELQKENSKRWNPEIQYTSNF
223_10           QILIKNTPVPANPPEVFTPAKFASFITQYSTGQVSVEIEWELQKENSKRWNPEIQYTSNF
223_2            QILIKNTPVPANPPEVFTPAKFASFITQYSTGQVSVEIEWELQKENSKRWNPEIQYTSNF
223_7            QILIKNTPVPANPPEVFTPAKIASFITQYSTGQVSVEIEWELQKENSKRWNPEIQYTSNF
223_6            QILIKNTPVPANPPEVFTPAKLASFITQYSTGQVSVEIEWELQKENSKRWNPEIQYTSNF
44_1             QILIKNTPVPADPPTTFSQAKLASFITQYSTGQVSVEIEWELQKENSKRWNPEIQYTSNY
44_5             QILIKNTPVPADPPTTFSQAKLASFITQYSTGQVSVEIEWELQKENSKRWNPEIQYTSNY
44_2             QILIKNTPVPADPPTTFSQAKLASFITQYSTGQVSVEIEWELQKENSKRWNPEIQYTSNY
29.3\VP1         QILIKNTPVPADPPTTFSQAKLASFITQYSTGQVSVEIEWELQKENSKRWNPEIQYTSNY
29.5\VP1         QILIKNTPVPADPPTTFSQAKLASFITQYSTGQVSVEIEWELQKENSKRWNPEIQYTSNY
42_15            QILIKNTPVPADPPTTFSQAKLASFITQYSTGQVSVEIEWELQKENSKRWNPEIQYTSNY
42_8             QILIKNTPVPADPPTTFSQAKLASFITQYSTGQVSVEIEWELQKENSKRWNPEIQYTSNY
42_13            QILIKNTPVPADPPTTFSQAKLASFITQYSTGQVSVEIEWELQKENSKRWNPEIQYTSNY
42_3A            QILIKNTPVPADPPTTFSQAKLASFITQYSTGQVSVEIEWELQKENSKRWNPEIQYTSNY
42_4             QILIKNTPVPADPPTTFSQAKPASFITQYSTGQVSVEIEWELQKENSKRWNPEIQYTSNY
42_5A            QILIKNTPVPADPPTTFSQAKLASFITQYSTGQVSVEIEWELQKENSKRWNPEIQYTSNY
42_1B            QILIKNTPVPADPPTTFSQAKLASFITQYSTGQVSVEIEWELQKENSKRWNPEIQYTSNY
42_5B            QILIKNTPVPADPPTTFSQAKLASFITQYSTGQVSVEIEWELQKENSKRWNPEIQYTSNY
43_1             QILVKNTPVPADPPTTFSQAKLASFITQYSTGQVSVEIEWELQKENSKRWNPEIQYTSNY
43_12            QILVKNTPVPADPPTTFSQAKLASFITQYSTGQVSVEIEWELQKENSKRWNPEIQYTSNY
43_5             QILVKNTPVPADPPTTFSQAKLASFITQYSTGQVSVEIEWELQKENSKRWNPEIQYTSNY
AAV8             QILIKNTPVPADPPTTFNQSKLNSFITQYSTGQVSVEIEWELQKENSKRWNPEIQYTSNY
43_21            QILIKNTPVPADPPLTFNQAKLNSFITQYSTGQVSVEIEWELQKENSKRWNPEIQYTSNY
43_25            QILIKNTPVPADPPLTFNQAKLNSFITQYSTGQVSVEIEWELQKENSKRWNPEIQYTSNY
43_23            QILIKNTPVPADPPLTFNQAKLNSFITQYSTGQVSVEIEWELQKENSKRWNPEIQYTSNY
43_20            QILIKNTPVPADPPLTFNQAKLNSFITQYSTGQVSVEIEWELQKENSKRWNPEIQYTSNY
AAV_9            QILIKNTPVPADPPLTFNQAKLNSFITQYSTGQVSVEIEWELQKENSKRWNPEIQYTSNY
24.1             QILIKNTPVPANPPEVFTPAKFASFITQYSTGQVSVEIEWELQKENSKRWNPEIQYTSNY
42.2REAL         QILIKNTPVPANPPEVFTPAKFASFITQYSTGQVSVEIEWELQKENSKRWNPEIQYTSNY
7.2\VP1          QILIKNTPVPANPPEVFTPAKFASFITQYSTGQVSVEIEWELQKENSKRWNPEIQYTSNY
27.3\VP1         QILIKNTPVPANPPEVFTPAKFASFITQYSTGQVSVEIEWELQKENSKRWNPEIQYTSNY
16.3\VP1         QILIKNTPVPANPPGVFTPALFASFITQYSTGQVSVEIEWELQKENSKRWNPEIQYTSNY
42_10            QILIKNTPVPANPPEVFTPAKFASFITQYSTGQVSVEIEWELQKENSKRWNPEIQYTSNY
42_3B            QILIKNTPVPANPPEVFTPAKFASFITQYSTGQVSVEIEWELQKENSKRWNPEIQYTSNY
42_11            QILIKNTPVPANPPEVFTPAKFASFITQYSTGQVSVEIEWELQKENSKRWNPEIQYTSNY
F1\VP1           QILIKNTPVPANPPEVFTPAKFASFITQYSTGQVSVEIEWELQKENSKRWNPEIQYTSNY
F5\VP1@3         QILIKNTPVPANPPEVFTPAKFASFITQYSTGQVSVEIEWELQKENSKRWNPEIQYTSNY
F3\VP1           QILIKNTPVPANPPEVFTPAKFASFITQYSTGQVSVEIEWELQKENSKRWNPEIQYTSNY
42_6B            QILIKNTPVPANPPEVFTPAKFASFITQYSTGQVSVEIEWELQKENSKRWNPEIQYTSNY
42_12            QIILK-------------------------------------------------YTSNY
AAV5\CAP         MMLIKNTPVPGN-ITSFSDVPVSSFITQYSTGQVTVEMEWELKKENSKRWNPEIQYTNNY
```

FIG. 2L

```
                         730       740       750
                    ....|....|....|....|....|....|.
C1\VP1      GNQSSMLWAPDTTGKYTEPRVIGSRYLTNHL
C2\VP1      GNQSSMLWAPDTTGKYTEPRVIGSRYLTNHL
C5\VP1@2    GNQSSMLWAPDTTGKYTEPRVIGSRYLTNHL
AAV4\VP1    GQQNSLLWAPDAAGKYTEPRAIGTRYLTHHL
AAV1        AKSANVDFTVDNNGLYTEPRPIGTRYLTRPL
AAV6\VP1    AKSANVDFTVDNNGLYTEPRPIGTRYLTRPL
A3_3        NKSVNVEFTVDANGVYSEPRPIGTRYLTRNL
A3_7        NKSVNVEFTVDANGVYSEPRPIGTRYLTRNL
A3_4        NKSVNVEFTVDANGVYSEPRPIGTRYLTRNL
A3_5        NKSVNVEFTVDANGVYSEPRPIGTRYLTRNL
AAV2        NKSVNVDFTVDTNGVYSEPRPIGTRYLTRNL
AAV3        NKSVNVDFTVDTNGVYSEPRPIGTRYLTRNL
13.3b\VP1   EKQTGVDFAVDSQGVYSEPRPIGTRYLTRNL
AAV7        EKQTGVDFAVDSQGVYSEPRPIGTRYLTRNL
223_4       DKQTGVDFAVDSQGVYSEP------------
223_5       DKQTGVDFAVDSQGVYSEP------------
223_10      DKQTGVDFAVDSQGVYSEP------------
223_2       DKQTGVDFAVDSQGVYSEP------------
223_7       DKQTGVDFAVDSQGVYSEP------------
223_6       DKQTGVDFAVDSQGVYSEP------------
44_1        YKSTNVDFAVNTDGTYSEPRPIGTRYLTRNL
44_5        YKSTNVDFAVNTDGTYSEPRPIGTRYLTRNL
44_2        YKSTNVDFAVNTDGTYSEPRPIGTRYLTRNL
29.3\VP1    YKSTNVDFAVNTDGTYSEPRPIGTRYLTRNL
29.5\VP1    YKSTNVDFAVNTDGTYSEPRPIGTRYLTRNL
42_15       YKSTNVDFAVNTEGTYSEPRPIGTRYLTRNL
42_8        YKSTNVDFAVNTEGTYSEPRPIGTRYLTRNL
42_13       YKSTNVDFAVNTEGTYSEPRPIGTRYLTRSL
42_3A       YKSTNVDFAVNTEGTYSEPRPIGTRYLTRNL
42_4        YKSTNVDFAVNTEGTYSEPRPIGTRYLTRNL
42_5A       YKSTNVDFAVNTEGTYSEPRPIGTRYLTRNL
42_1B       YKSTNVDFAVNTEGTYSEPRPIGTRYLTRNL
42_5B       YKSTNVDFAVNTEGTYSEPRPIGTRYLTRNL
43_1        YKSTNVDFAVNTEGTYSEPRPIGTRYLTRNL
43_12       YKSTNVDFAVNTEGTYSEPRPIGTRYLTRNL
43_5        YKSTNVDFAVNTEGTYSEPRPIGTRYLTRNL
AAV8        YKSTSVDFAVNTEGVYSEPRPIGTRYLTRNL
43_21       YKSTNVDFAVNTEGVYSEPRPIGTRYLTRNL
43_25       YKSTNVDFAVNTEGVYSEPRPIGTRYLTRNL
43_23       YKSTNVDFAVNTEGVYSEPRPIGTRYLTRNL
43_20       YKSTNVDFAVNTEGVYSEPRPIGTRYLTRNL
AAV_9       YKSTNVDFAVNTEGVYSEPRPIGTRYLTRNL
24.1        AKSNNVEFAVNNEGVYTEPRPIGTRYLTRNL
42.2REAL    AKSNNVEFAVNNEGVYTEPRPIGTRYLTRNL
7.2\VP1     AKSNNVEFAVNNEGVYTEPRPIGTRYLTRNL
27.3\VP1    AKSNNVEFAVNNEGVYTEPRPIGTRYLTRNL
16.3\VP1    AKSNNVEFAVNNEGVYTEPRPIGTRYLTRNL
42_10       AKSNNVEFAVNNEGVYTEPRPIGTRYLTRNL
42_3B       AKSNNVEFAVNNEGVYTEPRPIGTRYLTRNL
42_11       AKSNNVEFAVNNEGVYTEPRPIGTRYLTRNL
F1\VP1      AKSNNVEFAVNPDGVYTEPRPIGTRYLPRNL
F5\VP1@3    AKSNNVEFAVNPDGVYTEPRPIGTRYLTRNL
F3\VP1      AKSNNVEFAVNPDGVYTEPRPIGTRYLTRNL
42_6B       AKSNNVEFAVNNEGVYTEPRPIGTRYLTRNL
42_12       YKSTNVDFAVNTEGTYSEPRPIGTRYLTRNL
AAV5\CAP    NDPQFVDFAPDSTGEYRTTRPIGTRYLTRPL
```

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
            50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
            85                  90                  95

Thr Thr Gly Val Lys Ser Met Val Leu Gly Arg Phe Leu Ser Gln Ile
            100                 105                 110

Arg Glu Lys Leu Val Gln Thr Ile Tyr Arg Gly Val Glu Pro Thr Leu
            115                 120                 125

Pro Asn Trp Phe Ala Val Thr Lys Thr Arg Asn Gly Ala Gly Gly Gly
            130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
            165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
            195                 200                 205

Pro Asn Ser Asp Ala Pro Val Ile Arg Ser Lys Thr Ser Ala Arg Tyr
            210                 215                 220
```

Fig. 3B

```
Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
            245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ser
            275                 280                 285

Leu Pro Ala Asp Ile Lys Thr Asn Arg Ile Tyr Arg Ile Leu Glu Leu
        290                 295                 300

Asn Gly Tyr Asp Pro Ala Tyr Ala Gly Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445
```

Fig. 3C

Glu Leu Thr Arg Arg Leu Glu His Asp Phe Gly Lys Val Thr Lys Gln
    450             455             460

Glu Val Lys Glu Phe Phe Arg Trp Ala Ser Asp His Val Thr Glu Val
465             470             475             480

Ala His Glu Phe Tyr Val Arg Lys Gly Gly Ala Ser Lys Arg Pro Ala
            485             490             495

Pro Asp Asp Ala Asp Ile Ser Glu Pro Lys Arg Ala Cys Pro Ser Val
            500             505             510

Ala Asp Pro Ser Thr Ser Asp Ala Glu Gly Ala Pro Val Asp Phe Ala
            515             520             525

Asp Arg Tyr Gln Asn Lys Cys Ser Arg His Ala Gly Met Ile Gln Met
    530             535             540

Leu Phe Pro Cys Lys Thr Cys Glu Arg Met Asn Gln Asn Phe Asn Ile
545             550             555             560

Cys Phe Thr His Gly Val Arg Asp Cys Leu Glu Cys Phe Pro Gly Val
            565             570             575

Ser Glu Ser Gln Pro Val Val Arg Lys Lys Thr Tyr Arg Lys Leu Cys
            580             585             590

Ala Ile His His Leu Leu Gly Arg Ala Pro Glu Ile Ala Cys Ser Ala
            595             600             605

Cys Asp Leu Val Asn Val Asp Leu Asp Asp Cys Val Ser Glu Gln
    610             615             620

US 10,041,090 B2

METHOD OF DETECTING AND/OR IDENTIFYING ADENO-ASSOCIATED VIRUS (AAV) SEQUENCES AND ISOLATING NOVEL SEQUENCES IDENTIFIED THEREBY

BACKGROUND OF THE INVENTION

Adeno-associated virus (AAV), a member of the Parvovirus family, is a small nonenveloped, icosahedral virus with single-stranded linear DNA genomes of 4.7 kilobases (kb) to 6 kb. AAV is assigned to the genus, *Dependovirus*, because the virus was discovered as a contaminant in purified adenovirus stocks. AAV's life cycle includes a latent phase at which AAV genomes, after infection, are site specifically integrated into host chromosomes and an infectious phase in which, following either adenovirus or herpes simplex virus infection, the integrated genomes are subsequently rescued, replicated, and packaged into infectious viruses. The properties of non-pathogenicity, broad host range of infectivity, including non-dividing cells, and potential site-specific chromosomal integration make AAV an attractive tool for gene transfer.

Recent studies suggest that AAV vectors may be the preferred vehicle for gene therapy. To date, there have been 6 different serotypes of AAVs isolated from human or non-human primates (NHP) and well characterized. Among them, human serotype 2 is the first AAV that was developed as a gene transfer vector; it has been widely used for efficient gene transfer experiments in different target tissues and animal models. Clinical trials of the experimental application of AAV2 based vectors to some human disease models are in progress, and include such diseases as cystic fibrosis and hemophilia B.

What are desirable are AAV-based constructs for gene delivery.

SUMMARY OF THE INVENTION

In one aspect, the invention provides a novel method of detecting and identifying AAV sequences from cellular DNAs of various human and non-human primate (NHP) tissues using bioinformatics analysis, PCR based gene amplification and cloning technology, based on the nature of latency and integration of AAVs in the absence of helper virus co-infection.

In another aspect, the invention provides method of isolating novel AAV sequences detected using the above described method of the invention. The invention further comprises methods of generating vectors based upon these novel AAV serotypes, for serology and gene transfer studies solely based on availability of capsid gene sequences and structure of rep/cap gene junctions.

In still another aspect, the invention provides a novel method for performing studies of serology, epidemiology, biodistribution and mode of transmission, using reagents according to the invention, which include generic sets of primers/probes and quantitative real time PCR.

In yet another aspect, the invention provides a method of isolating complete and infectious genomes of novel AAV serotypes from cellular DNA of different origins using RACE and other molecular techniques.

In a further aspect, the invention provides a method of rescuing novel serotypes of AAV genomes from human and NHP cell lines using adenovirus helpers of different origins.

In still a further aspect, the invention provides novel AAV serotypes, vectors containing same, and methods of using same.

These and other aspects of the invention will be readily apparent from the following detailed description of the invention.

BRIEF DESCRIPTION OF THE DRAWINGS

FIGS. 2A through 2M are an alignment of the amino acid sequences of the proteins of the vp1 capsid proteins of previously published AAV serotypes 1 [SEQ ID NO:64], AAV2 [SEQ ID NO:70], AAV3 [SEQ ID NO: 71], AAV4 [SEQ ID NO:63], AAV5 [SEQ ID NO:114], and AAV6 [SEQ ID NO:65] and novel AAV sequences of the invention, including: C1 [SEQ ID NO:60], C2 [SEQ ID NO:61], C5 [SEQ ID NO:62], A3-3 [SEQ ID NO:66], A3-7 [SEQ ID NO:67], A3-4 [SEQ ID NO:68], A3-5 [SEQ ID NO: 69], 3.3b [SEQ ID NO: 62], 223.4 [SEQ ID NO: 73], 223-5 [SEQ ID NO:74], 223-10 [SEQ ID NO:75], 223-2 [SEQ ID NO:76], 223-7 [SEQ ID NO: 77], 223-6 [SEQ ID NO: 78], 44-1 [SEQ ID NO: 79], 44-5 [SEQ ID NO:80], 44-2 [SEQ ID NO:81], 42-15 [SEQ ID NO: 84], 42-8 [SEQ ID NO: 85], 42-13 [SEQ ID NO:86], 42-3A [SEQ ID NO:87], 42-4 [SEQ ID NO:88], 42-5A [SEQ ID NO:89], 42-1B [SEQ ID NO:90], 42-5B [SEQ ID NO:91], 43-1 [SEQ ID NO: 92], 43-12 [SEQ ID NO: 93], 43-5 [SEQ ID NO:94], 43-21 [SEQ ID NO:96], 43-25 [SEQ ID NO: 97], 43-20 [SEQ ID NO:99], 24.1 [SEQ ID NO: 101], 42.2 [SEQ ID NO:102], 7.2 [SEQ ID NO: 103], 27.3 [SEQ ID NO: 104], 16.3 [SEQ ID NO: 105], 42.10 [SEQ ID NO: 106], 42-3B [SEQ ID NO: 107], 42-11 [SEQ ID NO: 108], F1 [SEQ ID NO: 109], F5 [SEQ ID NO: 110], F3 [SEQ ID NO:111], 42-6B [SEQ ID NO: 112], 42-12 [SEQ ID NO: 113]. Novel serotypes AAV8

Figure 1E:
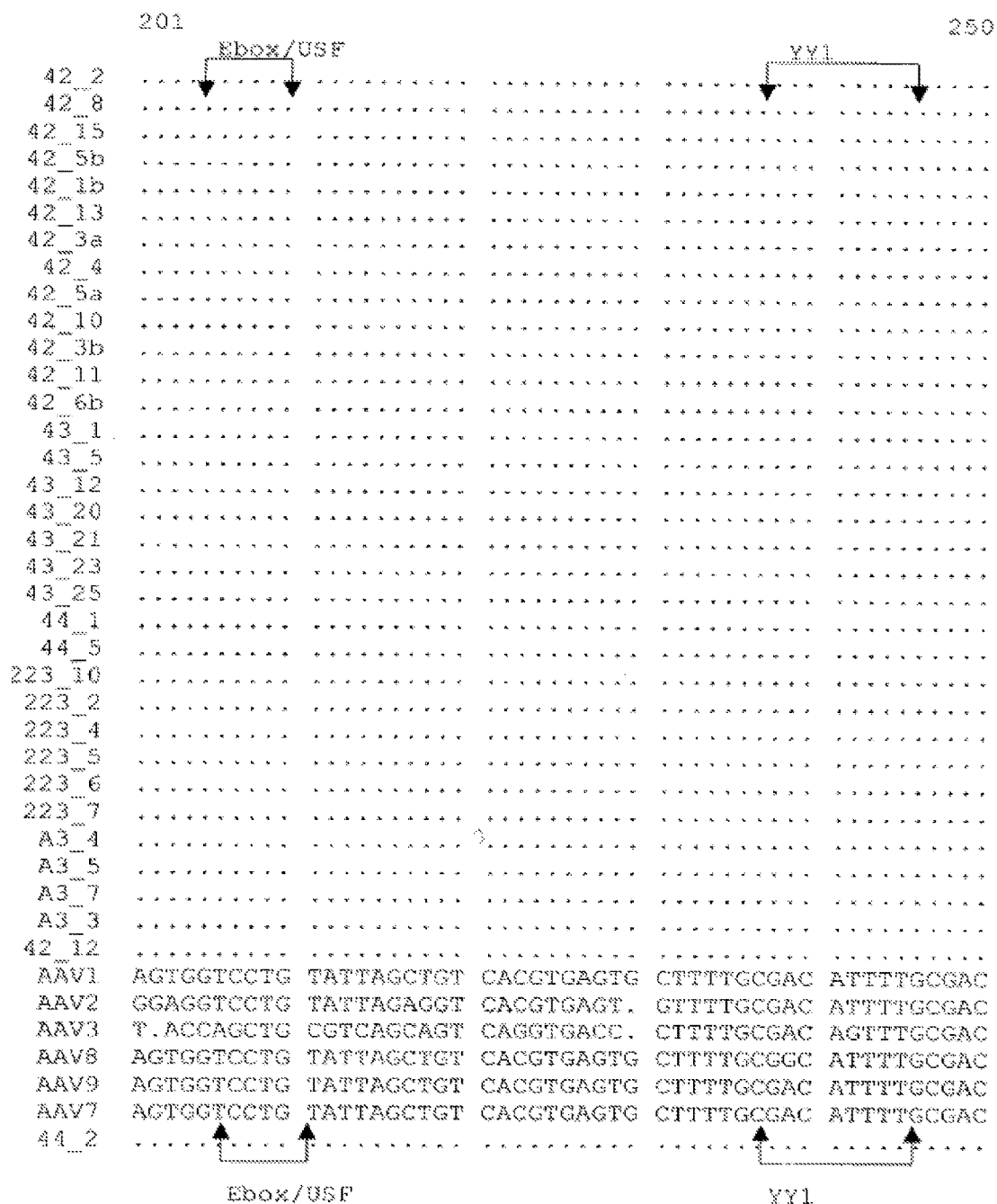
FIGS. 1A through 1AAAR provide an alignment of the nucleic acid sequences encoding at least the cap proteins for the AAV serotypes. The full-length sequences including the ITRs, the rep region, and the capsid region are provided for novel AAV serotype 7 [SEQ ID NO:1], and for previously published AAV1 [SEQ IN NO:6], AAV2 [SEQ ID NO:7]; and AAV3 [SEQ ID NO:8]. Novel AAV serotypes AAV8 [SEQ ID NO:4] and AAV9 [SEQ ID NO:5] are the subject of co-filed applications. The other novel clones of the invention provided in this alignment include: 42-2 [SEQ ID NO:9], 42-8 [SEQ ID NO:27], 42-15 [SEQ ID NO:28], 42-5b [SEQ ID NO: 29], 42-1b [SEQ ID NO:30]; 42-13 [SEQ ID NO: 31], 42-3a [SEQ ID NO: 32], 42-4 [SEQ ID NO:33], 42-5a [SEQ ID NO: 34], 42-10 [SEQ ID NO:35], 42-3b [SEQ ID NO: 36], 42-11 [SEQ ID NO: 37], 42-6b [SEQ ID NO:38], 43-1 [SEQ ID NO: 39], 43-5 [SEQ ID NO: 40], 43-12 [SEQ ID NO:41], 43-20 [SEQ ID NO:42], 43-21 [SEQ ID NO: 43], 43-23 [SEQ ID NO:44], 43-25 [SEQ ID NO: 45], 44.1 [SEQ ID NO:47], 44.5 [SEQ ID NO:47], 223.10 [SEQ ID NO:48], 223.2 [SEQ ID NO:49], 223.4 [SEQ ID NO:50], 223.5 [SEQ ID NO: 51], 223.6 [SEQ ID NO: 52], 223.7 [SEQ ID NO: 53], A3.4 [SEQ ID NO: 54], A3.5 [SEQ ID NO:55], A3.7 [SEQ ID NO: 56], A3.3 [SEQ ID NO:57], 42.12 [SEQ ID NO: 58], 44.2 [SEQ ID NO: 59]. The nucleotide sequences of the signature regions of AAV10 [SEQ ID NO: 117], AAV11 [SEQ ID NO: 118] and AAV12 [SEQ ID NO:119] are provided in this figure. Critical landmarks in the structures of AAV genomes are shown. Gaps are demonstrated by dots. The 3' ITR of AAV1 [SEQ ID NO:6] is shown in the same configuration as in the published sequences. TRS represents terminal resolution site. Notice that AAV7 is the only AAV reported that uses GTG as the initiation codon for VP3.

[SEQ ID NO:95] and AAV9 [SEQ ID NO:100] are the subject of co-filed patent applications.

FIGS. 3A through 3C provide the amino acid sequences of the AAV7 rep proteins [SEQ ID NO:3].

DETAILED DESCRIPTION OF THE INVENTION

In the present invention, the inventors have found a method which takes advantage of the ability of adeno-associated virus (AAV) to penetrate the nucleus, and, in the absence of a helper virus co-infection, to integrate into cellular DNA and establish a latent infection. This method utilizes a polymerase chain reaction (PCR)-based strategy for detection, identification and/or isolation of sequences of AAVs from DNAs from tissues of human and non-human primate origin as well as from other sources. Advantageously, this method is also suitable for detection, identification and/or isolation of other integrated viral and non-viral sequences, as described below.

The invention further provides nucleic acid sequences identified according to the methods of the invention. One such adeno-associated virus is of a novel serotype, termed herein serotype 7 (AAV7). Other novel adeno-associated virus serotypes provided herein include AAV10, AAV11, and AAV12. Still other novel AAV serotypes identified according to the methods of the invention are provided in the present specification. See, Figures and Sequence Listing, which is incorporated by reference.

Also provided are fragments of these AAV sequences. Among particularly desirable AAV fragments are the cap proteins, including the vp1, vp2, vp3, the hypervariable regions, the rep proteins, including rep 78, rep 68, rep 52, and rep 40, and the sequences encoding these proteins. Each of these fragments may be readily utilized in a variety of vector systems and host cells. Such fragments may be used alone, in combination with other AAV sequences or fragments, or in combination with elements from other AAV or non-AAV viral sequences. In one particularly desirable embodiment, a vector contains the AAV cap and/or rep sequences of the invention.

As described herein, alignments are performed using any of a variety of publicly or commercially available Multiple Sequence Alignment Programs, such as AClustal W≅, accessible through Web Servers on the internet. Alternatively, Vector NTI utilities are also used. There are also a number of algorithms known in the art which can be used to measure nucleotide sequence identity, including those contained in the programs described above. As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Similar programs are available for amino acid sequences, e.g., the "Clustal X" program. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs.

The term "substantial homology" or "substantial similarity," when referring to a nucleic acid, or fragment thereof, indicates that, when optimally aligned with appropriate nucleotide insertions or deletions with another nucleic acid (or its complementary strand), there is nucleotide sequence identity in at least about 95 to 99% of the aligned sequences. Preferably, the homology is over full-length sequence, or an open reading frame thereof, or another suitable fragment which is at least 15 nucleotides in length. Examples of suitable fragments are described herein.

The term "substantial homology" or "substantial similarity," when referring to amino acids or fragments thereof, indicates that, when optimally aligned with appropriate amino acid insertions or deletions with another amino acid, there is amino acid sequence identity in at least about 95 to 99% of the aligned sequences. Preferably, the homology is over full-length sequence, or a protein thereof, e.g., a cap protein, a rep protein, or a fragment thereof which is at least 8 amino acids, or more desirably, at least 15 amino acids in length. Examples of suitable fragments are described herein.

By the term "highly conserved" is meant at least 80% identity, preferably at least 90% identity, and more preferably, over 97% identity. Identity is readily determined by one of skill in the art by resort to algorithms and computer programs known by those of skill in the art.

The term "percent sequence identity" or "identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to about 700 amino acids. Examples of suitable fragments are described herein.

The AAV sequences and fragments thereof are useful in production of rAAV, and are also useful as antisense delivery vectors, gene therapy vectors, or vaccine vectors. The invention further provides nucleic acid molecules, gene delivery vectors, and host cells which contain the AAV sequences of the invention.

As described herein, the vectors of the invention containing the AAV capsid proteins of the invention are particularly well suited for use in applications in which the neutralizing antibodies diminish the effectiveness of other AAV serotype based vectors, as well as other viral vectors. The rAAV vectors of the invention are particularly advantageous in rAAV readministration and repeat gene therapy.

These and other embodiments and advantages of the invention are described in more detail below. As used throughout this specification and the claims, the terms Acomprising≅ and "including" and their variants are inclusive of other components, elements, integers, steps and the like. Conversely, the term "consisting" and its variants is exclusive of other components, elements, integers, steps and the like.

I. Methods of the Invention

A. Detection of Sequences Via Molecular Cloning

In one aspect, the invention provides a method of detecting and/or identifying target nucleic acid sequences in a sample. This method is particularly well suited for detection of viral sequences which are integrated into the chromosome of a cell, e.g., adeno-associated viruses (AAV) and retroviruses, among others. The specification makes reference to AAV, which is exemplified herein. However, based on this information, one of skill in the art may readily perform the methods of the invention on retroviruses [e.g., feline leukemia virus (FeLV), HTLVI and HTLVII], and lentivirinae [e.g., human immunodeficiency virus (HIV), simian immunodeficiency virus (SIV), feline immunodeficiency virus (FIV), equine infectious anemia virus, and spumavirinal)], among others. Further, the method of the invention may also be used for detection of other viral and non-viral sequences, whether integrated or non-integrated into the genome of the host cell.

As used herein, a sample is any source containing nucleic acids, e.g., tissue, tissue culture, cells, cell culture, and biological fluids including, without limitation, urine and blood. These nucleic acid sequences may be DNA or RNA from plasmids, natural DNA or RNA from any source, including bacteria, yeast, viruses, and higher organisms such as plants or animals. DNA or RNA is extracted from the sample by a variety of techniques known to those of skill in the art, such as those described by Sambrook, Molecular Cloning: A Laboratory Manual (New York: Cold Spring Harbor Laboratory). The origin of the sample and the method by which the nucleic acids are obtained for application of the method of the invention is not a limitation of the present invention. Optionally, the method of the invention can be performed directly on the source of DNA, or on nucleic acids obtained (e.g., extracted) from a source.

The method of the invention involves subjecting a sample containing DNA to amplification via polymerase chain reaction (PCR) using a first set of primers specific for a first region of double-stranded nucleic acid sequences, thereby obtaining amplified sequences.

As used herein, each of the Aregions≅ is predetermined based upon the alignment of the nucleic acid sequences of at least two serotypes (e.g., AAV) or strains (e.g., lentiviruses), and wherein each of said regions is composed of sequences having a 5' end which is highly conserved, a middle which is preferably, but necessarily, variable, and a 3' end which is highly conserved, each of these being conserved or variable relative to the sequences of the at least two aligned AAV serotypes. Preferably, the 5' and/or 3' end is highly conserved over at least about 9, and more preferably, at least 18 base pairs (bp). However, one or both of the sequences at the 5= or 3= end may be conserved over more than 18 bp, more than 25 bp, more than 30 bp, or more than 50 bp at the 5' end. With respect to the variable region, there is no requirement for conserved sequences, these sequences may be relatively conserved, or may have less than 90, 80, or 70% identity among the aligned serotypes or strains.

Each of the regions may span about 100 bp to about 10 kilobase pairs in length. However, it is particularly desirable that one of the regions is a Asignature region≅, i.e., a region which is sufficiently unique to positively identify the amplified sequence as being from the target source. For example, in one embodiment, the first region is about 250 bp in length, and is sufficiently unique among known AAV sequences, that it positively identifies the amplified region as being of AAV origin. Further, the variable sequences within this region are sufficiently unique that can be used to identify the serotype from which the amplified sequences originate. Once amplified (and thereby detected), the sequences can be identified by performing conventional restriction digestion and comparison to restriction digestion patterns for this region in any of AAV1, AAV2, AAV3, AAV4, AAVS, or AAV6, or that of AAV7, AAV10, AAV11, AAV12, or any of the other novel serotypes identified by the invention, which is predetermined and provided by the present invention.

Given the guidance provided herein, one of skill in the art can readily identify such regions among other integrated viruses to permit ready detection and identification of these sequences. Thereafter, an optimal set of generic primers located within the highly conserved ends can be designed and tested for efficient amplification of the selected region from samples. This aspect of the invention is readily adapted to a diagnostic kit for detecting the presence of the target sequence (e.g., AAV) and for identifying the AAV serotype, using standards which include the restriction patterns for the AAV serotypes described herein or isolated using the techniques described herein. For example, quick identification or molecular serotyping of PCR products can be accomplished by digesting the PCR products and comparing restriction patterns.

Thus, in one embodiment, the "signature region" for AAV spans about by 2800 to about 3200 of AAV 1 [SEQ ID NO:6], and corresponding base pairs in AAV 2, AAV3, AAV4, AAV5, and AAV6. More desirably, the region is about 250 bp, located within by 2886 to about 3143 bp of AAV 1 [SEQ ID NO:6], and corresponding base pairs in AAV 2 [SEQ ID NO:7], AAV3 [SEQ ID NO8], and other AAV serotypes. See, FIG. 1. To permit rapid detection of AAV in the sample, primers which specifically amplify this signature region are utilized. However, the present invention is not limited to the exact sequences identified herein for the AAV signature region, as one of skill in the art may readily alter this region to encompass a shorter fragment, or a larger fragment of this signature region.

The PCR primers are generated using techniques known to those of skill in the art. Each of the PCR primer sets is composed of a 5' primer and a 3' primer. See, e.g., Sambrook et al, cited herein. The term "primer" refers to an oligonucleotide which acts as a point of initiation of synthesis when placed under conditions in which synthesis of a primer extension product which is complementary to a nucleic acid strand is induced. The primer is preferably single stranded. However, if a double stranded primer is utilized, it is treated to separate its strands before being used to prepare extension products. The primers may be about 15 to 25 or more nucleotides, and preferably at least 18 nucleotides. However, for certain applications shorter nucleotides, e.g., 7 to 15 nucleotides are utilized.

The primers are selected to be sufficiently complementary to the different strands of each specific sequence to be amplified to hybridize with their respective strands. Therefore, the primer sequence need not reflect the exact sequence of the region being amplified. For example, a non-complementary nucleotide fragment may be attached to the 5' end of the primer, with the remainder of the primer sequence being completely complementary to the strand. Alternatively, non-complementary bases or longer sequences can be interspersed into the primer, provided that the primer sequence has sufficient complementarity with the sequence of the strand to be amplified to hybridize therewith and form a template for synthesis of the extension product of the other primer.

The PCR primers for the signature region according to the invention are based upon the highly conserved sequences of two or more aligned sequences (e.g., two or more AAV serotypes). The primers can accommodate less than exact identity among the two or more aligned AAV serotypes at the 5' end or in the middle. However, the sequences at the 3' end of the primers correspond to a region of two or more aligned AAV serotypes in which there is exact identity over at least five, preferably, over at least nine base pairs, and more preferably, over at least 18 base pairs at the 3' end of the primers. Thus, the 3' end of the primers is composed of sequences with 100% identity to the aligned sequences over at least five nucleotides. However, one can optionally utilize one, two, or more degenerate nucleotides at the 3' end of the primer.

For example, the primer set for the signature region of AAV was designed based upon a unique region within the AAV capsid, as follows. The 5' primer was based upon nt 2867-2891 of AAV2 [SEQ ID NO:7], 5'-GGTAATTCCTC-CGGAAATTGGCATT3'. See, FIG. 1. The 3' primer was designed based upon nt 3096-3122 of AAV2 [SEQ ID NO:7], 5'-GACTCATCAACAACAACTGGGGATTC-3'. However, one of skill in the art may have readily designed the primer set based upon the corresponding regions of AAV 1, AAV3, AAV4, AAV5, AAV6, or based upon the information provided herein, AAV7, AAV10, AAV11, AAV12, or another novel AAV of the invention. In addition, still other primer sets can be readily designed to amplify this signature region, using techniques known to those of skill in the art.

B. Isolation of Target Sequences

As described herein, the present invention provides a first primer set which specifically amplifies the signature region of the target sequence, e.g., an AAV serotype, in order to permit detection of the target. In a situation in which further sequences are desired, e.g., if a novel AAV serotype is identified, the signature region may be extended. Thus, the invention may further utilize one or more additional primer sets.

Suitably, these primer sets are designed to include either the 5' or 3' primer of the first primer set and a second primer unique to the primer set, such that the primer set amplifies a region 5' or 3' to the signature region which anneals to either the 5' end or the 3' end of the signature region. For example, a first primer set is composed of a 5' primer, P1 and a 3' primer P2 to amplify the signature region. In order to extend the signature region on its 3' end, a second primer set is composed of primer P1 and a 3' primer P4, which amplifies the signature region and contiguous sequences downstream of the signature region. In order to extend the signature region on its 5' end, a third primer set is composed of a 5' primer, P5, and primer P2, such that the signature region and contiguous sequences upstream of the signature region are amplified. These extension steps are repeated (or performed at the same time), as needed or desired. Thereafter, the products results from these amplification steps are fused using conventional steps to produce an isolated sequence of the desired length.

The second and third primer sets are designed, as with the primer set for the signature region, to amplify a region having highly conserved sequences among the aligned sequences. Reference herein to the term "second" or "third" primer set is for each of discussion only, and without regard to the order in which these primers are added to the reaction mixture, or used for amplification. The region amplified by the second primer set is selected so that upon amplification it anneals at its 5' end to the 3' end of the signature region. Similarly, the region amplified by the third primer set is selected so that upon amplification it anneals at its 3' end anneals to the 5' end of the signature region. Additional primer sets can be designed such that the regions which they amplify anneal to the either the 5' end or the 3' end of the extension products formed by the second or third primer sets, or by subsequent primer sets.

For example, where AAV is the target sequence, a first set of primers (P1 and P2) are used to amplify the signature region from the sample. In one desirable embodiment, this signature region is located within the AAV capsid. A second set of primers (P1 and P4) is used to extend the 3' end of the signature region to a location in the AAV sequence which is just before the AAV 3' ITR, i.e., providing an extension product containing the entire 3' end of the AAV capsid when using the signature region as an anchor. In one embodiment, the P4 primer corresponds to nt 4435 to 4462 of AAV2 [SEQ ID NO:7], and corresponding sequences in the other AAV serotypes. This results in amplification of a region of about 1.6 kb, which contains the 0.25 kb signature region. A third set of primers (P3 and P2) is used to extend the 5' end of signature region to a location in the AAV sequences which is in the 3' end of the rep genes, i.e., providing an extension product containing the entire 5' end of the AAV capsid when using the signature region as an anchor. In one embodiment, the P3 primer corresponds to nt 1384 to 1409 of AAV2 [SEQ ID NO:7], and corresponding sequences in the other AAV serotypes. This results in amplification of a region of about 1.7 kb, which contains the 0.25 kb signature region. Optionally, a fourth set of primers are used to further extend the extension product containing the entire 5' end of the AAV capsid to also include the rep sequences. In one embodiment, the primer designated P5 corresponds to nt 108 to 133 of AAV2 [SEQ ID NO:7], and corresponding sequences in the other AAV serotypes and is used in conjunction with the P2 primer.

Following completion of the desired number of extension steps, the various extension products are fused, making use of the signature region as an anchor or marker, to construct an intact sequence. In the example provided herein, AAV sequences containing, at a minimum, an intact AAV cap gene are obtained. Larger sequences may be obtained, depending upon the number of extension steps performed.

Suitably, the extension products are assembled into an intact AAV sequence using methods known to those of skill in the art. For example, the extension products may be digested with DraIII, which cleaves at the DraIII site located within the signature region, to provide restriction fragments which are re-ligated to provide products containing (at a minimum) an intact AAV cap gene. However, other suitable techniques for assembling the extension products into an intact sequence may be utilized. See, generally, Sambrook et al, cited herein.

As an alternative to the multiple extension steps described above, another embodiment of the invention provides for direct amplification of a 3.1 kb fragment which allows isolation of full-length cap sequences. To directly amplify a 3.1 kb full-length cap fragment from NHP tissue and blood DNAs, two other highly conserved regions were identified in AAV genomes for use in PCR amplification of large fragments. A primer within a conserved region located in the middle of the rep gene is utilized (AV1ns: 5' GCTGCGT-CAACTGGACCAATGAGAAC 3', nt of SEQ ID NO:6) in combination with the 3' primer located in another conserved region downstream of the Cap gene (AV2cas: 5' CGCAGA-GACCAAAGTTCAACTGAAACGA 3', SEQ ID NO: 7) for amplification of AAV sequences including the full-length AAV cap. Typically, following amplification, the products are cloned and sequence analysis is performed with an accuracy of ≥99.9%. Using this method, the inventors have isolated at least 50 capsid clones which have subsequently been characterized. Among them, 37 clones were derived from Rhesus macaque tissues (rh.1-rh.37), 6 clones from cynomologous macaques (cy.1-cy.6), 2 clones from Baboons (bb.1 and bb.2) and 5 clones from Chimps (ch.1-ch.5). These clones are identified elsewhere in the specification, together with the species of animal from which they were identified and the tissues in that animal these novel sequences have been located.

C. Alternative Method for Isolating Novel AAV

In another aspect, the invention provides an alternative method for isolating novel AAV from a cell. This method involves infecting the cell with a vector which provides helper functions to the AAV; isolating infectious clones containing AAV; sequencing the isolated AAV; and comparing the sequences of the isolated AAV to known AAV serotypes, whereby differences in the sequences of the isolated AAV and known AAV serotypes indicates the presence of a novel AAV.

In one embodiment, the vector providing helper functions provides essential adenovirus functions, including, e.g., E1a, E1b, E2a, E4ORF6. In one embodiment, the helper functions are provided by an adenovirus. The adenovirus may be a wild-type adenovirus, and may be of human or non-human origin, preferably non-human primate (NHP) origin. The DNA sequences of a number of adenovirus types are available from Genbank, including type Ad5 [Genbank Accession No. M73260]. The adenovirus sequences may be obtained from any known adenovirus serotype, such as serotypes 2, 3, 4, 7, 12 and 40, and further including any of the presently identified human types [see, e.g., Horwitz, cited above]. Similarly adenoviruses known to infect non-human animals (e.g., chimpanzees) may also be employed in the vector constructs of this invention. See, e.g., U.S. Pat. No. 6,083,716. In addition to wild-type adenoviruses, recombinant viruses or non-viral vectors (e.g., plasmids, episomes, etc.) carrying the necessary helper functions may be utilized. Such recombinant viruses are known in the art and may be prepared according to published techniques. See, e.g., U.S. Pat. No. 5,871,982 and U.S. Pat. No. 6,251, 677, which describe a hybrid Ad/AAV virus. The selection of the adenovirus type is not anticipated to limit the following invention. A variety of adenovirus strains are available from the American Type Culture Collection, Manassas, Va., or available by request from a variety of commercial and institutional sources. Further, the sequences of many such strains are available from a variety of databases including, e.g., PubMed and GenBank.

In another alternative, infectious AAV may be isolated using genome walking technology (Siebert et al., 1995, *Nucleic Acid Research*, 23:1087-1088, Friezner-Degen et al., 1986, *J. Biol. Chem.* 261:6972-6985, BD Biosciences Clontech, Palo Alto, Calif.). Genome walking is particularly well suited for identifying and isolating the sequences adjacent to the novel sequences identified according to the method of the invention. For example, this technique may be useful for isolating inverted terminal repeat (ITRs) of the novel AAV serotype, based upon the novel AAV capsid and/or rep sequences identified using the methods of the invention. This technique is also useful for isolating sequences adjacent to other AAV and non-AAV sequences identified and isolated according to the present invention. See, Examples 3 and 4.

The methods of the invention may be readily used for a variety of epidemiology studies, studies of biodistribution, monitoring of gene therapy via AAV vectors and vector derived from other integrated viruses. Thus, the methods are well suited for use in pre-packaged kits for use by clinicians, researchers, and epidemiologists.

II. Diagnostic Kit

In another aspect, the invention provides a diagnostic kit for detecting the presence of a known or unknown adeno-associated virus (AAV) in a sample. Such a kit may contain a first set of 5' and 3' PCR primers specific for a signature region of the AAV nucleic acid sequence. Alternatively, or additionally, such a kit can contain a first set of 5' and 3' PCR primers specific for the 3.1 kb fragment which includes the full-length AAV capsid nucleic acid sequence identified herein (e.g., the AV1 ns and AV2cas primers.) Optionally, a kit of the invention may further contain two or more additional sets of 5' and 3' primers, as described herein, and/or PCR probes. These primers and probes are used according to the present invention amplify signature regions of each AAV serotype, e.g., using quantitative PCR.

The invention further provides a kit useful for identifying an AAV serotype detected according to the method of the invention and/or for distinguishing novel AAV from known AAV. Such a kit may further include one or more restriction enzymes, standards for AAV serotypes providing their "signature restriction enzyme digestions analyses", and/or other means for determining the serotype of the AAV detected.

In addition, kits of the invention may include, instructions, a negative and/or positive control, containers, diluents and buffers for the sample, indicator charts for signature comparisons, disposable gloves, decontamination instructions, applicator sticks or containers, and sample preparator cups, as well as any desired reagents, including media, wash reagents and concentration reagents. Such reagents may be readily selected from among the reagents described herein, and from among conventional concentration reagents. In one desirable embodiment, the wash reagent is an isotonic saline solution which has been buffered to physiologic pH, such as phosphate buffered saline (PBS); the elution reagent is PBS containing 0.4 M NaCl, and the concentration reagents and devices. For example, one of skill in the art will recognize that reagents such as polyethylene glycol (PEG), or $NH_4SO_4$ may be useful, or that devices such as filter devices. For example, a filter device with a 100 K membrane would concentrate rAAV.

The kits provided by the present invention are useful for performing the methods described herein, and for study of biodistribution, epidemiology, mode of transmission of novel AAV serotypes in human and NHPs.

Thus, the methods and kits of the invention permit detection, identification, and isolation of target viral sequences, particularly integrated viral sequences. The methods and kits are particularly well suited for use in detection, identification and isolation of AAV sequences, which may include novel AAV serotypes.

In one notable example, the method of the invention facilitated analysis of cloned AAV sequences by the inventors, which revealed heterogeneity of proviral sequences between cloned fragments from different animals, all of which were distinct from the known six AAV serotypes, with the majority of the variation localized to hypervariable regions of the capsid protein. Surprising divergence of AAV sequences was noted in clones isolated from single tissue sources, such as lymph node, from an individual rhesus monkey. This heterogeneity is best explained by apparent evolution of AAV sequence within individual animals due, in part, to extensive homologous recombination between a limited number of co-infecting parenteral viruses. These studies suggest sequence evolution of widely disseminated virus during the course of a natural AAV infection that presumably leads to the formation of swarms of quasispecies which differ from one another in the array of capsid hypervariable regions. This is the first example of rapid molecular evolution of a DNA virus in a way that formerly was thought to be restricted to RNA viruses.

Sequences of several novel AAV serotypes identified by the method of the invention and characterization of these serotypes is provided.

III. Novel AAV Serotypes

A. Nucleic Acid Sequences

Nucleic acid sequences of novel AAV serotypes identified by the methods of the invention are provided. See, SEQ ID NO:1, 9-59, and 117-120, which are incorporated by reference herein. See also, FIG. 1 and the sequence listing.

For novel serotype AAV7, the full-length sequences, including the AAV 5' ITRs, capsid, rep, and AAV 3' ITRs are provided in SEQ ID NO:1.

For other novel AAV serotypes of the invention, the approximately 3.1 kb fragment isolated according to the method of the invention is provided. This fragment contains sequences encoding full-length capsid protein and all or part of the sequences encoding the rep protein. These sequences include the clones identified below.

For still other novel AAV serotypes, the signature region encoding the capsid protein is provided. For example, the AAV10 nucleic acid sequences of the invention include those illustrated in FIG. 1 [See, SEQ ID NO:117, which spans 255 bases]. The AAV11 nucleic acid sequences of the invention include the DNA sequences illustrated in FIG. 1 [See, SEQ ID NO:118 which spans 258 bases]. The AAV12 nucleic acid sequences of the invention include the DNA sequences illustrated in FIG. 1 [See, SEQ ID NO:119, which consists of 255 bases]. Using the methodology described above, further AAV10, AAV11 and AAV12 sequences can be readily identified and used for a variety of purposes, including those described for AAV7 and the other novel serotypes herein.

Figure 1F:
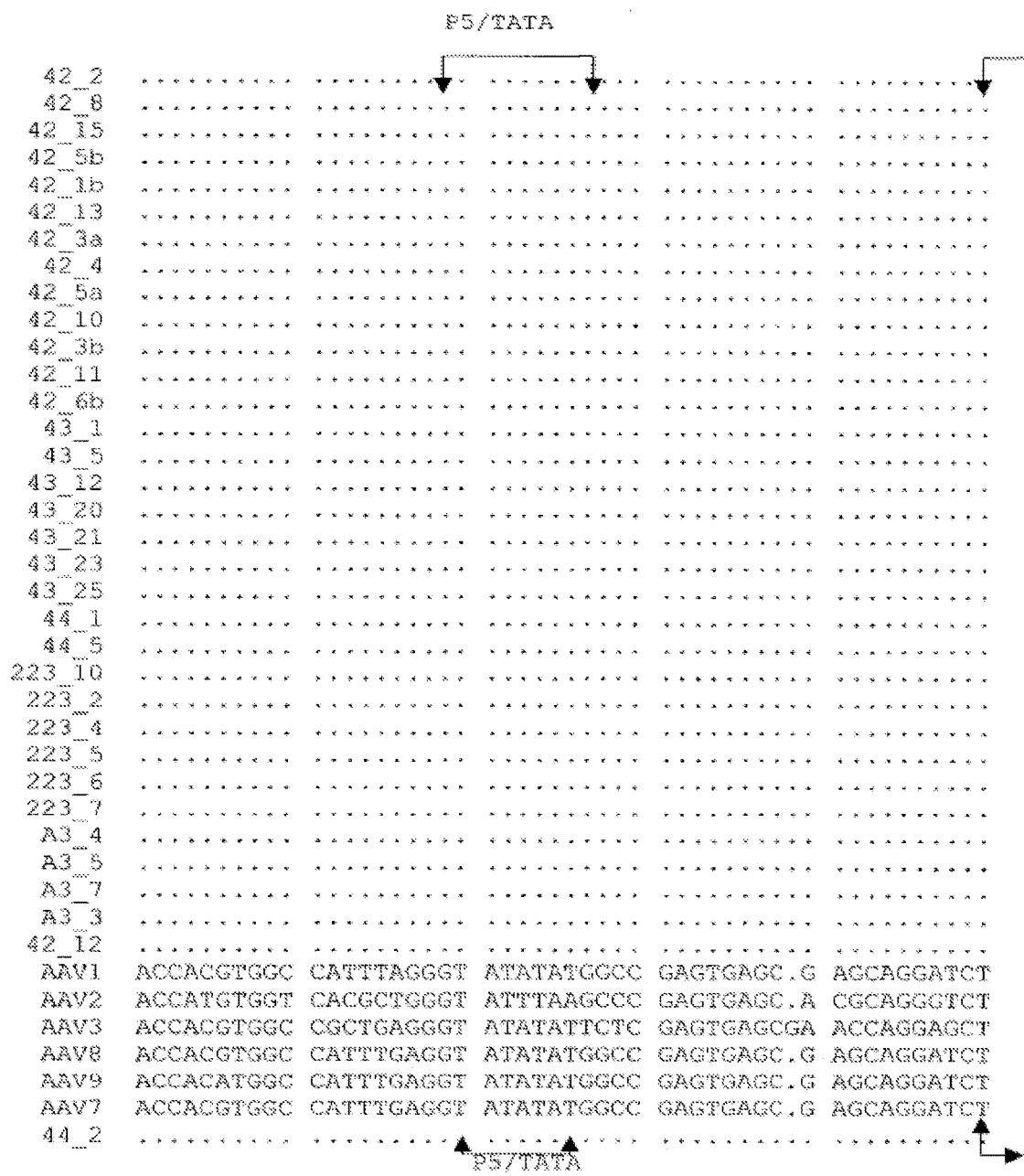
Figure 1G:
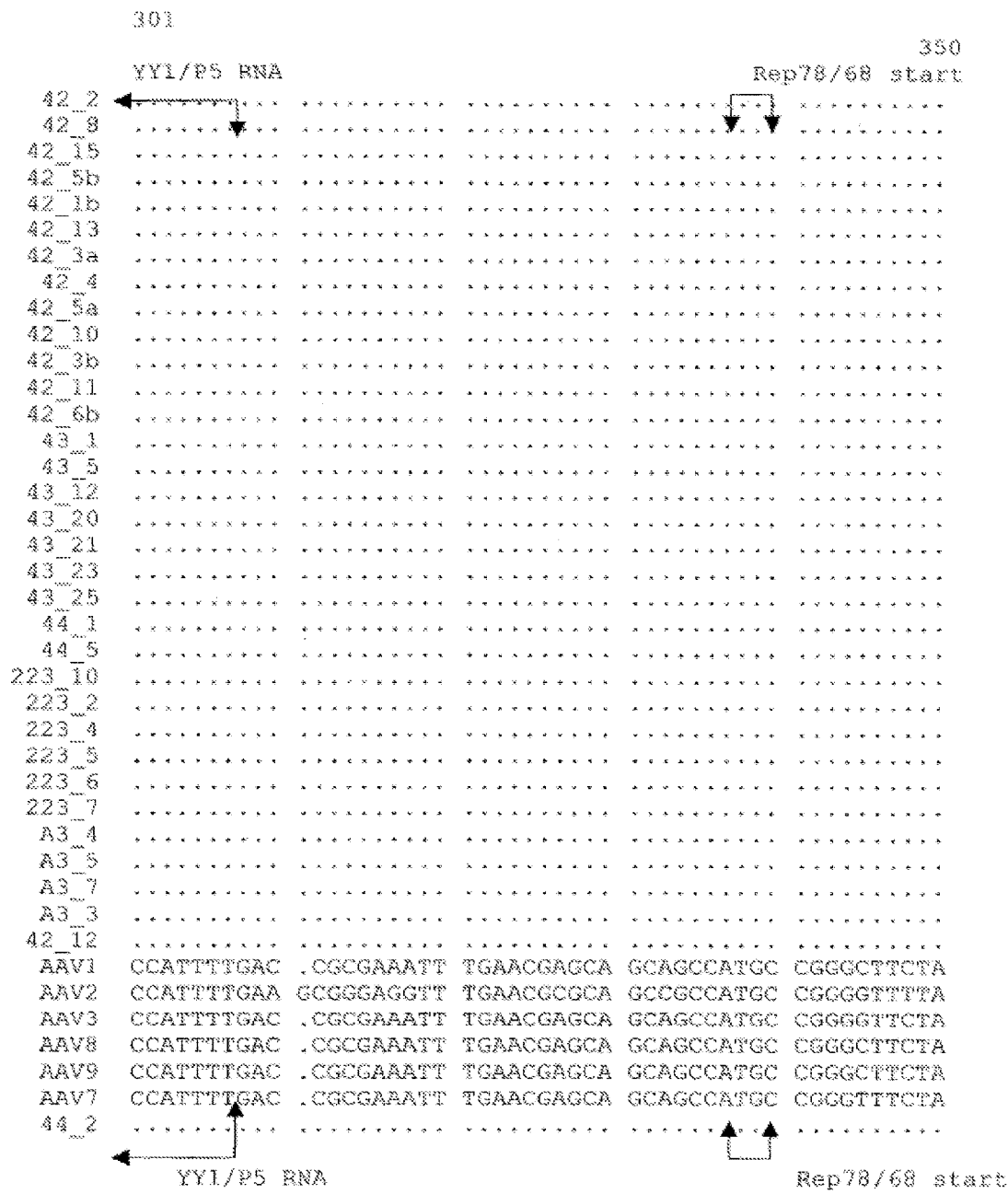

FIG. 1 provides the non-human primate (NHP) AAV nucleic acid sequences of the invention in an alignment with the previously published AAV serotypes, AAV 1 [SEQ ID NO:6], AAV2 [SEQ ID NO:7], and AAV3 [SEQ ID NO:8]. These novel NHP sequences include those provided in the following Table I, which are identified by clone number:

TABLE 1

| AAV Cap Sequence | Clone Number | Source Species | Tissue | SEQ ID NO (DNA) |
|---|---|---|---|---|
| Rh.1 | Clone 9 (AAV9) | Rhesus | Heart | 5 |
| Rh.2 | Clone 43.1 | Rhesus | MLN | 39 |
| Rh.3 | Clone 43.5 | Rhesus | MLN | 40 |
| Rh.4 | Clone 43.12 | Rhesus | MLN | 41 |
| Rh.5 | Clone 43.20 | Rhesus | MLN | 42 |
| Rh.6 | Clone 43.21 | Rhesus | MLN | 43 |
| Rh.7 | Clone 43.23 | Rhesus | MLN | 44 |
| Rh.8 | Clone 43.25 | Rhesus | MLN | 45 |
| Rh.9 | Clone 44.1 | Rhesus | Liver | 46 |
| Rh.10 | Clone 44.2 | Rhesus | Liver | 59 |
| Rh.11 | Clone 44.5 | Rhesus | Liver | 47 |
| Rh.12 | Clone 42.1B | Rhesus | MLN | 30 |
| Rh.13 | 42.2 | Rhesus | MLN | 9 |
| Rh.14 | Clone 42.3A | Rhesus | MLN | 32 |
| Rh.15 | Clone 42.3B | Rhesus | MLN | 36 |
| Rh.16 | Clone 42.4 | Rhesus | MLN | 33 |
| Rh.17 | Clone 42.5A | Rhesus | MLN | 34 |
| Rh.18 | Clone 42.5B | Rhesus | MLN | 29 |
| Rh.19 | Clone 42.6B | Rhesus | MLN | 38 |
| Rh.20 | Clone 42.8 | Rhesus | MLN | 27 |
| Rh.21 | Clone 42.10 | Rhesus | MLN | 35 |
| Rh.22 | Clone 42.11 | Rhesus | MLN | 37 |
| Rh.23 | Clone 42.12 | Rhesus | MLN | 58 |
| Rh.24 | Clone 42.13 | Rhesus | MLN | 31 |
| Rh.25 | Clone 42.15 | Rhesus | MLN | 28 |
| Rh.26 | Clone 223.2 | Rhesus | Liver | 49 |
| Rh.27 | Clone 223.4 | Rhesus | Liver | 50 |
| Rh.28 | Clone 223.5 | Rhesus | Liver | 51 |
| Rh.29 | Clone 223.6 | Rhesus | Liver | 52 |
| Rh.30 | Clone 223.7 | Rhesus | Liver | 53 |
| Rh.31 | Clone 223.10 | Rhesus | Liver | 48 |
| Rh.32 | Clone C1 | Rhesus | Spleen, Duo, Kid & Liver | 19 |
| Rh.33 | Clone C3 | Rhesus | | 20 |
| Rh.34 | Clone C5 | Rhesus | | 21 |
| Rh.35 | Clone F1 | Rhesus | Liver | 22 |
| Rh.36 | Clone F3 | Rhesus | | 23 |
| Rh.37 | Clone F5 | Rhesus | | 24 |
| Cy.1 | Clone 1.3 | Cyno | Blood | 14 |
| Cy.2 | Clone 13.3B | Cyno | Blood | 15 |
| Cy.3 | Clone 24.1 | Cyno | Blood | 16 |
| Cy.4 | Clone 27.3 | Cyno | Blood | 17 |
| Cy.5 | Clone 7.2 | Cyno | Blood | 18 |
| Cy.6 | Clone 16.3 | Cyno | Blood | 10 |
| bb.1 | Clone 29.3 | Baboon | Blood | 11 |
| bb.2 | Clone 29.5 | Baboon | Blood | 13 |
| Ch.1 | Clone A3.3 | Chimp | Blood | 57 |
| Ch.2 | Clone A3.4 | Chimp | Blood | 54 |
| Ch.3 | Clone A3.5 | Chimp | Blood | 55 |
| Ch.4 | Clone A3.7 | Chimp | Blood | 56 |

A novel NHP clone was made by splicing capsids fragments of two chimp adenoviruses into an AAV2 rep construct. This new clone, A3.1, is also termed Ch.5 [SEQ ID NO:20]. Additionally, the present invention includes two human AAV sequences, termed H6 [SEQ ID NO:25] and H2 [SEQ ID NO:26].

The AAV nucleic acid sequences of the invention further encompass the strand which is complementary to the strands provided in the sequences provided in FIG. 1 and the Sequence Listing [SEQ ID NO:1, 9-59, 117-120], nucleic acid sequences, as well as the RNA and cDNA sequences corresponding to the sequences provided in FIG. 1 and the Sequence Listing [SEQ ID NO:1, 9-59, 117-120], and their complementary strands. Also included in the nucleic acid sequences of the invention are natural variants and engineered modifications of the sequences of FIG. 1 and the Sequence Listing [SEQ ID NO:1, 9-59, 117-120], and their complementary strands. Such modifications include, for example, labels which are known in the art, methylation, and substitution of one or more of the naturally occurring nucleotides with a degenerate nucleotide.

Further included in this invention are nucleic acid sequences which are greater than 85%, preferably at least about 90%, more preferably at least about 95%, and most preferably at least about 98 to 99% identical or homologous to the sequences of the invention, including FIG. 1 and the Sequence Listing [SEQ ID NO:1, 9-59, 117-120]. These terms are as defined herein.

Also included within the invention are fragments of the novel AAV sequences identified by the method described herein. Suitable fragments are at least 15 nucleotides in length, and encompass functional fragments, i.e., fragments which are of biological interest. In one embodiment, these fragments are fragments of the novel sequences of FIG. 1 and the Sequence Listing [SEQ ID NO:1, 9-59, 117-120], their complementary strands, cDNA and RNA complementary thereto.

Examples of suitable fragments are provided with respect to the location of these fragments on AAV1, AAV2, or AAV7. However, using the alignment provided herein (obtained using the Clustal W program at default settings), or similar techniques for generating an alignment with other novel serotypes of the invention, one of skill in the art can readily identify the precise nucleotide start and stop codons for desired fragments.

Examples of suitable fragments include the sequences encoding the three variable proteins (vp) of the AAV capsid which are alternative splice variants: vp1 [e.g., nt 825 to 3049 of AAV7, SEQ ID NO: 1]; vp2 [e.g., nt 1234-3049 of AAV7, SEQ ID NO: 1]; and vp 3 [e.g., nt 1434-3049 of AAV7, SEQ ID NO:1]. It is notable that AAV7 has an unusual GTG start codon. With the exception of a few house-keeping genes, such a start codon has not previously been reported in DNA viruses. The start codons for vp1, vp2 and vp3 for other AAV serotypes have been believed to be such that they permit the cellular mechanism of the host cell in which they reside to produce vp1, vp2 and vp3 in a ratio of 10%:10%:80%, respectively, in order to permit efficient assembly of the virion. However, the AAV7 virion has been found to assemble efficiently even with this rare GTG start codon. Thus, the inventors anticipate this it is desirable to alter the start codon of the vp3 of other AAV serotypes to contain this rare GTG start codon, in order to improve packaging efficiency, to alter the virion structure and/or to alter location of epitopes (e.g., neutralizing antibody epitopes) of other AAV serotypes. The start codons may be altered using conventional techniques including, e.g., site directed mutagenesis. Thus, the present invention encompasses altered AAV virions of any selected serotype, composed of a vp 3, and/or optionally, vp 1 and/or vp2 having start codons altered to GTG.

Other suitable fragments of AAV, include a fragment containing the start codon for the AAV capsid protein [e.g., nt 468 to 3090 of AAV7, SEQ ID NO:1, nt 725 to 3090 of AAV7, SEQ ID NO: 1, and corresponding regions of the other AAV serotypes]. Still other fragments of AAV7 and the other novel AAV serotypes identified using the methods described herein include those encoding the rep proteins, including rep 78 [e.g., initiation codon 334 of FIG. 1 for AAV7], rep 68 [initiation codon nt 334 of FIG. 1 for AAV7], rep 52 [initiation codon 1006 of FIG. 1 for AAV7], and rep 40 [initiation codon 1006 of FIG. 1 for AAV7] Other fragments of interest may include the AAV 5' inverted terminal repeats ITRs, [nt 1 to 107 of FIG. 1 for AAV7]; the AAV 3' ITRs [nt 4704 to 4721 of FIG. 1 for AAV7], P19 sequences, AAV P40 sequences, the rep binding site, and the terminal resolute site (TRS). Still other suitable fragments will be readily apparent to those of skill in the art. The corresponding regions in the other novel serotypes of the invention can be readily determined by reference to FIG. 1, or by utilizing conventional alignment techniques with the sequences provided herein.

In addition to including the nucleic acid sequences provided in the figures and Sequence Listing, the present invention includes nucleic acid molecules and sequences which are designed to express the amino acid sequences, proteins and peptides of the AAV serotypes of the invention. Thus, the invention includes nucleic acid sequences which encode the following novel AAV amino acid sequences: C1 [SEQ ID NO:60], C2 [SEQ ID NO:61], C5 [SEQ ID NO:62], A3-3 [SEQ ID NO:66], A3-7 [SEQ ID NO:67], A3-4 [SEQ ID NO:68], A3-5 [SEQ ID NO: 69], 3.3b [SEQ ID NO: 62], 223.4 [SEQ ID NO: 73], 223-5 [SEQ ID NO:74], 223-10 [SEQ ID NO:75], 223-2 [SEQ ID NO:76], 223-7 [SEQ ID NO: 77], 223-6 [SEQ ID NO: 78], 44-1 [SEQ ID NO: 79], 44-5 [SEQ ID NO:80], 44-2 [SEQ ID NO:81], 42-15 [SEQ ID NO: 84], 42-8 [SEQ ID NO: 85], 42-13 [SEQ ID NO:86], 42-3A [SEQ ID NO:87], 42-4 [SEQ ID NO:88], 42-5A [SEQ ID NO:89], 42-1B [SEQ ID NO:90], 42-5B [SEQ ID NO:91], 43-1 [SEQ ID NO: 92], 43-12 [SEQ ID NO: 93], 43-5 [SEQ ID NO:94], 43-21 [SEQ ID NO:96], 43-25 [SEQ ID NO: 97], 43-20 [SEQ ID NO:99], 24.1 [SEQ ID NO: 101], 42.2 [SEQ ID NO:102], 7.2 [SEQ ID NO: 103], 27.3 [SEQ ID NO: 104], 16.3 [SEQ ID NO: 105], 42.10 [SEQ ID NO: 106], 42-3B [SEQ ID NO: 107], 42-11 [SEQ ID NO: 108], F1 [SEQ ID NO: 109], F5 [SEQ ID NO: 110], F3 [SEQ ID NO:111], 42-6B [SEQ ID NO: 112], and/or 42-12 [SEQ ID NO: 113], and artificial AAV serotypes generated using these sequences and/or unique fragments thereof.

As used herein, artificial AAV serotypes include, without limitation, AAV with a non-naturally occurring capsid protein. Such an artificial capsid may be generated by any suitable technique, using a novel AAV sequence of the invention (e.g., a fragment of a vp1 capsid protein) in combination with heterologous sequences which may be obtained from another AAV serotype (known or novel), non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid.

B. AAV Amino Acid Sequences, Proteins and Peptides

The invention provides proteins and fragments thereof which are encoded by the nucleic acid sequences of the novel AAV serotypes identified herein, including, e.g., AAV7 [nt 825 to 3049 of AAV7, SEQ ID NO: 1] the other novel serotypes provided herein. Thus, the capsid proteins of the novel serotypes of the invention, including: H6 [SEQ ID NO: 25], H2 [SEQ ID NO: 26], 42-2 [SEQ ID NO:9], 42-8 [SEQ ID NO:27], 42-15 [SEQ ID NO:28], 42-5b [SEQ ID NO: 29], 42-1b [SEQ ID NO:30]; 42-13 [SEQ ID NO: 31], 42-3a [SEQ ID NO: 32], 42-4 [SEQ ID NO:33], 42-5a [SEQ ID NO: 34], 42-10 [SEQ ID NO:35], 42-3b [SEQ ID NO: 36], 42-11 [SEQ ID NO: 37], 42-6b [SEQ ID NO:38], 43-1 [SEQ ID NO: 39], 43-5 [SEQ ID NO: 40], 43-12 [SEQ ID NO:41], 43-20 [SEQ ID NO:42], 43-21 [SEQ ID NO: 43], 43-23 [SEQ ID NO:44], 43-25 [SEQ ID NO: 45], 44.1 [SEQ ID NO:47], 44.5 [SEQ ID NO:47], 223.10 [SEQ ID NO:48], 223.2 [SEQ ID NO:49], 223.4 [SEQ ID NO:50], 223.5 [SEQ ID NO: 51], 223.6 [SEQ ID NO: 52], 223.7 [SEQ ID NO: 53], A3.4 [SEQ ID NO: 54], A3.5 [SEQ ID NO:55], A3.7 [SEQ ID NO: 56], A3.3 [SEQ ID NO:57], 42.12 [SEQ ID NO: 58], and 44.2 [SEQ ID NO: 59], can be readily generated using conventional techniques from the open reading frames provided for the above-listed clones.

The invention further encompasses AAV serotypes generated using sequences of the novel AAV serotypes of the invention, which are generated using synthetic, recombinant or other techniques known to those of skill in the art. The invention is not limited to novel AAV amino acid sequences, peptides and proteins expressed from the novel AAV nucleic acid sequences of the invention and encompasses amino acid sequences, peptides and proteins generated by other methods known in the art, including, e.g., by chemical synthesis, by other synthetic techniques, or by other methods. For example, the sequences of any of C1 [SEQ ID NO:60], C2 [SEQ ID NO:61], C5 [SEQ ID NO:62], A3-3 [SEQ ID NO:66], A3-7 [SEQ ID NO:67], A3-4 [SEQ ID NO:68], A3-5 [SEQ ID NO: 69], 3.3b [SEQ ID NO: 62], 223.4 [SEQ ID NO: 73], 223-5 [SEQ ID NO:74], 223-10 [SEQ ID NO:75], 223-2 [SEQ ID NO:76], 223-7 [SEQ ID NO: 77], 223-6 [SEQ ID NO: 78], 44-1 [SEQ ID NO: 79], 44-5 [SEQ ID NO:80], 44-2 [SEQ ID NO:81], 42-15 [SEQ ID NO: 84], 42-8 [SEQ ID NO: 85], 42-13 [SEQ ID NO:86], 42-3A [SEQ ID NO:87], 42-4 [SEQ ID NO:88], 42-5A [SEQ ID NO:89], 42-1B [SEQ ID NO:90], 42-5B [SEQ ID NO:91], 43-1 [SEQ ID NO: 92], 43-12 [SEQ ID NO: 93], 43-5 [SEQ ID NO:94], 43-21 [SEQ ID NO:96], 43-25 [SEQ ID NO: 97], 43-20 [SEQ ID NO:99], 24.1 [SEQ ID NO: 101], 42.2 [SEQ ID NO:102], 7.2 [SEQ ID NO: 103], 27.3 [SEQ ID NO: 104], 16.3 [SEQ ID NO: 105], 42.10 [SEQ ID NO: 106], 42-3B [SEQ ID NO: 107], 42-11 [SEQ ID NO: 108], F1 [SEQ ID NO: 109], F5 [SEQ ID NO: 110], F3 [SEQ ID NO:111], 42-6B [SEQ ID NO: 112], and/or 42-12 [SEQ ID NO: 113] by be readily generated using a variety of techniques.

Suitable production techniques are well known to those of skill in the art. See, e.g., Sambrook et al, Molecular Cloning: A Laboratory Manual, Cold Spring Harbor Press (Cold Spring Harbor, N.Y.). Alternatively, peptides can also be synthesized by the well known solid phase peptide synthesis methods (Merrifield, *J. Am. Chem. Soc.*, 85:2149 (1962); Stewart and Young, Solid Phase Peptide Synthesis (Freeman, San Francisco, 1969) pp. 27-62). These and other suitable production methods are within the knowledge of those of skill in the art and are not a limitation of the present invention.

Particularly desirable proteins include the AAV capsid proteins, which are encoded by the nucleotide sequences identified above. The sequences of many of the capsid proteins of the invention are provided in an alignment in FIG. 2 and/or in the Sequence Listing, SEQ ID NO: 2 and 60 to 115, which is incorporated by reference herein. The AAV capsid is composed of three proteins, vp1, vp2 and vp3, which are alternative splice variants. The full-length sequence provided in these figures is that of vp1. Based on the numbering of the AAV7 capsid [SEQ ID NO:2], the sequences of vp2 span amino acid 138-737 of AAV7 and the sequences of vp3 span amino acids 203-737 of AAV7. With this information, one of skill in the art can readily determine the location of the vp2 and vp3 proteins for the other novel serotypes of the invention.

Other desirable proteins and fragments of the capsid protein include the constant and variable regions, located between hypervariable regions (HPV) and the sequences of the HPV regions themselves. An algorithm developed to determine areas of sequence divergence in AAV2 has yielded 12 hypervariable regions (HVR) of which 5 overlap or are part of the four previously described variable regions. [Chiorini et al, *J. Virol*, 73:1309-19 (1999); Rutledge et al, *J. Virol.*, 72:309-319] Using this algorithm and/or the alignment techniques described herein, the HVR of the novel AAV serotypes are determined. For example, with respect to the number of the AAV2 vp1 [SEQ ID NO:70], the HVR are located as follows: HVR1, aa 146-152; HVR2, aa 182-186; HVR3, aa 262-264; HVR4, aa 381-383; HVR5, aa 450-474; HVR6, aa 490-495; HVR7, aa500-504; HVR8, aa 514-522; HVR9, aa 534-555; HVR10, aa 581-594; HVR11, aa 658-667; and HVR12, aa 705-719. Utilizing an alignment prepared in accordance with conventional methods and the novel sequences provided herein [See, e.g., FIG. 2], one can readily determine the location of the HVR in the novel AAV serotypes of the invention. For example, utilizing FIG. 2, one can readily determine that for AAV7 [SEQ ID NO:2], HVR1 is located at aa 146-152; HVR2 is located at 182-187; HVR3 is located at aa 263-266, HVR4 is located at aa 383-385, HVR5 is located at aa 451-475; HVR6 is located at aa 491-496 of AAV7; HVR7 is located at aa 501-505; HVR8 is located at aa 513-521; HVR9 is located at 533-554; HVR10 is located at aa 583-596; HVR11 is located at aa 660-669; HVR12 is located at aa 707-721. Using the information provided herein, the HVRs for the other novel serotypes of the invention can be readily determined.

In addition, within the capsid, amino acid cassettes of identity have been identified. These cassettes are of particular interest, as they are useful in constructing artificial serotypes, e.g., by replacing a HVR1 cassette of a selected serotype with an HVR1 cassette of another serotype. Certain of these cassettes of identity are noted in FIG. 2. See, FIG. 2, providing the Clustal X alignment, which has a ruler is displayed below the sequences, starting at 1 for the first residue position. The line above the ruler is used to mark strongly conserved positions. Three characters (*, :, .) are used. "*" indicates positions which have a single, fully conserved residue. ":" indicates that a "strong" group is fully conserved "." Indicates that a "weaker" group is fully conserved. These are all the positively scoring groups that occur in the Gonnet Pam250 matrix. The strong groups are defined as a strong score >0.5 and the weak groups are defined as weak score <0.5.

Additionally, examples of other suitable fragments of AAV capsids include, with respect to the numbering of AAV2 [SEQ ID NO:70], aa 24-42, aa 25-28; aa 81-85; aa133-165; aa 134-165; aa 137-143; aa 154-156; aa 194-208; aa 261-274; aa 262-274; aa 171-173; aa 413-417; aa 449-478; aa 494-525; aa 534-571; aa 581-601; aa 660-671; aa 709-723. Still other desirable fragments include, for example, in AAV7, amino acids 1 to 184 of SEQ ID NO:2, amino acids 199 to 259; amino acids 274 to 446; amino acids 603 to 659; amino acids 670 to 706; amino acids 724 to 736; aa 185 to 198; aa 260 to 273; aa447 to 477; aa495 to 602; aa660 to 669; and aa707 to 723. Still other desirable regions, based on the numbering of AAV7 [SEQ ID NO:2], are selected from among the group consisting of aa 185 to 198; aa 260 to 273; aa447 to 477; aa495 to 602; aa660 to 669; and aa707 to 723. Using the alignment provided herein performed using the Clustal X program at default settings, or using other commercially or publicly available alignment programs at default settings, one of skill in the art can readily determine corresponding fragments of the novel AAV capsids of the invention.

Other desirable proteins are the AAV rep proteins [aa 1 to 623 of SEQ ID NO:3 for AAV7] and functional fragments thereof, including, e.g., aa 1 to 171, aa 172 to 372, aa 373 to 444, aa 445 to 623 of SEQ ID NO:3, among others. Suitably, such fragments are at least 8 amino acids in length. See, FIG. 3. Comparable regions can be identified in the proteins of the other novel AAV of the invention, using the techniques described herein and those which are known in the art. In addition, fragments of other desired lengths may be readily utilized. Such fragments may be produced recombinantly or by other suitable means, e.g., chemical synthesis.

The sequences, proteins, and fragments of the invention may be produced by any suitable means, including recombinant production, chemical synthesis, or other synthetic means. Such production methods are within the knowledge of those of skill in the art and are not a limitation of the present invention.

IV. Production of rAAV with novel AAV capsids

The invention encompasses novel, wild-type AAV serotypes identified by the invention, the sequences of which wild-type AAV serotypes are free of DNA and/or cellular material with these viruses are associated in nature. In another aspect, the present invention provides molecules which utilize the novel AAV sequences of the invention, including fragments thereof, for production of molecules useful in delivery of a heterologous gene or other nucleic acid sequences to a target cell.

The molecules of the invention which contain sequences of a novel AAV serotype of the invention include any genetic element (vector) which may be delivered to a host cell, e.g., naked DNA, a plasmid, phage, transposon, cosmid, episome, a protein in a non-viral delivery vehicle (e.g., a lipid-based carrier), virus, etc. which transfer the sequences carried thereon. The selected vector may be delivered by any suitable method, including transfection, electroporation, liposome delivery, membrane fusion techniques, high velocity DNA-coated pellets, viral infection and protoplast fusion. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y.

In one embodiment, the vectors of the invention contain sequences encoding a novel AAV capsid of the invention (e.g., AAV7 capsid, AAV 44-2 (rh.10), an AAV10 capsid, an AAV11 capsid, an AAV12 capsid), or a fragment of one or more of these AAV capsids. Alternatively, the vectors may contain the capsid protein, or a fragment thereof, itself.

Optionally, vectors of the invention may contain sequences encoding AAV rep proteins. Such rep sequences may be from the same AAV serotype which is providing the cap sequences. Alternatively, the present invention provides vectors in which the rep sequences are from an AAV serotype which differs from that which is providing the cap sequences. In one embodiment, the rep and cap sequences are expressed from separate sources (e.g., separate vectors, or a host cell and a vector). In another embodiment, these rep sequences are expressed from the same source as the cap sequences. In this embodiment, the rep sequences may be fused in frame to cap sequences of a different AAV serotype to form a chimeric AAV vector. Optionally, the vectors of the invention further contain a minigene comprising a selected transgene which is flanked by AAV 5' ITR and AAV 3' ITR.

Thus, in one embodiment, the vectors described herein contain nucleic acid sequences encoding an intact AAV capsid which may be from a single AAV serotype (e.g., AAV7 or another novel AAV). Alternatively, these vectors contain sequences encoding artificial capsids which contain one or more fragments of the AAV7 (or another novel AAV) capsid fused to heterologous AAV or non-AAV capsid proteins (or fragments thereof). These artificial capsid proteins are selected from non-contiguous portions of the AAV7 (or another novel AAV) capsid or from capsids of other AAV serotypes. For example, it may be desirable to modify the coding regions of one or more of the AAV vp1, e.g., in one or more of the hypervariable regions (i.e., HPV1-12), or vp2, and/or vp3. In another example, it may be desirable to alter the start codon of the vp3 protein to GTG. These modifications may be to increase expression, yield, and/or to improve purification in the selected expression systems, or for another desired purpose (e.g., to change tropism or alter neutralizing antibody epitopes).

The vectors described herein, e.g., a plasmid, are useful for a variety of purposes, but are particularly well suited for use in production of a rAAV containing a capsid comprising AAV sequences or a fragment thereof. These vectors, including rAAV, their elements, construction, and uses are described in detail herein.

In one aspect, the invention provides a method of generating a recombinant adeno-associated virus (AAV) having an AAV serotype 7 (or another novel AAV) capsid, or a portion thereof. Such a method involves culturing a host cell which contains a nucleic acid sequence encoding an adeno-associated virus (AAV) serotype 7 (or another novel AAV) capsid protein, or fragment thereof, as defined herein; a functional rep gene; a minigene composed of, at a minimum, AAV inverted terminal repeats (ITRs) and a transgene; and sufficient helper functions to permit packaging of the minigene into the AAV7 (or another novel AAV) capsid protein.

The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing the rAAV of the invention may be delivered to the packaging host cell in the form of any genetic element which transfer the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, *J. Vivol.*, 70:520-532 (1993) and U.S. Pat. No. 5,478,745.

A. The Minigene

The minigene is composed of, at a minimum, a transgene and its regulatory sequences, and 5= and 3=AAV inverted terminal repeats (ITRs). It is this minigene which is packaged into a capsid protein and delivered to a selected host cell.

1. The Transgene

The transgene is a nucleic acid sequence, heterologous to the vector sequences flanking the transgene, which encodes a polypeptide, protein, or other product, of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, one type of transgene sequence includes a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc.

These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is green fluorescent protein or luciferase, the vector carrying the signal may be measured visually by color or light production in a luminometer.

However, desirably, the transgene is a non-marker sequence encoding a product which is useful in biology and medicine, such as proteins, peptides, RNA, enzymes, or catalytic RNAs. Desirable RNA molecules include tRNA, dsRNA, ribosomal RNA, catalytic RNAs, and antisense RNAs. One example of a useful RNA sequence is a sequence which extinguishes expression of a targeted nucleic acid sequence in the treated animal.

The transgene may be used to correct or ameliorate gene deficiencies, which may include deficiencies in which normal genes are expressed at less than normal levels or deficiencies in which the functional gene product is not expressed. A preferred type of transgene sequence encodes a therapeutic protein or polypeptide which is expressed in a host cell. The invention further includes using multiple transgenes, e.g., to correct or ameliorate a gene defect caused by a multi-subunit protein. In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., M. L. Donnelly, et al, *J. Gen. Virol.,* 78(Pt 1):13-21 (January 1997); Furler, S., et al, *Gene Ther.,* 8(11):864-873 (June 2001); Klump H., et al., *Gene Ther.,* 8(10):811-817 (May 2001). This 2A peptide is significantly smaller than an IRES, making it well suited for use when space is a limiting factor. However, the selected transgene may encode any biologically active product or other product, e.g., a product desirable for study.

Suitable transgenes may be readily selected by one of skill in the art. The selection of the transgene is not considered to be a limitation of this invention.

2. Regulatory Elements

In addition to the major elements identified above for the minigene, the vector also includes conventional control elements necessary which are operably linked to the transgene in a manner which permits its transcription, translation and/or expression in a cell transfected with the plasmid vector or infected with the virus produced by the invention. As used herein, Aoperably linked≅ sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell,* 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system [WO 98/10088]; the ecdysone insect promoter [No et al, *Proc. Natl. Acad. Sci. USA,* 93:3346-3351 (1996)], the tetracycline-repressible system [Gossen et al, *Proc. Natl. Acad. Sci. USA,* 89:5547-5551 (1992)], the tetracycline-inducible system [Gossen et al, Science, 268:1766-1769 (1995), see also Harvey et al, *Curr. Opin. Chem. Biol.,* 2:512-518 (1998)], the RU486-inducible system [Wang et al, *Nat. Biotech.,* 15:239-243 (1997) and Wang et al, *Gene Ther.,* 4:432-441 (1997)] and the rapamycin-inducible system [Magari et al, *J. Clin. Invest.,* 100:2865-2872 (1997)]. Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a transgene operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally-occurring promoters (see Li et al., *Nat. Biotech.*, 17:241-245 (1999)). Examples of promoters that are tissue-specific are known for liver (albumin, Miyatake et al., *J. Virol.*, 71:5124-32 (1997); hepatitis B virus core promoter, Sandig et al., *Gene Ther.*, 3:1002-9 (1996); alpha-fetoprotein (AFP), Arbuthnot et al., *Hum. Gene Ther.*, 7:1503-14 (1996)), bone osteocalcin (Stein et al., *Mol. Biol. Rep.*, 24:185-96 (1997)); bone sialoprotein (Chen et al., *J. Bone Miner. Res.*, 11:654-64 (1996)), lymphocytes (CD2, Hansal et al., *J. Immunol.*, 161:1063-8 (1998); immunoglobulin heavy chain; T cell receptor α chain), neuronal such as neuron-specific enolase (NSE) promoter (Andersen et al., *Cell. Mol. Neurobiol.*, 13:503-15 (1993)), neurofilament light-chain gene (Piccioli et al., *Proc. Natl. Acad. Sci. USA*, 88:5611-5 (1991)), and the neuron-specific vgf gene (Piccioli et al., *Neuron*, 15:373-84 (1995)), among others.

Optionally, plasmids carrying therapeutically useful transgenes may also include selectable markers or reporter genes may include sequences encoding geneticin, hygromicin or purimycin resistance, among others. Such selectable reporters or marker genes (preferably located outside the viral genome to be rescued by the method of the invention) can be used to signal the presence of the plasmids in bacterial cells, such as ampicillin resistance. Other components of the plasmid may include an origin of replication. Selection of these and other promoters and vector elements are conventional and many such sequences are available [see, e.g., Sambrook et al, and references cited therein].

The combination of the transgene, promoter/enhancer, and 5= and 3=ITRs is referred to as a "minigene" for ease of reference herein. Provided with the teachings of this invention, the design of such a minigene can be made by resort to conventional techniques.

3. Delivery of the Minigene to a Packaging Host Cell

The minigene can be carried on any suitable vector, e.g., a plasmid, which is delivered to a host cell. The plasmids useful in this invention may be engineered such that they are suitable for replication and, optionally, integration in prokaryotic cells, mammalian cells, or both. These plasmids (or other vectors carrying the 5' AAV ITR-heterologous molecule-3'ITR) contain sequences permitting replication of the minigene in eukaryotes and/or prokaryotes and selection markers for these systems. Selectable markers or reporter genes may include sequences encoding geneticin, hygromicin or purimycin resistance, among others. The plasmids may also contain certain selectable reporters or marker genes that can be used to signal the presence of the vector in bacterial cells, such as ampicillin resistance. Other components of the plasmid may include an origin of replication and an amplicon, such as the amplicon system employing the Epstein Barr virus nuclear antigen. This amplicon system, or other similar amplicon components permit high copy episomal replication in the cells. Preferably, the molecule carrying the minigene is transfected into the cell, where it may exist transiently. Alternatively, the minigene (carrying the 5' AAV ITR-heterologous molecule-3' ITR) may be stably integrated into the genome of the host cell, either chromosomally or as an episome. In certain embodiments, the minigene may be present in multiple copies, optionally in head-to-head, head-to-tail, or tail-to-tail concatamers. Suitable transfection techniques are known and may readily be utilized to deliver the minigene to the host cell.

Generally, when delivering the vector comprising the minigene by transfection, the vector is delivered in an amount from about 5 μg to about 100 μg DNA, and preferably about 10 to about 50 μg DNA to about $1\times10^4$ cells to about $1\times10^{13}$ cells, and preferably about $10^5$ cells. However, the relative amounts of vector DNA to host cells may be adjusted, taking into consideration such factors as the selected vector, the delivery method and the host cells selected.

B. Rep and Cap Sequences

In addition to the minigene, the host cell contains the sequences which drive expression of the novel AAV capsid protein (e.g., AAV7 or other novel AAV capsid or an artificial capsid protein comprising a fragment of one or more of these capsids) in the host cell and rep sequences of the same serotype as the serotype of the AAV ITRs found in the minigene. The AAV cap and rep sequences may be independently obtained from an AAV source as described above and may be introduced into the host cell in any manner known to one in the art as described above. Additionally, when pseudotyping a novel AAV capsid of the invention, the sequences encoding each of the essential rep proteins may be supplied by the same AAV serotype, or the sequences encoding the rep proteins may be supplied by different AAV serotypes (e.g., AAV1, AAV2, AAV3, AAV4, AAV5, AAV6, or one of the novel serotypes identified herein). For example, the rep78/68 sequences may be from AAV2, whereas the rep52/40 sequences may from AAV1.

In one embodiment, the host cell stably contains the capsid protein under the control of a suitable promoter, such as those described above. Most desirably, in this embodiment, the capsid protein is expressed under the control of an inducible promoter. In another embodiment, the capsid protein is supplied to the host cell in trans. When delivered to the host cell in trans, the capsid protein may be delivered via a plasmid which contains the sequences necessary to direct expression of the selected capsid protein in the host cell. Most desirably, when delivered to the host cell in trans, the plasmid carrying the capsid protein also carries other sequences required for packaging the rAAV, e.g., the rep sequences.

In another embodiment, the host cell stably contains the rep sequences under the control of a suitable promoter, such as those described above. Most desirably, in this embodiment, the essential rep proteins are expressed under the control of an inducible promoter. In another embodiment, the rep proteins are supplied to the host cell in trans. When delivered to the host cell in trans, the rep proteins may be delivered via a plasmid which contains the sequences necessary to direct expression of the selected rep proteins in the host cell. Most desirably, when delivered to the host cell in trans, the plasmid carrying the capsid protein also carries other sequences required for packaging the rAAV, e.g., the rep and cap sequences.

Thus, in one embodiment, the rep and cap sequences may be transfected into the host cell on a single nucleic acid molecule and exist stably in the cell as an episome. In another embodiment, the rep and cap sequences are stably integrated into the genome of the cell. Another embodiment has the rep and cap sequences transiently expressed in the host cell. For example, a useful nucleic acid molecule for such transfection comprises, from 5' to 3', a promoter, an optional spacer interposed between the promoter and the start site of the rep gene sequence, an AAV rep gene sequence, and an AAV cap gene sequence.

Optionally, the rep and/or cap sequences may be supplied on a vector that contains other DNA sequences that are to be introduced into the host cells. For instance, the vector may contain the rAAV construct comprising the minigene. The vector may comprise one or more of the genes encoding the helper functions, e.g., the adenoviral proteins E1, E2a, and E4ORF6, and the gene for VAI RNA.

Preferably, the promoter used in this construct may be any of the constitutive, inducible or native promoters known to one of skill in the art or as discussed above. In one embodiment, an AAV P5 promoter sequence is employed. The selection of the AAV to provide any of these sequences does not limit the invention.

In another preferred embodiment, the promoter for rep is an inducible promoter, as are discussed above in connection with the transgene regulatory elements. One preferred promoter for rep expression is the T7 promoter. The vector comprising the rep gene regulated by the T7 promoter and the cap gene, is transfected or transformed into a cell which either constitutively or inducibly expresses the T7 polymerase. See WO 98/10088, published Mar. 12, 1998.

The spacer is an optional element in the design of the vector. The spacer is a DNA sequence interposed between the promoter and the rep gene ATG start site. The spacer may have any desired design; that is, it may be a random sequence of nucleotides, or alternatively, it may encode a gene product, such as a marker gene. The spacer may contain genes which typically incorporate start/stop and polyA sites. The spacer may be a non-coding DNA sequence from a prokaryote or eukaryote, a repetitive non-coding sequence, a coding sequence without transcriptional controls or a coding sequence with transcriptional controls. Two exemplary sources of spacer sequences are the λ, phage ladder sequences or yeast ladder sequences, which are available commercially, e.g., from Gibco or Invitrogen, among others. The spacer may be of any size sufficient to reduce expression of the rep78 and rep68 gene products, leaving the rep52, rep40 and cap gene products expressed at normal levels. The length of the spacer may therefore range from about 10 bp to about 10.0 kbp, preferably in the range of about 100 bp to about 8.0 kbp. To reduce the possibility of recombination, the spacer is preferably less than 2 kbp in length; however, the invention is not so limited.

Although the molecule(s) providing rep and cap may exist in the host cell transiently (i.e., through transfection), it is preferred that one or both of the rep and cap proteins and the promoter(s) controlling their expression be stably expressed in the host cell, e.g., as an episome or by integration into the chromosome of the host cell. The methods employed for constructing embodiments of this invention are conventional genetic engineering or recombinant engineering techniques such as those described in the references above. While this specification provides illustrative examples of specific constructs, using the information provided herein, one of skill in the art may select and design other suitable constructs, using a choice of spacers, P5 promoters, and other elements, including at least one translational start and stop signal, and the optional addition of polyadenylation sites.

In another embodiment of this invention, the rep or cap protein may be provided stably by a host cell.

C. The Helper Functions

The packaging host cell also requires helper functions in order to package the rAAV of the invention. Optionally, these functions may be supplied by a herpesvirus. Most desirably, the necessary helper functions are each provided from a human or non-human primate adenovirus source, such as those described above and/or are available from a variety of sources, including the American Type Culture Collection (ATCC), Manassas, Va. (US). In one currently preferred embodiment, the host cell is provided with and/or contains an E1a gene product, an E1b gene product, an E2a gene product, and/or an E4 ORF6 gene product. The host cell may contain other adenoviral genes such as VAI RNA, but these genes are not required. In a preferred embodiment, no other adenovirus genes or gene functions are present in the host cell.

By Aadenoviral DNA which expresses the E1a gene product=, it is meant any adenovirus sequence encoding E1a or any functional E1a portion. Adenoviral DNA which expresses the E2a gene product and adenoviral DNA which expresses the E4 ORF6 gene products are defined similarly. Also included are any alleles or other modifications of the adenoviral gene or functional portion thereof. Such modifications may be deliberately introduced by resort to conventional genetic engineering or mutagenic techniques to enhance the adenoviral function in some manner, as well as naturally occurring allelic variants thereof. Such modifications and methods for manipulating DNA to achieve these adenovirus gene functions are known to those of skill in the art.

The adenovirus E1a, E1b, E2a, and/or E4ORF6 gene products, as well as any other desired helper functions, can be provided using any means that allows their expression in a cell. Each of the sequences encoding these products may be on a separate vector, or one or more genes may be on the same vector. The vector may be any vector known in the art or disclosed above, including plasmids, cosmids and viruses. Introduction into the host cell of the vector may be achieved by any means known in the art or as disclosed above, including transfection, infection, electroporation, liposome delivery, membrane fusion techniques, high velocity DNA-coated pellets, viral infection and protoplast fusion, among others. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously-added factors, for example.

D. Host Cells And Packaging Cell Lines

The host cell itself may be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, BHK, MDCK, COS 1, COS 7, BSC 1, BSC 40, BMT 10, VERO, WI38, HeLa, 293 cells (which express functional adenoviral E1), Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc. The most desirable cells do not carry any adenovirus gene other than E1, E2a and/or E4 ORF6; nor do they contain any other virus gene which could result in homologous recombination of a contaminating virus during the production of rAAV; and it is capable of infection or transfection of DNA and expression of the transfected DNA. In a preferred embodiment, the host cell is one that has rep and cap stably transfected in the cell.

One host cell useful in the present invention is a host cell stably transformed with the sequences encoding rep and cap, and which is transfected with the adenovirus E1, E2a, and E4ORF6 DNA and a construct carrying the minigene as described above. Stable rep and/or cap expressing cell lines, such as B-50 (PCT/US98/19463), or those described in U.S. Pat. No. 5,658,785, may also be similarly employed. Another desirable host cell contains the minimum adenoviral DNA which is sufficient to express E4 ORF6. Yet other cell lines can be constructed using the novel AAV rep and/or novel AAV cap sequences of the invention.

The preparation of a host cell according to this invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus and AAV genomes, combined with polymerase chain reaction, synthetic methods, and any other suitable methods which provide the desired nucleotide sequence.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation, and/or infection by hybrid adenovirus/AAV vectors into cell lines such as the human embryonic kidney cell line HEK 293 (a human kidney cell line containing functional adenovirus E1 genes which provides trans-acting E1 proteins).

These novel AAV-based vectors which are generated by one of skill in the art are beneficial for gene delivery to selected host cells and gene therapy patients since no neutralization antibodies to AAV7 have been found in the human population. Further, early studies show no neutralizing antibodies in cyno monkey and chimpanzee populations, and less than 15% cross-reactivity of AAV 7 in rhesus monkeys, the species from which the serotype was isolated. One of skill in the art may readily prepare other rAAV viral vectors containing the AAV7 capsid proteins provided herein using a variety of techniques known to those of skill in the art. One may similarly prepare still other rAAV viral vectors containing AAV7 sequence and AAV capsids of another serotype. Similar advantages are conferred by the vectors based on the other novel AAV of the invention.

Thus, one of skill in the art will readily understand that the AAV7 sequences of the invention can be readily adapted for use in these and other viral vector systems for in vitro, ex vivo or in vivo gene delivery. Similarly, one of skill in the art can readily select other fragments of the novel AAV genome of the invention for use in a variety of rAAV and non-rAAV vector systems. Such vectors systems may include, e.g., lentiviruses, retroviruses, poxviruses, vaccinia viruses, and adenoviral systems, among others. Selection of these vector systems is not a limitation of the present invention.

Thus, the invention further provides vectors generated using the nucleic acid and amino acid sequences of the novel AAV of the invention. Such vectors are useful for a variety of purposes, including for delivery of therapeutic molecules and for use in vaccine regimens. Particularly desirable for delivery of therapeutic molecules are recombinant AAV containing capsids of the novel AAV of the invention. These, or other vector constructs containing novel AAV sequences of the invention may be used in vaccine regimens, e.g., for co-delivery of a cytokine, or for delivery of the immunogen itself.

V. Recombinant Viruses And Uses Thereof

Using the techniques described herein, one of skill in the art may generate a rAAV having a capsid of a novel serotype of the invention, or a novel capsid containing one or more novel fragments of an AAV serotype identified by the method of the invention. In one embodiment, a full-length capsid from a single serotype, e.g., AAV7 [SEQ ID NO: 2] can be utilized. In another embodiment, a full-length capsid may be generated which contains one or more fragments of a novel serotype of the invention fused in frame with sequences from another selected AAV serotype. For example, a rAAV may contain one or more of the novel hypervariable region sequences of an AAV serotype of the invention. Alternatively, the unique AAV serotypes of the invention may be used in constructs containing other viral or non-viral sequences.

It will be readily apparent to one of skill in the art one embodiment, that certain serotypes of the invention will be particularly well suited for certain uses. For example, vectors based on AAV7 capsids of the invention are particularly well suited for use in muscle; whereas vectors based on rh.10 (44-2) capsids of the invention are particularly well suited for use in lung. Uses of such vectors are not so limited and one of skill in the art may utilize these vectors for delivery to other cell types, tissues or organs. Further, vectors based upon other capsids of the invention may be used for delivery to these or other cells, tissues or organs.

A. Delivery of Transgene

In another aspect, the present invention provides a method for delivery of a transgene to a host which involves transfecting or infecting a selected host cell with a vector generated with the sequences of the AAV of the invention. Methods for delivery are well known to those of skill in the art and are not a limitation of the present invention.

In one desirable embodiment, the invention provides a method for AAV-mediated delivery of a transgene to a host. This method involves transfecting or infecting a selected host cell with a recombinant viral vector containing a selected transgene under the control of sequences which direct expression thereof and AAV capsid proteins.

Optionally, a sample from the host may be first assayed for the presence of antibodies to a selected AAV serotype. A variety of assay formats for detecting neutralizing antibodies are well known to those of skill in the art. The selection of such an assay is not a limitation of the present invention. See, e.g., Fisher et al, *Nature Med.*, 3(3):306-312 (March 1997) and W. C. Manning et al, *Human Gene Therapy*, 9:477-485 (Mar. 1, 1998). The results of this assay may be used to determine which AAV vector containing capsid proteins of a particular serotype are preferred for delivery, e.g., by the absence of neutralizing antibodies specific for that capsid serotype.

In one aspect of this method, the delivery of vector with a selected AAV capsid proteins may precede or follow delivery of a gene via a vector with a different serotype AAV capsid protein. Similarly, the delivery of vector with other novel AAV capsid proteins of the invention may precede or follow delivery of a gene via a vector with a different serotype AAV capsid protein. Thus, gene delivery via rAAV vectors may be used for repeat gene delivery to a selected host cell. Desirably, subsequently administered rAAV vectors carry the same transgene as the first rAAV vector, but the subsequently administered vectors contain capsid proteins of serotypes which differ from the first vector. For example, if a first vector has AAV7 capsid proteins [SEQ ID NO:2], subsequently administered vectors may have capsid proteins selected from among the other serotypes, including AAV1, AAV2, AAV3A, AAV3B, AAV4, AAV6, AAV10, AAV11, and AAV12, or any of the other novel AAV capsids identified herein including, without limitation: A3.1, H2, H6, C1, C2, C5, A3-3, A3-7, A3-4, A3-5, 3.3b, 223.4, 223-5, 223-10, 223-2, 223-7, 223-6, 44-1, 44-5, 44-2, 42-15, 42-8, 42-13, 42-3A, 42-4, 42-5A, 42-1B, 42-5B, 43-1, 43-12, 43-5, 43-21, 43-25, 43-20, 24.1, 42.2, 7.2, 27.3, 16.3, 42.10, 42-3B, 42-11, F1, F5, F3, 42-6B, and/or 42-12.

The above-described recombinant vectors may be delivered to host cells according to published methods. The rAAV, preferably suspended in a physiologically compatible carrier, may be administered to a human or non-human mammalian patient. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The viral vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, and other parental routes of administration. Routes of administration may be combined, if desired.

Dosages of the viral vector will depend primarily on factors such as the condition being treated, the age, weight and health of the patient, and may thus vary among patients. For example, a therapeutically effective human dosage of the viral vector is generally in the range of from about 1 ml to about 100 ml of solution containing concentrations of from about $1 \times 10^9$ to $1 \times 10^{16}$ genomes virus vector. A preferred human dosage may be about $1 \times 10^{13}$ to $1 \times 10^{16}$ AAV genomes. The dosage will be adjusted to balance the therapeutic benefit against any side effects and such dosages may vary depending upon the therapeutic application for which the recombinant vector is employed. The levels of expression of the transgene can be monitored to determine the frequency of dosage resulting in viral vectors, preferably AAV vectors containing the minigene. Optionally, dosage regimens similar to those described for therapeutic purposes may be utilized for immunization using the compositions of the invention.

Examples of therapeutic products and immunogenic products for delivery by the AAV-containing vectors of the invention are provided below. These vectors may be used for a variety of therapeutic or vaccinal regimens, as described herein. Additionally, these vectors may be delivered in combination with one or more other vectors or active ingredients in a desired therapeutic and/or vaccinal regimen.

B. Therapeutic Transgenes

Useful therapeutic products encoded by the transgene include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor α (TGFα), platelet-derived growth factor (PDGF), insulin growth factors I and II (IGF-I and IGF-II), any one of the transforming growth factor β superfamily, including TGF β, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including, IL-2, IL-4, IL-12, and IL-18), monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation, including the low density lipoprotein (LDL) receptor, high density lipoprotein (HDL) receptor, the very low density lipoprotein (VLDL) receptor, and the scavenger receptor. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence. Still other useful gene products include enzymes such as may be useful in enzyme replacement therapy, which is useful in a variety of conditions resulting from deficient activity of enzyme. For example, enzymes that contain mannose-6-phosphate may be utilized in therapies for lysosomal storage diseases (e.g., a suitable gene includes that encoding β-glucuronidase (GUSB)).

Other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene is particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce Aself≈-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

C. Immunogenic Transgenes

Alternatively, or in addition, the vectors of the invention may contain AAV sequences of the invention and a transgene encoding a peptide, polypeptide or protein which induces an immune response to a selected immunogen. For example, immunogens may be selected from a variety of viral families. Example of desirable viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Another viral family includes the calcivirus family, which encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, Ross-River virus, and Venezuelan, Eastern & Western Equine encephalitis, and rubivirus, including Rubella virus. The flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinating encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis. Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the rhabdovirus family, which includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus may be a suitable source of antigens. The paramyxovirus family includes parainfluenza Virus Type 1, parainfluenza Virus Type 3, bovine parainfluenza Virus Type 3, rubulavirus (mumps virus, parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. The reovirus family includes the genera reovirus, rotavirus (which causes acute gastroenteritis in children), orbiviruses, and cultivirus (Colorado Tick fever, Lebombo (humans), equine encephalosis, blue tongue).

The retrovirus family includes the sub-family oncoriviral which encompasses such human and veterinary diseases as feline leukemia virus, HTLVI and HTLVII, lentivirinal (which includes human immunodeficiency virus (HIV), simian immunodeficiency virus (SIV), feline immunodeficiency virus (FIV), equine infectious anemia virus, and spumavirinal). Between the HIV and SIV, many suitable antigens have been described and can readily be selected. Examples of suitable HIV and SIV antigens include, without limitation the gag, pol, Vif, Vpx, VPR, Env, Tat and Rev proteins, as well as various fragments thereof. In addition, a variety of modifications to these antigens have been described. Suitable antigens for this purpose are known to those of skill in the art. For example, one may select a sequence encoding the gag, pol, Vif, and Vpr, Env, Tat and Rev, amongst other proteins. See, e.g., the modified gag protein which is described in U.S. Pat. No. 5,972,596. See, also, the HIV and SIV proteins described in D. H. Barouch et al, J. Virol., 75(5):2462-2467 (March 2001), and R. R. Amara, et al, Science, 292:69-74 (6 Apr. 2001). These proteins or subunits thereof may be delivered alone, or in combination via separate vectors or from a single vector.

The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus family feline parvovirus (feline enteritis), feline panleucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (HCMV, muromegalovirus) and the sub-family gammaherpesvirinae, which includes the genera lymphocryptovirus, EBV (Burkitts lymphoma), infectious rhinotracheitis, Marek=s disease virus, and rhadinovirus. The poxvirus family includes the sub-family chordopoxvirinae, which encompasses the genera orthopoxvirus (Variola (Smallpox) and Vaccinia (Cowpox)), parapoxvirus, avipoxvirus, capripoxvirus, leporipoxvirus, suipoxvirus, and the sub-family entomopoxvirinae. The hepadnavirus family includes the Hepatitis B virus. One unclassified virus which may be suitable source of antigens is the Hepatitis delta virus. Still other viral sources may include avian infectious bursal disease virus and porcine respiratory and reproductive syndrome virus. The alphavirus family includes equine arteritis virus and various Encephalitis viruses.

The present invention may also encompass immunogens which are useful to immunize a human or non-human animal against other pathogens including bacteria, fungi, parasitic microorganisms or multicellular parasites which infect human and non-human vertebrates, or from a cancer cell or tumor cell. Examples of bacterial pathogens include pathogenic gram-positive cocci include pneumococci; staphylococci; and streptococci. Pathogenic gram-negative cocci include meningococcus; gonococcus. Pathogenic enteric gram-negative bacilli include enterobacteriaceae; *pseudomonas,* acinetobacteria and eikenella; melioidosis; *salmonella; shigella; haemophilus; moraxella; H. ducreyi* (which causes chancroid); *brucella; Franisella tularensis* (which causes tularemia); *yersinia (pasteurella); streptobacillus moniliformis* and *spirillum*; Gram-positive bacilli include *listeria monocytogenes*; erysipelothrix rhusiopathiae; *Corynebacterium diphtheria* (diphtheria); cholera; *B. anthracis* (anthrax); donovanosis (granuloma inguinale); and bartonellosis. Diseases caused by pathogenic anaerobic bacteria include tetanus; botulism; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever, and Rickettsialpox. Examples of *mycoplasma* and chlamydial infections include: *mycoplasma pneumoniae*; lymphogranuloma venereum; psittacosis; and perinatal chlamydial infections. Pathogenic eukaryotes encompass pathogenic protozoans and helminths and infections produced thereby include: amebiasis; malaria; leishmaniasis; trypanosomiasis; toxoplasmosis; *Pneumocystis carinii*; Trichans; *Toxoplasma gondii*; babesiosis; giardiasis; trichinosis; filariasis; schistosomiasis; nematodes; trematodes or flukes; and cestode (tapeworm) infections.

Many of these organisms and/or toxins produced thereby have been identified by the Centers for Disease Control [(CDC), Department of Heath and Human Services, USA], as agents which have potential for use in biological attacks. For example, some of these biological agents, include, *Bacillus anthracia* (anthrax), *Clostridium botulinum* and its toxin (botulism), *Yersinia pestis* (plague), variola major (smallpox), *Francisella tularensis* (tularemia), and viral hemorrhagic fever, all of which are currently classified as Category A agents; *Coxiella burnetti* (Q fever); *Brucella* species (brucellosis), *Burkholderia mallei* (glanders), *Ricinus communis* and its toxin (ricin toxin), *Clostridium perfringens* and its toxin (epsilon toxin), *Staphylococcus* species and their toxins (enterotoxin B), all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

Administration of the vectors of the invention to deliver immunogens against the variable region of the T cells elicit an immune response including CTLs to eliminate those T cells. In rheumatoid arthritis (RA), several specific variable regions of T cell receptors (TCRs) which are involved in the disease have been characterized. These TCRs include V-3, V-14, V-17 and Vα-17. Thus, delivery of a nucleic acid sequence that encodes at least one of these polypeptides will elicit an immune response that will target T cells involved in RA. In multiple sclerosis (MS), several specific variable regions of TCRs which are involved in the disease have been characterized. These TCRs include V-7 and Vα-10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V-6, V-8, V-14 and Vα-16, Vα-3C, Vα-7, Vα-14, Vα-15, Vα-16, Vα-28 and Vα-12. Thus, delivery of a nucleic acid molecule that encodes at least one of these polypeptides will elicit an immune response that will target T cells involved in scleroderma.

Optionally, vectors containing AAV sequences of the invention may be delivered using a prime-boost regimen. A variety of such regimens have been described in the art and may be readily selected. See, e.g., WO 00/11140, published Mar. 2, 2000, incorporated by reference.

Such prime-boost regimens typically involve the administration of a DNA (e.g., plasmid) based vector to prime the immune system to second, booster, administration with a traditional antigen, such as a protein or a recombinant virus carrying the sequences encoding such an antigen. In one embodiment, the invention provides a method of priming and boosting an immune response to a selected antigen by delivering a plasmid DNA vector carrying said antigen, followed by boosting, e.g., with a vector containing AAV sequences of the invention.

In one embodiment, the prime-boost regimen involves the expression of multiproteins from the prime and/or the boost vehicle. See, e.g., R. R. Amara, Science, 292:69-74 (6 Apr. 2001) which describes a multiprotein regimen for expression of protein subunits useful for generating an immune response against HIV and SIV. For example, a DNA prime may deliver the Gag, Pol, Vif, VPX and Vpr and Env, Tat, and Rev from a single transcript. Alternatively, the SIV Gag, Pol and HIV-1 Env is delivered.

However, the prime-boost regimens are not limited to immunization for HIV or to delivery of these antigens. For example, priming may involve delivering with a first chimp vector of the invention followed by boosting with a second chimp vector, or with a composition containing the antigen itself in protein form. In one or example, the prime-boost regimen can provide a protective immune response to the virus, bacteria or other organism from which the antigen is derived. In another desired embodiment, the prime-boost regimen provides a therapeutic effect that can be measured using convention assays for detection of the presence of the condition for which therapy is being administered.

The priming vaccine may be administered at various sites in the body in a dose dependent manner, which depends on the antigen to which the desired immune response is being targeted. The invention is not limited to the amount or situs of injection(s) or to the pharmaceutical carrier. Rather, the priming step encompasses treatment regimens which include a single dose or dosage which is administered hourly, daily, weekly or monthly, or yearly. As an example, the mammals may receive one or two priming injection containing between about 10 μg to about 50 μg of plasmid in carrier. A desirable priming amount or dosage of the priming DNA vaccine composition ranges between about 1 μg to about 10,000 μg of the DNA vaccine. Dosages may vary from about 1 μg to 1000 μg DNA per kg of subject body weight. The amount or site of injection is desirably selected based upon the identity and condition of the mammal being vaccinated.

The dosage unit of the DNA vaccine suitable for delivery of the antigen to the mammal is described herein. The DNA vaccine is prepared for administration by being suspended or dissolved in a pharmaceutically or physiologically acceptable carrier such as isotonic saline, isotonic salts solution or other formulations which will be apparent to those skilled in such administration. The appropriate carrier will be evident to those skilled in the art and will depend in large part upon the route of administration. The compositions of the invention may be administered to a mammal according to the routes described above, in a sustained release formulation using a biodegradable biocompatible polymer, or by on-site delivery using micelles, gels and liposomes.

Optionally, the priming step of this invention also includes administering with the priming DNA vaccine composition, a suitable amount of an adjuvant, such as are defined herein.

Preferably, a boosting composition is administered about 2 to about 27 weeks after administering the priming DNA vaccine to the mammalian subject. The administration of the boosting composition is accomplished using an effective amount of a boosting vaccine composition containing or capable of delivering the same antigen as administered by the priming DNA vaccine. The boosting composition may be composed of a recombinant viral vector derived from the same viral source or from another source. Alternatively, the "boosting composition" can be a composition containing the same antigen as encoded in the priming DNA vaccine, but in the form of a protein or peptide, which composition induces an immune response in the host. In another embodiment, the boosting vaccine composition includes a composition containing a DNA sequence encoding the antigen under the control of a regulatory sequence directing its expression in a mammalian cell, e.g., vectors such as well-known bacterial or viral vectors. The primary requirements of the boosting vaccine composition are that the antigen of the vaccine composition is the same antigen, or a cross-reactive antigen, as that encoded by the DNA vaccine.

Suitably, the vectors of the invention are also well suited for use in regimens which use non-AAV vectors as well as proteins, peptides, and/or other biologically useful therapeutic or immunogenic compounds. These regimens are particularly well suited to gene delivery for therapeutic poses and for immunization, including inducing protective immunity Such uses will be readily apparent to one of skill in the art.

Further, a vector of the invention provides an efficient gene transfer vehicle which can deliver a selected transgene to a selected host cell in vivo or ex vivo even where the organism has neutralizing antibodies to one or more AAV serotypes. In one embodiment, the vector (e.g., an rAAV) and the cells are mixed ex vivo; the infected cells are cultured using conventional methodologies; and the transduced cells are re-infused into the patient. Further, the vectors of the invention may also be used for production of a desired gene product in vitro. For in vitro production, a desired product (e.g., a protein) may be obtained from a desired culture following transfection of host cells with a rAAV containing the molecule encoding the desired product and culturing the cell culture under conditions which permit expression. The expressed product may then be purified and isolated, as desired. Suitable techniques for transfection, cell culturing, purification, and isolation are known to those of skill in the art.

The following examples illustrate several aspects and embodiments of the invention.

EXAMPLES

Example 1: PCR Amplification, Cloning and Characterization of Novel AAV Sequences Tissues from nonhuman primates were screened for AAV sequences using a PCR method based on oligonucleotides to highly conserved regions of known AAVs. A stretch of AAV sequence spanning 2886 to 3143 bp of AAV1 [SEQ ID NO:6] was selected as a PCR amplicon in which a hypervariable region of the capsid protein (Cap) that is unique to each known AAV serotype, which is termed herein a "signature region," is flanked by conserved sequences. In later analysis, this signature region was shown to be located between conserved residues spanning hypervariable region 3.

An initial survey of peripheral blood of a number of nonhuman primate species revealed detectable AAV in a subset of animals from species such as rhesus macaques, cynomologous macaques, chimpanzees and baboons. However, there were no AAV sequences detected in some other species tested, including Japanese macaques, pig-tailed macaques and squirrel monkeys. A more extensive analysis of vector distribution was conducted in tissues of rhesus monkeys of the University of Pennsylvania and Tulane colonies recovered at necropsy. This revealed AAV sequence throughout a wide array of tissues.

A. Amplification of an AAV Signature Region

DNA sequences of AAV1-6 and AAVs isolated from Goose and Duck were aligned to each other using "Clustal W" at default settings. The alignment for AAV1-6, and including the information for the novel AAV7, is provided in FIG. 1. Sequence similarities among AAVs were compared.

In the line of study, a 257 bp region spanning 2886 bp to 3143 bp of AAV 1 [SEQ ID NO: 6], and the corresponding region in the genomes of AAV 2-6 genomes [See, FIG. 1], was identified by the inventors. This region is located with the AAV capsid gene and has highly conserved sequences among at both 5' and 3' ends and is relatively variable sequence in the middle. In addition, this region contains a DraIII restriction enzyme site (CACCACGTC, SEQ ID NO:15). The inventors have found that this region serves as specific signature for each known type of AAV DNA. In other words, following PCR reactions, digestion with endonucleases that are specific to each known serotypes and gel electrophoresis analysis, this regions can be used to definitively identify amplified DNA as being from serotype 1, 2, 3, 4, 5, 6, or another serotype.

The primers were designed, validated and PCR conditions optimized with AAV1, 2 and 5 DNA controls. The primers were based upon the sequences of AAV2: 5' primer, 1S: by 2867-2891 of AAV2 (SEQ ID NO:7) and 3' primer, 18as, by 3095-3121 of AAV2 (SEQ ID NO:7).

Cellular DNAs from different tissues including blood, brain, liver, lung, testis, etc. of different rhesus monkeys were studied utilizing the strategy described above. The results revealed that DNAs from different tissues of these monkeys gave rise to strong PCR amplifications. Further restriction analyses of PCR products indicated that they were amplified from AAV sequences different from any published AAV sequences.

PCR products (about 255 bp in size) from DNAs of a variety of monkey tissues have been cloned and sequenced. Bioinformatics study of these novel AAV sequences indicated that they are novel AAV sequences of capsid gene and distinct from each other. FIG. 1 includes in the alignment the novel AAV signature regions for AAV10-12 [SEQ ID NO:117, 118 and 119, respectively]. Multiple sequence alignment analysis was performed using the Clustal W (1.81) program. The percentage of sequence identity between the signature regions of AAV 1-7 and AAV 10-12 genomes is provided below.

TABLE 2

| Sequences for Analysis | | |
|---|---|---|
| Sequence # | AAV Serotype | Size (bp) |
| 1 | AAV1 | 258 |
| 2 | AAV2 | 255 |
| 3 | AAV3 | 255 |
| 4 | AAV4 | 246 |
| 5 | AAV5 | 258 |
| 6 | AAV6 | 258 |
| 7 | AAV7 | 258 |
| 10 | AAV10 | 255 |
| 11 | AAV11 | 258 |
| 12 | AAV12 | 255 |

TABLE 3

| Pairwise Alignment (Percentage of Identity) | | | | | | | | | |
|---|---|---|---|---|---|---|---|---|---|
|  | AAV2 | AAV3 | AAV4 | AAV5 | AAV6 | AAV7 | AAV10 | AAV11 | AAV12 |
| AAV1 | 90 | 90 | 81 | 76 | 97 | 91 | 93 | 94 | 93 |
| AAV2 |  | 93 | 79 | 78 | 90 | 90 | 93 | 93 | 92 |
| AAV3 |  |  | 80 | 76 | 90 | 92 | 92 | 92 | 92 |
| AAV4 |  |  |  | 76 | 81 | 84 | 82 | 81 | 79 |
| AAV5 |  |  |  |  | 75 | 78 | 79 | 79 | 76 |
| AAV6 |  |  |  |  |  | 91 | 92 | 94 | 94 |
| AAV7 |  |  |  |  |  |  | 94 | 92 | 92 |
| AAV10 |  |  |  |  |  |  |  | 95 | 93 |
| AAV11 |  |  |  |  |  |  |  |  | 94 |

Over 300 clones containing novel AAV serotype sequences that span the selected 257 bp region were isolated and sequenced. Bioinformatics analysis of these 300+ clones suggests that this 257 bp region is critical in serving as a good land marker or signature sequence for quick isolation and identification of novel AAV serotype.

B. Use of the Signature Region for PCR Amplification.

The 257 bp signature region was used as a PCR anchor to extend PCR amplifications to 5' of the genome to cover the junction region of rep and cap genes (1398 bp-3143 bp, SEQ ID NO:6) and 3' of the genome to obtain the entire cap gene sequence (2866 bp-4600 bp, SEQ ID NO:6). PCR amplifications were carried out using the standard conditions, including denaturing at 95° C. for 0.5-1 min, annealing at 60-65° C. for 0.5-1 min and extension at 72° C. for 1 min per kb with a total number of amplification cycles ranging from 28 to 42.

Using the aligned sequences as described in "A", two other relative conserved regions were identified in the sequence located in 3' end of rep genes and 5' to the 257 bp region and in the sequence down stream of the 257 bp fragment but before the AAV' 3 ITR. Two sets of new primers were designed and PCR conditions optimized for recovery of entire capsid and a part of rep sequences of novel AAV serotypes. More specifically, for the 5' amplification, the 5' primer, AV1Ns, was GCTGCGTCAACTG-GACCAATGAGAAC [nt 1398-1423 of AAV1, SEQ ID NO:6] and the 3' primer was 18as, identified above. For the 3' amplification, the 5' primer was 1s, identified above, and the 3' primer was AV2Las, TCGTTTCAGTTGAACTTTG-GTCTCTGCG [nt 4435-4462 of AAV2, SEQ ID NO:7].

In these PCR amplifications, the 257 bp region was used as a PCR anchor and land marker to generate overlapping fragments to construct a complete capsid gene by fusion at the DraIII site in the signature region following amplification of the 5' and 3' extension fragments obtained as described herein. More particularly, to generate the intact AAV7 cap gene, the three amplification products (a) the sequences of the signature region; (b) the sequences of the 5' extension; and (c) the sequences of the 3' extension were cloned into a pCR4-Topo [Invitrogen] plasmid backbone according to manufacturer's instructions. Thereafter, the plasmids were digested with DraIII and recombined to form an intact cap gene.

In this line of work, about 80% of capsid sequences of AAV7 and AAV 8 were isolated and analyzed. Another novel serotype, AAV9, was also discovered from Monkey #2.

Using the PCR conditions described above, the remaining portion of the rep gene sequence for AAV7 is isolated and cloned using the primers that amplify 108 bp to 1461 bp of AAV genome (calculated based on the numbering of AAV2, SEQ ID NO:7). This clone is sequenced for construction of a complete AAV7 genome without ITRs.

C. Direct Amplification of 3.1 kb Cap Fragment

To directly amplify a 3.1 kb full-length Cap fragment from NHP tissue and blood DNAs, two other highly conserved regions were identified in AAV genomes for use in PCR amplification of large fragments. A primer within a conserved region located in the middle of the rep gene was selected (AV1 ns: 5' GCTGCGTCAACTGGACCAAT-GAGAAC 3', nt 1398-1423 of SEQ ID NO:6) in combination with the 3' primer located in another conserved region downstream of the Cap gene (AV2cas: 5' CGCAGAGAC-CAAAGTTCAACTGAAACGA 3', SEQ ID NO:7) for amplification of full-length cap fragments. The PCR products were Topo-cloned according to manufacturer's directions (Invitrogen) and sequence analysis was performed by Qiagengenomics (Qiagengenomics, Seattle, Wash.) with an accuracy of ≥99.9%. A total of 50 capsid clones were isolated and characterized. Among them, 37 clones were derived from Rhesus macaque tissues (rh.1-rh.37), 6 clones from cynomologous macaques (cy.1-cy.6), 2 clones from Baboons (bb.1 and bb.2) and 5 clones from Chimps (ch.1-ch.5).

To rule out the possibility that sequence diversity within the novel AAV family was not an artifact of the PCR, such as PCR-mediated gene splicing by overlap extension between different partial DNA templates with homologous sequences, or the result of recombination process in bacteria, a series of experiments were performed under identical conditions for VP1 amplification using total cellular DNAs. First, intact AAV7 and AAV8 plasmids were mixed at an equal molar ratio followed by serial dilutions. The serially diluted mixtures were used as templates for PCR amplification of 3.1 kb VP1 fragments using universal primers and identical PCR conditions to that were used for DNA amplifications to see whether any hybrid PCR products were generated. The mixture was transformed into bacteria and isolated transformants to look for hybrid clones possibly derived from recombination process in bacterial cells. In a different experiment, we restricted AAV7 and AAV8 plasmids with Msp I, Ava I and HaeI, all of which cut both genomes multiple times at different positions, mixed the digestions in different combinations and used them for PCR amplification of VP1 fragments under the same conditions to test whether any PCR products could be generated through overlap sequence extension of partial AAV sequences. In another experiment, a mixture of gel purified 5' 1.5 kb AAV7 VP1 fragment and 3' 1.7 kb AAV8 VP1 fragment with overlap in the signature region was serially diluted and used for PCR amplification in the presence and absence of 200 ng cellular DNA extracted from a monkey cell line that was free of AAV sequences by TaqMan analysis. None of these experiments demonstrated efficient PCR-mediated overlap sequence production under the conditions of the genomic DNA Cap amplification (data not shown). As a further confirmation, 3 pairs of primers were designed, which were located at different HVRs, and were sequence specific to the variants of clone 42s from Rhesus macaque F953, in different combinations to amplify shorter fragments from mesenteric lymph node (MLN) DNA from F953 from which clone 42s were isolated. All sequence variations identified in full-length Cap clones were found in these short fragments (data not shown).

Example 2: Adeno-Associated Viruses Undergo Substantial Evolution in Primates During Natural Infections Sequence analysis of selected AAV isolates revealed divergence throughout the genome that is most concentrated in hypervariable regions of the capsid proteins. Epidemiologic data indicate that all known serotypes are endemic to primates, although isolation of clinical isolates has been restricted to AAV2 and AAV3 from anal and throat swabs of human infants and AAV5 from a human condylomatous wart. No known clinical sequalae have been associated with AAV infection.

In an attempt to better understand the biology of AAV, nonhuman primates were used as models to characterize the sequlae of natural infections. Tissues from nonhuman primates were screened for AAV sequences using the PCR method of the invention based on oligonucleotides to highly conserved regions of known AAVs (see Example 1). A stretch of AAV sequence spanning 2886 to 3143 bp of AAV1 [SEQ ID NO:6] was selected as a PCR amplicon in which conserved sequences are flanked by a hypervariable region that is unique to each known AAV serotype, termed herein a "signature region."

An initial survey of peripheral blood of a number of nonhuman primate species including rhesus monkeys, cynomologous monkeys, chimpanzees, and baboons revealed detectable AAV in a subset of animals from all species. A more extensive analysis of vector distribution was conducted in tissues of rhesus monkeys of the University of Pennsylvania and Tulane colonies recovered at necropsy. This revealed AAV sequence throughout a wide array of tissues.

The amplified signature sequences were subcloned into plasmids and individual transformants were subjected to sequence analysis. This revealed substantial variation in nucleotide sequence of clones derived from different animals. Variation in the signature sequence was also noted in clones obtained within individual animals. Tissues harvested from two animals in which unique signature sequences were identified (i.e., colon from 98E044 and heart from 98E056) were further characterized by expanding the sequence amplified by PCR using oligonucleotides to highly conserved sequences. In this way, complete proviral structures were reconstructed for viral genomes from both tissues as described herein. These proviruses differ from the other known AAVs with the greatest sequence divergence noted in regions of the Cap gene.

Additional experiments were performed to confirm that AAV sequences resident to the nonhuman primate tissue represented proviral genomes of infectious virus that is capable of being rescued and form virions. Genomic DNA from liver tissue of animal 98E056, from which AAV8 signature sequence was detected, was digested with an endonuclease that does not have a site within the AAV sequence and transfected into 293 cells with a plasmid containing an E1 deleted genome of human adenovirus serotype 5 as a source of helper functions. The resulting lysate was passaged on 293 cells once and the lysate was recovered and analyzed for the presence of AAV Cap proteins using a broadly reacting polyclonal antibody to Cap proteins and for the presence and abundance of DNA sequences from the PCR amplified AAV provirus from which AAV8 was derived. Transfection of endonuclease restricted heart DNA and the adenovirus helper plasmid yielded high quantities of AAV8 virus as demonstrated by the detection of Cap proteins by Western blot analysis and the presence of $10^4$ AAV8 vector genomes per 293 cell. Lysates were generated from a large-scale preparation and the AAV was purified by cesium sedimentation. The purified preparation demonstrated 26 nm icosohedral structures that look identical to those of AAV serotype 2. Transfection with the adenovirus helper alone did not yield AAV proteins or genomes, ruling out contamination as a source of the rescued AAV.

To further characterize the inter and intra animal variation of AAV signature sequence, selected tissues were subjected to extended PCR to amplify entire Cap open reading frames.

The resulting fragments were cloned into bacterial plasmids and individual transformants were isolated and fully sequenced. This analysis involved mesenteric lymph nodes from three rhesus monkeys (Tulane/V223—6 clones; Tulane/T612—7 clones; Tulane/F953—14 clones), liver from two rhesus monkeys (Tulane/N251—3 clones; Penn/00E033—3 clones), spleen from one rhesus monkey (Penn/97E043—3 clones), heart from one rhesus monkey (IHGT/98E046—1 clone) and peripheral blood from one chimpanzee (New Iberia/X133—5 clones), six cynomologous macaques (Charles River/A1378, A3099, A3388, A3442, A2821, A3242—6 clones total) and one Baboon (SFRB/8644—2 clones). Of the 50 clones that were sequenced from 15 different animals, 30 were considered non-redundant based on the finding of at least 7 amino acid differences from one another. The non-redundant VP1 clones are numbered sequentially as they were isolated, with a prefix indicating the species of non-human primate from which they were derived. The structural relationships between these 30 non-redundant clones and the previously described 8 AAV serotypes were determined using the SplitsTree program [Huson, D. H. SplitsTree: analyzing and visualizing evolutionary data. *Bioinformatics* 14, 68-73 (1998)] with implementation of the method of split decomposition. The analysis depicts homoplasy between a set of sequences in a tree-like network rather than a bifurcating tree. The advantage is to enable detection of groupings that are the result of convergence and to exhibit phylogenetic relationships even when they are distorted by parallel events. Extensive phylogenetic research will be required in order to elucidate the AAV evolution, whereas the intention here only is to group the different clones as to their sequence similarity.

To confirm that the novel VP1 sequences were derived from infectious viral genomes, cellular DNA from tissues with high abundance of viral DNA was restricted with an endonuclease that should not cleave within AAV and transfected into 293 cells, followed by infection with adenovirus. This resulted in rescue and amplification of AAV genomes from DNA of tissues from two different animals (data not shown).

VP1 sequences of the novel AAVs were further characterized with respect to the nature and location of amino acid sequence variation. All 30 VP1 clones that were shown to differ from one another by greater than 1% amino acid sequence were aligned and scored for variation at each residue. An algorithm developed to determine areas of sequence divergence yielded 12 hypervariable regions (HVR) of which 5 overlap or are part of the 4 previously described variable regions [Kotin, cited above; Rutledge, cited above]. The three-fold-proximal peaks contain most of the variability (HVR5-10). Interestingly the loops located at the 2 and 5 fold axis show intense variation as well. The HVRs 1 and 2 occur in the N-terminal portion of the capsid protein that is not resolved in the X-ray structure suggesting that the N-terminus of the VP1 protein is exposed on the surface of the virion.

Real-time PCR was used to quantify AAV sequences from tissues of 21 rhesus monkeys using primers and probes to highly conserved regions of Rep (one set) and Cap (two sets) of known AAVs. Each data point represents analysis from tissue DNA from an individual animal. This confirmed the wide distribution of AAV sequences, although the quantitative distribution differed between individual animals. The source of animals and previous history or treatments did not appear to influence distribution of AAV sequences in rhesus macaques. The three different sets of primers and probes used to quantify AAV yielded consistent results. The highest levels of AAV were found consistently in mesenteric lymph nodes at an average of 0.01 copies per diploid genome for 13 animals that were positive. Liver and spleen also contained high abundance of virus DNA. There were examples of very high AAV, such as in heart of rhesus macaque 98E056, spleen of rhesus macaque 97E043 and liver of rhesus macaque RQ4407, which demonstrated 1.5, 3 and 20 copies of AAV sequence per diploid genome respectively. Relatively low levels of virus DNA were noted in peripheral blood mononuclear cells, suggesting the data in tissue are not due to resident blood components (data not shown). It should be noted that this method would not necessarily capture all AAVs resident to the nonhuman primates since detection requires high homology to both the oligonucleotides and the real time PCR probe. Tissues from animals with high abundance AAV DNA was further analyzed for the molecular state of the DNA, by DNA hybridization techniques, and its cellular distribution, by in situ hybridization.

The kind of sequence variation revealed in AAV proviral fragments isolated from different animals and within tissues of the same animals is reminiscent of the evolution that occurs for many RNA viruses during pandemics or even within the infection of an individual. In some situations the notion of a wild-type virus has been replaced by the existence of swarms of quasispecies that evolve as a result of rapid replication and mutations in the presence of selective pressure. One example is infection by HIV, which evolves in response to immunologic and pharmacologic pressure. Several mechanisms contribute to the high rate of mutations in RNA viruses, including low fidelity and lack of proof reading capacity of reverse transcriptase and non-homologous and homologous recombination.

Evidence for the formation of quasispecies of AAV was illustrated in this study by the systematic sequencing of multiple cloned proviral fragments. In fact, identical sequences could not be found within any extended clones isolated between or within animals. An important mechanism for this evolution of sequence appears to be a high rate of homologous recombination between a more limited number of parenteral viruses. The net result is extensive swapping of hypervariable regions of the Cap protein leading to an array of chimeras that could have different tropisms and serologic specificities (i.e., the ability to escape immunologic responses especially as it relates to neutralizing antibodies). Mechanisms by which homologous recombination could occur are unclear. One possibility is that + and − strands of different single stranded AAV genomes anneal during replication as has been described during high multiplicity of infections with AAV recombinants. It is unclear if other mechanisms contribute to sequence evolution in AAV infections. The overall rate of mutation that occurs during AAV replication appears to be relatively low and the data do not suggest high frequencies of replication errors. However, substantial rearrangements of the AAV genome have been described during lytic infection leading to the formation of defective interfering particles. Irrespective of the mechanisms that lead to sequence divergence, with few exceptions, vp1 structures of the quasispecies remained intact without frameshifts or nonsense mutations suggesting that competitive selection of viruses with the most favorable profile of fitness contribute to the population dynamics.

These studies have implications in several areas of biology and medicine. The concept of rapid virus evolution, formerly thought to be a property restricted to RNA viruses, should be considered in DNA viruses, which classically have been characterized by serologic assays. It will be important in terms of parvoviruses to develop a new method for describing virus isolates that captures the complexity of its structure and biology, such as with HIV, which are categorized as general families of similar structure and function called Clades. An alternative strategy is to continue to categorize isolates with respect to serologic specificity and develop criteria for describing variants within serologic groups.

Example 3: Vectorology of Recombinant AAV Genomes Equipped with AAV2 ITRs Using Chimeric Plasmids Containing AAV2 Rep and Novel AAV Cap Genes for Serological and Gene Transfer Studies in Different Animal Models Chimeric packaging constructs are generated by fusing AAV2 rep with cap sequences of novel AAV serotypes. These chimeric packaging constructs are used, initially, for pseudotyping recombinant AAV genomes carrying AAV2 ITRs by triple transfection in 293 cell using Ad5 helper plasmid. These pseudotyped vectors are used to evaluate performance in transduction-based serological studies and evaluate gene transfer efficiency of novel AAV serotypes in different animal models including NHP and rodents, before intact and infectious viruses of these novel serotypes are isolated.

A. pAAV2GFP

The AAV2 plasmid which contains the AAV2 ITRs and green fluorescent protein expressed under the control of a constitutitive promoter. This plasmid contains the following elements: the AAV2 ITRs, a CMV promoter, and the GFP coding sequences.

B. Cloning of Trans Plasmid

To construct the chimeric trans-plasmid for production of recombinant pseudotyped AAV7 vectors, p5E18 plasmid (Xiao et al., 1999, *J. Virol* 73:3994-4003) was partially digested with Xho I to linearize the plasmid at the Xho I site at the position of 3169 bp only. The Xho I cut ends were then filled in and ligated back. This modified p5E18 plasmid was restricted with Xba I and Xho I in a complete digestion to remove the AAV2 cap gene sequence and replaced with a 2267 bp Spe I/Xho I fragment containing the AAV7 cap gene which was isolated from pCRAAV7 6-5+15-4 plasmid.

The resulting plasmid contains the AAV2 rep sequences for Rep78/68 under the control of the AAV2 P5 promoter, and the AAV2 rep sequences for Rep52/40 under the control of the AAV2 P19 promoter. The AAV7 capsid sequences are under the control of the AAV2 P40 promoter, which is located within the Rep sequences. This plasmid further contains a spacer 5' of the rep ORF.

C. Production of Pseudotyped rAAV

The rAAV particles (AAV2 vector in AAV7 capsid) are generated using an adenovirus-free method. Briefly, the cis plasmid (pAAV2.1 lacZ plasmid containing AAV2 ITRs), and the trans plasmid pCRAAV7 6-5+15-4 (containing the AAV2 rep and AAV7 cap) and a helper plasmid, respectively, were simultaneously co-transfected into 293 cells in a ratio of 1:1:2 by calcium phosphate precipitation.

For the construction of the pAd helper plasmids, pBG10 plasmid was purchased from Microbix (Canada). A RsrII fragment containing L2 and L3 was deleted from pBHG10, resulting in the first helper plasmid, pAdΔF13. Plasmid AdΔ F1 was constructed by cloning Asp700/SalI fragment with a PmeI/SgfI deletion, isolating from pBHG10, into Bluescript. MLP, L2, L2 and L3 were deleted in the pAdΔF1. Further deletions of a 2.3 kb NruI fragment and, subsequently, a 0.5 kb RsrII/NruI fragment generated helper plasmids pAdΔF5 and pAdΔF6, respectively. The helper plasmid, termed pΔF6, provides the essential helper functions of E2a and E4 ORF6 not provided by the E1-expressing helper cell, but is deleted of adenoviral capsid proteins and functional E1 regions).

Typically, 50 µg of DNA (cis:trans:helper) was transfected onto a 150 mm tissue culture dish. The 293 cells were harvested 72 hours post-transfection, sonicated and treated with 0.5% sodium deoxycholate (37EC for 10 min.) Cell lysates were then subjected to two rounds of a CsCl gradient. Peak fractions containing rAAV vector are collected, pooled and dialyzed against PBS.

Example 4: Creation of Infectious Clones Carrying Intact Novel AAV Serotypes for Study of Basic Virology in Human and NHP Derived Cell Lines and Evaluation of Pathogenesis of Novel AAV Serotypes in NHP and Other Animal Models To achieve this goal, the genome walker system is employed to obtain 5' and 3' terminal sequences (ITRs) and complete construction of clones containing intact novel AAV serotype genomes.

Briefly, utilizing a commercially available Universal Genome Walker Kit [Clontech], genomic DNAs from monkey tissues or cell lines that are identified as positive for the presence of AAV7 sequence are digested with Dra I, EcoR V, Pvu II and Stu I endonucleases and ligated to Genome Walker Adaptor to generate 4 individual Genome Walker Libraries (GWLs). Using DNAs from GWLs as templates, AAV7 and adjacent genomic sequences will be PCR-amplified by the adaptor primer 1 (AP1, provided in the kit) and an AAV7 specific primer 1, followed by a nested PCR using the adaptor primer 2 (AP2) and another AAV7 specific primer 2, both of which are internal to the first set of primers. The major PCR products from the nested PCR are cloned and characterized by sequencing analysis.

In this experiment, the primers covering the 257 bp or other signature fragment of a generic AAV genome are used for PCR amplification of cellular DNAs extracted from Human and NHP derived cell lines to identify and characterize latent AAV sequences. The identified latent AAV genomes are rescued from the positive cell lines using adenovirus helpers of different species and strains.

Genome copy (GC) titers of AAV vectors were determined by TaqMan analysis using probes and primers targeting SV40 poly A region as described previously [Gao, G., et al., (2000) *Hum Gene Ther* 11, 2079-91].

Vectors were constructed for each serotype for a number of in vitro and in vivo studies. Eight different transgene cassettes were incorporated into the vectors and recombinant virions were produced for each serotype. The recovery of virus, based on genome copies, is summarized in Table 4 below. The yields of vector were high for each serotype with no consistent differences between serotypes. Data presented in the table are average genome copy yields with standard deviation $\times 10^{13}$ of multiple production lots of 50 plate (150 mm) transfections.

TABLE 4

| | Production of Recombinant Vectors | | | | |
|---|---|---|---|---|---|
| | AAV2/1 | AAV2/2 | AAV2/5 | AAV2/7 | AAV2/8 |
| CMV LacZ | 7.30 ± 4.33 (n = 9) | 4.49 ± 2.89 (n = 6) | 5.19 ± 5.19 (n = 8) | 3.42 (n = 1) | 0.87 (n = 1) |
| CMV EGFP | 6.43 ± 2.42 (n = 2) | 3.39 ± 2.42 (n = 2) | 5.55 ± 6.49 (n = 4) | 2.98 ± 2.66 (n = 2) | 3.74 ± 3.88 (n = 2) |
| TBG LacZ | 4.18 (n = 1) | 0.23 (n = 1) | 0.704 ± 0.43 (n = 2) | 2.16 (n = 1) | 0.532 (n = 1) |
| Alb A1AT | 4.67 ± 0.75 (n = 2) | 4.77 (n = 1) | 4.09 (n = 1) | 5.04 (n = 1) | 2.02 (n = 1) |
| CB A1AT | 0.567 (n = 1) | 0.438 (n = 1) | 2.82 (n = 1) | 2.78 (n = 1) | 0.816 ± 0.679 (n = 2) |
| TBG rhCG | 8.51 ± 6.65 (n = 6) | 3.47 ± 2.09 (n = 5) | 5.26 ± 3.85 (n = 4) | 6.52 ± 3.08 (n = 4) | 1.83 ± 0.98 (n = 5) |
| TBG cFIX | 1.24 ± 1.29 (n = 3) | 0.63 ± 0.394 (n = 6) | 3.74 ± 2.48 (n = 7) | 4.05 (n = 1) | 15.8 ± 15.0 (n = 5) |

To isolate infectious AAV clones from NHP derived cell lines, a desired cell line is obtained from ATCC and screened by PCR to identify the 257 bp amplicon, i.e., signature region of the invention. The 257 bp PCR product is cloned and serotyped by sequencing analysis. For these cell lines containing the AAV7 sequence, the cells are infected with SV-15, a simian adenovirus purchased from ATCC, human Ad5 or transfected with plasmid construct housing the human Ad genes that are responsible for AAV helper functions. At 48 hour post infection or transfection, the cells are harvested and Hirt DNA is prepared for cloning of AAV7 genome following Xiao et al., 1999, J. Virol, 73:3994-4003.

Example 5: Production of AAV Vectors

A pseudotyping strategy similar to that of Example 3 for AAV1/7 was employed to produce AAV2 vectors packaged with AAV1, AAV5 and AAV8 capsid proteins. Briefly, recombinant AAV genomes equipped with AAV2 ITRs were packaged by triple transfection of 293 cells with cis-plasmid, adenovirus helper plasmid and a chimeric packaging construct where the AAV2 rep gene is fused with cap genes of novel AAV serotypes. To create the chimeric packaging constructs, the Xho I site of p5E18 plasmid at 3169 bp was ablated and the modified plasmid was restricted with Xba I and Xho I in a complete digestion to remove the AAV2 cap gene and replace it with a 2267 bp Spe I/Xho I fragment containing the AAV8 cap gene [Xiao, W., et al., (1999) *J Virol* 73, 3994-4003]. A similar cloning strategy was used for creation of chimeric packaging plasmids of AAV2/1 and AAV2/5. All recombinant vectors were purified by the standard CsCl$_2$ sedimentation method except for AAV2/2, which was purified by single step heparin chromatography.

Example 6: Serologic Analysis of Pseudotyped Vectors

C57BL/6 mice were injected with vectors of different serotypes of AAVCBA1AT vectors intramuscularly ($5 \times 10^{11}$ GC) and serum samples were collected 34 days later. To test neutralizing and cross-neutralizing activity of sera to each serotype of AAV, sera was analyzed in a transduction based neutralizing antibody assay [Gao, G. P., et al., (1996) *J Vivol* 70, 8934-43]. More specifically, the presence of neutralizing antibodies was determined by assessing the ability of serum to inhibit transduction of 84-31 cells by reporter viruses (AAVCMVEGFP) of different serotypes. Specifically, the reporter virus AAVCMVEGFP of each serotype [at multiplicity of infection (MOI) that led to a transduction of 90% of indicator cells] was pre-incubated with heat-inactivated serum from animals that received different serotypes of AAV or from naïve mice. After 1-hour incubation at 37° C., viruses were added to 84-31 cells in 96 well plates for 48 or 72-hour, depending on the virus serotype. Expression of GFP was measured by Fluorolmagin (Molecular Dynamics) and quantified by Image Quant Software. Neutralizing antibody titers were reported as the highest serum dilution that inhibited transduction to less than 50%.

The availability of GFP expressing vectors simplified the development of an assay for neutralizing antibodies that was based on inhibition of transduction in a permissive cell line (i.e., 293 cells stably expressing E4 from Ad5). Sera to selected AAV serotypes were generated by intramuscular injection of the recombinant viruses. Neutralization of AAV transduction by 1:20 and 1:80 dilutions of the antisera was evaluated (See Table 5 below). Antisera to AAV1, AAV2, AAV5 and AAV8 neutralized transduction of the serotype to which the antiserum was generated (AAV5 and AAV8 to a lesser extent than AAV1 and AAV2) but not to the other serotype (i.e., there was no evidence of cross neutralization suggesting that AAV 8 is a truly unique serotype).

sion for 7 weeks. Animals were then treated with AAV2/8TBGcFIX intraportally and studied for cFIX gene expression.

ELISA based assays were performed to quantify serum levels of hA1AT, rhCG and cFIX proteins as described

TABLE 5

Serological Analysis of New AAV Serotypes.

| | | % Infection on 84-31 cells with AAVCMVEGFP virus: | | | | | | | | |
|---|---|---|---|---|---|---|---|---|---|---|
| | | AAV2/1 | | AAV2/2 | | AAV2/5 | | AAV2/7 | | AAV2/8 |
| | Immunization | Serum dilution: | | Serum dilution: | | Serum dilution: | | Serum dilution: | | Serum dilution: |
| Sera: | Vector | 1/20 | 1/80 | 1/20 | 1/80 | 1/20 | 1/80 | 1/20 | 1/80 | 1/20 | 1/80 |
| Group 1 | AAV2/1 | 0 | 0 | 100 | 100 | 100 | 100 | 100 | 100 | 100 | 100 |
| Group 2 | AAV2/2 | 100 | 100 | 0 | 0 | 100 | 100 | 100 | 100 | 100 | 100 |
| Group 3 | AAV2/5 | 100 | 100 | 100 | 100 | 16.5 | 16.5 | 100 | 100 | 100 | 100 |
| Group 4 | AAV2/7 | 100 | 100 | 100 | 100 | 100 | 100 | 61.5 | 100 | 100 | 100 |
| Group 5 | AAV2/8 | 100 | 100 | 100 | 100 | 100 | 100 | 100 | 100 | 26.3 | 60 |

Human sera from 52 normal subjects were screened for neutralization against selected serotypes. No serum sample was found to neutralize AAV2/7 and AAV2/8 while AAV2/2 and AAV2/1 vectors were neutralized in 20% and 10% of sera, respectively. A fraction of human pooled IgG representing a collection of 60,000 individual samples did not neutralize AAV2/7 and AAV2/8, whereas AAV2/2 and AAV2/1 vectors were neutralized at titers of serum equal to $1/1280$ and $1/640$, respectively.

Example 7: In Vivo Evaluation of Different Serotypes of AAV Vectors

In this study, 7 recombinant AAV genomes, AAV2CBhA1AT, AAV2A1bhA1AT, AAV2CMVrhCG, AAV2TBGrhCG, AAV2TBGcFIX, AAV2CMVLacZ and AAV2TBGLacZ were packaged with capsid proteins of different serotypes. In all 7 constructs, minigene cassettes were flanked with AAV2 ITRs. cDNAs of human α-antitrypsin (A1AT) [Xiao, W., et al., (1999) J Virol 73, 3994-4003] β-subunit of rhesus monkey choriogonadotropic hormone (CG) [Zoltick, P. W. & Wilson, J. M. (2000) Mol Ther 2, 657-9] canine factor IX [Wang, L., et al., (1997) Proc Natl Acad Sci USA 94, 11563-6] and bacterial β-galactosidase (i.e., Lac Z) genes were used as reporter genes. For liver-directed gene transfer, either mouse albumin gene promoter (Alb) [Xiao, W. (1999), cited above] or human thyroid hormone binding globulin gene promoter (TBG) [Wang (1997), cited above] was used to drive liver specific expression of reporter genes. In muscle-directed gene transfer experiments, either cytomegalovirus early promoter (CMV) or chicken β-actin promoter with CMV enhancer (CB) was employed to direct expression of reporters.

For muscle-directed gene transfer, vectors were injected into the right tibialis anterior of 4-6 week old NCR nude or C57BL/6 mice (Taconic, Germantown, N.Y.). In liver-directed gene transfer studies, vectors were infused intraportally into 7-9 week old NCR nude or C57BL/6 mice (Taconic, Germantown, N.Y.). Serum samples were collected intraorbitally at different time points after vector administration. Muscle and liver tissues were harvested at different time points for cryosectioning and Xgal histochemical staining from animals that received the lacZ vectors. For the re-administration experiment, C56BL/6 mice initially received AAV2/1, 2/2, 2/5, 2/7 and 2/8CBA1AT vectors intramuscularly and followed for A1AT gene exprespreviously [Gao, G. P., et al., (1996) J Virol 70, 8934-43; Zoltick, P. W. & Wilson, J. M. (2000) Mol Ther 2, 657-9; Wang, L., et al., Proc Nati Acad Sci USA 94, 11563-6]. The experiments were completed when animals were sacrificed for harvest of muscle and liver tissues for DNA extraction and quantitative analysis of genome copies of vectors present in target tissues by TaqMan using the same set of primers and probe as in titration of vector preparations [Zhang, Y., et al., (2001) Mol Ther 3, 697-707].

The performance of vectors base on the new serotypes were evaluated in murine models of muscle and liver-directed gene transfer and compared to vectors based on the known serotypes AAV1, AAV2 and AAV5. Vectors expressing secreted proteins (alpha-antitrypsin (A1AT) and chorionic gonadotropin (CG)) were used to quantitate relative transduction efficiencies between different serotypes through ELISA analysis of sera. The cellular distribution of transduction within the target organ was evaluated using lacZ expressing vectors and X-gal histochemistry.

The performance of AAV vectors in skeletal muscle was analyzed following direct injection into the tibialis anterior muscles. Vectors contained the same AAV2 based genome with the immediate early gene of CMV or a CMV enhanced β-actin promoter driving expression of the transgene. Previous studies indicated that immune competent C57BL/6 mice elicit limited humoral responses to the human A1AT protein when expressed from AAV vectors [Xiao, W., et al., (1999) J Virol 73, 3994-4003].

In each strain, AAV2/1 vector produced the highest levels of A1AT and AAV2/2 vector the lowest, with AAV2/7 and AAV2/8 vectors showing intermediate levels of expression. Peak levels of CG at 28 days following injection of nu/nu NCR mice showed the highest levels from AAV2/7 and the lowest from AAV2/2 with AAV2/8 and AAV2/1 in between. Injection of AAV2/1 and AAV2/7 lacZ vectors yielded gene expression at the injection sites in all muscle fibers with substantially fewer lacZ positive fibers observed with AAV2/2 and AAV 2/8 vectors. These data indicate that the efficiency of transduction with AAV2/7 vectors in skeletal muscle is similar to that obtained with AAV2/1, which is the most efficient in skeletal muscle of the previously described serotypes [Xiao, W. (1999), cited above; Chao, H., et al., (2001) Mol Ther 4, 217-22; Chao, H., et al., (2000) Mol Ther 2, 619-23].

Similar murine models were used to evaluate liver-directed gene transfer. Identical doses of vector based on genome copies were infused into the portal veins of mice that were analyzed subsequently for expression of the transgene. Each vector contained an AAV2 based genome using previously described liver-specific promoters (i.e., albumin or thyroid hormone binding globulin) to drive expression of the transgene. More particularly, CMVCG and TBGCG minigene cassettes were used for muscle and liver-directed gene transfer, respectively. Levels of rhCG were defined as relative units (RUs×10$^3$). The data were from assaying serum samples collected at day 28, post vector administration (4 animals per group). As shown in Table 3, the impact of capsid proteins on the efficiency of transduction of A1AT vectors in nu/nu and C57BL/6 mice and CG vectors in C57BL/6 mice was consistent (See Table 6).

TABLE 6

Expression of β-unit of Rhesus Monkey Chorionic Gonadotropin (rhCG)

| Vector | Muscle | Liver |
|---|---|---|
| AAV2/1 | 4.5 ± 2.1 | 1.6 ± 1.0 |
| AAV2 | 0.5 ± 0.1 | 0.7 ± 0.3 |
| AAV2/5 | ND* | 4.8 ± 0.8 |
| AAV2/7 | 14.2 ± 2.4 | 8.2 ± 4.3 |
| AAV2/8 | 4.0 ± 0.7 | 76.0 ± 22.8 |

*Not determined in this experiment.

In all cases, AAV2/8 vectors yielded the highest levels of transgene expression that ranged from 16 to 110 greater than what was obtained with AAV2/2 vectors; expression from AAV2/5 and AAV2/7 vectors was intermediate with AAV2/7 higher than AAV2/5. Analysis of X-Gal stained liver sections of animals that received the corresponding lacZ vectors showed a correlation between the number of transduced cells and overall levels of transgene expression. DNAs extracted from livers of C57BL/6 mice who received the A1AT vectors were analyzed for abundance of vector DNA using real time PCR technology.

The amount of vector DNA found in liver 56 days after injection correlated with the levels of transgene expression (See Table 7). For this experiment, a set of probe and primers targeting the SV40 polyA region of the vector genome was used for TaqMan PCR. Values shown are means of three individual animals with standard deviations. The animals were sacrificed at day 56 to harvest liver tissues for DNA extraction. These studies indicate that AAV8 is the most efficient vector for liver-directed gene transfer due to increased numbers of transduced hepatocytes.

TABLE 7

Real Time PCR Analysis for Abundance of AAV Vectors in nu/nu Mouse Liver Following Injection of 1 × 10$^{11}$ Genome Copies of Vector.

| AAV vectors/Dose | Genome Copies per Cell |
|---|---|
| AAV2/1AlbA1AT | 0.6 ± 0.36 |
| AAV2AlbA1AT | 0.003 ± 0.001 |
| AAV2/5AlbA1AT | 0.83 ± 0.64 |
| AAV2/7AlbA1AT | 2.2 ± 1.7 |
| AAV2/8AlbA1AT | 18 ± 11 |

The serologic data described above suggest that AAV2/8 vector should not be neutralized in vivo following immunization with the other serotypes. C57BL/6 mice received intraportal injections of AAV2/8 vector expressing canine factor IX (10$^{11}$ genome copies) 56 days after they received intramuscular injections of A1AT vectors of different serotypes. High levels of factor IX expression were obtained 14 days following infusion of AAV2/8 into naïve animals (17±2 µg/ml, n=4) which were not significantly different that what was observed in animals immunized with AAV2/1 (31±23 µg/ml, n=4), AAV2/2 (16 µg/ml, n=2), and AAV2/7 (12 µg/ml, n=2). This contrasts to what was observed in AAV2/8 immunized animals that were infused with the AAV2/8 factor IX vector in which no detectable factor IX was observed (<0.1 µg/ml, n=4).

Oligonucleotides to conserved regions of the cap gene did amplify sequences from rhesus monkeys that represented unique AAVs. Identical cap signature sequences were found in multiple tissues from rhesus monkeys derived from at least two different colonies. Full-length rep and cap open reading frames were isolated and sequenced from single sources. Only the cap open reading frames of the novel AAVs were necessary to evaluate their potential as vectors because vectors with the AAV7 or AAV8 capsids were generated using the ITRs and rep from AAV2. This also simplified the comparison of different vectors since the actual vector genome is identical between different vector serotypes. In fact, the yields of recombinant vectors generated using this approach did not differ between serotypes.

Vectors based on AAV7 and AAV8 appear to be immunologically distinct (i.e., they are not neutralized by antibodies generated against other serotypes). Furthermore, sera from humans do not neutralize transduction by AAV7 and AAV8 vectors, which is a substantial advantage over the human derived AAVs currently under development for which a significant proportion of the human population has pre-existing immunity that is neutralizing [Chirmule, N., et al., (1999) Gene Ther 6, 1574-83].

The tropism of each new vector is favorable for in vivo applications. AAV2/7 vectors appear to transduce skeletal muscle as efficiently as AAV2/1, which is the serotype that confers the highest level of transduction in skeletal muscle of the primate AAVs tested to date [Xiao, W., cited above; Chou (2001), cited above, and Chou (2000), cited above]. Importantly, AAV2/8 provides a substantial advantage over the other serotypes in terms of efficiency of gene transfer to liver that until now has been relatively disappointing in terms of the numbers of hepatocytes stably transduced. AAV2/8 consistently achieved a 10 to 100-fold improvement in gene transfer efficiency as compared to the other vectors. The basis for the improved efficiency of AAV2/8 is unclear, although it presumably is due to uptake via a different receptor that is more active on the basolateral surface of hepatocytes. This improved efficiency will be quite useful in the development of liver-directed gene transfer where the number of transduced cells is critical, such as in urea cycle disorders and familial hypercholesterolemia.

Thus, the present invention provides a novel approach for isolating new AAVs based on PCR retrieval of genomic sequences. The amplified sequences were easily incorporated into vectors and tested in animals. The lack of pre-existing immunity to AAV7 and the favorable tropism of the vectors for muscle indicates that AAV7 is suitable for use as a vector in human gene therapy and other in vivo applications. Similarly, the lack of pre-existing immunity to the AAV serotypes of the invention, and their tropisms, renders them useful in delivery of therapeutic molecules and other useful molecules.

Example 9: Tissue Tropism Studies

In the design of a high throughput functional screening scheme for novel AAV constructs, a non-tissue specific and highly active promoter, CB promoter (CMV enhanced chicken β actin promoter) was selected to drive an easily detectable and quantifiable reporter gene, human α antitrypsin gene. Thus only one vector for each new AAV clone needs to be made for gene transfer studies targeting 3 different tissues, liver, lung and muscle to screen for tissue tropism of a particular AAV construct. The following table summarizes data generated from 4 novel AAV vectors in the tissue tropism studies (AAVCBA1AT), from which a novel AAV capsid clone, 44.2, was found to be a very potent gene transfer vehicle in all 3 tissues with a big lead in the lung tissue particularly. Table 8 reports data obtained (in μg A1AT/mL serum) at day 14 of the study.

TABLE 8

| Vector | Target Tissue | | |
|---|---|---|---|
| | Lung | Liver | Muscle |
| AAV2/1 | ND | ND | 45 ± 11 |
| AAV2/5 | 0.6 ± 0.2 | ND | ND |
| AAV2/8 | ND | 84 ± 30 | ND |
| AAV2/rh.2 (43.1) | 14 ± 7 | 25 ± 7.4 | 35 ± 14 |
| AAV2/rh.10 (44.2) | 23 ± 6 | 53 ± 19 | 46 ± 11 |
| AAV2/rh.13 (42.2) | 3.5 ± 2 | 2 ± 0.8 | 3.5 ± 1.7 |
| AAV2/rh.21 (42.10) | 3.1 ± 2 | 2 ± 1.4 | 4.3 ± 2 |

A couple of other experiments were then performed to confirm the superior tropism of AAV 44.2 in lung tissue. First, AAV vector carried CC10hA1AT minigene for lung specific expression were pseudotyped with capsids of novel AAVs were given to Immune deficient animals (NCR nude) in equal volume (50 μl each of the original preps without dilution) via intratracheal injections as provided in the following table. In Table 9, 50 μl of each original prep per mouse, NCR Nude, detection limit ≥0.033 μg/ml, Day 28

TABLE 9

| Vector | Total GC in 50 μl vector | μg of A1AT/ml with 50 μl vector | μg of A1AT/ml with 1 × 10$^{11}$ vector | Relative Gene transfer as compared to rh.10 (clone 44.2) |
|---|---|---|---|---|
| 2/1 | 3 × 10$^{12}$ | 2.6 ± 0.5 | 0.09 ± 0.02 | 2.2 |
| 2/2 | 5.5 × 10$^{11}$ | <0.03 | <0.005 | <0.1 |
| 2/5 | 3.6 × 10$^{12}$ | 0.65 ± 0.16 | 0.02 ± 0.004 | 0.5 |
| 2/7 | 4.2 × 10$^{12}$ | 1 ± 0.53 | 0.02 ± 0.01 | 0.5 |
| 2/8 | 7.5 × 10$^{11}$ | 0.9 ± 0.7 | 0.12 ± 0.09 | 2.9 |
| 2/ch.5 (A.3.1) | 9 × 10$^{12}$ | 1 ± 0.7 | 0.01 ± 0.008 | 0.24 |
| 2/rh.8 (43.25) | 4.6 × 10$^{12}$ | 26 ± 21 | 0.56 ± 0.46 | 13.7 |
| 2/rh.10 (44.2) | 2.8 × 10$^{12}$ | 115 ± 38 | 4.1 ± 1.4 | 100 |
| 2/rh.13 (42.2) | 6 × 10$^{12}$ | 7.3 ± 0.8 | 0.12 ± 0.01 | 2.9 |
| 2/rh.21 (42.10) | 2.4 × 10$^{12}$ | 9 ± 0.9 | 0.38 ± 0.04 | 9.3 |
| 2/rh.22 (42.11) | 2.6 × 10$^{12}$ | 6 ± 0.4 | 0.23 ± 0.02 | 5.6 |
| 2/rh.24 (42.13) | 1.1 × 10$^{11}$ | 0.4 ± 0.3 | 0.4 ± 0.3 | 1 |

The vectors were also administered to immune competent animals (C57BL/6) in equal genome copies (1×10$^{11}$ GC) as shown in the Table 10. (1×10$^{11}$ GC per animal, C57BL/6, day 14, detection limit ≥0.033 μg/ml)

TABLE 10

| AAV Vector | μg of A1AT/ml with 1 × 10$^{11}$ vector | Relative Gene transfer as compared to rh.10 (clone 44.2) |
|---|---|---|
| 2/1 | 0.076 ± 0.031 | 2.6 |
| 2/2 | 0.1 ± 0.09 | 3.4 |
| 2/5 | 0.084 0.033 | 2.9 |
| 2/7 | 0.33 ± 0.01 | 11 |
| 2/8 | 1.92 ± 1.3 | 2.9 |
| 2/ch.5 (A.3.1) | 0.048 ± 0.004 | 1.6 |
| 2/rh.8 (43.25) | 1.7 ± 0.7 | 58 |
| 2/rh.10 (44.2) | 2.93 ± 1.7 | 100 |
| 2/rh.13 (42.2) | 0.45 ± 0.15 | 15 |
| 2/rh.21 (42.10) | 0.86 ± 0.32 | 29 |
| 2/rh.22 (42.11) | 0.38 ± 0.18 | 13 |
| 2/rh.24 (42.13) | 0.3 ± 0.19 | 10 |

The data from both experiments confirmed the superb tropism of clone 44.2 in lung-directed gene transfer.

Interestingly, performance of clone 44.2 in liver and muscle directed gene transfer was also outstanding, close to that of the best liver transducer, AAV8 and the best muscle transducer AAV1, suggesting that this novel AAV has some intriguing biological significance.

To study serological properties of those novel AAVs, pseudotyped AAVGFP vectors were created for immunization of rabbits and in vitro transduction of 84-31 cells in the presence and absence of antisera against different capsids. The data are summarized below:

TABLE 11a

| | Cross-NAB assay in 8431 cells and adenovirus (Adv) coinfection Infection in 8431 cells (coinfected with Adv) with: | | | |
|---|---|---|---|---|
| Serum from rabbit immunized with: | 10$^9$ GC rh.13 AAV2/ 42.2 | 10$^9$ GC rh.21 AAV2/ 42.10 | 10$^9$ GC rh.22 AAV2/ 42.11 | 10$^{10}$ GC rh.24 AAV2/ 42.13 |
| AAV2/1 | 1/20 | 1/20 | 1/20 | No NAB |
| AAV2/2 | 1/640 | 1/1280 | 1/5120 | No NAB |
| AAV2/5 | No NAB | 1/40 | 1/160 | No NAB |
| AAV2/7 | 1/81920 | 1/81920 | 1/40960 | 1/640 |
| AAV2/8 | 1/640 | 1/640 | 1/320 | 1/5120 |
| Ch.5 | 1/20 | 1/160 | 1/640 | 1/640 |
| AAV2/A3 | | | | |

TABLE 11a-continued

| | Cross-NAB assay in 8431 cells and adenovirus (Adv) coinfection Infection in 8431 cells (coinfected with Adv) with: | | | |
|---|---|---|---|---|
| Serum from rabbit immunized with: | 10$^9$ GC rh.13 AAV2/ 42.2 | 10$^9$ GC rh.21 AAV2/ 42.10 | 10$^9$ GC rh.22 AAV2/ 42.11 | 10$^{10}$ GC rh.24 AAV2/ 42.13 |
| rh.8 AAV2/43.25 | 1/20 | 1/20 | 1/20 | 1/320 |
| rh.10 AAV2/44.2 | No NAB | No NAB | No NAB | 1/5120 |
| rh.13 AAV2/42.2 | 1/5120 | 1/5120 | 1/5120 | No NAB |
| rh.21 AAV2/42.10 | 1/5120 | 1/10240 | 1/5120 | 1/20 |
| rh.22 AAV2/42.11 | 1/20480 | 1/20480 | 1/40960 | No NAB |
| rh.24 AAV2/42.13 | No NAB | 1/20 | 1/20 | 1/5120 |

TABLE 11b

Cross-NAB assay in 8431 cells and Adv coinfection
Infection in 8431 cells (coinfected with Adv) with:

| Serum from rabbit immunized with: | $10^9$ GC rh.12 AAV2/42.1B | $10^{10}$ GC ch.5 AAV2/A3 | $10^{10}$ GC rh.8 AAV2/43.25 | $10^9$ GC rh.10 AAV2/44.2 | $10^9$ GC rh.20 AAV2/42.8.2 |
|---|---|---|---|---|---|
| AAV2/1 | No NAB | 1/20480 | No NAB | 1/80 | ND |
| AAV2/2 | 1/20 | No NAB | No NAB | No NAB | ND |
| AAV2/5 | No NAB | 1/320 | No NAB | No NAB | ND |
| AAV2/7 | 1/2560 | 1/640 | 1/160 | 1/81920 | ND |
| AAV2/8 | 1/10240 | 1/2560 | 1/2560 | 1/81920 | ND |
| ch.5 AAV2/A3 | 1/1280 | 1/10240 | ND | 1/5120 | 1/320 |
| rh.8 AAV2/43.25 | 1/1280 | ND | 1/20400 | 1/5120 | 1/2560 |
| rh.10 AAV2/44.2 | 1/5120 | ND | ND | 1/5120 | 1/5120 |
| rh.13 AAV2/42.2 | 1/20 | ND | ND | No NAB | 1/320 |
| rh.21 AAV2/42.10 | 1/20 | ND | ND | 1/40 | 1/80 |
| rh.22 AAV2/42.11 | No NAB | ND | ND | ND | No NAB |
| rh.24 AAV2/42.13 | 1/5120 | ND | ND | ND | 1/2560 |

TABLE 12

| | Titer of rabbit sera | | Titer after |
|---|---|---|---|
| | Vector | Titer d21 | Boosting |
| ch.5 | AAV2/A3 | 1/10,240 | 1/40,960 |
| rh.8 | AAV2/43.25 | 1/20,400 | 1/163,840 |
| rh.10 | AAV2/44.2 | 1/10,240 | 1/527,680 |
| rh.13 | AAV2/42.2 | 1/5,120 | 1/20,960 |
| rh.21 | AAV2/42.10 | 1/20,400 | 1/81,920 |
| rh.22 | AAV2/42.11 | 1/40,960 | ND |
| rh.24 | AAV2/42.13 | 1/5,120 | ND |

TABLE 13 a

Infection in 8431 cells (coinfected with Adv) with GFP

| | $10^9$ GC/well AAV2/1 | $10^9$ GC/well AAV2/2 | $10^9$ GC/well AAV2/5 | $10^9$ GC/well AAV2/7 | $10^9$ GC/well AAV2/8 | $10^9$ GC/well ch.5 AAV2/A3 |
|---|---|---|---|---|---|---|
| # GFU/field | 128 | >200 | 95 | 56 | 13 | 1 |
| | 83 | >200 | 65 | 54 | 11 | 1 |

TABLE 13b

Infection in 8431 cells (coinfected with Adv) with GFP

| | $10^9$ GC/well rh.8 AAV2/43.25 | $10^9$ GC/well rh.10 AAV2/44.2 | $10^9$ GC/well rh.13 AAV2/42.2 | $10^9$ GC/well rh.21 AAV2/42.10 | $10^9$ GC/well rh.22 AAV2/42.11 | $10^9$ GC/well rh.24 AAV2/42.13 | $10^9$ GC/well rh.12 AAV2/42.1B |
|---|---|---|---|---|---|---|---|
| # GFU/field | 3 | 13 | 54 | 62 | 10 | 3 | 18 |
| | 2 | 12 | 71 | 60 | 14 | 2 | 20 |
| | | | 48 | 47 | 16 | 3 | 12 |

Example 10: Mouse Model of Familial Hypercholesterolemia

The following experiment demonstrates that the AAV2/7 construct of the invention delivers the LDL receptor and express LDL receptor in an amount sufficient to reduce the levels of plasma cholesterol and triglycerides in animal models of familial hypercholesterolemia.

A. Vector Construction

AAV vectors packaged with AAV7 or AAV8 capsid proteins were constructed using a pseudotyping strategy [Hildinger M, et al., *J. Virol* 2001; 75:6199-6203]. Recombinant AAV genomes with AAV2 inverted terminal repeats (ITR) were packaged by triple transfection of 293 cells with the cis-plasmid, the adenovirus helper plasmid and a chimeric packaging construct, a fusion of the capsids of the novel AAV serotypes with the rep gene of AAV2. The chimeric packaging plasmid was constructed as previously described [Hildinger et al, cited above]. The recombinant vectors were purified by the standard $CsCl_2$ sedimentation method. To determine the yield TaqMan (Applied Biosystems) analysis was performed using probes and primers targeting the SV40 poly(A) region of the vectors [Gao G P, et al., *Hum Gene Ther.* 2000 Oct. 10; 11(15):2079-91]. The resulting vectors express the transgene under the control of the human thyroid hormone binding globulin gene promoter (TBG).

B. Animals

LDL receptor deficient mice on the C57Bl/6 background were purchased from the Jackson Laboratory (Bar Harbor, Me., USA) and maintained as a breeding colony. Mice were given unrestricted access to water and obtained a high fat Western Diet (high % cholesterol) starting three weeks prior vector injection. At day –7 as well at day 0, blood was obtained via retroorbital bleeds and the lipid profile evaluated. The mice were randomly divided into seven groups. The vector was injected via an intraportal injection as previously described ([Chen S J et al., *Mol Therapy* 2000; 2(3), 256-261]. Briefly, the mice were anaesthetized with ketamine and xylazine. A laparotomy was performed and the portal vein exposed. Using a 30 g needle the appropriate dose of vector diluted in 100 ul PBS was directly injected into the portal vein. Pressure was applied to the injection site to ensure a stop of the bleeding. The skin wound was closed and draped and the mice carefully monitored for the following day. Weekly bleeds were performed starting at day 14 after liver directed gene transfer to measure blood lipids. Two animals of each group were sacrificed at the time points week 6 and week 12 after vector injection to examine atherosclerotic plaque size as well as receptor expression.

The remaining mice were sacrificed at week 20 for plaque measurement and determination of transgene expression.

TABLE 14

| | Vector | dose | n |
|---|---|---|---|
| Group 1 | AAV2/7-TBG-hLDLr | $1 \times 10^{12}$ gc | 12 |
| Group 2 | AAV2/7-TBG-hLDLr | $3 \times 10^{11}$ gc | 12 |
| Group 3 | AAV2/7-TBG-hLDLr | $1 \times 10^{11}$ gc | 12 |
| Group 4 | AAV2/8-TBG-hLDLr | $1 \times 10^{12}$ gc | 12 |
| Group 5 | AAV2/8-TBG-hLDLr | $3 \times 10^{11}$ gc | 12 |
| Group 6 | AAV2/8-TBG-hLDLr | $1 \times 10^{11}$ gc | 12 |
| Group 7 | AAV2/7-TBG-LacZ | $1 \times 10^{11}$ gc | 16 |

C. Serum Lipoprotein and Liver Function Analysis

Blood samples were obtained from the retroorbital plexus after a 6 hour fasting period. The serum was separated from the plasma by centrifugation. The amount of plasma lipoproteins and liver transaminases in the serum were detected using an automatized clinical chemistry analyzer (ACE, Schiapparelli Biosystems, Alpha Wassermann)

D. Detection of Transgene Expression

LDL receptor expression was evaluated by immunofluorescence staining and Western blotting. For Western Blot frozen liver tissue was homogenized with lysis buffer (20 mM Tris, pH7.4, 130 mM NaCl, 1% Triton X 100, proteinase inhibitor (complete, EDTA-free, Roche, Mannheim, Germany). Protein concentration was determined using the Micro BCA Protein Assay Reagent Kit (Pierce, Rockford, Ill.). 40 µg of protein was resolved on 4-15% Tris-HCl Ready Gels (Biorad, Hercules, Calif.) and transferred to a nitrocellulose membrane (Invitrogen,). To generate Anti-hLDL receptor antibodies a rabbit was injected intravenously with an AdhLDLr prep ($1\times10^{13}$ GC). Four weeks later the rabbit serum was obtained and used for Western Blot. A 1:100 dilution of the serum was used as a primary antibody followed by a HRP-conjugated anti-rabbit IgG and ECL chemiluminescent detection (ECL Western Blot Detection Kit, Amersham, Arlington Heights, Ill.).

E. Immunocytochemistry

For determination of LDL receptor expression in frozen liver sections immunohistochemistry analyses were performed. 10 um cryostat sections were either fixed in acetone for 5 minutes, or unfixed. Blocking was obtained via a 1 hour incubation period with 10% of goat serum. Sections were then incubated for one hour with the primary antibody at room temperature. A rabbit polyclonal antibody anti-human LDL (Biomedical Technologies Inc., Stoughton, Mass.) was used diluted accordingly to the instructions of the manufacturer. The sections were washed with PBS, and incubated with 1:100 diluted fluorescein goat anti-rabbit IgG (Sigma, St Louis, Mo.). Specimens were finally examined under fluorescence microscope Nikon Microphot-FXA. In all cases, each incubation was followed by extensive washing with PBS. Negative controls consisted of preincubation with PBS, omission of the primary antibody, and substitution of the primary antibody by an isotype-matched non-immune control antibody. The three types of controls mentioned above were performed for each experiment on the same day.

F. Gene Transfer Efficiency

Liver tissue was obtained after sacrificing the mice at the designated time points. The tissue was shock frozen in liquid nitrogen and stored at –80° C. until further processing. DNA was extracted from the liver tissue using a QIAamp DNA Mini Kit (QIAGEN GmbH, Germany) according to the manufacturers protocol. Genome copies of AAV vectors in the liver tissue were evaluated using Taqman analysis using probes and primers against the SV40 poly(A) tail as described above.

G. Atherosclerotic Plaque Measurement

For the quantification of the atherosclerotic plaques in the mouse aorta the mice were anaesthetized (10% ketamine and xylazine, ip), the chest opened and the arterial system perfused with ice-cold phosphate buffered saline through the left ventricle. The aorta was then carefully harvested, slit down along the ventral midline from the aortic arch down to the femoral arteries and fixed in formalin. The lipid-rich atherosclerotic plaques were stained with Sudan IV (Sigma, Germany) and the aorta pinned out flat on a black wax surface. The image was captured with a Sony DXC-960 MD color video camera. The area of the plaque as well as of the complete aortic surface was determined using Phase 3 Imaging Systems (Media Cybernetics).

H. Clearance of $I^{125}$ LDL

Two animals per experimental group were tested. A bolus of $I^{125}$-labeled LDL (generously provided by Dan Rader, U Penn) was infused slowly through the tail vein over a period of 30 sec (1,000,000 counts of $[I^{125}]$-LDL diluted in 100 µl sterile PBS/animal). At time points 3 min, 30 min, 1.5 hr, 3 hr, 6 hr after injection a blood sample was obtained via the retro-orbital plexus. The plasma was separated off from the whole blood and 10 µl plasma counted in the gamma counter. Finally the fractional catabolic rate was calculated from the lipoprotein clearance data.

I. Evaluation of Liver Lipid Accumulation

Oil Red Staining of frozen liver sections was performed to determine lipid accumulation. The frozen liver sections were briefly rinsed in distilled water followed by a 2 minute incubation in absolute propylene glycol. The sections were then stained in oil red solution (0.5% in propylene glycol) for 16 hours followed by counterstaining with Mayer's hematoxylin solution for 30 seconds and mounting in warmed glycerin jelly solution.

For quantification of the liver cholesterol and triglyceride content liver sections were homogenized and incubated in chloroform/methanol (2:1) overnight. After adding of 0.05% $H_2SO_4$ and centrifugation for 10 minutes, the lower layer of each sample was collected, divided in two aliquots and dried under nitrogen. For the cholesterol measurement the dried lipids of the first aliquot were dissolved in 1% Triton X-100 in chloroform. Once dissolved, the solution was dried under nitrogen. After dissolving the lipids in ddH$_2$O and incubation for 30 minutes at 37° C. the total cholesterol concentration was measured using a Total Cholesterol Kit (Wako Diagnostics). For the second aliquot the dried lipids were dissolved in alcoholic KOH and incubated at 60° C. for 30 minutes. Then 1M MgCl2 was added, followed by incubation on ice for 10 minutes and centrifugation at 14,000 rpm for 30 minutes. The supernatant was finally evaluated for triglycerides (Wako Diagnostics).

All of the vectors pseudotyped in an AAV2/8 or AAV2/7 capsid lowered total cholesterol, LDL and triglycerides as compared to the control. These test vectors also corrected phenotype of hypercholesterolemia in a dose-dependent manner. A reduction in plaque area for the AAV2/8 and AAV2/7 mice was observed in treated mice at the first test (2 months), and the effect was observed to persist over the length of the experiment (6 months).

Example 10: Functional Factor IX Expression and Correction of Hemophilia

A. Knock-Out Mice

Functional canine factor IX (FIX) expression was assessed in hemophilia B mice. Vectors with capsids of AAV1, AAV2, AAV5, AAV7 or AAV8 were constructed to deliver AAV2 5' ITR-liver-specific promoter [LSP]-canine FIX-woodchuck hepatitis post-regulatory element (WPRE)-AAV2 3' ITR. The vectors were constructed as described in Wang et al, 2000, *Molecular Therapy* 2: 154-158), using the appropriate capsids.

Knock-out mice were generated as described in Wang et al, 1997. *Proc. Natl. Acad. Sci. USA* 94: 11563-11566. This model closely mimic the phenotypes of hemophilia B in human.

Vectors of different serotypes (AAV1, AAV2, AAV5, AAV7 and AAV8) were delivered as a single intraportal injection into the liver of adult hemophiliac C57Bl/6 mice in a dose of $1 \times 10^{11}$ GC/mouse for the five different serotypes and one group received an AAV8 vector at a lower dose, $1 \times 10^{10}$ GC/mouse. Control group was injected with $1 \times 10^{11}$ GC of AAV2/8 TBG LacZ3. Each group contains 5-10 male and female mice. Mice were bled bi-weekly after vector administration.

1. ELISA

The canine FIX concentration in the mouse plasma was determined by an ELISA assay specific for canine factor IX, performed essentially as described by Axelrod et al, 1990, *Proc. Natl. Acad. Sci. USA*, 87:5173-5177 with modifications. Sheep anti-canine factor IX (Enzyme Research Laboratories) was used as primary antibody and rabbit anti-canine factor IX ((Enzyme Research Laboratories) was used as secondary antibody. Beginning at two weeks following injection, increased plasma levels of cFIX were detected for all test vectors. The increased levels were sustained at therapeutic levels throughout the length of the experiment, i.e., to 12 weeks. Therapeutic levels are considered to be 5% of normal levels, i.e., at about 250 ng/mL.

The highest levels of expression were observed for the AAV2/8 (at 10") and AAV2/7 constructs, with sustained superphysiology levels cFIX levels (ten-fold higher than the normal level). Expression levels for AAV2/8 ($10^{11}$) were approximately 10 fold higher than those observed for AAV2/2 and AAV2/8 ($10^{10}$). The lowest expression levels, although still above the therapeutic range, were observed for AAV2/5.

2. In Vitro Activated Partial Thromboplastin Time (aPTT) Assay

Functional factor IX activity in plasma of the FIX knock-out mice was determined by an in vitro activated partial thromboplastin time (aPTT) assay—Mouse blood samples were collected from the retro-orbital plexus into $\frac{1}{10}$ volume of citrate buffer. The aPTT assay was performed as described by Wang et al, 1997, *Proc. Natl. Acad. Sci. USA* 94: 11563-11566.

Clotting times by aPTT on plasma samples of all vector injected mice were within the normal range (approximately 60 sec) when measured at two weeks post-injection, and sustained clotting times in the normal or shorter than normal range throughout the study period (12 weeks).

Lowest sustained clotting times were observed in the animals receiving AAV2/8 ($10^{11}$) and AAV2/7. By week 12, AAV2/2 also induced clotting times similar to those for AAV2/8 and AAV2/7. However, this lowered clotting time was not observed for AAV2/2 until week 12, whereas lowered clotting times (in the 25-40 sec range) were observed for AAV2/8 and AAV2/7 beginning at week two.

Immuno-histochemistry staining on the liver tissues harvested from some of the treated mice is currently being performed. About 70-80% of hepatocytes are stained positive for canine FIX in the mouse injected with AAV2/8.cFIX vector.

B. Hemophilia B Dogs

Dogs that have a point mutation in the catalytic domain of the F.IX gene, which, based on modeling studies, appears to render the protein unstable, suffer from hemophilia B [Evans et al, 1989, Proc. Natl. Acad. Sci. USA, 86:10095-10099). A colony of such dogs has been maintained for more than two decades at the University of North Carolina, Chapel Hill. The homeostatic parameters of these dogs are well described and include the absence of plasma F.IX antigen, whole blood clotting times in excess of 60 minutes, whereas normal dogs are 6-8 minutes, and prolonged activated partial thromboplastin time of 50-80 seconds, whereas normal dogs are 13-28 seconds. These dogs experience recurrent spontaneous hemorrhages. Typically, significant bleeding episodes are successfully managed by the single intravenous infusion of 10 ml/kg of normal canine plasma; occasionally, repeat infusions are required to control bleeding.

Four dogs are injected intraportally with AAV.cFIX according to the schedule below. A first dog receives a single injection with AAV2/2.cFIX at a dose of $3.7 \times 10^{11}$ genome copies (GC)/kg. A second dog receives a first injection of AAV2/2.cFIX ($2.8 \times 10^{11}$ GC/kg), followed by a second injection with AAV2/7.cFIX ($2.3 \times 10^{13}$ GC/kg) at day 1180. A third dog receives a single injection with AAV2/2.cFIX at a dose of $4.6 \times 10^{12}$ GC/kg. The fourth dog receives an injection with AAV2/2.cFIX ($2.8 \times 10^{12}$ GC/kg) and an injection at day 995 with AAV2/7.cFIX ($5 \times 10^{12}$ GC/kg).

The abdomen of hemophilia dogs are aseptically and surgically opened under general anesthesia and a single infusion of vector is administered into the portal vein. The animals are protected from hemorrhage in the peri-operative period by intravenous administration of normal canine plasma. The dog is sedated, intubated to induce general anesthesia, and the abdomen shaved and prepped. After the abdomen is opened, the spleen is moved into the operative field. The splenic vein is located and a suture is loosely placed proximal to a small distal incision in the vein. A needle is rapidly inserted into the vein, then the suture loosened and a 5 F cannula is threaded to an intravenous location near the portal vein threaded to an intravenous location near the portal vein bifurcation. After hemostasis is secured and the catheter balloon inflated, approximately 5.0 ml of vector diluted in PBS is infused into the portal vein over a 5 minute interval. The vector infusion is followed by a 5.0 ml infusion of saline. The balloon is then deflated, the callula removed and venous hemostasis is secured. The spleen is then replaced, bleeding vessels are cauterized and the operative wound is closed. The animal is extubated having tolerated the surgical procedure well. Blood samples are analyzed as described. [Wang et al, 2000, *Molecular Therapy* 2: 154-158]

Results showing correction or partial correction are anticipated for AAV2/7.

All publications cited in this specification including priority applications, U.S. patent application Ser. No. 13/633,971, U.S. patent application Ser. No. 12/962,793, U.S. patent application Ser. No. 10/291,583, and U.S. provisional patent application Nos. 60/386,675, 60/377,066, 60/341,117, and 60/350,607, are incorporated herein by reference. While the invention has been described with reference to particularly preferred embodiments, it will be appreciated that modifications can be made without departing from the spirit of the invention. Such modifications are intended to fall within the scope of the claims.

SEQUENCE LISTING

<160> NUMBER OF SEQ ID NOS: 120

<210> SEQ ID NO 1
<211> LENGTH: 4721
<212> TYPE: DNA
<213> ORGANISM: Unknown
<220> FEATURE:
<223> OTHER INFORMATION: adeno-associated virus serotype 7

<400> SEQUENCE: 1

| | | | | |
|---|---|---|---|---|
| ttggccactc | cctctatgcg | cgctcgctcg | ctcggtgggg | cctgcggacc | aaaggtccgc | 60 |
| agacggcaga | gctctgctct | gccggccccca | ccgagcgagc | gagcgcgcat | agagggagtg | 120 |
| gccaactcca | tcactagggg | taccgcgaag | cgcctcccac | gctgccgcgt | cagcgctgac | 180 |
| gtaaatcacg | tcataggggga | gtggtcctgt | attagctgtc | acgtgagtgc | ttttgcgaca | 240 |
| ttttgcgaca | ccacgtggcc | atttgaggta | tatatggccg | agtgagcgag | caggatctcc | 300 |
| attttgaccg | cgaaatttga | acgagcagca | gccatgccgg | gtttctacga | gatcgtgatc | 360 |
| aaggtgccga | gcgacctgga | cgagcacctg | ccgggcattt | ctgactcgtt | tgtgaactgg | 420 |
| gtggccgaga | aggaatggga | gctgccccccg | gattctgaca | tggatctgaa | tctgatcgag | 480 |
| caggcacccc | tgaccgtggc | cgagaagctg | cagcgcgact | tcctggtcca | atggcgccgc | 540 |
| gtgagtaagg | ccccggaggc | cctgttcttt | gttcagttcg | agaagggcga | gagctacttc | 600 |
| caccttcacg | ttctggtgga | gaccacgggg | gtcaagtcca | tggtgctagg | ccgcttcctg | 660 |
| agtcagattc | gggagaagct | ggtccagacc | atctaccgcg | gggtcgagcc | cacgctgccc | 720 |
| aactggttcg | cggtgaccaa | gacgcgtaat | ggcgccggcg | ggggaacaa | ggtggtggac | 780 |
| gagtgctaca | tccccaacta | cctcctgccc | aagacccagc | ccgagctgca | gtgggcgtgg | 840 |
| actaacatgg | aggagtatat | aagcgcgtgt | ttgaacctgg | ccgaacgcaa | acggctcgtg | 900 |
| gcgcagcacc | tgacccacgt | cagccagacg | caggagcaga | acaaggagaa | tctgaacccc | 960 |
| aattctgacg | cgcccgtgat | caggtcaaaa | acctccgcgc | gctacatgga | gctggtcggg | 1020 |
| tggctggtgg | accgggggcat | cacctccgag | aagcagtgga | tccaggagga | ccaggcctcg | 1080 |
| tacatctcct | tcaacgccgc | ctccaactcg | cggtcccaga | tcaaggccgc | gctggacaat | 1140 |
| gccggcaaga | tcatggcgct | gaccaaatcc | gcgcccgact | acctggtggg | gcccgcgctg | 1200 |
| cccgcggaca | ttaaaaccaa | ccgcatctac | cgcatcctgg | agctgaacgg | gtacgatcct | 1260 |
| gcctacgccg | gctccgtctt | tctcggctgg | gcccagaaaa | agttcgggaa | gcgcaacacc | 1320 |
| atctggctgt | ttgggcccgc | caccaccggc | aagaccaaca | ttgcggaagc | catcgcccac | 1380 |
| gccgtgccct | tctacggctg | cgtcaactgg | accaatgaga | ctttcccctt | caacgattgc | 1440 |
| gtcgacaaga | tggtgatctg | gtgggaggag | ggcaagatga | cggccaaggt | cgtggagtcc | 1500 |
| gccaaggcca | ttctcggcgg | cagcaaggtg | cgcgtggacc | aaaagtgcaa | gtcgtccgcc | 1560 |
| cagatcgacc | ccaccccccgt | gatcgtcacc | tccaacacca | acatgtgcgc | cgtgattgac | 1620 |
| gggaacagca | ccaccttcga | gcaccagcag | ccgttgcagg | accggatgtt | caaatttgaa | 1680 |
| ctcacccgcc | gtctggagca | cgactttggc | aaggtgacga | agcaggaagt | caaagagttc | 1740 |
| ttccgctggg | ccagtgatca | cgtgaccgag | gtggcgcatg | agttctacgt | cagaaagggc | 1800 |
| ggagccagca | aaagacccgc | ccccgatgac | gcggatataa | gcgagcccaa | gcgggcctgc | 1860 |
| ccctcagtcg | cggatccatc | gacgtcagac | gcggaaggag | ctccggtgga | ctttgccgac | 1920 |
| aggtaccaaa | acaaatgttc | tcgtcacgcg | ggcatgattc | agatgctgtt | tccctgcaaa | 1980 |
| acgtgcgaga | gaatgaatca | gaatttcaac | atttgcttca | cacacggggt | cagagactgt | 2040 |

```
ttagagtgtt tccccggcgt gtcagaatct caaccggtcg tcagaaaaaa gacgtatcgg    2100
aaactctgcg cgattcatca tctgctgggg cgggcgcccg agattgcttg ctcggcctgc    2160
gacctggtca acgtggacct ggacgactgc gtttctgagc aataaatgac ttaaaccagg    2220
tatggctgcc gatggttatc ttccagattg gctcgaggac aacctctctg agggcattcg    2280
cgagtggtgg gacctgaaac ctggagcccc gaaacccaaa gccaaccagc aaaagcagga    2340
caacggccgg ggtctggtgc ttcctggcta caagtacctc ggaccccttca acggactcga    2400
caagggggag cccgtcaacg cggcggacgc agcggccctc gagcacgaca aggcctacga    2460
ccagcagctc aaagcgggtg acaatccgta cctgcggtat aaccacgccg acgccgagtt    2520
tcaggagcgt ctgcaagaag atacgtcatt tgggggcaac ctcgggcgag cagtcttcca    2580
ggccaagaag cgggttctcg aacctctcgg tctggttgag gaaggcgcta agacggctcc    2640
tgcaaagaag agaccggtag agccgtcacc tcagcgttcc cccgactcct ccacgggcat    2700
cggcaagaaa ggccagcagc ccgccagaaa gagactcaat tcggtcaga ctggcgactc    2760
agagtcagtc cccgaccctc aacctctcgg agaacctcca gcagcgccct ctagtgtggg    2820
atctggtaca gtggctgcag gcggtggcgc accaatggca gacaataacg aaggtgccga    2880
cggagtgggt aatgcctcag gaaattgcca ttgcgattcc acatggctgg gcgacagagt    2940
cattaccacc agcaccccgaa cctgggcccct gcccacctac aacaaccacc tctacaagca    3000
aatctccagt gaaactgcag gtagtaccaa cgacaacacc tacttcggct acagcacccc    3060
ctgggggtat tttgacttta acagattcca ctgccacttc tcaccacgtg actggcagcg    3120
actcatcaac aacaactggg gattccggcc caagaagctg cggttcaagc tcttcaacat    3180
ccaggtcaag gaggtcacga cgaatgacgg cgttacgacc atcgctaata accttaccag    3240
cacgattcag gtattctcgg actcggaata ccagctgccg tacgtcctcg gctctgcgca    3300
ccagggctgc ctgcctccgt tcccggcgga cgtcttcatg attcctcagt acggctacct    3360
gactctcaac aatggcagtc agtctgtggg acgttcctcc ttctactgcc tggagtactt    3420
cccctctcag atgctgagaa cgggcaacaa ctttgagttc agctacagct cgaggacgt    3480
gcctttccac agcagctacg cacacagcca gagcctggac cggctgatga atcccctcat    3540
cgaccagtac ttgtactacc tggccagaac acagagtaac ccaggaggca cagctggcaa    3600
tcgggaactg cagttttacc agggcgggcc ttcaactatg gccgaacaag ccaagaattg    3660
gttacctgga ccttgcttcc ggcaacaaag agtctccaaa acgctggatc aaaacaacaa    3720
cagcaacttt gcttggactg gtgccaccaa atatcacctg aacggcagaa actcgttggt    3780
taatcccggc gtcgccatgg caactcacaa ggacgacgag gaccgcttt tcccatccag    3840
cggagtcctg atttttggaa aaactggagc aactaacaaa actacattgg aaaatgtgtt    3900
aatgacaaat gaagaagaaa ttcgtcctac taatcctgta gccacggaag aatacgggat    3960
agtcagcagc aacttacaag cggctaatac tgcagcccag acacaagttg tcaacaacca    4020
gggagcctta cctggcatgg tctggcagaa ccggacgtg tacctgcagg gtcccatctg    4080
ggccaagatt cctcacacgg atggcaactt tcacccgtct cctttgatgg gcggctttgg    4140
acttaaacat ccgcctcctc agatcctgat caagaacact cccgttcccg ctaatcctcc    4200
ggaggtgttt actcctgcca gtttgcttc gttcatcaca cagtacagca ccggacaagt    4260
cagcgtggaa atcgagtggg agctgcagaa ggaaaacagc aagcgctgga accgggagat    4320
tcagtacacc tccaactttg aaaagcagac tggtgtggac tttgccgttg acagccaggg    4380
tgtttactct gagcctcgcc ctattggcac tcgttacctc acccgtaatc tgtaattgca    4440
```

```
tgttaatcaa taaaccggtt gattcgtttc agttgaactt tggtctcctg tgcttcttat    4500
cttatcggtt tccatagcaa ctggttacac attaactgct tgggtgcgct tcacgataag    4560
aacactgacg tcaccgcggt acccctagtg atggagttgg ccactccctc tatgcgcgct    4620
cgctcgctcg gtggggcctg cggaccaaag gtccgcagac ggcagagctc tgctctgccg    4680
gccccaccga gcgagcgagc gcgcatagag ggagtggcca a                        4721

<210> SEQ ID NO 2
<211> LENGTH: 737
<212> TYPE: PRT
<213> ORGANISM: Unknown
<220> FEATURE:
<223> OTHER INFORMATION: capsid protein of adeno-associated virus
      serotpye 7

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300
```

```
Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
            325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
            405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
            435                 440                 445

Arg Thr Gln Ser Asn Pro Gly Gly Thr Ala Gly Asn Arg Glu Leu Gln
450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
            485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
            515                 520                 525

His Lys Asp Asp Glu Asp Arg Phe Phe Pro Ser Ser Gly Val Leu Ile
            530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
            565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
            595                 600                 605

Gln Asn Arg Asp Val Tyr Leu Gln Gly Pro Ile Trp Ala Lys Ile Pro
610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
            645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
            690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
```

725                 730                 735

Leu

<210> SEQ ID NO 3
<211> LENGTH: 623
<212> TYPE: PRT
<213> ORGANISM: Unknown
<220> FEATURE:
<223> OTHER INFORMATION: rep protein of adeno-associated virus serotype
      7

<400> SEQUENCE: 3

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
            100                 105                 110

Arg Glu Lys Leu Val Gln Thr Ile Tyr Arg Gly Val Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ser
        275                 280                 285

Leu Pro Ala Asp Ile Lys Thr Asn Arg Ile Tyr Arg Ile Leu Glu Leu
    290                 295                 300

Asn Gly Tyr Asp Pro Ala Tyr Ala Gly Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro

```
                340                 345                 350
Phe Tyr Gly Cys Val Asn Trp Thr Asn Glu Asn Phe Pro Phe Asn Asp
            355                 360                 365
Cys Val Asp Lys Met Val Ile Trp Trp Glu Glu Gly Lys Met Thr Ala
        370                 375                 380
Lys Val Glu Ser Ala Lys Ala Ile Leu Gly Gly Ser Lys Val Arg
385                 390                 395                 400
Val Asp Gln Lys Cys Lys Ser Ser Ala Gln Ile Asp Pro Thr Pro Val
                405                 410                 415
Ile Val Thr Ser Asn Thr Asn Met Cys Ala Val Ile Asp Gly Asn Ser
            420                 425                 430
Thr Thr Phe Glu His Gln Gln Pro Leu Gln Asp Arg Met Phe Lys Phe
        435                 440                 445
Glu Leu Thr Arg Arg Leu Glu His Asp Phe Gly Lys Val Thr Lys Gln
    450                 455                 460
Glu Val Lys Glu Phe Phe Arg Trp Ala Ser Asp His Val Thr Glu Val
465                 470                 475                 480
Ala His Glu Phe Tyr Val Arg Lys Gly Gly Ala Ser Lys Arg Pro Ala
                485                 490                 495
Pro Asp Asp Ala Asp Ile Ser Glu Pro Lys Arg Ala Cys Pro Ser Val
            500                 505                 510
Ala Asp Pro Ser Thr Ser Asp Ala Glu Gly Ala Pro Val Asp Phe Ala
        515                 520                 525
Asp Arg Tyr Gln Asn Lys Cys Ser Arg His Ala Gly Met Ile Gln Met
    530                 535                 540
Leu Phe Pro Cys Lys Thr Cys Glu Arg Met Asn Gln Asn Phe Asn Ile
545                 550                 555                 560
Cys Phe Thr His Gly Val Arg Asp Cys Leu Glu Cys Phe Pro Gly Val
                565                 570                 575
Ser Glu Ser Gln Pro Val Val Arg Lys Lys Thr Tyr Arg Lys Leu Cys
            580                 585                 590
Ala Ile His His Leu Leu Gly Arg Ala Pro Glu Ile Ala Cys Ser Ala
        595                 600                 605
Cys Asp Leu Val Asn Val Asp Leu Asp Asp Cys Val Ser Glu Gln
    610                 615                 620
```

<210> SEQ ID NO 4
<211> LENGTH: 4393
<212> TYPE: DNA
<213> ORGANISM: Unknown
<220> FEATURE:
<223> OTHER INFORMATION: adeno-associated virus serotype 8

<400> SEQUENCE: 4
cagagaggga gtggccaact ccatcactag gggtagcgcg aagcgcctcc cacgctgccg     60
cgtcagcgct gacgtaaatt acgtcatagg ggagtggtcc tgtattagct gtcacgtgag    120
tgcttttgcg gcattttgcg acaccacgtg gccatttgag gtatatatgg ccgagtgagc    180
gagcaggatc tccattttga ccgcgaaatt tgaacgagca gcagccatgc gggcttcta    240 cgagatcgtg atcaaggtgc gagcgacct ggacgagcac ctgccgggca tttctgactc    300
gtttgtgaac tgggtggccg agaaggaatg ggagctgccc ccggattctg acatggatcg    360
gaatctgatc gagcaggcac ccctgaccgt ggccgagaag ctgcagcgcg acttcctggt    420
ccaatggcgc gcgtgagta aggcccccgga ggccctcttc tttgttcagt tcgagaaggg    480

```
cgagagctac tttcacctgc acgttctggt cgagaccacg ggggtcaagt ccatggtgct      540
aggccgcttc ctgagtcaga ttcgggaaaa gcttggtcca gaccatctac ccgcggggtc      600
gagccccacc ttgcccaact ggttcgcggt gaccaaagac gcggtaatgg cgccggcggg      660
ggggaacaag gtggtggacg agtgctacat ccccaactac ctcctgccca agactcagcc      720
cgagctgcag tgggcgtgga ctaacatgga ggagtatata agcgcgtgct tgaacctggc      780
cgagcgcaaa cggctcgtgg cgcagcacct gacccacgtc agccagacgc aggagcagaa      840
caaggagaat ctgaacccca attctgacgc gcccgtgatc aggtcaaaaa cctccgcgcg      900
ctatatggag ctggtcgggt ggctggtgga ccggggcatc acctccgaga agcagtggat      960
ccaggaggac caggcctcgt acatctcctt caacgccgcc tccaactcgc ggtcccagat     1020
caaggccgcg ctgacaatg ccggcaagat catggcgctg accaaatccg cgcccgacta      1080
cctggtgggg ccctcgctgc ccgcggacat tacccagaac cgcatctacc gcatcctcgc     1140
tctcaacggc tacgaccctg cctacgccgg ctccgtcttt ctcggctggg ctcagaaaaa     1200
gttcgggaaa cgcaacacca tctggctgtt tggacccgcc accaccggca agaccaacat     1260
tgcggaagcc atcgcccacg ccgtgccctt ctacggctgc gtcaactgga ccaatgagaa     1320
cttccccttc aatgattgcg tcgacaagat ggtgatctgg tgggaggagg caagatgac      1380 ggccaaggtc gtggagtccg ccaaggccat tctcggcggc agcaaggtgc gcgtggacca     1440
aaagtgcaag tcgtccgccc agatcgaccc cacccccgtg atcgtcacct ccaacaccaa     1500
catgtgcgcc gtgattgacg ggaacagcac caccttcgag caccagcagc ctctccagga     1560
ccggatgttt aagttcgaac tcacccgccg tctggagcac gactttggca aggtgacaaa     1620
gcaggaagtc aaagagttct ccgctgggc cagtgatcac gtgaccgagg tggcgcatga     1680
gttttacgtc agaaagggcg gagccagcaa aagacccgcc cccgatgacg cggataaaag     1740
cgagcccaag cgggcctgcc cctcagtcgc ggatccatcg acgtcagacg cggaaggagc     1800
tccggtggac tttgccgaca ggtaccaaaa caaatgttct cgtcacgcgg gcatgcttca     1860
gatgctgttt ccctgcaaaa cgtgcgagag aatgaatcag aatttcaaca tttgcttcac     1920
acacggggtc agagactgct cagagtgttt ccccggcgtg tcagaatctc aaccggtcgt     1980
cagaaagagg acgtatcgga aactctgtgc gattcatcat ctgctggggc gggctcccga     2040
gattgcttgc tcggcctgcg atctggtcaa cgtggacctg gatgactgtg tttctgagca     2100
ataaatgact taaaccaggt atggctgccg atggttatct tccagattgg ctcgaggaca     2160
acctctctga gggcattcgc gagtggtggg cgctgaaacc tggagccccg aagcccaaag     2220
ccaaccagca aaagcaggac gacggccggg gtctggtgct tcctggctac aagtacctcg     2280
gacccttcaa cggactcgac aagggggagc cgtcaacgc ggcggacgca gcggccctcg      2340
agcacgacaa ggcctacgac cagcagctgc aggcgggtga caatccgtac ctgcggtata     2400
accacgccga cgccgagttt caggagcgtc tgcaagaaga cgtctttttt ggggcaacc     2460 tcgggcgagc agtcttccag gccaagaagc gggttctcga acctctcggt ctggttgagg     2520
aaggcgctaa gacggctcct ggaaagaaga ggccggtaga gccatcaccc cagcgttctc     2580
cagactcctc tacgggcatc ggcaagaaag gccaacagcc cgccagaaaa agactcaatt     2640
ttggtcagac tggcgactca gagtcagttc agacccctca acctctcgga gaacctccag     2700
cagcgccctc tggtgtggga cctaatacaa tggctgcagg cggtggcgca ccaatggcag     2760
acaataacga aggcgccgac ggagtgggta gttcctcggg aaattggcat gcgattcca     2820 catggctggg cgacagagtc atcaccacca gcaccgaac ctgggccctg cccacctaca     2880
```

-continued

```
acaaccacct ctacaagcaa atctccaacg ggacatcggg aggagccacc aacgacaaca    2940
cctacttcgg ctacagcacc ccctgggggt attttgactt taacagattc cactgccact    3000
tttcaccacg tgactggcag cgactcatca acaacaactg gggattccgg cccaagagac    3060
tcagcttcaa gctcttcaac atccaggtca aggaggtcac gcagaatgaa ggcaccaaga    3120
ccatcgccaa taacctcacc agcaccatcc aggtgtttac ggactcggag taccagctgc    3180
cgtacgttct cggctctgcc caccaggct gcctgcctcc gttcccggcg gacgtgttca    3240
tgattcccca gtacggctac ctaacactca acaacggtag tcaggccgtg gacgctcct    3300 ccttctactg cctggaatac tttccttcgc agatgctgag aaccggcaac aacttccagt    3360
ttacttacac cttcgaggac gtgcctttcc acagcagcta cgcccacagc cagagcttgg    3420
accggctgat gaatcctctg attgaccagt acctgtacta cttgtctcgg actcaaacaa    3480
caggaggcac ggcaaatacg cagactctgg gcttcagcca aggtgggcct aatacaatgg    3540
ccaatcaggc aaagaactgg ctgccaggac cctgttaccg ccaacaacgc gtctcaacga    3600
caaccgggca aaacaacaat agcaactttg cctggactgc tgggaccaaa taccatctga    3660
atggaagaaa ttcattggct aatcctggca tcgctatggc aacacacaaa gacgacgagg    3720
agcgtttttt tcccagtaac gggatcctga tttttggcaa acaaaatgct gccagagaca    3780
atgcggatta cagcgatgtc atgctcacca gcgaggaaga aatcaaaacc actaaccctg    3840
tggctacaga ggaatacggt atcgtggcag ataacttgca gcagcaaaac acggctcctc    3900
aaattggaac tgtcaacagc caggggggcct acccggtat ggtctggcag aaccgggacg    3960
tgtacctgca gggtcccatc tgggccaaga ttcctcacac ggacggcaac ttccacccgt    4020
ctccgctgat gggcggcttt ggcctgaaac atcctccgcc tcagatcctg atcaagaaca    4080
cgcctgtacc tgcggatcct ccgaccacct tcaaccagtc aaagctgaac tctttcatca    4140
cgcaatacag caccggacag gtcagcgtgg aaattgaatg ggagctgcag aaggaaaaca    4200
gcaagcgctg gaaccccgag atccagtaca cctccaacta ctacaaatct acaagtgtgg    4260
actttgctgt taatacagaa ggcgtgtact ctgaaccccg ccccattggc acccgttacc    4320
tcacccgtaa tctgtaattg cctgttaatc aataaaccgg ttgattcgtt tcagttgaac    4380
tttggtctct gcg                                                      4393
```

<210> SEQ ID NO 5
<211> LENGTH: 4385
<212> TYPE: DNA
<213> ORGANISM: Unknown
<220> FEATURE:
<223> OTHER INFORMATION: adeno-associated virus serotype 9

<400> SEQUENCE: 5

```
cagagaggga gtggccaact ccatcactag gggtaatcgc gaagcgcctc ccacgctgcc      60
gcgtcagcgc tgacgtagat tacgtcatag gggagtggtc ctgtattagc tgtcacgtga     120
gtgcttttgc gacattttgc gacaccacat ggccatttga ggtatatatg gccgagtgag     180
cgagcaggat ctccattttg accgcgaaat ttgaacgagc agcagccatg ccgggcttct     240
acgagattgt gatcaaggtg ccgagcgacc tggacgagca cctgccgggc atttctgact     300
cttttgtgaa ctgggtggcc gagaaggaat gggagctgcc cccggattct gacatggatc     360
ggaatctgat cgagcaggca cccctgaccg tggccgagaa gctgcagcgc gacttcctgg     420
tccaatggcg ccgcgtgagt aaggcccggg aggccctctt ctttgttcag ttcgagaagg     480
```

```
gcgagagcta ctttcacctg cacgttctgg tcgagaccac gggggtcaag tccatggtgc      540
taggccgctt cctgagtcag attcgggaga agctggtcca gaccatctac cgcgggatcg      600
agccgaccct gcccaactgg ttcgcggtga ccaagacgcg taatggcgcc ggcggggggga     660 acaaggtggt ggacgagtgc tacatcccca actacctcct gcccaagact cagcccgagc      720
tgcagtgggc gtggactaac atggaggagt atataagcgc gtgcttgaac ctggccgagc      780
gcaaacggct cgtggcgcag cacctgaccc acgtcagcca gacgcaggag cagaacaagg      840
agaatctgaa ccccaattct gacgcgcccg tgatcaggtc aaaaacctcc gcgcgctaca      900
tggagctggt cgggtggctg gtggaccggg gcatcacctc cgagaagcag tggatccagg      960
aggaccaggc ctcgtacatc tccttcaacg ccgcctccaa ctcgcggtcc cagatcaagg     1020
ccgcgctgga caatgccggc aagatcatgg cgctgaccaa atccgcgccc gactacctgg     1080
taggcccttc acttccggtg acattacgc agaaccgcat ctaccgcatc ctgcagctca      1140
acggctacga ccctgcctac gccggctccg tctttctcgg ctgggcacaa aagaagttcg     1200
ggaaacgcaa caccatctgg ctgtttgggc cggccaccg gggaaagacc aacatcgcag      1260
aagccattgc ccacgccgtg cccttctacg gctgcgtcaa ctggaccaat gagaactttc     1320
ccttcaacga ttgcgtcgac aagatggtga tctggtggga ggagggcaag atgacggcca     1380
aggtcgtgga gtccgccaag gccattctcg gcggcagcaa ggtgcgcgtg gaccaaaagt     1440
gcaagtcgtc cgcccagatc gaccccactc ccgtgatcgt cacctccaac accaacatgt     1500
gcgccgtgat tgacgggaac agcaccacct tcgagcacca gcagcctctc caggaccgga     1560
tgtttaagtt cgaactcacc cgccgtctgg agcacgactt tggcaaggtg acaaagcagg     1620
aagtcaaaga gttcttccgc tgggccagtg atcacgtgac cgaggtggcg catgagtttt     1680
acgtcagaaa gggcggagcc agcaaaagac ccgcccccga tgacgcggat aaaagcgagc     1740
ccaagcgggc ctgcccctca gtcgcggatc catcgacgtc agacgcggaa ggagctccgg     1800
tggactttgc cgacaggtac caaaacaaat gttctcgtca cgcgggcatg cttcagatgc     1860
tgcttccctg caaaacgtgc gagagaatga atcagaattt caacatttgc ttcacacacg     1920
gggtcagaga ctgctcagag tgtttccccg gcgtgtcaga atctcaaccg gtcgtcagaa     1980
agaggacgta tcggaaactc tgtgcgattc atcatctgct ggggcgggct cccgagattg     2040
cttgctcggc ctgcgatctg gtcaacgtgg acctggatga ctgtgtttct gagcaataaa     2100
tgacttaaac caggtatggc tgccgatggt tatcttccag attggctcga ggacaacctc     2160
tctgagggca ttcgcgagtg gtgggcgctg aaacctggag ccccgaagcc aaagccaac      2220 cagcaaaagc aggacgacgg ccggggtctg gtgcttcctg gctacaagta cctcggaccc     2280
ttcaacggac tcgacaaggg ggagcccgtc aacgcggcgg acgcagcggc cctcgagcac     2340
ggcaaggcct acgaccagca gctgcaggcg ggtgacaatc cgtacctgcg gtataaccac     2400
gccgacgccg agtttcagga gcgtctgcaa gaagatacgt cttttggggg caacctcggg     2460
cgagcagtct tccaggccaa gaagcgggtt ctcgaacctc tcggtctggt tgaggaaggc     2520
gctaagacgg ctcctggaaa gaagagaccg gtagagccat caccccagcg ttctccagac     2580
tcctctacgg gcatcggcaa gaaaggccaa cagcccgcca gaaaaagact caattttggt     2640
cagactggcg actcagagtc agttccagac cctcaacctc tcggagaacc tccagcagcg     2700
ccctctggtg tgggacctaa tacaatggct gcaggcggtg gcgcaccaat ggcagacaat     2760
aacgaaggcg ccgacggagt gggtaattcc tcggaaaatt ggcattgcga ttccacatgg     2820
ctgggggaca gagtcatcac caccagcacc cgaacctggg cattgcccac ctacaacaac     2880
```

```
cacctctaca agcaaatctc caatggaaca tcgggaggaa gcaccaacga caacacctac    2940
tttggctaca gcacccoctg ggggtatttt gacttcaaca gattccactg ccacttctca    3000
ccacgtgact ggcagcgact catcaacaac aactggggat tccggccaaa gagactcaac    3060
ttcaagctgt tcaacatcca ggtcaaggag gttacgacga acgaaggcac caagaccatc    3120
gccaataacc ttaccagcac cgtccaggtc tttacggact cggagtacca gctaccgtac    3180
gtcctaggct ctgcccacca aggatgcctg ccaccgtttc tgcagacgt cttcatggtt    3240 cctcagtacg gctacctgac gctcaacaat ggaagtcaag cgttaggacg ttcttctttc    3300
tactgtctgg aatacttccc ttctcagatg ctgagaaccg gcaacaactt tcagttcagc    3360
tacactttcg aggacgtgcc tttccacagc agctacgcac acagccagag tctagatcga    3420
ctgatgaacc ccctcatcga ccagtaccta tactacctgg tcagaacaca gacaactgga    3480
actgggggaa ctcaaacttt ggcattcagc caagcaggcc ctagctcaat ggccaatcag    3540
gctagaaact gggtacccgg gccttgctac cgtcagcagc gcgtctccac aaccaccaac    3600
caaaataaca acagcaactt tgcgtggacg ggagctgcta aattcaagct gaacgggaga    3660
gactcgctaa tgaatcctgg cgtggctatg gcatcgcaca aagacgacga ggaccgcttc    3720
tttccatcaa gtggcgttct catatttggc aagcaaggag ccgggaacga tggagtcgac    3780
tacagccagg tgctgattac agatgaggaa gaaattaaag ccaccaaccc tgtagccaca    3840
gaggaatacg agcagtggc catcaacaac caggccgcta acgcaggc gcaaactgga    3900 cttgtgcata accagggagt tattcctggt atggtctggc agaaccggga cgtgtacctg    3960
cagggcccta tttgggctaa aatacctcac acagatggca actttcaccc gtctcctctg    4020
atgggtggat ttggactgaa acacccacct ccacagattc taattaaaaa tacaccagtg    4080
ccggcagatc ctcctcttac cttcaatcaa gccaagctga actctttcat cacgcagtac    4140
agcacgggac aagtcagcgt ggaaatcgag tgggagctgc agaaagaaaa cagcaagcgc    4200
tggaatccag agatccagta tacttcaaac tactacaaat ctacaaatgt ggactttgct    4260
gtcaatacca aaggtgttta ctctgagcct cgccccattg gtactcgtta cctcacccgt    4320
aatttgtaat tgcctgttaa tcaataaacc ggttaattcg tttcagttga actttggtct    4380
ctgcg                                                                4385
```

<210> SEQ ID NO 6
<211> LENGTH: 4718
<212> TYPE: DNA
<213> ORGANISM: Unknown
<220> FEATURE:
<223> OTHER INFORMATION: adeno-associated virus serotype 1

<400> SEQUENCE: 6

```
ttgcccactc cctctctgcg cgctcgctcg ctcggtgggg cctgcggacc aaaggtccgc      60
agacggcaga gctctgctct gccggcccca ccgagcgagc gagcgcgcag agagggagtg     120
ggcaactcca tcactagggg taatcgcgaa gcgcctccca cgctgccgcg tcagcgctga     180
cgtaaattac gtcataggg agtggtcctg tattagctgt cacgtgagtg cttttgcgac     240
attttgcgac accacgtggc catttagggt atatatggcc gagtgagcga gcaggatctc     300
cattttgacc gcgaaatttg aacgagcagc agccatgccg gcttctacg agatcgtgat     360 caaggtgccg agcgacctgg acgagcacct gccgggcatt tctgactcgt ttgtgagctg     420
ggtggccgag aaggaatggg agctgccccc ggattctgac atggatctga atctgattga     480
```

```
gcaggcaccc ctgaccgtgg ccgagaagct gcagcgcgac ttcctggtcc aatggcgccg    540
cgtgagtaag gccccggagg ccctcttctt tgttcagttc gagaagggcg agtcctactt    600
ccacctccat attctggtgg agaccacggg ggtcaaatcc atggtgctgg ccgcttcct    660 gagtcagatt agggacaagc tggtgcagac catctaccgc gggatcgagc cgaccctgcc    720
caactggttc gcggtgacca agacgcgtaa tggcgccgga ggggggaaca aggtggtgga    780
cgagtgctac atccccaact acctcctgcc caagactcag cccgagctgc agtgggcgtg    840
gactaacatg gaggagtata taagcgcctg tttgaacctg gccgagcgca acggctcgt    900 ggcgcagcac ctgacccacg tcagccagac ccaggagcag aacaaggaga atctgaaccc    960
caattctgac gcgcctgtca tccggtcaaa aacctccgcg cgctacatgg agctggtcgg   1020
gtggctggtg gaccggggca tcacctccga agcagtggg atccaggagg accaggcctc   1080
gtacatctcc ttcaacgccg cttccaactc gcggtcccag atcaaggccg ctctggacaa   1140
tgccggcaag atcatggcgc tgaccaaatc cgcgcccgac tacctggtag gccccgctcc   1200
gcccgcggac attaaaacca accgcatcta ccgcatcctg gagctgaacg gctacgaacc   1260
tgcctacgcc ggctccgtct tctcggctg ggcccagaaa aggttcggga agcgcaacac   1320
catctggctg tttgggccgg ccaccacggg caagaccaac atcgcggaag ccatcgccca   1380
cgccgtgccc ttctacggct gcgtcaactg gaccaatgag aactttccct tcaatgattg   1440
cgtcgacaag atggtgatct ggtgggagga gggcaagatg acggccaagg tcgtggagtc   1500
cgccaaggcc attctcggcg gcagcaaggt gcgcgtggac caaaagtgca agtcgtccgc   1560
ccagatcgac cccacccccg tgatcgtcac ctccaacacc aacatgtgcg ccgtgattga   1620
cgggaacagc accaccttcg agcaccagca gccgttgcag gaccggatgt tcaaatttga   1680
actcacccgc cgtctggagc atgactttgg caaggtgaca aagcaggaag tcaaagagtt   1740
cttccgctgg gcgcaggatc acgtgaccga ggtggcgcat gagttctacg tcagaaaggg   1800
tggagccaac aaaagacccg ccccgatga gcgggataaa agcgagccca agcgggcctg   1860 ccctcagtc gcggatccat cgacgtcaga gcgaaggag gctccggtgg actttgccga   1920
caggtaccaa aacaaatgtt tcgtcacgc gggcatgctt cagatgctgt ttccctgcaa   1980
gacatgcgag agaatgaatc agaatttcaa catttgcttc acgcacggga cgagagactg   2040
ttcagagtgc ttccccggcg tgtcagaatc tcaaccggtc gtcagaaaga ggacgtatcg   2100
gaaactctgt gccattcatc atctgctggg gcgggctccc gagattgctt gctcggcctg   2160
cgatctggtc aacgtggacc tggatgactg tgtttctgag caataaatga cttaaaccag   2220
gtatggctgc cgatggttat cttccagatt ggctcgagga caacctctct gagggcattc   2280
gcgagtggtg ggacttgaaa cctggagccc cgaagcccaa agccaaccag caaaagcagg   2340
acgacggccg gggtctggtg cttcctggct acaagtacct cggacccttc aacggactcg   2400
acaaggggga gcccgtcaac gcggcggacg cagcggccct cgagcacgac aaggcctacg   2460
accagcagct caaagcgggt gacaatccgt acctgcggta taaccacgcc gacgccgagt   2520
ttcaggagcg tctgcaagaa gatacgtctt ttgggggcaa cctcgggcga gcagtcttcc   2580
aggccaagaa gcgggttctc gaacctctcg gtctggttga ggaagcgct aagacggctc   2640 ctggaaagaa acgtccggta gagcagtcgc acaagagcc agactcctcc tcgggcatcg   2700
gcaagacagg ccagcagccc gctaaaaaga gactcaatt tggtcagact ggcgactcag   2760
agtcagtccc cgatccacaa cctctcggag aacctccagc aaccccgct gctgtgggac   2820 ctactacaat ggcttcaggc ggtggcgcac caatggcaga caataacgaa ggcgccgacg   2880
```

```
gagtgggtaa tgcctcagga aattggcatt gcgattccac atggctgggc gacagagtca    2940
tcaccaccag cacccgcacc tgggccttgc ccacctacaa taaccacctc tacaagcaaa    3000
tctccagtgc ttcaacgggg gccagcaacg acaaccacta cttcggctac agcaccccct    3060
gggggtattt tgatttcaac agattccact gccacttttc accacgtgac tggcagcgac    3120
tcatcaacaa caattgggga ttccggccca agagactcaa cttcaaactc ttcaacatcc    3180
aagtcaagga ggtcacgacg aatgatgcg tcacaaccat cgctaataac cttaccagca    3240
cggttcaagt cttctcggac tcggagtacc agcttccgta cgtcctcggc tctgcgcacc    3300
agggctgcct ccctccgttc ccggcggacg tgttcatgat tccgcaatac ggctacctga    3360
cgctcaacaa tggcagccaa gccgtgggac gttcatcctt ttactgcctg aatatttcc     3420 cttctcagat gctgagaacg ggcaacaact ttaccttcag ctacaccttt gaggaagtgc    3480 cttttccacag cagctacgcg cacagccaga gcctggaccg gctgatgaat cctctcatcg   3540
accaatacct gtattacctg aacagaactc aaaatcagtc cggaagtgcc caaaacaagg    3600
acttgctgtt tagccgtggg tctccagctg gcatgtctgt tcagcccaaa aactggctac   3660
ctggaccctg ttatcggcag cagcgcgttt ctaaaacaaa aacagacaac aacaacagca    3720
attttacctg gactggtgct tcaaaatata acctcaatgg gcgtgaatcc atcatcaacc    3780
ctggcactgc tatggcctca cacaaagacg acgaagacaa gttcttccc atgagcggtg     3840 tcatgatttt tggaaaagag agcgccggag cttcaaacac tgcattggac aatgtcatga    3900
ttacagacga agaggaaatt aaagccacta accctgtggc caccgaaaga tttgggaccg    3960
tggcagtcaa tttccagagc agcagcacag accctgcgac cggagatgtg catgctatgg    4020
gagcattacc tggcatggtg tggcaagata gagacgtgta cctgcagggt cccatttggg   4080
ccaaaattcc tcacacagat ggacactttc acccgtctcc tcttatgggc ggctttggac    4140
tcaagaaccc gcctcctcag atcctcatca aaaacacgcc tgttcctgcg aatcctccgg    4200
cggagttttc agctacaaag tttgcttcat tcatcaccca atactccaca ggacaagtga    4260
gtgtggaaat tgaatgggag ctgcagaaag aaaacagcaa gcgctggaat cccgaagtgc    4320
agtacacatc caattatgca aaatctgcca acgttgattt tactgtggac aacaatggac    4380
tttatactga gctcgcccc attggcaccc gttaccttac ccgtcccctg taattacgtg     4440
ttaatcaata aaccggttga ttcgtttcag ttgaactttg gtctcctgtc cttcttatct    4500
tatcggttac catggttata gcttacacat taactgcttg gttgcgcttc gcgataaaag    4560
acttacgtca tcgggttacc cctagtgatg gagttgccca ctccctctct gcgcgctcgc    4620
tcgctcggtg gggcctgcgg accaaggtc cgcagacggc agagctctgc tctgccggcc     4680
ccaccgagcg agcgagcgcg cagagaggga gtgggcaa                           4718
```

<210> SEQ ID NO 7
<211> LENGTH: 4675
<212> TYPE: DNA
<213> ORGANISM: adeno-associated virus 2

<400> SEQUENCE: 7

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctggagg ggtggagtcg tgacgtgaat tacgtcatag    180
ggttagggag gtcctgtatt agaggtcacg tgagtgtttt gcgacatttt gcgacaccat    240
```

| | |
|---|---|
| gtggtcacgc tgggtattta agcccgagtg agcacgcagg gtctccattt tgaagcggga | 300 |
| ggtttgaacg cgcagccgcc atgccggggt tttacgagat tgtgattaag gtccccagcg | 360 |
| accttgacgg gcatctgccc ggcatttctg acagctttgt gaactgggtg gccgagaagg | 420 |
| aatgggagtt gccgccagat tctgacatgg atctgaatct gattgagcag gcacccctga | 480 |
| ccgtggccga aagctgcag cgcgactttc tgacggaatg gcgccgtgtg agtaaggccc | 540 |
| cggaggcccct tttctttgtg caatttgaga agggagagag ctacttccac atgcacgtgc | 600 |
| tcgtggaaac caccggggtg aaatccatgg ttttgggacg tttcctgagt cagattcgcg | 660 |
| aaaaactgat tcagagaatt taccgcggga tcgagccgac tttgccaaac tggttcgcgg | 720 |
| tcacaaagac cagaaatggc gccggaggcg ggaacaaggt ggtggatgag tgctacatcc | 780 |
| ccaattactt gctccccaaa acccagcctg agctccagtg ggcgtggact aatatggaac | 840 |
| agtatttaag cgcctgtttg aatctcacgg agcgtaaacg gttggtggcg cagcatctga | 900 |
| cgcacgtgtc gcagacgcag gagcagaaca aagagaatca gaatcccaat tctgatgcgc | 960 |
| cggtgatcag atcaaaaact tcagccaggt acatggagct ggtcgggtgg ctcgtggaca | 1020 |
| aggggattac ctcggagaag cagtggatcc aggaggacca ggcctcatac atctccttca | 1080 |
| atgcggcctc caactcgcgg tcccaaatca aggctgcctt ggacaatgcg ggaaagatta | 1140 |
| tgagcctgac taaaaccgcc cccgactacc tggtgggcca gcagcccgtg gaggacattt | 1200 |
| ccagcaatcg gatttataaa attttggaac taaacgggta cgatcccaa tatgcggctt | 1260 |
| ccgtctttct gggatgggcc acgaaaaagt tcggcaagag gaacaccatc tggctgtttg | 1320 |
| ggcctgcaac taccgggaag accaacatcg cggaggccat agcccacact gtgcccttct | 1380 |
| acgggtgcgt aaactggacc aatgagaact ttcccttcaa cgactgtgtc gacaagatgg | 1440 |
| tgatctggtg ggaggagggg aagatgaccg ccaaggtcgt ggagtcggcc aaagccattc | 1500 |
| tcggaggaag caaggtgcgc gtggaccaga aatgcaagtc ctcggcccag atagacccga | 1560 |
| ctcccgtgat cgtcacctcc aacaccaaca tgtgcgccgt gattgacggg aactcaacga | 1620 |
| ccttcgaaca ccagcagccg ttgcaagacc ggatgttcaa atttgaactc acccgccgtc | 1680 |
| tggatcatga ctttgggaag gtcaccagc aggaagtcaa agacttttttc cggtgggcaa | 1740 |
| aggatcacgt ggttgaggtg gagcatgaat tctacgtcaa aaagggtgga gccaagaaaa | 1800 |
| gacccgcccc cagtgacgca gatataagtg agcccaaacg ggtgcgcgag tcagttgcgc | 1860 |
| agccatcgac gtcagacgcg gaagcttcga tcaactacgc agacaggtac caaaacaaat | 1920 |
| gttctcgtca cgtgggcatg aatctgatgc tgtttccctg cagacaatgc gagagaatga | 1980 |
| atcagaattc aaatatctgc ttcactcacg gacagaaaga ctgtttagag tgctttcccg | 2040 |
| tgtcagaatc tcaacccgtt tctgtcgtca aaaaggcgta tcagaaactg tgctacattc | 2100 |
| atcatatcat gggaaaggtg ccagacgctt gcactgcctg cgatctggtc aatgtggatt | 2160 |
| tggatgactg catctttgaa caataaatga tttaaatcag gtatggctgc cgatggttat | 2220 |
| cttccagatt ggctcgagga cactctctct gaaggaataa gacagtggtg gaagctcaaa | 2280 |
| cctggcccac caccaccaaa gcccgcagag cggcataagg acgacagcag gggtcttgtg | 2340 |
| cttcctgggt acaagtacct cggacccttc aacggactcg acaagggaga gccggtcaac | 2400 |
| gaggcagacg ccgcggccct cgagcacgta caaagcctac gaccggcagc tcgacagcgg | 2460 |
| agacaacccg tacctcaagt acaaccacgc cgacgcggag tttcaggagc gccttaaaga | 2520 |
| agatacgtct tttgggggca acctcggacg agcagtcttc caggcgaaaa agagggttct | 2580 |
| tgaacctctg ggcctggttg aggaacctgt taagacggct ccgggaaaaa agaggccggt | 2640 |

```
agagcactct cctgtggagc cagactcctc ctcgggaacc ggaaaggcgg gccagcagcc    2700
tgcaagaaaa agattgaatt ttggtcagac tggagacgca gactcagtac ctgacccca    2760 gcctctcgga cagccaccag cagccccctc tggtctggga actaatacga tggctacagg    2820
cagtggcgca ccaatggcag acaataacga gggcgccgac ggagtgggta attcctccgg    2880
aaattggcat tgcgattcca catggatggg cgacagagtc atcaccacca gcacccgaac    2940
ctgggccctg cccacctaca caaccacct ctacaaacaa atttccagcc aatcaggagc    3000
ctcgaacgac aatcactact ttggctacag cacccttgg gggtattttg acttcaacag    3060
attccactgc cacttttcac cacgtgactg gcaaagactc atcaacaaca actggggatt    3120
ccgacccaag agactcaact tcaagctctt taacattcaa gtcaaagagg tcacgcagaa    3180
tgacggtacg acgacgattg ccaataacct taccagcacg gttcaggtgt ttactgactc    3240
ggagtaccag ctcccgtacg tcctcggctc ggcgcatcaa ggatgcctcc cgccgttccc    3300
agcagacgtc ttcatggtgc acagtatgg atacctcacc ctgaacaacg ggagtcaggc    3360
agtaggacgc tcttcatttt actgcctgga gtactttcct tctcagatgc tgcgtaccgg    3420
aaacaacttt accttcagct cacttttga ggacgttcct ttccacagca gctacgctca    3480
cagccagagt ctggaccgtc tcatgaatcc tctcatcgac cagtacctgt attacttgag    3540
cagaacaaac actccaagtg aaccaccac gcagtcaagg cttcagtttt tcaggccgg    3600 agcgagtgac attcgggacc agtctaggaa ctggcttcct ggaccctgtt accgccagca    3660
gcgagtatca agacatctg cggataacaa caacagtgaa tactcgtgga ctggagctac    3720
caagtaccac ctcaatggca gagactctct ggtgaatccg ccatggcaa gccacaagga    3780 cgatgaagaa aagttttttc ctcagagcgg ggttctcatc tttgggaagc aaggctcaga    3840
gaaaacaaat gtgaacattg aaaaggtcat gattacagac gaagaggaaa tcggaacaac    3900
caatcccgtg gctacggagc agtatggttc tgtatctacc aacctccaga gaggcaacag    3960
acaagcagct accgcagatg tcaacacaca aggcgttctt ccaggcatgg tctggcagga    4020
cagagatgtg taccttcagg ggcccatctg ggcaaagatt ccacacacgg acggacattt    4080 tcaccctct ccctcatgg gtggattcgg acttaaacac cctctccac agattctcat    4140 caagaacacc ccggtacctg cgaatccttc gaccaccttc agtgcggcaa agtttgcttc    4200
cttcatcaca cagtactcca cgggacacg tcagcgtgga gatcgagtgg gagctgcaga    4260
aggaaaacag caaacgctgg aatcccgaaa ttcagtacac ttccaactac aacaagtctg    4320
ttaatcgtgg acttaccgtg gatactaatg gcgtgtattc agagcctcgc cccattggca    4380
ccagatacct gactcgtaat ctgtaattgc ttgttaatca ataaaccgtt taattcgttt    4440
cagttgaact ttggtctctg cgtatttctt tcttatctag tttccatggc tacgtagata    4500
agtagcatgg cgggttaatc attaactaca aggaacccct agtgatggag ttggccactc    4560
cctctctgcg cgctcgctcg ctcactgagg ccgggcgacc aaaggtcgcc cgacgcccgg    4620
gctttgcccg gcggcctca gtgagcgagc gagcgcgcag agagggagtg gccaa         4675

<210> SEQ ID NO 8
<211> LENGTH: 4726
<212> TYPE: DNA
<213> ORGANISM: adeno-associated virus 3

<400> SEQUENCE: 8
ttggccactc cctctatgcg cactcgctcg ctcggtgggg cctggcgacc aaaggtcgcc       60
```

```
agacggacgt gctttgcacg tccggcccca ccgagcgagc gagtgcgcat agagggagtg    120
gccaactcca tcactagagg tatggcagtg acgtaacgcg aagcgcgcga agcgagacca    180
cgcctaccag ctgcgtcagc agtcaggtga ccctttttgcg acagtttgcg acaccacgtg    240
gccgctgagg gtatatattc tcgagtgagc gaaccaggag ctccattttg accgcgaaat    300
ttgaacgagc agcagccatg ccggggttct acgagattgt cctgaaggtc ccgagtgacc    360
tggacgagcg cctgccgggc atttctaact cgtttgttaa ctgggtggcc gagaaggaat    420
gggacgtgcc gccggattct gacatggatc cgaatctgat tgagcaggca cccctgaccg    480
tggccgaaaa gcttcagcgc gagttcctgg tggagtggcg ccgcgtgagt aaggccccgg    540
aggccctctt ttttgtccag ttcgaaaagg gggagaccta cttccacctg cacgtgctga    600
ttgagaccat cggggtcaaa tccatggtgg tcggccgcta cgtgagccag attaaagaga    660
agctggtgac ccgcatctac cgcggggtcg agccgcagct tccgaactgg ttcgcggtga    720
ccaaaacgcg aaatggcgcc gggggcggga acaaggtggt ggacgactgc tacatcccca    780
actacctgct ccccaagacc cagccccgagc tccagtgggg gtggactaac atggaccagt    840
atttaagcgc ctgtttgaat ctcgcggagc gtaaacggct ggtggcgcag catctgacgc    900
acgtgtcgca gacgcaggag cagaacaaag agaatcagaa ccccaattct gacgcgccgg    960
tcatcaggtc aaaaacctca gccaggtaca tggagctggt cgggtggctg gtggaccgcg   1020
ggatcacgtc agaaaagcaa tggattcagg aggaccaggc ctcgtacatc tccttcaacg   1080
ccgcctccaa ctcgcggtcc cagatcaagg ccgcgctgga caatgcctcc aagatcatga   1140
gcctgacaaa gacggctccg gactacctgg tgggcagcaa cccgccggag gacattacca   1200
aaaatcggat ctaccaaatc ctggagctga acgggtacga tccgcagtac gcggcctccg   1260
tcttcctggg ctgggcgcaa aagaagttcg ggaagaggaa caccatctgg ctctttgggc   1320
cggccacgac gggtaaaacc aacatcgcgg aagccatcgc ccacgccgtg cccttctacg   1380
gctgcgtaaa ctgaccaat gagaactttc ccttcaacga ttgcgtcgac aagatggtga   1440
tctggtggga ggagggcaag atgacggcca aggtcgtgga gagcgccaag gccattctgg   1500
gcggaagcaa ggtgcgcgtg gaccaaaagt gcaagtcatc ggcccagatc gaacccactc   1560
ccgtgatcgt cacctccaac accaacatgt gcgccgtgat tgacgggaac agcaccacct   1620
tcgagcatca gcgccgctg caggaccgga tgtttgaatt tgaacttacc cgccgtttgg   1680
accatgactt tgggaaggtc accaaacagg aagtaaagga cttttttccgg tgggcttccg   1740 atcacgtgac tgacgtggct catgagttct acgtcagaaa gggtgagct aagaaacgcc   1800 ccgcctccaa tgacgcggat gtaagcgagc caaaacggga gtgcacgtca cttgcgcagc   1860
cgacaacgtc agacgcggaa gcaccggcgg actacgcgga caggtaccaa aacaaatgtt   1920
ctcgtcacgt gggcatgaat ctgatgcttt ttccctgtaa aacatgcgag agaatgaatc   1980 aaattttccaa tgtctgtttt acgcatggtc aaagagactg tggggaatgc ttccctggaa   2040
tgtcagaatc tcaacccgtt tctgtcgtca aaaagaagac ttatcagaaa ctgtgtccaa   2100
ttcatcatat cctgggaagg gcacccgaga ttgcctgttc ggcctgcgat ttggccaatg   2160
tggacttgga tgactgtgtt tctgagcaat aaatgactta aaccaggtat ggctgctgac   2220
ggttatcttc cagattggct cgaggacaac ctttctgaag gcattcgtga gtggtgggct   2280
ctgaaacctg gagtccctca acccaaagcg aaccaacaac accaggacaa ccgtcggggt   2340
cttgtgcttc cgggttacaa atacctcgga cccggtaacg gactcgacaa aggagagccg   2400
gtcaacgagg cggacgcggc agccctcgaa cacgacaaag cttacgacca gcagctcaag   2460
```

```
gccggtgaca acccgtacct caagtacaac cacgccgacg ccgagtttca ggagcgtctt    2520
caagaagata cgtcttttgg gggcaacctt ggcagagcag tcttccaggc caaaaagagg    2580
atccttgagc tcttggtct  ggttgaggaa gcagctaaaa cggctcctgg aaagaagggg    2640
gctgtagatc agtctcctca ggaaccggac tcatcatctg gtgttggcaa atcgggcaaa    2700
cagcctgcca gaaaaagact aaatttcggt cagactggag actcagagtc agtcccagac    2760
cctcaacctc tcggagaacc accagcagcc cccacaagtt tgggatctaa tacaatggct    2820
tcaggcggtg gcgcaccaat ggcagacaat aacgagggtg ccgatggagt gggtaattcc    2880
tcaggaaatt ggcattgcga ttcccaatgg ctgggcgaca gagtcatcac caccagcacc    2940
agaacctggg ccctgcccac ttacaacaac catctctaca gcaaatctc  cagccaatca    3000 ggagcttcaa acgacaacca ctactttggc tacagcaccc cttgggggta ttttgacttt    3060
aacagattcc actgccactt ctcaccacgt gactggcagc gactcattaa caacaactgg    3120
ggattccggc ccaagaaact cagcttcaag ctcttcaaca tccaagttag aggggtcacg    3180
cagaacgatg gcacgacgac tattgccaat aaccttacca gcacggttca agtgtttacg    3240
gactcggagt atcagctccc gtacgtgctc gggtcggcgc accaaggctg tctcccgccg    3300
tttccagcgg acgtcttcat ggtccctcag tatggatacc tcaccctgaa caacggaagt    3360
caagcggtgg gacgctcatc ttttactgc  ctggagtact tcccttcgca gatgctaagg    3420
actggaaata acttccaatt cagctatacc ttcgaggatg tacctttcca gcagctac     3480 gctcacagcc agagtttgga tcgcttgatg aatcctctta ttgatcagta tctgtactac    3540
ctgaacagaa cgcaaggaac aacctctgga acaaccaacc aatcacggct gcttttagc    3600 caggctgggc ctcagtctat gtcttttcag ccagaaatt  ggctacctgg gccctgctac    3660
cggcaacaga gactttcaaa gactgctaac gacaacaaca acagtaactt ccttggaca    3720 gcggccagca aatatcatct caatggccgc gactcgctgg tgaatccagg accagctatg    3780
gccagtcaca aggacgatga agaaaaattt ttccctatgc acggcaatct aatatttggc    3840
aaagaaggga caacggcaag taacgcgaaa ttagataatg taatgattac ggatgaagaa    3900
gagattcgta ccaccaatcc tgtggcaaca gagcagtatg gaactgtggc aaataacttg    3960
cagagctcaa atacagctcc cacgactgga actgtcaatc atcagggggc cttacctggc    4020
atggtgtggc aagatcgtga cgtgtacctt caaggaccta tctgggcaaa gattcctcac    4080
acggatggac actttcatcc ttctcctctg atgggaggct ttggactgaa acatccgcct    4140
cctcaaatca tgatcaaaaa tactccggta ccggcaaatc ctccgacgac tttcagcccg    4200
gccaagtttg cttcatttat cactcagtac tccactggac aggtcagcgt ggaaattgag    4260
tgggagctac agaagaaaa  cagcaaacgt tggaatccag agattcagta cacttccaac    4320
tacaacaagt ctgttaatgt ggactttact gtagacacta atggtgttta tagtgaacct    4380
cgccctattg aacccggta  tctcacacga aacttgtgaa tcctggttaa tcaataaacc    4440
gtttaattcg tttcagttga actttggctc ttgtgcactt ctttatcttt atcttgtttc    4500
catggctact gcgtagataa gcagcggcct gcggcgcttg cgcttcgcgg tttacaactg    4560
ctggttaata tttaactctc gccataccct tagtgatgga gttggccact ccctctatgc    4620
gcactcgctc gctcggtggg gcctggcgac caaaggtcgc cagacggacg tgctttgcac    4680
gtccggcccc accgagcgag cgagtgcgca tagagggagt ggccaa              4726
```

<210> SEQ ID NO 9

<211> LENGTH: 3098
<212> TYPE: DNA
<213> ORGANISM: Unknown
<220> FEATURE:
<223> OTHER INFORMATION: AAV serotype, clone 42.2

<400> SEQUENCE: 9

| | | | | | |
|---|---|---|---|---|---|
| gaattcgccc | tttctacggc | tgcgtcaact | ggaccaatga | gaactttccc | ttcaacgatt | 60 |
| gcgtcgacaa | gatggtgatc | tggtgggagg | agggcaagat | gacggccaag | gtcgtggagt | 120 |
| ccgccaaggc | cattctcggc | ggcagcaagg | tgcgcgtgga | ccaaaagtgc | aagtcttccg | 180 |
| cccagatcga | tcccaccccc | gtgatcgtca | cttccaacac | caacatgtgc | gctgtgattg | 240 |
| acgggaacag | caccaccttc | gagcaccagc | agccgttaca | agaccggatg | ttcaaatttg | 300 |
| aactcacccg | ccgtctggag | cacgactttg | gcaaggtgac | aaagcaggaa | gtcaaagagt | 360 |
| tcttccgctg | ggcgcaggat | cacgtgaccg | aggtggcgca | tgagttctac | gtcagaaagg | 420 |
| gtggagccaa | caagagaccc | gcccccgatg | acgcggataa | aagcgagccc | aagcgggcct | 480 |
| gcccctcagt | cgcggatcca | tcgacgtcag | acgcggaagg | agctccggtg | actttgccg | 540 |
| acaggtacca | aaacaaatgt | tctcgtcacg | cgggcatgct | tcagatgctg | tttccctgca | 600 |
| agacatgcga | gagaatgaat | cagaatttca | acatttgctt | cacgcacggg | accagagact | 660 |
| gttcagaatg | tttccccggc | gtgtcagaat | ctcaaccggt | cgtcagaaag | aggacgtatc | 720 |
| ggaaactctg | tgccattcat | catctgctgg | ggcgggctcc | cgagattgct | tgctcggcct | 780 |
| gcgatctggt | caacgtggac | ctggatgacc | gtgtttctga | caataaatg | acttaaacca | 840 |
| ggtatggctg | ccgatggtta | tcttccagat | tggctcgagg | acaacctctc | tgagggcatt | 900 |
| cgcgagtggt | gggacttgaa | acctggagcc | ccgaaaccca | agccaaccca | gcaaaagcag | 960 |
| gacgacggcc | ggggtctggt | gcttcctggc | tacaagtacc | tcggacccct | caacggactc | 1020 |
| gacaagggag | agccggtcaa | cgaggcagac | gccgcggccc | tcgagcacga | caaggcctac | 1080 |
| gacaagcagc | tcgagcaggg | ggacaacccg | tacctcaagt | acaaccacgc | cgacgccgag | 1140 |
| tttcaggagc | gtcttcaaga | agatacgtct | ttgggggca | acctcggcg | agcagtcttc | 1200 |
| caggccaaga | agcgggttct | cgaacctctc | ggtctggttg | aggaaggcgc | taagacggct | 1260 |
| cctggaaaga | agagacccat | agaatccccc | gactcctcca | cgggcatcgg | caagaaaggc | 1320 |
| cagcagcccg | ctaaaaagaa | gctcaacttt | gggcagactg | gcgactcaga | gtcagtgccc | 1380 |
| gacccccaac | ctctcggaga | acctccgcc | gcgccctcag | gtctgggatc | tggtacaatg | 1440 |
| gctgcaggcg | gtggcgcacc | aatggcagac | aataacgaag | gcgccgacgg | agtgggtaat | 1500 |
| gcctccggaa | attggcattg | cgattccaca | tggctgggcg | acagagtcat | caccaccagc | 1560 |
| acccgcacct | gggcgctgcc | cacctacaac | aaccacctct | acaagcagat | atcaagtcag | 1620 |
| agcggggcta | ccaacgacaa | ccacttcttc | ggctacagca | cccctgggg | ctattttgac | 1680 |
| ttcaacagat | tccactgcca | cttctcacca | cgtgactggc | agcgactcat | caacaacaac | 1740 |
| tggggattcc | ggcccagaa | gctgcggttc | aagttgttca | acatccaggt | caaggaggtc | 1800 |
| acgacgaacg | acggcgttac | gaccatcgct | aataaccta | ccagcacgat | tcaggtcttc | 1860 |
| tcggactcgg | agtaccaact | gccgtacgtc | ctcggctctg | cgcaccaggg | ctgcctccct | 1920 |
| ccgttccctg | cggacgtgtt | catgattcct | cagtacggat | atctgactct | aaacaacggc | 1980 |
| agtcagtctg | tgggacgttc | ctccttctac | tgcctggagt | actttccttc | tcagatgctg | 2040 |
| agaacgggca | taactttga | attcagctac | acctttgagg | aagtgccttt | ccacagcagc | 2100 |
| tatgcgcaca | gccagagcct | ggaccggctg | atgaatcccc | tcatcgacca | gtacctgtac | 2160 |

| | |
|---|---|
| tacctggccc ggacccagag cactacgggg tccacaaggg agctgcagtt ccatcaggct | 2220 |
| gggcccaaca ccatggccga gcaatcaaag aactggctgc ccggaccctg ttatcggcag | 2280 |
| cagagactgt caaaaaacat agacagcaac aacaacagta actttgcctg gaccggggcc | 2340 |
| actaaatacc atctgaatgg tagaaaattca ttaaccaacc cgggcgtagc catggccacc | 2400 |
| aacaaggacg acgaggacca gttctttccc atcaacggag tgctggtttt tggcgaaacg | 2460 |
| ggggctgcca acaagacaac gctggaaaac gtgctaatga ccagcgagga ggagatcaaa | 2520 |
| accaccaatc ccgtggctac agaagaatac ggtgtggtct ccagcaacct gcaatcgtct | 2580 |
| acggccggac cccagacaca gactgtcaac agccaggggg ctctgcccgg catggtctgg | 2640 |
| cagaaccggg acgtgtacct gcagggtccc atctgggcca aaattcctca cacggacggc | 2700 |
| aactttcacc cgtctcccct gatgggcgga tttggactca acacccgcc tcctcaaatt | 2760 |
| ctcatcaaaa acaccccggt acctgctaat cctccagagg tgtttactcc tgccaagttt | 2820 |
| gcctcattta tcacgcagta cagcaccggc caggtcagcg tggagatcga gtgggaactg | 2880 |
| cagaaagaaa acagcaaacg ctggaatcca gagattcagt acacctcaaa ttatgccaag | 2940 |
| tctaataatg tggaatttgc tgtcaacaac gaagggggttt atactgagcc tcgcccccatt | 3000 |
| ggcacccgtt acctcacccg taacctgtaa ttgcctgtta atcaataaac cggttaattc | 3060 |
| gtttcagttg aactttggtc tctgcgaagg gcgaattc | 3098 |

<210> SEQ ID NO 10
<211> LENGTH: 3098
<212> TYPE: DNA
<213> ORGANISM: Unknown
<220> FEATURE:
<223> OTHER INFORMATION: AAV serotype, clone 16.3

<400> SEQUENCE: 10

| | |
|---|---|
| gaattcgccc ttcgcagaga ccaaagttca actgaaacga atcaaccggt ttattgatta | 60 |
| acaagtaatt acaggttacg ggtgaggtaa cgggtgccaa tggggcgagg ctcagtataa | 120 |
| accccttcgt tgttgacagc aaattccaca ttattagact tggcataatt tgaggtgtac | 180 |
| tgaatctctg gattccagcg tttgctgttt tctttctgca gttccactc gatctccacg | 240 |
| ctgacctggc cggtgctgta ctgcgtgata aatgaggcaa actaggcagg agtaaacacc | 300 |
| cctggaggat tagcaggtac cggggtgttt ttgatgagaa tttgaggagg cgggtgtttg | 360 |
| agtccaaatc cgcccatcag gggagacggg tgaaagttgc cgtccgtgtg aggaattttg | 420 |
| gcccagatgg gaccctgcag gtacacgtcc cggttctgcc agaccatgcc gggcagagcc | 480 |
| ccctggctgt tgacagtctg tgtctggggt ccggccgtag acgattgcag gttgctggag | 540 |
| accacaccgt attcttctgt agccacggga ttggtggttt tgatctcctc ctcgctggtc | 600 |
| attagcacgt tttccagcgt tgtcttgttg gcagcccccg ttttgccaaa aaccagcact | 660 |
| ccgttgatgg gaaagaactg gccctcgtcg tccttgttgg tggccatggc tacgcccggg | 720 |
| ttggttaatg aatttctacc attcagatgg tatttagtgg ccccggtcca ggcaaagtta | 780 |
| ctgttgttgt tgctgtctat gtttttttgac agtctctgct gccgataaca gggtccgggc | 840 |
| agccagttct tgattgctcg gccatggtgt ttgggcccag cctgatgaa ctgcagctcc | 900 |
| cttgtggacc ccgtagtgct ctgggtccgg gccaggtagt acaggtactg gtcgatgagg | 960 |
| ggattcatca gccggtccag gctctggctg tgcgcatagc tgctgtggaa aggcacttcc | 1020 |
| tcaaaggtgt agctgaattc aaagttattg cccgttctca gcatctgaga aggaaagtac | 1080 |

```
tccaggcagt agaaggagga acgtcccata gactgactgc cgttgtttag agtcagatat    1140
ccgtactgag gaatcatgaa cacgtccgca gggaacggag ggaggcagcc ctggtgcgca    1200
gagccgagga cgtacggcag ttggtactcc gagtccgaga agacctgaat cgtgctggta    1260
aggttattag cgatggtcgt aacgccgtcg ttcgtcgtga cctccttgac ctggatgttg    1320
aacaacttga accgcagctt tctgggccgg aatccccagt tgttgttgat gagtcgctgc    1380
cagtcacgtg gtgagaagtg gcagtggaat ctgttgaagt caaaatagcc caggggggtg    1440
ctgtagccga agaagtggtt gtcgttggta gccccgctct gacttgatat ctgcttgtag    1500
aggtggttgt tgtaggtggg cagggcccag gtgcgggtgc tggtggtgat gactctgtcg    1560
cccagccatg tggaatcgca atgccaattt ccggaggcat acccactcc gtcggcgcct    1620 tcgttattgt ctgccattgg tgcgccaccg cctgcagcca ttgtaccaga tcccagacct    1680
gagggcgcgg cgggaggttc tccgagaggt tgggggtcgg gcactgactc tgagtcgcca    1740
gtctgcccaa agttgagctt cttttttagcg ggctgctggc cttcttgcc gatgcccgtg    1800 gaggagtcgg gggattctat gggtctcttc tttccaggag ccgtcttagc gccttcctca    1860
accagaccga gaggttcgag aacccgcttc ttggcctgga agactgctcg cccgaggttg    1920
cccccaaaag acgtatcttc ttgaagacgc tcctgaaact cagcgtcggc gtggttgtac    1980
ttgaggtacg ggttgtcccc ctgctcgagc tgcttgtcgt aggccttgtc gtgctcgagg    2040
gccgcggcgt ctgcctcgtt gaccggctct cccttgtcga gtccgttgaa gggtccgagg    2100
tacttgtagc caggaagcac cagaccccgg ccgtcgtcct gcttttgctg gttggctttg    2160
ggtttcgggg ctccaggttt caagtcccac cactcgcgaa tgccctcaga gaggttgtcc    2220
tcgagccaat ctggaagata accatcggca gccataccctg gtttaagtca tttattgctc    2280
agaaacacag tcatccaggt ccacgttgac cagatcgcag gccagcaag caatctcggg    2340 agcccgcccc agcagatgat gaatggcaca gagtttccga tacgtcctct ttctgacgac    2400
cggttgagat tctgacacgc cggggaaaca ttctgaacag tctctggtcc cgtgcgtgaa    2460
gcaaatgttg aaattctgat tcattctctc gcatgtcttg cagggaaaca gcatctgaag    2520
catgcccgcg tgacgagaac atttgttttg gtacctgtcg gcaaagtcca ccggagctcc    2580
ttccgcgtct gacgtcgatg gatccgcgac tgaggggcag gcccgcttgg gctcgctttt    2640
atccgcgtca tcggggcgg gcctcttgtt ggctccaccc tttctgacgt agaactcatg    2700
cgccacctcg gtcacgtgat cctgcgccca gcggaagaac tctttgactt cctgctttgt    2760
caccttgcca aagtcctgct ccagacgcg ggtgagttca aatttgaaca tccggtcttg    2820
taacggctgc tggtgctcga aggtggtgct gttcccgtca atcacggcgc acatgttggt    2880
gttggaagtg acgatcacgg gggtgggatc gatctgggcg gacgacttgc acttttggtc    2940
cacgcgcacc ttgctgccgc cgagaatggc cttggcggac tccacgacct tggccgtcat    3000
cttgccctcc tcccaccaga tcaccatctt gtcgacgcaa tcgttgaagg gaaagttctc    3060
attggtccag ttgacgcagc cgtagaaagg gcgaattc                            3098
```

<210> SEQ ID NO 11
<211> LENGTH: 3121
<212> TYPE: DNA
<213> ORGANISM: Unknown
<220> FEATURE:
<223> OTHER INFORMATION: AAV serotype, clone 29.3

<400> SEQUENCE: 11

```
gaattcgccc ttcgcagaga ccaaagttca actgaaacga atcaaccggt ttattgatta     60
```

```
acaagcaatt acagattacg ggtgaggtaa cgggtgccga tggggcgagg ctcagaataa      120
gtgccatctg tgttaacagc aaagtccaca tttgtagatt tgtagtagtt ggaagtgtat      180
tgaatctctg ggttccagcg tttgctgttt tctttctgca gctcccattc aatttccacg      240
ctgacctgtc cggtgctgta ctgcgtgatg aacgacgcca gcttagcttg actgaaggta      300
gttggaggat ccgcgggaac aggtgtattc ttaatcagga tctgaggagg cgggtgtttc      360
agtccaaagc cccccatcag cggcgaggga tgaaagtttc cgtccgtgtg aggaatcttg      420
gcccagatag gaccctgcag gtacacgtcc cggttctgcc agaccatgcc aggtaaggct      480
ccttgactgt tgacgccccc tacaatagga gcggcgtttt gctgttgcag gttatcggcc      540
accacgccgt actgttctgt ggccactggg ttggtggttt taatttcttc ctcactggtt      600
agcataacgc tgctatagtc cacgttgcct tttccagctc cctgtttccc aaacattaag      660
actccgctgg acggaaaaaa tcgctcttcg tcgtccttgt gggttgccat agcgacaccg      720
ggatttacca gagagtctct gccattcaga tgatacttgg tggcaccggt ccaggcaaag      780
ttgctgttgt tattttgcga cagtgtcgtg agacgcgtt gctgccggta gcagggcccg       840
ggtagccagt ttttggcctg agccgacatg ttattaggcc cggcctgaga aaatagcaac      900
tgctgagttc ctgcggtacc tcccgtggac tgagtccgag acaggtagta caggtactgg      960
tcgatgaggg ggttcatcag ccggtccagg ctttggctgt gcgcgtagct gctgtgaaaa     1020
ggcacgtcct caaactggta gctgaactca agttgttgc ccgttctcag catttgagaa      1080
ggaaagtact ccaggcagta aaggaggaa cggcccacgg cctgactgcc attgttcaga      1140
gtcaggtacc cgtactgagg aatcatgaag acgtccgccg ggaacggagg caggcagccc     1200
tggcgcgcag agccgaggac gtacgggagc tggtattccg agtccgtaaa gacctgaatc     1260
gtgctggtaa ggttattggc gatggtcttg gtgccttcat tctgcgtgac ctccttgacc     1320
tggatgttga agagcttgaa gttgagtctc ttgggccgga atccccagtt gttgttgatg     1380
agtcgctgcc agtcacgtgg tgagaagtgg cagtggaatc tgttaaagtc aaaataccc      1440 caggggtgc tgtagccgaa gtaggtgttg tcgttggtgc ttcctcccga agtcccgttg      1500
gagatttgct tgtagaggtg gttgttgtag gtggggaggg cccaggttcg ggtgctggtg     1560
gtgatgactc tgtcgcccag ccatgtggaa tcgcaatgcc aatttcctga ggaactaccc     1620
actccgtcgg cgccttcgtt attgtctgcc attggagcgc caccgcctgc agccattgta     1680
ccagatccca gaccagaggg gcctgcgggg ggttctccga ttggttgagg gtcgggcact     1740
gactctgagt cgccagtctg cccaaagttg agtctctttt tcgcgggctg ctggcctttc     1800
ttgccgatgc ccgtagtgga gtctggagaa cgctggggtg atggctctac cggtctcttc     1860
tttccaggag ccgtcttagc gccttcctca accagaccga gaggtcgag aacccgcttc       1920 ttggcctgga agactgctcg tccgaggttg cccccaaaag acgtatcttc ttgcagacgc     1980
tcctgaaact cggcgtcggc gtggttatac cgcaggtacg gattgtcacc cgctttgagc     2040
tgctggtcgt aggccttgtc gtgctcgagg gccgctgcgt ccgccgcgtt gacgggctcc     2100
cccttgtcga gtccgttgaa gggtccgagg tacttgtagc caggaagcac cagaccccgg     2160
ccgtcgtcct gcttttgctg gttggctttg ggcttcgggg ctccaggttt cagcgcccac     2220
cactcgcgaa tgccctcaga gaggttgtcc tcgagccaat ctggaagata accatcggca     2280
gccatacctg atctaaatca tttattgttc aaagatgcag tcatccaaat ccacattgac     2340
cagatcgcag gcagtgcaag cgtctggcac cttcccatg atatgatgaa tgtagcacag      2400
```

```
tttctgatac gccttttga cgacagaaac gggttgagat tctgacacgg gaaagcactc    2460
taaacagtct ttctgtccgt gagtgaagca gatatttgaa ttctgattca ttctctcgca    2520
ttgtctgcag ggaaacagca tcagattcat gcccacgtga cgagaacatt tgttttggta    2580
cctgtccgcg tagttgatcg aagcttccgc gtctgacgtc gatggctgcg caactgactc    2640
gcgcacccgt ttgggctcac ttatatctgc gtcactgggg gcgggtcttt tcttggctcc    2700
accctttttg acgtagaatt catgctccac ctcaaccacg tgatcctttg cccaccggaa    2760
aaagtctttg acttcctgct tggtgacctt cccaaagtca tgatccagac ggcgggtgag    2820
ttcaaatttg aacatccggt cttgcaacgg ctgctggtgt tcgaaggtcg ttgagttccc    2880
gtcaatcacg gcgcacatgt tggtgttgga ggtgacgatc acgggagtcg ggtctatctg    2940
ggccgaggac ttgcatttct ggtccacgcg caccttgctt cctccagaaa tggctttggc    3000
cgactccacg accttggcgg tcatcttccc ctcctcccac cagatcacca tcttgtcgac    3060
acagtcgttg aagggaaagt tctcattggt ccagttgacg cagccgtaga agggcgaatt    3120
c                                                                    3121

<210> SEQ ID NO 12
<211> LENGTH: 3121
<212> TYPE: DNA
<213> ORGANISM: Unknown
<220> FEATURE:
<223> OTHER INFORMATION: AAV serotype, clone 29.4

<400> SEQUENCE: 12
gaattcgccc ttctacggct gcgtcaactg gaccaatgag aactttccct tcaacgactg     60
tgtcgacaag atggtgatct ggtgggagga ggggaagatg accgccaagg tcgtggagtc    120
ggccaaagcc attctcggag gaagcaaggt gcgcgtggac cagaaatgca agtcctcggc    180
ccagatagac ccgactcccg tgatcgtcac ctccaacacc aacatgtgcg ccgtgattga    240
cgggaactca cgaccttcg aacaccagca gccgttgcaa gaccggatgt tcaaatttga    300
actcacccgc cgtctggatc atgactttgg gaaggtcacc aagcaggaag tcaaagactt    360
tttccggtgg gcaaaggatc acgtggttga ggtggagcac gaattctacg tcaaaaaggg    420
tggagccaag aaaagacccg ccccagtga cgcagatata agtgagccca acgggtgcg    480 cgagtcagtt gcgcagccat cgacgtcaga gcgggaagct tcgatcaact acgcagacag    540
gtaccaaaac aaatgttctc gtcacgcggg catgaatctg atgctgtttc cctgcagaca    600
atgcgagaga atgaatcaga attcaaatat ctgcttcact cacggacaga agactgttt    660 agagtgctt cccgtgtcag aatctcaacc cgtttctgtc gtcaaaaagg cgtatcagaa    720
actgtgctac attcatcata tcatgggaaa ggtgccagac gcttgcactg cctgcgatct    780
ggtcgatgtg gatttggatg actgcatctt tgaacaataa atgatttaaa tcaggtatgg    840
ctgccgatgg ttatcttcca gattggctcg aggacaaccct ctctgagggc attcgcgagt    900
ggtgggcgct gaaacctgga gccccgaagc ccaaagccaa ccagcaaaag caggacggcg    960
gccggggtct ggtgcttcct ggctacaagt acctcggacc cttcaacgga ctcgacaagg   1020
gggagcccgt caacgcggcg gacgcagcgg ccctcgagca cgacaaggcc tacgaccagc   1080
agctcaaagc gggtgacaat ccgtacctgc ggtataacca cgccgacgcc gagtttcagg   1140
agcgtctgca agaagatacg tcttttgggg caacctcgg gcgagcagtc ttccaggcca   1200
agaagcgggt tctcgaacct ctcggtctgg ttgaggaagg cgctaagacg gctcctggaa   1260
agaagagacc ggtagagcca tcaccccagc gttctccaga ctcctctacg ggcatcggca   1320
```

```
agaaaggcca gcagcccgcg aaaaagagac tcaactttgg gcagactggc gactcagagt    1380
cagtgcccga ccctcaacca atcggagaac cccccgcagg cccctctggt ctgggatctg    1440
gtacaatggc tgcaggcggt ggcgctccaa tggcagacaa taacgaaggc gccgacggag    1500
tgggtagttc ctcaggaaat tggcattgcg attccacatg gctgggcgac tgagtcatca    1560
ccaccagcac ccgaacctgg gccctcccca cctacaacaa ccacctctac aagcaaatct    1620
ccaacgggac ttcgggagga agcaccaacg acaacaccta cttcggctac agcacccccct   1680
```



```
agaaaggcca gcagcccgcg aaaaagagac tcaactttgg gcagactggc gactcagagt    1380
cagtgcccga ccctcaacca atcggagaac cccccgcagg cccctctggt ctgggatctg    1440
gtacaatggc tgcaggcggt ggcgctccaa tggcagacaa taacgaaggc gccgacggag    1500
tgggtagttc ctcaggaaat tggcattgcg attccacatg gctgggcgac tgagtcatca    1560
ccaccagcac ccgaacctgg gccctcccca cctacaacaa ccacctctac aagcaaatct    1620
ccaacgggac ttcgggagga agcaccaacg acaacaccta cttcggctac agcaccccct    1680
gggggtattt tgactttaac agattccact gccacttctc accacgtgac tggcagcgac    1740
tcatcaacaa caactgggga ttccggccca agagactcaa cttcaagctc ttcaacatcc    1800
aggtcaagga ggtcacgcag aatgaaggca ccaagaccat cgccaataac cttaccagca    1860
cgattcaggt ctttacggac tcggaatacc agctcccgta cgtcctcggc tctgcgcacc    1920
agggctgcct gcctccgttc ccggcggacg tcttcatgat tcctcagtac gggtacctga    1980
ctctgaacaa tggcagtcag gccgtgggcc gttcctcctt ctactgcctg gagtactttc    2040
cttctcaaat gctgagaacg ggcaacaact ttgagttcag ctaccagttt gaggacgtgc    2100
cttttcacag cagctacgcg cacagccaaa gcctggaccg gctgatgaac ccctcatcg     2160 accagtacct gtactacctg tctcggactc agtccacggg aggtaccgca ggaactcagc    2220
agttgctatt ttctcaggcc gggcctaata acatgtcggc tcaggccaaa aactggctac    2280
ccgggccctg ctaccggcag taacgcgtct ccacgacact gtcgcaaaat aacaacagca    2340
actttgtctg gaccggtgcc accaagtatc atctgaatgg cagagactct ctggtagatc    2400
ccggtgtcgc tatggcaacc cacaaggacg acgaagagcg attttttccg tccagcggag    2460
tcataatgtt tgggaaacag gggagctgaa aagacaacgt ggactatagc agcgtcatgc    2520
taaccagtga ggaagaaatt aaaaccacca acccagtggc cacagaacag tacggcgtgg    2580
tggccgataa cctgcaacag caaaacgccg ctcctattgt aggggccgtc aacagtcaag    2640
gagccttacc tggcatggtc tggcagaacc gggacgtgta cctgcagggt cctacctggg    2700
ccaagattcc tcacacggac ggaaactttc atccctcgcc gctgatggga ggctttggac    2760
tgaaacaccc gcctcctcag atcctgatta agaatacacc tgttcccgcg atcctccaa    2820 ctaccttcag tcaagctaag ctggcgtcgt tcatcacgca gtacagcacc ggacaggtca    2880
gcgtggaaat tgaatgggag ctgcaggaag aaaacagcaa acgctggaac ccagagattc    2940
aatacactcc caactactac aaatctacaa atgtggactt tgctgttaac acagatggca    3000
cttattctga gcctcgcccc atcggcaccc gttacctcac ccgtaatctg taattgcttg    3060
ttaatcaata aaccggttga ttcgtttcag ttgaactttg gtctctgcga agggcgaatt    3120
c                                                                    3121
```

<210> SEQ ID NO 13
<211> LENGTH: 3121
<212> TYPE: DNA
<213> ORGANISM: Unknown
<220> FEATURE:
<223> OTHER INFORMATION: AAV serotype, clone 29.5

<400> SEQUENCE: 13

```
gaattcgccc ttcgcgagac caaagttcaa ctgaaacgaa tcaaccggtt tattgattaa      60
caagcaatta cagattacgg gtgaggtaac gggtgccgat ggggcgaggc tcagaataag    120
tgccatctgt gttaacagca aagtccacat ttgtagattt gtagtagttg gaagtgtatt    180
```

```
gaatctctgg gttccagcgt tgctgttttt ctttctgcag ctcccattca atttccacgc    240
tgacctgtcc ggtgctgtac tgcgtgatga acgacgccag cttagcttga ctgaaggtag    300
ttggaggatc cgcgggaaca ggtgtattct taatcaggat ctgaggaggc gggtgtttca    360
gtccaaagcc tcccatcagc ggcgagggat gaaagtttcc gtccgtgtga ggaatcttgg    420
cccagatagg accctgcagg tacacgtccc ggttctgcca gaccatgcca ggtaaggctc    480
cttgactgtt gacggcccct acaataggag cggcgttttg ctgttgcagg ttatcggcca    540
ccacgccgta ctgttctgtg gccactgggt tggtggtttt aatttcttcc tcactggtta    600
gcataacgct gctatagtcc acgttgtctt ttccagctcc ctgtttccca aacattaaga    660
ctccgctgga cggaaaaaat cgctcttcgt cgtccttgtg ggttgccata gcgacaccgg    720
gatttaccag agagtctctg ccattcagat gatacttggt ggcaccggtc caggcaaagt    780
tgctgttgtc attttgcgac agtgtcgtgg agacgcgttg ctgccggtag cagggcccgg    840
gtagccagtt tttggcctga ccgacatgt tattaggccc ggcctgagaa aatagcaact    900
gctgagttcc tgcggtacct cccgtggact gagtccgaga caggtagtac aggtactggt    960
cgatgagggg gttcatcagc cggtccaggc tttggctgtg cgcgtagctg ctgtgaaaag    1020
gcacgtcctc aaactggtag ctgaactcaa agttgttgcc cgttctcagc atttgagaag    1080
gaaagtactc caggcagtag aaggaggaac ggcccacggc ctgactgcca ttgttcagag    1140
tcaggtaccc gtactgagga atcatgaaga cgtccgccgg gaacggaggc aggcagccct    1200
ggtgcgcaga gccgaggacg tacgggagct ggtattccga gtccgtaaag acctgaatcg    1260
tgctggtaag gttattggcg atggtcttgg tgccttcatt ctgcgtgacc tccttgacct    1320
ggatgttgaa gagcttgaag ttgaggctct gggccggaa tccccagttg ttgttgatga    1380
gtcgctgcca gtcacgtggt gagaagtggc agtggaatct gttaaagtca aaataccccc    1440
aggggggtgct gtagccgaag taggtgttgt cgttggtgct tcctcccgaa gtcccgttgg    1500
agatttgctt gtagaggtgg ttgttgtagg tgggagggc ccaggttcgg gtgctggtgg    1560
tgatgactcc gtcgcccagc catgtggaat cgcaatgcca atttcctgag gaactaccca    1620
ctccgtcggc gccttcgtta ttgtctgcca ttggagcgcc accgcctgca gccattgtac    1680
cagatcccag accagagggg cctgcggggg gttctccgat tggttgaggg tcgggcactg    1740
actctgagtc gccagtctgc ccaaagttga gtctcttttt cgcgggctgc tggccttttct    1800
tgccgatgcc cgtagaggag tctggagaac gctggggtga tggctctacc ggtctcttct    1860
ttccaggagc cgtcttagcg ccttcctcaa ccagaccgag aggttcgaga acccgcttct    1920
tggcctggaa gactgctcgc ccgaggttgc ccccaaaaga cgtatcttct tgcagacgct    1980
cctgaaactc ggcgtcggcg tggttatacc gcaggtacgg attgtcaccc gctttgagct    2040
gctggtcgta ggccttgtcg tgctcgaggg ccgctgcgtc cgccgcgttg acgggctccc    2100
ccttgtcgag tccgttgaag ggtccgaggt acttgtagcc aggaagcacc agaccccggc    2160
cgtcgtcctg cttttgctgg ttggcttggg gcttcggggc tccaggtttc agcgcccacc    2220
actcgcgaat gccctcagag aggttgtcct cgagccaatc tggaagataa ccatcggcag    2280
ccatacctga tttaaatcat ttattgttca aagatgcagt catccaaatc cacattgacc    2340
agatcgcagg cagtgcaagc gtctggcacc tttcccatga tatgatgaat gtagcacagt    2400
ttctgatacg ccttttttgac gacagaaacg ggttgagatt ctgacacggg aaagcactct    2460
aaacagtctt tctgtccgtg agtgaagcag atatttgaat tctgattcat tctctcgcat    2520
tgtctgcagg gaaacagcat cagattcatg cccacgtgac gagaacattt gttttggtac    2580
```

-continued

| | | |
|---|---|---|
| ctgtctgcgt agttgatcga agcttccgcg tctgacgtcg atggctgcgc aactgactcg | 2640 |
| cgcacccgtt tgggctcact tatatctgcg tcactggggg cgggtctttt cttggctcca | 2700 |
| cccttttga cgtagaattc atgctccacc tcaaccacgt gatcctttgc ccaccggaaa | 2760 |
| aagtctttga cttcctgctt ggtgaccttc ccaaagtcat gatccagacg gcgggtgagt | 2820 |
| tcaaatttga acatccggtc ttgcaacggc tgctggtgtt cgaaggtcgt tgagttcccg | 2880 |
| tcaatcacgg cgcacatgtt ggtgttggag gtgacgatca cggagtcgg gtctatctgg | 2940 |
| gccgaggact tgcatttctg gtccacgcgc accttgcttc ctccgagaat ggctttggcc | 3000 |
| gactccacga ccttggcggt catcttcccc tcctcccacc agatcaccat cttgtcgaca | 3060 |
| cagtcgttga agggaaagtt ctcattggtc cagttgacgc agccgtagaa agggcgaatt | 3120 |
| c | 3121 |

<210> SEQ ID NO 14
<211> LENGTH: 3131
<212> TYPE: DNA
<213> ORGANISM: Unknown
<220> FEATURE:
<223> OTHER INFORMATION: AAV serotype, clone 1-3

<400> SEQUENCE: 14

| | | |
|---|---|---|
| gcggccgcga attcgccctt ggctgcgtca actggaccaa tgagaacttt cccttcaatg | 60 |
| attgcgtcga caagatggtg atctggtggg aggagggcaa gatgacggcc aaggtcgtgg | 120 |
| agtccgccaa ggccattctc ggcggcagca aggtgcgcgt ggaccaaaag tgcaagtcgt | 180 |
| ccgcccagat cgaccccacc ccgtgatcg tcacctccaa caccaacatg tgcgccgtga | 240 |
| ttgacgggaa cagcaccacc ttcgagcacc agcagcctct ccaggaccgg atgtttaagt | 300 |
| tcgaactcac ccgccgtctg gagcacgact ttggcaaggt gacaaagcag gaagtcaaag | 360 |
| agttcttccg ctgggccagt gatcacgtga ccgaggtggc gcatgagttt acgtcagaa | 420 |
| agggcggagc cagcaaaaga cccgcccccg atgacgcgga taaaagcgag cccaagcggg | 480 |
| cctgccctc agtcgcggat ccatcgacgt cagacgcgga aggagctccg gtggactttg | 540 |
| ccgacaggta ccaaaacaaa tgttctcgtc acgcgggcat gcttcagatg ctgtttccct | 600 |
| gcaaaacgtg cgagagaatg aatcggaatt caacatttg cttcacacac ggggtcagag | 660 |
| actgctcaga gtgtttcccc ggcgtgtcag aatctcaacc ggtcgtcaga aagaggacgt | 720 |
| atcggaaact ccgtgcgatt catcatctgc tggggcgggc tcccgagatt gcttgctcgg | 780 |
| cctgcgatct ggtcaacgtg gacctggatg actgtgtttc tgagcaataa atgacttaaa | 840 |
| ccaggtatgg ctgccgatgg ttatcttcca gattggctcg aggacaacct ctctgagggc | 900 |
| attcgcgagt ggtgggcgct gaaacctgga gccccgaagc caaagccaa ccagcaaaag | 960 |
| caggacgacg gccggggtct ggtgcttcct ggctacaagt acctcggacc cttcaacgga | 1020 |
| ctcgacaagg gggagcccgt caacgcggcg gacgcagcgg ccctcgagca cgacaaggct | 1080 |
| tacgaccagc agctgcaggc gggtgacaat ccgtacctgc ggtataacca cgccgacgcc | 1140 |
| gagtttcagg agcgtctgca agaagatacg tcttttgggg gcaacctcgg gcagcagtc | 1200 |
| ttccaggcca agaagcgggt tctcgaacct ctcggtctgg ttgaggaagg cgctaagacg | 1260 |
| gctcctggaa agaagagacc ggtagagcca tcaccccagc gttctccaga ctcctctacg | 1320 |
| ggcatcggca agaaggcca acagcccgcc agaaaaagac tcaattttgg tcagactggc | 1380 |
| gactcagagt cagttccaga ccctcaacct ctcggagaac ctccagcagc gccctctggt | 1440 |

```
gtgggaccta atacaatggc tgcaggcggt ggcgcaccaa tggcagacaa taacgaaggc    1500
gccgacggag tgggtagttc ctcgggaaat tggcattgcg attccacatg gctgggcgac    1560
agagtcatca ccaccagcac ccgaacctgg gccctgccca cctacaacaa ccacctctac    1620
aagcaaatct ccaacgggac atcgggagga gccaccaacg acaacaccta cttcggctac    1680
agcaccccct gggggtattt tgactttaac agattccact gccacctttc accacgtgac    1740
tggcagcgac tcatcaacaa caactgggga ttccgaccca agagactcag cttcaagctc    1800
ttcaacatcc aggtcaagga ggtcacgcag aatgaaggca ccaagaccat cgccaataac    1860
ctcaccagca ccatccaggt gtttacggac tcggagtacc agctgccgta cgttctcggc    1920
tctgtccacc agggctgcct gcctccgttc ccggcggacg tgttcatgat tccccagtac    1980
ggctacctaa cactcaacaa cggtagtcag gccgtgggac gctcctcctt ctactgcctg    2040
gaatactttc cttcgcagat gctgagaacc ggcaacaact tccagtttac ttacaccttc    2100
gaggacgtgc ctttccacag cagctacgcc cacagctaga gcttggaccg gctgatgaat    2160
cctctgattg accagtacct gtactacttg tctcggactc aaacaacagg aggcacggca    2220
aatacgcaga ctctgggctt cagccaaggt gggcctaata caatggccaa tcaggcaaag    2280
aactggctgc aggaccctg ttaccgccaa caacgcgtct caacgacaac cgggcaaaac    2340
aacaatagca ctttgcctg gactgctggg accaaatacc atctgaatgg aagaaattca    2400
ttggctaatc ctggcatcgc tatggcaaca cacaaagacg acgaggagcg ttttttttccc    2460 agtaacggga tcctgatttt tggcaaacaa aatgctgcca gagacaatgc ggattacagc    2520
gatgtcatgc tcaccagcga ggaagaaatc aaaaccacta ccctgtggc tacagaggaa    2580 tacggtatcg tggcagataa cttgcagcag caaaacacgg ctcctcaaat tggaactgtc    2640
aacagccagg gggccttacc cggtatggtc tggcagaacc gggacgtgta cctgcagggt    2700
cccatctggg ccaagattcc tcacacggac ggcaacttcc acccgtctcc gctgatgggc    2760
ggctttggcc tgaaacatcc tccgcctcag atcctgatca agaacacgcc tgtacctgcg    2820
gatcctccga ccaccttcaa ccagtcaaag ctgaactctt tcatcacgca atacagcacc    2880
ggacaggtca gcgtggaaat tgaatggag ctgcagaagg aaaacagcaa gcgctggaac    2940
cccgagatcc agtacaccctc caactactac aaatctataa gtgtggactt tgctgttaat    3000
acagaaggcg tgtactctga accccgcccc attggcaccc gttacctcac ccgtaatctg    3060
taattgcctg ttaatcaata aaccggttga ttcgtttcag ttgaactttg gtctctgcga    3120
agggcgaatt c    3131
```

<210> SEQ ID NO 15
<211> LENGTH: 3127
<212> TYPE: DNA
<213> ORGANISM: Unknown
<220> FEATURE:
<223> OTHER INFORMATION: AAV serotype, clone 13-3b

<400> SEQUENCE: 15

```
gcggccgcga attcgcccctt cgcagagacc aaagttcaac tgaaacgaat caaccggttt     60
attgattaac atgcaattac agattacggg tgaggtaacg agtgccaata gggcgaggct    120
cagagtaaac accctggctg tcaacggcaa agtccacacc agtctgcttt tcaaagttgg    180
aggtgtactg aatctccggg tcccagcgct tgctgttttc cttctgcagc tcccactcga    240
tttccacgct gacttgtccg gtgctgtact gtgtgatgaa cgaagcaaac ttggcaggag    300 taaacaccctc cggaggatta gcgggaacgg gagtgttctt gatcaggatc tgaggaggcg    360
```

```
gatgtttaag tccaaagccg cccatcaaag gagacgggtg aaagttgcca tccgtgtgag    420
gaatcttggc ccagatggga ccctgcaggt acacgtcccg gttctgccag accatgccag    480
gtaaggctcc ctggttgttg acaacttgtg tctgggctgc agtattagcc gcttgtaagt    540
tgctgctgac tatcccgtat tcttccgtgg ctacaggatt agtaggacga atttcttctt    600
catttgtcat taacacattt tccaatgtag ttttgttagt tgctccagtt tttccaaaaa    660
tcaggactcc gctggatggg aaaaagcggt cctcgtcgtc cttgtgagtt gccatggcga    720
cgccgggatt aaccaacgag tttctgccgt tcaggtgata tttggtggca ccagtccaag    780
caaagttgct gttgttgttt tgatccagcg ttttggagac cctttgttgc cggaagcagg    840
gtccaggtaa ccaattcttg gcttgttcgg ccatagttga aggcccgccc tggtaaaact    900
gcagttcccg attgccagct gtgcctcctg ggtcactctg tgttctggcc aggtagtaca    960
agtactggtc gatgagggga ttcatcagcc ggtccaggct ctggctgtgt gcgtagctgc   1020
tgtggaaagg cacgtcctcg aagctgtagc tgaactcaaa gttgttgccc gttctcagca   1080
tctgagaggg gaagtactcc aggcagtaga aggaggaacg tcccacagac tgactgccat   1140
tgttgagagt caggtagccg tactgaggaa tcatgaagac gtccgccggg aacggaggca   1200
ggcagccctg gtgcgcagag ccgaggacgt acggcagctg gtattccgag tccgagaata   1260
cctgaatcgt gctggtaagg ttattagcga tggtcgtaac gccgtcattc gtcgtgacct   1320
ccttgacctg gatgttgaag agcttgaacc gcagcttctt gggccggaat ccccagttgt   1380
tgttgatgag tcgctgccag tcacgtggtg agaagtggca gtggaatctg ttaaagtcaa   1440 aatacccca gggggtgctg tagccgaagt aggtgttgtc gttggtacta cctgcagttt   1500
cactggagat ttgctcgtag aggtggttgt tgtaggtggg cagggcccag gttcgggtgc   1560
tggtggtaat gactctgtcg cccagccatg tggaatcgca atgccaattt cctgaggcat   1620 taccactcc gtcggcacct tcgttattgt ctgccattgg tgcgccaccg cctgcagcca   1680
ctgtaccaga tcccacacta gagggcgctg ctggaggttc tccgagaggt tgagggtcgg   1740
ggactgactc tgagtcgcca gtctgaccga aattgagtct cttctgcgcg gctgctggc    1800 ccttcttgcc gatgcccgtg gaggagtcgg gggaacgctg aggtgacggc tctaccggtc   1860
tcttctttgc aggagccgtc ttagcgcctt cctcaaccag accgagaggt tcgagaaccc   1920
gcttcttggc ctggaagact gctcgcccga ggttgccccc aaatgacgta tcttcttgca   1980
gacgctcctg aaactcggcg tcggcgtggt tataccgcag gtacgggttg tcacccgcat   2040
tgagctgctg gtcgtaggcc ttgtcgtgct cgagggccgc tgcgtccgcc gcgttgacgg   2100
gctccccctt gtcgagtccg ttgaagggtc cgaggtactt gtagccagga agcaccagac   2160
cccggccgtt gtcctgcttt tgctggttgg ctttgggttt cgggctcca ggtttcaggt    2220 cccaccactc gcgaatgccc tcagagaggt tgtcctcgag ccaatctgga agataaccat   2280
cggcagccat acctgattta aatcatttat tgttcaaaga tgcagtcatc caaatccaca   2340
ttgaccagat cgcaggcagt gcaagcgtct ggcacctttc ccatgatatg atgaatgtag   2400
cacagtttct gatacgcctt tttgacgaca gaaacgggtt tagattctga cacgggaaag   2460
cactctaaac agtctttctg tccgtgagtg aagcagatat ttgaattctg attcattctc   2520
tcgcattgtc tgcagggaaa cagcatcaga ttcatgccca cgtgacgaga acatttgttt   2580
tggtacctgt ctgcgtagtt gatcgaagct tccgcgtctg acgtcgatgg ctgcgcaact   2640
gactcgcgca cccgtttggg ctcacttata tctgcgtcac tggggcgggg tcttttcttg   2700
```

```
gctccaccct ttttgacgta gaattcatgc tccacctcaa ccacgtaatc ctttgcccac    2760
cggaaaaagt ctttgacttc ctgcttggtg accttcccaa agtcatgatc cagacggcgg    2820
gtgagttcaa atttgaacat ccggtcttgc aacggctgct ggtgttcgaa ggtcgttgag    2880
ttcccgtcga tcacggcgca catgttggtg ttggagatga cgatcgcggg agtcgggtct    2940
atctgggccg aggacttgca tttctggtcc acgcgcacct tgcttcctcc gagaatggct    3000
ttggccgact ccacgacctt ggcggtcatc ttccctcct cccaccagat caccatcttg    3060
tcgacacagt cgttgaaggg aaagttctca ttggtccagt tgacgcagcc gtagaaaggg    3120
cgaattc                                                              3127

<210> SEQ ID NO 16
<211> LENGTH: 3106
<212> TYPE: DNA
<213> ORGANISM: Unknown
<220> FEATURE:
<223> OTHER INFORMATION: AAV serotype, clone 24-1

<400> SEQUENCE: 16
gcggccgcga attcgccctt cgcagagacc aaagttcaac tgaaacgaat caaccggttt      60
attgattaac aagtaattac aggttacggg tgaggtaacg ggtgccaatg gggcgaggct     120
cagtataaac cccttcgttg ttgacagcaa attccacatt attagacttg cataatttg     180 aggtgtactg aatctctgga ttccagcgtt tgctgttttc tttctgcagt cccactcga     240 tctccacgct gacctggccg gtgctgtact gcgtgataaa tgaggcaaac ttggcaggag     300
taaacacctc tggaggatta gcaggtaccg gggtgttttt gatgagaatt tgaggaggcg     360
ggtgtttgag tccaaatccg cccatcaggg gagacgggtg aaagttgccg tccgtgtgag     420
gaattttggc ccagatggga ccctgcaggc acacgtcccg gttctgccag accatgccgg     480
gcagagcccc ctggctgttg acagtctgtg tctggggtcc ggccgtagac gattgcaggt     540
tgctggagac cacaccgtat tcttctgtag ccacgggatt ggtggttttg atctcctcct     600
cgctggtcat tagcacgttt ccagcgttg tcttgttggc agccccgtt tgccaaaaa       660 ccagcactcc gttgatggga agaactggt cctcgtcgtc cttgttggtg gccatggcta     720
cgcccgggtt ggttaatgaa tttctaccat tcagatggta tttagtggcc ccggtccagg     780
caaagttact gttgttgttg ctgtctatgt tttttgacag tctctgctgc cgataacagg     840
gtccgggcag ccagttcttt gattgctcgg ccatggtgtt gggcccagcc tgatggaact     900
gcagctccct tgtggacccc gtagtgctct gggtccgggc caggtagtac aggtactggt     960
cgatgagggg attcatcagc cggtctaggc tctggctgtg cacatagctg ctgtggaaag    1020
gcacttcctc aaaggtgtag ctgaattcaa agttattgcc cgttctcagc atctgagaag    1080
gaaagtactc caggcagtag aaggaggaac gtcccacaga ctgactgccg ttgtttagag    1140
tcagatatcc gtactgagga atcatgaaca cgtccgcagg gaacggaggg aggcagccct    1200
ggtgcgcaga gccgaggacg tacggcagtt ggtactccga gtccgagaag acctgaatcg    1260
tgctggtaag gttattagcg atggtcgtaa cgccgtcgtt cgtcgtgacc tccttgacct    1320
ggatgttgaa caacttgaac cgcagctttc tgggccggaa tccccagttg ttgttgatga    1380
gtcgctgcca gtcacgtggt gagaagtggc agtggaatct gttgaagtca aaatagcccc    1440
agggggtgct gtagctgaag aagtggttgt cgttggtagc cccgctctga cttgatatct    1500
gcttgtagag gtggttgttg taggtgggca gggcccaggt gcgggtgctg gtggtgatga    1560
ctctgtcgcc cagccatgtg gaatcgcaat gccaatttcc ggaggcatta cccactccgt    1620
```

```
cggcgccttc gttattgtct gccattggtg cgccaccgcc tgcagccatt gtaccagatc    1680
ccagacctga gggcgcggcg ggaggttctc cgagaggttg ggggtcgggc actgactctg    1740
agtcgccagt ctgcccaaag ttgagcttct ttttagcggg ctgctggcct ttcttgccga    1800
tgcccgtgga ggagtcgggg gattctatgg gtctcttctt tccaggagcc gtcttagcga    1860
cttcctcaac cagaccgaga ggttcgagaa cccgcttctt ggcctggaag actgctcgcc    1920
cgaggttgcc cccaaaagac gtatcttctt gaagacgctc ctgaaactcg cgtcggcgt     1980 ggttgtactt gaggtacggg ttgtcccct gctcgagctg cttgtcgtag gccttgtcgt     2040
gctcgagggc cgcggcgtct gcctcgttga ccggctctcc cttgtcgagt ccgttgaagg    2100
gtctgaggta cttgtagcca ggaagcacca gaccccggcc gtcgtcctgc ttttgctggt    2160
tggctttggg tttcggggct ccaggtttca agtcccacca ctcgcgaatg ccctcagaga    2220
ggttgtcctc gagccaatct ggaagataac catcggcagc catacctggt ttaagtcatt    2280
tattgctcag aaacacagtc atccaggtcc acgttgacca gatcgcaggc cgagcaagca    2340
atctcgggag cccgccccag cagatgatga atggcacaga gtttccgata cgtcctcttt    2400
ctgacgaccg gttgagattc tgacacgccg gggaaacatt ctgaacagtc tctggtcccg    2460
tgcgtgaagc aaatgttgaa attctgattc actctctcgc atgtcttgca gggaaacagc    2520
atctgaagca tgcccgcgtg acgagaacat ttgttttggt acctgtcggc aaagtccacc    2580
ggagctcctt ccgcgtctga cgtcgatgga ttcgcgactg aggggcaggc ccgcttgggc    2640
tcgcttttat ccgcgtcatc gggggcgggt ctcttgttgg ccccacccu tctgacgtag    2700 aacccatgcg ccacctcggt cacgtgatcc tgcgcccagc ggaagaacct tttgacttcc    2760
tgctttgtca ccttgccaaa gttatgctcc agacggcggg tggttcaaa tttgaacatc     2820 cggtcctgca acggctgctg gtgctcgaag gtggcgctgt tcccgtcaat cacggcgcac    2880
atgttggtgt tggaggtgac ggtcacgggg gtggggtcga tctgggcgga cgacttgcac    2940
ttttggtcca cgcgcacctt gctgccgccg agaatggcct tggcggactc cacgaccttg    3000
gccgtcatct tgccctcctc ccaccagatc accatcttgt cggcgcaatc gttgaaggga    3060
aagttctcat tggtccagtt gacgcagccg tagaaagggc gaattc                  3106
```

<210> SEQ ID NO 17
<211> LENGTH: 3102
<212> TYPE: DNA
<213> ORGANISM: Unknown
<220> FEATURE:
<223> OTHER INFORMATION: AAV serotype, clone 27-3

<400> SEQUENCE: 17

```
gcggccgcga attcgccctt cgcagagacc aaagttcaac tgaaacgaat caaccggttt      60
attgattaac aagtaattac aggttacggg tgaggtaacg ggtgccaatg gggcgaggct     120
cagtataaac cccttcgttg ttgacagcaa attccacatt attagacttg cataatttg     180 aggtgtactg aatctctgga ttccagcgtt tgctgttttc tttctgcagt tcccactcga    240
tctccacgct gacctggccg gtgctgtact gcgtgataaa tgaggcaaac ttggcaggag    300
taaacacctc tggaggatta gcaggtaccg gggtgttttt tgatgagaat tgaggaggcg    360
ggtgtttgag tccaaatccg cccatcaggg gagacgggtg aaagttgccg tccgtgtgag    420
gaatttcggc ccagatggga ccctgcaggt acacgtcccg gttctgccag accatgccgg    480
gcagagcccc ctggctgttg acagtctgtg tccggggtcc ggccgtagac gattgcaggt    540
```

```
tgctggagac cacaccgtat tcttctgtag ccacgggatt ggtggttttg atctcctcct    600
cgctggtcat tagcacgttt tccagcgttg tcttgttggc agccccgtt  ttgccaaaaa    660
ccagcactcc gttgatggga aggaactggt cctcgtcgtc cttgttggtg gccatggcta    720
cgcccgggtt ggttaatgaa tttctaccat tcagatggta tttagtggcc ccggtccagg    780
caaagttact gttgttgttg ctgtctatgt tttttgacag tctctgctgc cgataacagg    840
gtccgggcag ccagttcttt gattgctcgg ccacggtgtt gggcccagcc tgatggaact    900
gcagctccct tgtggacccc gtagtgctct gggtccgggc caggtagtac aggtactggt    960
cgatgagggg attcatcagc cggtccaggc tctggctgtg cgcatagctg ctgtggaaag   1020
gcacttcctc aaaggtgtag ctgaattcaa agttattgcc cgttctcagc atctgagaag   1080
gaaagtactc caggcagcag aaggaggaac gtcccacaga ctgactgccg ttgtttagag   1140
tcagatatcc gtactgagga atcatgaaca cgtccgcagg aacggaggg  aggcagccct   1200
ggtgcgcaga gccgaggacg tacgcagtt  ggtactccga gtccgagaag acctgaatcg   1260
tgctggtaag gttattagcg atggtcgtaa cgccgtcgtt cgtcgtgacc tccttgacct   1320
ggatgttgaa caacttgaac cgcagctttc tgggccggaa tccccagttg ttgttgatga   1380
gtcgctgcca gtcacgtggt gagaagtggc agtggaatct gttgaagtca aaatagcccc   1440
agggggtgct gtagccgaag aagtggttgt cgttggtagc cccgctctga cttgatatct   1500
gcttgtagag gtggttgttg taggtgggca gggcccaggt gcgggtgctg gtggtgatga   1560
ctctgtcgcc cagccatgtg gaatcgcaat gccaatttcc ggaggcatta cccactccgt   1620
cggcgccttc gttattgtct gccattggtg cgccaccgcc tgcagccatt gtaccagatc   1680
ccagacctga gggcgcggcg ggaggttctc cgagaggttg gggtcgggc  actgactctg   1740
agtcgccagt ctgcccaaag ttgagcttct ttttagcggg ctgctggcct ttcttgccga   1800
tgcccgtgga ggagtcgggg gattctatgg gtctcttctt tccggaagcc gtcttagcgc   1860
cttcctcaac cagaccgaga ggttcgagaa cccgcttctt ggcctggaag actgctcgcc   1920
cgaggttgcc cccaaaagac gtatcttctt gaagacgctc ctgaaactcg cgtcggcgt   1980
ggttgtactt gaggtacggg ttgtcccccct gctcgagctg cttgtcgtag ccttgtcgt   2040
gctcgagggc cgcggcgtct gcctcgttga ccggctctcc cttgtcgagt ccgttgaagg   2100
gtccgaggta cttgtagcca ggaagcacca gaccccggcc gtcgtcctgc ttttgctggt   2160
tggctttggg tttcggggct ccaggtttca gtcccacca  ctcgcgaatg ccctcagaga   2220
ggttgtcctc gagccaatct ggaagataac catcggcagc catacctggt ttaagtcatt   2280
tattgctcag aaacacagtc atccaggtcc acgttgacca gatcgcaggc cgagcaagca   2340
atctcgggag cccgcccag  cagatgatga atggcacaga gtttccgata cgtcctcttt   2400
ctgacgaccg gttgagattc tgacacgccg gggaaacatt ctgaacagtc tctggtcccg   2460
tgcgtgaagc aaatgttgaa attctgattc attctctcgc atgtcttgca gggaaacagc   2520
atctgaagca tgcccgcgtg acgagaacat ttgttttggt acctgtcggc aaagtccacc   2580
ggagctcctt ccgcgtctga cgtcgatgga tccgcgactg aggggcaagc ccgcttgggc   2640
tcgctttat  ccgcgtcatc gggggcgggt ctcttgttgg ctccacccct tctgacgtag   2700
aactcatgcg ccacctcggt cacgtgatcc tgcgcccagc ggaagaactc tttgacttcc   2760
tgctttgtca ccttgccaaa gtcatgctcc agacggcggg tgagttcaaa tttgaacatc   2820
cggtcttgta acgctgctg  gtgctcgaag gtggtgctgt tccgtcaat  cacgcgcac   2880
atgttggtgt tggaagtgac gatcacgggg gtgggatcga tctgggcgga cgacttgcac   2940
```

```
ttttggtcca cgcgcacctt gctgccgccg agaatggcct tggcggactc cacgaccttg    3000
gccgtcatct tgccctcctc ccaccagatc accatcttgt cgacgcaatc gttgaaggga    3060
aagttctcat tggtccagtt gacgcagccg aagggcgaat tc                      3102
```

<210> SEQ ID NO 18
<211> LENGTH: 3106
<212> TYPE: DNA
<213> ORGANISM: Unknown
<220> FEATURE:
<223> OTHER INFORMATION: AAV serotype, clone 7-2

<400> SEQUENCE: 18

```
gcggccgcga attcgccctt cgcagagacc aaagttcaac tgaaacgaat cagccggttt      60
attgattaac aagtaattac aggttacggg tgaggtaacg ggtgccaatg gggcgaggct     120
cagtataaac cccttcgttg ttgacagcaa attccacatt attagacttg cataaatttg     180
aggtgtactg aatctctgga ttccagcgtt tgctgttttc tttctgcagt tcccactcga     240
tctccacgct gacctggccg gtgctgtact gcgtgataaa tgaggcaaac ttggcaggag     300
taaacacctc tggaggatta gcaggtaccg gggtgttttt gatgagaatt tgaggaggcg     360
ggtgtttgag tccaaatccg cccatcaggg gagacgggtg aaagttgccg tccgtgtgag     420
gaattttggc ccagatggga ccctgcaggt acacgtcccg gttctgccag accatgccgg     480
gcagagcccc ctggctgttg acagtctgtg tctggggtcc ggccgtagac gattgcaggt     540
tgctggagac cacaccgtat tcttctgtag ccacgggatt ggtggttttg atctcctcct     600
cgctggtcat tagcacgttt ccagcgttg tcttgttggc agccccgtt ttgccaaaaa      660 ccagcactcc gttgatggga aagaactggt cctcgtcgtc cttgttggtg gccatggcta     720
cgcccgggtt ggttaatgaa tttctaccat tcagatggta tttagtggcc ccggtccagg     780
caaagttact gttgttgttg ctgtctatgt ttttgacag tctctgctgc cgataacagg      840
gtccgggcag ccagttcttt gattgctcgg ccatggtgtt gggcccagcc tgatggaact     900
gcagctccct tgtggacccc gtagtgctct gggtccgggc caggtagtac aggtactggt     960
cgatgagggg attcatcagc cggtccaggc tctggctgtg cgcatagctg ctgtggaaag    1020
gcacttcctc aaaggtgtag ctgaattcaa agttatcgcc cgttctcagc atctgagaag    1080
gaaagtactc caggcagtag aaggaggaac gtcccacaga ctgactgccg ttgtttagag    1140
tcagatatcc gtactgagga atcatgaaca cgtccgcagg gaacggaggg aggcagccct    1200
ggtgcgcaga gccgaggacg tacggcagtt ggtactccga gtccgagaag acctgaatcg    1260
tgctggtaag gttattagcg atggtcgtaa cgccgtcgtt cgtcgtgacc tccttgacct    1320
ggatgttgaa caacttgaac cgcagctttc tgggccggaa tccccagttg ttgttgatga    1380
gtcgctgcca gtcacgtggt gagaagtggc agtggaatct gttgaagtca aaatagcccc    1440
agggggtgct gtagccgaag aagtggttgt cgttggtagc cccgctctga cttgatatct    1500
gcttgtagag gtggttgttg taggtgggca gggcccaggt gcgggtgctg gtggtgatga    1560
ctctgtcgcc cagccatgtg gaatcgcaat gccaatttcc ggaggcatta cccactccgt    1620
cggcgccttc gttattgtct gccattggtg cgccaccgcc tgcagccatt gtaccagatc    1680
ccagacctga gggcgcggcg ggaggttctc cgagaggttg ggggtcgggc actgactctg    1740
agtcgccagt ctgcccaaag ttgagcttct ttttagcggg cggctggccg ttcttgccga    1800
tgcccgtgga ggagtcgggg gattctatgg gtctcttctt tccaggagcc gtcttagcgc    1860
```

-continued

| | |
|---|---|
| cttcctcaac cagaccgaga ggttcgagaa cccgcttctt ggcctggaag actgctcgcc | 1920 |
| cgaggttgcc cccaaaagac gtatcttctt gaagacgctc ctgaaactcg cgtcggcgt | 1980 |
| ggttgtactt gaggtacggg ttgtccccct gctcgagctg cttgtcgtag gccttgtcgt | 2040 |
| gctcgagggc cgcggcgtct gcctcgttga ccggctctcc cttgtcgagt ccgttgaagg | 2100 |
| gtccgaggta cctgtagcca ggaagcacca gaccccggcc gtcgtcctgc ttttgctggt | 2160 |
| tggctttggg tttcggggct ccaggtttca agtcccacca ctcgcgaatg ccctcagaga | 2220 |
| ggttgccctc gagccaatct ggaagataac catcggcagc catacctggt ttaagtcatt | 2280 |
| tattgctcag aaacacagtc atccaggtcc acgttggcca gatcgcaggc cgagcaagca | 2340 |
| atctcgggag cccgccccag cagatgatga atggcacaga gtttccgata cgtcctcttt | 2400 |
| ctgacgaccg gttgagattc tgacacgccg gggaaacatt ctgaacagtc tctggtcccg | 2460 |
| tgcgtgaagc aaatgttgaa attctgattc attctctcgc atgtcttgca ggggaacagc | 2520 |
| atctgaagca tgcccgcgtg acgagaacat ttgttttggt acctgtcggc aaagtccacc | 2580 |
| ggagctcctt ccgcgtctga cgtcgatgga tccgcgactg aggggcaggc ccgcttgggc | 2640 |
| tcgctttat ccgcgtcatc gggggcgggt ctcttgttgg ctccacccct tctgacgtag | 2700 |
| aactcatacg ccacctcggt cacgtgatcc tgcgcccagc ggaagaactc tttgacttcc | 2760 |
| tgctttgtca ccttgccaaa gtcatgctcc agacggcggg tgagttcaaa tttgaacatc | 2820 |
| cggtcttgta acggctgctg gtgctcgaag gtggtgctgt tcccgtcaat cacggcgcac | 2880 |
| atgttggtgt tggaagtgac gatcacgggg gtgggatcga tctgggcgga cgacttgcac | 2940 |
| ttttggtcca cgcgcacctt gctgccgccg agaatggcct tggcggactc cacgaccttg | 3000 |
| gccgtcatcc tgccctcctc ccaccagatc accatcttgt cgacgcaatc gttgaaggga | 3060 |
| aagttctcat tggtccagtt gacgcagccg tagaaagggc gaattc | 3106 |

<210> SEQ ID NO 19
<211> LENGTH: 3105
<212> TYPE: DNA
<213> ORGANISM: Unknown
<220> FEATURE:
<223> OTHER INFORMATION: AAV serotype, clone C1

<400> SEQUENCE: 19

| | |
|---|---|
| gaattcgccc ttgctgcgtc aactggacca atgagaactt tcccttcaac gattgcgtcg | 60 |
| acaagatggt gatctggtgg gaggagggca agatgaccgc caaggtcgtg gagtccgcca | 120 |
| aggccattct gggcggaagc aaggtgcgcg tggaccaaaa gtgcaagtca tcggcccaga | 180 |
| tcgaccccac gcccgtgatc gtcacctcca acaccaacat gtgcgccgtg atcgacggga | 240 |
| acagcaccac cttcgagcac cagcagccgc tgcaggaccg catgttcaag ttcgagctca | 300 |
| cccgccgtct ggagcacgac tttggcaagg tgaccaagca ggaagtcaaa gagttcttcc | 360 |
| gctgggctca ggatcacgtg actgaggtgg cgcatgagtt ctacgtcaga aagggcggag | 420 |
| ccaccaaaag acccgccccc agtgacgcgg atataagcga gcccaagcgg gcctgcccct | 480 |
| cagttgcgga gccatcgacg tcagacgcgg aagcaccggt ggactttgcg gacaggtacc | 540 |
| aaaacaaatg ttctcgtcac gcgggcatgc ttcagatgct gtttccctgc aagacatgcg | 600 |
| agagaatgaa tcagaatttc aacgtctgct tcacgcacgg ggtcagagac tgctcagagt | 660 |
| gcttccccgg cgcgtcagaa tctcaacccg tcgtcagaaa aaagacgtat cagaaactgt | 720 |
| gcgcgattca tcatctgctg gggcgggcac ccgagattgc gtgttcggcc cgcgatctcg | 780 |
| tcaacgtgga cttggatgac tgtgtttctg agcaataaat gacttaaacc aggtatggct | 840 |

```
gctgacggtt atcttccaga ttggctcgag acaacctct ctgagggcat tcgcgagtgg      900
tgggacctga aacctggagc ccccaagccc aaggccaacc agcagaagca ggacgacggc      960
cggggtctgg tgcttcctgg ctacaagtac ctcggaccct tcaacggact cgacaagggg     1020
gagcccgtca acgcggcgga cgcagcggcc ctcgagcacg acaaggccta cgaccagcag     1080
ctcaaagcgg gtgacaatcc gtacctgcgg tataaccacg ccgacgccga gtttcaggag     1140
cgtctgcaag aagatacgtc ttttgggggc aacctcgggc gagcagtctt ccaggccaag     1200
aagagggtac tcgaacctct gggcctggtt gaagaaggtg ctaagacggc tcctggaaag     1260
aagagaccgt tagagtcacc acaagagccc gactcctcct caggaatcgg caaaaaaggc     1320
aaacaaccag ccaaaaagag actcaacttt gaagaggaca ctggagccgg agacggaccc     1380
cctgaaggat cagataccag cgccatgtct tcagacattg aaatgcgtgc agcaccgggc     1440
ggaaatgctg tcgatgcggg acaaggttcc gatggagtgg gtaatgcctc gggtgattgg     1500
cattgcgatt ccacctggtc tgagggcaag gtcacaacaa cctcgaccag aacctgggtc     1560
ttgcccacct acaacaacca cttgtacctg cggctcggaa caacatcaaa cagcaacacc     1620
tacaacggat tctccacccc ctggggatac tttgacttta acagattcca ctgtcacttc     1680
tcaccacgtg actggcaaag actcatcaac aacaactggg gactacgacc aaaagccatg     1740
cgcgttaaaa tcttcaatat ccaagttaag gaggtcacaa cgtcgaacgg cgagactacg     1800
gtcgctaata accttaccag cacggttcag atatttgcgg actcgtcgta tgagctcccg     1860
tacgtgatgg acgctggaca agagggaagt ctgtctcctt tccccaatga cgtcttcatg     1920
gtgcctcaat atggctactg tggcattgtg actggcgaaa atcagaacca gacggacaga     1980
aatgctttct actgcctgga gtattttcct tcacaaatgc tgagaactgg caataacttt     2040
gaaatggctt acaactttgg gaaggtgccg ttccactcaa tgtatgctta cagccagagc     2100
ccggacagac tgatgaatcc cctcctggac cagtacctgt ggcacttaca gtcgaccacc     2160
tctggagaga ctctgaatca aggcaatgca gcaaccacat ttggaaaaat caggagtgga     2220
gactttgcct tttacagaaa gaactggctg cctgggcctt gtgttaaaca gcagagactc     2280
tcaaaaactg ccagtcaaaa ttacaagatt cctgccagcg ggggcaacgc tctgttaaag     2340
tatgacaccc actatacctt aaacaaccgc tggagcaaca tagcgcctgg acctccaatg     2400
gcaacagctg gaccttcaga tgggactttc agcaacgccc agctcatctt ccctggacca     2460
tcagtcaccg gaaacacaac aacctcagca acaatctgt tgtttacatc agaagaagaa     2520
attgctgcca ccaacccaag agacacggac atgtttggtc agattgctga caataatcag     2580
aatgctacaa ctgctcccat aaccggcaac gtgactgcta tgggagtgct tcctggcatg     2640
gtgtggcaaa acagagacat ttactaccaa gggccaattt gggccaagat cccacacgcg     2700
gacggacatt ttcatccttc accgctaatt ggcggttttg gactgaaaca tccgcctccc     2760
cagatattta tcaaaaacac ccccgtacct gccaatcctg cgacaacctt cactgcagcc     2820
agagtggact cttttcatca acaatacagc accggccagg tcgctgttca gattgaatgg     2880
gaaatcgaaa aggaacgctc caaacgctgg aatcctgaag tgcagtttac ttcaaactat     2940
gggaaccagt cttctatgtt gtgggctccc gatacaactg gaagtatac agagccgcgg     3000
gttattggct ctcgttattt gactaatcat ttgtaactgc ctagttaatc aataaaccgt     3060
gtgattcgtt tcagttgaac tttggtctct gcgaagggcg aattc                    3105
```

<210> SEQ ID NO 20

<211> LENGTH: 3105
<212> TYPE: DNA
<213> ORGANISM: Unknown
<220> FEATURE:
<223> OTHER INFORMATION: AAV serotype, clone C3

<400> SEQUENCE: 20

| | |
|---|---|
| gaattcgccc ttgctgcgtc aactggacca atgagaactt tcccttcaac gattgcgtcg | 60 |
| acaagatggt gatctggtgg gaggagggca agatgaccgc caaggtcgtg gagtccgcca | 120 |
| aggccattct gggcggaagc aaggtgcgcg tggaccaaaa gtgcaagtca tcggcccaga | 180 |
| tcgaccccac gcccgtgatc gtcacctcca acaccaacat gtgcgccgtg atcgacggga | 240 |
| acagcaccac cttcgagcac cagcagccgc tgcaggaccg catgttcaag ttcgagctca | 300 |
| cccgccgtct ggagcacgac tttgcaagg tgaccaagca ggaagtcaaa gagttcttcc | 360 |
| gctgggctca ggatcacgtg actgaggtgg cgcatgagtt ctacgtcaga aagggcggag | 420 |
| ccaccaaaag acccgccccc agtgacgcgg atataagcga gcccaagcgg gcctgcccct | 480 |
| cagttgcgga gccatcgacg tcagacgcgg aagcaccggt ggactttgcg acaggtacc | 540 |
| aaaacaaatg ttctcgtcac gcgggcatgc ttcagatgct gtttccctgc aagacatgcg | 600 |
| agagaatgaa tcagaatttc aacgtctgct tcacgcacgg ggtcagagac tgctcagagt | 660 |
| gcttccccgg cgcgtcagaa tctcaacccg tcgtcagaaa aaagacgtat cagaaactgt | 720 |
| gcgcgattca tcatctgctg gggcgggcac ccgagattgc gtgttcggcc tgcgatctcg | 780 |
| tcaacgtgga cttggatgac tgtgtttctg agcaataaat gacttaaacc aggtatggct | 840 |
| gctgacggtt atcttccaga ttggctcgag gacaacctct ctgagggcat cgcgagtgg | 900 |
| tgggacctga aacctggagc ccccaagctc aaggccaacc agcagaagca ggacgacggc | 960 |
| cggggtctgt gcttcctgg ctacaagtac ctcggaccct ccacggact cgacaagggg | 1020 |
| gagcccgtca acgcggcgga cgcagcggcc ctcgagcacg acaaggccta cgaccagcag | 1080 |
| ctcaaagcgg gtgacaatcc gtacctgcgg tataaccacg ccgacgccga gtttcaggag | 1140 |
| cgtctgcaag aagatacgtc ttttgggggc aacctcgggc gagcagtctt ccaggccaag | 1200 |
| aagagggtac tcgaaccact gggcctggtt gaagaaggtg ctaagacggc tcctggaaag | 1260 |
| aagagaccgt tagagtcacc acaagagccc gactcctcct caggaatcgg caaaaaaggc | 1320 |
| aaacaaccag ccaaaaagag actcaacttt gaagaggaca ctggagccgg agacggaccc | 1380 |
| cctgaaggat cagataccag cgccatgtct tcagacattg aaatgcgtgc agcaccgggc | 1440 |
| ggaaatgctg tcgatgcggg acaaggttcc gatggagtgg gtaatgcctc gggtgattgg | 1500 |
| cattgcgatt ccacctggtc tgagggcaag gtcacaacaa cctcgaccag aacctgggtc | 1560 |
| ttgcccacct acaacaacca cttgtacctg cggctcggaa caacatcaaa cagcaacacc | 1620 |
| tacaacggat tctccacccc ctggggatac tttgactta acagattcca ctgtcacttc | 1680 |
| tcaccacgtg actggcaaag actcatcaac aacaactggg gactacgacc aaaagccatg | 1740 |
| cgcgttaaaa tcttcaatat ccaagttaag gaggtcacaa cgtcgaacgg cgagactacg | 1800 |
| gtcgctaata accttaccag cacggttcag atatttgcgg actcgtcgta tgagctcccg | 1860 |
| tacgtgatgg acgctggaca agagggaagt ctgcctcctt tccccaatga cgtcttcatg | 1920 |
| gtgcctcaat atggctactg tggcattgtg actggcgaaa atcagaacca gacggacaga | 1980 |
| aatgcttct actgcctgga gtattttcct tcacaaatgc tgagaactgg caataacttt | 2040 |
| gaaatggctt acaactttga gaaggtgccg ttccactcaa tgtatgctca cagccagagc | 2100 |
| ctggacagac tgatgaatcc cctcctggac cagtaccgt ggcacttaca gtcgaccacc | 2160 |

```
tctggagaga ctctgaatca aggcaatgca gcaaccacat ttggaaaaat caggagtgga    2220
gactttgcct tttacagaaa gaactggctg cctgggcctt gtgttaaaca gcagagattc    2280
tcaaaaactg ccagtcaaaa ttacaagatt cctgccagcg ggggcaacgc tctgttaaag    2340
tatgacaccc actatacctt aaacaaccgc tggagcaaca tagcgcctgg acctccaatg    2400
gcaacagctg gaccttcaga tggggacttc agcaacgccc agctcatctt ccctggacca    2460
tcagtcaccg gaaacacaac aacctcagca aacaatctgt tgtttacatc agaaggagaa    2520
attgctgcca ccaacccaag agacacggac atgtttggtc agattgctga caataatcag    2580
aatgctacaa ctgctcccat aaccggcaac gtgactgcta tgggagtgct tcctggcatg    2640
gtgtggcaaa acagagacat ttactaccaa gggccaattt gggccaagat cccacacgcg    2700
gacggacatt tcatccttc  accgctaatt ggcggttttg gactgaaaca tccgcctccc    2760
cagatattta tcaaaaacac ccccgtacct gccaatcctg cgacaacctt cactgcagcc    2820
agagtggact ctttcatcac acaatacagc accggccagg tcgctgttca gattgaatgg    2880
gaaatcgaaa aggaacgctc caaacgccgg aatcctgaag tgcagtttac ttcaaactat    2940
gggaaccagt cttctatgtt gtgggctccc gatacaactg gaagtatac agagccgcgg     3000 gttattggct ctcgttattt gactaatcat tgtaactgc ctagttaatc aataaaccgt     3060
gtgattcgtt tcagttgaac tttggtctct gcgaagggcg aattc                   3105
```

<210> SEQ ID NO 21
<211> LENGTH: 3105
<212> TYPE: DNA
<213> ORGANISM: Unknown
<220> FEATURE:
<223> OTHER INFORMATION: AAV serotype, clone C5

<400> SEQUENCE: 21

```
gaattcgccc ttcgcagaga ccaaagttca actgaaacga atcacacggt ttattgatta      60
actaggcagt tacaaatgat tagtcaaata acgagagcca ataacccgcg gctctgtata     120
cttcccagtt gtatcgggag cccacaacat agaagactgg ttcccacagt ttgaagtaaa     180
ctgcacttca ggattccagc gtttggagcg ttccttttcg atttcccatt caatctgaac     240
agcgacctgg ccggtgctgt attgtgtgat gaaagagtcc actctggctg cagtgaaggt     300
tgtcgcagga taggcaggta cgggggtgtt tttgataaat atctggggag gcggatgttt     360
cagtccaaaa ccgccaatta gcggtgaagg atgaaaatgt ccgtccgcgt gtgggatctt     420
ggcccaaatt ggcccttggt agtaaatgtc tctgttttgc cacaccatgc caggaagcac     480
tcccatagca gtcacgttgc cggttatggg agcagttgta gcattctgat tattgtcagc     540
aatctgacca acatgtccg tgtctcttgg gttggtggca gcaatttctt cttctgatgt      600
aaacaacaga ttgtttgctg aggttgttgt gtttccggtg actgatggtc cagggaagat     660
gagctgggcg ttgctgaagt ccccatctga aggtccagct gttgccattg gaggtccagg     720
cgctatgttg ctccagcggt tgtttaaggt atagtgggtg tcatacttta acagagcgtt     780
gcccccgctg gcaggaatct tgtaattttg actggcagtt tttgagaatc tctgctgttt     840
aacacaaggc ccaggcagcc agttctttct gtaaaaggca aagtctccac tcctgatttt     900
tccaaatgtg gttgctgcat tgccttgatt cagagtctct ccagaggtgg tcgactgtaa     960
gtgccacagg tactggtcca ggaggggatt catcagtccg tccaggctct ggctgtgagc    1020
atacattgag tggaacggca ccttctcaaa gttgtaagcc gtttcaaagt tattgccagt    1080
```

```
tctcagcatt tgtgaaggaa atactccag  gcagtagaaa gcatttctgt ccgtctggtt    1140
ctgattttcg ccagtcacaa tgccacagta gccatattga ggcaccatga agacgtcatt    1200
ggggaaagga ggcagacttc cctcttgtcc agcgtccatc acgtacggga gctcatacga    1260
cgagtccgca aatatctgaa ccgtgctggt aaggttatta gcgaccgtag tctcgccgtt    1320
cgacgttgtg acctccttaa cttggatatt gaagatttta acgcgcatgg cttttggtcg    1380
tagtccccag ttgttgttga tgagtctttg ccagtcacgt ggtgagaagt gacagtggaa    1440
tctgttaaag tcaaagtatc cccaggggt  ggagaatccg ttgtaggtgt tgctgtttga    1500
tgttgttccg agccgcaggt acaagtggtt gttgtaggtg ggcaagaccc aggttctggt    1560
cgaggttgtt gtgaccttgc cctcagacca ggtggaatcg caatgccaat cacccgaggc    1620
attacccact ccatcggaac cttgtcccgc atcgacagca tttccgcccg gtgctgcacg    1680
catttcaatg tctgaagaca tggcgctggt atctgatcct tcaggggtc  cgtctccggc    1740 tccagtgtcc tcttcaaagt tgagtctctt tttggctggt tgtttgcctt ttttgccgat    1800
tcctgaggag gagtcgggct cttgtggtga ctctaacggt ctcttctttc caggagccgt    1860
cttagcacct tcttcaacca ggcccagagg ttcgagtacc ctcttcttgg cctggaagac    1920
tgctcgcccg aggttgcccc caaaagacgt atcttcttgc agacgctcct gaaactcggc    1980
gtcggcgtgg ttataccgca ggtacggatt gtcacccgct ttgagctgct ggtcgtaggc    2040
cttgtcgtgc tcgagggccg ctgcgtccgc cgcgttgacg ggctcccct  tgtcgagtcc    2100 gttgaagggt ccgaggtact cgtagccagg aagcaccaga ccccggccgt cgtcctgctt    2160
ctgctggttg gccttgggct tgggggctcc aggtttcagg tcccaccact cgcgaatgcc    2220
ctcagagagg ttgtcctcga gccaatctgg aagataaccg tcagcagcca tacctggttt    2280
aagtcattta ttgctcagaa acacagtcat ccaagtccac gttgacgaga tcgcaggccg    2340
aacacgcaat ctcgggtgcc cgccccagca gatgatgaat cgcgcacagt ttctgatacg    2400
tcttttttct gacgacgggt tgagattctg acgcgccggg gaagcactct gagcagtctc    2460
tgaccccgtg cgtgaagcag acgttgaaat tctgattcat tctctcgcat gtcttgcagg    2520
gaaacagcat ctgaagcatg cccgcgtgac gagaacattt gttttggtac ctgtccgcaa    2580
ggtccaccgg tgcttccgcg tctgacgtcg atggctccgc aactgagggg caggcccgct    2640
tgggctcgct tatatccgcg tcactggggg cgggtctttt ggtggctccg ccctttctga    2700
cgtagaactc atgcgccacc tcagtcacgt gatcctgagc ccagcggaag aactctttga    2760
cttcctgctt ggtcaccttg ccaaagtcgt gctccagacg gcgggtgagc tcgaacttga    2820
acatgcggtc ctgcagcggc tgctggtgct cgaaggtggt gctgttcccg tcgatcacgg    2880
cgcacatgtt ggtgttggag gtgacgatca cgggcgtggg gtcgatctgg gccgatgact    2940
tgcacttttg gtccacgcgc accttgcttc cgcccagaat ggccttggcg gactccacga    3000
ccttggcggt catcttgccc tcctcccacc agatcaccat cttgtcgacg caatcgttga    3060
agggaaagtt ctcattggtc cagttgacgc agcaagggcg aattc                    3105
```

<210> SEQ ID NO 22
<211> LENGTH: 3094
<212> TYPE: DNA
<213> ORGANISM: Unknown
<220> FEATURE:
<223> OTHER INFORMATION: AAV serotype, clone F1

<400> SEQUENCE: 22

```
gaattcgccc ttgctgcgtc aactggacca agagaacttt cccttcaacg attgcgtcga    60
```

```
caagatggtg atctggtggg aggagggcaa gatgacggcc aaggtcgtgg agtccgccaa    120
agccattctg ggcggaagca aggtgcgcgt cgaccaaaag tgcaagtcct cggcccagat    180
cgatcccacc cccgtgatcg tcacctccaa caccaacatg tgcgccgtga tcgacgggaa    240
cagcaccacc ttcgagcacc agcagccgtt gcaggaccgg atgttcaaat ttgaactcac    300
ccgccgtctg gaacacgact ttggcaaggt gaccaagcag gaagtcaaag agttcttccg    360
ctgggctagt gatcacgtga ctgaggtgac gcatgagttc tacgtcagaa agggcggagc    420
cagcaaaaga cccgcccccg atgacgcgga tataagcgag cccaagcggg cctgtccctc    480
agtcacggac ccatcgacgt cagacgcgga aggagctccg gtggactttg ccgacaggta    540
ccaaaacaaa tgttctcgtc acgcgggcat gcttcagatg ctgtttccct gcaaaacgtg    600
cgagagaatg aatcagaatt tcaacatttg cttcacgcac ggggtcagag actgtttaga    660
atgtttcccc ggcgtgtcag aatctcaacc ggtcgtcaga aaaagacgt atcggaagct    720 gtgtgcgatt catcatctgc tggggcgggc acccgagatt gcttgctcgg cctgcgacct    780
ggtcaacgtg gacctggacg actgtgtttc tgagcaataa atgacttaaa ccgggtatgg    840
ctgccgatgg ttatcttcca gattggctcg aggacaacct ctctgagggc attcgcgagt    900
ggtgggacct gaaacctgga gccccgaaac ccaaagccaa ccagcaaaag caggacgacg    960 gccgggtct ggtgcttcct ggctacaagt acctcggacc cttcaacgga ctcgacaagg   1020
gggagcccgt caacgcggcg gacgcagcgg ccctcgagca cgacaaggcc tacgaccagc   1080
agctcaaagc gggtgacaat ccgtacctgc ggtataacca cgccgacgcc gagtttcagg   1140
agcgtctgca agaagatacg tcatttgggg gcaacctcgg gcgagcagtc ttccaggcca   1200
agaagcgggt tctcgaacct ctcggtctgg ttgaggaagg cgctaagacg gctcctggaa   1260
agaagagacc catagactct ccagactcct ccacgggcat cggcaaaaaa ggccagcagc   1320
ccgctaaaaa gaagctcaat tttggtcaga ctggcgactc agagtcagtc cccgaccctc   1380
aacctcttgg agaacctcca gcagcgccct ctagtgtggg atctggtaca atggctgcag   1440
gcggtggcgc accaatggca gacaataacg aaggtgccga cggagtgggt aatgcctcag   1500
gaaattggca ttgcgattcc acatggctgg gcgacagagt catcaccacc agcaccagaa   1560
cctgggccct ccccacctac aacaaccacc tctacaagca aatctccagc agcagctcag   1620
gagccaccaa tgacaaccac tacttcggct acagcacccc ctgggggtat ttgacttta   1680 acagattcca ctgccacttc tcaccacgtg actggcagcg actcatcaac aacaactggg   1740
gattccggcc caagaagctg cggttcaagc tcttcaacat ccaggtcaag gaggtcacaa   1800
cgaatgacgg cgtcacgacc atcgctaata accttaccag cacggttcag gtcttctcgg   1860
actcggaata ccagctgccg tacgtcctcg gctctgcgca ccagggctgc ctgcctccgt   1920
tcccggcgga cgtcttcatg attcctcagt acggctacct gactctgaac aacggcagcc   1980
aatcggtggg ccgttcctcc ttctactgcc tggaatattt cccctctcaa atgctgagaa   2040
cgggcaacaa ctttgagttc agttacagct tcgaggacgt gcctttccac agcagctacg   2100
cgcacagcca gagcctagac cggctgatga accctctcat cgaccagtac ctgtactacc   2160
tggcccggac ccagagcacc acgggttcca ccagggaact gcaatttcat caagctgggc   2220
ccaatactat ggccgagcag tcaaagaact ggctgcctgg accctgctat aggcaacagg   2280
gactgtcaaa gaacttggac tttaacaaca cagcaatttt gcctggact gctgccacta   2340 aatatcatct gaatggcaga aactctttga ccaatcctgg cattcccatg gcaaccaaca   2400
```

-continued

```
aggatgatga ggaccagttc tttcccatca acggggtact ggttttttggc aagacgggag    2460 ctgccaacaa aactacgctg gaaaacgttc tgatgaccag cgaggaggag atcaagacca    2520
ctaaccctgt ggctacagaa gaatacggtg tggtctccag caacctgcag ccgtctacag    2580
ccgggcctca atcacagact atcaacagcc agggagcact gcctggcatg gtctggcaga    2640
accgggacgt gtatctgcag ggtcccatct gggccaaaat tcctcacacg gatggcaact    2700
ttcacccgtc tcctctgatg ggcggttttg gactcaaaca cccgcctcca cagatcctga    2760
tcaaaaacac acctgtacct gctaatcctc cggaggtgtt tactcctgcc aagtttgcct    2820
ccttcatcac gcagtacagc accggacaag tcagcgtgga aatcgagtgg gagctgcaga    2880
aagaaaacag caagcgctgg aacccagaaa ttcagtatac ttccaattat gccaagtcta    2940
ataatgttga atttgctgtg aaccctgatg gtgtttatac tgagcctcgc cccattggca    3000
ctcgttacct cccccgtaat ctgtaattgc ttgttaatca ataaaccggt tgattcgttt    3060
cagttgaact ttggtctctg cgaagggcga attc    3094
```

<210> SEQ ID NO 23
<211> LENGTH: 3095
<212> TYPE: DNA
<213> ORGANISM: Unknown
<220> FEATURE:
<223> OTHER INFORMATION: AAV serotype, clone F3

<400> SEQUENCE: 23

```
gaattcgccc ttcgcagaga ccaaagttca actgaaacga atcaaccggt ttattgatta     60
acaagcaatt acagattacg ggtgaggtaa cgagtgccaa tggggcgagg ctcagtataa    120
acaccatcag ggttcacagc aaattcaaca ttattagact tggcataatt ggaagtatac    180
tgaatttctg ggttccagcg cttgctgttt tctttctgca gctcccactc gatttccacg    240
ctgacttgtc cggtgctgta ctgcgtgatg aaggaggcaa acttggcagg agtaaacacc    300
tccggaggat tagcaggtac agtgtgtttt ttgatcagga tctgtggagg cgggtgtttg    360
agtccaaaac cgcccatcag aggagacggg tgaaagttgc catccgtgtg aggaattttg    420
gcccagatgg gaccctgcag atacacgtcc cggttctgcc agaccatgcc aggcagtgct    480
ccctggctgt tgatagtctg tgattgaggc ccggctgtag acgactgcag gttgctggag    540
accacaccgt attcttctgt agccacaggg ttagtggtct tgatctcctc ctcgctggtc    600
atcagaacgt tttccagcgt agttttgttg gcagctcccg tcttgccaaa aaccagtacc    660
ccgttgatgg gaaagaactg gtcctcatca tccttgttgg ttgccatggg aatgccagga    720
ttggtcaaag agtttctgcc attcagatga tatttagtgg cagcagtcca ggcaaaattg    780
ctgttgttgt taaagtccaa gttctttgac agtctctgtt gcctatagca gggtccaggc    840
agccagttct ttgactgctc ggccatagta ttgggcccag cttgatgaaa ttgcagttcc    900
ctggtggaac ccgtggtgct ctgggtccgg gccaggtagt acaggtactg gtcgatgaga    960
gggttcatca gccggtctag gctctggctg tgcgcgtagc tgctgtggaa aggcacgtcc   1020
tcgaagctgt aactgaactc aaagttgttg cccgttctca gcatttgaga ggggaaatat   1080
tccaggcagt agaaggagga acggcccacc gattggctgc cgttgtccag agtcaggtag   1140
ccgtactgag gaatcatgaa gacgtccgcc gggaacggag gcaggcagcc ctggtgcgca   1200
gagccgagga cgtacggcag ctggtattcc gagtccgaga agacctgaac cgtgctggta   1260
aggttattag cgatggtcgt gacgccgtca ttcgttgtga cctccttgac ctggatgttg   1320
aggagcttga accgcagctt cttgggccgg aatcccagt tgttgttgat gagtcgctgc   1380
```

```
cagtcacgtg gtgagaagtg gcagtggaat ctgttaaagt caaaatcccc ccagggggtg    1440
ctgtagccga agtagtggtt gtcattggtg gctcctgagc tgctgctgga gatttgcttg    1500
tagaggtggt tgttgtaggt ggggagggcc caggttctgg tgctggtggt gatgactctg    1560
tcgcccagcc atgtggaatc gcaatgccaa tttcctgagg cattacccac tccgtcggca    1620
ccttcgttat tgtctgccat tggtgcgcca ccgcctgcag ccattgtacc agatcccaca    1680
ctagagggcg ctgctggagg ttctccaaga ggttgagggt cggggactga ctctgagtcg    1740
ccagtctgac caaaattgag cttcttttta gcgggctgct ggccttttt gccgatgccc    1800 gtggaggagt ctggagagcc tatgggtctc ttctttccag gagccgtctt agcgccttcc    1860
tcaaccagac cgagaggttc gagaacccgc ttcttggcct ggaagactgc tcgcccgagg    1920
ttgcccccaa atgacgtatc ttcttgcaga cgctcctgaa actcggcgtc ggcgtggtta    1980
taccgcaggt acggattgtc acccgctttg agctgctggt cgtaggcctt gtcgtgctcg    2040
agggccgctg cgtccgccgc gttgacgggc tcccccttgt cgagtccgtt gaagggtccg    2100
aggtacttgt agccaggaag caccagaccc cggccgtcgt cctgcttttg ctggttggct    2160
ttgggtttcg gggctccagg tttcaggtcc caccactcgc gaatgccctc agagaggttg    2220
tcctcgagcc aatctggaag ataaccatcg gcagccatac ctggtttaag tcatttattg    2280
ctcagaaaca cagtcgtcca ggtccacgtt gaccaggtcg caggccgagc aagcaatctc    2340
gggtgcccgc cccagcagat gatgaatcgc acacagcttc cgatacgtct ttttctgac    2400 gaccggttga gattctgaca cgccggggaa acattctaaa cagtctctga ccccgtgcgt    2460
gaagcaaatg ttgaaattct gattcattct ctcgcacgtt ttgcagggaa acagcacctg    2520
aagcatgccc gcgtgacgag aacatttgtt ttggtacctg tcggcaaagt ccaccggagc    2580
tccttccgcg tctgacgtcg atgggtccgt gactgaggga cgggcccgct tgggctcgct    2640
tatatccgcg tcatcggggg cgggtctttt gctggctccg ccctttctga cgtagaactc    2700
atgcgtcacc tcagtcacgt gatcactagc ccagcggaag aactctttga cttcctgctt    2760
tgtcaccttg ccaaagtcgt gttccagacg gcgggtgagt tcaaatttga acatccggtc    2820
ctgcaacggt tgctggtgct cgaaggtggt gctgttcccg tcgatcacgg cgcacatgtt    2880
ggtgttggag gtgacgatca cggggtggg atcgatctgg gcggacgact tgcactttg     2940 gtccacgcgc accttgctgc cgccgagaat ggccttggcg gactccacga ccttggccgt    3000
catcttgccc tcctcccacc agatcaccat cttgtcgacg caatcgttga agggaaagtt    3060
ctcattggtc cagttgacgc agcaagggcg aattc                              3095
```

<210> SEQ ID NO 24
<211> LENGTH: 3095
<212> TYPE: DNA
<213> ORGANISM: Unknown
<220> FEATURE:
<223> OTHER INFORMATION: AAV serotype, clone F5

<400> SEQUENCE: 24

```
gaattcgccc ttcgcagaga ccaaagttca actgaaacga atcaaccggt ttattgatta      60
acaagcaatt acagattacg ggtgaggtaa cgagtgccaa tggggcgagg ctcagtataa     120
acaccatcag ggttcacagc aaattcaaca ttattagact tggcataatt ggaagtatac     180
tgaatttctg ggttccagcg cttgctgttt tctttctgca gctcccactc gatttccacg     240
ctgacttgtc cggtgctgta ctgcgtgatg aaggaggcaa acttggcagg agtaaacacc     300
```

```
tccggaggat tagcaggtac aggtgtgttt tgatcagga tctgtggagg cgggtgttcg      360
agtccaaaac cgcccatcag aggagacggg tgaaagttgc catccgtgtg aggaattttg    420
gcccagatgg gaccctgcag atacacgtcc cggttctgcc agaccatgcc aggcagtgct    480
ccctggctgt tgatagtctg tgattgaggc cggctgtag acgactgcag gttgctggag     540
accacaccgt attcttctgt agccacaggg ttagtggtct tgatctcctc ctcgctggtc    600
atcagaacgt tttccagcgt agttttgttg gcagctcccg tcttgccaaa aaccagtacc    660
ccgttgatgg gaaagaactg gtcctcatca tccttgttgg ttgccatggg aatgccagga    720
ttggtcaaag agtttctgcc attcagatga tatttagtgg cagcagtcca ggcaaaattg    780
ctgttgttgt taaagtccaa gttctttgac agtctctgtt gcctatagca gggtccaggc    840
agccagttct ttgactgctc ggccatagta ttgggcccag cttgatgaaa ttgcagttcc    900
ctggtggaac ccgtggtgct ctgggtccgg gccaggtagt acaggtactg gtcgatgaga    960
gggttcatca gccggtctag gctctggctg tgcgcgtagc tgctgtggaa aggcacgtcc   1020
tcgaagctgt aactgaactc aaagttgttg cccgttctca gcatttgaga ggggaaatat   1080
tccaggcagt agaaggagga acggcccacc gattggctgc cgttgttcag agtcaggtag   1140
ccgtactgag gaatcatgaa gacgtccgcc gggaacggag gcaggcagcc ctggtgcgca   1200
gagccgagga cgtacggcag ctggtattcc gagtccgaga agacctgaac cgtgctggta   1260
aggttattag cgatggtcgt gacgccgtca ttcgttgtga cctccttgac ctggatgttg   1320
aagagcttga accgcagctt cttgggccgg aatccccagt tgttgttgat gagtcgctgc   1380
cagtcacgtg gtgagaagtg gcagtggaat ctgttaaagt caaaataccc ccaggggtg    1440
ctgtagccga agtagtggtt gtcattggtg gctcctgagc tgctgctgga gatttgcttg   1500
tagaggtggt tgttgtaggt ggggagggcc caggttctgg tgctggtggt gatgactctg   1560
tcgcccagcc atgtggaatc gcaatgccaa tttcctgagg cattacccac tccgtcggca   1620
ccttcgttat tgtctgccgt tggtgcgcca ccgcctgcag ccattgtacc agatcccaca   1680
ctagagggcg ctgctggagg ttctccaaga ggttgagggt cggggactga ctctgagtcg   1740
ccagtctgac caaaattgag cttctttta gcgggctgct ggccttttt gccgatgccc     1800
gtggaggagt ctggagagtc tatgggtctc ttctttccag gagccgtctt agccgccttcc  1860
tcaaccagac cgagaggttc gagaacccgc ttccttggcct ggaagactgc tcgcccgagg  1920
ttgcccccaa atgacgtatc ttcttgcagg cgctcctgaa actcggcgtc ggcgtggtta   1980
taccgcaggt acggattgtc acccgctttg agctgctggt cgtaggcctt gtcgtgctcg   2040
agggccgctg cgtccgccgc gttgacgggc tccccttgt cgagtccgtt gaagggtccg    2100
aggtacttgt agccaggaag caccagaccc cggccgtcgt cctgcttttg ctggttggct   2160
ttgggtttcg gggctccagg tttcaggtcc caccactcgc gaatgccctc agagaggttg   2220
tcctcgagcc aatctggaag ataaccatcg gcagccatac ctggtttaag ccatttattg   2280
ctcagaaaca cagtcgtcca ggtccacgtt gaccaggtcg caggccgagc aggcaatctc   2340
gggtgcccgc cccagcagat gatgaatcgc acacagcttc cgatacgtct tttttctgac   2400
gaccggttga gattctgaca cgccggggaa acattctaaa cagtctctga ccccgtgcgt   2460
gaagcaaatg ttgaaattct gattcattct ctcgcacgtt ttgcagggaa acagcatctg   2520
aagcatgccc gcgtggcgag aacatttgtt ttggtacctg tcggcaaagt ccaccggagc   2580
tccttccgcg tctgacgtcg atgggtccgt gactgaggga caggcccgct tgggctcgct   2640
tatatccgcg tcatcggggg cgggtctttt gctggctccg ccctttctga cgtagaactc   2700
```

```
atgcgtcacc tcagtcacgt gatcactagc ccagcggaag aactctttga cttcctgctt    2760
tgtcaccttg ccaaagtcgt gttccagacg gcgggtgagt tcaaatttga acatccggtc    2820
ctgcaacggc tgctggtgct cgaaggtggt gctgttcccg tcgatcacgg cgcgcatgtt    2880
ggtgttggag gtgacgatca cggggtgggg atcgatctgg gcggacgact tgcacttttg    2940
gtccacgcgc accttgctgc cgccgagaat ggccttggcg gactccacga ccttggccgt    3000
catcttgccc tcctcccacc agatcaccat cttgtcgacg caatcgttga agggaaagtt    3060
ctcattggtc cagttgacgc agcaagggcg aattc                               3095
```

<210> SEQ ID NO 25
<211> LENGTH: 3142
<212> TYPE: DNA
<213> ORGANISM: Unknown
<220> FEATURE:
<223> OTHER INFORMATION: AAV serotype, clone H6

<400> SEQUENCE: 25

```
aaaacgacgg gccagtgatt gtaatacgac tcactatagg gcgaaattga aattagcggc     60
cgcgaattcg cctttcgcag agaccaaagt tcaactgaaa cgaattaaac ggtttattga    120
ttaacaagca attacagatt acgagtcagg tatctggtgc caatggggcg aggctctgaa    180
tacacaccat tagtgtccac agtaaagtcc acattaacag acttgttgta gttgaagtg     240 tactgaattt cgggattcca gcgtttgctg ttctccttct gcagctccca ctcgatctcc    300
acgctgacct gtcccgtgga atactgtgtg atgaaagaag caaacttggc agaactgaag    360
tttgtgggag gattggctgg aacgggagtg ttttgatca tgatctgagg aggcgggtgt     420
ttgagtccaa aacctcccat cagtgggaaa ggatgaaagt gtccatcggt gtgaggaatc    480
ttggcccaaa tgggtccctg caggtacacg tctcgatcct gccacaccat accaggtaac    540
gctccttggt gattgacagt tccagtagtt ggaccagtgt tgagttttg caaattattt     600 gacacagtcc cgtactgctc cgtagccacg ggattggtgg ccctgatttc ttcttcatct    660
gtaatcatga catttttccaa atccgcgtcg ttggcatttg ttccttgttt accaaatatc    720
agggttccat gcatggggaa aaacttttct tcgtcatcct tgtgactggc catagctggt    780
cctggattaa ccaacgagtc ccggccattt agatgatact ttgtagctgc agtccaggga    840
aagttgctgt tgttgttgtc gtttgcctgt tttgacagac gctgctgtct gtagcaaggt    900
ccaggcagcc agtttttagc ttgaagagac atgttggttg gtccagcttg ctaaacagt     960 agccgagact gctgaagagt tccactattt gtttgtgtct tgttcagata atacaggtac   1020
tggtcgatca gaggattcat cagccgatcc agactctggc tgtgagcgta gctgctgtgg   1080
aaaggcacgt cttcaaaagt gtagctgaac tgaaagttgt ttccagtacg cagcatctga   1140
gaaggaaagt actccaggca gtaaaaggaa gagcgtccta ccgcctgact cccgttgttc   1200
agggtgaggt atccatactg tgggaccatg aagacgtccg ctggaaacgg cgggaggcat   1260
ccttgatgcg ccgagcccag gacgtacggg agctggtact ccgagtcagt aaacacctga   1320
accgtgctgg taaggttatt ggcaatcgtc gtcgtaccgt cattctgcgt gacctctttg   1380
acttgaatat taaagagctt gaagttgagt cttttgggcc ggaatcccg gttgttgttg    1440 acgagtcttt gccagtcacg tggtgaaaag tggcagtgga atctgttgaa gtcaaaatac   1500 ccccagggg tgctgtagcc aaagtagtgg ttgtcgttgc tggctcctga ttggctggag    1560
atttgcttgt agaggtggtt gttgtatgtg ggcagggcc aggttcgggt gctggtggtg    1620
```

| | |
|---|---|
| atgactctgt cgcccagcca ttgggaatcg caatgccaat ttcctgagga attacccact | 1680 |
| ccatcggcac cctcgttatt gtctgccatt ggtgcgccac tgcctgtagc cattgtagta | 1740 |
| gatcccagac cagaggggc tgctggtggc tgtccgagag gctgggggtc aggtacggag | 1800 |
| tctgcgtctc cagtctgacc aaaatttaat cttttcttg caggctgctg gcccgctttt | 1860 |
| ccggttcccg aggaggagtc tggctccaca ggagagtgct ctaccggcct cttttttccc | 1920 |
| ggagccgtct taacaggctc ctcaaccagg cccagaggtt caagaaccct cttttcgcc | 1980 |
| tggaagactg ctcgtccgag gttgcccca aaagacgtat cttctttaag gcgctcctga | 2040 |
| aactctgcgt cggcgtggtt gtacttgagg tacgggttgt ctccgctgtc gagctgccgg | 2100 |
| tcgtaggcct tgtcgtgctc gagggccgcg gcgtctgcct cgttgaccgg ctccccttg | 2160 |
| tcgagtccgt tgaagggtcc gaggtacttg tacccaggaa gcacaagacc cctgctgtcg | 2220 |
| tccttatgcc gctctgcggg cttggtggt ggtgggccag gtttgagctt ccaccactgt | 2280 |
| cttattcctt cagagagagt gtcctcgagc caatctggaa gataaccatc ggcagccata | 2340 |
| cctgatttaa atcatttatt gttcagagat gcagtcatcc aaatccacat tgaccagatc | 2400 |
| gcaggcagtg caagcgtctg gcacctttcc catgatatga tgaatgtagc acagtttctg | 2460 |
| atacgccttt ttgacgacag aaacggttg agattctgac acgggaaagc actctaaaca | 2520 |
| gtctttctgt ccgtgagtga agcagatatt tgaattctga ttcattctct cgcattgtct | 2580 |
| gcagggaaac agcatcagat tcatgcccac gtgacgagaa catttgtttt ggtacctgtc | 2640 |
| cgcgtagttg atcgaagctt ccgcgtctga cgtcgatggc tgcgcaactg actcgcgcgc | 2700 |
| ccgtttgggc tcacttatat ctgcgtcact ggggcgggt cttttcttag ctccacccctt | 2760 |
| tttgacgtag aattcatgct ccacctcaac cacgtgatcc tttgcccacc ggaaaaagtc | 2820 |
| tttcacttcc tgcttggtga cctttccaaa gtcatgatcc agacggcggg taagttcaaa | 2880 |
| tttgaacatc cggtcttgca acggctgctg gtgctcgaag gtcgttgagt tcccgtcaat | 2940 |
| cacggcgcac atgttggtgt tggaggtgac gatcacggga gtcgggtcta tctgggccga | 3000 |
| ggacttgcat ttctggtcca cacgcacctt gcttcctcca agaatggctt tggccgactc | 3060 |
| cacgaccttg gcggtcatct tcccctcctc ccaccagatc accatcttgt cgacgcaatg | 3120 |
| gtaaaaggaa agttctcatt gg | 3142 |

<210> SEQ ID NO 26
<211> LENGTH: 3075
<212> TYPE: DNA
<213> ORGANISM: Unknown
<220> FEATURE:
<223> OTHER INFORMATION: AAV serotype, clone H2

<400> SEQUENCE: 26

| | |
|---|---|
| tgagaactt cctttcaacg attgcgtcgg acaagatggt gatctggtgg gaggagggga | 60 |
| agatgaccgc caaggtcgtg gagtcggcca agccattct ggaggaagc aaggtgcgtg | 120 |
| tggaccagaa atgcaagtcc tcggcccaga tagacccgac tcccgtgatc gtcacctcca | 180 |
| acaccaacat gtgcgccgtg attgacggga actcaacgac cttcgagcac cagcagccgt | 240 |
| tgcaagaccg gatgttcaaa tttgaactta cccgccgtct ggatcatgac tttgaaaagg | 300 |
| tcaccaagca ggaagtgaaa gactttttcc ggtgggcaaa ggatcacgtg gttgaggtgg | 360 |
| agcatgaatt ctacgtcaaa aagggtggag ctaagaaaag accgcccccc agtgacgcag | 420 |
| atataagtga gcccaaacgg gcgcgcgagt cagttgcgca gccatcaacg tcagacgcgg | 480 |
| aagcttcgat caactacgcg gacaggtacc aaaaacaaat gttctcgtca cgtgggcatg | 540 |

```
aatctgatgc tgtttccctg cagacaatgc gagagaatga atcagaattc aaatatctgc    600
ttcactcacg gacagaaaga ctgtttagag tgctttcccg tgtcagaatc tcaacccgtt    660
tctgtcgtca aaaggcgta tcagaaactg tgctacattc atcatatcat gggaaaggtg    720
ccagacgctt gcactgcctg cgatctggtc aatgtggatt tggatgactg catctctgaa    780
caataaatga tttaaatcag gtatggctgc cgatggttat cctccagatt ggctcgagga    840
cactctctct gaagggataa gacagtggtg gaagctcaaa cctggcccac caccaccaaa    900
gcccgcagag cggcataagg acgacagcag gggtcttgtg cttcctgggt acaagtacct    960
cggacccttc aacggactcg acaaggggga gccggtcaac gaggcagacg ccgcggccct    1020
cgagcacgac aaggcctacg accggcagct cgacagcgga gacaacccgt acctcaagta    1080
caaccacgcc gacgcagagt ttcaggagcg ccttaaagaa gatacgtctt ttggggcaa    1140
cctcggacga gcagtcttcc aggcgaaaaa gagggttctt gaacctctgg gcctggttga    1200
ggaacctgtt aagacggctc cgggaaaaaa gaggccggta gagcactctc ctgtggagcc    1260
agactcctcc tcgggaaccg gaaaagcggg ccagcggcct gcaagaaaaa gattaaattt    1320
tggtcagact ggagacgcag actccgtacc tgacccccag cctctcggac agccaccagc    1380
agcccctct ggtctgggat ctactacaat ggctacaggc agtggcgcac caatggcaga    1440
caataacgag ggtgccgatg gagtgggtaa ttcctcagga aattggcatt gcgattccca    1500
atggctgggc gacagagtca tcaccaccag cacccgaacc tgggccctgc ccacatacaa    1560
caaccacctc tacaagcaaa tctccagcca atcaggagcc agcaacgaca ccactactt    1620
tggctacagc accccctggg ggtattttga cttcaacaga ttccactgcc acttttcacc    1680
acgtgactgg caaagactca tcaacaacaa ctgggggattc cggcccaaaa gactcaactt    1740
caagctcttt aatattcaag tcaaagaggt cacgcagaat gacggtacga cgacgattgc    1800
caataacctt accagcacgg ttcaggtgtt tactgactcg gagtaccagc tcccgtacgt    1860
cctgggctcg gcgcatcaag gatgcctccc gccgtttcca gcggacgtct tcatggtccc    1920
acagtatgga tacctcaccc tgaacaacgg gagtcaggcg gtaggacgct cttccttta    1980
ctgcctggag tactttcctt ctcagatgct gcgtactgga aacaactttc agttcagcta    2040
cacttttgaa gacgtgcctt tccacagcag ctacgctcac agccagagtc tggatcggct    2100
gatgaatcct ctgatcgacc agtacctgta ttatctgaac aagacacaaa caaatagtgg    2160
aactcttcag cagtctcggc tactgtttag ccaagctgga ccaaccaaca tgtctcttca    2220
agctaaaaac tggctgcctg gaccttgcta cagacagcag cgtctgtcaa acaggcaaa    2280
cgacaacaac aacagcaact ttccctggac tgcagctaca agtatcatc taaatggccg    2340
ggactcgttg gttaatccag gaccagctat ggccagtcac aaggatgacg aagaaaagtt    2400
tttcccatg catggaaccc tgatatttgg taaacaagga acaaatgcca acgacgcgga    2460
tttgaaaat gtcatgatta cagatgaaga agaaatcagg gccaccaatc ccgtggctac    2520
ggagcagtac gggactgtgt caaataattt gcaaaactca aacactggtc caactactgg    2580
aactgtcaat cgccaaggag cgttacctgg tatggtgtgg caggatcgag acgtgtacct    2640
gcagggaccc atttgggcca agattcctca caccgatgga cactttcatc cttctccact    2700
gatgggaggt tttggactca aacacccgcc tcctcagatc atgatcaaaa acactcccgt    2760
tccagccaat cctcccacaa acttcagttc tgccaagttt gcttctttca tcacacagta    2820
ttccacggga caggtcagcg tggagatcga gtgggagctg cagaaggaga acagcaaacg    2880
```

-continued

```
ctggaatccc gaaattcagt acacttccaa ctacaacaag tctgttaatg tggactttac      2940
tgtggacact aatggtgtgt attcagagcc tcgccccatt ggcaccagat acctgactcg      3000
taatctgtaa ttgcttgtta atcaataaac cgtttaattc gtttcagttg aactttggtc      3060
tctgcgaagg gcgaa                                                        3075
```

<210> SEQ ID NO 27
<211> LENGTH: 3128
<212> TYPE: DNA
<213> ORGANISM: Unknown
<220> FEATURE:
<223> OTHER INFORMATION: AAV serotype, clone 42.8

<400> SEQUENCE: 27

```
gaattcgccc tttctacggc tgcgtcaact ggaccaatga gaactttccc ttcaacgatt        60
gcgtcgacaa gatggtgatc tggtgggagg agggcaagat gacggccaag gtcgtggagt       120
ccgccaaggc cattctcggc ggcagcaagg tgcgcgtgga ccaaaagtgc aagtcttccg       180
cccagatcga tcccaccccc gtgatcgtca cttccaacac caacatgtgc gccgtgattg       240
acgggaacag caccaccttc gagcaccagc agccgttaca agaccggatg ttcaaatttg       300
aactcacccg ccgtctggag cacgactttg caaggtgac aaagcaggaa gtcaaagagt       360
tcttccgctg ggcgcaggat cacgtgaccg aggtggcgca tgagttctac gtcagaaagg       420
gtggagccaa cagagaccc gccccgatg acgcggataa aagcgagccc aagcgggcct        480 gccctcagt cgcggatcca tcgacgtcag acgcggaagg agctccggtg actttgccg        540 acaggtacca aaacaaatgt tctcgtcacg cgggcatgct tcagatgctg tttccctgca       600
agacatgcga gagaatgaat cagaatttca acatttgctt cacgcacggg accagagact       660
gttcagaatg tttccccggc gtgtcagaat ctcaaccggt cgtcagaaag aggacgtatc       720
ggaaactctg tgccattcat catctgctag gcgggctcc cgagattgct tgctcggcct       780
gcgatctggt caacgtggac ctggatgact gtgtttctga gcaataaatg acttaaacca       840
ggtatggctg ccgatggtta tcttccagat tggctcgagg acaacctctc tgagggcatt       900
cgcgagtggt gggacttgaa acctggagcc ccgaaaccca agccaaccca gcaaaagcag       960
gacgacggcc ggggtctggt gcttcctggc tacaagtacc tcggacccttt caacggactc      1020 gacaaggggg agcccgtcaa cgcggcggac gcagcggccc tcgagcacga caaggcctac      1080
gaccagcagc tcaaagcggg tgacaatccg tacctgcggt ataaccacgc cgacgccgag      1140
tttcaggagc gtctgcaaga agatacgtct tttgggggca acctcgggcg agcagtcttc      1200
caggccaaga agcgggttct cgaacctctc ggtctggttg aggaaggcgc taagacggct      1260
cctggaaaga agagaccggt agagccatca ccccagcgtt ctccagactc ctctacgggc      1320
atcggcaaga caggccagca gcccgcgaaa aagagactca actttggca gactggcgac      1380 tcagagtcag tgcccgaccc tcaaccaatc ggagaacccc cgcaggccc ctctggtctg      1440 ggatctggta caatggctgc aggcggtggc gctccaatgg cagacaataa cgaaggcgcc      1500
gacggagtgg gtagttcctc aggaaattgg cattgcgatt ccacatggct gggcgacaga      1560
gtcatcacca ccagcacccg aacctgggcc ctccccacct acaacaacca cctctacaag      1620
caaatctcca cgggacatc gggaggaagc accaacgaca cacctactt cggctacagc      1680 accccctggg ggtattttga ctttaacaga ttccactgcc acttctcacc acgtgactgg      1740
cagcgactca tcaacaacaa ctggggattc cggcccaaga gactcaactt caagctcttc      1800
aacatccagg tcaaggaggt cacgcagaat gaaggcacca agaccatcgc caataacctt      1860
```

```
accagcacga ttcaggtctt tacggactcg gaataccagc tcccgtacgt cctcggctct    1920
gcgcaccagg gctgcctgcc tccgttcccg gcggacgtct tcatgattcc tcagtacggg    1980
tacctgactc tgaacaacgg cagtcaggcc gtgggccgtt cctccttcta ctgcctggag    2040
tactttcctt ctcaaatgct gagaacgggc aacaactttg agttcagcta ccagtttgag    2100
gacgtgcctt ttcacagcag ctacgcgcac agccaaagcc tggaccggct gatgaacccc    2160
ctcatcgacc agtacctgta ctacctgtct cggactcagt ccacgggagg taccgcagga    2220
actcagcagt tgctattttc tcaggccggg cctaataaca tgtcggctca ggccaaaaac    2280
tggctacccg gccctgcta ccggcagcaa cgcgtctcca cgacactgtc gcaaaataac    2340
aacagcaact tgcttggac cggtgccacc aagtatcatc tgaatggcag agactctctg    2400
gtaaatcccg tgtcgctat ggcaacgcac aaggacgacg aagagcgatt ttttccatcc    2460
agcggagtct tgatgtttgg gaaacaggga gctggaaaag acaacgtgga ctatagcagc    2520
gttatgctaa ccagtgagga agaaatcaaa accaccaacc cagtggccac agaacagtac    2580
ggcgtggtgg ccgataacct gcaacagcaa aacgccgctc ctattgtagg ggccgtcaac    2640
agtcaaggag ccttacctgg catggtctgg cagaaccggg acgtgtacct gcagggtcct    2700
atctgggcca agattcctca cacggacggc aactttcatc cttcgccgct gatgggaggc    2760
tttggactga aacacccgcc tcctcagatc ctgattaaga atacacctgt tcccgcggat    2820
cctccaacta ccttcagtca agccaagctg gcgtcgttca tcacgcagta cagcaccgga    2880
caggtcagcg tggaaattga atgggagctg cagaaagaga acagcaagcg ctggaaccca    2940
gagattcagt atacttccaa ctactacaaa tctacaaatg tggactttgc tgtcaatact    3000
gagggtactt attcagagcc tcgccccatt ggcacccgtt acctcacccg taacctgtaa    3060
ttgcctgtta atcaataaac cggctaattc gtttcagttg aactttggtc tctgcgaagg    3120
gcgaattc                                                             3128

<210> SEQ ID NO 28
<211> LENGTH: 3128
<212> TYPE: DNA
<213> ORGANISM: Unknown
<220> FEATURE:
<223> OTHER INFORMATION: AAV serotype, clone 42.15

<400> SEQUENCE: 28
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgcgtgga ccaaaagtgc aagtcgtccg     180
cccagatcga ccccaccccc gtgatcgtca cctccaacac caacatgtgc gccgtgattg     240
acgggaacag caccaccttc gagcaccagc agccgttgca ggaccggatg ttcaaatttg     300
aactcacccg ccgtctggag catgactttg gcaaggtgac aaagcaggaa gtcaaagagt     360
tcttccgctg ggcgcaggat cacgtgaccg aggtggcgca tgagttctac gtcagaaagg     420
gtggagccaa caagagaccc gcccccgatg acgcggataa aagcgagccc aagcgggcct     480
gcccctcagt cgcggatcca tcgacgtcag acgcggaagg agctccggtg actttgccg     540 acaggtacca aaacaaatgt tctcgtcacg cgggcatgct tcagatgctg tttcccctgca    600 agacatgcga gagaatgaat cagaatttca acatttgctt cacgcgcggg accagagact    660
gttcagaatg tttcccgggc gtgtcagaat ctcaaccggt cgtcagaaag aggacgtatc    720
```

```
ggaaactctg tgccattcat catctgctgg ggcgggctcc cgagattgct tgctcggcct      780
gcgatctggt caacgtggac ctggatgact gtgtttctga gcaataaatg acttaaacca      840
ggtatggctg ccgatggtta tcttccagat tggctcgagg acaacctctc tgagggcatt      900
cgcgagtggt gggacttgaa acctggagcc ccgaaaccca agccaaacca gcaaaagcag      960
gacgacggcc ggggtctggt gcttcctggc tacaagtacc tcggacccttt caacggactc     1020 gacaagggga gcccgtcaa cgcggcggac gcagcggccc tcgagcacga caaggcctac      1080
gaccagcagc tcaaagcggg tgacaatccg tacctgcggt ataaccacgc cgacgccgag      1140
tttcaggagc gtctgcaaga agatacgtct tttgggggca acctcgggcg agcagtcttc      1200
caggccaaga agcgggttct cgaacctctc ggtctggttg aggaaggcgc taagacggct      1260
cctggaaaga gagaccggt agagccatca ccccagcgtt ctccagactc ctctacgggc      1320
atcggcaaga caggccagca gcccgcgaaa aagagactca actttgggca gactggcgac      1380
tcagagtcag tgcccgaccc tcaaccaatc ggagaacccc ccgcaggccc ctctggtctg      1440
ggatctggta caatggctgc aggcggtggc gctccaatgg cagacaataa cgaaggcgcc      1500 gacgagtgg gtagttcctc aggaaattgg cattgcgatt ccacatggct gggcgacaga      1560
gtcatcacca ccagcacccg aacctgggcc ctccccacct acaacaacca cctctacaag      1620
caaatctcca cgggacatc gggaggaagc accaacgaca cacctactt cggctacagc      1680 accccctggg ggtattttga ctttaacaga ttccactgcc acttctcacc acgtgactgg      1740
cagcgactca tcaacaacaa ctggggattc cggcccaaga gactcaactt caagctcttc      1800
aacatccagg tcaaggaggt cacgcagaat gaaggcacca gaccatcgc caataacctt      1860 accagcacga ttcaggtctt tacggactcg aataccagc tcccgtacgt cctcggctct      1920
gcgcaccagg gctgcccgcc tccgttcccg cggacgtct tcatgattcc tcagtacggg      1980
tacctgactc tgaacaacgg cagtcaggcc gtgggccgtt cctccttcta ctgcctggag      2040
tactttcctt ctcaaatgcg gagaacgggc aacaactttg agttcagcta ccagtttgag      2100
gacgtgcctt ttcacagcag ctacgcgcat agccaaagcc tggaccggct gatgaacccc      2160
ctcatcgacc agtacctgta ctacctgtct cggactcagt ccacgggagg taccgcagga      2220
actcagcagt tgctattttc tcaggccggg cctaataaca tgtcggctca ggccaaaaac      2280
tggctacccg ggcctgcta ccggcagcaa cgcgtctcca cgacactgtc gcaaaataac      2340
aacagcaact tgcttggac cggtgccacc aagtatcatc tgaatggcag agactctctg      2400
gtaaatcccg tgtcgctat ggcaacgcac aaggacgacg aagagcgatt ttttccatcc      2460
agcggagtct tgatgtttgg gaaacaggga gctggaaaag acaacgtgga ctatagcagc      2520
gttatgctaa ccagtgagga gaaaatcaaa accaccaacc cagtggccac agaacagtac      2580
ggcgtggtgg ccgataacct gcaacagcaa acgccgctc ctattgtagg ggccgtcaac      2640
agtcaaggag ccttacctgg catggtctgg cagaaccggg acgtgtacct gcagggtcct      2700
atctgggcca agattcctca cacggacggc aactttcatc cttcgccgct gatgggaggc      2760
tttggactga aacacccgcc tcctcagatc ctgattaaga atacacctgt tcccgcggat      2820
cctccaacta ccttcagtca agccaagctg gcgtcgttca tcacgcagta cagcaccgga      2880
caggtcagcg tggaaattga atgggagctg cagaaagaga acagcaagcg ctggaaccca      2940
gagattcagt atacttccaa ctactacaaa tctacaaatg tggactttgc tgtcaatact      3000
gagggtactt attcagagcc tcgcccccatt ggcacccgtt acctcacccg taacctgtaa      3060
ttgcctgtta atcaataaac cggttaattc gttcagttg aactttggtc tctgcgaagg      3120
``` gcgaattc                                                              3128

<210> SEQ ID NO 29
<211> LENGTH: 3197
<212> TYPE: DNA
<213> ORGANISM: Unknown
<220> FEATURE:
<223> OTHER INFORMATION: AAV serotype. clone 42.5b

<400> SEQUENCE: 29
gaattcgccc tttctacggc tgcgtcaact ggaccaatga aactttccc ttcaacgatt        60
gcgtcgacaa gatggtgatc tggtgggagg agggcaagat gacggccaag gtcgtggagt       120
ccgccaaggc cattctcggc ggcagcaagg tgcgcgtgga ccaaaagtgc aagtcgtccg       180
cccagatcga ccccaccccc gtgatcgtca cctccaacac caacatgtgc gccgtgattg       240
acgggaacag caccaccttc gagcaccagc agccgttaca agaccggatg ttcaaatttg       300
aactcacccg ccgtctggag cacgactttg caaggtgac aaagcaggaa gtcaaagagt        360
tcttccgctg ggcgcaggat cacgtgaccg aggtggcgca tgagttctac gtcagaaagg       420
gtggagccaa caagagaccc gccccgatg acgcggataa aagcgagccc aagcgggcct        480
gccccctcagt cgcggatcca tcgacgtcag acgcggaagg agctccggtg actttgccg       540
acaggtacca aaacaaatgt tctcgtcacg cgggcatgct tcagatgctg tttccctgca       600
agacatgcga gagaatgaat cagaatttca acatttgctt cacgcacggg accagagact       660
gttcagaatg tttccccggc gtgtcagaat ctcaaccggt cgtcagaaag aggacgtatc       720
ggaaactctg tgccattcat catctgctgg ggcgggctcc cgagattgct tgctcggcct       780
gcgatctggt caacgtggac ctggatgact gtgtttctga gcaataaatg acttaaacca       840
ggtatggctg ccgatggtta tcttccagat tggctcgagg acaacctctc tgagggcatt       900
cgcgagtggt gggacttgaa acctggagcc ccgaaaccca agccaaccca gcaaaagcag       960
gacgacggcc ggggtctggt gcttcctggc tacaagtacc tcggacccctt caacggactc      1020
gacaagggag agccggtcaa cgaggcagac gccgcggccc tcgagcacga caaggcctac      1080
gacaagcagc tcgagcaggg ggacaacccg tacctcaagt acaaccacgc cgacgccgag      1140
tttcaggagc gtcttcaaga agatacgtct tttggggca acctcgggcg agcagtcttc      1200
caggccaaga agcgggttct cgaacctctc ggtctggttg aggaaggcgc taagacggct      1260
cctggaaaga gagaccggt agagccatca ccccagcgtt ctccagactc ctctacgggc      1320
atcggcaaga caggccagca gcccgcgaaa aagagactca actttgggca gactggcgac      1380
tcagagtcag tgcccgaccc tcaaccaatc ggagaacccc ccgcaggccc ctctggtctg      1440
ggatctggta caatggctgc aggcggtggc gctccaatgg cagacaataa cgaaggcgcc      1500
gacggagtgg gtagttcctc aggaaattgg cattgcgatt ccacatggct gggcgacaga      1560
gtcatcacca ccagcacccg aacctgggcc ctccccacct acaacaacca cctctacaag      1620
caaatctcca cgggacatc ggaggaagc accaacgaca cacctactt cggctacagc      1680
acccccctggg ggtatttga ctttaacaga ttccactgcc acttctcacc acgtgactgg      1740
cagcgactca tcaacaacaa ctgggggattc cggcccaaga gactcaactt caagctcttc      1800
aacatccagg tcaaggaggt cacgcagaat gaaggcacca gaccatcgc caataacctt      1860
accagcacga ttcaggtctt tacgactcg gaataccagc tcccgtacgt cctcggctct      1920
gcgcaccagg gctgcctgcc tccgttcccg gcggacgtct tcatgattcc tcagtacggg      1980

| | |
|---|---:|
| tacctgactc tgaacaacgg cagtcaggcc gtgggccgtt cctccttcta ctgcctggag | 2040 |
| tactttcctt ctcaaatgct gagaacgggc aacaactttg agttcagcta ccagtttgag | 2100 |
| gacgtgcctt ttcacagcag ctacgcgcac agccaaagcc tggaccggct gatgaacccc | 2160 |
| ctcatcgacc agtacctgta ctacctgtct cggactcagt ccacgggagg taccgcagga | 2220 |
| actcagcagt tgctatttc tcaggccggg cctaataaca tgtcggctca ggccaaaaac | 2280 |
| tggctacccg ggccctgcta ccggcagcaa cgcgtctcca cgacactgtc gcaaaataac | 2340 |
| aacagcaact ttgcttggac cggtgccacc aagtatcatc tgaatggcag agactctctg | 2400 |
| gtaaatcccg gtgtcgctat ggcaacgcac aaggacgacg aagagcgatt ttttccatcc | 2460 |
| agcggagtct tgatgtttgg gaaacaggga gctggaaaag acaacgtgga ctatagcagc | 2520 |
| gttatgctaa ccagtgagga gaaaatcaaa accaccaacc cagtggccac agaacagtac | 2580 |
| ggcgtggtgg ccgataacct gcaacagcaa aacgccgctc ctattgtagg ggccgtcaac | 2640 |
| agtcaaggag ccttacctgg catggtctgg cagaaccggg acgtgtacct gcagggtcct | 2700 |
| atctgggcca agattcctca cacggacggc aactttcatc cttcgccgct gatgggaggc | 2760 |
| tttggactga acacccgcc tcctcagatc ctgattaaga atacacctgt cccgcggat | 2820 |
| cctccaacta ccttcagtca agccaagctg gcgtcgttca tcacgcagta cagcaccgga | 2880 |
| caggtcagcg tggaaattga atgggagctg cagaaagaga acagcaagcg ctggaaccca | 2940 |
| gagattcagt atacttccaa ctactacaaa tctacaaatg tggactttgc tgtcaatact | 3000 |
| gagggtactt attcagagcc tcgccccatt ggcacccgtt acctcacccg taacctgtaa | 3060 |
| ttgcctgtta atcaataaac cggttaattc gtttcagttg aactttggtc tctgcgaagg | 3120 |
| gcgaattcgt ttaaacctgc aggactagtc cctttagtga gggttaattc tgagcttggc | 3180 |
| gtaatcatgg gtcatag | 3197 |

<210> SEQ ID NO 30
<211> LENGTH: 2501
<212> TYPE: DNA
<213> ORGANISM: Unknown
<220> FEATURE:
<223> OTHER INFORMATION: AAV serotype, clone 42.1b

<400> SEQUENCE: 30

| | |
|---|---:|
| gaattcgccc ttggctgcgt caactggacc aatgagaact ttcccttcaa cgattgcgtc | 60 |
| gacaagatgg tgatctggtg ggaggagggc aagatgacgg ccaaggtcgt ggagtccgcc | 120 |
| aaggccattc atcatctgct ggggcgggct cccgagattg cttgctcggc ctgcgatctg | 180 |
| gtcaacgtgg acctggatga ctgtgtttct gagcaataaa tgacttaaac caggtatggc | 240 |
| tgccgatggt tatcttccag attggctcga ggacaacctc tctgagggca ttcgcgagtg | 300 |
| gtgggacttg agacctggag ccccgaaacc caaagccaac cagcaaaagc aggacgacgg | 360 |
| ccggggtctg gtgcttcctg gctacaagta cctcggaccc ttcaacggac tcgacaaggg | 420 |
| agagccggtc aacgaggcag acgccgcggc cctcgagcac gacaaggcct acgacaagca | 480 |
| gctcgagcag ggggacaacc cgtacctcaa gtacaaccac gccgacgccg agtttcagga | 540 |
| gcgtcttcaa gaagatacgt cttttgggg caacctcggg cgagcagtct tccaggccaa | 600 |
| gaagcgggtt ctcgaacctc tcggtctggt tgaggaaggc gctaagacgg ctcctggaaa | 660 |
| gaagagaccc atagaatccc ccgactcctc cacgggcatc ggcaagaaag gccagcagcc | 720 |
| cgctaaaaag agactcaact ttgggcagac tggcgactca gagtcagtgc ccgaccctca | 780 |
| accaatcgga gaacccccg caggcccctc tggtctggga tctggcacaa tggctgcagg | 840 |

-continued

```
cggtggcgct ccaatggcag acaataacga aggcgccgac ggagtgggta gttcctcagg    900
aaattggcat tgcgattcca catggctggg cgacagagtc atcaccacca gcacccgaac    960
ctgggccctc cccacctaca acaaccacct ctacaagcaa atctccaacg ggacatcggg   1020
aggaagcacc aacgacaaca cctacttcgg ctacagcacc ccctgggggt attttgactt   1080
taacagattc cactgccact tctcaccacg tgactggcag cgactcatca acaacaactg   1140
gggattccgg cccaagagac tcaacttcaa gctcttcaac atccaggtca aggaggtcac   1200
gcagaatgaa ggcaccaaga ccatcgccaa taaccttacc agcacgattc aggtctttac   1260
ggactcggaa taccagctcc cgtacgtcct cggctctgcg caccagggct gcctgcctcc   1320
gttcccggcg gacgtcttca tgattcctca gtacgggtac ctgactctga caacggcag   1380 tcaggccgtg ggccgttcct ccttctactg cctggagtac tttccttctc aaatgctgag   1440
aacgggcaac aactttgagt tcagctacca gtttgaggac gtgccttttc acagcagcta   1500
tgcgcacagc caaagcctgg accggctgat gaacccctc atcgaccagt acctgtacta   1560
cctgtctcgg actcagtcca cgggaggtac cgcaggaact cagcagttgc tattttctca   1620
ggccgggcct aataacatgt cggctcaggc caaaaactgg ctacccgggc cctgctaccg   1680
gcagcaacgc gtctccacga cagtgtcgca aaataacaac agcaactttg cttggaccgg   1740
tgccaccaag tatcatctga atggcagaga ctctctggta atcccggtg tcgctatggc   1800 aacgcacaag ggcgacgaag agcgattttt tccatccagc ggagtcttga tgtttgggaa   1860
acagggagct ggaaaagaca acgtagacta tagcagcgtt atgctaacca gtgaggaaga   1920
aatcaaaacc accaacccag tggccacaga acagtacggc gtggtggccg ataacctgca   1980
acagcaaaac gccgctccta ttgtaggggc cgtcaacagt caaggagcct acctggcat   2040 ggtctggcag aaccgggacg tgtacctgca gggtcctatc tgggccaaga ttcctcacac   2100
ggacggcaac tttcatcctt cgccgctgat gggaggcttt ggactgaaac acccgcctcc   2160
tcagatcctg attaagaata cacctgttcc cgcggatcct ccaactacct tcagtcaagc   2220
caagctggcg tcgttcatca cgcagtacag caccggacag gtcagcgtgg aaattgaatg   2280
ggagctgcag aaagagaaca gcaagcgctg gaacccagag attcagtata cttccaacta   2340
ctacaaatct acaaatgtgg actttgctgt caatactgag ggtacttatt cagagcctcg   2400
ccccattggc acccgttacc tcacccgtaa cctgtaattg cctgttaatc aataaaccgg   2460
ttgattcgtt tcagttgaac tttggtctca agggcgaatt c                       2501
```

<210> SEQ ID NO 31
<211> LENGTH: 3113
<212> TYPE: DNA
<213> ORGANISM: Unknown
<220> FEATURE:
<223> OTHER INFORMATION: AAV serotype, clone 42.13

<400> SEQUENCE: 31

```
gaattcgccc tttctacggc tgcgtcaact ggaccaatga gaactttccc ttcaacgatt    60
gcgtcgacaa gatggtgatc tggtgggagg agggcaagat gacggccaag gtcgtggagt   120
ccgccaaggc cattctcggc ggcagcaagg tgcgcgtgga ccaaaagtgc aagtcgtccg   180
cccagatcga tcccaccccc gtgatcgtca cttccaacac caacatgtgc gccgtgattg   240 acggaacag caccaccttc gagcaccagc agccgttaca agaccggatg ttcaaatttg   300
aactcacccg ccgtctggag catgactttg gcaaggtgac aaagcaggaa gtcaaagagt   360
```

```
tcttccgctg gcgcaggat cacgtgaccg aggtggcgca tgagttctac gtcagaaagg    420
gtggagccaa caagagaccc gccccgatg acgcggataa agcgagccc aagcgggcct    480
gccctcagt cgcggatcca tcgacgtcag acgcggaagg agctccggtg gactttgccg    540
acaggtacca aaacaaatgt tctcgtcacg cgggcatgct tcagatgctg tttccctgca    600
agacatgcga gagaatgaat cagaatttca acatttgctt cacgcacggg accagagact    660
gttcagaatt ttccccggc gtgtcagaat ctcaaccggt cgtcagaaag aggacgtatc    720
ggaaactctg tgccattcat catctgctgg ggcgggctcc cgagattgct tgctcggcct    780
gcgatctggt caacgtggac ctggatgact gtgtttctga gcaataaatg acttaaacca    840
ggtatggctg ccgatggtta tcttccagat tggctcgagg acaacctctc tgagggcatt    900
cgcgagtggt gggacttgaa acctggagcc ccgaaaccca agccaaacca gcaaaagcag    960
gacgacggcc ggggtctggt gcttcctggc tacaagtacc tcggacccttt caacggactc   1020
gacaaggggg agcccgtcaa cgcggcggac gcagcggccc tcgagcacga caaggcctac   1080
gaccagcagc tcaaagcggg tgacaatccg tacctgcggt ataaccacgc cgacgccgag   1140
tttcaggagc gtcttcaaga agatacgtct tttgggggca acctcgggcg agcagtcttc   1200
caggccaaga agcgggttct cgaacctctc ggtctggttg aggaaggcgc taagacggct   1260
cctggaaaga agagacccat agaatccccc gactcctcca cgggcatcgg caagaaaggc   1320
cagcagcccg ctaaaaagaa gctcaacttt gggcagactg gcgactcaga gtcagtgccc   1380
gaccctcaac caatcggaga accccgca ggccctctg gtctgggatc tggtacaatg    1440
gctgcaggcg gtggcgctcc aatggcagac aataacgaag cgccgacgg agtgggtagt   1500
tcctcaggaa attggcattg cgattccaca tggctgggcg acagagtcat caccaccagc   1560
acccgaacct gggccctccc cacctacaac aaccacctct acaagcaaat ctccaacggg   1620
acatcgggag gaagcaccaa cgacaacacc tacttcggct acagcacccc ctgggggtat   1680
tttgactttta acagattcca ctgccacttc tcaccacgtg actggcagcg actcatcaac   1740
aacaactggg gattccggcc caagagactc aacttcaagc tcttcaacat ccaggtcaag   1800
gaggtcacgc agaatgaagg caccaagacc atcgccaata accttaccag cacgattcag   1860
gtctttacgg actcggaata ccagctcccg tacgtcctcg gctctgcgca ccagggctgc   1920
ctgcctccgt tccggcgga cgtcttcatg attcctcagt acgggtacct gactctgaac   1980
aacggcagtc aggccgtggg ccgttcctcc ttctactgcc tggagtactt tccttctcaa   2040
atgctgagaa cgggcaacaa cttgagttc agctaccagt ttgaggacgt gccttttcac   2100
agcagctatg cgcacagcca aagcctggac cggctgatga cccctctcat cgaccagtac   2160
ctgtactacc tgtctcggac tcagtccacg ggaggtaccg caggaactca gcagttgcta   2220
tttttctcagg ccgggcctaa taacatgtcg gctcaggcca aaaactggct acccgggccc   2280
tgctaccggc agcaacgcgt ctccacgaca gtgtcgcaaa ataacaacag caactttgct   2340
tggaccggtg ccaccaagta tcatctgaat ggcagagact ctctggtaaa tcccggtgtc   2400
gctatggcaa cgcacaaggg cgacgaagag cgatttttc catccagcgg agtcttgatg   2460
tttgggaaac agggagctgg aaaagacaac gtggactata gcagcgttat gctaaccagt   2520
gaggaagaaa tcaaaaccac caacccagtg gccacagaac agtacggcgt ggtggccgat   2580
aacctgcaac agcaaaacgc cgctccattt gtaggggccg tcaacagtca aggagcctta   2640
cctggcatgg tctggcagaa ccgggacgtg tacctgcagg gtcctatctg ggccaagatt   2700
cctcacacgg acggcaactt tcatccttcg ccgctgatgg gaggctttgg actgaaacac   2760
```

```
ccgcctcctc agatcctgat taagaataca cctgttcccg cggatcctcc aactaccttc    2820
agtcaagcca agctggcgtc gttcatcacg cagtacagca ccggacaggt cagcgtggaa    2880
attgaatggg agctgcagaa agagaacagc aagcgctgga acccagagat tcagtatact    2940
tccaactact acaaatctac aaatgtggac tttgctgtca atactgaggg tacttattca    3000
gagcctcgcc ccattggcac ccgttacctc acccgtagcc tgtaattgcc tgttaatcaa    3060
taaaccggtt gattcgtttc agttgaactt tggtctctgc gaagggcgaa ttc           3113
```

<210> SEQ ID NO 32
<211> LENGTH: 3113
<212> TYPE: DNA
<213> ORGANISM: Unknown
<220> FEATURE:
<223> OTHER INFORMATION: AAV serotype, clone 42.3a

<400> SEQUENCE: 32

```
gaattcgccc tttctacggc tgcgtcaact ggaccaatga gaactttccc ttcaacgatt     60
gcgtcgacaa gatggtgatc tggtgggagg agggcaagat gacggccaag gtcgtggagt    120
ccgccaaggc cattctcggc ggcagcaagg tgcgcgtgga ccaaaagtgc aagtcgtccg    180
cccagatcga tcccaccccc gtgatcgtca cttccaacac caacatgtgc gccgtgattg    240
acgggaacag caccaccttc gagcaccagc agccgttaca agaccggatg ttcaaatttg    300
aactcacccg ccgtctggag catgactttg caaggtgac aaagcaggaa gtcaaagagt    360
tcttccgctg ggcgcaggat cacgtgaccg aggtggcgca tgagttctac gtcagaaagg    420
gtggagccaa caagagaccc gcccccgatg acgcggataa aagcgagccc aagcgggcct    480
gcccctcagt cgcggatcca tcgacgtcag acgcggaagg agctccggtg gactttgccg    540
acaggtacca aaacaaatgt tctcgtcacg cgggcatgct tcagatgctg cttccctgca    600
agacatgcga gaatgaat cagaatttca gcatttgctt cacgcacggg accagagact    660
gttcagaatg tttccccggc gtgtcagaat ctcaaccggt cgtcagaaag aggacgtatc    720
ggaaactctg tgccattcat catctgctgg ggcgggctcc cgagattgct tgctcggcct    780
gcgatctggt caacgtggac ctggatgact gtgtttctga caataaatg acttaaacca    840 ggtatggctg ccgatggtca tcttccagat tggctcgagg acaacctctc tgagggcatt    900
cgcgagtggt gggacttgaa acctggagcc ccgaaaccca agccaaccag caaaagcag    960 gacgacggcc ggggtctggt gcttcctggc tacaagtacc tcggaccctt caacggactc    1020
gacaagggga gcccgtcaa cgcggcggac gcagcggccc tcgagcacga caaggcctac    1080
gaccagcagc tcaaagcggg tgacaatccg tacctgcggt ataaccacgc cgacgccgag    1140
tttcaggagc gtcttcaaga agatacgtct tttgggggca acctcgggcg agcagtcttc    1200
caggccaaga agcgggttct cgaacctctc ggtctggttg aggaaggcgc taagacggct    1260
cctggaaaga gagacccat agaatccccc gactcctcca cgggcatcgg caagaaaggc    1320
cagcagcccg ctaaaaagaa gctcaacttt gggcagactg gcgactcaga gtcagtgccc    1380
gaccctcaac caatcggaga accccccgca ggcccctctg gtctgggatc tggtacaatg    1440
gctgcaggcg gtggcgctcc aatggcagac aataacgaag cgccgacgg agtgggtagt    1500 tcctcaggaa attggcattg cgattccaca tagctgggcg acagagtcat caccaccagc    1560
acccgaacct gggccctccc cacctacaac aaccacctct acaagcaaat ctccaacggg    1620
acatcgggag gaagcaccaa cgacaacacc tacttcggct acagcacccc ctgggggtat    1680
```

```
tttgacttta acagattcca ctgccacttc tcaccacgtg actggcagcg actcatcaac    1740
aacagctggg gattccggcc caagagactc aacttcaagc tcttcaacat ccaggtcaag    1800
gaggtcacgc agaatgaagg caccaagacc atcgccaata accttaccag cacgattcag    1860
gtctttacgg actcggaata ccagctcccg tacgtcctcg gctctgcgca ccagggctgc    1920
ctgcctccgt tcccggcgga cgtcttcatg attcctcagt acgggtacct gactctgaac    1980
aacggcagtc aggccgtggg ccgttcctcc ttctactgcc tggagtactt tccttctcaa    2040
atgctgagaa cgggcaacaa ctttgagttc agctaccagt ttgaggacgt gccttttcac    2100
agcagctacg cgcacagcca aagcctggac cggctgatga ccccctcat cgaccagtac    2160 ctgtactacc tgtctcggac tcagtccacg ggaggtaccg caggaactca gcagttgcta    2220
ttttctcagg ccgggcctaa taacatgtcg gctcaggcca aaaactggct acccgggccc    2280
tgctaccggc agcaacgcgt ctccacgaca ctgtcgcaaa ataacaacag caactttgct    2340
tggaccggtg ccaccaagta tcatctgaat ggcagagact ctctggtaaa tcccggtgtc    2400
gctatggcaa cgcacaagga cgacgaagag cgattttttc catccagcgg agtcttgatg    2460
tttgggaaac agggagctgg aaaagacaac gtggactata gcagcgttat gctaaccagt    2520
gaggaagaaa tcaaaaccac caacccagtg gccacagaac agtacggcgt ggtggccgat    2580
aacctgcaac agcaaaacgc cgctcctatt gtaggggccg tcaacagtca aggagcctta    2640
cctggcatgg tctggcagaa ccgggacgtg tacctgcagg gtcctatctg gccaagatt    2700 cctcacacgg acggcaactt tcatccttcg ccgctgatgg gaggctttgg actgaaacac    2760
ccgcctcctc agatcctgat taagaataca cctgttcccg cggatcctcc aactaccttc    2820
agtcaagcca agctggcgtc gttcatcacg cagtacagca ccggacaggt cagcgtggaa    2880
attgaatggg agctgcagaa agagaacagc aagcgctgga acccagagat tcagtatact    2940
tccaactact acaaatctac aaatgtggac tttgctgtca atactgaggg tacttattca    3000
gagcctcgcc ccattggcac ccgttacctc acccgtaacc tgtaattgcc tgttaatcaa    3060
taaaccggtt aattcgtttc agttgaactt tggtctctgc gaagggcgaa ttc          3113
```

<210> SEQ ID NO 33
<211> LENGTH: 2504
<212> TYPE: DNA
<213> ORGANISM: Unknown
<220> FEATURE:
<223> OTHER INFORMATION: AAV serotype, clone 42.4

<400> SEQUENCE: 33

```
gaattcgccc tttctacggc tgcgtcaact ggaccaatga gaactttccc ttcaacgatt     60
gcgtcgacaa gatggtgatc tggtgggagg agggcaagat gacggccaag gtcgtggagt    120
ccgccaaggc cattcatcat ctgctggggc gggctcccga gattgcttgc tcggcctgcg    180
atctggtcaa cgtggacctg gatgactgtg tttctgagca ataaatgact taaaccaggt    240
atggctgccg atggttatct tccagattgg ctcgaggaca acctctctga gggcattcgc    300
gagtggtggg acttgaaacc tggagccccg aaacccaaag ccaaccagca aaagcaggac    360
gacgccgggg tctggtgct tcctggctac aagtacctcg acccttcaa cggactcgac    420 aagggagagc cggtcaacga ggcagacgcc gcggccctcg agcacgacaa ggcctacgac    480
aagcagctcg agcagggggga caacccgtac ctcaagtaca accacgccga cgccgagttt    540
caggagcgtc ttcaagaaga tacgtctttt ggggggcaacc tcgggcgagc agtcttccag    600
gccaagaagc gggttctcga acctctcggt ctggttgagg aaggcgctaa gacggctcct    660
```

```
ggaaagaaga gacccataga atcccccgac tcctccacgg gcatcggcaa gaaaggccag    720
cagcccgcta aaagaagct caactttggg cagactggcg actcagagtc agtgcccgac    780
cctcaaccaa tcggagaacc ccccgcaggc ccctctggtc tgggatctgg tacaatggct    840
gcaggcggtg gcgctccaat ggcagacaat aacgaaggcg ccgacggagt gggtaatgcc    900
tccggaaatt ggcattgcga ttccacatgg ctgggcgaca gagtcatcac caccagcacc    960
cgcacctggg ccctgcccac ctacaacaac cacctctaca gcagatatc aagtcagagc   1020 ggggctacca acgacaacca cttcttcggc tacagcaccc cctggggcta ttttgacttc   1080
aacagattcc actgccactt ctcatcacgt gactggcagc gactcatcaa caacaactgg   1140
ggattccggc caagagact caacttcaag ctcttcaaca tccaggtcaa ggaggtcacg   1200
cagaatgaag gcaccaagac catcgccaat aaccttacca gcacgattca ggtctttacg   1260
gactcggaat accggctccc gtacgtcctc ggctctgcgc accagggctg cctgcctccg   1320
ttcccggcgg acgtcttcat gattcctcag tacgggtacc tgactctgaa caacggcagt   1380
caggccgtgg gccgttcctc cttctactgc ctggagtact ttccttctca aatgctgaga   1440
acgggcaaca actttgagtt cagctaccag tttgaggacg tgccttttca cagcagctac   1500
gcgcacagcc aaagcctgga ccggctgatg aaccccctca tcgaccagta cctgtactac   1560
ctgtctcgga ctcagtccac gggaggtacc gcaggaactc agcagttgct attttctcag   1620
gccgggccta ataacatgtc ggctcaggcc aaaaactggc tacccgggcc ctgctaccgg   1680
cagcaacgcg tctccacgac actgtcgcaa aataacaaca gcaactttgc cttggaccgg   1740
gccaccaagt atcatctgaa tggcagagac tctctggtaa atcccggtgt cgctatggca   1800
acgcacaagg acgacgaaga gcgattttt ccatccagcg gagtcttgat gtttgggaaa   1860
cagggagctg aaaagacaa cgtggactat agcagcgtta tgctaaccag tgaggaagaa   1920
atcaaaacca ccaacccagt ggccacagaa cagtacggcg tggtggccga taacctgcaa   1980
cagcaaaacg ccgctcctat tgtaggggcc gtcaacagtc aaggagcctt acctggcatg   2040
gtctggcaga accgggacgt gtacctgcag ggtcctatct gggccaagat tcctcacacg   2100
gacggcaact tcatccttc gccgctgatg ggaggctttg gactgaaaca cccgcctcct   2160
cagatcctga ttaagaatac acctgttccc gcggatcctc caactacctt cagtcaagcc   2220
aagccggcgt cgttcatcac gcagtacagc accggacagg tcagcgtgga aattgaatgg   2280
gagctgcaga aagagaacag caagcgctgg aacccagaga ttcagtatac ttccaactac   2340
tacaaatcta caaatgtgga ctttgctgtc aatactgagg gtacttattc agagcctcgc   2400
cccattggca cccgttacct cacccgtaac ctgtaattgc ctgttaatca ataaaccggt   2460
taattcgttt cagttgaact ttggtctctg cgaagggcga attc                   2504
```

<210> SEQ ID NO 34
<211> LENGTH: 3106
<212> TYPE: DNA
<213> ORGANISM: Unknown
<220> FEATURE:
<223> OTHER INFORMATION: AAV serotype, clone 42.5a

<400> SEQUENCE: 34

```
gaattcgccc ttctacggct gcgtcaactg gaccaatgag aactttccct tcaacgattg     60
cgtcgacaag atggtgatct ggtgggagga gggcaagatg acggccaagg tcgtggagtc    120
cgccaaggcc attctcggcg gcagcaaggt gcgcgtggac caaaagtgca gtcgtccgc    180
```

```
ccagatcgac cccacccccg tgatcgtcac ctccaacacc aacatgtgcg ccgtgattga    240
cgggaacagc accaccttcg agcaccagca gccgttgcag gaccggatgt tcaaatttga    300
actcacccgc cgtctggagc atgactttgg caaggcgaca agcaggaag tcaaagagtt    360 cttccgctgg gcgcaggatc acgtgaccga ggtggcgcat gagttctacg tcagaaaggg    420
tggagccaac aagagacccg cccccgatga cgcggataaa agcgagccca agcgggcccg    480
cccctcagtc gcggatccat cgacgtcaga gcggaagga gctccggtgg actttgccga    540
caggtaccaa aacaaatgtt ctcgtcacgc gggcatgctt cagatgctgt ttccctgcaa    600
aacatgcgag agaatgaatc agaatttcaa catttgcttc acgcacggga ccagagactg    660
ttcagaatgt ttccccggcg tgtcagaatc tcaaccggtc gtcagaaaga ggacgtatcg    720
gaaactctgt gccattcatc atctgctggg gcgggctccc gagattgctt gctcggcctg    780
cgatctggtc aacgtggacc tggatgactg tgtttctgag caataaatga cttaaaccag    840
gtatggctgc cgatggttat cttccagatt ggctcgagga caacctctct gagggcattc    900
gcgagtggtg ggacttgaaa cctggagccc cgaaacccaa agccaaccag caaaagcagg    960
acgacggccg gggtctggtg cttcctggct acaagtacct cggacccttc aacggactcg    1020
acaagggaga gccggtcaac gaggcagacg ccgcggccct cgagcacgac aaggcctacg    1080
acaagcagct cgagcagggg gacaacccgt acctcaagta caaccacgcc gacgccgagt    1140 tcaggagcg tcttcaagaa gatacgtctt ttggggggcaa cctcgggcga gcagtcttcc    1200
gggccaagaa gcgggttctc gaacctctcg gtctggttga ggaaggcgct aagacggctc    1260
ctggaaagaa gagacccata gaatccccg actcctccac gggcatcggc aagaaaggcc    1320
agcagcccgc taaaaagaag ctcaactttg gcagactgg cgactcagag tcagtgcccg    1380 accccccaacc tctcggagaa cctccgccg cgccctcagg tctgggatct ggtacaatgg    1440
ctgcaggcgg tggcgcacca atggcagaca ataacgaagg cgccgacgga gtgggtaatg    1500
cctccggaaa ttggcattgc gattccacat ggctgggcga cagagtcatc accaccagca    1560
cccgcacctg ggcccctgcc cctacaaca accacctcta caagcagata tcaagtcaga    1620
gcggggctac caacgacaac cacttcttcg gctacagcac cccctggggc tatttttgact    1680 tcaacagatt ccactgccac ttctcaccac gtgactggca gcgactcatc aacaacaacc    1740
ggggattccg gccagaaag ctgcggttca gttgttcaa catccaggtc aaggaggtca    1800
cgacgaacga cggcgttacg accatcgcta ataaccttac cagcacgatt caggtcttct    1860
cggactcgga gtaccaactg ccgtacgtcc tcggctctgc gcaccaggc tgcctccctc    1920 cgttccctgc ggacgtgttc atgattcctc agtacggata tctgactcta aacaacggca    1980
gtcagtctgt gggacgttcc tccttctact gcctggagta ctttcctcct cagatgctga    2040
gaacgggcaa taactttgaa ttcagctacc agtttgagga cgtgccctt cacagcagct    2100 acgcgcacag ccaaagccctg gaccggctga tgaacccct catcgaccag tacctgtact    2160
acctgtctcg gactcagtcc acgggaggta ccgcaggaac tcagcagttg ctattttctc    2220
aggccgggcc taataacatg tcggctcagg ccaaaactg gctacccggg ccctgctacc    2280
ggcagcaacg cgtctccacg cacactgtcg caaaataacaa cagcaacttt gcttggaccg    2340
gtgccaccaa gtatcatctg aatggcagag actctctggt aaatcccggt gtcgctatgg    2400
caacgcacaa ggacgacgaa gagcgatttt ttccatccag cggagtcttg atgtttggga    2460
aacagggagc tggaaaagac aacgtggact atagcagcgt tatgctaacc agtgaggaag    2520
aaatcaaaac caccaaccca gtggccacag aacagtacgg cgtggtggcc gataacctgc    2580
```

```
aacagcaaaa cgccgctcct attgtagggg ccgtcaacag tcaaggagcc ttacctggca    2640
tggcctggca gaaccgggac gtgtacctgc agggtcctat ctgggccaag attcctcaca    2700
cggacggcaa ctttcatcct tcgccgctga tgggaggctt tggactgaaa cacccgcctc    2760
ctcagatcct gattaagaat acacctgttc ccgcggatcc tccaactacc ttcagtcaag    2820
ccaagctggc gtcgttcatc acgcagtaca gcaccggaca ggtcagcgtg gaaattgaat    2880
gggagctgca gaaagagaac agcaagcgct ggaacccaga gattcagtat acttccaact    2940
actacaaatc tacaaatgtg gactttgctg tcaatactga gggtacttat tcagagcctc    3000
gccccattgg cacccgttac ctcacccgta acctgtaatt gcctgttaat caataaaccg    3060
gttaattcgt ttcagttgaa ctttggtctc tgcgaagggc gaattc                   3106

<210> SEQ ID NO 35
<211> LENGTH: 2489
<212> TYPE: DNA
<213> ORGANISM: Unknown
<220> FEATURE:
<223> OTHER INFORMATION: AAV serotype, clone 42.10

<400> SEQUENCE: 35
gaattcgccc tttctacggc tgcgtcaact ggaccaatga gaactttccc ttcaacgatt      60
gcgtcgacaa gatggtgatc tggtgggagg agggcaagat gacggccaag gtcgtgaagt     120
ccgccaaggc cattcatcat ctgctggggc gggctcccga gattgcttgc tcggcctgcg     180
atctggtcaa cgtggacctg atgactgtgt ttctgagca ataaatgact taaaccaggt      240
atggctgccg atggttatct tccagattgg ctcgaggaca acctctctga gggcattcgc     300
gagtggtggg acttgaaacc tggagccccg aaacccaaag ccaaccagca aaagcaggac     360
gacggccggg gtctggtgct tcctggctac aagtaccctcg gaccctcaa cggactcgac     420 aagggagagc cggtcaacga ggcagacgcc gcggccctcg agcacgacaa ggcctacgac     480
aagcagctcg agcaggggga caacccgtac ctcaagtaca ccacgccga cgccgagttt     540 caggagcgtc ttcaagaaga tacgtctttt gggggcaacc tcgggcgagc agtcttccag     600
gccaagaagc gggttctcga acctctcggt ctggttgagg aaggcgctaa gacggctcct     660
ggaaagaaga gacccataga atccccgac tcctccacgg gcatcggcag gaaaggccag     720
cagcccgcta aaaagaagct caactttggg cagactggcg actcagagtc agtgcccgac     780
cctcaaccaa tcggagaacc ccccgcaggc ccctctggtc tgggatctgg tacaatggct     840
gcaggcggtg gcgctccaat ggcagacaat aacgaaggcg ccgacggagt gggtaatgcc     900
tccggaaatt ggcattgcga ttccacatgg ctgggcgaca gagtcatcac caccagcacc     960
cgcacctggg ccctgccac ctacaacaac cacctctaca gcagatatc aagtcagagc    1020 ggggctacca acgacaacca cttcttcggc tacagcaccc cctggggcta ttttgacttc    1080
aacagattcc actgccactt ctcaccacgt gactggcagc gactcatcaa caacaactgg    1140
ggattccggc ccagaaagct gcggttcaag ttgttcaaca tccaggtcaa ggaggtcacg    1200
acgaacgacg gcgttacgac catcgccaat aaccttacca gcacgattca ggtcttctcg    1260
gactcggagt accaactgcc gtacgtcctc ggctctgcgc accagggctg cctcccctcg    1320
ttccctgcgg acgtgttcat gattcctcag tacggatatc tgactctaaa caacggcagt    1380
cagtctgtgg gacgttcctc cttctactgc ctggagtact tccttctca gatgctgaga    1440 acgggcaata actttgaatt cagctacacc tttgaggaag tgcctttcca cagcagctat    1500
```

```
gcgcacagcc agagcctgga ccggctgatg aatcccctca tcgaccagta cctgtactac    1560
ctggcccgga cccagagcac tacggggtcc acaagggagc tgcagttcca tcaggctggg    1620
cccaacacca tggccgagca atcaaagaac tggctgcccg accctgttac tcggcagcag    1680
agactgtcaa aaacatagac agcaacaaca acagtaact ttgcctggac cggggccact    1740
aaataccatc tgaatggtag aaattcatta accaacccgg gcgtagccat ggccaccaac    1800
aaggacgacg aggaccagtt ctttcccatc aacggagtgc tggtttttgg caaaacgggg    1860
gctgccaaca agacaacgct ggaaaacgtg ctaatgacca gcgaggagga gatcaaaacc    1920
accaatcccg tggctacaga agaatacggt gtggtctcca gcaacctgca atcgtctacg    1980
gccggacccc agacacagac tgtcaacagc caggggggctc tgcccggcat ggtctggcag    2040
aaccgggacg tgtacctgca gggtcccatc tgggccaaaa ttcctcacac ggacggcaac    2100
tttcacccgt ctcccctgat gggcggattt ggactcaaac accgcctcc tcaaattctc    2160 atcaaaaaca ccccggtacc tgctaatcct ccagaggtgt ttactcctgc caagtttgcc    2220
tcatttatca cgcagtacag caccggccag gtcagcgtgg agatcgagtg gaactgcag    2280 aaagaaaaca gcaaacgctg gaatccagag attcagtaca cctcaaatta tgccaagtct    2340
aataatgtgg aatttgctgt caacaacgaa gggggttata ctgagcctcg ccccattggc    2400
acccgttacc tcacccgtaa cctgtaattg cctgttaatc aataaaccgg ttaattcgtt    2460
tcagttgaac tttggtcaag ggcgaattc                                     2489
```

<210> SEQ ID NO 36
<211> LENGTH: 2495
<212> TYPE: DNA
<213> ORGANISM: Unknown
<220> FEATURE:
<223> OTHER INFORMATION: AAV serotype, clone 42.3b

<400> SEQUENCE: 36

```
gaattcgccc tttctacggc tgcgtcaact agaccaatga gaactttccc ttcaacgatt      60
gcgtcgacaa gatggtgatc tggtgggagg agggcaagat gacggccaag gtcgtggagt     120
ccgccaaggc cattcatcat ctgctgggggc gggctcccga gattgcttgc tcggcctgcg     180
atctggtcaa cgtggacctg atgactgtg tttctgagca ataaatgact taaaccaggt     240
atggctgccg atggttatct tccagattgg ctcgaggaca acctctctga gggcattcgc     300
gagtggtggg acttgaaacc tggagccccg aaacccaaag ccaaccagca aaagcaggac     360
gacggccggg gtctggtgct tcctggctac aagtacctcg acccttcaa cggactcgac     420 aagggagagc cggtcaacga ggcagacgcc gcggccctcg agcacgacaa ggcctacgac     480
aagcagctcg agcagggga caacccgtac ctcaagtaca accacgccga cgccgagttt     540
caggagcgtc ttcaagaaga tacgtctttt gggggcaacc tcgggcgagc agtcttccag     600
gccaagaagc gggttctcga acctctcggt ctggttgagg aaggcgctaa gacggctcct     660
ggaaagaaga gacccataga atcccccgac tcctccacgg gcatcggcaa gaaaggccag     720
cagcccgcta aaaagaagct caactttggg cagactggcg actcagagtc agtgcccgac     780
cctcaaccaa tcggagaacc cccgcaggcc cctctggtc tgggatctgg tacaatggct     840
gcaggcggtg gcgctccaat ggcagacaat aacgaaggcg ccgacggagt gggtaatgcc     900
tccggaaatt ggcattgcga ttccacatgg ctgggcgaca gagtcatcac caccagcacc     960
cgcacctggg ccctgcccac ctacaacaac cacctctaca gcagatatc aagtcagagc    1020 ggggctacca acgacaacca cttcttcggc tacagcaccc cctggggcta ttttgacttc    1080
```

-continued

```
aacagattcc actgccactt ctcaccacgt gactggcagc gactcatcaa caacaactgg    1140
ggattccggc ccagaaagct gcggttcaag ttgttcaaca tccaggtcaa ggaggtcacg    1200
acgaacgacg gcgttacgac catcgctaat aaccttacca gcacgattca ggtcttctcg    1260
gactcggagt accaactgcc gtacgtcctc ggctctgcgc accagggctg cctccctccg    1320
ttccctgcgg acgtgttcat gattcctcag tacggatatc tgactctaaa caacggcagt    1380
cagtctgtgg acgttcctc cttctactgc ctggagtact ttccttctca gatgctgaga    1440
acgggcaata actttgaatt cagctacacc tttgaggaag tgcctttcca cagcagctat    1500
gcgcacagcc agagcctgga ccggctgatg aatcccctca tcgaccagta cctgtactac    1560
ctggcccgga cccagagcac tacggggtcc acaagggagc tgcagttcca tcaggctggg    1620
cccaacacca tggccgagca atcaaagaac tggctgcccg gaccctgtta tcggcagcag    1680
agactgtcaa aaacatgaa cagcaacaac accagtaact ttgcctggac cggggccact    1740
aaataccatc tgaatggtag aaattcatta accaacccgg gcgtagccat ggccaccaac    1800
aaggacgacg aggaccagtt cttttcccatc aacggagtgc tggttttgg caaaacgggg    1860 gctgccaaca agacaacgct ggaaaacgtg ctaatgacca gcgaggagga gatcaaaacc    1920
accaatcccg tggctacaga acagtacggt gtggtctcca gcaacctgca atcgtctacg    1980
gccggacccc agacacagac tgtcaacagc aggggggctc tgcccggcat ggtctggcag    2040
aaccgggacg tgtacctgca gggtcccatc tgggccaaaa ttcctcacac ggacggcaac    2100
tttcacccgt ctccctgat gggcggattt ggactcaaac accgcctcc tcaaattctc    2160 atcaaaaaca ccccggtacc tgctaatcct ccagaggtgt ttactcctgc caagtttgcc    2220
tcatttatca cgcagtacag caccggccag gtcagcgtgg agatcgagtg gaactgcag    2280 aaagaaaaca gcaaacgctg gaatccagag attcagtaca cctcaaatta tgccaagtct    2340
aataatgtgg aatttgctgt caacaacgaa gggggtttata ctgagcctcg ccccattggc    2400
acccgttacc tcacccgtaa cctgtaattg cctgttaatc aataaaccgg ttaattcgtt    2460
tcagttgaac tttggtctct gcgaagggcg aattc                              2495
```

<210> SEQ ID NO 37
<211> LENGTH: 3098
<212> TYPE: DNA
<213> ORGANISM: Unknown
<220> FEATURE:
<223> OTHER INFORMATION: AAV serotype, clone 42.11

<400> SEQUENCE: 37

```
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgcgtgga ccaaaagtgc aagtcttccg     180
cccagatcga tccccccccc gtgatcgtca cttccaacac caacatgtgc gccgtgattg     240
acgggaacag caccacccttc gagcaccagc agccgttaca agaccggatg ttcaaatttg     300
aactcacccg ccgtctggag cacgactttg gcaaggtgac aaagcaggaa gtcaaagagt     360
tcttccgctg ggcgcaggat cacgtgaccg aggtggcgca tgagttctac gtcagaaagg     420
gtggagccaa caagagaccc gcccccgatg acgcggataa agcgagccc aagcgggcct     480 gccccctcagt cgcggatcca tcgacgtcag acgcggaagg agctccggtg gactttgccg     540
acaggtacca aaacaaatgt tctcgtcacg cgggcatgct tcagatgctg tttcccctgca     600
```

```
agacatgcga gagaatgaat cagaatttca acatttgctt cacgcacggg accggagact    660
gttcagaatg tttccccggc gtgtcagaat ctcaaccggt cgtcagaaag aggacgtatc    720
ggaaactctg tgccattcat catctgctgg ggcgggctcc cgagattgct tgctcggcct    780
gcgatctggt caacgtggac ctggatgact gtgtttctga gcaataaatg acttaaacca    840
ggtatggctg ccgatggtta tcttccagat tggctcgagg acaacctctc tgagggcatt    900
cgcgagtggt gggacttgaa acctggagcc ccgaaaccca agccaaacca gcaaaagcag    960
gacgacggcc ggggtctggt gcttcctggc tacaagtacc tcggacccct caacggactc   1020
gacaagggag agccggtcaa cgcggcggac gcagcggccc tcgagcacga caaggcctac   1080
gaccagcagc tcaaagcggg tgacaatccg tacctgcggt ataaccacgc cgacgccgag   1140
tttcaggagc gtcttcaaga agatacgtct tttgggggca acctcgggcg agcagtcttc   1200
caggccaaga agcgggttct cgaacctctc ggtctggttg aggaaggcgc taagacggct   1260
cctggaaaga agagacccat agaatccccc gactcctcca cgggcatcgg caagaaaggc   1320
cagcagcccg ctaaaagaa gctcaacttt gggcagactg gcgactcaga gtcagtgccc   1380
gaccctcaac caatcggaga acccccgca ggcccctctg gtctgggatc tggtacaatg   1440
gctgcaggcg gtggcgctcc aatggcagac aataacgaag cgccgacgg agtgggtaat   1500 gcctccggaa attggcattg cgattccaca tggctgggcg acagagtcat caccaccagc   1560
acccgcacct gggccctgcc cacctacaac aaccacctct acaagcagat atcaagtcag   1620
agcggggcta ccaacgacaa ccacttcttc ggctacagca ccccctgggg ctattttgac   1680
ttcaacagat tccactgcca cttctcacca cgtgactggc agcgactcat caacaacaac   1740
tggggattcc ggcccagaaa gctgcggttc aagttgttca acatccaggt caaggaggtc   1800
acgacgaacg acggcgttac gaccatcgct aataacctta ccagcacgat tcaggtcttc   1860
tcggactcgg agtaccaact gccgtacgtc ctcggctctg cgcaccaggg ctgcctccct   1920
ccgttccctg cggacgtgtt catgattcct cagtacggat atctgactct aaacaacggc   1980
agtcagtctg tgggacgttc ctccttctac tgcctggagt actttccttc tcagatgctg   2040
agaacgggca taactttga attcagctac acctttgagg aagtgccttt ccacagcagc   2100
tatgcgcaca gccagagcct ggaccggctg atgaatcccc tcatcgacca gtacctgtac   2160
tacctggccc ggaccagag cactacgggg tccacaaggg agctgcagtt ccatcaggct   2220
gggcccaaca ccatggccga gcaatcaaag aactggctgc ccggaccctg ttatcggcgg   2280
cagagactgt caaagacat agacagcaac aacaacagta actttgcctg gaccggggcc   2340
actaaatacc atctgaatgg tagaaattca ttaaccaacc cgggcgtagc catggccacc   2400
aacaaggacg acgaggacca gttctttccc atcaacggag tgctggtttt tggcaaaacg   2460
ggggctgcca acaagacaac gctggaaaac gtgctaatga ccagcgagga ggagatcaaa   2520
accaccaatc ccgtggctac agaagaatac ggtgtggtct ccagcaacct gcaatcgtct   2580
acggccggac cccagacaca gactgtcaac agccagggg ctctgcccgg catggtctgg   2640
cagaaccggg acgtgtacct gcagggtccc atctgggcca aaattcctca cacggacggc   2700
aactttcacc cgtctcccct gatgggcgga tttggactca acacccgcc tcctcaaatt   2760 ctcatcaaaa acacccggt acctgctaat cctccagagg tgtttactcc tgccaagttt   2820
gcctcattta tcacgcagta cagcaccggc caggtcagcg tggagatcga gtgggaactg   2880
cagaaagaga acagcaaacg ctggaatcca gagattcagt acacctcaaa ttatgccaag   2940
tctaataatg tggaatttgc tgtcaacaac gaagggggttt atactgagcc tcgccccatt   3000
```

```
ggcacccgtt acctcacccg taacctgtaa ttacttgtta atcaataaac cggttgattc    3060
gtttcagttg aactttggtc tctgcgaagg gcgaattc                            3098

<210> SEQ ID NO 38
<211> LENGTH: 3276
<212> TYPE: DNA
<213> ORGANISM: Unknown
<220> FEATURE:
<223> OTHER INFORMATION: AAV serotype, clone 42.6a

<400> SEQUENCE: 38
gaattcgccc ttcgcagaga ccaaagttca actgaaacga attaaccggt ttattgatta      60
acaggcaatt acaggttacg ggtgaggtaa cgggtgccaa tggggcgagg ctcagtataa     120
accccttcgt tgttgacagc aaattccaca ttattagact tggcataatt tgaggtgtac     180
tgaatctctg gattccagcg tttgctgttt tctttctgca gttcccactc gatctccacg     240
ctgacctggc cggtgctgta ctgcgtgata aatgaggcaa acttggcagg agtaaacacc     300
tctggaggat tagcaggtac cggggtgttt ttgatgagaa tttgaggagg cgggtgtttg     360
agtccaaatc cgtccatcag gggagacggg tgaaagttgc cgtccgtgtg aggaattttg     420
gcccagatgg gaccctgcag gtacacgtcc cggttctgcc agaccatgcc gggcagagcc     480
ccctggctgt tgacagtctg tgtctggggt ccggccgtag acgattgcag gttgctggag     540
accacaccgt attcttctgt agccacggga ttggtggttt tgatctcctc ctcgctggtc     600
attagcacgt tttccagcgt tgtcttgttg gcagcccccg ttttgccaaa aaccagcact     660
ccgttgatgg gaaagaactg gtcctcgtcg tccttgttgg tggccatggc tacgcccggg     720
ttggttaatg aatttctacc attcagatgg tatttagtgg ccccggtcca ggcaaagtta     780
ctgttgttgt tgctgtctat gttttttgac agtctctgct gccgataaca gggtccgggc     840
agccagttct ttgattgctc ggccatggtg ttgggcccag cctgatggaa ctgcagctcc     900
cttgtggacc ccgtagtgct ctgggtccgg gccaggtagt acaggtactg gtcgatgagg     960
ggattcatca gccggtccag gctctggcta tgcgcatagc tgctgtggaa aggcacttcc    1020
tcaaaggtgt agctgaattc aaagttattg cccgttctca gcatctgaga aggaaagtac    1080
tccaggcagt agaaggagga acgtcccaca gactgactgc cgttgtttag agtcagatat    1140
ccgtactgag gaatcatgaa cacgtccgca gggaacggag ggaggcagcc ctggtgcgca    1200
gagccgagga cgtacggcag ttggtactcc gagtccgaga agacctgaat cgtgctggta    1260
aggttattag cgatggtcgt aacgccgtcg tccgtcgtga cctccttgac ctggatgttg    1320
aacaacttga accgcagctt tctgggccgg aatccccagt tgttgttgat gagtcgctgc    1380
cagtcacgtg gtgagaagtg gcagtggaat ctgttaaagt caaataccc caggggtg     1440 ctgtagccga agtaggtgtt gtcgttggtg cttcctcccg atgtcccgtt ggagatttgc    1500
ttgtagaggt ggttgttgta ggtgggagg gcccaggttc gggtgctggt ggtgatgact    1560
ctgtcgccca gccatgtgga atcgcaatgc caatttcctg aggaactacc cactccgtcg    1620
gcgccttcgt tattgtctgc cattggagcg ccaccgcctg cagccattgt accagatccc    1680
agaccagagg ggcctgcggg gggttctccg attggttgag ggtcgggcac tgactctgag    1740
tcgccagtct gcccaaagtt gagtctcttt ttcgcgggct gctggcctgt cttgccgatg    1800
cccgtagagg agtctggaga acgctggggt gatggctcta ccggtctctt ctttccagga    1860
gccgtcttag cgccttcctc aaccagaccg agaggttcga gaacccgctt cttggcctgg    1920
```

| | |
|---|---|
| aagactgctc gcccgaggtt gcccccaaaa gacgtatctt cttgaagacg ctcctgaaac | 1980 |
| tcggcgtcgg cgtggttgta cttgaggtac gggttgtccc cctgctcgag ctgcttgtcg | 2040 |
| taggccttgt cgtgctcgag ggccgcggcg tctgcctcgt tgaccggctc tcccttgtcg | 2100 |
| agtccgttga agggtccgag gtacttgtag ccaggaagca ccagaccccg gccgtcgtcc | 2160 |
| tgcttttgct ggttggcttt gggtttcggg gctccaggtt tcaagtccca ccactcgcga | 2220 |
| atgccctcag agaggttgtc ctcgagccaa tctggaagat aaccatcggc agccatacct | 2280 |
| ggtttaagtc atttattgct cagaaacaca gtcatccagg tccacgttga ccagatcgca | 2340 |
| ggccgagcaa gcaatctcgg gagcccgccc cagcagatga tgaatggcac agagtttccg | 2400 |
| atacgtcctc tttctgacga ccggttgaga ttctgacacg ccggggaaac attctgaaca | 2460 |
| gtctctggtc ccgtgcgtga agcaaatgtt gaaattctga ttcattctct cgcatgtctt | 2520 |
| gcagggaaac agcatctgaa gcatgcccgc gtgacgagaa cacttgtttt ggtacctgtc | 2580 |
| ggcaaagtcc accggagctc cttccgcgtc tgacgtcgat ggatgcaaaa tgtcgcaaaa | 2640 |
| gcactcacgt gacagctaat acaggaccac tcccctatga cgtgatttac gtcagcgcta | 2700 |
| tgcccgcgtg acgagaacat ttgttttggt acctgtcggc aaagtccacc ggagctcctt | 2760 |
| ccgcgtctga cgtcgatgga tccgcgactg aggggcaggc ccgcttgggc tcgcttttat | 2820 |
| ccgcgtcatc gggggcgggt ctcttgttgg ctccacccctt tctgacgtag aactcatgcg | 2880 |
| ccacctcggt cacgtgatcc tgcgcccagc ggaagaactc tttgacttcc tgctttgtca | 2940 |
| ccttgccaaa gtcatgctcc agacggcggg tgagttcaaa tttgaacatc cggtcctgca | 3000 |
| acggctgctg gtgctcgaag gtggtgctgt tcccgtcaat cacggcgcac atgttggtgt | 3060 |
| tggaagtgac gatcacgggg gtgggatcga tctgggcgga agacttgcac ttttggtcca | 3120 |
| cgcgcacctt gctgccgccg agaatggcct tggcggactc cacgaccttg gccgtcatct | 3180 |
| tgccctcctc ccaccagatc accatcttgt cgacgcaatc gttgaaggga agttctcat | 3240 |
| tggtccagtt gacgcagccg tagaaagggc gaattc | 3276 |

<210> SEQ ID NO 39
<211> LENGTH: 3084
<212> TYPE: DNA
<213> ORGANISM: Unknown
<220> FEATURE:
<223> OTHER INFORMATION: AAV serotype, clone 43.1

<400> SEQUENCE: 39

| | |
|---|---|
| gaattcgccc tttctacggc tgcatcaact ggaccaatga gaactttccc ttcaacgatt | 60 |
| gcgtcgacaa gatggtgatc tggtgggagg agggcaagat gacggccaag gtcgtggagt | 120 |
| ccgccaaggc cattctcggc ggcagcaagg tgcgcgtgga ccaaaagtgc aagtcgtccg | 180 |
| cccagatcga ccccaccccc gtgatcgtca cctccaacac caacatgtgc gccgtgattg | 240 |
| acgggaacag caccaccttc gagcaccagc agccgttgca ggaccggatg ttcaagttcg | 300 |
| aactcacccg ccgtctggag cacgactttg gcaaggtgac caagcaggaa gtcaaagagt | 360 |
| tcttccgctg ggcgcaggat cacgtgaccg aggtggcgca tgagttctac gtcagaaagg | 420 |
| gcggagccag caaaagaccc gccccgatg acgcggatat aagcgagccc aagcgggcct | 480 |
| gccccctcagt cgcggatcca tcgacgtcag acgcggaagg agctccggtg gactttgccg | 540 |
| acaggtacca aaacaaatgt tctcgtcacg cgggcatgct tcagatgctg tttccctgca | 600 |
| aaacgtgcga gaaatgaat cagaatttca acatttgctt cacgcacggg gtcagagact | 660 |
| gctcagaatg tttccccggt gcatcagaat ctcaaccggt cgtcagaaaa aaaacgtatc | 720 |

```
agaaactgtg tgccattcat catctgctgg ggcgggcacc cgagattgct tgctcggcct    780
gcgatctggt caacgtggac ctggacgact gtgtttctga gcaataaatg acttaaacca    840
ggtatggctg ccgatggtta tcttccagat tggcttgagg acaacctctc tgagggcatt    900
cgcgagtggt gggacctgaa acctggagcc ccgaaaccca agccaaccca gcaaaagcag    960
gacgacggcc ggggtctggt gcttcctggc tacaagtacc tcggacccct caacggactc   1020
gacaagggg agcccgtcaa cgcggcggac gcagcggccc tcgagcacga caaggcctac   1080
gaccagcagc tcaaagcggg tgacaatccg tacctgcggt ataaccacgc cgacgccgag   1140
tttcaggagc gtctgcaaga agatacgtct tttgggggca acctcgggcg agcagtcttc   1200
caggccaaga agcgggttct cgaacctctc ggtctggttg aggaaggcgc taagacggct   1260
cctgaaaga agagaccggt agagccatca cctcagcgtt cccccgactc ctccacgggc   1320
atcggcaaga aaggccacca gcccgcgaga aagagactga actttgggca gactggcgac   1380
tcggagtcag tccccgaccc tcaaccaatc ggagaaccac cagcaggccc ctctggtctg   1440
ggatctggta caatggctgc aggcggtggc gctccaatgg cagacaataa cgaaggcgcc   1500
gacgagtgg gtagttcctc aggaaattgg cattgcgatt ccacatggct gggcgacaga   1560
gtcatcacca ccagcacccg aacctgggcc ctgcccacct acaacaacca tctctacaag   1620
caaatctcca cgggacatc gggaggaagc actaacgaca cacctactt tggctacagc   1680
accccctgg ggtattttga cttcaacaga ttccactgcc acttctcacc acgtgactgg   1740
cagcgactca tcaacaataa ctggggattc cggcccaaga gactcaactt caagctcttc   1800
aacatccagg tcaaggaggt cacgcagaat gaaggcacca agaccatcgc caataacctt   1860
accagcacga ttcaggtgtt tacgactcg gaataccagc tcccgtacgt ccccggctct   1920
gcgcaccagg gctgcctccc tccgttcccg gcggacgtct tcatgattcc tcagtacggg   1980
tatctgaccc taaacaatgg cagtcaggct gtgggccgtt cctccttcta ctgcctggaa   2040
tacttcccctt ctcaaatgct gaggacgggc aacaactttg aattcagcta caccttcgag   2100
gacgtgcctt tccacagcag ctacgcgcac agccagagcc tggaccggct gatgaaccct   2160
ctcatcgacc agtacctgta ttacttatcc agaactcagt ccacaggagg aactcaaggt   2220
actcagcaat tgttattttc tcaagccggg cccgcaaaca tgtcggctca ggccaagaac   2280
tggctacctg gaccgtgtta ccgtcagcaa cgagtttcca cgacactgtc gcaaaacaac   2340
aacagcaatt ttgcttggac cggtgccacc aagtatcacc tgaatggcag agactccctg   2400
gttaatcccg cgcgttgccat ggctacccac aaggacgacg aggagcgctt cttcccgtca   2460
agcggagttc taatgtttgg caagcagggg gctggaaaag acaatgtgga ctacagcagc   2520
gtgatgctca ccagcgaaga agaaattaaa actactaacc cagtggctac agagcagtat   2580
ggtgtggtgg cagacaacct gcagcagacc aacggagctc ccattgtggg aactgtcaac   2640
agccaggggg ccttacctgg tatggtctgg caaaaccggg acgtgtacct gcagggcccc   2700
atctgggcca aaattcctca cacggacggc aactttcatc cttcgccgct gatgggaggc   2760
tttggactga aacacccgcc tcctcagatc ctggtgaaaa acactcctgt tcctgcggat   2820
cctccgacca cccttcagcca ggccaagctg gcttctttta tcacgcagta cagcaccgga   2880
caggtcagcg tggaaatcga atgggagctg cagaaagaaa acagcaagcg ctggaaccca   2940
gagattcagt atacttccaa ctactacaaa tctacaaatg tggactttgc tgtcaatact   3000
gagggtactt attcagagcc tcgcccatt ggcactcgtt atctcacccg taatctgtaa   3060
```

```
ttgcttgtta atcaataaac cggt                                          3084

<210> SEQ ID NO 40
<211> LENGTH: 2370
<212> TYPE: DNA
<213> ORGANISM: Unknown
<220> FEATURE:
<223> OTHER INFORMATION: AAV serotype, clone 43.5

<400> SEQUENCE: 40
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgcgtgga ccaaaagtgc aagtcgtccg     180
cccagatcga ccccaccccc gtgatcgtca cctccaacac caacatgtgc gccgtgattg     240
acgggaacag caccaccttc gagcaccagc agccgttgca ggaccggatg ttcaagttcg     300
aactcacccg ccgtctggag cacgactttg gcaaggtgac caagcaggaa gtcaaagagt     360
tcttccgctg ggcgcaggat cacgtgaccg aggtggcgca tgagttctac gtcagaaagg     420
gcggagccag caaaagaccc gcccccgatg acgcggatat aagcgagccc aagcgggcct     480
gcccctcagt cgcggatcca tcgacgtcag acgcggaagg agctccggtg gactttgccg     540
acaggtacca aaacaaatgt tctcgtcacg cgggcatgct tcagacgctg tttccctgca     600
aaacgtgcga gagaatgaat cagaatttca acatttgctt cacgcacggg gtcagagact     660
gctcagaatg tttccccggt gcatcagaat ctcaaccggt cgtcagaaaa aaacgtatc      720 agaaactgtg tgccattcat catctgctgg ggcgggcacc cgagattgct tgctcggcct     780
gcgatctggt caacgtggac ctggacgact gtgtttctga gcaataaatg acttaaacca     840
ggtatggctg ccgatggtta tcttccagat tggcttgagg acaacctctc tgagggcatt     900
cgcgagtggt gggacctgaa acctggagcc cgaaacccaa agccaaccag caaaagcag      960 gacgacggcc ggggtctggt gcttcctggc tacaagtacc tcggacccct caacggactc    1020
gacaaggggg agcccgtcaa cgcggcggac gcagcggccc tcgagcacga caaggcctac    1080
gaccagcagc tcaaagcggg tgacaatccg tacctgcgct ataaccacgc cgacgccgag    1140
tttcaggagc gtctgcaaga agatacgtct tttgggggca acctcgggcg agcagtcttc    1200
caggccaaga agcgggttct cgaacctctc ggtctggttg aggaaggcgc taagacggct    1260
cctggaaaga gagaccggt agagccatca cctcagcgtt cccccgactc ctccacgggc    1320
atcggcaaga aggccacca gcccgcgaga aagagactga actttgggca gactggcgac    1380
tcggagtcag tccccgaccc tcaaccaatc ggagaaccac cagcaggccc ctctggtctg    1440
ggatctggta caatggctgc aggcggtggc gctccaatgg cagacaataa cgaaggcgcc    1500
gacggagtgg gtagttcctc aggaaattgg cattgcgatt ccacatggct gggcgacaga    1560
gtcatcacca ccagcacccg aacctgggcc ctgcccacct acaacaacca tctctacaag    1620
caaatctcca cgggacatc gggaggaagc actaacgaca cacctactt tggctacagc    1680 accccctggg ggtattttga cttcaacaga ttccactgcc acttctcacc acgtgactgg    1740
cagcgactca tcaacaataa ctggggattc cggcccaaga gactcaactt caagctcttc    1800
aacatccagg tcaaggaggt cacgcagaat gaaggcacca agaccatcgc caataacctt    1860
accagcacga ttcaggtgtt tacgactcg gaataccagc tcccgtacgt cctcggctct    1920
gcgcaccagg gctgcctccc tccgttcccg cgggacgtct tcatgattcc tcagtacggg    1980
tatctgaccc taaacaatgg cagtcaggct gtgggccgtt cctccttcta ctgcctggaa    2040
```

```
tacttcccett ctcaaatgct gaggacgggc aacaactttg aattcagcta caccttcgag    2100
gacgtgcctt tccacagcag ctacgcgcac agccagagcc tggaccggct gatgaaccct    2160
ctcatcgacc agtacctgta ttacttatcc agaactcagt ccacaggagg aactcaaggt    2220
actcagcaat tgttattttc tcaagccggg cccgcaaaca tgtyggctca ggccaagaac    2280
tggctacctg gaccgtgtta ccgtcagcaa cgagtttcca cgacactgtc gcaaaacaac    2340
aacagcaatt ttgctggacc ggtgccacca                                     2370
```

<210> SEQ ID NO 41
<211> LENGTH: 3123
<212> TYPE: DNA
<213> ORGANISM: Unknown
<220> FEATURE:
<223> OTHER INFORMATION: AAV serotype, clone 43.12

<400> SEQUENCE: 41

```
gaattcgccc ttggctgcgt caactggacc aatgagaact tcccttcaa cgattgcgtc      60 gacaagatgg tgatctggtg ggaggagggc aagatgacgg ccaaggtcgt ggagtccgcc    120
aaggccattc tcggcggcag caaggtgcgc gtggaccaaa agtgcaagtc gtccgcccag    180
atcgacccca cccccgtgat cgtcacctcc aacaccaaca tgtgcgccgt gattgacggg    240
aacagcacca ccttcgagca ccagcagccg ttgcaggacc ggatgttcaa gttcgaactc    300
acccgccgtc tggagcacga ctttggcaag gtgaccaagc aggaagtcaa agagttcttc    360
cgctgggcgc aggatcacgt gaccgaggtg gcgcatgagt tctacgtcag aaagggcgga    420
gccagcaaaa gacccgcccc cgatgacgcg gatataagcg agcccaagcg ggcctgcccc    480
tcagtcgcgg atccatcgac gtcagacgcg aaggagctc cggtggactt tgccgacagg    540
taccaaaaca atgttctcg tcacgcgggc atgctccaga tgctgtttcc ctgcaaaacg    600
tgcgagagaa tgaatcagaa tttcaacatt tgcttcacgc acgggtcag agactgctca    660 gaatgtttcc ccggtgcatc agaatctcaa ccggtcgtca gaaaaaaaac gtatcagaaa    720
ctgtgtgcca ttcatcatct gctggggcgg gcacccgaga ttgcttgctc ggcctgcgat    780
ctggtcaacg tggacctgga cgactgtgtt tctgagcaat aaatgactta aaccaggtat    840
ggctgccgat ggttatcttc cagattggct tgaggacaac ctctctgagg gcattcgcga    900
gtggtgggac ctgaaacctg agccccgaa acccaaagcc aaccagcaaa agcaggacga    960
cggccggggt ctggtgcttc ctggctacaa gtacctcgga cccttcaacg gactcgacaa    1020
gggggagccc gtcaacgcgg cggacgcagc ggccctcgag cacgacaagg cctacgacca    1080
gcagctcaaa gcgggtgaca atccgtacct gcggtataac acgccgacg ccgagtttca    1140 ggagcgtctg caagaagata cgtcttttgg gggcaacctc gggcgagcag tcttccaggc    1200
caagaagcgg gttctcgaac ctctcggtct ggttgaggaa ggcgctaaga cggctcctgg    1260
aaagaagaga ccggtagagc catcacctca gcgttccccc gactcctcca cgggcatcgg    1320
caagaaaggc caccagcccg cgagaaagag actgaacttt ggcagactg gcgactcgga    1380 gtcagtcccc gaccctcaac caatcggaga accaccagca ggccctctg gtctgggatc    1440 tggtacaatg gctgcaggcg gtggcgctcc aatggcagac aataacgaag cgccgacgg    1500 agtgggtagt tcctcaggaa attggcattg cgattccaca tggctgggcg acagagtcat    1560
caccaccagc acccgaacct gggccctgcc cacctacaac aaccatctct acaagcaaat    1620
ctccaacggg acatcgggag gaagcactaa cgacaacacc tactttggct acagcacccc    1680
```

| | |
|---|---|
| ctgggggtat tttgacttca acagattcca ctgccacttc tcaccacgtg actggcagcg | 1740 |
| actcatcaac aataactggg gattccggcc caagagactc aacttcaagc tcttcaacat | 1800 |
| ccaggtcaag gaggtcacgc agaatgaagg caccaagacc atcgccaata accttaccag | 1860 |
| cacgattcag gtgtttacgg actcggaata ccagctcccg tacgtcctcg gctctgcgca | 1920 |
| ccagggctgc ctccctccgt tcccggcgga cgtcttcatg attcctcagt acgggtatct | 1980 |
| gaccctaaac aatggcagtc aggctgtggg ccgttcctcc ttctactgcc tggaatactt | 2040 |
| cccttctcaa atgctgagga cgggcaacaa ctttgaattc agctacacct tcgaggacgt | 2100 |
| gcctttccac agcagctacg cgcacagcca gagcctggac cggctgatga ccctctcat | 2160 |
| cgaccagtac ctgtattact tatccagaac tcagtccaca ggaggaactc aaggtactca | 2220 |
| gcaattgtta ttttctcaag ccgggcccgc aaacatgtcg gctcaggcca gaactggct | 2280 |
| acctggaccg tgttaccgtc agcaacgagt ttccacgaca ctgtcgcaaa acaacaacag | 2340 |
| caattttgct tggaccggtg ccaccaagta tcacctgaat ggcagagact ccctggttaa | 2400 |
| tcccggcgtt gccatggcta cccacaagga cgacgaggag cgcttcttcc cgtcaagcgg | 2460 |
| agttctaatg tttggcaagc aggggctgg aaaagacaat gtggactaca gcagcgtgat | 2520 |
| gctcaccagc gaagaagaaa ttaaaaactac taacccagtg ctacagagc agtatggtgt | 2580 |
| ggtggcagac aacctgcagc agaccaacgg agctcccatt gtgggaactg tcaacagcca | 2640 |
| gggggcctta cctggtatgg tctggcaaaa ccggacgtg tacctgcagg ccccatctg | 2700 |
| ggccaaaatt cctcacacgg acggcaactt tcatccttcg ccgctgatgg gaggctttgg | 2760 |
| actgaaacac ccgcctcctc agatcctggt gaaaaacact cctgttcctg cggatcctcc | 2820 |
| gaccaccttc agccaggcca agctggcttc ttttatcacg cagtacagca ccggacaggt | 2880 |
| cagcgtggaa atcgaatggg agctgcagaa agaaaacagc aagcgctgga acccagagat | 2940 |
| tcagtatact tccaactact acaaatctac aaatgtggac tttgctgtca atactgaggg | 3000 |
| tacttattca gagcctcgcc ccattggcac tcgttatctc acccgtaatc tgtaattgct | 3060 |
| tgttaatcaa taaaccggtt aattcgtttc agttgaactt tggtctctgc gaagggcgaa | 3120 |
| ttc | 3123 |

<210> SEQ ID NO 42
<211> LENGTH: 3122
<212> TYPE: DNA
<213> ORGANISM: Unknown
<220> FEATURE:
<223> OTHER INFORMATION: AAV serotype, clone 43.20

<400> SEQUENCE: 42

| | |
|---|---|
| gaattcgccc tttctacggc tgcgtcaact ggaccaatga gaactttccc ttcaacgatt | 60 |
| gcgtcgacaa gatggtgatc tggtgggagg agggcaagat gacggccaag gtcgtggagt | 120 |
| ccgccaaggc cattctcggc ggcagcaagg tgcgtgtgga ccaaaagtgc aagtcttccg | 180 |
| cccagatcga tcccaccccc gtgatcgtca cctccaacac caacatgtgc gccgtgattg | 240 |
| acgggaacag cgccaccttc gagcaccagc agccgttgca ggaccggatg ttcaaatttg | 300 |
| aactcacccg ccgtctggag catgactttg gcaaggtgac gaagcaggaa gtcaaagagt | 360 |
| tcttccgctg ggcgcaggat cacgtgaccg aggtggcgca tgagttccac gtcagaaagg | 420 |
| gtggagccaa caagacccc gcccccgatg acgcggatat aagcgagccc aagcgggcct | 480 |
| gcccctcagt cgcggatcca tcgacgtcag acgcggaagg agctccggtg actttgccg | 540 |
| acaggtacca aaacaaatgt ctctgtcacg cgggcatgct tcagatgctg tttccctgca | 600 |

```
agacatgcga gagaatgaat cagaatttca acatttgctt cacgcacggg accagagact    660
gttcagaatg tttccccggc gtgtcagaat ctcaaccggt cgtcagaaag aggacgtatc    720
ggaaactctg tgcgattcat catctgctgg ggcgggctcc cgagattgct tgctcggcct    780
gcgatctggt caacgtggac ctggatgact gtgtttctga gcaataaatg acttaaacca    840
ggtatggctg ccgatggtta tcttccagat tggctcgagg acaacctctc tgagggcatt    900
cgcgagtggt gggacttgaa acctggagcc ccgaaaccca agccaaccca gcaaaagcag    960
gacgacggcc ggggtctggt gcttcctggc tacaagtacc tcggacccct caacggactc   1020
gacaagggg agcccgtcaa cgcggcggac gcagcggccc tcgagcacga caaagcctac   1080
gaccagcagc tcaaagcggg tgacaatccg tacctgcggt ataatcacgc cgacgccgag   1140
tttcaggagc gtctgcaaga agatacgtct ttgggggca acctcgggcg agcagtcttc   1200
caggccaaga agcgggttct cgaacctctc ggtctggttg aggaaggcgc taagacggct   1260
cctggaaaga agagactggt agagcagtcg ccacaagagc cagactcctc ctcgggcatc   1320
ggcaagacag gccagcagcc cgctaaaaag agactcaatt ttggtcagac tggcgactca   1380
gagtcagtcc ccgacccaca acctctcgga gaacctccag cagcccctc aggtctggga   1440
cctaatacaa tggcttcagg cggtggcgct ccaatggcag acaataacga aggcgccgac   1500
ggagtgggta attcctcggg aaattggcat gcgattcca catggctggg ggacagagtc   1560
atcaccacca gcacccgaac ctgggccctg cccacctaca caaccacct ctacaagcaa   1620
atctccaacg gcacctcggg aggaagcacc aacgacaaca cctatttgg ctacagcacc   1680
ccctgggggt attttgactt caacagattc cactgtcact tttcaccacg tgactggcaa   1740
cgactcatca caacaattg gggattccgg cccaaaagac tcaacttcaa gctgttcaac   1800
atccaggtca aggaagtcac gacgaacgaa ggcaccaaga ccatcgccaa taatctcacc   1860
agcaccgtgc aggtctttac ggactcgag taccagttac cgtacgtgct aggatccgct   1920
caccagggat gtctgcctcc gttcccggcg gacgtcttca cggttcctca gtacggctat   1980
ttaactttaa acaatggaag ccaagccctg ggacgttcct ccttctactg tctggagtat   2040
ttcccatcgc agatgctgag aaccggcaac aactttcagt tcagctacac cttcgaggac   2100
gtgcctttcc acagcagcta cgcgcacagc cagagcctgg acaggctgat gaatcccctc   2160
atcgaccagt acctgtacta cctggtcaga acgcaaacga ctggaactgg agggacgcag   2220
actctggcat tcagccaagc gggtcctagc tcaatggcca accaggctag aaattgggtg   2280
cccgaccctt gctaccggca gcagcgcgtc tccacgacaa ccaaccagaa caacaacagc   2340
aactttgcct ggacgggagc tgccaagttt aagctgaacg gccgagactc tctaatgaat   2400
ccgggcgtgg caatggcttc ccacaaggat gacgacgacc gcttcttccc ttcgagcggg   2460
gtcctgattt ttggcaagca aggagccggg aacgatggag tggattacag ccaagtgctg   2520
attacagatg aggaagaaat caaggctacc aaccccgtgg ccacagaaga atatggagca   2580
gtggccatca caaccaggc cgccaatacg caggcgcaga ccggactcgt gcacaaccag   2640
ggggtgattc ccggcatggt gtggcagaat agagacgtgt acctgcaggg tcccatctgg   2700
gccaaaattc ctcacacgga cggcaacttt caccgtctc cctgatggg cggctttgga   2760
ctgaagcacc cgcctcctca aattctcatc aagaacacac cggttccagc ggacccgccg   2820
cttaccttca accaggccaa gctgaactct ttcatcacgc agtacagcac cggacaggtc   2880
agcgtggaaa tcgagtggga gctgcagaaa gaaaacagca acgctggaa tccagagatt   2940
```

```
caatacactt ccaactacta caaatctaca aatgtggact ttgctgtcaa cacggaagga   3000
gtttatagcg agcctcgccc cattggcacc cgttacctca cccgcaacct gtaattacat   3060
gttaatcaat aaaccggtta attcgtttca gttgaacttt ggtctctgcg aagggcgaat   3120
tc                                                                 3122

<210> SEQ ID NO 43
<211> LENGTH: 3117
<212> TYPE: DNA
<213> ORGANISM: Unknown
<220> FEATURE:
<223> OTHER INFORMATION: AAV serotype, clone 43.21

<400> SEQUENCE: 43
gaattcgccc ttggctgcgt caactggacc aatgagaact ttcccttcaa cgattgcgtc     60
gacaagatgg tgatctggtg ggaggagggc aagatgacgg ccaaggtcgt ggagtccgcc    120
aaggccattc tcggcggcag caaggtgcgt gtggaccaaa agtgcaagtc ttccgcccag    180
atcgatccca cccccgtgat cgtcacctcc aacaccaaca tgtgcgccgt gattgacggg    240
aacagcacca ccttcgagca ccagcagccg ttgcaggacc ggatgttcaa atttgaactc    300
acccgccgtc tggagcatga ctttggcaag gtgacgaagc aggaagtcaa agagttcttc    360
cgctgggcgc aggatcacgt gaccgaggtg gcgcatgagt ccacgtcag aaagggtgga    420 gccaacaaga gacccgcccc cgatgacgcg gatataagcg agcccaagcg ggcctgcccc    480
tcagtcgcgg atccatcgac gtcagacgcg aaggagctcc ggtggactt tgccgacagg    540 taccaaaaca aatgttctcg tcacgcgggc atgcttcaga tgctgtttcc ctgcaagaca    600
tgcgagagaa tgaatcagaa tttcaacatt tgcttcacgc acgggaccag agactgttca    660
gaatgtttcc ccggcgtgtc agaatctcaa ccggtcgtca gaaagaggac gtatcggaaa    720
ctctgtgcga ttcatcatct gctggggcgg gctcccgaga ttgcttgctc ggcctgcgat    780
ctggtcaacg tggacctgga tgactgtgtt tctgagcaat aaatgactta aaccaggtat    840
ggctgccgat ggttatcttc cagattggct cgaggacaac ctctctgagg gcattcgcga    900
gtggtgggac ttgaaacctg gagccccgaa acccaaagcc aaccagcaaa agcaggacga    960 cggccgggt ctggtgcttc ctggctacaa gtacctcgga cccttcaacg gactcgacaa   1020
gggggagccc gtcaacgcgg cggacgcagc ggccctcgag cacgacaaag cctacgacca   1080
gcagctcaaa gcgggtgaca atccgtacct gcggtataat cacgccgacg ccgagtttca   1140
ggagcgtctg caagaagata cgtcttttgg gggcaacctc gggcgagcag tcttccaggc   1200
caagaagcgg gttctcgaac ctctcggtct ggttgaggaa ggcgctaaga cggctcctgg   1260
aaagaagaga ccggtagagc agtcgccaca agagccagac tcctcctcgg catcggcaa   1320 gacaggccag cagcccgcta aaaagagact caattttggt cagactggcg actcagagtc   1380
agtccccgac ccacaacctc tcggagaacc tccagcagcc cctcaggtc tgggacctaa   1440 tacaatggct tcaggcggtg cgctccaat ggcagacaat aacgaaggcg ccgacggagt   1500
gggtaattcc tcgggaaatt ggcattgcga ttccacatgg ctgggggaca gagtcatcac   1560
caccagcacc cgaacctggg ccctgcccac ctacaacaac cacctctaca gcaaatctc   1620 caacggcacc tcgggaggaa gcaccaacga caacacctat tttggctaca gcaccccctg   1680
ggggtatttt gacttcaaca gattccactg tcactttca ccacgtgact ggcaacgact   1740
catcaacaac aattgggat ccggcccaa aagactcaac ttcaagctgt tcaacatcca   1800
ggtcaaggaa gtcacgacga acgaaggcac caagaccatc gccaataatc tcaccagcac   1860
```

-continued

```
cgtgcgggtc tttacggact cggagtacca gttaccgtac gtgctaggat ccgctcacca    1920
gggatgtctg cctccgttcc cggcggacgt cttcatggtt cctcagtacg gctatttaac    1980
tttaaacaat ggaagccaag ccctgggacg ttcctccttc tactgtctgg agtatttccc    2040
atcgcagatg ctgagaaccg gcaacaactt tcagttcagc tacaccttcg aggacgtgcc    2100
tttccacagc agctacgcgc acagccagag cctggacagg ctgatgaatc ccctcatcga    2160
ccagtacctg tactacctgg tcagaacgca aacgactgga actggaggga cgcagactct    2220
ggcattcagc caagcgggtc ctagctcaat ggccaaccag ctagaaatt gggtgcccgg     2280 accttgctac cggcagcagc gcgtctccac gacaaccaac cagagcaaca acagcaactt    2340
tgcctggacg ggagctgcca gtttaagct gaacggccga gactctctaa tgaatccggg     2400
cgtggcaatg gcttcccaca aggatgacga cgaccgcttc ttcccttcga gcggggtcct    2460 gattttggc aagcaaggag ccgggaacga tggagtggat tacagccaag tgctgattac     2520
agatgaggaa gaaatcaagg ctaccaaccc cgtggccaca aagaatatg gagcagtggc     2580 catcaacaac caggccgcca atacgcaggc gcagaccgga ctcgtgcaca accagggggt    2640
gattcccggc atggtgtggc agaatagaga cgtgtacctg cagggtccca tctgggccaa    2700
aattcctcac acggacggca actttcaccc gtctcccctg atgggcggct ttggactgaa    2760
gcacccgcct cctcaaattc tcatcaagaa cacaccggtt ccagcggacc cgccgcttac    2820
cttcaaccag gccaagctga actctttcat cacgcagtac agcaccggac aggtcagcgt    2880
ggaaatcgag tgggagctgc agaaagaaaa cagcaaacgc tggaatccag agattcaata    2940
cacttccaac tactacaaat ctacaaatgt ggactttgct gtcaacacgg aaggagttta    3000
tagcgagcct cgccccattg gcacccgtta cctcacccgc aacctgtaat tacatgttaa    3060
tcaataaacc ggttaattcg tttcagttga actttggtct ctgcgaaggg cgaattc      3117
```

<210> SEQ ID NO 44
<211> LENGTH: 3121
<212> TYPE: DNA
<213> ORGANISM: Unknown
<220> FEATURE:
<223> OTHER INFORMATION: AAV serotype, clone 43.23

<400> SEQUENCE: 44

```
gaattcgccc ttctacggct gcgtcaactg gaccaatgag aactttccct caacgattg      60 cgtcgacaag atggtgatct ggtgggagga gggcaagatg acggccaagg tcgtggagtc    120
cgccaaggcc attctcggcg gcagcaaggt gcgtgtggca caaaagtgca agtcttccgc    180
ccagatcgat cccacccccg tgatcgtcac ctccaacacc aacatgtgcg ccgtgattga    240
cgggaacagc accaccttcg agcaccagca gccgttgcag gaccggatgt tcaaatttga    300
actcacccgc cgtctggagc atgactttgg caaggtgacg aagcaggaag tcaaagagtt    360
cttccgctgg gcgcaggatc acgtgaccga ggtggcgcat gagttccacg tcagaaaggg    420
tggcgccaac aagagacccg cccccgatga cgcggatata agcgagccca gcgggcctg    480 cccctcagtc gcggatccat cgacgtcaga cgcggaagga gctccggtgg actttgccga    540
caggtaccaa aacaaatgtt ctcgtcacgc gggcatgctt cagatgctgt ttccctgcaa    600
gacatgcgag agaatgaatc agaatttcaa catttgcttc acgcacggga ccagagactg    660
ttcagaatgt tttccccggcg tgtcagaatc tcaaccggtc gtcagaaaga ggacgtatcg    720
gaaactctgt gcgattcatc atctgctggg gcgggctccc gagattgctt gctcggcctg    780
```

```
cgatctggtc aacgtggacc tggatgactg tgtttctgag caataaatga cttaaaccag    840
gtatggctgc cgatggttat cttccagatt ggctcgagga caacctctct gagggcattc    900
gcgagtggtg ggacttgaaa cctggagccc cgaaacccaa agccaaccag caaaagcagg    960
acgacggccg gggtctggtg cttcctggct acaagtacct cggacccttc aacggactcg   1020
acaagggga gcccgtcaac gcggcggacg cagcggccct cgagcacgac aaagcctacg   1080
accagcagct caaagcgggt gacaatccgt acctgcggta taatcacgcc gacgccgagt   1140
ttcaggagcg tctgcaagaa gatacgtcct ttgggggcaa cctcgggcga gcagtcttcc   1200
aggccaagaa gcgggttctc gaacctctcg gtctggttga ggaaggcgct aagacggctc   1260
ctggaaagaa gagaccggta gagcagtcgc cacaagagcc agactcctcc tcgggcatcg   1320
gcaagacagg ccagcagccc gctaaaaaga gactcaattt tggtcagact ggcgactcag   1380
agtcagtccc cgacccacaa cctctcggag aacctccagc agcccctca ggtctgggac   1440
ctaatacaat ggcttcaggc ggtggcgctc caatggcaga caataacgaa ggcgccgacg   1500
gagtgggtaa ttcctcggga aattggcatt gcgattccac atggctgggg gacagagtca   1560
tcaccaccag cacccgaacc tgggccctgc ccacctacaa caaccacctc tacaagcaaa   1620
tctccaacgg cacctcggga ggaagcacca acgacaacac ctattttggc tacagcaccc   1680
cctgggggta ttttgacttc aacagattcc actgtcactt ttcaccacgt gactggcaac   1740
gactcatcaa caacaattgg ggattccggc ccaaaagact caacttcaag ctgttcaaca   1800
tccaggtcaa ggaagtcacg acgaacgaag gcaccaagac catcgccaat aatctcacca   1860
gcaccgtgca ggtctttacg gacttggagt accagttacc gtacgtgcta ggatccgctc   1920
accagggatg tctgcctccg ttcccggcgg acgtcttcat ggttcctcag tacggctatt   1980
taactttaaa caatggaagc caagccctgg gacgttcctc cttctactgt ctggagtatt   2040
tcccatcgca gatgccgaga accggcaaca actttcagtt cagctacacc ttcgaggacg   2100
tgcctttcca cagcagctac gcgcacagcc agagcctgga caggctgatg aatcccctca   2160
tcgaccagta cctgtactac ctggtcagaa cgcaaacgac tggaactgga gggacgcaga   2220
ctctggcatt cagccaagcg gtcctagct caatggccaa ccaggctaga aattgggtgc   2280
ccggaccttg ctaccggcag cagcgcgtct ccacgacaac caaccagaac aacaacagca   2340
actttgcctg gacgggagct gccaagttta gctgaacgg ccgagactct ctaatgaatc   2400
cgggcgtggc aatggcttcc cacaaggatg acgacgaccg cttcttccct tcgagcgggg   2460
tcctgatttt tggcaagcaa ggagccggga acgatgagt ggattacagc caagtgctga   2520
ttacagatga ggaagaaatc aaggctacca accccgtggc cacagaagaa tatggagcag   2580
tggccatcaa caaccaggcc gccaatacgc aggcgcagac cggactcgtg cacaaccagg   2640
gggtgattcc cggcatggtg tggcagaata gagacgtgta cctgcagggt cccatctggg   2700
ccaaaattcc tcacacggac ggcaacttc accgtctcc cctgatgggc ggctttggac   2760
tgaagcaccc gcctcctcaa attctcatca agaacacacc ggttccagcg gacccgccgc   2820
ttaccttcaa ccaggccaag ctgaactctt tcatcacgca gtacagcacc ggacaggtca   2880
gcgtggaaat cgagtgggag ctgcagaaag aaaacagcaa acgctggaat ccagagattc   2940
aatacacttc caactactac aaatctacaa atgtggactt tgctgtcaac acggaaggag   3000
tttatagcga gcctcgcccc attggcaccc gttacctcac ccgcaacctg taattacatg   3060
ttaatcaata aaccggttaa ttcgtttcag ttgaactttg gtctctgcga agggcgaatt   3120
c                                                                   3121
```

<210> SEQ ID NO 45
<211> LENGTH: 3122
<212> TYPE: DNA
<213> ORGANISM: Unknown
<220> FEATURE:
<223> OTHER INFORMATION: AAV serotype, clone 43.25

<400> SEQUENCE: 45

```
gaattcgccc tttctacggc tgcgtcaact ggaccaatga aactttcccc ttcaacgatt      60
gcgtcgacaa gatggtgatc tggtgggagg agggcaagat gacggccaag gtcgtggagt     120
ccgccaaggc cattctcggc ggcagcaagg tgcgtgtgga ccaaaagtgc aagtcttccg     180
cccagatcga tcccaccccc gtgatcgtca cctccaacac caacatgtgc gccgtgattg     240
acgggaacag caccaccttc gagcaccagc agccgttgca ggaccggatg ttcaaatttg     300
aactcacccg ccgtctggag catgactttg gcaaggtgac gaagcaggaa gtcaaagggt     360
tcttccgctg ggcgcaggat cacgtgaccg aggtggcgca tgagttccac gtgcgagccc     420
aagcgggcct gccctcagt cgcggatcca tcgacgtcag accagaaagg gtggagccaa     480
caagagaccc gccccgatg acgcggatat aagcggaagg agctccggtg gactttgccg     540
acaggtacca aaacaaatgt tctcgtcacg cgggcatgct tcagatgctg tttccctgca     600
agacatgcga gagaatgaat cagaatttca acatttgctt cacgcacggg accagagact     660
gttcagaatg ttccccggc gtgtcagaat ctcaaccggt cgtcagaaag aggacgtatc     720
ggaaactctg tgcgattcat catctgctgg ggcgggctcc cgagattgct tgctcggcct     780
gcgatctggt caacgtggac ctggatgact gtgtttctga caataaatg acttaaacca     840
ggtatgctg ccgatggtta tcttccagat tggctcgagg acaacctctc tgagggcatt     900
cgcgagtggt gggacttgaa acctggagcc ccgaaaccca agccaaccca gcaaaagcag     960
gacgacggcc ggggtctggt gcttcctggc tacaagtacc tcggacccctt caacggactc    1020
gacaaggggg agcccgtcaa cgcggcggac gcagcggccc tcgagcacga caaagcctac    1080
gaccagcagc tcaaagcggg tgacaatccg tacctgcggt ataatcacgc cgacgccgag    1140
tttcaggagc gtctgcaaga agatacgtct tttgggggca acctcgggcg agcagtcttc    1200
caggccaaga agcgggttct cgaacctctc ggtctggttg aggaaggcgc taagacggct    1260
cctgaaaga agagaccggt agagcagtcg ccacaagagc cagactcctc ctcgggcatc    1320
ggcaagacag gccagcagcc cgctaaaaag agactcaatt ttggtcagac tggcgactca    1380
gagtcagtcc ccgacccaca acctctcgga gaacctccag cagcccctc aggtctggga    1440
cctaatacaa tggcttcagg cggtggcgct ccaatggcag acaataacga aggcgccgac    1500
ggagtgggta ttcctcgggg aaattggcat gcgattccca catggctggg gacagagtc    1560
atcaccacca gcacccgaac ctgggccctg cccacctaca acaaccacct ctacaagcaa    1620
atctccaacg gcacctcggg aggaagcacc aacgacaaca cctatttgg ctacagcacc    1680
cccctgggt attttgactt caacagattc cactgtcact tttcaccacg tgactggcaa    1740
cgactcatca caacaattg gggattccgg cccaaaagac tcaacttcaa gctgttcaac    1800
atccaggtca aggaagtcac gacgaacgaa ggcaccaaga ccatcgccaa taatctcacc    1860
agcaccgtgc aggtctttac ggactcggag taccagttac cgtacgtgct aggatccgct    1920
caccagggat gtctgcctcc gttccgcgcg acgtcttca tggttcctca gtacggctat    1980
ttaactttaa acaatggaag ccaagccctg ggacgttcct ccttctactg tctggagtat    2040
```

```
ttcccatcgc agatgctgag aaccggcaac aactttcagt tcagctacac cttcgaggac    2100
gtgcctttcc acagcagcta cgcgcacagc cagagcctgg acaggctgat gaatcccctc    2160
atcgaccagt acctgtacta cctggtcaga acgcaaacga ctggaactgg agggacgcag    2220
actctggcat tcagccaagc gggtcctagc tcaatggcca accaggctag aaattgggtg    2280
cccggacctt gctaccggca gcagcgcgtc tccacgacaa ccaaccagaa caacaacagc    2340
aactttgcct ggacgggagc tgccaagttt aagctgaacg gccgagactc tctaatgaat    2400
ccgggcgtgg caatggcttc ccacaaggat gacgacgacc gcttcttccc ttcgagcggg    2460
gtcctgattt ttggcaagca aggagccggg aacgatggag tggattacag ccaagtgctg    2520
attacagatg aggaagaaat caaggctacc aaccccgtgg ccacagaaga atatggagca    2580
gtggccatca acaaccaggc cgccaatacg caggcgcaga ccggactcgt gcacaaccag    2640
ggggtgattc ccggcatggt gtggcagaat agagacgtgt acctgcaggg tcccatctgg    2700
gccaaaattc ctcacacgga cggcaacttt caccgtctc ccctgatggg cggctttgga    2760
ctgaagcacc cgcctcctca aattctcatc aagaacacac cggttccagc ggacccgccg    2820
cttaccttca accaggccaa gctgaactct ttcatcacgc agtacagcac cggacaggtc    2880
agcgtggaaa tcgagtggga gctgcagaaa gaaaacagca acgctggaa tccagagatt    2940
caatacactt ccaactacta caaatctaca aatgtggact ttgctgtcaa cacggagggg    3000
gtttatagcg agcctcgccc cattggcacc cgttacctca cccgcaacct gtaattacat    3060
gttaatcaat aaaccggtta attcgtttca gttgaacttt ggtctctgcg aagggcgaat    3120
tc                                                                   3122

<210> SEQ ID NO 46
<211> LENGTH: 3128
<212> TYPE: DNA
<213> ORGANISM: Unknown
<220> FEATURE:
<223> OTHER INFORMATION: AAV serotype, clone 44.1

<400> SEQUENCE: 46
gaattcgccc tttctacggc tgcgtcaact ggaccaatga gaactttccc ttcaacgatt      60
gcgtcgacaa gatgttgatc tggtgggagg agggcaagat gacggccaag gtcgtggagt     120
ccgccaaggc cattctcggc ggcagcaaag tgcgcgtgga ccaaaagtgc aagccgtccg     180
cccagatcga ccccaccccc gtgatcgtca cctccaacac caacatgtgc gccgtgattg     240
acgggaacag caccaccttc gagcaccagc agccgttgcg ggaccggatg ttcaagtttg     300
aactcacccg ccgtctggag cacgactttg gcaaggtgac aaagcaggaa gtcagagagt     360
tcttccgctg ggcgcaggat cacgtgaccg aggtggcgca cgagttctac gtcagaaagg     420
gtggagccaa caagagaccc gcccccgatg acgcggataa aagcgagccc aagcgggcct     480
gcccctcagt cgcggatcca tcgacgtcag acgcggaagg agctccggtg gactttgccg     540
acaggtacca aaacaaatgt ctcgtcacg cgggcatgct tcagatgctg tttcctgca      600
aaacatgcga gagaatgaat cagaatttca acatttgctt cacgcacggg accagagact     660
gttcagaatt tttccccggc gtgtcagaat ctcaaccggt cgtcagaaaa agacgtatc      720
ggaaactctg tgcgattcat catctgctgg ggcgggcacc cgagattgct tgctcggcct     780
gcgatctggt caacgtggac ctagatgact gtgtttctga gcaataaatg acttaaacca     840
ggtatggctc cgatggtta tcttccagat tggctcgagg acaacctctc tgagggcatt     900
cgcgagtggt gggacttgaa acctggagcc ccgaaaccca agccaaccca gcaaaagcag    960
```

```
gacgacggcc ggggtctggt gcttcctggc tacaagtacc tcggacccct caacggactc   1020 gacaagggg agcccgtcaa cgcggcggac gcagcggccc tcgagcacga caaggcctac   1080
gaccagcagc tcaaagcggg tgacaatccg tacctgcggt ataaccacgc cgacgccgag   1140
tttcaggagc gtctgcaaga agatacgtct tttgggggca acctcgggcg agcagtcttc   1200
caggccaaga agcgggttct cgaacctctc ggtctggttg aggaaggcgc taagacggct   1260 cctgaaaga agagaccggt agagccatca ccccagcgtt ctccagactc ctctacgggc   1320
atcggcaaga aaggccagca gcccgcgaaa aagagactca actttgggca gactggcgac   1380
tcagagtcag tgcccgaccc tcaaccaatc ggagaacccc ccgcaggccc ctctggtctg   1440
ggatctggta caatggctgc aggcggtggc gctccaatgg cagacaataa cgaaggcgcc   1500
gacggagtgg gtagttcctc aggaaattgg cattgcgatt ccacatggct gggcgacaga   1560
gtcatcacca ccagcacccg aacctgggcc ctccccacct acaacaacca cctctacaag   1620
caaatctcca cgggacttc gggaggaagc accaacgaca cacctactt cggctacagc   1680 accccctggg ggtattttga ctttaacaga ttccactgcc acttctcacc acgtgactgg   1740
cagcgactca tcaacaacaa ctggggattc cggcccaaga gactcaactt caagctcttc   1800
aacatccagg tcaaggaggt cacgcagaat gaaggcacca agaccatcgc caataacctt   1860
accagcacga ttcaggtctt tacgactcg gaataccagc tcccgtacgt cctcggctct   1920
gcgcaccagg gctgcctgcc tccgttcccg gcggacgtct tcatgattcc tcagtacggg   1980
tacctgactc tgaacaatgg cagtcaggcc gtgggccgtt cctccttcta ctgcctggag   2040
tactttcctt ctcaaatgct gagaacgggc aacaactttg agttcagcta ccagtttgag   2100
gacgtgcctt ttcacagcag ctacgcgcac agccaaagcc tggaccggct gatgaacccc   2160
ctcatcgacc agtacctgta ctacctgtct cggactcagt ccacgggagg taccgcagga   2220
actcagcagt tgctattttc tcaggccggg cctaataaca gtcggctca ggccaaaaac   2280 tggctacccg ggccctgcta ccggcagcaa cgcgtctcca cgacactgtc gcaaaataac   2340
aacagcaact gtaaatcccg tgtcgctat ggcaacccac aaggacgacg aagagcgatt   2400
ttgcctggac cggtgccacc aagtatcatc tgaatggcag agactctctg ttttccgtcc   2460
agcggagtct taatgtttgg gaaacaggga gctggaaaag acaacgtgga ctatagcagc   2520
gttatgctaa ccagtgagga agaaattaaa accaccaacc cagtggccac ggaacagtac   2580
ggcgtggtgg ccgataaccct gcaacagcaa aacgccgctc ctattgtagg ggccgtcaac   2640
agtcaaggag ccttacctgg catggtctgg cagaaccggg acgtgtacct gcagggtcct   2700
atctgggcca agattcctca cacggacgga aactttcatc cctcgccgct gatgggaggc   2760 tttgactga aacacccgcc tcctcagatc ctgattaaga atacacctgt tcccgcggat   2820
cctccaacta ccttcagtca agctaagctg cgtcgttca tcacgcagta cagcaccgga   2880
caggtcagcg tggaaattga atgggagctg cagaaagaaa acagcaaacg ctggaaccca   2940
gagattcaat acacttccaa ctactacaaa tctacaaatg tggacttcgc tgttaacaca   3000
gatggcactt attctgagcc tcgccccatt ggcacccgtt acctcacccg taatctgtaa   3060
ttgctcgtta atcaataaac cggttgattc gtttcagttg aactttggtc tctgcgaagg   3120
gcgaattc                                                            3128

<210> SEQ ID NO 47
<211> LENGTH: 3128
<212> TYPE: DNA
```

<213> ORGANISM: Unknown
<220> FEATURE:
<223> OTHER INFORMATION: AAV serotype, clone 44.5

<400> SEQUENCE: 47

```
gaattcgccc tttctacggc tgcgtcaact ggaccaatga aactttccc ttcaacgatt       60
gcgtcgacaa gatggtgatc tggtgggagg agggcaagat gacggccaag gtcgtggagt      120
ccgccaaggc cattctcggc ggcagcaaag tgcgcgtgga ccaaaagtgc aagtcgtccg      180
cccagatcga ccccaccccc gtgatcgtca cctccaacac caacatgtgc gccgtgattg      240
acgggaacag caccaccttc gagcaccagc agccgttgca ggaccggatg ttcaagtttg      300
aactcacccg ccgtctggag cacgactttg gcaaggtgac aaagcaggaa gtcagagagt      360
tcttccgctg ggcgcaggat cacgtgaccg aggtggcgca cgagttctac gtcagaaagg      420
gtggagccaa caagagaccc gccccgatg acgcggataa agcgagccc aagcgggcct       480
gccctcagt cgcggatcca tcgacgtcag acgcggaagg agctccggtg gactttgccg       540
acaggtacca aaacaaatgt tctcgtcacg cgggcatgct tcagatgctg tttccctgca      600
aaacatgcga gagaatgaat cagaatttca catttgctt cacgcacggg accagagact      660
gttcagaatg tttccccggc gtgtcagaat ctcaaccggt tgtcagaaaa aagacgtatc      720
ggaaactctg tgcgattcat catctgctgg ggcgggcacc cgagattgct tgctcggcct      780
gcgatctggt caacgtggac ctagatgact gtgtttctga gcaataaatg acttaaacca      840
ggtatggctg ccgatggtta tcttccagat tggctcgagg acaacctctc tgagggcatt      900
cgcgagtggt gggacttgaa acctggagcc ccgaaaccca agccaacca gcaaaagcag       960
gacgacggcc ggggtctggt gcttcctggc tacaagtacc tcggaccctt caacggactc     1020
gacaagggg agcccgtcaa cgcggcggac gcagcggccc tcgagcacga caaggcctac     1080
gaccagcagc tcaaagcggg tgacaatccg tacctgcggt ataaccacgc cgacgccgag     1140
tttcaggagc gtctgcaaga agatacgtct tttggggggca acctcgggcg agcagtcttc     1200
caggccaaga agcgggttct cgaacctctc ggtctggttg aggaaggcgc taagacggct     1260
cctggaaaga agagaccggt agagccatca ccccagcgtt ctccagactc ctctacgggc     1320
atcggcaaga aaggccagca gcccgcgaaa aagagactca actttgggca gactggcgac     1380
tcagagtcag tgcccgaccc tcaaccaatc ggagaacccc ccgcaggccc ctctggtctg     1440
ggatctggta caatggctgc aggcggtggc gctccaatgg cagacaataa cgaaggcgcc     1500
gacgagtgg gtagttcctc aggaaattgg cattgcgatt ccacatggct gggcgacaga     1560
gtcatcacca ccagcacccg aacctgggcc ctccccacct acaacaacca cctctacaag     1620
caaatctcca cgggactc gggaggaagc accaacgaca cacctactt cggctacagc       1680
accccctggg ggtattttga ctttaacaga ttccactgcc acttctcacc acgtgactgg     1740
cagcgactca tcaacaacaa ctggggattc cggcccaaga gacccaactt caagctcttc     1800
aacatccagg tcaaggaggt cacgcagaat gaaggcacca gaccatcgc caataacctt     1860
accagcacga ttcaggtctt tacggactcg aataccagc tcccgtacgt cctcggctct     1920
gcgcaccagg gctgcctgcc tccgttcccg cggacgtct tcatgattcc tcagtacggg     1980
tacctgactc tgaacaatgg cagtcaggcc gtgggccgtt cctccttcta ctgcctggag     2040
tactttcctt ctcaaatgct gagaacgggc aacaactttg agttcagcta ccagtttgag     2100
gacgtgcctt tcacagcag ctacgcgcac agccaaagcc tggaccggct gatgaacccc     2160
ctcatcgacc agtacctgta ctacctgtct cggactcagt ccacgggagg taccgcagga     2220
```

```
actcagcagt tgctatttc tcaggccggg cctaataaca tgtcggctca ggccaaaaac    2280
tggctacccg ggccctgcta ccggcagcaa cgcgtctcca cgacactgtc gcaaaataac    2340
aacagcaact ttgcctggac cggtgccacc aagtatcatc tgaatggcag agactctctg    2400
gtaaatcccg tgtcgctat ggcaacccac aaggacgacg aagagcgatt ttttccgtcc    2460
agcggagtct taatgtttgg gaaacaggga gctggaaaag acaacgtgga ctatagcagc    2520
gttatgctaa ccagtgagga agaaattaaa ccaccaacc cagtggccac agaacagtac     2580
ggcgtggtgg ccgataacct gcaacagcaa acgccgctc ctattgtagg ggccgtcaac     2640
agtcaaggag ccttacctgg catggtctgg cagaaccggg acgtgtacct gcagggtcct    2700
atctgggcca agattcctca cacggacgga aactttcatc cctcgccgct gatgggaggc    2760
tttggactga aacacccgcc tcctcagatc ctgattaaga atacacctgt tcccgcggat    2820
cctccaacta ccttcagtca agctaagctg gcgtcgttca tcacgcagta cagcaccgga    2880
caggtcagcg tggaaattga atgggagctg cagaaagaaa acagcaaacg ctggaaccca    2940
gagattcaat acacttccaa ctactacaaa tctacaaatg tggactttgc tgttaacaca    3000
gatggcactt attctgagcc tcgccccatt ggcacccgtt acctcacccg taatctgtaa    3060
ttgcttgtta atcaataaac cggttgattc gtttcagttg aactttggtc tctgcgaagg    3120
gcgaattc                                                             3128

<210> SEQ ID NO 48
<211> LENGTH: 1933
<212> TYPE: DNA
<213> ORGANISM: Unknown
<220> FEATURE:
<223> OTHER INFORMATION: AAV serotype, clone 223.10
<220> FEATURE:
<221> NAME/KEY: misc_feature
<222> LOCATION: (1302)..(1302)
<223> OTHER INFORMATION: can be a, c, g or t

<400> SEQUENCE: 48
caaggcctac gaccagcagc tcaaagcggg tgacaatccg tacctgcggt ataaccacgc     60
cgacgccgag tttcaggagc gtcttcaaga agatacgtct tttgggggca acctcgggcg    120
agcagtcttc caggccaaaa agcgggttct cgaacctctt ggtctggttg agacgccagc    180
taagacggca cctggaaaga gcgaccggt agactcgcca gactccacct cgggcatcgg    240
caagaaaggc cagcagcccg cgaaaaagag actcaacttt gggcagactg gcgactcaga    300
gtcagtcccc gaccctcaac caatcggaga accaccagca ggcccctctg tgtctgggatc    360
tggtacaatg gctgcaggcg gtggcgcacc aatggctgac aataacgagg gcgccgacgg    420
agtgggtaat gcctcaggaa attggcattg cgattccaca tggctgggcg acagagtcat    480
caccaccagc acccgaacct gggccctgcc cacctacaac aaccacctct acaagcaaat    540
ctccagtcag tcagcaggga gcaccaacga taacgtctat ttcggctaca gcacccctg    600
ggggtatttt gacttcaaca gattccattg ccacttctca ccacgtgact ggcagcgact    660
tatcaacaac aactgggat tccggcccaa gaagctcaac ttcaagctct tcaacatcca    720
ggtcaaggag gtcacgacga atgacggtgt cacaaccatc gctaataacc ttaccagcac    780
ggttcaggtc ttttcggact cggaatatca actgccgtac gtcctcggct ccgcgcacca    840
gggctgcctg cctccgttcc cggcagacgt gttcatgatt ccgcagtacg gatacctgac    900
tctgaacaat ggcagccaat cggtaggccg ttcctccttc tactgcctgg agtactttcc    960
```

-continued

```
ttctcagatg ctgagaacgg gcaacaactt cacctttagc tacaccttcg aggacgtgcc      1020
tttccacagc agctacgcgc acagccagag tctggaccgg ctgatgaatc ccctcatcga      1080
ccagtacctg tactacttgg ccagaacaca gagcaacgca ggaggtactg ctggcaatcg      1140
ggaactgcag ttttatcagg gcggacctac caccatggcc gaacaagcaa agaactggct      1200
gcccggacct tgcttccggc aacagagagt atccaagacg ctggatcaaa ataacaacag      1260
caactttgcc tggactggtg ccacaaaata ccatttaaat gnaagaaatt cattggttaa      1320
tcccggtgtc gccatggcaa cccacaagga cgacgaggaa cgcttcttcc cttcgagcgg      1380
agttctaatt tttggcaaaa ctggagcagc taataaaact acattagaaa acgtgctcat      1440
gacaaatgaa gaagaaattc gtcctaccaa cccggtagct accgaggaat acgggattgt      1500
aagcagcaac ttgcaggcgg ctagcaccgc agcccagaca caagttgtta caaccaggg       1560 agccttacct ggcatggtct ggcagaaccg ggacgtgtac ctgcaaggtc ccatttgggc      1620
caagattcct cacacggacg gcaactttca cccgtctcct ctaatgggtg gctttggact      1680
gaaacacccg cctccccaga tcctgatcaa aaacacaccg gtacctgcta atcctccaga      1740
agtgtttact cctgccaagt ttgcttcctt catcacgcag tacagcaccg gcaagtcag       1800 cgttgagatc gagtgggagc tgcagaaaga aacagcaag cgctggaacc cagagattca      1860
gtacacctcc aactttgaca aacagactgg agtggacttt gctgttgaca gccagggtgt      1920
ttactctgag cct                                                         1933
```

<210> SEQ ID NO 49
<211> LENGTH: 1933
<212> TYPE: DNA
<213> ORGANISM: Unknown
<220> FEATURE:
<223> OTHER INFORMATION: AAV serotype, clone 223.2

<400> SEQUENCE: 49

```
caaggcctac gaccagcagc tcaaagcggg tgacaatccg tacctgcggt ataaccacgc        60
cgacgccgag tttcaggagt gtcttcaaga agatacgtct tttgggggca acctcgggcg      120
agcagtcttc caggccaaaa agcgggttct cgaacctctt ggtctggttg agacgccagc      180
taagacggca cctggaaaga agcgaccggt agactcgcca gactccacct cgggcatcgg      240
caagaaaggc cagcagcccg cgaaaaagag actcaacttt gggcagactg gcgactcaga      300
gtcagtcccc gaccctcaac caatcggaga accaccagca ggcccctctg tctctgggatc      360 tggtacaatg gttgcaggcg gtggcgcacc aatggctgac aataacgagg gcgccgacgg      420
agtgggtaat gcctcaggaa attggcattg cgattccaca tggctgggcg acagagtcat      480
caccaccagc cccgaacct gggccctgcc cacctcaac aaccacctct acaagcaaat       540
ctccagtcag tcagcaggga gcaccaacga taacgtctat ttcggctaca gcaccccctg      600
ggggtatttt gacttcaaca gattccattg ccacttctca ccacgtgact ggcagcgact      660
tatcaacaac aactggggat ccggcccaa gaagctcaac ttcaagctct tcaacatcca      720
ggtcaaggag gtcacgacga atgacggtgt cacaaccatc gctaataacc ttaccagcac      780
ggttcaggtc ttttcggact cggaatatca actgccgtac gtcctcggct ccgcgcacca      840
gggctgcctg cctccgttcc cggcagacgt gttcatgatt ccgcagtacg gatacctgac      900
tctgaacaat ggcagccaat cggtaggcc ttcctcctc tactgcctgg agtactttcc      960
ttctcagatg ctgagaacgg gcaacaactt cacctttagc tacaccttcg aggacgtgcc     1020
tttccacagc agctacgcgc acagccagag tctggaccgg ctgatgaatc ccctcatcga     1080
```

```
ccagtacctg tactacttgg ccagaacaca gagcaacgca ggaggtactg ctggcaatcg    1140
ggaactgcag ttttatcagg gcggacctac caccatggcc gaacaagcaa agaactggct    1200
gcccggacct tgcttccggc aacagagagt atccaagacg ctggatcaaa ataacaacag    1260
caactttgcc tggactggtg ccacaaaata ccatttaaat ggaagaaatt cattggttaa    1320
tcccggtgtc gccatggcaa cccacaagga cgacgaggaa cgcttctccc cttcgagcgg    1380
agttctaatt tttggcaaaa ctggagcagc taataaaact acattagaaa acgtgctcat    1440
gacaaatgaa gaagaaattc gtcctaccaa cccggtagct accgaggaat acgggattgt    1500
aagcagcaac ttgcaggcgg ctagcaccgc agcccagaca caagttgtta caaccaggg    1560 agccttacct ggcatggtct ggcagaaccg ggacgtgtac ctgcaaggtc ccatttgggc    1620
caagattcct cacacggacg caactttca cccgtctcct ctaatgggtg ctttggact    1680 gaaacacccg cctccccaga tcctgatcaa aaacacgccg gtacctgcta atcctccaga    1740
agtgtttact cctgccaagt ttgcttcctt catcacgcag tacagcaccg ggcaagtcag    1800
cgttgagatc gagtgggagc tgcagaaaga gaacagcaag cgctggaacc cagagattca    1860 gtacaccctcc aactttgaca aacagactgg agtggactt gctgttgaca gccagggtgt    1920
ttactctgag cct                                                       1933

<210> SEQ ID NO 50
<211> LENGTH: 1933
<212> TYPE: DNA
<213> ORGANISM: Unknown
<220> FEATURE:
<223> OTHER INFORMATION: AAV serotype, clone 223.4

<400> SEQUENCE: 50
caaggcctac gaccagcagc tcaaagcggg tgacaatccg tacctgcggt ataaccacgc      60
cgacgccgag tttcaggagc gtcttcaaga agatacgtct tttggggca acctcgggcg     120 agcagtcttc caggccaaaa agcgggttct cgaacctctt ggtctggttg agacgccagc     180
taagacggca cctggaaaga gcgaccggt agactcgcca gactccacct cgggcatcgg     240
caagaaaggc cagcagcccg cgaaaaagag actcaacttt gggcagactg gcgactcaga     300
gccagtcccc gaccctcaac caatcggaga accaccagca ggcccctctg gtctgggatc     360
tggtacaatg gctgcaggcg gtggcgcacc aatggctgac aataacgagg cgccgacgg     420 agtgggtaat gcctcaggaa attggcattg cgattccaca cggctgggcg acagagtcat     480
caccaccagc acccgaacct gggccctgcc cacctacaac aaccacctct acaagcaaat     540
ctccagtcag tcagcaggga gcaccaacga taacgtctat ttcggctaca gcaccccctg     600
ggggtatttt gacttcaaca gattccattg ccacttctca ccacgtgact ggcagcgact     660
tatcaacaac aactggggat tccggcccaa gaagctcaac ttcaagctct caacatcca     720 ggtcaaggag gtcacgacga tgacggcgt cacaaccatc gctaataacc ttaccagcac     780
ggttcaggtc ttttcggact cggaatatca actgccgtac gtcctcggct ccgcgcacca     840
gggctgcctg cctccgttcc cggcagacgt gttcatgatt ccgcagtacg gatacctgac     900
tctgaacaat ggcagccaat cggtaggccg ttcctccttc tactgcctgg agtactttcc     960
ttctcagatg ctgagaacgg caacaacttt cacctttagc tacaccttcg aggacgtgcc    1020
tttccacagc agctacgcgc acagccagag tctgggccgg ctgatgaatc ccctcatcga    1080
ccagtacctg tactacttgg ccagaacaca gagcaacgca ggaggtactg ctggcaatcg    1140
```

```
ggaactgcag ttttatcagg gcggacctac caccatggcc gaacaagcaa agaactggct    1200
gcccggacct tgcttccggc aacagagagt atccaagacg ctggatcaaa ataacaacag    1260
caactttgcc tggactggtg ccacaaaata ccatttaaat ggaagaaatt cattggttaa    1320
tcccggtgtc gccatggcaa cccacaagga cgacgaggaa cgcttcttcc cttcgagcgg    1380
agttctaatt tttggcaaaa ctggagcagc taataaaact acattagaaa acgtgctcat    1440
gacaaatgaa gaagaaattc gtcctaccaa cccggtagct accgaggaat acggggattgt    1500
aagcagcaac ttgcaggcgg ctagcaccgc agcccagaca caagttgtta caaccaggg    1560
agccttacct ggcatggtct ggcagaaccg ggacgtgtac ctgcaaggtc ccatttgggc    1620
caagattcct cacacggacg gcaactttca cccgtctcct ctaatgggtg gctttggact    1680
gaaacacccg cctccccaga tcctgatcaa aaacacaccg gtacctgcta atcctccaga    1740
agtgtttact cctgccaagt tgcttccctt catcacgcag tacagcaccg ggcaagtcag    1800
cgttgagatc gaatgggagc tgcagaaaga gaacagcaag cgctggaacc cagagattca    1860
gtacacctcc aactttgaca aacagactgg agtggacttt gctgttgaca gccagggtgt    1920
ttactctgag cct                                                        1933

<210> SEQ ID NO 51
<211> LENGTH: 1933
<212> TYPE: DNA
<213> ORGANISM: Unknown
<220> FEATURE:
<223> OTHER INFORMATION: AAV serotype, clone 223.5

<400> SEQUENCE: 51
caaggcctac gaccagcagc tcaaagcggg tgacaatccg tacctgcggt ataaccacgc    60
cgacgccgag tttcaggagc gtcttcaaga agatacgtct tttggggca acctcgggcg    120
agcagtcttc caggccaaaa agcgggttct cgaacctctt ggtctggttg agacgccagc    180
taagacggca cctggaaaga gcgaccggt agactcgcca gactccacct cgggcatcgg    240
caagaaaggc cagcagcccg cgaaaaagag actcaactt gggcagactg gcgactcaga    300
gccagtcccc gaccctcaac caatcggaga ccaccagca ggcccctctg tctgggatc    360
tggtacaatg gctgcaggcg gtggcgcacc aatggctgac aataacgagg gcgccgacgg    420
agtgggtaat gcctcaggaa attggcattg cgattccaca cggctgggcg acagagtcat    480
caccaccagc acccgaacct gggccctgcc cacctacaac aaccacctct acaagcaaat    540
ctccagtcag tcagcaggga gcaccaacga taacgtctat ttcggctaca gcaccccctg    600
ggggtatttt gacttcaaca gattccattg ccacttctca ccacgtgact ggcagcgact    660
tatcaacaac aactgggat ccggcccaa gaagctcaac ttcaagctct caacatcca    720
ggtcaaggag gtcacgacga tgacggcgt cacaaccatc gctaataacc ttaccagcac    780
ggttcaggtc ttttcggact cggaatatca actgccgtac gtcctcggct ccgcgcacca    840
gggctgcctg cctccgttcc cggcagacgt gttcatgatt ccgcagtacg gatacctgac    900
tctgaacaat ggcagccaat cggtaggccg ttcctccttc tactgcctgg agtactttcc    960
ttctcagatg ctgagaacgg gcaacaactt cacctttagc tacaccttcg aggacgtgcc    1020
tttccacagc agctacgcgc acagccagag tctgggccgg ctgatgaatc ccctcatcga    1080
ccagtacctg tactacttgg ccagaacaca gagcaacgca ggaggtactg ctggcaatcg    1140
ggaactgcag ttttatcagg gcggacctac caccatggcc gaacaagcaa agaactggct    1200
gcccggacct tgcttccggc aacagagagt atccaagacg ctggatcaaa ataacaacag    1260
```

-continued

```
caactttgcc tggactggtg ccacaaaata ccatttaaat ggaagaaatt cattggttaa    1320
tcccggtgtc gccatggcaa cccacaagga cgacgaggaa cgcttcttcc cttcgagcgg    1380
agttctaatt tttggcaaaa ctggagcagc taataaaact acattagaaa acgtgctcat    1440
gacaaatgaa gaagaaattc gtcctaccaa cccggtagct accgaggaat acgggattgt    1500
aagcagcaac ttgcaggcgg ctagcaccgc agcccagaca caagttgtta caaccaggg     1560 agccttacct ggcatggtct ggcagaaccg ggacgtgtac ctgcaaggtc ccatttgggc    1620
caagattcct cacacggacg gcaactttca cccgtctcct ctaatgggtg ctttggact     1680 gaaacacccg cctccccaga tcctgatcaa aaacacaccg gtacctgcta atcctccaga    1740
agtgtttact cctgccaagt ttgcttcctt catcacgcag tacagcaccg ggcaagtcag    1800
cgttgagatc gaatgggagc tgcagaaaga gaacagcaag cgctggaacc cagagattca    1860
gtacacctcc aactttgaca aacagactgg agtggacttt gctgttgaca gccagggtgt    1920
ttactctgag cct                                                       1933
```

<210> SEQ ID NO 52
<211> LENGTH: 1933
<212> TYPE: DNA
<213> ORGANISM: Unknown
<220> FEATURE:
<223> OTHER INFORMATION: AAV serotype, clone 223.6

<400> SEQUENCE: 52

```
caaggcctac gaccagcagc tcaaagcggg tgacaatccg tacctgcggt ataaccacgc      60
cgacgccgag tttcaggagc gtcttcaaga agatacgtct tttgggggca acctcgggcg     120
agcagtcttc caggccaaaa agcgggttct cgaacctctt ggtctggttg agacgccagc     180
taagacggca cctggaaaga agcgaccggt agactcgcca gactccacct cgggcatcgg     240
caagaaaggc cagcagcccg cgaaaaagag actcaacttt gggcagactg gcgactcaga     300
gtcagtcccc gaccctcaac caatcggaga accaccagca ggcccctctg gtctgggatc     360
tggtacaatg gctgcaggcg gtggcgcacc aatggctgac aatagcgagg cgccgacgg      420 agtgggtaat gcctcaggaa attggcattg cgattccaca tggctgggcg acagagtcat     480
caccaccagc acccgaacct gggccctgcc cacctacaac aaccacctct acaagcaaat     540
ctccagtcag tcagcaggga gcaccaacga taacgtctat ttcggctaca gcaccccctg     600
ggggtatttt gacttcaaca gattccattg ccacttctca ccacgtgact ggcagcgact     660
tatcaacaac aactggggat ccggcccaa gaagctcaac ttcaagctct caacatcca      720 ggtcaaggag gtcacgacga atgacggtgt cacaaccatc gctaataacc ttaccagcac     780
ggttcaggtc ttttcggact cggaatatca actgccgtac gtcctcggct ccgcgcacca    840
gggctgcctg cctccgttcc cggcagacgt gttcatgatt ccgcagtacg gataccctgac   900 tctgaacaat ggcagccaat cggtaggcgg ttcctccttc tactgcctgg agtactttcc    960
ttctcagatg ctgagaacgg gcaacaactt caccttttagc tacaccttcg aggacgtgcc   1020
tttccacagc agctacgcgc acagccagag tctggaccgg ctgatgaatc ccctcatcga   1080
ccagtacctg tactacttgg ccagaacaca gagcaacgca ggaggtactg ctggcaatcg   1140
ggaactgcag ttttatcagg gcggacctac caccatggcc gaacaagcaa agaactggct    1200
gcccggacct tgcttccggc aacagagagt atccaagacg ctggatcaaa ataacaacag    1260
caactttgcc tggactggtg ccacaaaata ccatttaaat ggaagaaatt cattggttaa    1320
```

| | |
|---|---|
| tcccggtgtc gccatggcaa cccacaagga cgacgaggaa cgcttcttcc cttcgagcgg | 1380 |
| agttctaatt tttggcaaaa ctggagcagc taataaaact acattagaaa acgtgctcat | 1440 |
| gacaaatgaa gaagaaattc gtcctaccaa cccggtagct accgaggaat acgggattgt | 1500 |
| aagcagcaac ttgcaggcgg ctagcaccgc agcccagaca caagttgtta caaccaggg | 1560 |
| agccttacct ggcatggtct ggcagaaccg ggacgtgtac ctgcaaggtc ccatttgggc | 1620 |
| caagattcct cacacggacg gcaactttca cccgtctcct ctaatgggtg ctttggact | 1680 |
| gaaacacccg cctccccaga tcctgatcaa aaacacaccg gtacctgcta atcctccaga | 1740 |
| agtgttact cctgccaagc ttgcttcctt catcacgcag tacagcaccg ggcaagtcag | 1800 |
| cgttgagatc gagtgggagc tgcagaaaga gaacagcaag cgctggaacc cagagattca | 1860 |
| gtacacctcc aactttgaca aacagactgg agtggacttt gctgttgaca gccagggtgt | 1920 |
| ttactctgag cct | 1933 |

<210> SEQ ID NO 53
<211> LENGTH: 1933
<212> TYPE: DNA
<213> ORGANISM: Unknown
<220> FEATURE:
<223> OTHER INFORMATION: AAV serotype, clone 223.7

<400> SEQUENCE: 53

| | |
|---|---|
| caaggcctac gaccagcagc tcaaagcggg tgacaatccg tacctgcggt ataaccacgc | 60 |
| cgacgccgag tttcaggagc gtcttcaaga agatacgtct tttgggggca acctcgggcg | 120 |
| agcagtcttc caggccaaaa agcgggttct cgaacctctt ggtctggttg agacgccagc | 180 |
| taagacggca cctggaaaga agcgaccggt agactcgcca gactccacct cgggcatcgg | 240 |
| caagaaaggc cagcagcccg cgaaaaagag actcaacttt gggcagactg gcgactcaga | 300 |
| gtcagtcccc gaccctcaac caatcggaga accaccagca ggcccctctg tctgggatc | 360 |
| tggtacaatg gctgcaggcg gtggcgcacc aatggctgac aataacgagg gcgccgacgg | 420 |
| agtgggtaat gcctcaggaa attggcattg cgattccaca tggctgggcg acagagtcat | 480 |
| caccaccagc acccgaacct gggccctgcc cacctacaac aaccacctct acaagcaaat | 540 |
| ctccagtcag tcagcaggga gcaccaacga taacgtctat ttcggctaca gcacccctg | 600 |
| ggggtatttt gacttcaaca gattccattg ccacttctca ccacgtgact ggcagcgact | 660 |
| tatcaacaac aactgggga tccggcccaa gaagctcaac ttcaagctct tcaacatcca | 720 |
| ggtcaaggag gtcacgacga tgacggcgt cacaaccatc gctaataacc ttaccagcac | 780 |
| ggttcaggtc ttttcggacc cggaatatca actgccgtac gtcctcggct ccgcgcacca | 840 |
| gggctgcctg cctccgttcc cggcagacgt gttcatgatt ccgcagtacg gatacctgac | 900 |
| tctgaacaat ggcagccaat cggtaggccg ttcctccttc tactgcctgg agtactttcc | 960 |
| ttctcagatg ctgagaacgg gcaacaactt caccttagc tacaccttcg aggacgtgcc | 1020 |
| tttccacagc agctacgcgc acagccagag tctggaccgg ctgatgaatc ccctcatcga | 1080 |
| ccagtacctg tactacttgg ccagaacaca gagcaacgca ggaggtactg ctggcaatcg | 1140 |
| ggaactgcag ttttatcagg gcggacctac caccatggcc gaacaagcaa gaactggct | 1200 |
| gcccggacct tgcttccggc aacagagagt atccaagacg ctggatcaaa ataacaacag | 1260 |
| caactttgcc tggactggtg ccacaaaata ccatttaaat ggaagaaatt cattggttaa | 1320 |
| tcccggtgtc gccatggcaa cccacaagga cgacgaggaa cgcttcttcc cttcgagcgg | 1380 |
| agttctaatt tttggcaaaa ctggagcagc taataaaact acattagaaa acgtgctcat | 1440 |

```
gacaaatgaa gaagaaattc gtcctaccaa cccggtagct accgaggaat acgggattgt    1500
aagcagcaac ttgcaggcgg ctagcaccgc agcccagaca caagttgtta acaaccaggg    1560
agccttacct ggcatggtct ggcagaaccg ggacgtgtac ctgcaaggtc ccatttgggc    1620
caagattcct cacacggacg gcaactttca cccgtctcct ctaatgggtg ctttggact     1680 gaaacacccg cctccccaga tcctgatcaa aaacacaccg gtacctgcta atcctccaga    1740
agtgtttact cctgccaaga ttgcttcctt catcacgcag tacagcaccg ggcaagtcag    1800
cgttgagatc gagtgggagc tgcagaaaga aacagcaag cgctggaacc cagagattca    1860 gtacaccctcc aactttgaca aacagactgg agtggacttt gctgttgaca gccagggtgt   1920
ttactctgag cct                                                        1933
```

```
<210> SEQ ID NO 54
<211> LENGTH: 3123
<212> TYPE: DNA
<213> ORGANISM: Unknown
<220> FEATURE:
<223> OTHER INFORMATION: AAV serotype, clone A3.4

<400> SEQUENCE: 54
```

```
gaattcgccc tttctacggc tgcgtcaact ggaccaatga aaactttccc ttcaacgatt     60
gcgtcgacaa gatggtgatc tggtgggagg agggaaagat gaccgccaag gtcgtggaat    120
ctgccaaagc cattctgggt ggaagcaagg ttcgtgtgga ccagaaatgc aagtcttcgg    180
cccagatcga cccgactccg gtgattgtca cctctaacac caacatgtgc gccgtgattg    240
acggaaactc gaccaccttc gagcaccagc agccgttgca agaccggatg ttcaaatttg    300
aacttacccg ccgtttggat catgactttg ggaaggtcac caagcaggaa gtcaaagact    360 tttttccggtg ggctcaagat cacgtgactg aggtggagca tgagttctac gtcaaaaagg    420
gtggagccaa gaaaaggccc gcccccgatg atgtatatat aaatgagccc aagcgggcgc    480
gcgagtcagt tgcgcagcca tcgacgtcag acgcggaagc ttcgataaac tacgcgggca    540
ggtaccaaaa caaatgttct cgtcacgtgg gcatgaatct gatgctgttt ccctgtcgac    600
aatgcgaaag aatgaatcag aattcaaata tctgcttcac acacgggcaa aaagactgtt    660
tggaatgctt tccccgtgtca gaatctcaac ccgttttcgt cgtcagaaaa acgtatcaga    720
aactttgtta cattcatcat atcatgggaa aagaaccaga cgcctgcact gcctgcgacc    780
tggtaaatgt ggacttggat gactgtattt ctgagcaata atgacttaa atcaggtatg    840 gctgctgacg gttatcttcc agattggctc gaggacactc tctctgaagg aatcagacag    900
tggtggaagc tcaaacctgg cccaccaccg ccgaaaccta accaacaaca ccgggacgac    960 agtagggtc ttgtgcttcc tgggtacaag taccctcggac ccttcaacgg actcgacaaa    1020
ggagagccgg tcaacgaggc agacgccgcg gccctcgagc acgacaaagc ctacgaccac    1080
cagctcaagc aaggggacaa cccgtacctc aaatacaacc acgcggacgc tgaatttcag    1140
gagcgtcttc aagaagatac gtctttcggg ggcaacctcg ggcgagcagt cttccaggcc    1200
aaaaagaggg tactcgagcc tcttggtctg gttgaggaag ctgttaagac ggctcctgga    1260
aaaaagagac ctatagagca gtcctctgca gaaccggact cttcctcggg catcggcgaa    1320
tcaggccagc agcccgctaa gaaaagactc aattttggtc agactggcga cacagagtca    1380
gtcccagacc ctcaaccaat cggagaaccc cccgcagccc cctctggtgt gggatctaat    1440
acaatggctt caggcggtgg ggcaccaatg gcagacgata cgaaggcgc cgacggagtg    1500
```

| | |
|---|---:|
| ggtaattcct cgggaaattg gcattgcgat tccacatgga tgggcgacag agttatcacc | 1560 |
| accagcacaa gaacctgggc cctccccacc tacaataatc acctctacaa gcaaatctcc | 1620 |
| agcgaatcgg gagccaccaa cgacaaccac tacttcggct acagcacccc ctgggggtat | 1680 |
| tttgactta acagattcca ctgtcacttc tcaccacgtg actggcagcg actcatcaac | 1740 |
| aacaactggg gatttagacc caagaaactc aatttcaagc tcttcaacat ccaagtcaag | 1800 |
| gaggtcacgc agaatgatgg aaccacgacc atcgccaata accttaccag cacggtgcag | 1860 |
| gtcttcacag actctgagta ccagctgccc tacgtcctcg gttcggctca ccagggctgc | 1920 |
| cttccgccgt tcccagcaga cgtcttcatg attcctcagt acggctactt gactctgaac | 1980 |
| aatggcagcc aagcggtagg acgttcttca ttctactgtc tagagtattt tccctctcag | 2040 |
| atgctgagga cggaaacaa cttcaccttc agctacactt ttgaagacgt gccttttccac | 2100 |
| agcagctacg cgcacagcca gagtctggat cggctgatga atcctctcat tgaccagtac | 2160 |
| ctgtattacc tgagcaaaac tcagggtaca agtggaacaa cgcagcaatc gagactgcag | 2220 |
| ttcagccaag ctgggcctag ctccatggct cagcaggcca aaaactggct accgggaccc | 2280 |
| agctaccgac agcagcgaat gtctaagacg ctaatgaca caacaacag tgaatttgct | 2340 |
| tggactgcag ccaccaaata ttacctgaat ggaagaaatt ctctggtcaa tcccgggccc | 2400 |
| ccaatggcca gtcacaagga cgatgaggaa aagtatttcc ccatgcacgg aaatctcatc | 2460 |
| tttgaaaac aaggcacagg aactaccaat gtggacattg aatcagtgct tattacagac | 2520 |
| gaagaagaaa tcagaacaac taatcctgtg gctacagaac aatacggaca ggttgccacc | 2580 |
| aaccatcaga gtcaggacac cacagcttcc tatggaagtg tggacagcca gggaatctta | 2640 |
| cctggaatgg tgtggcagga ccgcgatgtc tatcttcaag gtcccatttg gccaaaaact | 2700 |
| cctcacacgg acgacactt tcatccttct ccgctcatgg gaggctttgg actgaaacac | 2760 |
| cctcctcccc agatcctgat caaaaacaca cctgtgccag cgaatcccgc gaccactttc | 2820 |
| actcctggaa gttttgcttc gttcattacc cagtattcca ccggacaggt cagcgtggaa | 2880 |
| atagagtggg agctgcagaa agaaaacagc aaacgctgga acccagaaat tcagtacacc | 2940 |
| tccaactaca acaagtcggt gaatgtggag tttaccgtgg acgcaaacgg tgtttattct | 3000 |
| gaaccccgcc ctattggcac tcgttacctt acccggaact tgtaatttcc tgttaatgaa | 3060 |
| taaaccgatt tatgcgtttc agttgaactt tggtctctgc gaagggcgaa ttcgcggccg | 3120 |
| cta | 3123 |

```
<210> SEQ ID NO 55
<211> LENGTH: 3113
<212> TYPE: DNA
<213> ORGANISM: Unknown
<220> FEATURE:
<223> OTHER INFORMATION: AAV serotype, clone A3.5

<400> SEQUENCE: 55
```

| | |
|---|---:|
| gaattcgccc tttctacggc tgcgtcaact ggaccaatga aaactttccc ttcaacgatt | 60 |
| gcgtcgacaa gatggtgatc tggtgggagg agggaaagat gaccgccaag gtcgtggaat | 120 |
| ctgccaaagc cattctgggt ggaagcaagg ttcgtgtgga ccagaaatgc aagtcttcgg | 180 |
| cccagatcga cccgactccg gtgattgtca cctctaacac caacatgtgc gccgtgattg | 240 |
| acggaaactc gaccaccttc gagcaccagc agccgttgca agaccggatg ttcaaatttg | 300 |
| aacttacccg ccgtttggat catgactttg gaaggtcac caagcaggaa gtcaaagact | 360 |
| tttccggtg ggctcaagat cacgtgactg aggtggagca tgagttctac gtcaaaaagg | 420 |

```
gtggagccaa gaaaaggccc gcccccgatg atgtatatat aaatgagccc aagcgggcgc    480
gcgagtcagt tgcgcagcca tcgacgtcag acgcggaagc ttcgataaac tacgcggaca    540
ggtaccaaaa caaatgttct cgtcacgtgg gcatgaatct gatgctgttt ccctgtcgac    600
aatgcgaaag aatgaatcag aattcaaata tctgcttcac acacgggcaa aaagactgtt    660
tggaatgctt tcccgtgtca gaatctcaac ccgttcctgt cgtcagaaaa acgtatcaga    720
aactttgtta cattcatcat atcatgggaa aagtaccaga cgcctgcact gcctgcgacc    780
tggtaaatgt ggacttggat gactgtattt ctgagcaata aatgacttaa atcaggtatg    840
gctgctgacg gttatcttcc agattggctc gaggacactc tctctgaagg aatcagacag    900
tggtggaagc tcaaacctgg cccaccaccg ccgaaaccta accaacaaca ccgggacgac    960
agtaggggtc ttgtgcttcc tgggtacaag tacctcggac ccttcaacgg actcgacaaa   1020
ggagagccgg tcaacgaggc agacgccgcg gccctcgagc acgacaaagc ctacgaccac   1080
cagctcaagc aaggggacaa cccgtacctc aaatacaacc acgcggacgc tgaatttcag   1140
gagcgtcttc aagaagatac gtctttcggg ggcaacctcg ggcgagcagt cttccaggcc   1200
aaaaagaggg tactcgagcc tcttggtctg gttgaggaag ctgttaagac ggctcctgga   1260
aaaaagagac ctatagagca gtcctcctgca gaaccggact cttcctcggg catcggcaaa   1320
tcaggccagc agcccgctaa gaaaagactc aatttggtc agactggcga cacagagtca    1380
gtcccagacc ctcaaccaat cggagaaccc cccgcagccc cctctggtgt gggatctaat   1440
acaatggctt caggcggtgg ggcaccaatg gcagacaata acgaaggcgc cgacggagtg   1500
ggtaattcct cgggaaattg gcattgcgat tccacatgga tgggcgacag agttatcacc   1560
accagcacaa gaacctgggc cctccccacc tacaataatc acctctacaa gcaaatctcc   1620
agcgaatcgg gagccaccaa cgacaaccac tacttcggct acagcacccc ctgggggtat   1680 tttgactttta acagattcca ctgtcacttc tcaccgcgtg actggcagcg actcatcaat   1740
aacaactggg gatttagacc caagaaactc aatttcaagc tcttcaacat ccaagtcaag   1800
gaggtcacgc agaatgatgg aaccacgacc atcgccaata accttaccag cacggtgcag   1860
gtcttcacag actctgagta ccagctgccc tacgtcctcg gttcggctca ccagggctgc   1920
cttccgccgt tcccagcaga cgtcttcatg attcctcagt acggctactt gactctgaac   1980 aatgcagcc aagcggtagg acgttcttca ttctactgtc tagagtattt tccctctcag   2040
atgctgagga cgggaaacaa cttcaccttc agctacactt ttgaagacgt gcctttccac   2100
agcagctacg cgcacagcca gagtctggat cggctgatga atcctctcat tgaccagtac   2160
ctgtattacc tgagcaaaac tcagggtaca agtggaacaa cgcagcaatc gagactgcag   2220
ttcaaccaag ctgggcctag ctccatggct cagcaggcca aaaactggct accgggaccc   2280
agctaccgac agcagcgaat gtctaagacg gctaatgaca acaacaacag tgaatttgct   2340
tggactgcag ccaccaaata ttaccccgaat ggaagaaatt ctctggtcaa tcccgggccc   2400
ccaatggcca gtcacaagga cgatgaggaa aagtatttcc ccatgcacgg aaatctcatc   2460
tttggaaaac aaggcacagg aactaccaat gtggacattg aatcagtgct tattacagac   2520
gaagaagaaa tcagaacgac taatcctgtg gctacagaac aatacggaca ggttgccacc   2580
aaccgtcaga gtcagaacac cacagcttcc tatggaagtg tggacagcca gggaatctta   2640
cctggaatgg tgtggcagga ccgcgatgtc tatcttcaag gtcccatttg gccaaaaact   2700
cctcacacgg acggacactt tcatccttct ccgctcatgg gaggctttgg actgaaacac   2760
```

```
cctcctcccc agatcctgat caaaaacaca cctgtgccag cgaatcccgc gaccactttc    2820
actcctggaa gtttgcttc gttcattacc cagtattcca ccggacaggt cagcgtggaa     2880
atagagtggg agctgcagaa agaaaacagc aaacgctgga acccggaaat tcagtacacc    2940
tccaactaca acaagtcggt gaatgtggag tttaccgtgg acgcaaacgg tgtttattct    3000
gaaccccgcc ctattggcac tcgttacctt acccggaact tgtaatttcc tgttaatgaa    3060
taaaccgatt tatgcgtttc agttgaactt tggtctctgc gaagggcgaa ttc           3113
```

<210> SEQ ID NO 56
<211> LENGTH: 3122
<212> TYPE: DNA
<213> ORGANISM: Unknown
<220> FEATURE:
<223> OTHER INFORMATION: AAV serotype, clone A3.7

<400> SEQUENCE: 56

```
agcggccgcg aattcgccct ttctacggct gcgtcaactg gaccaatgaa aactttccct     60
tcaacgattg cgtcgacaag atggtgatct ggtgggagga gggaaagatg accgccaagg    120
tcgtggaatc tgccaaagcc attctgggtg gaagcaaggt tcgtgtggac cagaaatgca    180
ggtcttcggc ccagatcgac ccgactccgg tgattgtcac ctctaacacc aacatgtgcg    240
ccgtgattga cggaaaactcg accaccttcg agcaccagca gccgttgcaa gaccggatgt    300
tcaaatttga acttacccgc cgtttggatc atgactttgg gaaggtcacc aagcaggaag    360
tcaaagactt tttccggtgg gctcaagatc acgtgactga ggtggagcat gagttctacg    420
tcaaaaaggg tggagccaag aaaaggcccg cccccgatga tgtatatata aatgagccca    480
agcgggcgcg cgagtcagtt gcgcagccat cgacgtcaga gcggaagct tcgataaact     540 acgcggacag gtaccaaaac aaatgttctc gtcacgtggg catgaatctg atgctgtttc    600
cctgtcgaca atgcgaaaga atgaatcaga attcaaatat ctgcttcaca cacgggcaaa    660
aagactgttt ggaatgcttt cccgtgtcag aatctcaacc cgtttctgtc gtcagaaaaa    720
cgtatcagaa actttgttac attcatcata tcatgggaaa agtaccagac gcctgcactg    780
cctgcgacct ggtaaatgtg gacttggatg actgtatttc tgagcaataa atgacttaaa    840
tcaggtatgg ctgctgacgg ttatcttcca gattggctcg aggacactct ctctgaagga    900
atcagacagt ggtggaagct caaacctggc ccaccaccgc cgaaacctaa ccaacaacac    960
cgggacgaca gtagggggtct tgtgcttcct gggtacaagt acctcggacc cttcaacgga    1020
ctcgacaaag gagagccggt caacgaggca gacgccgcgg ccctcgagca cgacaaagcc    1080
tacgaccacc agctcaagca aggggacaac ccgtacctca aatacaacca cgcggacgct    1140
gaatttcagg agcgtcttca agaagatacg tcttttcgggg gcaacctcgg gcgagcagtc    1200
ttccaggcca aaaagagggt actcgagcct cttggtctgg ttgaggaagc tgttaagacg    1260
gctcctggaa aaaagagacc tatagagcag tctcctgcag aaccggactc ttcctcgggc    1320
atcggcaaat caggccagca gcccgctaag aaaagactca attttggtca gactggcgac    1380
acagagtcag tcccagaccc tcaaccaatc ggagaacccc ccgcagcccc tctggtgtg    1440 ggatctaata caatggcttc aggcggtggg gcaccaatgg cagacaataa cgaaggcgcc    1500
gacggagtgg gtaattcctc gggaaattgg cattgcgatt ccacatggat gggcgacaga    1560
gttatcacca ccagcacaag aacctgggcc ctccccacct acaataatcg cctctacaag    1620
caaatctcca gcgaatcggg agccaccaac gacaaccact acttcggcta cagcaccccc    1680
tgggggtatt ttgactttaa cagattccac tgtcacttct caccacgtga ctggcagcga    1740
```

```
ctcatcaaca acaactgggg atttagaccc aagaaactca atttcaagct cttcaacatc    1800
caagtcaagg aggtcacgca gaatgatgga accacgacca tcgccaataa ccttaccagc    1860
acggtgcagg tcttcacaga ctctgagtac cagctgcect acgtcctcgg ttcggctcac    1920
cagggctgcc ttccgccgtt cccagcagac gtcttcatga ttcctcagta cggctacttg    1980
actctgaaca atggcagcca agcggtagga cgttcttcat tctactgtct agagtatttt    2040
ccctctcaga tgctgaggac gggaaacaac ttcaccttca gctacacttt tgaagacgtg    2100
cctttccaca gcagctacgc gcacagccag agtctggatc ggctgatgaa tcctctcatt    2160
gaccagtacc tgtattacct gagcaaaact cagggtacaa gtggaacaac gcagcaatcg    2220
agactgcagt tcagccaagc tgggcctagc tccatggctc agcaggccaa aaactggcta    2280
ccgggaccca gctaccgaca gcagcgaatg tctaagacgg ctaatgacaa caacaacagt    2340
gaatttgctt ggactgcagc caccaaatat acctgaatg gaagaaattc tctggtcaat    2400
cccgggcccc caatgccag tcacaaggac gatgaggaaa agtatttccc catgcacgga    2460
aatctcatct ttggaaaaca aggcacagga actaccaatg tggacattga atcagtgctt    2520
attacagacg aagaagaaat cagaacaact aatcctgtgg ctacagaaca atacggacag    2580
gttgccacca accatcagag tcagaacacc acagcttcct atggaagtgt ggacagccag    2640
ggaatcttac ctggaatggt gtggcaggac cgcgatgtct atcttcaagg tcccatttgg    2700
gccaaaactc ctcacacgga cggacacttt catccttctc cgctcatggg aggctttgga    2760
ctgaaacacc ctcctcccca gatcctgatc aaaaacacac ctgtgccagc gaatcccgcg    2820
accactttca ctcctggaaa gtttgcttcg ttcattaccc agtattccac cggacaggtc    2880
agcgtggaaa tagagtggga gctgcagaaa gaaaacagca aacgctggaa cccagaaatt    2940
cagtacacct ccaactacaa caagtcggtg aatgtggagt ttaccgtgga cgcaaacggt    3000
gtttattctg aaccccgccc tattggcact cgttacctta cccggaactt gtaatttcct    3060
gttaatgaat aaaccgattt atgcgtttca gttgaacttt ggtctctgcg aagggcgaat    3120
tc                                                                  3122
```

<210> SEQ ID NO 57
<211> LENGTH: 3123
<212> TYPE: DNA
<213> ORGANISM: Unknown
<220> FEATURE:
<223> OTHER INFORMATION: AAV serotype, clone A3.3

<400> SEQUENCE: 57

```
gaattcgccc tttctacggc tgcgtcaact ggaccaatga aaactttccc ttcaacgatt     60
gcgtcgacaa gatggtgatc tggtgggagg agggaaagat gaccgccaag gtcgtggaat    120
ctgccaaagc cattctgggt ggaggcaagg ttcgtgtgga ccagaaatgc aagtcttcgg    180
cccagatcga cccgactccg gtgattgtca cctctaacac caacatgtgc gccgtgattg    240
acggaaactc gaccaccttc gagcaccagc agccgttgca agaccggatg ttcaaatttg    300
aacttacccg ccgtttggat catgactttg gaaggtcac caagcaggaa gtcaaagact    360
ttttccggtg ggctcaagat cacgtgactg aggtggagca tgagttctac gtcaaaaagg    420
gtggagccaa gaaaaggccc gcccccgatg atgtatatat aaatgagccc aagcgggcgc    480
gcgagtcagt tgcgcagcca tcgacgtcag acgcggaagc ttcgataaac tacgcggaca    540
ggtaccaaaa caaatgttct cgtcacgtgg gcatgaatct gatgctgttt ccctgtcgac    600
```

```
aatgcgaaag aatgaatcag aattcaaata tctgcttcac acacgggcaa aaagactgtt    660
tggaatgctt tcccgtgtca gaatctcaac ccgtttctgt cgtcagaaaa acgtatcaga    720
aactttgtta cattcatcat atcatgggaa aagtaccaga cgcctgcact gcctgcgacc    780
tggtaaatgt ggacttggat gactgtattt ctgagcaata aatgacttaa atcaggtatg    840
gctgctgacg gttatcttcc agattggctc gaggacactc tctctgaagg aatcagacag    900
tggtggaagc tcaaacctgg cccaccaccg ccgaaaccta accaacaaca ccgggacgac    960
agtaggggtc ttgtgcttcc tgggtacaag tacctcggac ccttcaacgg actcgacaaa   1020
ggagagccgg tcaacgaggc agacgccgcg ccccctgagc acgacaaagc ctacgaccac   1080
cagctcaagc aaggggacaa cccgtacctc aaatacaacc acgcggacgc tgaatttcag   1140
gagcgtcttc aagaagatac gtctttcggg ggcaacctcg ggcgagcagt cttccaggcc   1200
aaaaagaggg tactcgagcc tcttggtctg gttgaggaag ctgttaagac ggctcctgga   1260
aaaaagagac ctatagagca gtctcctgca gaaccggact cttcctcggg catcggcaaa   1320
tcaggccagc agcccgctaa gaaaagactc aattttggtc agactggcga cacagagtca   1380
gtcccaggcc ctcaaccaat cggagaaccc cccgcagccc cctctggtgt gggatctaat   1440
acaatggctt caggcggtgg ggcaccaatg gcagacaata cgaaggcgc cgacggagtg   1500 ggtaattcct cgggaaattg gcattgcgat tccacatgga tgggcgacag agttatcacc   1560
accagcacaa gaacctgggc cctccccacc tacaataatc acctctacaa gcaaatctcc   1620
agcgaatcgg gagccaccaa cgacaaccac tacttcggct acagcacccc ctgggggtat   1680
tttgacttta acagattcca ctgtcacttc tcaccacgtg actggcagcg actcatcaac   1740
aacaactggg gatttagacc caagaaactc aatttcaagc tcttcaacat ccaagtcaag   1800
gaggtcacgc agaatgatgg aaccacgacc atcgccaata accttaccag cgcggtgcag   1860
gtcttcacag actctgagta ccagctgccc tacgtcctcg gttcggctca ccagggctgc   1920
cttccgccgt tcccagcaga cgtcttcatg attcctcagt acggctactt gactctgaac   1980
aatggcagcc aagcggtagg acgttcttca ttctactgtc tagagtattt tccctctcag   2040
atgctgagga cgggaaacaa cttcaccttc agctacactt ttgaagacgt gcctttccac   2100
agcagctacg cgcacagcca gagtctggat cggctgatga atcctctcat tgaccagtac   2160
ctgtattacc tgagcaaaac tcagggtaca agtggaacaa cgcagcaatc gagactgcag   2220
ttcagccaag ctgggcctag ctccatggct cagcaggcca aaaactggct accgggaccc   2280
agctaccgac agcagcgaat gtctaagacg gctaatgaca caacaacag tgaatttgct   2340 tggactgcag ccaccaaata ttacctgaat ggaagaaatt ctctggtcaa tcccgggccc   2400
ccagtggcca gtcacaagga cgatgaggaa aagtatttcc ccatgcacgg aaatctcatc   2460
tttggaaaac aaggcacagg aactaccaat gtggacattg aatcagtgct tattacagac   2520
gaagaagaaa tcagaacaac taatcctgtg gctacagaac aatacggaca ggttgccacc   2580
aaccatcaga gtcagaacac cacagcttcc tatgaagtg tggacagcca gggaatctta   2640
cctggaatgg tgtggcagga ccgcgatgtc tatcttcaag gtcccatttg gccaaaaact   2700
cctcacacgg acggacactt tcatccttct ccgctcatgg gaggctttgg actgaaacac   2760
cctcctcccc agatcctgat caaaaacaca cctgtgccag cgaatcccgc gaccactttc   2820
actcctggaa agtttgcttc gttcattacc cagtattcca cctgacaggt cagcgtggaa   2880
atagagtggg agctgcagaa agaaaacagc aaacgctgga acccagaaat tcagtacacc   2940
tccaactaca acaagtcggt gaatgtggag tttaccgtgg acgcaaacgg tgtttattct   3000
```

```
gaaccccgcc ctattggcac tcgttacctt acccggaact tgtaatttcc tgttaatgaa    3060
taagccgatt tatgcgtttc agttgaactt tggtctctgc gaagggcgaa ttcgtttaaa    3120
cct                                                                 3123
```

<210> SEQ ID NO 58
<211> LENGTH: 2969
<212> TYPE: DNA
<213> ORGANISM: Unknown
<220> FEATURE:
<223> OTHER INFORMATION: AAV serotype, clone 42.12

<400> SEQUENCE: 58

```
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgcgtgga ccaaaagtgc aagtcgtccg     180
cccagatcga ccccaccccc gtgatcgtca cctccaacac caacatgtgc gccgtgattg     240
acgggaacag caccaccttc gagcaccagc agccgttaca agaccggatg ttcaaatttg     300
aactcacccg ccgtctggag cacgactttg gcaaggtgac aaagcaggaa gtcaaagagt     360
tcttccgctg ggcgcaggat cacgtgaccg aggtggcgca tgagttctac gtcagaaagg     420
gtggagccaa caagagaccc gcccccgatg acgcggataa aagcgagccc aagcgggcct     480 gccccctcagt cgcggatcca tcgacgtcag acgcggaagg agctccggtg gactttgccg     540
acaggtacca aaacaaatgt tctcgtcacg cgggcatgct tcagatgctg tttccctgca     600
agacatgcga gagaatgaat cagaatttca acatttgctt cacgcacggg accagagact     660
gttcagaatg tttccccggc gtgtcagaat ctcaaccggt cgtcagaaag aggacgtatc     720
ggaaactctg tgccattcat catctgctgg ggcgggctcc cgagattgct tgctcggcct     780
gcgatctggt caacgtggac ctggatgact gtgtttctga gcaataaatg acttaaacca     840
ggtatggctg ccgatggtta tcttccagat tggctcgagg acaacctctc tgagggcatc     900
cgcgagtggt gggacttgaa acctggagcc ccgaaaccca agccaaccag gcaaaagcag     960
gacgacggcc ggggtctggt gcttcctggc tacaagtacc tcggaccctt caacggactc    1020
gacaagggag agccggtcaa cgaggcagac gccgcggccc tcgagcacga caaggcctac    1080
gacaagcagc tcgagcaggg ggacaacccg tacctcaagt acaaccacgc cgacgccgag    1140
tttcaggagc gtcttcaaga agatacgtct tttgggggca acctcggcg agcagtcttc    1200 caggccaaga gcgggttcct cgaacctctc ggtctggttg aggaaggcgc taagacggct    1260
cctggaaaga gagaccggt agagccatca ccccagcgtt ctccagactc ctctacgggc    1320
atcggcaaga caggccagca gcccgcgaaa aagagactca actttgggca gactggcgac    1380
tcagagtcag tgcccgaccc tcaaccaatc ggagaacccc ccgcaggccc ctctggtctg    1440
ggatctggta caatggctgc aggcggtggc gctccaatgg cagacaataa cgaaggcgcc    1500
gacggagtgg gtagttcctc aggaaattgg cattgcgatt ccacatggct gggcgacaga    1560
gtcatcacca ccagcacccg aacctgggcc ctccccacct acaacaacca cctctacaag    1620
caaatctcca cgggacatc gggaggaagc accaacgaca cacctacctt cggctacagc    1680
accccctggg ggtattttga ctttaacaga ttccactgcc acttctcacc acgtgactgg    1740
cagcgactca tcaacaacaa ctggggattc cggcccaaga gactcaactt caagctcttc    1800
aacatccagg tcaaggaggt cacgcagaat gaaggcacca agaccatcgc caataacctt    1860
```

```
accagcacga ttcaggtctt tacggactcg gaataccagc tcccgtacgt cctcggctct   1920
gcgcaccagg gctgcctgcc tccgttcccg gcggacgtct tcatgattcc tcagtacggg   1980
tacctgactc tgaacaacgg cagtcaggcc gtgggccgtt cctccttcta ctgcctggag   2040
tactttcctt ctcaaatgct gagaacgggc aacaactttg agttcagcta ccagtttgag   2100
gacgtgcctt ttcacagcag ctacgcgcac agccaaagcc tggaccggct gacgaacccc   2160
ctcatcgacc agtacctgta ctacctggcc cggacccaga gcactacggg gtccacaagg   2220
gggctgcagt tccatcaggc tgggcccaac accatggccg agcaatcaaa gaactggctg   2280
cccggacccct gttatcggca gcagagactg tcaaaaaaca tagacagcaa caacaacagt   2340
aactttgcct ggaccggggc cactaaatac catctgaatg gtagaaattc attaaccaac   2400
ccgggcgtag ccatggccac caacaaggac gacgaggacc agttcttcc catcaacgga   2460
gtgctggttt ttggcaaaac gggggctgcc aacaagacaa cgctggaaaa cgtgctaatg   2520
accagcgagg aggagatcaa aaccaccaat cccgtggcta cagaagaata cggtgtggtc   2580
tccagcaacc tgcaatcgtc tacggccgga ccccagacac agactgtcaa cagccagggg   2640
gctctgcccg gcatggtctg gcagaaccgg gacgtgtacc tgcagggtcc catctgggcc   2700
aaaattcctc acacggacgg caactttcac ccgtctcccc tgatgggcgg atttggactc   2760
aaacacccgc tcctcaaat tctcatcaag tatacttcca actactacaa atctacaaat   2820
gtggactttg ctgtcaatac tgagggtact tattcagagc tcgccccat ggcacccgt   2880
tacctcaccc gtaacctgta attgcctgtt aatcaataaa ccggttaatt cgtttcagtt   2940
gaactttggt ctctgcgaag ggcgaattc                                     2969
```

<210> SEQ ID NO 59
<211> LENGTH: 3129
<212> TYPE: DNA
<213> ORGANISM: Unknown
<220> FEATURE:
<223> OTHER INFORMATION: AAV serotype, clone 44.2

<400> SEQUENCE: 59

```
gaattcgccc tttctacggc tgcgtcaact ggaccaatga gaactttccc ttcaacgatt     60
gcgtcgacaa gatggtgatc tggtgggagg agggcaagat gacggccaag gtcgtggagt    120
ccgccaaggc cattctcggc ggcagcaaag tgcgcgtgga ccaaaagtgc aagtcgtccg    180
cccagatcga ccccaccccc gtgatcgtca cctccaacac caacatgtgc gccgtgattg    240
acggaacag caccaccttc gagcaccagc agccgttgca ggaccggatg ttcaagtttg    300
aactcacccg ccgtctggag cacgactttg gcaaggtgac aaagcaggaa gtcagagagt    360
tcttccgctg ggcgcaggat cacgtgaccg aggtggcgca cgagttctac gtcagaaagg    420
gtggagccaa caagagaccc gcccccgatg acgcggataa aagcgagccc aagcgggcct    480
gccccctcagt cgcggatcca tcgacgtcag acgcggaagg agctccggtg actttgccg    540
acaggtacca aaacaaatgt tctcgtcacg cgggcatgct tcagatgctg tttccctgca    600
aaacatgcga gagaatgaat cagaatttca catttgcttc cacgcacggg accagagact    660
gttcagaatg tttccccggc gtgtcagaat ctcaaccggt cgtcagaaaa aagacgtatc    720
ggaaactctg tgcgattcat catctgctgg gggcgggcac ccgagattgc ttgctcggcc    780
tgcgatctgg tcaacgtgga cctagatgac tgtgtttctg agcaataaat gacttaaacc    840
aggtatggct gccgatggtt atcttccaga ttggctcgag gacaacctct ctgagggcat    900
tcgcgagtgg tgggacttga aacctggagc cccgaaaccc aaagccaacc agcaaaagca    960
```

```
ggacgacggc cggggtctgg tgcttcctgg ctacaagtac ctcggaccct tcaacggact    1020
cgacaagggg gagcccgtca acgcggcgga cgcagcggcc ctcgagcacg acaaggccta    1080
cgaccagcag ctcaaagcgg gtgacaatcc gtacctgcgg tataaccacg ccgacgccga    1140
gtttcaggag cgtctgcaag aagatacgtc ttttgggggc aacctcgggc gagcagtctt    1200
ccaggccaag aagcgggttc tcgaacctct cggtctggtt gaggaaggcg ctaagacggc    1260
tcctggaaaa aagagaccgg tagagccatc accccagcgt tctccagact cctctacggg    1320
catcggcaag aaaggccagc agcccgcgaa aaagagactc aactttgggc agactggcga    1380
ctcagagtca gtgcccgacc ctcaaccaat cggagaaccc cccgcaggcc cctctggtct    1440
gggatctggt acaatggctg caggcggtgg cgctccaatg gcagacaata cgaaggcgc     1500 cgacggagtg ggtagttcct caggaaattg gcattgcgat tccacatggc tgggcgacag    1560
agtcatcacc accagcaccc gaacctgggc cctccccacc tacaacaacc acctctacaa    1620
gcaaatctcc aacgggactt cgggaggaag caccaacgac aacacctact tcggctacag    1680 cacccctgg gggtattttg actttaacag attccactgc cacttctcac cacgtgactg     1740
gcagcgactc atcaacaaca actgggggatt ccggcccaag agactcaact tcaagctctt    1800
caacatccag gtcaaggagg tcacgcagaa tgaaggcacc aagaccatcg ccaataacct    1860
taccagcacg attcaggtct ttacggactc ggaataccag ctcccgtacg tcctcggctc    1920
tgcgcaccag ggctgcctgc ctccgttccc ggcggacgtc ttcatgattc ctcagtacgg    1980
gtacctgact ctgaacaatg gcagtcaggc cgtgggccgt tcctccttct actgcctgga    2040
gtactttcct tctcaaatgc tgagaacggg caacaacttt gagttcagct accagtttga    2100
ggacgtgcct tttcacagca gctacgcgca cagccaaagc ctggaccggc tgatgaaccc    2160
cctcatcgac cagtacctgt actacctgtc tcggactcag tccacgggag gtaccgcagg    2220
aactcagcag ttgctatttt ctcaggccgg gcctaataac atgtcggctc aggccaaaaa    2280
ctggctaccc gggccctgct accggcagca acgcgtctcc acgacactgt cgcaaaataa    2340
caacagcaac tttgcctgga ccggtgccac caagtatcat ctgaatggca gagactctct    2400
ggtaaatccc ggtgtcgcta tggcaaccca caaggacgac gaagagcgat ttttccgtc     2460 cagcggagtc ttaatgtttg ggaaacaggg agctggaaaa gacaacgtgg actatagcag    2520
cgttatgcta accagtgagg aagaaattaa aaccaccaac ccagtggcca cagaacagta    2580
cggcgtggtg gccgataacc tgcaacagca aaacgccgct cctattgtag ggccgtcaa     2640 cagtcaagga gccttacctg gcatggtctg cagaaccgg gacgtgtacc tgcagggtcc     2700
tatctgggcc aagattcctc acacggacgg aaactttcat ccctcgccgc tgatgggagg    2760
ctttggactg aaacacccgc ctcctcagat cctgattaag aatacacctg ttcccgcgga    2820
tcctccaact accttcagtc aagctaagct ggcgtcgttc atcacgcagt acagcaccgg    2880
acaggtcagc gtgaaattg aatgggagct gcagaaagaa aacagcaaac gctggaaccc     2940
agagattcaa tacacttcca actactacaa atctacaaat gtggactttg ctgttaacac    3000
agatggcact tattctgagc ctcgccccat cggcacccgt tacctcaccc gtaatctgta    3060
attgcttgtt aatcaataaa ccggttgatt cgtttcagtt gaactttggt ctctgcgaag    3120
ggcgaattc                                                             3129
```

<210> SEQ ID NO 60
<211> LENGTH: 733
<212> TYPE: PRT

<213> ORGANISM: Unknown
<220> FEATURE:
<223> OTHER INFORMATION: capsid protein of AAV serotype, clone C1VP1

<400> SEQUENCE: 60

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Leu Glu Ser Pro Gln Glu Pro Asp Ser Ser Gly Ile Gly Lys
145                 150                 155                 160

Lys Gly Lys Gln Pro Ala Lys Lys Arg Leu Asn Phe Glu Glu Asp Thr
                165                 170                 175

Gly Ala Gly Asp Gly Pro Pro Glu Gly Ser Asp Thr Ser Ala Met Ser
            180                 185                 190

Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
    210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                245                 250                 255

Thr Ser Asn Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Leu Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Ser Pro Phe Pro Asn Asp Val Phe Met Val Pro Gln Tyr Gly Tyr
        355                 360                 365

Cys Gly Ile Val Thr Gly Glu Asn Gln Asn Gln Thr Asp Arg Asn Ala
    370                 375                 380

Phe Tyr Cys Leu Glu Tyr Phe Pro Ser Gln Met Leu Arg Thr Gly Asn
```

```
            385                 390                 395                 400
Asn Phe Glu Met Ala Tyr Asn Phe Gly Lys Val Pro Phe His Ser Met
                405                 410                 415

Tyr Ala Tyr Ser Gln Ser Pro Asp Arg Leu Met Asn Pro Leu Leu Asp
                420                 425                 430

Gln Tyr Leu Trp His Leu Gln Ser Thr Thr Ser Gly Glu Thr Leu Asn
                435                 440                 445

Gln Gly Asn Ala Ala Thr Thr Phe Gly Lys Ile Arg Ser Gly Asp Phe
450                 455                 460

Ala Phe Tyr Arg Lys Asn Trp Leu Pro Gly Pro Cys Val Lys Gln Gln
465                 470                 475                 480

Arg Leu Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
                500                 505                 510

Trp Ser Asn Ile Ala Pro Gly Pro Met Ala Thr Ala Gly Pro Ser
                515                 520                 525

Asp Gly Asp Phe Ser Asn Ala Gln Leu Ile Phe Pro Gly Pro Ser Val
530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
                580                 585                 590

Val Thr Ala Met Gly Val Leu Pro Gly Met Val Trp Gln Asn Arg Asp
                595                 600                 605

Ile Tyr Tyr Gln Gly Pro Ile Trp Ala Lys Ile Pro His Ala Asp Gly
                610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
                660                 665                 670

Thr Gly Gln Val Ala Val Gln Ile Glu Trp Glu Ile Glu Lys Glu Arg
                675                 680                 685

Ser Lys Arg Trp Asn Pro Glu Val Gln Phe Thr Ser Asn Tyr Gly Asn
                690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730

<210> SEQ ID NO 61
<211> LENGTH: 733
<212> TYPE: PRT
<213> ORGANISM: Unknown
<220> FEATURE:
<223> OTHER INFORMATION: capsid protein of AAV serotype, clone C2VP1

<400> SEQUENCE: 61

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Leu
```

-continued

```
                20                  25                  30
Lys Ala Asn Gln Gln Lys Gln Asp Asp Gly Arg Gly Leu Val Leu Pro
            35                  40                  45
Gly Tyr Lys Tyr Leu Gly Pro Phe His Gly Leu Asp Lys Gly Glu Pro
     50                  55                  60
Val Asn Ala Ala Asp Ala Ala Leu Glu His Asp Lys Ala Tyr Asp
 65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
    130                 135                 140
Pro Leu Glu Ser Pro Gln Glu Pro Asp Ser Ser Ser Gly Ile Gly Lys
145                 150                 155                 160
Lys Gly Lys Gln Pro Ala Lys Lys Arg Leu Asn Phe Glu Glu Asp Thr
                165                 170                 175
Gly Ala Gly Asp Gly Pro Pro Glu Gly Ser Asp Thr Ser Ala Met Ser
            180                 185                 190
Ser Asp Ile Glu Met Arg Ala Ala Pro Gly Gly Asn Ala Val Asp Ala
        195                 200                 205
Gly Gln Gly Ser Asp Gly Val Gly Asn Ala Ser Gly Asp Trp His Cys
    210                 215                 220
Asp Ser Thr Trp Ser Glu Gly Lys Val Thr Thr Thr Ser Thr Arg Thr
225                 230                 235                 240
Trp Val Leu Pro Thr Tyr Asn Asn His Leu Tyr Leu Arg Leu Gly Thr
                245                 250                 255
Thr Ser Asn Ser Asn Thr Tyr Asn Gly Phe Ser Thr Pro Trp Gly Tyr
            260                 265                 270
Phe Asp Phe Asn Arg Phe His Cys His Phe Ser Pro Arg Asp Trp Gln
        275                 280                 285
Arg Leu Ile Asn Asn Asn Trp Gly Leu Arg Pro Lys Ala Met Arg Val
    290                 295                 300
Lys Ile Phe Asn Ile Gln Val Lys Glu Val Thr Thr Ser Asn Gly Glu
305                 310                 315                 320
Thr Thr Val Ala Asn Asn Leu Thr Ser Thr Val Gln Ile Phe Ala Asp
                325                 330                 335
Ser Ser Tyr Glu Leu Pro Tyr Val Met Asp Ala Gly Gln Glu Gly Ser
            340                 345                 350
Leu Pro Pro Phe Pro Asn Asp Val Phe Met Val Pro Gln Tyr Gly Tyr
        355                 360                 365
Cys Gly Ile Val Thr Gly Glu Asn Gln Asn Gln Thr Asp Arg Asn Ala
    370                 375                 380
Phe Tyr Cys Leu Glu Tyr Phe Pro Ser Gln Met Leu Arg Thr Gly Asn
385                 390                 395                 400
Asn Phe Glu Met Ala Tyr Asn Phe Glu Lys Val Pro Phe His Ser Met
                405                 410                 415
Tyr Ala His Ser Gln Ser Leu Asp Arg Leu Met Asn Pro Leu Leu Asp
            420                 425                 430
Gln Tyr Leu Trp His Leu Gln Ser Thr Thr Ser Gly Glu Thr Leu Asn
        435                 440                 445
```

```
Gln Gly Asn Ala Ala Thr Thr Phe Gly Lys Ile Arg Ser Gly Asp Phe
    450                 455                 460
Ala Phe Tyr Arg Lys Asn Trp Leu Pro Gly Pro Cys Val Lys Gln Gln
465                 470                 475                 480
Arg Phe Ser Lys Thr Ala Ser Gln Asn Tyr Lys Ile Pro Ala Ser Gly
                485                 490                 495
Gly Asn Ala Leu Leu Lys Tyr Asp Thr His Tyr Thr Leu Asn Asn Arg
            500                 505                 510
Trp Ser Asn Ile Ala Pro Gly Pro Pro Met Ala Thr Ala Gly Pro Ser
        515                 520                 525
Asp Gly Asp Phe Ser Asn Ala Gln Leu Ile Phe Pro Gly Pro Ser Val
    530                 535                 540
Thr Gly Asn Thr Thr Thr Ser Ala Asn Asn Leu Leu Phe Thr Ser Glu
545                 550                 555                 560
Gly Glu Ile Ala Ala Thr Asn Pro Arg Asp Thr Asp Met Phe Gly Gln
                565                 570                 575
Ile Ala Asp Asn Asn Gln Asn Ala Thr Thr Ala Pro Ile Thr Gly Asn
            580                 585                 590
Val Thr Ala Met Gly Val Leu Pro Gly Met Val Trp Gln Asn Arg Asp
        595                 600                 605
Ile Tyr Tyr Gln Gly Pro Ile Trp Ala Lys Ile Pro His Ala Asp Gly
    610                 615                 620
His Phe His Pro Ser Pro Leu Ile Gly Gly Phe Gly Leu Lys His Pro
625                 630                 635                 640
Pro Pro Gln Ile Phe Ile Lys Asn Thr Pro Val Pro Ala Asn Pro Ala
                645                 650                 655
Thr Thr Phe Thr Ala Ala Arg Val Asp Ser Phe Ile Thr Gln Tyr Ser
            660                 665                 670
Thr Gly Gln Val Ala Val Gln Ile Glu Trp Glu Ile Glu Lys Glu Arg
        675                 680                 685
Ser Lys Arg Arg Asn Pro Glu Val Gln Phe Thr Ser Asn Tyr Gly Asn
    690                 695                 700
Gln Ser Ser Met Leu Trp Ala Pro Asp Thr Thr Gly Lys Tyr Thr Glu
705                 710                 715                 720
Pro Arg Val Ile Gly Ser Arg Tyr Leu Thr Asn His Leu
                725                 730

<210> SEQ ID NO 62
<211> LENGTH: 733
<212> TYPE: PRT
<213> ORGANISM: Unknown
<220> FEATURE:
<223> OTHER INFORMATION: capsid protein of AAV serotype, clone C5VP1[@0002]

<400> SEQUENCE: 62

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Glu Tyr Leu Gly Pro Phe Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
```

```
Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Leu Glu Ser Pro Gln Glu Pro Asp Ser Ser Ser Gly Ile Gly Lys
145                 150                 155                 160

Lys Gly Lys Gln Pro Ala Lys Lys Arg Leu Asn Phe Glu Glu Asp Thr
                165                 170                 175

Gly Ala Gly Asp Gly Pro Pro Glu Gly Ser Asp Thr Ser Ala Met Ser
            180                 185                 190

Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                245                 250                 255

Thr Ser Asn Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Leu Arg Pro Lys Ala Met Arg Val
290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Ile Val Thr Gly Glu Asn Gln Asn Gln Thr Asp Arg Asn Ala
370                 375                 380

Phe Tyr Cys Leu Glu Tyr Phe Pro Ser Gln Met Leu Arg Thr Gly Asn
385                 390                 395                 400

Asn Phe Glu Thr Ala Tyr Asn Phe Glu Lys Val Pro Phe His Ser Met
                405                 410                 415

Tyr Ala His Ser Gln Ser Leu Asp Gly Leu Met Asn Pro Leu Leu Asp
            420                 425                 430

Gln Tyr Leu Trp His Leu Gln Ser Thr Thr Ser Gly Glu Thr Leu Asn
        435                 440                 445

Gln Gly Asn Ala Ala Thr Thr Phe Gly Lys Ile Arg Ser Gly Asp Phe
450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495
```

```
Gly Asn Ala Leu Leu Lys Tyr Asp Thr His Tyr Thr Leu Asn Asn Arg
                500                 505                 510

Trp Ser Asn Ile Ala Pro Gly Pro Met Ala Thr Ala Gly Pro Ser
        515                 520                 525

Asp Gly Asp Phe Ser Asn Ala Gln Leu Ile Phe Pro Gly Pro Ser Val
    530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
                595                 600                 605

Ile Tyr Tyr Gln Gly Pro Ile Trp Ala Lys Ile Pro His Ala Asp Gly
            610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Tyr Pro Ala
                645                 650                 655

Thr Thr Phe Thr Ala Ala Arg Val Asp Ser Phe Ile Thr Gln Tyr Ser
                660                 665                 670

Thr Gly Gln Val Ala Val Gln Ile Glu Trp Glu Ile Glu Lys Glu Arg
            675                 680                 685

Ser Lys Arg Trp Asn Pro Glu Val Gln Phe Thr Ser Asn Cys Gly Asn
        690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730

<210> SEQ ID NO 63
<211> LENGTH: 734
<212> TYPE: PRT
<213> ORGANISM: Unknown
<220> FEATURE:
<223> OTHER INFORMATION: capsid protein of AAV serotype, clone AAV4VP1

<400> SEQUENCE: 63

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
                20                  25                  30

Ala Asn Gln Gln His Gln Asp Asn Ala Arg Gly Leu Val Leu Pro Gly
            35                  40                  45

Tyr Lys Tyr Leu Gly Pro Gly Asn Gly Leu Asp Lys Gly Glu Pro Val
        50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
        115                 120                 125
```

```
Gly Leu Val Glu Gln Ala Gly Glu Thr Ala Pro Gly Lys Lys Arg Pro
130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Leu Val Phe Glu Asp Glu Thr
                165                 170                 175

Gly Ala Gly Asp Gly Pro Pro Glu Gly Ser Thr Ser Gly Ala Met Ser
                180                 185                 190

Asp Asp Ser Glu Met Arg Ala Ala Gly Ala Ala Val Glu Gly
        195                 200                 205

Gly Gln Gly Ala Asp Gly Val Gly Asn Ala Ser Gly Asp Trp His Cys
    210                 215                 220

Asp Ser Thr Trp Ser Glu Gly His Val Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
                260                 265                 270

Phe Asp Phe Asn Arg Phe His Cys His Phe Ser Pro Arg Asp Trp Gln
        275                 280                 285

Arg Leu Ile Asn Asn Asn Trp Gly Met Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
                340                 345                 350

Leu Pro Pro Phe Pro Asn Asp Val Phe Met Val Pro Gln Tyr Gly Tyr
            355                 360                 365

Cys Gly Leu Val Thr Gly Asn Thr Ser Gln Gln Thr Asp Arg Asn
370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
            435                 440                 445

Asn Ala Gly Thr Ala Thr Thr Asn Phe Thr Lys Leu Arg Pro Thr Asn
450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
            485                 490                 495

Gly Ser Asp Ser Leu Ile Lys Tyr Glu Thr His Ser Thr Leu Asp Gly
            500                 505                 510

Arg Trp Ser Ala Leu Thr Pro Gly Pro Pro Met Ala Thr Ala Gly Pro
            515                 520                 525

Ala Asp Ser Lys Phe Ser Asn Ser Gln Leu Ile Phe Ala Gly Pro Lys
530                 535                 540

Gln Asn Gly Asn Thr Ala Thr Val Pro Gly Thr Leu Ile Phe Thr Ser
```

-continued

```
                545                 550                 555                 560
Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
                580                 585                 590

Arg Leu Thr Ala Leu Gly Ala Val Pro Gly Met Val Trp Gln Asn Arg
                595                 600                 605

Asp Ile Tyr Tyr Gln Gly Pro Ile Trp Ala Lys Ile Pro His Thr Asp
                610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
                660                 665                 670

Ser Thr Gly Gln Val Ser Val Gln Ile Asp Trp Glu Ile Gln Lys Glu
                675                 680                 685

Arg Ser Lys Arg Trp Asn Pro Glu Val Gln Phe Thr Ser Asn Tyr Gly
                690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                725                 730

<210> SEQ ID NO 64
<211> LENGTH: 736
<212> TYPE: PRT
<213> ORGANISM: Unknown
<220> FEATURE:
<223> OTHER INFORMATION: capsid protein of AAV serotype, clone AAV1

<400> SEQUENCE: 64

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
                35                  40                  45

Gly Tyr Lys Tyr Leu Gly Pro Phe Asn Gly Leu Asp Lys Gly Glu Pro
                50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
                130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
```

```
            180                 185                 190
Ala Thr Pro Ala Ala Val Gly Pro Thr Thr Met Ala Ser Gly Gly Gly
            195                 200                 205
Ala Pro Met Ala Asp Asn Asn Glu Gly Ala Asp Gly Val Gly Asn Ala
            210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Ala Ser Thr Gly Ala Ser Asn Asp Asn His
                260                 265                 270
Tyr Phe Gly Tyr Ser Thr Pro Trp Gly Tyr Phe Asp Phe Asn Arg Phe
            275                 280                 285
His Cys His Phe Ser Pro Arg Asp Trp Gln Arg Leu Ile Asn Asn Asn
            290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
                325                 330                 335
Leu Thr Ser Thr Val Gln Val Phe Ser Asp Ser Glu Tyr Gln Leu Pro
                340                 345                 350
Tyr Val Leu Gly Ser Ala His Gln Gly Cys Leu Pro Pro Phe Pro Ala
            355                 360                 365
Asp Val Phe Met Ile Pro Gln Tyr Gly Tyr Leu Thr Leu Asn Asn Gly
            370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
                405                 410                 415
Glu Glu Val Pro Phe His Ser Ser Tyr Ala His Ser Gln Ser Leu Asp
            420                 425                 430
Arg Leu Met Asn Pro Leu Ile Asp Gln Tyr Leu Tyr Tyr Leu Asn Arg
            435                 440                 445
Thr Gln Asn Gln Ser Gly Ser Ala Gln Asn Lys Asp Leu Leu Phe Ser
            450                 455                 460
Arg Gly Ser Pro Ala Gly Met Ser Val Gln Pro Lys Asn Trp Leu Pro
465                 470                 475                 480
Gly Pro Cys Tyr Arg Gln Gln Arg Val Ser Lys Thr Lys Thr Asp Asn
                485                 490                 495
Asn Asn Ser Asn Phe Thr Trp Thr Gly Ala Ser Lys Tyr Asn Leu Asn
                500                 505                 510
Gly Arg Glu Ser Ile Ile Asn Pro Gly Thr Ala Met Ala Ser His Lys
            515                 520                 525
Asp Asp Glu Asp Lys Phe Phe Pro Met Ser Gly Val Met Ile Phe Gly
            530                 535                 540
Lys Glu Ser Ala Gly Ala Ser Asn Thr Ala Leu Asp Asn Val Met Ile
545                 550                 555                 560
Thr Asp Glu Glu Glu Ile Lys Ala Thr Asn Pro Val Ala Thr Glu Arg
                565                 570                 575
Phe Gly Thr Val Ala Val Asn Phe Gln Ser Ser Ser Thr Asp Pro Ala
            580                 585                 590
Thr Gly Asp Val His Ala Met Gly Ala Leu Pro Gly Met Val Trp Gln
            595                 600                 605
```

```
Asp Arg Asp Val Tyr Leu Gln Gly Pro Ile Trp Ala Lys Ile Pro His
        610                 615                 620

Thr Asp Gly His Phe His Pro Ser Pro Leu Met Gly Gly Phe Gly Leu
625                 630                 635                 640

Lys Asn Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
        690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 65
<211> LENGTH: 736
<212> TYPE: PRT
<213> ORGANISM: Unknown
<220> FEATURE:
<223> OTHER INFORMATION: capsid protein of AAV serotype, clone AAV6VP1

<400> SEQUENCE: 65

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240
```

```
Thr Thr Ser Thr Arg Thr Trp Ala Leu Pro Thr Tyr Asn Asn His Leu
            245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
            325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
            450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
            515                 520                 525

Asp Asp Lys Asp Lys Phe Phe Pro Met Ser Gly Val Met Ile Phe Gly
            530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
            565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
            645                 650                 655
```

```
Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
        690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 66
<211> LENGTH: 735
<212> TYPE: PRT
<213> ORGANISM: Unknown
<220> FEATURE:
<223> OTHER INFORMATION: capsid protein of AAV serotype, clone A3.3

<400> SEQUENCE: 66

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Asn Gln Gln His Arg Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

His Gln Leu Lys Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Val Lys Thr Ala Pro Gly Lys Lys Arg
    130                 135                 140

Pro Ile Glu Gln Ser Pro Ala Glu Pro Asp Ser Ser Ser Gly Ile Gly
145                 150                 155                 160

Lys Ser Gly Gln Gln Pro Ala Lys Lys Arg Leu Asn Phe Gly Gln Thr
                165                 170                 175

Gly Asp Thr Glu Ser Val Pro Gly Pro Gln Pro Ile Gly Glu Pro Pro
            180                 185                 190

Ala Ala Pro Ser Gly Val Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Glu Ser Gly Ala Thr Asn Asp Asn His Tyr
            260                 265                 270

Phe Gly Tyr Ser Thr Pro Trp Gly Tyr Phe Asp Phe Asn Arg Phe His
        275                 280                 285
```

```
Cys His Phe Ser Pro Arg Asp Trp Gln Arg Leu Ile Asn Asn Asn Trp
    290                 295                 300

Gly Phe Arg Pro Lys Lys Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Ala Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Ile Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Lys Thr
                435                 440                 445

Gln Gly Thr Ser Gly Thr Thr Gln Gln Ser Arg Leu Gln Phe Ser Gln
450                 455                 460

Ala Gly Pro Ser Ser Met Ala Gln Gln Ala Lys Asn Trp Leu Pro Gly
465                 470                 475                 480

Pro Ser Tyr Arg Gln Gln Arg Met Ser Lys Thr Ala Asn Asp Asn Asn
                485                 490                 495

Asn Ser Glu Phe Ala Trp Thr Ala Ala Thr Lys Tyr Tyr Leu Asn Gly
                500                 505                 510

Arg Asn Ser Leu Val Asn Pro Gly Pro Pro Val Ala Ser His Lys Asp
                515                 520                 525

Asp Glu Glu Lys Tyr Phe Pro Met His Gly Asn Leu Ile Phe Gly Lys
530                 535                 540

Gln Gly Thr Gly Thr Thr Asn Val Asp Ile Glu Ser Val Leu Ile Thr
545                 550                 555                 560

Asp Glu Glu Glu Ile Arg Thr Thr Asn Pro Val Ala Thr Glu Gln Tyr
                565                 570                 575

Gly Gln Val Ala Thr Asn His Gln Ser Gln Asn Thr Thr Ala Ser Tyr
                580                 585                 590

Gly Ser Val Asp Ser Gln Gly Ile Leu Pro Gly Met Val Trp Gln Asp
                595                 600                 605

Arg Asp Val Tyr Leu Gln Gly Pro Ile Trp Ala Lys Thr Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ala Thr Thr Phe Thr Pro Gly Lys Phe Ala Ser Phe Ile Thr Gln
                660                 665                 670

Tyr Ser Thr Gly Gln Val Ser Val Glu Ile Glu Trp Glu Leu Gln Lys
                675                 680                 685

Glu Asn Ser Lys Arg Trp Asn Pro Glu Ile Gln Tyr Thr Ser Asn Tyr
690                 695                 700

Asn Lys Ser Val Asn Val Glu Phe Thr Val Asp Ala Asn Gly Val Tyr
```

```
                705                 710                 715                 720
Ser Glu Pro Arg Pro Ile Gly Thr Arg Tyr Leu Thr Arg Asn Leu
                725                 730                 735

<210> SEQ ID NO 67
<211> LENGTH: 735
<212> TYPE: PRT
<213> ORGANISM: Unknown
<220> FEATURE:
<223> OTHER INFORMATION: capsid protein of  AAV serotype, clone A3.7

<400> SEQUENCE: 67

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Asn Gln Gln His Arg Asp Ser Arg Gly Leu Val Leu Pro
        35                  40                  45

Gly Tyr Lys Tyr Leu Gly Pro Phe Asn Gly Leu Asp Lys Gly Glu Pro
50                  55                  60

Val Asn Glu Ala Asp Ala Ala Leu Glu His Asp Lys Ala Tyr Asp
65                  70                  75                  80

His Gln Leu Lys Gln Gly Asp Asn Pro Tyr Leu Lys Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
    115                 120                 125

Leu Gly Leu Val Glu Glu Ala Val Lys Thr Ala Pro Gly Lys Lys Arg
130                 135                 140

Pro Ile Glu Gln Ser Pro Ala Glu Pro Asp Ser Ser Ser Gly Ile Gly
145                 150                 155                 160

Lys Ser Gly Gln Gln Pro Ala Lys Lys Arg Leu Asn Phe Gly Gln Thr
            165                 170                 175

Gly Asp Thr Glu Ser Val Pro Asp Pro Gln Pro Ile Gly Glu Pro Pro
        180                 185                 190

Ala Ala Pro Ser Gly Val Gly Ser Asn Thr Met Ala Ser Gly Gly Gly
    195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn Arg Leu
            245                 250                 255

Tyr Lys Gln Ile Ser Ser Glu Ser Gly Ala Thr Asn Asp Asn His Tyr
        260                 265                 270

Phe Gly Tyr Ser Thr Pro Trp Gly Tyr Phe Asp Phe Asn Arg Phe His
    275                 280                 285

Cys His Phe Ser Pro Arg Asp Trp Gln Arg Leu Ile Asn Asn Asn Trp
290                 295                 300

Gly Phe Arg Pro Lys Lys Leu Asn Phe Lys Leu Phe Asn Ile Gln Val
305                 310                 315                 320

Lys Glu Val Thr Gln Asn Asp Gly Thr Thr Thr Ile Ala Asn Asn Leu
            325                 330                 335

Thr Ser Thr Val Gln Val Phe Thr Asp Ser Glu Tyr Gln Leu Pro Tyr
```

```
                340             345             350
Val Leu Gly Ser Ala His Gln Gly Cys Leu Pro Phe Pro Ala Asp
            355             360             365
Val Phe Met Ile Pro Gln Tyr Gly Tyr Leu Thr Leu Asn Asn Gly Ser
        370             375             380
Gln Ala Val Gly Arg Ser Ser Phe Tyr Cys Leu Glu Tyr Phe Pro Ser
385             390             395             400
Gln Met Leu Arg Thr Gly Asn Asn Phe Thr Phe Ser Tyr Thr Phe Glu
            405             410             415
Asp Val Pro Phe His Ser Ser Tyr Ala His Ser Gln Ser Leu Asp Arg
        420             425             430
Leu Met Asn Pro Leu Ile Asp Gln Tyr Leu Tyr Tyr Leu Ser Lys Thr
            435             440             445
Gln Gly Thr Ser Gly Thr Thr Gln Gln Ser Arg Leu Gln Phe Ser Gln
        450             455             460
Ala Gly Pro Ser Ser Met Ala Gln Gln Ala Lys Asn Trp Leu Pro Gly
465             470             475             480
Pro Ser Tyr Arg Gln Gln Arg Met Ser Lys Thr Ala Asn Asp Asn Asn
            485             490             495
Asn Ser Glu Phe Ala Trp Thr Ala Ala Thr Lys Tyr Tyr Leu Asn Gly
        500             505             510
Arg Asn Ser Leu Val Asn Pro Gly Pro Pro Met Ala Ser His Lys Asp
            515             520             525
Asp Glu Glu Lys Tyr Phe Pro Met His Gly Asn Leu Ile Phe Gly Lys
        530             535             540
Gln Gly Thr Gly Thr Thr Asn Val Asp Ile Glu Ser Val Leu Ile Thr
545             550             555             560
Asp Glu Glu Glu Ile Arg Thr Thr Asn Pro Val Ala Thr Glu Gln Tyr
            565             570             575
Gly Gln Val Ala Thr Asn His Gln Ser Gln Asn Thr Thr Ala Ser Tyr
        580             585             590
Gly Ser Val Asp Ser Gln Gly Ile Leu Pro Gly Met Val Trp Gln Asp
            595             600             605
Arg Asp Val Tyr Leu Gln Gly Pro Ile Trp Ala Lys Thr Pro His Thr
        610             615             620
Asp Gly His Phe His Pro Ser Pro Leu Met Gly Gly Phe Gly Leu Lys
625             630             635             640
His Pro Pro Pro Gln Ile Leu Ile Lys Asn Thr Pro Val Pro Ala Asn
            645             650             655
Pro Ala Thr Thr Phe Thr Pro Gly Lys Phe Ala Ser Phe Ile Thr Gln
        660             665             670
Tyr Ser Thr Gly Gln Val Ser Val Glu Ile Glu Trp Glu Leu Gln Lys
            675             680             685
Glu Asn Ser Lys Arg Trp Asn Pro Glu Ile Gln Tyr Thr Ser Asn Tyr
        690             695             700
Asn Lys Ser Val Asn Val Glu Phe Thr Val Asp Ala Asn Gly Val Tyr
705             710             715             720
Ser Glu Pro Arg Pro Ile Gly Thr Arg Tyr Leu Thr Arg Asn Leu
            725             730             735

<210> SEQ ID NO 68
<211> LENGTH: 735
<212> TYPE: PRT
<213> ORGANISM: Unknown
```

<220> FEATURE:
<223> OTHER INFORMATION: capsid protein of AAV serotype, clone A3.4

<400> SEQUENCE: 68

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Asn Gln Gln His Arg Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

His Gln Leu Lys Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Val Lys Thr Ala Pro Gly Lys Lys Arg
    130                 135                 140

Pro Ile Glu Gln Ser Pro Ala Glu Pro Asp Ser Ser Ser Gly Ile Gly
145                 150                 155                 160

Glu Ser Gly Gln Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Glu Ser Gly Ala Thr Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Ile Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Phe Thr Phe Ser Tyr Thr Phe Glu
                405                 410                 415

Asp Val Pro Phe His Ser Ser Tyr Ala His Ser Gln Ser Leu Asp Arg
        420                 425                 430

Leu Met Asn Pro Leu Ile Asp Gln Tyr Leu Tyr Tyr Leu Ser Lys Thr
            435                 440                 445

Gln Gly Thr Ser Gly Thr Thr Gln Gln Ser Arg Leu Gln Phe Ser Gln
    450                 455                 460

Ala Gly Pro Ser Ser Met Ala Gln Gln Ala Lys Asn Trp Leu Pro Gly
465                 470                 475                 480

Pro Ser Tyr Arg Gln Gln Arg Met Ser Lys Thr Ala Asn Asp Asn Asn
                485                 490                 495

Asn Ser Glu Phe Ala Trp Thr Ala Thr Lys Tyr Tyr Leu Asn Gly
        500                 505                 510

Arg Asn Ser Leu Val Asn Pro Gly Pro Pro Met Ala Ser His Lys Asp
            515                 520                 525

Asp Glu Glu Lys Tyr Phe Pro Met His Gly Asn Leu Ile Phe Gly Lys
    530                 535                 540

Gln Gly Thr Gly Thr Thr Asn Val Asp Ile Glu Ser Val Leu Ile Thr
545                 550                 555                 560

Asp Glu Glu Ile Arg Thr Thr Asn Pro Val Ala Thr Glu Gln Tyr
                565                 570                 575

Gly Gln Val Ala Thr Asn His Gln Ser Gln Asp Thr Thr Ala Ser Tyr
        580                 585                 590

Gly Ser Val Asp Ser Gln Gly Ile Leu Pro Gly Met Val Trp Gln Asp
            595                 600                 605

Arg Asp Val Tyr Leu Gln Gly Pro Ile Trp Ala Lys Thr Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ala Thr Thr Phe Thr Pro Gly Lys Phe Ala Ser Phe Ile Thr Gln
        660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
    690                 695                 700

Asn Lys Ser Val Asn Val Glu Phe Thr Val Asp Ala Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 69
<211> LENGTH: 735
<212> TYPE: PRT
<213> ORGANISM: Unknown
<220> FEATURE:
<223> OTHER INFORMATION: capsid protein of AAV serotype, clone A3.5

<400> SEQUENCE: 69

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

-continued

Lys Pro Asn Gln Gln His Arg Asp Asp Ser Arg Gly Leu Val Leu Pro
         35                  40                  45

Gly Tyr Lys Tyr Leu Gly Pro Phe Asn Gly Leu Asp Lys Gly Glu Pro
 50                  55                  60

Val Asn Glu Ala Asp Ala Ala Leu Glu His Asp Lys Ala Tyr Asp
 65              70                  75                  80

His Gln Leu Lys Gln Gly Asp Asn Pro Tyr Leu Lys Tyr Asn His Ala
             85                  90                  95

Asp Ala Glu Phe Gln Glu Arg Leu Gln Glu Asp Thr Ser Phe Gly Gly
             100                 105                 110

Asn Leu Gly Arg Ala Val Phe Gln Ala Lys Lys Arg Val Leu Glu Pro
             115                 120                 125

Leu Gly Leu Val Glu Glu Ala Val Lys Thr Ala Pro Gly Lys Lys Arg
     130                 135                 140

Pro Ile Glu Gln Ser Pro Ala Glu Pro Asp Ser Ser Ser Gly Ile Gly
145                 150                 155                 160

Lys Ser Gly Gln Gln Pro Ala Lys Lys Arg Leu Asn Phe Gly Gln Thr
                 165                 170                 175

Gly Asp Thr Glu Ser Val Pro Asp Pro Gln Pro Ile Gly Glu Pro Pro
             180                 185                 190

Ala Ala Pro Ser Gly Val Gly Ser Asn Thr Met Ala Ser Gly Gly Gly
             195                 200                 205

Ala Pro Met Ala Asp Asn Asn Glu Gly Ala Asp Gly Val Gly Asn Ser
     210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                 245                 250                 255

Tyr Lys Gln Ile Ser Ser Glu Ser Gly Ala Thr Asn Asp Asn His Tyr
             260                 265                 270

Phe Gly Tyr Ser Thr Pro Trp Gly Tyr Phe Asp Phe Asn Arg Phe His
             275                 280                 285

Cys His Phe Ser Pro Arg Asp Trp Gln Arg Leu Ile Asn Asn Asn Trp
     290                 295                 300

Gly Phe Arg Pro Lys Lys Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                 325                 330                 335

Thr Ser Thr Val Gln Val Phe Thr Asp Ser Glu Tyr Gln Leu Pro Tyr
             340                 345                 350

Val Leu Gly Ser Ala His Gln Gly Cys Leu Pro Pro Phe Pro Ala Asp
             355                 360                 365

Val Phe Met Ile Pro Gln Tyr Gly Tyr Leu Thr Leu Asn Asn Gly Ser
     370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                 405                 410                 415

Asp Val Pro Phe His Ser Ser Tyr Ala His Ser Gln Ser Leu Asp Arg
             420                 425                 430

Leu Met Asn Pro Leu Ile Asp Gln Tyr Leu Tyr Tyr Leu Ser Lys Thr
             435                 440                 445

```
Gln Gly Thr Ser Gly Thr Thr Gln Gln Ser Arg Leu Gln Phe Asn Gln
            450                 455                 460
Ala Gly Pro Ser Ser Met Ala Gln Gln Ala Lys Asn Trp Leu Pro Gly
465                 470                 475                 480
Pro Ser Tyr Arg Gln Gln Arg Met Ser Lys Thr Ala Asn Asp Asn Asn
                485                 490                 495
Asn Ser Glu Phe Ala Trp Thr Ala Ala Thr Lys Tyr Tyr Pro Asn Gly
            500                 505                 510
Arg Asn Ser Leu Val Asn Pro Gly Pro Pro Met Ala Ser His Lys Asp
                515                 520                 525
Asp Glu Glu Lys Tyr Phe Pro Met His Gly Asn Leu Ile Phe Gly Lys
530                 535                 540
Gln Gly Thr Gly Thr Thr Asn Val Asp Ile Glu Ser Val Leu Ile Thr
545                 550                 555                 560
Asp Glu Glu Glu Ile Arg Thr Thr Asn Pro Val Ala Thr Glu Gln Tyr
                565                 570                 575
Gly Gln Val Ala Thr Asn Arg Gln Ser Gln Asn Thr Thr Ala Ser Tyr
                580                 585                 590
Gly Ser Val Asp Ser Gln Gly Ile Leu Pro Gly Met Val Trp Gln Asp
            595                 600                 605
Arg Asp Val Tyr Leu Gln Gly Pro Ile Trp Ala Lys Thr Pro His Thr
                610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ala Thr Thr Phe Thr Pro Gly Lys Phe Ala Ser Phe Ile Thr Gln
            660                 665                 670
Tyr Ser Thr Gly Gln Val Ser Val Glu Ile Glu Trp Glu Leu Gln Lys
            675                 680                 685
Glu Asn Ser Lys Arg Trp Asn Pro Glu Ile Gln Tyr Thr Ser Asn Tyr
690                 695                 700
Asn Lys Ser Val Asn Val Glu Phe Thr Val Asp Ala Asn Gly Val Tyr
705                 710                 715                 720
Ser Glu Pro Arg Pro Ile Gly Thr Arg Tyr Leu Thr Arg Asn Leu
                725                 730                 735

<210> SEQ ID NO 70
<211> LENGTH: 735
<212> TYPE: PRT
<213> ORGANISM: Unknown
<220> FEATURE:
<223> OTHER INFORMATION: capsid protein of AAV serotype, clone AAV2

<400> SEQUENCE: 70

Met Ala Ala Asp Gly Tyr Leu Pro Asp Trp Leu Glu Asp Thr Leu Ser
1               5                   10                  15
Glu Gly Ile Arg Gln Trp Trp Lys Leu Lys Pro Gly Pro Pro Pro Pro
                20                  25                  30
Lys Pro Ala Glu Arg His Lys Asp Asp Ser Arg Gly Leu Val Leu Pro
            35                  40                  45
Gly Tyr Lys Tyr Leu Gly Pro Phe Asn Gly Leu Asp Lys Gly Glu Pro
        50                  55                  60
Val Asn Glu Ala Asp Ala Ala Ala Leu Glu His Asp Lys Ala Tyr Asp
65                  70                  75                  80
```

-continued

```
Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
```

```
                500             505             510
Arg Asp Ser Leu Val Asn Pro Gly Pro Ala Met Ala Ser His Lys Asp
            515             520             525

Asp Glu Glu Lys Phe Phe Pro Gln Ser Gly Val Leu Ile Phe Gly Lys
            530             535             540

Gln Gly Ser Glu Lys Thr Asn Val Asp Ile Glu Lys Val Met Ile Thr
545             550             555             560

Asp Glu Glu Ile Arg Thr Thr Asn Pro Val Ala Thr Glu Gln Tyr
            565             570             575

Gly Ser Val Ser Thr Asn Leu Gln Arg Gly Asn Arg Gln Ala Ala Thr
            580             585             590

Ala Asp Val Asn Thr Gln Gly Val Leu Pro Gly Met Val Trp Gln Asp
            595             600             605

Arg Asp Val Tyr Leu Gln Gly Pro Ile Trp Ala Lys Ile Pro His Thr
            610             615             620

Asp Gly His Phe His Pro Ser Pro Leu Met Gly Gly Phe Gly Leu Lys
625             630             635             640

His Pro Pro Pro Gln Ile Leu Ile Lys Asn Thr Pro Val Pro Ala Asn
            645             650             655

Pro Ser Thr Thr Phe Ser Ala Ala Lys Phe Ala Ser Phe Ile Thr Gln
            660             665             670

Tyr Ser Thr Gly Gln Val Ser Val Glu Ile Glu Trp Glu Leu Gln Lys
            675             680             685

Glu Asn Ser Lys Arg Trp Asn Pro Glu Ile Gln Tyr Thr Ser Asn Tyr
            690             695             700

Asn Lys Ser Val Asn Val Asp Phe Thr Val Asp Thr Asn Gly Val Tyr
705             710             715             720

Ser Glu Pro Arg Pro Ile Gly Thr Arg Tyr Leu Thr Arg Asn Leu
            725             730             735

<210> SEQ ID NO 71
<211> LENGTH: 736
<212> TYPE: PRT
<213> ORGANISM: Unknown
<220> FEATURE:
<223> OTHER INFORMATION: capsid protein of AAV serotype, clone AAV3

<400> SEQUENCE: 71

Met Ala Ala Asp Gly Tyr Leu Pro Asp Trp Leu Glu Asp Asn Leu Ser
1               5               10              15

Glu Gly Ile Arg Glu Trp Trp Ala Leu Lys Pro Gly Val Pro Gln Pro
            20              25              30

Lys Ala Asn Gln Gln His Gln Asp Asn Arg Arg Gly Leu Val Leu Pro
            35              40              45

Gly Tyr Lys Tyr Leu Gly Pro Gly Asn Gly Leu Asp Lys Gly Glu Pro
        50              55              60

Val Asn Glu Ala Asp Ala Ala Leu Glu His Asp Lys Ala Tyr Asp
65              70              75              80

Gln Gln Leu Lys Ala Gly Asp Asn Pro Tyr Leu Lys Tyr Asn His Ala
            85              90              95

Asp Ala Glu Phe Gln Glu Arg Leu Gln Glu Asp Thr Ser Phe Gly Gly
            100             105             110

Asn Leu Gly Arg Ala Val Phe Gln Ala Lys Lys Arg Ile Leu Glu Pro
            115             120             125

Leu Gly Leu Val Glu Glu Ala Ala Lys Thr Ala Pro Gly Lys Lys Gly
```

-continued

```
              130                 135                 140
Ala Val Asp Gln Ser Pro Gln Glu Pro Asp Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Ala Pro Thr Ser Leu Gly Ser Asn Thr Met Ala Ser Gly Gly Gly
                195                 200                 205

Ala Pro Met Ala Asp Asn Asn Glu Gly Ala Asp Gly Val Gly Asn Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
        290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
        450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
                500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
        530                 535                 540

Lys Glu Gly Thr Thr Ala Ser Asn Ala Glu Leu Asp Asn Val Met Ile
545                 550                 555                 560
```

-continued

```
Thr Asp Glu Glu Glu Ile Arg Thr Thr Asn Pro Val Ala Thr Glu Gln
                565                 570                 575
Tyr Gly Thr Val Ala Asn Asn Leu Gln Ser Ser Asn Thr Ala Pro Thr
            580                 585                 590
Thr Gly Thr Val Asn His Gln Gly Ala Leu Pro Gly Met Val Trp Gln
        595                 600                 605
Asp Arg Asp Val Tyr Leu Gln Gly Pro Ile Trp Ala Lys Ile Pro His
    610                 615                 620
Thr Asp Gly His Phe His Pro Ser Pro Leu Met Gly Gly Phe Gly Leu
625                 630                 635                 640
Lys His Pro Pro Gln Ile Met Ile Lys Asn Thr Pro Val Pro Ala
                645                 650                 655
Asn Pro Pro Thr Thr Phe Ser Pro Ala Lys Phe Ala Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Ile Gln Tyr Thr Ser Asn
    690                 695                 700
Tyr Asn Lys Ser Val Asn Val Asp Phe Thr Val Asp Thr Asn Gly Val
705                 710                 715                 720
Tyr Ser Glu Pro Arg Pro Ile Gly Thr Arg Tyr Leu Thr Arg Asn Leu
                725                 730                 735

<210> SEQ ID NO 72
<211> LENGTH: 737
<212> TYPE: PRT
<213> ORGANISM: Unknown
<220> FEATURE:
<223> OTHER INFORMATION: capsid protein of AAV serotype, clone 3.3bVP1

<400> SEQUENCE: 72

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asn Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Asn Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Ala Lys Lys Arg
    130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Arg Lys Arg Leu Asn Phe Gly Gln
                165                 170                 175
Thr Gly Asp Ser Glu Ser Val Pro Asp Pro Gln Pro Leu Gly Glu Pro
            180                 185                 190
```

```
Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Glu Gln Ile Ser Ser Glu Thr Ala Gly Ser Thr Asn Asp Asn
                260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
        370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
            435                 440                 445

Arg Thr Gln Ser Asp Pro Gly Gly Thr Ala Gly Asn Arg Glu Leu Gln
        450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Asp Arg Phe Phe Pro Ser Ser Gly Val Leu Ile
        530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
        595                 600                 605
```

```
Gln Asn Arg Asp Val Tyr Leu Gln Gly Pro Ile Trp Ala Lys Ile Pro
            610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
            645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asp Pro Gly Ile Gln Tyr Thr Ser
690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu
```

<210> SEQ ID NO 73
<211> LENGTH: 644
<212> TYPE: PRT
<213> ORGANISM: Unknown
<220> FEATURE:
<223> OTHER INFORMATION: capsid protein of AAV serotype, clone 223-4

<400> SEQUENCE: 73

```
Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Arg Leu Gln Glu Asp Thr
            20                  25                  30

Ser Phe Gly Gly Asn Leu Gly Arg Ala Val Phe Gln Ala Lys Lys Arg
        35                  40                  45

Val Leu Glu Pro Leu Gly Leu Val Glu Thr Pro Ala Lys Thr Ala Pro
    50                  55                  60

Gly Lys Lys Arg Pro Val Asp Ser Pro Asp Ser Thr Ser Gly Ile Gly
65                  70                  75                  80

Lys Lys Gly Gln Gln Pro Ala Lys Lys Arg Leu Asn Phe Gly Gln Thr
                85                  90                  95

Gly Asp Ser Glu Pro Val Pro Asp Pro Gln Pro Ile Gly Glu Pro Pro
            100                 105                 110

Ala Gly Pro Ser Gly Leu Gly Ser Gly Thr Met Ala Ala Gly Gly Gly
        115                 120                 125

Ala Pro Met Ala Asp Asn Asn Glu Gly Ala Asp Gly Val Gly Asn Ala
    130                 135                 140

Ser Gly Asn Trp His Cys Asp Ser Thr Arg Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
            180                 185                 190

Tyr Phe Gly Tyr Ser Thr Pro Trp Gly Tyr Phe Asp Phe Asn Arg Phe
        195                 200                 205

His Cys His Phe Ser Pro Arg Asp Trp Gln Arg Leu Ile Asn Asn Asn
    210                 215                 220

Trp Gly Phe Arg Pro Lys Lys Leu Asn Phe Lys Leu Phe Asn Ile Gln
```

```
           225                 230                 235                 240
       Val Lys Glu Val Thr Thr Asn Asp Gly Val Thr Thr Ile Ala Asn Asn
                           245                 250                 255

Leu Thr Ser Thr Val Gln Val Phe Ser Asp Ser Glu Tyr Gln Leu Pro
                           260                 265                 270

Tyr Val Leu Gly Ser Ala His Gln Gly Cys Leu Pro Pro Phe Pro Ala
                           275                 280                 285

Asp Val Phe Met Ile Pro Gln Tyr Gly Tyr Leu Thr Leu Asn Asn Gly
                           290                 295                 300

Ser Gln Ser Val Gly Arg Ser Ser Phe Tyr Cys Leu Glu Tyr Phe Pro
       305                 310                 315                 320

Ser Gln Met Leu Arg Thr Gly Asn Asn Phe Thr Phe Ser Tyr Thr Phe
                           325                 330                 335

Glu Asp Val Pro Phe His Ser Ser Tyr Ala His Ser Gln Ser Leu Gly
                           340                 345                 350

Arg Leu Met Asn Pro Leu Ile Asp Gln Tyr Leu Tyr Tyr Leu Ala Arg
                           355                 360                 365

Thr Gln Ser Asn Ala Gly Gly Thr Ala Gly Asn Arg Glu Leu Gln Phe
                           370                 375                 380

Tyr Gln Gly Gly Pro Thr Thr Met Ala Glu Gln Ala Lys Asn Trp Leu
       385                 390                 395                 400

Pro Gly Pro Cys Phe Arg Gln Gln Arg Val Ser Lys Thr Leu Asp Gln
                           405                 410                 415

Asn Asn Asn Ser Asn Phe Ala Trp Thr Gly Ala Thr Lys Tyr His Leu
                           420                 425                 430

Asn Gly Arg Asn Ser Leu Val Asn Pro Gly Val Ala Met Ala Thr His
                           435                 440                 445

Lys Asp Asp Glu Glu Arg Phe Phe Pro Ser Ser Gly Val Leu Ile Phe
                           450                 455                 460

Gly Lys Thr Gly Ala Ala Asn Lys Thr Thr Leu Glu Asn Val Leu Met
       465                 470                 475                 480

Thr Asn Glu Glu Glu Ile Arg Pro Thr Asn Pro Val Ala Thr Glu Glu
                           485                 490                 495

Tyr Gly Ile Val Ser Ser Asn Leu Gln Ala Ala Ser Thr Ala Ala Gln
                           500                 505                 510

Thr Gln Val Val Asn Asn Gln Gly Ala Leu Pro Gly Met Val Trp Gln
                           515                 520                 525

Asn Arg Asp Val Tyr Leu Gln Gly Pro Ile Trp Ala Lys Ile Pro His
       530                 535                 540

Thr Asp Gly Asn Phe His Pro Ser Pro Leu Met Gly Gly Phe Gly Leu
       545                 550                 555                 560

Lys His Pro Pro Pro Gln Ile Leu Ile Lys Asn Thr Pro Val Pro Ala
                           565                 570                 575

Asn Pro Pro Glu Val Phe Thr Pro Ala Lys Phe Ala Ser Phe Ile Thr
                           580                 585                 590

Gln Tyr Ser Thr Gly Gln Val Ser Val Glu Ile Glu Trp Glu Leu Gln
                           595                 600                 605

Lys Glu Asn Ser Lys Arg Trp Asn Pro Glu Ile Gln Tyr Thr Ser Asn
                           610                 615                 620

Phe Asp Lys Gln Thr Gly Val Asp Phe Ala Val Asp Ser Gln Gly Val
       625                 630                 635                 640

Tyr Ser Glu Pro
```

<210> SEQ ID NO 74
<211> LENGTH: 644
<212> TYPE: PRT
<213> ORGANISM: Unknown
<220> FEATURE:
<223> OTHER INFORMATION: capsid protein of AAV serotype, clone 223-5

<400> SEQUENCE: 74

```
Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Arg Leu Gln Glu Asp Thr
            20                  25                  30

Ser Phe Gly Gly Asn Leu Gly Arg Ala Val Phe Gln Ala Lys Lys Arg
        35                  40                  45

Val Leu Glu Pro Leu Gly Leu Val Glu Thr Pro Ala Lys Thr Ala Pro
    50                  55                  60

Gly Lys Lys Arg Pro Val Asp Ser Pro Asp Ser Thr Ser Gly Ile Gly
65                  70                  75                  80

Lys Lys Gly Gln Gln Pro Ala Lys Lys Arg Leu Asn Phe Gly Gln Thr
                85                  90                  95

Gly Asp Ser Glu Pro Val Pro Asp Pro Gln Pro Ile Gly Glu Pro Pro
            100                 105                 110

Ala Gly Pro Ser Gly Leu Gly Ser Gly Thr Met Ala Ala Gly Gly Gly
        115                 120                 125

Ala Pro Met Ala Asp Asn Asn Glu Gly Ala Asp Gly Val Gly Asn Ala
    130                 135                 140

Ser Gly Asn Trp His Cys Asp Ser Thr Arg Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
            180                 185                 190

Tyr Phe Gly Tyr Ser Thr Pro Trp Gly Tyr Phe Asp Phe Asn Arg Phe
        195                 200                 205

His Cys His Phe Ser Pro Arg Asp Trp Gln Arg Leu Ile Asn Asn Asn
    210                 215                 220

Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
                245                 250                 255

Leu Thr Ser Thr Val Gln Val Phe Ser Asp Ser Glu Tyr Gln Leu Pro
            260                 265                 270

Tyr Val Leu Gly Ser Ala His Gln Gly Cys Leu Pro Pro Phe Pro Ala
        275                 280                 285

Asp Val Phe Met Ile Pro Gln Tyr Gly Tyr Leu Thr Leu Asn Asn Gly
    290                 295                 300

Ser Gln Ser Val Gly Arg Ser Ser Phe Tyr Cys Leu Glu Tyr Phe Pro
305                 310                 315                 320

Ser Gln Met Leu Arg Thr Gly Asn Asn Phe Thr Phe Ser Tyr Thr Phe
                325                 330                 335

Glu Asp Val Pro Phe His Ser Ser Tyr Ala His Ser Gln Ser Leu Gly
            340                 345                 350

Arg Leu Met Asn Pro Leu Ile Asp Gln Tyr Leu Tyr Tyr Leu Ala Arg
        355                 360                 365
```

-continued

```
Thr Gln Ser Asn Ala Gly Gly Thr Ala Gly Asn Arg Glu Leu Gln Phe
370                 375                 380
Tyr Gln Gly Gly Pro Thr Thr Met Ala Glu Gln Ala Lys Asn Trp Leu
385                 390                 395                 400
Pro Gly Pro Cys Phe Arg Gln Gln Arg Val Ser Lys Thr Leu Asp Gln
            405                 410                 415
Asn Asn Asn Ser Asn Phe Ala Trp Thr Gly Ala Thr Lys Tyr His Leu
            420                 425                 430
Asn Gly Arg Asn Ser Leu Val Asn Pro Gly Val Ala Met Ala Thr His
            435                 440                 445
Lys Asp Asp Glu Glu Arg Phe Phe Pro Ser Ser Gly Val Leu Ile Phe
450                 455                 460
Gly Lys Thr Gly Ala Ala Asn Lys Thr Thr Leu Glu Asn Val Leu Met
465                 470                 475                 480
Thr Asn Glu Glu Glu Ile Arg Pro Thr Asn Pro Val Ala Thr Glu Glu
                485                 490                 495
Tyr Gly Ile Val Ser Ser Asn Leu Gln Ala Ala Ser Thr Ala Ala Gln
                500                 505                 510
Thr Gln Val Val Asn Asn Gln Gly Ala Leu Pro Gly Met Val Trp Gln
            515                 520                 525
Asn Arg Asp Val Tyr Leu Gln Gly Pro Ile Trp Ala Lys Ile Pro His
530                 535                 540
Thr Asp Gly Asn Phe His Pro Ser Pro Leu Met Gly Gly Phe Gly Leu
545                 550                 555                 560
Lys His Pro Pro Gln Ile Leu Ile Lys Asn Thr Pro Val Pro Ala
                565                 570                 575
Asn Pro Pro Glu Val Phe Thr Pro Ala Lys Phe Ala Ser Phe Ile Thr
            580                 585                 590
Gln Tyr Ser Thr Gly Gln Val Ser Val Glu Ile Glu Trp Glu Leu Gln
            595                 600                 605
Lys Glu Asn Ser Lys Arg Trp Asn Pro Glu Ile Gln Tyr Thr Ser Asn
610                 615                 620
Phe Asp Lys Gln Thr Gly Val Asp Phe Ala Val Asp Ser Gln Gly Val
625                 630                 635                 640
Tyr Ser Glu Pro
```

```
<210> SEQ ID NO 75
<211> LENGTH: 644
<212> TYPE: PRT
<213> ORGANISM: Unknown
<220> FEATURE:
<223> OTHER INFORMATION: capsid protein of AAV serotype, clone 223-10
<220> FEATURE:
<221> NAME/KEY: MISC_FEATURE
<222> LOCATION: (434)..(434)
<223> OTHER INFORMATION: can be any amino acid

<400> SEQUENCE: 75
```

```
Lys Ala Tyr Asp Gln Gln Leu Lys Ala Gly Asp Asn Pro Tyr Leu Arg
1               5                   10                  15
Tyr Asn His Ala Asp Ala Glu Phe Gln Glu Arg Leu Gln Glu Asp Thr
                20                  25                  30
Ser Phe Gly Gly Asn Leu Gly Arg Ala Val Phe Gln Ala Lys Lys Arg
            35                  40                  45
Val Leu Glu Pro Leu Gly Leu Val Glu Thr Pro Ala Lys Thr Ala Pro
50                  55                  60
```

```
Gly Lys Lys Arg Pro Val Asp Ser Pro Asp Ser Thr Ser Gly Ile Gly
 65                  70                  75                  80

Lys Lys Gly Gln Gln Pro Ala Lys Lys Arg Leu Asn Phe Gly Gln Thr
             85                  90                  95

Gly Asp Ser Glu Ser Val Pro Asp Pro Gln Pro Ile Gly Glu Pro Pro
            100                 105                 110

Ala Gly Pro Ser Gly Leu Gly Ser Gly Thr Met Ala Ala Gly Gly Gly
        115                 120                 125

Ala Pro Met Ala Asp Asn Asn Glu Gly Ala Asp Gly Val Gly Asn Ala
        130                 135                 140

Ser Gly Asn Trp His Cys Asp Ser Thr Trp Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
            180                 185                 190

Tyr Phe Gly Tyr Ser Thr Pro Trp Gly Tyr Phe Asp Phe Asn Arg Phe
        195                 200                 205

His Cys His Phe Ser Pro Arg Asp Trp Gln Arg Leu Ile Asn Asn Asn
    210                 215                 220

Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
                245                 250                 255

Leu Thr Ser Thr Val Gln Val Phe Ser Asp Ser Glu Tyr Gln Leu Pro
            260                 265                 270

Tyr Val Leu Gly Ser Ala His Gln Gly Cys Leu Pro Pro Phe Pro Ala
        275                 280                 285

Asp Val Phe Met Ile Pro Gln Tyr Gly Tyr Leu Thr Leu Asn Asn Gly
    290                 295                 300

Ser Gln Ser Val Gly Arg Ser Ser Phe Tyr Cys Leu Glu Tyr Phe Pro
305                 310                 315                 320

Ser Gln Met Leu Arg Thr Gly Asn Asn Phe Thr Phe Ser Tyr Thr Phe
                325                 330                 335

Glu Asp Val Pro Phe His Ser Ser Tyr Ala His Ser Gln Ser Leu Asp
            340                 345                 350

Arg Leu Met Asn Pro Leu Ile Asp Gln Tyr Leu Tyr Tyr Leu Ala Arg
        355                 360                 365

Thr Gln Ser Asn Ala Gly Gly Thr Ala Gly Asn Arg Glu Leu Gln Phe
    370                 375                 380

Tyr Gln Gly Gly Pro Thr Thr Met Ala Glu Gln Ala Lys Asn Trp Leu
385                 390                 395                 400

Pro Gly Pro Cys Phe Arg Gln Gln Arg Val Ser Lys Thr Leu Asp Gln
                405                 410                 415

Asn Asn Asn Ser Asn Phe Ala Trp Thr Gly Ala Thr Lys Tyr His Leu
            420                 425                 430

Asn Xaa Arg Asn Ser Leu Val Asn Pro Gly Val Ala Met Ala Thr His
        435                 440                 445

Lys Asp Asp Glu Glu Arg Phe Phe Pro Ser Ser Gly Val Leu Ile Phe
    450                 455                 460

Gly Lys Thr Gly Ala Ala Asn Lys Thr Thr Leu Glu Asn Val Leu Met
465                 470                 475                 480

Thr Asn Glu Glu Glu Ile Arg Pro Thr Asn Pro Val Ala Thr Glu Glu
```

```
                485                 490                 495
Tyr Gly Ile Val Ser Ser Asn Leu Gln Ala Ala Ser Thr Ala Ala Gln
                500                 505                 510

Thr Gln Val Val Asn Asn Gln Gly Ala Leu Pro Gly Met Val Trp Gln
                515                 520                 525

Asn Arg Asp Val Tyr Leu Gln Gly Pro Ile Trp Ala Lys Ile Pro His
                530                 535                 540

Thr Asp Gly Asn Phe His Pro Ser Pro Leu Met Gly Gly Phe Gly Leu
545                 550                 555                 560

Lys His Pro Pro Gln Ile Leu Ile Lys Asn Thr Pro Val Pro Ala
                565                 570                 575

Asn Pro Pro Glu Val Phe Thr Pro Ala Lys Phe Ala Ser Phe Ile Thr
                580                 585                 590

Gln Tyr Ser Thr Gly Gln Val Ser Val Glu Ile Glu Trp Glu Leu Gln
                595                 600                 605

Lys Glu Asn Ser Lys Arg Trp Asn Pro Glu Ile Gln Tyr Thr Ser Asn
                610                 615                 620

Phe Asp Lys Gln Thr Gly Val Asp Phe Ala Val Asp Ser Gln Gly Val
625                 630                 635                 640

Tyr Ser Glu Pro

<210> SEQ ID NO 76
<211> LENGTH: 644
<212> TYPE: PRT
<213> ORGANISM: Unknown
<220> FEATURE:
<223> OTHER INFORMATION: capsid protein of AAV serotype, clone 223-2

<400> SEQUENCE: 76

Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Cys Leu Gln Glu Asp Thr
                20                  25                  30

Ser Phe Gly Gly Asn Leu Gly Arg Ala Val Phe Gln Ala Lys Lys Arg
        35                  40                  45

Val Leu Glu Pro Leu Gly Leu Val Glu Thr Pro Ala Lys Thr Ala Pro
    50                  55                  60

Gly Lys Lys Arg Pro Val Asp Ser Pro Asp Ser Thr Ser Gly Ile Gly
65                  70                  75                  80

Lys Lys Gly Gln Gln Pro Ala Lys Lys Arg Leu Asn Phe Gly Gln Thr
                85                  90                  95

Gly Asp Ser Glu Ser Val Pro Asp Pro Gln Pro Ile Gly Glu Pro Pro
                100                 105                 110

Ala Gly Pro Ser Gly Leu Gly Ser Gly Thr Met Val Ala Gly Gly Gly
        115                 120                 125

Ala Pro Met Ala Asp Asn Asn Glu Gly Ala Asp Gly Val Gly Asn Ala
    130                 135                 140

Ser Gly Asn Trp His Cys Asp Ser Thr Trp Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
                180                 185                 190

Tyr Phe Gly Tyr Ser Thr Pro Trp Gly Tyr Phe Asp Phe Asn Arg Phe
        195                 200                 205
```

```
His Cys His Phe Ser Pro Arg Asp Trp Gln Arg Leu Ile Asn Asn Asn
    210                 215                 220
Trp Gly Phe Arg Pro Lys Lys Leu Asn Phe Lys Leu Phe Asn Ile Gln
225                 230                 235                 240
Val Lys Glu Val Thr Thr Asn Asp Gly Val Thr Thr Ile Ala Asn Asn
                245                 250                 255
Leu Thr Ser Thr Val Gln Val Phe Ser Asp Ser Glu Tyr Gln Leu Pro
            260                 265                 270
Tyr Val Leu Gly Ser Ala His Gln Gly Cys Leu Pro Pro Phe Pro Ala
        275                 280                 285
Asp Val Phe Met Ile Pro Gln Tyr Gly Tyr Leu Thr Leu Asn Asn Gly
290                 295                 300
Ser Gln Ser Val Gly Arg Ser Ser Phe Tyr Cys Leu Glu Tyr Phe Pro
305                 310                 315                 320
Ser Gln Met Leu Arg Thr Gly Asn Asn Phe Thr Phe Ser Tyr Thr Phe
                325                 330                 335
Glu Asp Val Pro Phe His Ser Ser Tyr Ala His Ser Gln Ser Leu Asp
            340                 345                 350
Arg Leu Met Asn Pro Leu Ile Asp Gln Tyr Leu Tyr Tyr Leu Ala Arg
        355                 360                 365
Thr Gln Ser Asn Ala Gly Gly Thr Ala Gly Asn Arg Glu Leu Gln Phe
    370                 375                 380
Tyr Gln Gly Gly Pro Thr Thr Met Ala Glu Gln Ala Lys Asn Trp Leu
385                 390                 395                 400
Pro Gly Pro Cys Phe Arg Gln Gln Arg Val Ser Lys Thr Leu Asp Gln
                405                 410                 415
Asn Asn Asn Ser Asn Phe Ala Trp Thr Gly Ala Thr Lys Tyr His Leu
            420                 425                 430
Asn Gly Arg Asn Ser Leu Val Asn Pro Gly Val Ala Met Ala Thr His
        435                 440                 445
Lys Asp Asp Glu Glu Arg Phe Ser Pro Ser Ser Gly Val Leu Ile Phe
    450                 455                 460
Gly Lys Thr Gly Ala Ala Asn Lys Thr Thr Leu Glu Asn Val Leu Met
465                 470                 475                 480
Thr Asn Glu Glu Glu Ile Arg Pro Thr Asn Pro Val Ala Thr Glu Glu
                485                 490                 495
Tyr Gly Ile Val Ser Ser Asn Leu Gln Ala Ala Ser Thr Ala Ala Gln
            500                 505                 510
Thr Gln Val Val Asn Asn Gln Gly Ala Leu Pro Gly Met Val Trp Gln
        515                 520                 525
Asn Arg Asp Val Tyr Leu Gln Gly Pro Ile Trp Ala Lys Ile Pro His
    530                 535                 540
Thr Asp Gly Asn Phe His Pro Ser Pro Leu Met Gly Gly Phe Gly Leu
545                 550                 555                 560
Lys His Pro Pro Pro Gln Ile Leu Ile Lys Asn Thr Pro Val Pro Ala
                565                 570                 575
Asn Pro Pro Glu Val Phe Thr Pro Ala Lys Phe Ala Ser Phe Ile Thr
            580                 585                 590
Gln Tyr Ser Thr Gly Gln Val Ser Val Glu Ile Glu Trp Glu Leu Gln
        595                 600                 605
Lys Glu Asn Ser Lys Arg Trp Asn Pro Glu Ile Gln Tyr Thr Ser Asn
    610                 615                 620
```

Phe Asp Lys Gln Thr Gly Val Asp Phe Ala Val Asp Ser Gln Gly Val
625                 630                 635                 640

Tyr Ser Glu Pro

<210> SEQ ID NO 77
<211> LENGTH: 644
<212> TYPE: PRT
<213> ORGANISM: Unknown
<220> FEATURE:
<223> OTHER INFORMATION: capsid protein of AAV serotype, clone 223-7

<400> SEQUENCE: 77

Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Arg Leu Gln Glu Asp Thr
                20                  25                  30

Ser Phe Gly Gly Asn Leu Gly Arg Ala Val Phe Gln Ala Lys Lys Arg
            35                  40                  45

Val Leu Glu Pro Leu Gly Leu Val Glu Thr Pro Ala Lys Thr Ala Pro
50                  55                  60

Gly Lys Lys Arg Pro Val Asp Ser Pro Asp Ser Thr Ser Gly Ile Gly
65                  70                  75                  80

Lys Lys Gly Gln Gln Pro Ala Lys Lys Arg Leu Asn Phe Gly Gln Thr
                85                  90                  95

Gly Asp Ser Glu Ser Val Pro Asp Pro Gln Pro Ile Gly Glu Pro Pro
            100                 105                 110

Ala Gly Pro Ser Gly Leu Gly Ser Gly Thr Met Ala Ala Gly Gly Gly
        115                 120                 125

Ala Pro Met Ala Asp Asn Asn Glu Gly Ala Asp Gly Val Gly Asn Ala
130                 135                 140

Ser Gly Asn Trp His Cys Asp Ser Thr Trp Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
            180                 185                 190

Tyr Phe Gly Tyr Ser Thr Pro Trp Gly Tyr Phe Asp Phe Asn Arg Phe
        195                 200                 205

His Cys His Phe Ser Pro Arg Asp Trp Gln Arg Leu Ile Asn Asn Asn
210                 215                 220

Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
                245                 250                 255

Leu Thr Ser Thr Val Gln Val Phe Ser Asp Pro Glu Tyr Gln Leu Pro
            260                 265                 270

Tyr Val Leu Gly Ser Ala His Gln Gly Cys Leu Pro Pro Phe Pro Ala
        275                 280                 285

Asp Val Phe Met Ile Pro Gln Tyr Gly Tyr Leu Thr Leu Asn Asn Gly
290                 295                 300

Ser Gln Ser Val Gly Arg Ser Ser Phe Tyr Cys Leu Glu Tyr Phe Pro
305                 310                 315                 320

Ser Gln Met Leu Arg Thr Gly Asn Asn Phe Thr Phe Ser Tyr Thr Phe
                325                 330                 335

Glu Asp Val Pro Phe His Ser Ser Tyr Ala His Ser Gln Ser Leu Asp

```
            340                 345                 350
Arg Leu Met Asn Pro Leu Ile Asp Gln Tyr Leu Tyr Tyr Leu Ala Arg
            355                 360                 365

Thr Gln Ser Asn Ala Gly Gly Thr Ala Gly Asn Arg Glu Leu Gln Phe
    370                 375                 380

Tyr Gln Gly Gly Pro Thr Thr Met Ala Glu Gln Ala Lys Asn Trp Leu
385                 390                 395                 400

Pro Gly Pro Cys Phe Arg Gln Gln Arg Val Ser Lys Thr Leu Asp Gln
                405                 410                 415

Asn Asn Asn Ser Asn Phe Ala Trp Thr Gly Ala Thr Lys Tyr His Leu
            420                 425                 430

Asn Gly Arg Asn Ser Leu Val Asn Pro Gly Val Ala Met Ala Thr His
            435                 440                 445

Lys Asp Asp Glu Glu Arg Phe Phe Pro Ser Ser Gly Val Leu Ile Phe
    450                 455                 460

Gly Lys Thr Gly Ala Ala Asn Lys Thr Thr Leu Glu Asn Val Leu Met
465                 470                 475                 480

Thr Asn Glu Glu Glu Ile Arg Pro Thr Asn Pro Val Ala Thr Glu Glu
                485                 490                 495

Tyr Gly Ile Val Ser Ser Asn Leu Gln Ala Ala Ser Thr Ala Ala Gln
                500                 505                 510

Thr Gln Val Val Asn Asn Gln Gly Ala Leu Pro Gly Met Val Trp Gln
            515                 520                 525

Asn Arg Asp Val Tyr Leu Gln Gly Pro Ile Trp Ala Lys Ile Pro His
            530                 535                 540

Thr Asp Gly Asn Phe His Pro Ser Pro Leu Met Gly Gly Phe Gly Leu
545                 550                 555                 560

Lys His Pro Pro Pro Gln Ile Leu Ile Lys Asn Thr Pro Val Pro Ala
                565                 570                 575

Asn Pro Pro Glu Val Phe Thr Pro Ala Lys Ile Ala Ser Phe Ile Thr
            580                 585                 590

Gln Tyr Ser Thr Gly Gln Val Ser Val Glu Ile Glu Trp Glu Leu Gln
            595                 600                 605

Lys Glu Asn Ser Lys Arg Trp Asn Pro Glu Ile Gln Tyr Thr Ser Asn
    610                 615                 620

Phe Asp Lys Gln Thr Gly Val Asp Phe Ala Val Asp Ser Gln Gly Val
625                 630                 635                 640

Tyr Ser Glu Pro

<210> SEQ ID NO 78
<211> LENGTH: 644
<212> TYPE: PRT
<213> ORGANISM: Unknown
<220> FEATURE:
<223> OTHER INFORMATION: capsid protein of AAV serotype, clone 223-6

<400> SEQUENCE: 78

Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Arg Leu Gln Glu Asp Thr
            20                  25                  30

Ser Phe Gly Gly Asn Leu Gly Arg Ala Val Phe Gln Ala Lys Lys Arg
        35                  40                  45

Val Leu Glu Pro Leu Gly Leu Val Glu Thr Pro Ala Lys Thr Ala Pro
    50                  55                  60
```

```
Gly Lys Lys Arg Pro Val Asp Ser Pro Asp Ser Thr Ser Gly Ile Gly
 65                  70                  75                  80

Lys Lys Gly Gln Gln Pro Ala Lys Lys Arg Leu Asn Phe Gly Gln Thr
                 85                  90                  95

Gly Asp Ser Glu Ser Val Pro Asp Pro Gln Pro Ile Gly Glu Pro Pro
            100                 105                 110

Ala Gly Pro Ser Gly Leu Gly Ser Gly Thr Met Ala Ala Gly Gly Gly
        115                 120                 125

Ala Pro Met Ala Asp Asn Ser Glu Gly Ala Asp Gly Val Gly Asn Ala
    130                 135                 140

Ser Gly Asn Trp His Cys Asp Ser Thr Trp Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
                180                 185                 190

Tyr Phe Gly Tyr Ser Thr Pro Trp Gly Tyr Phe Asp Phe Asn Arg Phe
            195                 200                 205

His Cys His Phe Ser Pro Arg Asp Trp Gln Arg Leu Ile Asn Asn Asn
    210                 215                 220

Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
                245                 250                 255

Leu Thr Ser Thr Val Gln Val Phe Ser Asp Ser Glu Tyr Gln Leu Pro
                260                 265                 270

Tyr Val Leu Gly Ser Ala His Gln Gly Cys Leu Pro Pro Phe Pro Ala
            275                 280                 285

Asp Val Phe Met Ile Pro Gln Tyr Gly Tyr Leu Thr Leu Asn Asn Gly
    290                 295                 300

Ser Gln Ser Val Gly Arg Ser Ser Phe Tyr Cys Leu Glu Tyr Phe Pro
305                 310                 315                 320

Ser Gln Met Leu Arg Thr Gly Asn Asn Phe Thr Phe Ser Tyr Thr Phe
                325                 330                 335

Glu Asp Val Pro Phe His Ser Ser Tyr Ala His Ser Gln Ser Leu Asp
                340                 345                 350

Arg Leu Met Asn Pro Leu Ile Asp Gln Tyr Leu Tyr Tyr Leu Ala Arg
            355                 360                 365

Thr Gln Ser Asn Ala Gly Gly Thr Ala Gly Asn Arg Glu Leu Gln Phe
    370                 375                 380

Tyr Gln Gly Gly Pro Thr Thr Met Ala Glu Gln Ala Lys Asn Trp Leu
385                 390                 395                 400

Pro Gly Pro Cys Phe Arg Gln Gln Arg Val Ser Lys Thr Leu Asp Gln
                405                 410                 415

Asn Asn Asn Ser Asn Phe Ala Trp Thr Gly Ala Thr Lys Tyr His Leu
                420                 425                 430

Asn Gly Arg Asn Ser Leu Val Asn Pro Gly Val Ala Met Ala Thr His
            435                 440                 445

Lys Asp Asp Glu Glu Arg Phe Phe Pro Ser Ser Gly Val Leu Ile Phe
    450                 455                 460

Gly Lys Thr Gly Ala Ala Asn Lys Thr Thr Leu Glu Asn Val Leu Met
465                 470                 475                 480
```

Thr Asn Glu Glu Ile Arg Pro Thr Asn Pro Val Ala Thr Glu Glu
            485                 490                 495

Tyr Gly Ile Val Ser Ser Asn Leu Gln Ala Ala Ser Thr Ala Ala Gln
        500                 505                 510

Thr Gln Val Val Asn Asn Gln Gly Ala Leu Pro Gly Met Val Trp Gln
    515                 520                 525

Asn Arg Asp Val Tyr Leu Gln Gly Pro Ile Trp Ala Lys Ile Pro His
530                 535                 540

Thr Asp Gly Asn Phe His Pro Ser Pro Leu Met Gly Gly Phe Gly Leu
545                 550                 555                 560

Lys His Pro Pro Pro Gln Ile Leu Ile Lys Asn Thr Pro Val Pro Ala
                565                 570                 575

Asn Pro Pro Glu Val Phe Thr Pro Ala Lys Leu Ala Ser Phe Ile Thr
            580                 585                 590

Gln Tyr Ser Thr Gly Gln Val Ser Val Glu Ile Glu Trp Glu Leu Gln
        595                 600                 605

Lys Glu Asn Ser Lys Arg Trp Asn Pro Glu Ile Gln Tyr Thr Ser Asn
    610                 615                 620

Phe Asp Lys Gln Thr Gly Val Asp Phe Ala Val Asp Ser Gln Gly Val
625                 630                 635                 640

Tyr Ser Glu Pro

<210> SEQ ID NO 79
<211> LENGTH: 738
<212> TYPE: PRT
<213> ORGANISM: Unknown
<220> FEATURE:
<223> OTHER INFORMATION: capsid protein of AAV serotype, clone 44.1

<400> SEQUENCE: 79

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly

```
            195                 200                 205
Gly Ala Pro Met Ala Asp Asn Asn Glu Gly Ala Asp Gly Val Gly Ser
210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                    245                 250                 255
Leu Tyr Lys Gln Ile Ser Asn Gly Thr Ser Gly Gly Ser Thr Asn Asp
                260                 265                 270
Asn Thr Tyr Phe Gly Tyr Ser Thr Pro Trp Gly Tyr Phe Asp Phe Asn
                275                 280                 285
Arg Phe His Cys His Phe Ser Pro Arg Asp Trp Gln Arg Leu Ile Asn
                290                 295                 300
Asn Asn Trp Gly Phe Arg Pro Lys Arg Leu Asn Phe Lys Leu Phe Asn
305                 310                 315                 320
Ile Gln Val Lys Glu Val Thr Gln Asn Glu Gly Thr Lys Thr Ile Ala
                    325                 330                 335
Asn Asn Leu Thr Ser Thr Ile Gln Val Phe Thr Asp Ser Glu Tyr Gln
                340                 345                 350
Leu Pro Tyr Val Leu Gly Ser Ala His Gln Gly Cys Leu Pro Pro Phe
                355                 360                 365
Pro Ala Asp Val Phe Met Ile Pro Gln Tyr Gly Tyr Leu Thr Leu Asn
370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
                    405                 410                 415
Gln Phe Glu Asp Val Pro Phe His Ser Ser Tyr Ala His Ser Gln Ser
                420                 425                 430
Leu Asp Arg Leu Met Asn Pro Leu Ile Asp Gln Tyr Leu Tyr Tyr Leu
                435                 440                 445
Ser Arg Thr Gln Ser Thr Gly Gly Thr Ala Gly Thr Gln Gln Leu Leu
450                 455                 460
Phe Ser Gln Ala Gly Pro Asn Asn Met Ser Ala Gln Ala Lys Asn Trp
465                 470                 475                 480
Leu Pro Gly Pro Cys Tyr Arg Gln Gln Arg Val Ser Thr Thr Leu Ser
                    485                 490                 495
Gln Asn Asn Asn Ser Asn Phe Ala Trp Thr Gly Ala Thr Lys Tyr His
                500                 505                 510
Leu Asn Gly Arg Asp Ser Leu Val Asn Pro Gly Val Ala Met Ala Thr
                515                 520                 525
His Lys Asp Asp Glu Glu Arg Phe Phe Pro Ser Ser Gly Val Leu Met
530                 535                 540
Phe Gly Lys Gln Gly Ala Gly Lys Asp Asn Val Asp Tyr Ser Ser Val
545                 550                 555                 560
Met Leu Thr Ser Glu Glu Ile Lys Thr Thr Asn Pro Val Ala Thr
                    565                 570                 575
Glu Gln Tyr Gly Val Val Ala Asp Asn Leu Gln Gln Asn Ala Ala
                580                 585                 590
Pro Ile Val Gly Ala Val Asn Ser Gln Gly Ala Leu Pro Gly Met Val
                595                 600                 605
Trp Gln Asn Arg Asp Val Tyr Leu Gln Gly Pro Ile Trp Ala Lys Ile
610                 615                 620
```

```
Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
            645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 80
<211> LENGTH: 738
<212> TYPE: PRT
<213> ORGANISM: Unknown
<220> FEATURE:
<223> OTHER INFORMATION: capsid protein of AAV serotype, clone 44.5

<400> SEQUENCE: 80

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240
```

```
Ile Thr Thr Ser Thr Arg Thr Trp Ala Leu Pro Thr Tyr Asn Asn His
            245             250             255

Leu Tyr Lys Gln Ile Ser Asn Gly Thr Ser Gly Gly Ser Thr Asn Asp
        260             265             270

Asn Thr Tyr Phe Gly Tyr Ser Thr Pro Trp Gly Tyr Phe Asp Phe Asn
    275             280             285

Arg Phe His Cys His Phe Ser Pro Arg Asp Trp Gln Arg Leu Ile Asn
290             295             300

Asn Asn Trp Gly Phe Arg Pro Lys Arg Pro Asn Phe Lys Leu Phe Asn
305             310             315             320

Ile Gln Val Lys Glu Val Thr Gln Asn Glu Gly Thr Lys Thr Ile Ala
            325             330             335

Asn Asn Leu Thr Ser Thr Ile Gln Val Phe Thr Asp Ser Glu Tyr Gln
            340             345             350

Leu Pro Tyr Val Leu Gly Ser Ala His Gln Gly Cys Leu Pro Pro Phe
        355             360             365

Pro Ala Asp Val Phe Met Ile Pro Gln Tyr Gly Tyr Leu Thr Leu Asn
    370             375             380

Asn Gly Ser Gln Ala Val Gly Arg Ser Ser Phe Tyr Cys Leu Glu Tyr
385             390             395             400

Phe Pro Ser Gln Met Leu Arg Thr Gly Asn Asn Phe Glu Phe Ser Tyr
            405             410             415

Gln Phe Glu Asp Val Pro Phe His Ser Ser Tyr Ala His Ser Gln Ser
            420             425             430

Leu Asp Arg Leu Met Asn Pro Leu Ile Asp Gln Tyr Leu Tyr Tyr Leu
        435             440             445

Ser Arg Thr Gln Ser Thr Gly Gly Thr Ala Gly Thr Gln Gln Leu Leu
    450             455             460

Phe Ser Gln Ala Gly Pro Asn Asn Met Ser Ala Gln Ala Lys Asn Trp
465             470             475             480

Leu Pro Gly Pro Cys Tyr Arg Gln Gln Arg Val Ser Thr Thr Leu Ser
            485             490             495

Gln Asn Asn Asn Ser Asn Phe Ala Trp Thr Gly Ala Thr Lys Tyr His
        500             505             510

Leu Asn Gly Arg Asp Ser Leu Val Asn Pro Gly Val Ala Met Ala Thr
    515             520             525

His Lys Asp Asp Glu Glu Arg Phe Phe Pro Ser Ser Gly Val Leu Met
530             535             540

Phe Gly Lys Gln Gly Ala Gly Lys Asp Asn Val Asp Tyr Ser Ser Val
545             550             555             560

Met Leu Thr Ser Glu Glu Glu Ile Lys Thr Thr Asn Pro Val Ala Thr
            565             570             575

Glu Gln Tyr Gly Val Val Ala Asp Asn Leu Gln Gln Gln Asn Ala Ala
            580             585             590

Pro Ile Val Gly Ala Val Asn Ser Gln Gly Ala Leu Pro Gly Met Val
        595             600             605

Trp Gln Asn Arg Asp Val Tyr Leu Gln Gly Pro Ile Trp Ala Lys Ile
    610             615             620

Pro His Thr Asp Gly Asn Phe His Pro Ser Pro Leu Met Gly Gly Phe
625             630             635             640

Gly Leu Lys His Pro Pro Pro Gln Ile Leu Ile Lys Asn Thr Pro Val
            645             650             655

Pro Ala Asp Pro Pro Thr Thr Phe Ser Gln Ala Lys Leu Ala Ser Phe
```

```
                        660                 665                 670
Ile Thr Gln Tyr Ser Thr Gly Gln Val Ser Val Glu Ile Glu Trp Glu
                    675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                    725                 730                 735

Asn Leu

<210> SEQ ID NO 81
<211> LENGTH: 738
<212> TYPE: PRT
<213> ORGANISM: Unknown
<220> FEATURE:
<223> OTHER INFORMATION: capsid protein of AAV serotype, clone 44.2

<400> SEQUENCE: 81

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285
```

-continued

```
Arg Phe His Cys His Phe Ser Pro Arg Asp Trp Gln Arg Leu Ile Asn
            290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
            595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
690                 695                 700
```

-continued

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
            725                 730                 735

Asn Leu

<210> SEQ ID NO 82
<211> LENGTH: 738
<212> TYPE: PRT
<213> ORGANISM: Unknown
<220> FEATURE:
<223> OTHER INFORMATION: capsid protein of AAV serotype, clone 29.3VP1

<400> SEQUENCE: 82

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Thr Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala

-continued

```
                325                 330                 335
Asn Asn Leu Thr Ser Thr Ile Gln Val Phe Thr Asp Ser Glu Tyr Gln
            340                 345                 350
Leu Pro Tyr Val Leu Gly Ser Ala Arg Gln Gly Cys Leu Pro Pro Phe
            355                 360                 365
Pro Ala Asp Val Phe Met Ile Pro Gln Tyr Gly Tyr Leu Thr Leu Asn
            370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
            405                 410                 415
Gln Phe Glu Asp Val Pro Phe His Ser Ser Tyr Ala His Ser Gln Ser
            420                 425                 430
Leu Asp Arg Leu Met Asn Pro Leu Ile Asp Gln Tyr Leu Tyr Tyr Leu
            435                 440                 445
Ser Arg Thr Gln Ser Thr Gly Gly Thr Ala Gly Thr Gln Gln Leu Leu
            450                 455                 460
Phe Ser Gln Ala Gly Pro Asn Asn Met Ser Ala Gln Ala Lys Asn Trp
465                 470                 475                 480
Leu Pro Gly Pro Cys Tyr Arg Gln Gln Arg Val Ser Thr Thr Leu Ser
            485                 490                 495
Gln Asn Asn Asn Ser Asn Phe Ala Trp Thr Gly Ala Thr Lys Tyr His
            500                 505                 510
Leu Asn Gly Arg Asp Ser Leu Val Asn Pro Gly Val Ala Met Ala Thr
            515                 520                 525
His Lys Asp Asp Glu Glu Arg Phe Phe Pro Ser Ser Gly Val Leu Met
            530                 535                 540
Phe Gly Lys Gln Gly Ala Gly Lys Gly Asn Val Asp Tyr Ser Ser Val
545                 550                 555                 560
Met Leu Thr Ser Glu Glu Glu Ile Lys Thr Thr Asn Pro Val Ala Thr
            565                 570                 575
Glu Gln Tyr Gly Val Val Ala Asp Asn Leu Gln Gln Gln Asn Ala Ala
            580                 585                 590
Pro Ile Val Gly Ala Val Asn Ser Gln Gly Ala Leu Pro Gly Met Val
            595                 600                 605
Trp Gln Asn Arg Asp Val Tyr Leu Gln Gly Pro Ile Trp Ala Lys Ile
            610                 615                 620
Pro His Thr Asp Gly Asn Phe His Pro Ser Pro Leu Met Gly Gly Phe
625                 630                 635                 640
Gly Leu Lys His Pro Pro Pro Gln Ile Leu Ile Lys Asn Thr Pro Val
            645                 650                 655
Pro Ala Asp Pro Pro Thr Thr Phe Ser Gln Ala Lys Leu Ala Ser Phe
            660                 665                 670
Ile Thr Gln Tyr Ser Thr Gly Gln Val Ser Val Glu Ile Glu Trp Glu
            675                 680                 685
Leu Gln Lys Glu Asn Ser Lys Arg Trp Asn Pro Glu Ile Gln Tyr Thr
            690                 695                 700
Ser Asn Tyr Tyr Lys Ser Thr Asn Val Asp Phe Ala Val Asn Thr Asp
705                 710                 715                 720
Gly Thr Tyr Ser Glu Pro Arg Pro Ile Gly Thr Arg Tyr Leu Thr Arg
            725                 730                 735

Asn Leu
```

<210> SEQ ID NO 83
<211> LENGTH: 738
<212> TYPE: PRT
<213> ORGANISM: Unknown
<220> FEATURE:
<223> OTHER INFORMATION: capsid protein of AAV serotype, clone 29.5VP1

<400> SEQUENCE: 83

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Gly Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Ser Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365
```

```
Pro Ala Asp Val Phe Met Ile Pro Gln Tyr Gly Tyr Leu Thr Leu Asn
        370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asp Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
                515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
                580                 585                 590

Pro Ile Val Gly Ala Val Asn Ser Gln Gly Ala Leu Pro Gly Met Val
                595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 84
<211> LENGTH: 738
<212> TYPE: PRT
<213> ORGANISM: Unknown
<220> FEATURE:
<223> OTHER INFORMATION: capsid protein of AAV serotype, clone 42.15
```

```
<400> SEQUENCE: 84

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Thr Gly Gln Gln Pro Ala Lys Lys Arg Leu Asn Phe Gly Gln
            165                 170                 175

Thr Gly Asp Ser Glu Ser Val Pro Asp Pro Gln Pro Ile Gly Glu Pro
        180                 185                 190

Pro Ala Gly Pro Ser Gly Leu Gly Ser Gly Thr Met Ala Ala Gly Gly
    195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Asn Gly Thr Ser Gly Gly Ser Thr Asn Asp
        260                 265                 270

Asn Thr Tyr Phe Gly Tyr Ser Thr Pro Trp Gly Tyr Phe Asp Phe Asn
    275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Pro Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Arg Arg Thr Gly Asn Asn Phe Glu Phe Ser Tyr
                405                 410                 415
```

Gln Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 85
<211> LENGTH: 738
<212> TYPE: PRT
<213> ORGANISM: Unknown
<220> FEATURE:
<223> OTHER INFORMATION: capsid protein of AAV serotype, clone 42.8

<400> SEQUENCE: 85

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Gly Arg Gly Leu Val Leu Pro
                35                  40                  45
Gly Tyr Lys Tyr Leu Gly Pro Phe Asn Gly Leu Asp Lys Gly Glu Pro
 50                  55                  60
Val Asn Ala Ala Asp Ala Ala Leu Glu His Asp Lys Ala Tyr Asp
 65                  70                  75                  80
Gln Gln Leu Lys Ala Gly Asp Asn Pro Tyr Leu Arg Tyr Asn His Ala
                 85                  90                  95
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Val Leu Glu Pro
                115                 120                 125
Leu Gly Leu Val Glu Glu Gly Ala Lys Thr Ala Pro Gly Lys Lys Arg
    130                 135                 140
Pro Val Glu Pro Ser Pro Gln Arg Ser Pro Asp Ser Ser Thr Gly Ile
145                 150                 155                 160
Gly Lys Thr Gly Gln Gln Pro Ala Lys Lys Arg Leu Asn Phe Gly Gln
                165                 170                 175
Thr Gly Asp Ser Glu Ser Val Pro Asp Pro Gln Pro Ile Gly Glu Pro
                180                 185                 190
Pro Ala Gly Pro Ser Gly Leu Gly Ser Gly Thr Met Ala Ala Gly Gly
                195                 200                 205
Gly Ala Pro Met Ala Asp Asn Asn Glu Gly Ala Asp Gly Val Gly Ser
    210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ser Thr Asn Asp
                260                 265                 270
Asn Thr Tyr Phe Gly Tyr Ser Thr Pro Trp Gly Tyr Phe Asp Phe Asn
                275                 280                 285
Arg Phe His Cys His Phe Ser Pro Arg Asp Trp Gln Arg Leu Ile Asn
    290                 295                 300
Asn Asn Trp Gly Phe Arg Pro Lys Arg Leu Asn Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
                340                 345                 350
Leu Pro Tyr Val Leu Gly Ser Ala His Gln Gly Cys Leu Pro Pro Phe
                355                 360                 365
Pro Ala Asp Val Phe Met Ile Pro Gln Tyr Gly Tyr Leu Thr Leu Asn
    370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
                405                 410                 415
Gln Phe Glu Asp Val Pro Phe His Ser Ser Tyr Ala His Ser Gln Ser
                420                 425                 430
Leu Asp Arg Leu Met Asn Pro Leu Ile Asp Gln Tyr Leu Tyr Tyr Leu
                435                 440                 445
Ser Arg Thr Gln Ser Thr Gly Gly Thr Ala Gly Thr Gln Gln Leu Leu

```
            450                 455                 460
Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                    485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
                515                 520                 525

His Lys Asp Asp Glu Glu Arg Phe Phe Pro Ser Ser Gly Val Leu Met
                530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
                580                 585                 590

Pro Ile Val Gly Ala Val Asn Ser Gln Gly Ala Leu Pro Gly Met Val
                595                 600                 605

Trp Gln Asn Arg Asp Val Tyr Leu Gln Gly Pro Ile Trp Ala Lys Ile
                610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
                690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                    725                 730                 735

Asn Leu

<210> SEQ ID NO 86
<211> LENGTH: 733
<212> TYPE: PRT
<213> ORGANISM: Unknown
<220> FEATURE:
<223> OTHER INFORMATION: capsid protein of AAV serotype, clone 42.13

<400> SEQUENCE: 86

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80
```

-continued

```
Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Leu Asn Phe Gly Thr Gly Asp Ser Glu
                165                 170                 175

Ser Val Pro Asp Pro Gln Pro Ile Gly Glu Pro Ala Gly Pro Ser
            180                 185                 190

Gly Leu Gly Ser Gly Thr Met Ala Ala Gly Gly Ala Pro Met Ala
        195                 200                 205

Asp Asn Asn Glu Gly Ala Asp Gly Val Gly Ser Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Asn Gly Thr Ser Gly Ser Thr Asn Asp Asn Thr Tyr Phe Gly
            260                 265                 270

Tyr Ser Thr Pro Trp Gly Tyr Phe Asp Phe Asn Arg Phe His Cys His
        275                 280                 285

Phe Ser Pro Arg Asp Trp Gln Arg Leu Ile Asn Asn Asn Trp Gly Phe
    290                 295                 300

Arg Pro Lys Arg Leu Asn Phe Lys Leu Phe Asn Ile Gln Val Lys Glu
305                 310                 315                 320

Val Thr Gln Asn Glu Gly Thr Lys Thr Ile Ala Asn Asn Leu Thr Ser
                325                 330                 335

Thr Ile Gln Val Phe Thr Asp Ser Glu Tyr Gln Leu Pro Tyr Val Leu
            340                 345                 350

Gly Ser Ala His Gln Gly Cys Leu Pro Pro Phe Pro Ala Asp Val Phe
        355                 360                 365

Met Ile Pro Gln Tyr Gly Tyr Leu Thr Leu Asn Asn Gly Ser Gln Ala
    370                 375                 380

Val Gly Arg Ser Ser Phe Tyr Cys Leu Glu Tyr Phe Pro Ser Gln Met
385                 390                 395                 400

Leu Arg Thr Gly Asn Asn Phe Glu Phe Ser Tyr Gln Phe Glu Asp Val
                405                 410                 415

Pro Phe His Ser Ser Tyr Ala His Ser Gln Ser Leu Asp Arg Leu Met
            420                 425                 430

Asn Pro Leu Ile Asp Gln Tyr Leu Tyr Tyr Leu Ser Arg Thr Gln Ser
        435                 440                 445

Thr Gly Gly Thr Ala Gly Thr Gln Gln Leu Leu Phe Ser Gln Ala Gly
    450                 455                 460

Pro Asn Asn Met Ser Ala Gln Ala Lys Asn Trp Leu Pro Gly Pro Cys
465                 470                 475                 480

Tyr Arg Gln Gln Arg Val Ser Thr Thr Val Ser Gln Asn Asn Asn Ser
                485                 490                 495
```

```
Asn Phe Ala Trp Thr Gly Ala Thr Lys Tyr His Leu Asn Gly Arg Asp
                500                 505                 510

Ser Leu Val Asn Pro Gly Val Ala Met Ala Thr His Lys Gly Asp Glu
            515                 520                 525

Glu Arg Phe Phe Pro Ser Ser Gly Val Leu Met Phe Gly Lys Gln Gly
        530                 535                 540

Ala Gly Lys Asp Asn Val Asp Tyr Ser Ser Val Met Leu Thr Ser Glu
545                 550                 555                 560

Glu Glu Ile Lys Thr Thr Asn Pro Val Ala Thr Glu Gln Tyr Gly Val
                565                 570                 575

Val Ala Asp Asn Leu Gln Gln Gln Asn Ala Ala Pro Ile Val Gly Ala
            580                 585                 590

Val Asn Ser Gln Gly Ala Leu Pro Gly Met Val Trp Gln Asn Arg Asp
        595                 600                 605

Val Tyr Leu Gln Gly Pro Ile Trp Ala Lys Ile Pro His Thr Asp Gly
610                 615                 620

Asn Phe His Pro Ser Pro Leu Met Gly Gly Phe Gly Leu Lys His Pro
625                 630                 635                 640

Pro Pro Gln Ile Leu Ile Lys Asn Thr Pro Val Pro Ala Asp Pro Pro
                645                 650                 655

Thr Thr Phe Ser Gln Ala Lys Leu Ala Ser Phe Ile Thr Gln Tyr Ser
            660                 665                 670

Thr Gly Gln Val Ser Val Glu Ile Glu Trp Glu Leu Gln Lys Glu Asn
        675                 680                 685

Ser Lys Arg Trp Asn Pro Glu Ile Gln Tyr Thr Ser Asn Tyr Tyr Lys
690                 695                 700

Ser Thr Asn Val Asp Phe Ala Val Asn Thr Glu Gly Thr Tyr Ser Glu
705                 710                 715                 720

Pro Arg Pro Ile Gly Thr Arg Tyr Leu Thr Arg Ser Leu
                725                 730

<210> SEQ ID NO 87
<211> LENGTH: 733
<212> TYPE: PRT
<213> ORGANISM: Unknown
<220> FEATURE:
<223> OTHER INFORMATION: capsid protein of AAV serotype, clone 42.3A

<400> SEQUENCE: 87

Met Ala Ala Asp Gly His Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125
```

```
Leu Gly Leu Val Glu Glu Gly Ala Lys Thr Ala Pro Gly Lys Lys Arg
        130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Ile Gly Glu Pro Ala Gly Pro Ser
                180                 185                 190

Gly Leu Gly Ser Gly Thr Met Ala Ala Gly Gly Ala Pro Met Ala
        195                 200                 205

Asp Asn Asn Glu Gly Ala Asp Gly Val Gly Ser Ser Ser Gly Asn Trp
        210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Asn Gly Thr Ser Gly Gly Ser Thr Asn Asp Asn Thr Tyr Phe Gly
                260                 265                 270

Tyr Ser Thr Pro Trp Gly Tyr Phe Asp Phe Asn Arg Phe His Cys His
        275                 280                 285

Phe Ser Pro Arg Asp Trp Gln Arg Leu Ile Asn Asn Ser Trp Gly Phe
290                 295                 300

Arg Pro Lys Arg Leu Asn Phe Lys Leu Phe Asn Ile Gln Val Lys Glu
305                 310                 315                 320

Val Thr Gln Asn Glu Gly Thr Lys Thr Ile Ala Asn Asn Leu Thr Ser
                325                 330                 335

Thr Ile Gln Val Phe Thr Asp Ser Glu Tyr Gln Leu Pro Tyr Val Leu
                340                 345                 350

Gly Ser Ala His Gln Gly Cys Leu Pro Pro Phe Pro Ala Asp Val Phe
        355                 360                 365

Met Ile Pro Gln Tyr Gly Tyr Leu Thr Leu Asn Asn Gly Ser Gln Ala
370                 375                 380

Val Gly Arg Ser Ser Phe Tyr Cys Leu Glu Tyr Phe Pro Ser Gln Met
385                 390                 395                 400

Leu Arg Thr Gly Asn Asn Phe Glu Phe Ser Tyr Gln Phe Glu Asp Val
                405                 410                 415

Pro Phe His Ser Ser Tyr Ala His Ser Gln Ser Leu Asp Arg Leu Met
                420                 425                 430

Asn Pro Leu Ile Asp Gln Tyr Leu Tyr Tyr Leu Ser Arg Thr Gln Ser
                435                 440                 445

Thr Gly Gly Thr Ala Gly Thr Gln Gln Leu Leu Phe Ser Gln Ala Gly
        450                 455                 460

Pro Asn Asn Met Ser Ala Gln Ala Lys Asn Trp Leu Pro Gly Pro Cys
465                 470                 475                 480

Tyr Arg Gln Gln Arg Val Ser Thr Thr Leu Ser Gln Asn Asn Asn Ser
                485                 490                 495

Asn Phe Ala Trp Thr Gly Ala Thr Lys Tyr His Leu Asn Gly Arg Asp
                500                 505                 510

Ser Leu Val Asn Pro Gly Val Ala Met Ala Thr His Lys Asp Asp Glu
                515                 520                 525

Glu Arg Phe Phe Pro Ser Ser Gly Val Leu Met Phe Gly Lys Gln Gly
        530                 535                 540

Ala Gly Lys Asp Asn Val Asp Tyr Ser Ser Val Met Leu Thr Ser Glu
```

```
545                 550                 555                 560
Glu Glu Ile Lys Thr Thr Asn Pro Val Ala Thr Glu Gln Tyr Gly Val
                565                 570                 575

Val Ala Asp Asn Leu Gln Gln Gln Asn Ala Ala Pro Ile Val Gly Ala
                580                 585                 590

Val Asn Ser Gln Gly Ala Leu Pro Gly Met Val Trp Gln Asn Arg Asp
                595                 600                 605

Val Tyr Leu Gln Gly Pro Ile Trp Ala Lys Ile Pro His Thr Asp Gly
                610                 615                 620

Asn Phe His Pro Ser Pro Leu Met Gly Gly Phe Gly Leu Lys His Pro
625                 630                 635                 640

Pro Pro Gln Ile Leu Ile Lys Asn Thr Pro Val Pro Ala Asp Pro Pro
                645                 650                 655

Thr Thr Phe Ser Gln Ala Lys Leu Ala Ser Phe Ile Thr Gln Tyr Ser
                660                 665                 670

Thr Gly Gln Val Ser Val Glu Ile Glu Trp Glu Leu Gln Lys Glu Asn
                675                 680                 685

Ser Lys Arg Trp Asn Pro Glu Ile Gln Tyr Thr Ser Asn Tyr Tyr Lys
                690                 695                 700

Ser Thr Asn Val Asp Phe Ala Val Asn Thr Glu Gly Thr Tyr Ser Glu
705                 710                 715                 720

Pro Arg Pro Ile Gly Thr Arg Tyr Leu Thr Arg Asn Leu
                725                 730

<210> SEQ ID NO 88
<211> LENGTH: 731
<212> TYPE: PRT
<213> ORGANISM: Unknown
<220> FEATURE:
<223> OTHER INFORMATION: capsid protein of AAV serotype, clone 42.4

<400> SEQUENCE: 88

Met Ala Ala Asp Gly Tyr Leu Pro Asp Trp Leu Glu Asp Asn Leu Ser
1                   5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
                35                  40                  45

Gly Tyr Lys Tyr Leu Gly Pro Phe Asn Gly Leu Asp Lys Gly Glu Pro
50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
                130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Ile Gly Glu Pro Pro Ala Gly Pro Ser
```

```
                180             185             190
Gly Leu Gly Ser Gly Thr Met Ala Ala Gly Gly Ala Pro Met Ala
            195             200             205

Asp Asn Asn Glu Gly Ala Asp Gly Val Gly Asn Ala Ser Gly Asn Trp
210                 215                 220

His Cys Asp Ser Thr Trp Leu Gly Asp Arg Val Ile Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Gly Tyr Ser
            260                 265                 270

Thr Pro Trp Gly Tyr Phe Asp Phe Asn Arg Phe His Cys His Phe Ser
        275                 280                 285

Ser Arg Asp Trp Gln Arg Leu Ile Asn Asn Trp Gly Phe Arg Pro
        290                 295                 300

Lys Arg Leu Asn Phe Lys Leu Phe Asn Ile Gln Val Lys Glu Val Thr
305                 310                 315                 320

Gln Asn Glu Gly Thr Lys Thr Ile Ala Asn Asn Leu Thr Ser Thr Ile
                325                 330                 335

Gln Val Phe Thr Asp Ser Glu Tyr Arg Leu Pro Tyr Val Leu Gly Ser
            340                 345                 350

Ala His Gln Gly Cys Leu Pro Pro Phe Pro Ala Asp Val Phe Met Ile
            355                 360                 365

Pro Gln Tyr Gly Tyr Leu Thr Leu Asn Asn Gly Ser Gln Ala Val Gly
        370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Gln Phe Glu Asp Val Pro Phe
                405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Ser Arg Thr Gln Ser Thr Gly
            435                 440                 445

Gly Thr Ala Gly Thr Gln Gln Leu Leu Phe Ser Gln Ala Gly Pro Asn
        450                 455                 460

Asn Met Ser Ala Gln Ala Lys Asn Trp Leu Pro Gly Pro Cys Tyr Arg
465                 470                 475                 480

Gln Gln Arg Val Ser Thr Thr Leu Ser Gln Asn Asn Asn Ser Asn Phe
                485                 490                 495

Ala Trp Thr Gly Ala Thr Lys Tyr His Leu Asn Gly Arg Asp Ser Leu
            500                 505                 510

Val Asn Pro Gly Val Ala Met Ala Thr His Lys Asp Asp Glu Glu Arg
        515                 520                 525

Phe Phe Pro Ser Ser Gly Val Leu Met Phe Gly Lys Gln Gly Ala Gly
        530                 535                 540

Lys Asp Asn Val Asp Tyr Ser Ser Val Met Leu Thr Ser Glu Glu Glu
545                 550                 555                 560

Ile Lys Thr Thr Asn Pro Val Ala Thr Glu Gln Tyr Gly Val Val Ala
                565                 570                 575

Asp Asn Leu Gln Gln Gln Asn Ala Ala Pro Ile Val Gly Ala Val Asn
            580                 585                 590

Ser Gln Gly Ala Leu Pro Gly Met Val Trp Gln Asn Arg Asp Val Tyr
        595                 600                 605
```

-continued

Leu Gln Gly Pro Ile Trp Ala Lys Ile Pro His Thr Asp Gly Asn Phe
610                 615                 620

His Pro Ser Pro Leu Met Gly Gly Phe Gly Leu Lys His Pro Pro
625             630                 635                 640

Gln Ile Leu Ile Lys Asn Thr Pro Val Pro Ala Asp Pro Pro Thr Thr
        645                 650                 655

Phe Ser Gln Ala Lys Pro Ala Ser Phe Ile Thr Gln Tyr Ser Thr Gly
            660                 665                 670

Gln Val Ser Val Glu Ile Glu Trp Glu Leu Gln Lys Glu Asn Ser Lys
        675                 680                 685

Arg Trp Asn Pro Glu Ile Gln Tyr Thr Ser Asn Tyr Tyr Lys Ser Thr
    690                 695                 700

Asn Val Asp Phe Ala Val Asn Thr Glu Gly Thr Tyr Ser Glu Pro Arg
705                 710                 715                 720

Pro Ile Gly Thr Arg Tyr Leu Thr Arg Asn Leu
            725                 730

<210> SEQ ID NO 89
<211> LENGTH: 731
<212> TYPE: PRT
<213> ORGANISM: Unknown
<220> FEATURE:
<223> OTHER INFORMATION: capsid protein of AAV serotype, clone 42.5A

<400> SEQUENCE: 89

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Arg Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Pro Ala Ala Pro Ser
            180                 185                 190

Gly Leu Gly Ser Gly Thr Met Ala Ala Gly Gly Ala Pro Met Ala
        195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240

-continued

```
Arg Thr Trp Ala Leu Pro Thr Tyr Asn Asn His Leu Tyr Lys Gln Ile
            245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
            275                 280                 285

Pro Arg Asp Trp Gln Arg Leu Ile Asn Asn Arg Gly Phe Arg Pro
        290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
                340                 345                 350

Ala His Gln Gly Cys Leu Pro Pro Phe Pro Ala Asp Val Phe Met Ile
            355                 360                 365

Pro Gln Tyr Gly Tyr Leu Thr Leu Asn Asn Gly Ser Gln Ser Val Gly
        370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Gln Phe Glu Asp Val Pro Phe
                405                 410                 415

His Ser Ser Tyr Ala His Ser Gln Ser Leu Asp Arg Leu Met Asn Pro
                420                 425                 430

Leu Ile Asp Gln Tyr Leu Tyr Tyr Leu Ser Arg Thr Gln Ser Thr Gly
            435                 440                 445

Gly Thr Ala Gly Thr Gln Gln Leu Leu Phe Ser Gln Ala Gly Pro Asn
        450                 455                 460

Asn Met Ser Ala Gln Ala Lys Asn Trp Leu Pro Gly Pro Cys Tyr Arg
465                 470                 475                 480

Gln Gln Arg Val Ser Thr Thr Leu Ser Gln Asn Asn Asn Ser Asn Phe
                485                 490                 495

Ala Trp Thr Gly Ala Thr Lys Tyr His Leu Asn Gly Arg Asp Ser Leu
            500                 505                 510

Val Asn Pro Gly Val Ala Met Ala Thr His Lys Asp Asp Glu Glu Arg
            515                 520                 525

Phe Phe Pro Ser Ser Gly Val Leu Met Phe Gly Lys Gln Gly Ala Gly
        530                 535                 540

Lys Asp Asn Val Asp Tyr Ser Ser Val Met Leu Thr Ser Glu Glu Glu
545                 550                 555                 560

Ile Lys Thr Thr Asn Pro Val Ala Thr Glu Gln Tyr Gly Val Val Ala
                565                 570                 575

Asp Asn Leu Gln Gln Gln Asn Ala Ala Pro Ile Val Gly Ala Val Asn
            580                 585                 590

Ser Gln Gly Ala Leu Pro Gly Met Ala Trp Gln Asn Arg Asp Val Tyr
        595                 600                 605

Leu Gln Gly Pro Ile Trp Ala Lys Ile Pro His Thr Asp Gly Asn Phe
        610                 615                 620

His Pro Ser Pro Leu Met Gly Gly Phe Gly Leu Lys His Pro Pro Pro
625                 630                 635                 640

Gln Ile Leu Ile Lys Asn Thr Pro Val Pro Ala Asp Pro Pro Thr Thr
                645                 650                 655
```

```
Phe Ser Gln Ala Lys Leu Ala Ser Phe Ile Thr Gln Tyr Ser Thr Gly
            660                 665                 670

Gln Val Ser Val Glu Ile Glu Trp Glu Leu Gln Lys Glu Asn Ser Lys
        675                 680                 685

Arg Trp Asn Pro Glu Ile Gln Tyr Thr Ser Asn Tyr Tyr Lys Ser Thr
    690                 695                 700

Asn Val Asp Phe Ala Val Asn Thr Glu Gly Thr Tyr Ser Glu Pro Arg
705                 710                 715                 720

Pro Ile Gly Thr Arg Tyr Leu Thr Arg Asn Leu
                725                 730

<210> SEQ ID NO 90
<211> LENGTH: 733
<212> TYPE: PRT
<213> ORGANISM: Unknown
<220> FEATURE:
<223> OTHER INFORMATION: capsid protein of AAV serotype, clone 42.1B

<400> SEQUENCE: 90

Met Ala Ala Asp Gly Tyr Leu Pro Asp Trp Leu Glu Asp Asn Leu Ser
1               5                   10                  15

Glu Gly Ile Arg Glu Trp Trp Asp Leu Arg Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp Lys Gln
65                  70                  75                  80

Lys Gln Leu Glu Gln Gly Asp Asn Pro Tyr Leu Lys Tyr Asn His Ala
            85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Arg Leu Asn Phe Gly Gln Thr Gly Asp Ser Glu
                165                 170                 175

Ser Val Pro Asp Pro Gln Pro Ile Gly Glu Pro Pro Ala Gly Pro Ser
            180                 185                 190

Gly Leu Gly Ser Gly Thr Met Ala Ala Gly Gly Ala Pro Met Ala
        195                 200                 205

Asp Asn Asn Glu Gly Ala Asp Gly Val Gly Ser Ser Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Asn Gly Thr Ser Gly Gly Ser Thr Asn Asp Asn Thr Tyr Phe Gly
            260                 265                 270

Tyr Ser Thr Pro Trp Gly Tyr Phe Asp Phe Asn Arg Phe His Cys His
        275                 280                 285
```

```
Phe Ser Pro Arg Asp Trp Gln Arg Leu Ile Asn Asn Asn Trp Gly Phe
    290                 295                 300

Arg Pro Lys Arg Leu Asn Phe Lys Leu Phe Asn Ile Gln Val Lys Glu
305                 310                 315                 320

Val Thr Gln Asn Glu Gly Thr Lys Thr Ile Ala Asn Asn Leu Thr Ser
                325                 330                 335

Thr Ile Gln Val Phe Thr Asp Ser Glu Tyr Gln Leu Pro Tyr Val Leu
                340                 345                 350

Gly Ser Ala His Gln Gly Cys Leu Pro Pro Phe Pro Ala Asp Val Phe
            355                 360                 365

Met Ile Pro Gln Tyr Gly Tyr Leu Thr Leu Asn Asn Gly Ser Gln Ala
370                 375                 380

Val Gly Arg Ser Ser Phe Tyr Cys Leu Glu Tyr Phe Pro Ser Gln Met
385                 390                 395                 400

Leu Arg Thr Gly Asn Asn Phe Glu Phe Ser Tyr Gln Phe Glu Asp Val
                405                 410                 415

Pro Phe His Ser Ser Tyr Ala His Ser Gln Ser Leu Asp Arg Leu Met
            420                 425                 430

Asn Pro Leu Ile Asp Gln Tyr Leu Tyr Tyr Leu Ser Arg Thr Gln Ser
                435                 440                 445

Thr Gly Gly Thr Ala Gly Thr Gln Gln Leu Leu Phe Ser Gln Ala Gly
    450                 455                 460

Pro Asn Asn Met Ser Ala Gln Ala Lys Asn Trp Leu Pro Gly Pro Cys
465                 470                 475                 480

Tyr Arg Gln Gln Arg Val Ser Thr Thr Val Ser Gln Asn Asn Asn Ser
                485                 490                 495

Asn Phe Ala Trp Thr Gly Ala Thr Lys Tyr His Leu Asn Gly Arg Asp
            500                 505                 510

Ser Leu Val Asn Pro Gly Val Ala Met Ala Thr His Lys Gly Asp Glu
    515                 520                 525

Glu Arg Phe Phe Pro Ser Ser Gly Val Leu Met Phe Gly Lys Gln Gly
530                 535                 540

Ala Gly Lys Asp Asn Val Asp Tyr Ser Ser Val Met Leu Thr Ser Glu
545                 550                 555                 560

Glu Glu Ile Lys Thr Thr Asn Pro Val Ala Thr Glu Gln Tyr Gly Val
                565                 570                 575

Val Ala Asp Asn Leu Gln Gln Gln Asn Ala Ala Pro Ile Val Gly Ala
            580                 585                 590

Val Asn Ser Gln Gly Ala Leu Pro Gly Met Val Trp Gln Asn Arg Asp
    595                 600                 605

Val Tyr Leu Gln Gly Pro Ile Trp Ala Lys Ile Pro His Thr Asp Gly
610                 615                 620

Asn Phe His Pro Ser Pro Leu Met Gly Gly Phe Gly Leu Lys His Pro
625                 630                 635                 640

Pro Pro Gln Ile Leu Ile Lys Asn Thr Pro Val Pro Ala Asp Pro Pro
                645                 650                 655

Thr Thr Phe Ser Gln Ala Lys Leu Ala Ser Phe Ile Thr Gln Tyr Ser
            660                 665                 670

Thr Gly Gln Val Ser Val Glu Ile Glu Trp Glu Leu Gln Lys Glu Asn
    675                 680                 685

Ser Lys Arg Trp Asn Pro Glu Ile Gln Tyr Thr Ser Asn Tyr Tyr Lys
690                 695                 700

Ser Thr Asn Val Asp Phe Ala Val Asn Thr Glu Gly Thr Tyr Ser Glu
```

-continued

```
                705                 710                 715                 720

Pro Arg Pro Ile Gly Thr Arg Tyr Leu Thr Arg Asn Leu
                725                 730

<210> SEQ ID NO 91
<211> LENGTH: 738
<212> TYPE: PRT
<213> ORGANISM: Unknown
<220> FEATURE:
<223> OTHER INFORMATION: capsid protein of AAV serotype, clone 42.5B

<400> SEQUENCE: 91

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
```

```
                    340                 345                 350
Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
        370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 92
<211> LENGTH: 738
```

```
<212> TYPE: PRT
<213> ORGANISM: Unknown
<220> FEATURE:
<223> OTHER INFORMATION: capsid protein of AAV serotype, clone 43.1

<400> SEQUENCE: 92
```

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly His Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Pro Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
            405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Thr Gln Gly Thr Gln Gln Leu Leu
450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
            485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
            565                 570                 575

Glu Gln Tyr Gly Val Val Ala Asp Asn Leu Gln Gln Thr Asn Gly Ala
            580                 585                 590

Pro Ile Val Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Gln Ile Leu Val Lys Asn Thr Pro Val
            645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
            725                 730                 735

Asn Leu

<210> SEQ ID NO 93
<211> LENGTH: 738
<212> TYPE: PRT
<213> ORGANISM: Unknown
<220> FEATURE:
<223> OTHER INFORMATION: capsid protein of AAV serotype, clone 43.12

<400> SEQUENCE: 93

Met Ala Ala Asp Gly Tyr Leu Pro Asp Trp Leu Glu Asp Asn Leu Ser

-continued

```
1               5                   10                  15
Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
                35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
                130                 135                 140

Pro Val Glu Pro Ser Pro Gln Arg Ser Pro Asp Ser Ser Thr Gly Ile
145                 150                 155                 160

Gly Lys Lys Gly His Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
                180                 185                 190

Pro Ala Gly Pro Ser Gly Leu Gly Ser Gly Thr Met Ala Ala Gly Gly
                195                 200                 205

Gly Ala Pro Met Ala Asp Asn Asn Glu Gly Ala Asp Gly Val Gly Ser
                210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
                260                 265                 270

Asn Thr Tyr Phe Gly Tyr Ser Thr Pro Trp Gly Tyr Phe Asp Phe Asn
                275                 280                 285

Arg Phe His Cys His Phe Ser Pro Arg Asp Trp Gln Arg Leu Ile Asn
                290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
                370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
                420                 425                 430
```

```
Leu Asp Arg Leu Met Asn Pro Leu Ile Asp Gln Tyr Leu Tyr Tyr Leu
        435                 440                 445

Ser Arg Thr Gln Ser Thr Gly Gly Thr Gln Gly Thr Gln Gln Leu Leu
    450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
        530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Thr Asn Gly Ala
            580                 585                 590

Pro Ile Val Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Val Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 94
<211> LENGTH: 738
<212> TYPE: PRT
<213> ORGANISM: Unknown
<220> FEATURE:
<223> OTHER INFORMATION: capsid protein of AAV serotype, clone 43.5

<400> SEQUENCE: 94

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45
```

```
Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly His Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Gln Gly Thr Gln Gln Leu Leu
450                 455                 460

Phe Ser Gln Ala Gly Pro Ala Asn Met Ser Ala Gln Ala Lys Asn Trp
```

```
            465                 470                 475                 480
Leu Pro Gly Pro Cys Tyr Arg Gln Gln Arg Val Ser Thr Thr Leu Ser
                    485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
        530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                    565                 570                 575

Glu Gln Tyr Gly Val Val Ala Asp Asn Leu Gln Gln Thr Asn Gly Ala
                580                 585                 590

Pro Ile Val Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Val Lys Asn Thr Pro Val
                    645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                    725                 730                 735

Asn Leu

<210> SEQ ID NO 95
<211> LENGTH: 738
<212> TYPE: PRT
<213> ORGANISM: Unknown
<220> FEATURE:
<223> OTHER INFORMATION: capsid protein of AAV serotype, clone AAV8

<400> SEQUENCE: 95

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95
```

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510
```

```
Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
        530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
            565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
            645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
            725                 730                 735

Asn Leu

<210> SEQ ID NO 96
<211> LENGTH: 736
<212> TYPE: PRT
<213> ORGANISM: Unknown
<220> FEATURE:
<223> OTHER INFORMATION: capsid protein of AAV serotype, clone 43.21

<400> SEQUENCE: 96

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
```

```
                130               135               140
Pro Val Glu Gln Ser Pro Gln Glu Pro Asp Ser Ser Gly Ile Gly
145                 150               155               160

Lys Thr Gly Gln Gln Pro Ala Lys Lys Arg Leu Asn Phe Gly Gln Thr
                165                 170               175

Gly Asp Ser Glu Ser Val Pro Asp Pro Gln Pro Leu Gly Glu Pro Pro
            180                 185                 190

Ala Ala Pro Ser Gly Leu Gly Pro Asn Thr Met Ala Ser Gly Gly Gly
            195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Arg Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Val Pro Gln Tyr Gly Tyr Leu Thr Leu Asn Asn
    370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Val
        435                 440                 445

Arg Thr Gln Thr Thr Gly Thr Gly Gly Thr Gln Thr Leu Ala Phe Ser
    450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Thr Asn Gln Ser
                485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
        515                 520                 525

Asp Asp Asp Asp Arg Phe Phe Pro Ser Ser Gly Val Leu Ile Phe Gly
    530                 535                 540

Lys Gln Gly Ala Gly Asn Asp Gly Val Asp Tyr Ser Gln Val Leu Ile
545                 550                 555                 560
```

```
Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
            580                 585                 590

Thr Gly Leu Val His Asn Gln Gly Val Ile Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
        690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 97
<211> LENGTH: 736
<212> TYPE: PRT
<213> ORGANISM: Unknown
<220> FEATURE:
<223> OTHER INFORMATION: capsid protein of AAV serotype, clone 43.25

<400> SEQUENCE: 97

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190
```

```
Ala Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Gly Thr Ser Gly Ser Thr Asn Asp Asn
                260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Val Pro Gln Tyr Gly Tyr Leu Thr Leu Asn Asn
    370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
            405                 410                 415

Phe Glu Asp Val Pro Phe His Ser Ser Tyr Ala His Ser Gln Ser Leu
        420                 425                 430

Asp Arg Leu Met Asn Pro Leu Ile Asp Gln Tyr Leu Tyr Tyr Leu Val
    435                 440                 445

Arg Thr Gln Thr Thr Gly Thr Gly Gly Thr Gln Thr Leu Ala Phe Ser
450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Asn Gln Asn
            485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
    515                 520                 525

Asp Asp Asp Asp Arg Phe Phe Pro Ser Ser Gly Val Leu Ile Phe Gly
530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
            565                 570                 575

Tyr Gly Ala Val Ala Ile Asn Asn Gln Ala Ala Asn Thr Gln Ala Gln
            580                 585                 590

Thr Gly Leu Val His Asn Gln Gly Val Ile Pro Gly Met Val Trp Gln
            595                 600                 605
```

```
Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 98
<211> LENGTH: 736
<212> TYPE: PRT
<213> ORGANISM: Unknown
<220> FEATURE:
<223> OTHER INFORMATION: capsid protein of AAV serotype, clone 43.23

<400> SEQUENCE: 98

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240
```

-continued

Thr Thr Ser Thr Arg Thr Trp Ala Leu Pro Thr Tyr Asn Asn His Leu
            245                 250                 255

Tyr Lys Gln Ile Ser Asn Gly Thr Ser Gly Ser Thr Asn Asp Asn
        260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Gln Val Phe Thr Asp Leu Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Val Pro Gln Tyr Gly Tyr Leu Thr Leu Asn Asn
    370                 375                 380

Gly Ser Gln Ala Leu Gly Arg Ser Ser Phe Tyr Cys Leu Glu Tyr Phe
385                 390                 395                 400

Pro Ser Gln Met Pro Arg Thr Gly Asn Asn Phe Gln Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Val
        435                 440                 445

Arg Thr Gln Thr Thr Gly Thr Gly Gly Thr Gln Thr Leu Ala Phe Ser
    450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Thr Asn Gln Asn
                485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
        515                 520                 525

Asp Asp Asp Asp Arg Phe Phe Pro Ser Ser Gly Val Leu Ile Phe Gly
    530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
            580                 585                 590

Thr Gly Leu Val His Asn Gln Gly Val Ile Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr

```
                    660                 665                 670
Gln Tyr Ser Thr Gly Gln Val Ser Val Glu Ile Glu Trp Glu Leu Gln
                675                 680                 685
Lys Glu Asn Ser Lys Arg Trp Asn Pro Glu Ile Gln Tyr Thr Ser Asn
            690                 695                 700
Tyr Tyr Lys Ser Thr Asn Val Asp Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735

<210> SEQ ID NO 99
<211> LENGTH: 736
<212> TYPE: PRT
<213> ORGANISM: Unknown
<220> FEATURE:
<223> OTHER INFORMATION: capsid protein of AAV serotype, clone 43.20

<400> SEQUENCE: 99

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
    130                 135                 140
Leu Val Glu Gln Ser Pro Gln Glu Pro Asp Ser Ser Ser Gly Ile Gly
145                 150                 155                 160
Lys Thr Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Ala Pro Ser Gly Leu Gly Pro Asn Thr Met Ala Ser Gly Gly Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Gly Thr Ser Gly Gly Ser Thr Asn Asp Asn
            260                 265                 270
Thr Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
```

```
            290                 295                 300
Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Gln Val Phe Thr Asp Ser Glu Tyr Gln Leu
                340                 345                 350

Pro Tyr Val Leu Gly Ser Ala His Gln Gly Cys Leu Pro Pro Phe Pro
                355                 360                 365

Ala Asp Val Phe Thr Val Pro Gln Tyr Gly Tyr Leu Thr Leu Asn Asn
            370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Val
            435                 440                 445

Arg Thr Gln Thr Thr Gly Thr Gly Thr Gln Thr Leu Ala Phe Ser
450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Asn Gln Asn
                485                 490                 495

Asn Asn Ser Asn Phe Ala Trp Thr Gly Ala Ala Lys Phe Lys Leu Asn
                500                 505                 510

Gly Arg Asp Ser Leu Met Asn Pro Gly Val Ala Met Ala Ser His Lys
            515                 520                 525

Asp Asp Asp Asp Arg Phe Phe Pro Ser Ser Gly Val Leu Ile Phe Gly
530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
                580                 585                 590

Thr Gly Leu Val His Asn Gln Gly Val Ile Pro Gly Met Val Trp Gln
            595                 600                 605

Asn Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Tyr Lys Ser Thr Asn Val Asp Phe Ala Val Asn Thr Glu Gly Val
705                 710                 715                 720
```

Tyr Ser Glu Pro Arg Pro Ile Gly Thr Arg Tyr Leu Thr Arg Asn Leu
            725                 730                 735

<210> SEQ ID NO 100
<211> LENGTH: 736
<212> TYPE: PRT
<213> ORGANISM: Unknown
<220> FEATURE:
<223> OTHER INFORMATION: capsid protein of AAV serotype, clone AAV9

<400> SEQUENCE: 100

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Ser Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Glu Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Gln Val Phe Thr Asp Ser Glu Tyr Gln Leu
            340                 345                 350

```
Pro Tyr Val Leu Gly Ser Ala His Gln Gly Cys Leu Pro Phe Pro
        355                 360                 365

Ala Asp Val Phe Met Val Pro Gln Tyr Gly Tyr Leu Thr Leu Asn Asn
370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Val
            435                 440                 445

Arg Thr Gln Thr Thr Gly Thr Gly Gly Thr Gln Thr Leu Ala Phe Ser
        450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Thr Asn Gln Asn
                485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
        515                 520                 525

Asp Asp Glu Asp Arg Phe Phe Pro Ser Ser Gly Val Leu Ile Phe Gly
    530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
            580                 585                 590

Thr Gly Leu Val His Asn Gln Gly Val Ile Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 101
<211> LENGTH: 728
<212> TYPE: PRT
<213> ORGANISM: Unknown
<220> FEATURE:
```

<223> OTHER INFORMATION: capsid protein of AAV serotype, clone 24.1

<400> SEQUENCE: 101

| | | | | | | | | | | | | | | |
|---|---|---|---|---|---|---|---|---|---|---|---|---|---|---|
| Met<br>1 | Ala | Ala | Asp | Gly<br>5 | Tyr | Leu | Pro | Asp | Trp<br>10 | Leu | Glu | Asp | Asn | Leu<br>15 | Ser |
| Glu | Gly | Ile | Arg<br>20 | Glu | Trp | Trp | Asp | Leu<br>25 | Lys | Pro | Gly | Ala | Pro<br>30 | Lys | Pro |
| Lys | Ala | Asn<br>35 | Gln | Gln | Lys | Gln | Asp<br>40 | Asp | Gly | Arg | Gly | Leu<br>45 | Val | Leu | Pro |
| Gly | Tyr<br>50 | Lys | Tyr | Leu | Arg | Pro<br>55 | Phe | Asn | Gly | Leu | Asp<br>60 | Lys | Gly | Glu | Pro |
| Val<br>65 | Asn | Glu | Ala | Asp | Ala<br>70 | Ala | Ala | Leu | Glu | His<br>75 | Asp | Lys | Ala | Tyr | Asp<br>80 |
| Lys | Gln | Leu | Glu | Gln<br>85 | Gly | Asp | Asn | Pro | Tyr<br>90 | Leu | Lys | Tyr | Asn | His<br>95 | Ala |
| Asp | Ala | Glu | Phe<br>100 | Gln | Glu | Arg | Leu | Gln<br>105 | Glu | Asp | Thr | Ser | Phe<br>110 | Gly | Gly |
| Asn | Leu | Gly<br>115 | Arg | Ala | Val | Phe | Gln<br>120 | Ala | Lys | Lys | Arg | Val<br>125 | Leu | Glu | Pro |
| Leu | Gly<br>130 | Leu | Val | Glu | Glu | Val<br>135 | Ala | Lys | Thr | Ala | Pro<br>140 | Gly | Lys | Lys | Arg |
| Pro<br>145 | Ile | Glu | Ser | Pro | Asp<br>150 | Ser | Ser | Thr | Gly | Ile<br>155 | Gly | Lys | Lys | Gly | Gln<br>160 |
| Gln | Pro | Ala | Lys | Lys<br>165 | Lys | Leu | Asn | Phe | Gly<br>170 | Gln | Thr | Gly | Asp | Ser<br>175 | Glu |
| Ser | Val | Pro | Asp<br>180 | Pro | Gln | Pro | Leu | Gly<br>185 | Glu | Pro | Ala | Ala | Pro<br>190 | Ser |  |
| Gly | Leu | Gly<br>195 | Ser | Gly | Thr | Met | Ala<br>200 | Ala | Gly | Gly | Ala | Pro<br>205 | Met | Ala |  |
| Asp | Asn<br>210 | Asn | Glu | Gly | Ala | Asp<br>215 | Gly | Val | Gly | Asn | Ala<br>220 | Ser | Gly | Asn | Trp |
| His<br>225 | Cys | Asp | Ser | Thr | Trp<br>230 | Leu | Gly | Asp | Arg | Val<br>235 | Ile | Thr | Thr | Ser | Thr<br>240 |
| Arg | Thr | Trp | Ala | Leu<br>245 | Pro | Thr | Tyr | Asn | Asn<br>250 | His | Leu | Tyr | Lys | Gln<br>255 | Ile |
| Ser | Ser | Gln | Ser<br>260 | Gly | Ala | Thr | Asn | Asp<br>265 | Asn | His | Phe | Phe | Ser<br>270 | Tyr | Ser |
| Thr | Pro | Trp<br>275 | Gly | Tyr | Phe | Asp | Phe<br>280 | Asn | Arg | Phe | His | Cys<br>285 | His | Phe | Ser |
| Pro | Arg<br>290 | Asp | Trp | Gln | Arg | Leu<br>295 | Ile | Asn | Asn | Asn | Trp<br>300 | Gly | Phe | Arg | Pro |
| Arg<br>305 | Lys | Leu | Arg | Phe | Lys<br>310 | Leu | Phe | Asn | Ile | Gln<br>315 | Val | Lys | Glu | Val | Thr<br>320 |
| Thr | Asn | Asp | Gly | Val<br>325 | Thr | Thr | Ile | Ala | Asn<br>330 | Asn | Leu | Thr | Ser | Thr<br>335 | Ile |
| Gln | Val | Phe | Ser<br>340 | Asp | Ser | Glu | Tyr | Gln<br>345 | Leu | Pro | Tyr | Val | Leu<br>350 | Gly | Ser |
| Ala | His | Gln<br>355 | Gly | Cys | Leu | Pro | Pro<br>360 | Phe | Pro | Ala | Asp | Val<br>365 | Phe | Met | Ile |
| Pro | Gln<br>370 | Tyr | Gly | Tyr | Leu | Thr<br>375 | Leu | Asn | Asn | Gly | Ser<br>380 | Gln | Ser | Val | Gly |
| Arg<br>385 | Ser | Ser | Phe | Tyr | Cys<br>390 | Leu | Glu | Tyr | Phe | Pro<br>395 | Ser | Gln | Met | Leu | Arg<br>400 |

Thr Gly Asn Asn Phe Glu Phe Ser Tyr Thr Phe Glu Glu Val Pro Phe
                405                 410                 415

His Ser Ser Tyr Val His Ser Gln Ser Leu Asp Arg Leu Met Asn Pro
            420                 425                 430

Leu Ile Asp Gln Tyr Leu Tyr Tyr Leu Ala Arg Thr Gln Ser Thr Thr
        435                 440                 445

Gly Ser Thr Arg Glu Leu Gln Phe His Gln Ala Gly Pro Asn Thr Met
    450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Ser Asn Phe Ala Trp
            485                 490                 495

Thr Gly Ala Thr Lys Tyr His Leu Asn Gly Arg Asn Ser Leu Thr Asn
            500                 505                 510

Pro Gly Val Ala Met Ala Thr Asn Lys Asp Asp Glu Asp Gln Phe Phe
        515                 520                 525

Pro Ile Asn Gly Val Leu Val Phe Gly Lys Thr Gly Ala Ala Asn Lys
    530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
            565                 570                 575

Gln Ser Ser Thr Ala Gly Pro Gln Thr Gln Thr Val Asn Ser Gln Gly
            580                 585                 590

Ala Leu Pro Gly Met Val Trp Gln Asn Arg Asp Val Cys Leu Gln Gly
        595                 600                 605

Pro Ile Trp Ala Lys Ile Pro His Thr Asp Gly Asn Phe His Pro Ser
    610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Glu Val Phe Thr Pro
            645                 650                 655

Ala Lys Phe Ala Ser Phe Ile Thr Gln Tyr Ser Thr Gly Gln Val Ser
            660                 665                 670

Val Glu Ile Glu Trp Glu Leu Gln Lys Glu Asn Ser Lys Arg Trp Asn
        675                 680                 685

Pro Glu Ile Gln Tyr Thr Ser Asn Tyr Ala Lys Ser Asn Asn Val Glu
    690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 102
<211> LENGTH: 728
<212> TYPE: PRT
<213> ORGANISM: Unknown
<220> FEATURE:
<223> OTHER INFORMATION: capsid protein of AAV serotype, clone 42.2REAL

<400> SEQUENCE: 102

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

```
Lys Ala Asn Gln Gln Lys Gln Asp Gly Arg Gly Leu Val Leu Pro
             35                  40                  45

Gly Tyr Lys Tyr Leu Gly Pro Phe Asn Gly Leu Asp Lys Gly Glu Pro
 50                  55                  60

Val Asn Glu Ala Asp Ala Ala Leu Glu His Asp Lys Ala Tyr Asp
 65              70                  75                  80

Lys Gln Leu Glu Gln Gly Asp Asn Pro Tyr Leu Lys Tyr Asn His Ala
                 85                  90                  95

Asp Ala Glu Phe Gln Glu Arg Leu Gln Glu Asp Thr Ser Phe Gly Gly
             100                 105                 110

Asn Leu Gly Arg Ala Val Phe Gln Ala Lys Lys Arg Val Leu Glu Pro
             115                 120                 125

Leu Gly Leu Val Glu Glu Gly Ala Lys Thr Ala Pro Gly Lys Lys Arg
         130                 135                 140

Pro Ile Glu Ser Pro Asp Ser Ser Thr Gly Ile Gly Lys Lys Gly Gln
145                 150                 155                 160

Gln Pro Ala Lys Lys Leu Asn Phe Gly Gln Thr Gly Asp Ser Glu
                 165                 170                 175

Ser Val Pro Asp Pro Gln Pro Leu Gly Glu Pro Ala Ala Pro Ser
             180                 185                 190

Gly Leu Gly Ser Gly Thr Met Ala Ala Gly Gly Ala Pro Met Ala
         195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                 245                 250                 255

Ser Ser Gln Ser Gly Ala Thr Asn Asp Asn His Phe Phe Gly Tyr Ser
             260                 265                 270

Thr Pro Trp Gly Tyr Phe Asp Phe Asn Arg Phe His Cys His Phe Ser
         275                 280                 285

Pro Arg Asp Trp Gln Arg Leu Ile Asn Asn Asn Trp Gly Phe Arg Pro
    290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                 325                 330                 335

Gln Val Phe Ser Asp Ser Glu Tyr Gln Leu Pro Tyr Val Leu Gly Ser
             340                 345                 350

Ala His Gln Gly Cys Leu Pro Pro Phe Pro Ala Asp Val Phe Met Ile
         355                 360                 365

Pro Gln Tyr Gly Tyr Leu Thr Leu Asn Asn Gly Ser Gln Ser Val Gly
    370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Thr Phe Glu Glu Val Pro Phe
                 405                 410                 415

His Ser Ser Tyr Ala His Ser Gln Ser Leu Asp Arg Leu Met Asn Pro
             420                 425                 430

Leu Ile Asp Gln Tyr Leu Tyr Tyr Leu Ala Arg Thr Gln Ser Thr Thr
         435                 440                 445

Gly Ser Thr Arg Glu Leu Gln Phe His Gln Ala Gly Pro Asn Thr Met
```

```
                    450                 455                 460
Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Ser Asn Phe Ala Trp
            485                 490                 495

Thr Gly Ala Thr Lys Tyr His Leu Asn Gly Arg Asn Ser Leu Thr Asn
                500                 505                 510

Pro Gly Val Ala Met Ala Thr Asn Lys Asp Asp Glu Asp Gln Phe Phe
            515                 520                 525

Pro Ile Asn Gly Val Leu Val Phe Gly Glu Thr Gly Ala Ala Asn Lys
            530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
            565                 570                 575

Gln Ser Ser Thr Ala Gly Pro Gln Thr Gln Thr Val Asn Ser Gln Gly
                580                 585                 590

Ala Leu Pro Gly Met Val Trp Gln Asn Arg Asp Val Tyr Leu Gln Gly
            595                 600                 605

Pro Ile Trp Ala Lys Ile Pro His Thr Asp Gly Asn Phe His Pro Ser
            610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Pro Glu Val Phe Thr Pro
                645                 650                 655

Ala Lys Phe Ala Ser Phe Ile Thr Gln Tyr Ser Thr Gly Gln Val Ser
            660                 665                 670

Val Glu Ile Glu Trp Glu Leu Gln Lys Glu Asn Ser Lys Arg Trp Asn
            675                 680                 685

Pro Glu Ile Gln Tyr Thr Ser Asn Tyr Ala Lys Ser Asn Asn Val Glu
            690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 103
<211> LENGTH: 728
<212> TYPE: PRT
<213> ORGANISM: Unknown
<220> FEATURE:
<223> OTHER INFORMATION: capsid protein of AAV serotype, clone 7.2VP1

<400> SEQUENCE: 103

Met Ala Ala Asp Gly Tyr Leu Pro Asp Trp Leu Glu Gly Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Arg Tyr Leu Gly Pro Phe Asn Gly Leu Asp Lys Gly Glu Pro
        50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
```

-continued

```
            85                  90                  95
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
            130                 135                 140

Pro Ile Glu Ser Pro Asp Ser Ser Thr Gly Ile Gly Lys Asn Gly Gln
145                 150                 155                 160

Pro Pro Ala Lys Lys Lys Leu Asn Phe Gly Gln Thr Gly Asp Ser Glu
                165                 170                 175

Ser Val Pro Asp Pro Gln Pro Leu Gly Glu Pro Pro Ala Ala Pro Ser
            180                 185                 190

Gly Leu Gly Ser Gly Thr Met Ala Ala Gly Gly Gly Ala Pro Met Ala
            195                 200                 205

Asp Asn Asn Glu Gly Ala Asp Gly Val Gly Asn Ala Ser Gly Asn Trp
210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
            275                 280                 285

Pro Arg Asp Trp Gln Arg Leu Ile Asn Asn Asn Trp Gly Phe Arg Pro
290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
            340                 345                 350

Ala His Gln Gly Cys Leu Pro Pro Phe Pro Ala Asp Val Phe Met Ile
            355                 360                 365

Pro Gln Tyr Gly Tyr Leu Thr Leu Asn Asn Gly Ser Gln Ser Val Gly
            370                 375                 380

Arg Ser Ser Phe Tyr Cys Leu Glu Tyr Phe Pro Ser Gln Met Leu Arg
385                 390                 395                 400

Thr Gly Asp Asn Phe Glu Phe Ser Tyr Thr Phe Glu Glu Val Pro Phe
                405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Ala Arg Thr Gln Ser Thr Thr
            435                 440                 445

Gly Ser Thr Arg Glu Leu Gln Phe His Gln Ala Gly Pro Asn Thr Met
450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Asn Ser Asn Phe Ala Trp
                485                 490                 495

Thr Gly Ala Thr Lys Tyr His Leu Asn Gly Arg Asn Ser Leu Thr Asn
            500                 505                 510
```

```
Pro Gly Val Ala Met Ala Thr Asn Lys Asp Asp Glu Asp Gln Phe Phe
            515                 520                 525

Pro Ile Asn Gly Val Leu Val Phe Gly Lys Thr Gly Ala Ala Asn Lys
        530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
                565                 570                 575

Gln Ser Ser Thr Ala Gly Pro Gln Thr Gln Thr Val Asn Ser Gln Gly
            580                 585                 590

Ala Leu Pro Gly Met Val Trp Gln Asn Arg Asp Val Tyr Leu Gln Gly
        595                 600                 605

Pro Ile Trp Ala Lys Ile Pro His Thr Asp Gly Asn Phe His Pro Ser
        610                 615                 620

Pro Leu Met Gly Gly Phe Gly Leu Lys His Pro Pro Pro Gln Ile Leu
625                 630                 635                 640

Ile Lys Asn Thr Pro Val Pro Ala Asn Pro Pro Glu Val Phe Thr Pro
                645                 650                 655

Ala Lys Phe Ala Ser Phe Ile Thr Gln Tyr Ser Thr Gly Gln Val Ser
            660                 665                 670

Val Glu Ile Glu Trp Glu Leu Gln Lys Glu Asn Ser Lys Arg Trp Asn
        675                 680                 685

Pro Glu Ile Gln Tyr Thr Ser Asn Tyr Ala Lys Ser Asn Asn Val Glu
        690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 104
<211> LENGTH: 728
<212> TYPE: PRT
<213> ORGANISM: Unknown
<220> FEATURE:
<223> OTHER INFORMATION: capsid protein of AAV serotype, clone 27.3VP1

<400> SEQUENCE: 104

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Ser Gly Lys Lys Arg
    130                 135                 140
```

-continued

```
Pro Ile Glu Ser Pro Asp Ser Ser Thr Gly Ile Gly Lys Lys Gly Gln
145                 150                 155                 160

Gln Pro Ala Lys Lys Leu Asn Phe Gly Gln Thr Gly Asp Ser Glu
            165                 170                 175

Ser Val Pro Asp Pro Gln Pro Leu Gly Glu Pro Pro Ala Ala Pro Ser
            180                 185                 190

Gly Leu Gly Ser Gly Thr Met Ala Ala Gly Gly Ala Pro Met Ala
            195                 200                 205

Asp Asn Asn Glu Gly Ala Asp Gly Val Gly Asn Ala Ser Gly Asn Trp
210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
            245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
            275                 280                 285

Pro Arg Asp Trp Gln Arg Leu Ile Asn Asn Asn Trp Gly Phe Arg Pro
            290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
            325                 330                 335

Gln Val Phe Ser Asp Ser Glu Tyr Gln Leu Pro Tyr Val Leu Gly Ser
            340                 345                 350

Ala His Gln Gly Cys Leu Pro Pro Phe Pro Ala Asp Val Phe Met Ile
            355                 360                 365

Pro Gln Tyr Gly Tyr Leu Thr Leu Asn Asn Gly Ser Gln Ser Val Gly
            370                 375                 380

Arg Ser Ser Phe Cys Cys Leu Glu Tyr Phe Pro Ser Gln Met Leu Arg
385                 390                 395                 400

Thr Gly Asn Asn Phe Glu Phe Ser Tyr Thr Phe Glu Glu Val Pro Phe
            405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Ala Arg Thr Gln Ser Thr Thr
            435                 440                 445

Gly Ser Thr Arg Glu Leu Gln Phe His Gln Ala Gly Pro Asn Thr Val
450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Ser Asn Phe Ala Trp
            485                 490                 495

Thr Gly Ala Thr Lys Tyr His Leu Asn Gly Arg Asn Ser Leu Thr Asn
            500                 505                 510

Pro Gly Val Ala Met Ala Thr Asn Lys Asp Asp Glu Asp Gln Phe Leu
            515                 520                 525

Pro Ile Asn Gly Val Leu Val Phe Gly Lys Thr Gly Ala Ala Asn Lys
            530                 535                 540

Thr Thr Leu Glu Asn Val Leu Met Thr Ser Glu Glu Ile Lys Thr
545                 550                 555                 560
```

```
Thr Asn Pro Val Ala Thr Glu Glu Tyr Gly Val Ser Ser Asn Leu
                565                 570                 575
Gln Ser Ser Thr Ala Gly Pro Arg Thr Gln Thr Val Asn Ser Gln Gly
            580                 585                 590
Ala Leu Pro Gly Met Val Trp Gln Asn Arg Asp Val Tyr Leu Gln Gly
            595                 600                 605
Pro Ile Trp Ala Glu Ile Pro His Thr Asp Gly Asn Phe His Pro Ser
    610                 615                 620
Pro Leu Met Gly Gly Phe Gly Leu Lys His Pro Pro Gln Ile Leu
625                 630                 635                 640
Ile Lys Asn Thr Pro Val Pro Ala Asn Pro Pro Glu Val Phe Thr Pro
                645                 650                 655
Ala Lys Phe Ala Ser Phe Ile Thr Gln Tyr Ser Thr Gly Gln Val Ser
            660                 665                 670
Val Glu Ile Glu Trp Glu Leu Gln Lys Glu Asn Ser Lys Arg Trp Asn
        675                 680                 685
Pro Glu Ile Gln Tyr Thr Ser Asn Tyr Ala Lys Ser Asn Asn Val Glu
    690                 695                 700
Phe Ala Val Asn Asn Glu Gly Val Tyr Thr Glu Pro Arg Pro Ile Gly
705                 710                 715                 720
Thr Arg Tyr Leu Thr Arg Asn Leu
                725

<210> SEQ ID NO 105
<211> LENGTH: 728
<212> TYPE: PRT
<213> ORGANISM: Unknown
<220> FEATURE:
<223> OTHER INFORMATION: capsid protein of AAV serotype, clone 16.3VP1

<400> SEQUENCE: 105

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Glu Ala Asp Ala Ala Leu Glu His Asp Lys Ala Tyr Asp
65              70                  75                  80
Lys Gln Leu Glu Gln Gly Asp Asn Pro Tyr Leu Lys Tyr Asn His Ala
            85                  90                  95
Asp Ala Glu Phe Gln Glu Arg Leu Gln Glu Asp Thr Ser Phe Gly Gly
        100                 105                 110
Asn Leu Gly Arg Ala Val Phe Gln Ala Lys Lys Arg Val Leu Glu Pro
    115                 120                 125
Leu Gly Leu Val Glu Glu Gly Ala Lys Thr Ala Pro Gly Lys Lys Arg
130                 135                 140
Pro Ile Glu Ser Pro Asp Ser Ser Thr Gly Ile Gly Lys Lys Gly Gln
145                 150                 155                 160
Gln Pro Ala Lys Lys Lys Leu Asn Phe Gly Gln Thr Gly Asp Ser Glu
                165                 170                 175
Ser Val Pro Asp Pro Gln Pro Leu Gly Glu Pro Pro Ala Ala Pro Ser
            180                 185                 190
```

```
Gly Leu Gly Ser Gly Thr Met Ala Gly Gly Ala Pro Met Ala
            195                 200             205

Asp Asn Asn Glu Gly Ala Asp Gly Val Gly Asn Ala Ser Gly Asn Trp
210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
        275                 280                 285

Pro Arg Asp Trp Gln Arg Leu Ile Asn Asn Trp Gly Phe Arg Pro
290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
            340                 345                 350

Ala His Gln Gly Cys Leu Pro Pro Phe Pro Ala Asp Val Phe Met Ile
        355                 360                 365

Pro Gln Tyr Gly Tyr Leu Thr Leu Asn Asn Gly Ser Gln Ser Met Gly
        370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Thr Phe Glu Glu Val Pro Phe
                405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Ala Arg Thr Gln Ser Thr Thr
        435                 440                 445

Gly Ser Thr Arg Glu Leu Gln Phe His Gln Ala Gly Pro Asn Thr Met
450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Ser Asn Phe Ala Trp
                485                 490                 495

Thr Gly Ala Thr Lys Tyr His Leu Asn Gly Arg Asn Ser Leu Thr Asn
            500                 505                 510

Pro Gly Val Ala Met Ala Thr Asn Lys Asp Asp Glu Gly Gln Phe Phe
        515                 520                 525

Pro Ile Asn Gly Val Leu Val Phe Gly Lys Thr Gly Ala Ala Asn Lys
530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
                565                 570                 575

Gln Ser Ser Thr Ala Gly Pro Gln Thr Gln Thr Val Asn Ser Gln Gly
            580                 585                 590

Ala Leu Pro Gly Met Val Trp Gln Asn Arg Asp Val Tyr Leu Gln Gly
        595                 600                 605

Pro Ile Trp Ala Lys Ile Pro His Thr Asp Gly Asn Phe His Pro Ser
```

```
                 610              615              620
Pro Leu Met Gly Gly Phe Gly Leu Lys His Pro Pro Gln Ile Leu
625              630              635              640

Ile Lys Asn Thr Pro Val Pro Ala Asn Pro Pro Gly Val Phe Thr Pro
                 645              650              655

Ala Leu Phe Ala Ser Phe Ile Thr Gln Tyr Ser Thr Gly Gln Val Ser
                 660              665              670

Val Glu Ile Glu Trp Glu Leu Gln Lys Glu Asn Ser Lys Arg Trp Asn
                 675              680              685

Pro Glu Ile Gln Tyr Thr Ser Asn Tyr Ala Lys Ser Asn Asn Val Glu
                 690              695              700

Phe Ala Val Asn Asn Glu Gly Val Tyr Thr Glu Pro Arg Pro Ile Gly
705              710              715              720

Thr Arg Tyr Leu Thr Arg Asn Leu
                 725

<210> SEQ ID NO 106
<211> LENGTH: 728
<212> TYPE: PRT
<213> ORGANISM: Unknown
<220> FEATURE:
<223> OTHER INFORMATION: capsid protein of AAV serotype, clone 42.10

<400> SEQUENCE: 106

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Arg Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Ile Gly Glu Pro Ala Gly Pro Ser
            180                 185                 190

Gly Leu Gly Ser Gly Thr Met Ala Ala Gly Gly Ala Pro Met Ala
        195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
```

-continued

```
                245                 250                 255
    Ser Ser Gln Ser Gly Ala Thr Asn Asp Asn His Phe Gly Tyr Ser
                260                 265                 270

Thr Pro Trp Gly Tyr Phe Asp Phe Asn Arg Phe His Cys His Phe Ser
                275                 280                 285

Pro Arg Asp Trp Gln Arg Leu Ile Asn Asn Asn Trp Gly Phe Arg Pro
                290                 295                 300

Arg Lys Leu Arg Phe Lys Leu Phe Asn Ile Gln Val Lys Glu Val Thr
    305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
                340                 345                 350

Ala His Gln Gly Cys Leu Pro Pro Phe Pro Ala Asp Val Phe Met Ile
                355                 360                 365

Pro Gln Tyr Gly Tyr Leu Thr Leu Asn Asn Gly Ser Gln Ser Val Gly
                370                 375                 380

Arg Ser Ser Phe Tyr Cys Leu Glu Tyr Phe Pro Ser Gln Met Leu Arg
    385                 390                 395                 400

Thr Gly Asn Asn Phe Glu Phe Ser Tyr Thr Phe Glu Glu Val Pro Phe
                405                 410                 415

His Ser Ser Tyr Ala His Ser Gln Ser Leu Asp Arg Leu Met Asn Pro
                420                 425                 430

Leu Ile Asp Gln Tyr Leu Tyr Tyr Leu Ala Arg Thr Gln Ser Thr Thr
                435                 440                 445

Gly Ser Thr Arg Glu Leu Gln Phe His Gln Ala Gly Pro Asn Thr Met
    450                 455                 460

Ala Glu Gln Ser Lys Asn Trp Leu Pro Gly Pro Cys Tyr Arg Gln Gln
    465                 470                 475                 480

Arg Leu Ser Lys Asn Ile Asp Ser Asn Asn Asn Ser Asn Phe Ala Trp
                485                 490                 495

Thr Gly Ala Thr Lys Tyr His Leu Asn Gly Arg Asn Ser Leu Thr Asn
                500                 505                 510

Pro Gly Val Ala Met Ala Thr Asn Lys Asp Asp Glu Asp Gln Phe Phe
                515                 520                 525

Pro Ile Asn Gly Val Leu Val Phe Gly Lys Thr Gly Ala Ala Asn Lys
                530                 535                 540

Thr Thr Leu Glu Asn Val Leu Met Thr Ser Glu Glu Ile Lys Thr
    545                 550                 555                 560

Thr Asn Pro Val Ala Thr Glu Glu Tyr Gly Val Val Ser Ser Asn Leu
                565                 570                 575

Gln Ser Ser Thr Ala Gly Pro Gln Thr Gln Thr Val Asn Ser Gln Gly
                580                 585                 590

Ala Leu Pro Gly Met Val Trp Gln Asn Arg Asp Val Tyr Leu Gln Gly
                595                 600                 605

Pro Ile Trp Ala Lys Ile Pro His Thr Asp Gly Asn Phe His Pro Ser
                610                 615                 620

Pro Leu Met Gly Gly Phe Gly Leu Lys His Pro Pro Gln Ile Leu
    625                 630                 635                 640

Ile Lys Asn Thr Pro Val Pro Ala Asn Pro Pro Glu Val Phe Thr Pro
                645                 650                 655

Ala Lys Phe Ala Ser Phe Ile Thr Gln Tyr Ser Thr Gly Gln Val Ser
                660                 665                 670
```

-continued

Val Glu Ile Glu Trp Glu Leu Gln Lys Glu Asn Ser Lys Arg Trp Asn
           675                 680                 685

Pro Glu Ile Gln Tyr Thr Ser Asn Tyr Ala Lys Ser Asn Asn Val Glu
690                 695                 700

Phe Ala Val Asn Glu Gly Val Tyr Thr Glu Pro Arg Pro Ile Gly
705                 710                 715                 720

Thr Arg Tyr Leu Thr Arg Asn Leu
                725

<210> SEQ ID NO 107
<211> LENGTH: 728
<212> TYPE: PRT
<213> ORGANISM: Unknown
<220> FEATURE:
<223> OTHER INFORMATION: capsid protein of AAV serotype, clone 42.3B

<400> SEQUENCE: 107

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Ile Gly Glu Pro Pro Ala Gly Pro Ser
            180                 185                 190

Gly Leu Gly Ser Gly Thr Met Ala Ala Gly Gly Gly Ala Pro Met Ala
        195                 200                 205

Asp Asn Asn Glu Gly Ala Asp Gly Val Gly Asn Ala Ser Gly Asn Trp
210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
        275                 280                 285

Pro Arg Asp Trp Gln Arg Leu Ile Asn Asn Asn Trp Gly Phe Arg Pro
290                 295                 300

```
Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
            325                 330                 335

Gln Val Phe Ser Asp Ser Glu Tyr Gln Leu Pro Tyr Val Leu Gly Ser
            340                 345                 350

Ala His Gln Gly Cys Leu Pro Pro Phe Pro Ala Asp Val Phe Met Ile
            355                 360                 365

Pro Gln Tyr Gly Tyr Leu Thr Leu Asn Asn Gly Ser Gln Ser Val Gly
    370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Thr Phe Glu Glu Val Pro Phe
                405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Ala Arg Thr Gln Ser Thr Thr
        435                 440                 445

Gly Ser Thr Arg Glu Leu Gln Phe His Gln Ala Gly Pro Asn Thr Met
    450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Thr Ser Asn Phe Ala Trp
            485                 490                 495

Thr Gly Ala Thr Lys Tyr His Leu Asn Gly Arg Asn Ser Leu Thr Asn
            500                 505                 510

Pro Gly Val Ala Met Ala Thr Asn Lys Asp Asp Glu Asp Gln Phe Phe
        515                 520                 525

Pro Ile Asn Gly Val Leu Val Phe Gly Lys Thr Gly Ala Ala Asn Lys
    530                 535                 540

Thr Thr Leu Glu Asn Val Leu Met Thr Ser Glu Glu Glu Ile Lys Thr
545                 550                 555                 560

Thr Asn Pro Val Ala Thr Glu Gln Tyr Gly Val Val Ser Ser Asn Leu
            565                 570                 575

Gln Ser Ser Thr Ala Gly Pro Gln Thr Gln Thr Val Asn Ser Gln Gly
            580                 585                 590

Ala Leu Pro Gly Met Val Trp Gln Asn Arg Asp Val Tyr Leu Gln Gly
        595                 600                 605

Pro Ile Trp Ala Lys Ile Pro His Thr Asp Gly Asn Phe His Pro Ser
    610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Pro Glu Val Phe Thr Pro
            645                 650                 655

Ala Lys Phe Ala Ser Phe Ile Thr Gln Tyr Ser Thr Gly Gln Val Ser
            660                 665                 670

Val Glu Ile Glu Trp Glu Leu Gln Lys Glu Asn Ser Lys Arg Trp Asn
            675                 680                 685

Pro Glu Ile Gln Tyr Thr Ser Asn Tyr Ala Lys Ser Asn Asn Val Glu
    690                 695                 700

Phe Ala Val Asn Asn Glu Gly Val Tyr Thr Glu Pro Arg Pro Ile Gly
705                 710                 715                 720
```

-continued

```
Thr Arg Tyr Leu Thr Arg Asn Leu
                725

<210> SEQ ID NO 108
<211> LENGTH: 728
<212> TYPE: PRT
<213> ORGANISM: Unknown
<220> FEATURE:
<223> OTHER INFORMATION: capsid protein of AAV serotype, clone 42.11

<400> SEQUENCE: 108

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Ile Gly Glu Pro Pro Ala Gly Pro Ser
            180                 185                 190

Gly Leu Gly Ser Gly Thr Met Ala Ala Gly Gly Gly Ala Pro Met Ala
        195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
        275                 280                 285

Pro Arg Asp Trp Gln Arg Leu Ile Asn Asn Asn Trp Gly Phe Arg Pro
    290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
            340                 345                 350
```

```
Ala His Gln Gly Cys Leu Pro Pro Phe Pro Ala Asp Val Phe Met Ile
            355                 360                 365
Pro Gln Tyr Gly Tyr Leu Thr Leu Asn Asn Gly Ser Gln Ser Val Gly
370                 375                 380
Arg Ser Ser Phe Tyr Cys Leu Glu Tyr Phe Pro Ser Gln Met Leu Arg
385                 390                 395                 400
Thr Gly Asn Asn Phe Glu Phe Ser Tyr Thr Phe Glu Glu Val Pro Phe
                405                 410                 415
His Ser Ser Tyr Ala His Ser Gln Ser Leu Asp Arg Leu Met Asn Pro
            420                 425                 430
Leu Ile Asp Gln Tyr Leu Tyr Tyr Leu Ala Arg Thr Gln Ser Thr Thr
        435                 440                 445
Gly Ser Thr Arg Glu Leu Gln Phe His Gln Ala Gly Pro Asn Thr Met
450                 455                 460
Ala Glu Gln Ser Lys Asn Trp Leu Pro Gly Pro Cys Tyr Arg Arg Gln
465                 470                 475                 480
Arg Leu Ser Lys Asp Ile Asp Ser Asn Asn Ser Asn Phe Ala Trp
                485                 490                 495
Thr Gly Ala Thr Lys Tyr His Leu Asn Gly Arg Asn Ser Leu Thr Asn
                500                 505                 510
Pro Gly Val Ala Met Ala Thr Asn Lys Asp Asp Glu Asp Gln Phe Phe
            515                 520                 525
Pro Ile Asn Gly Val Leu Val Phe Gly Lys Thr Gly Ala Ala Asn Lys
        530                 535                 540
Thr Thr Leu Glu Asn Val Leu Met Thr Ser Glu Glu Ile Lys Thr
545                 550                 555                 560
Thr Asn Pro Val Ala Thr Glu Glu Tyr Gly Val Val Ser Ser Asn Leu
                565                 570                 575
Gln Ser Ser Thr Ala Gly Pro Gln Thr Gln Thr Val Asn Ser Gln Gly
            580                 585                 590
Ala Leu Pro Gly Met Val Trp Gln Asn Arg Asp Val Tyr Leu Gln Gly
        595                 600                 605
Pro Ile Trp Ala Lys Ile Pro His Thr Asp Gly Asn Phe His Pro Ser
610                 615                 620
Pro Leu Met Gly Gly Phe Gly Leu Lys His Pro Pro Gln Ile Leu
625                 630                 635                 640
Ile Lys Asn Thr Pro Val Pro Ala Asn Pro Pro Glu Val Phe Thr Pro
                645                 650                 655
Ala Lys Phe Ala Ser Phe Ile Thr Gln Tyr Ser Thr Gly Gln Val Ser
            660                 665                 670
Val Glu Ile Glu Trp Glu Leu Gln Lys Glu Asn Ser Lys Arg Trp Asn
        675                 680                 685
Pro Glu Ile Gln Tyr Thr Ser Asn Tyr Ala Lys Ser Asn Asn Val Glu
690                 695                 700
Phe Ala Val Asn Asn Glu Gly Val Tyr Thr Glu Pro Arg Pro Ile Gly
705                 710                 715                 720
Thr Arg Tyr Leu Thr Arg Asn Leu
                725

<210> SEQ ID NO 109
<211> LENGTH: 729
<212> TYPE: PRT
<213> ORGANISM: Unknown
<220> FEATURE:
<223> OTHER INFORMATION: capsid protein of AAV serotype, clone F1VP1
```

<400> SEQUENCE: 109

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Ile Asp Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Pro Ala Ala Pro Ser
            180                 185                 190

Ser Val Gly Ser Gly Thr Met Ala Ala Gly Gly Ala Pro Met Ala
        195                 200                 205

Asp Asn Asn Glu Gly Ala Asp Gly Val Gly Asn Ala Ser Gly Asn Trp
210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Ser Ser Ser Gly Ala Thr Asn Asp Asn His Tyr Phe Gly Tyr
            260                 265                 270

Ser Thr Pro Trp Gly Tyr Phe Asp Phe Asn Arg Phe His Cys His Phe
        275                 280                 285

Ser Pro Arg Asp Trp Gln Arg Leu Ile Asn Asn Asn Trp Gly Phe Arg
290                 295                 300

Pro Lys Lys Leu Arg Phe Lys Leu Phe Asn Ile Gln Val Lys Glu Val
305                 310                 315                 320

Thr Thr Asn Asp Gly Val Thr Thr Ile Ala Asn Asn Leu Thr Ser Thr
                325                 330                 335

Val Gln Val Phe Ser Asp Ser Glu Tyr Gln Leu Pro Tyr Val Leu Gly
            340                 345                 350

Ser Ala His Gln Gly Cys Leu Pro Pro Phe Pro Ala Asp Val Phe Met
        355                 360                 365

Ile Pro Gln Tyr Gly Tyr Leu Thr Leu Asn Asn Gly Ser Gln Ser Val
370                 375                 380

Gly Arg Ser Ser Phe Tyr Cys Leu Glu Tyr Phe Pro Ser Gln Met Leu
385                 390                 395                 400

Arg Thr Gly Asn Asn Phe Glu Phe Ser Tyr Ser Phe Glu Asp Val Pro

```
                    405                 410                 415
        Phe His Ser Ser Tyr Ala His Ser Gln Ser Leu Asp Arg Leu Met Asn
                        420                 425                 430

Pro Leu Ile Asp Gln Tyr Leu Tyr Tyr Leu Ala Arg Thr Gln Ser Thr
                        435                 440                 445

Thr Gly Ser Thr Arg Glu Leu Gln Phe His Gln Ala Gly Pro Asn Thr
                        450                 455                 460

Met Ala Glu Gln Ser Lys Asn Trp Leu Pro Gly Pro Cys Tyr Arg Gln
        465                 470                 475                 480

Gln Gly Leu Ser Lys Asn Leu Asp Phe Asn Asn Ser Asn Phe Ala
                        485                 490                 495

Trp Thr Ala Ala Thr Lys Tyr His Leu Asn Gly Arg Asn Ser Leu Thr
                        500                 505                 510

Asn Pro Gly Ile Pro Met Ala Thr Asn Lys Asp Glu Asp Gln Phe
                        515                 520                 525

Phe Pro Ile Asn Gly Val Leu Val Phe Gly Lys Thr Gly Ala Ala Asn
                        530                 535                 540

Lys Thr Thr Leu Glu Asn Val Leu Met Thr Ser Glu Glu Ile Lys
        545                 550                 555                 560

Thr Thr Asn Pro Val Ala Thr Glu Glu Tyr Gly Val Val Ser Ser Asn
                        565                 570                 575

Leu Gln Pro Ser Thr Ala Gly Pro Gln Ser Gln Thr Ile Asn Ser Gln
                        580                 585                 590

Gly Ala Leu Pro Gly Met Val Trp Gln Asn Arg Asp Val Tyr Leu Gln
                        595                 600                 605

Gly Pro Ile Trp Ala Lys Ile Pro His Thr Asp Gly Asn Phe His Pro
                        610                 615                 620

Ser Pro Leu Met Gly Gly Phe Gly Leu Lys His Pro Pro Gln Ile
        625                 630                 635                 640

Leu Ile Lys Asn Thr Pro Val Pro Ala Asn Pro Pro Glu Val Phe Thr
                        645                 650                 655

Pro Ala Lys Phe Ala Ser Phe Ile Thr Gln Tyr Ser Thr Gly Gln Val
                        660                 665                 670

Ser Val Glu Ile Glu Trp Glu Leu Gln Lys Glu Asn Ser Lys Arg Trp
                        675                 680                 685

Asn Pro Glu Ile Gln Tyr Thr Ser Asn Tyr Ala Lys Ser Asn Asn Val
                        690                 695                 700

Glu Phe Ala Val Asn Pro Asp Gly Val Tyr Thr Glu Pro Arg Pro Ile
        705                 710                 715                 720

Gly Thr Arg Tyr Leu Pro Arg Asn Leu
                        725

<210> SEQ ID NO 110
<211> LENGTH: 729
<212> TYPE: PRT
<213> ORGANISM: Unknown
<220> FEATURE:
<223> OTHER INFORMATION: capsid protein of AAV serotype, clone F5VP1[@0003]

<400> SEQUENCE: 110

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
```

-continued

```
            35                  40                  45
Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
                130                 135                 140

Pro Ile Asp Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Ala Ala Pro Ser
                180                 185                 190

Ser Val Gly Ser Gly Thr Met Ala Ala Gly Gly Ala Pro Thr Ala
                195                 200                 205

Asp Asn Asn Glu Gly Ala Asp Gly Val Gly Asn Ala Ser Gly Asn Trp
210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Ser Ser Ser Gly Ala Thr Asn Asp Asn His Tyr Phe Gly Tyr
                260                 265                 270

Ser Thr Pro Trp Gly Tyr Phe Asp Phe Asn Arg Phe His Cys His Phe
                275                 280                 285

Ser Pro Arg Asp Trp Gln Arg Leu Ile Asn Asn Asn Trp Gly Phe Arg
290                 295                 300

Pro Lys Lys Leu Arg Phe Lys Leu Phe Asn Ile Gln Val Lys Glu Val
305                 310                 315                 320

Thr Thr Asn Asp Gly Val Thr Thr Ile Ala Asn Asn Leu Thr Ser Thr
                325                 330                 335

Val Gln Val Phe Ser Asp Ser Glu Tyr Gln Leu Pro Tyr Val Leu Gly
                340                 345                 350

Ser Ala His Gln Gly Cys Leu Pro Pro Phe Pro Ala Asp Val Phe Met
                355                 360                 365

Ile Pro Gln Tyr Gly Tyr Leu Thr Leu Asn Asn Gly Ser Gln Ser Val
                370                 375                 380

Gly Arg Ser Ser Phe Tyr Cys Leu Glu Tyr Phe Pro Ser Gln Met Leu
385                 390                 395                 400

Arg Thr Gly Asn Asn Phe Glu Phe Ser Tyr Ser Phe Glu Asp Val Pro
                405                 410                 415

Phe His Ser Ser Tyr Ala His Ser Gln Ser Leu Asp Arg Leu Met Asn
                420                 425                 430

Pro Leu Ile Asp Gln Tyr Leu Tyr Tyr Leu Ala Arg Thr Gln Ser Thr
                435                 440                 445

Thr Gly Ser Thr Arg Glu Leu Gln Phe His Gln Ala Gly Pro Asn Thr
                450                 455                 460
```

```
Met Ala Glu Gln Ser Lys Asn Trp Leu Pro Gly Pro Cys Tyr Arg Gln
465                 470                 475                 480

Gln Arg Leu Ser Lys Asn Leu Asp Phe Asn Asn Ser Asn Phe Ala
        485                 490                 495

Trp Thr Ala Ala Thr Lys Tyr His Leu Asn Gly Arg Asn Ser Leu Thr
                500                 505                 510

Asn Pro Gly Ile Pro Met Ala Thr Asn Lys Asp Glu Asp Gln Phe
            515                 520                 525

Phe Pro Ile Asn Gly Val Leu Val Phe Gly Lys Thr Gly Ala Ala Asn
530                 535                 540

Lys Thr Thr Leu Glu Asn Val Leu Met Thr Ser Glu Glu Ile Lys
545                 550                 555                 560

Thr Thr Asn Pro Val Ala Thr Glu Glu Tyr Gly Val Val Ser Ser Asn
                565                 570                 575

Leu Gln Ser Ser Thr Ala Gly Pro Gln Ser Gln Thr Ile Asn Ser Gln
            580                 585                 590

Gly Ala Leu Pro Gly Met Val Trp Gln Asn Arg Asp Val Tyr Leu Gln
        595                 600                 605

Gly Pro Ile Trp Ala Lys Ile Pro His Thr Asp Gly Asn Phe His Pro
610                 615                 620

Ser Pro Leu Met Gly Gly Phe Gly Leu Glu His Pro Pro Gln Ile
625                 630                 635                 640

Leu Ile Lys Asn Thr Pro Val Pro Ala Asn Pro Pro Glu Val Phe Thr
                645                 650                 655

Pro Ala Lys Phe Ala Ser Phe Ile Thr Gln Tyr Ser Thr Gly Gln Val
            660                 665                 670

Ser Val Glu Ile Glu Trp Glu Leu Gln Lys Glu Asn Ser Lys Arg Trp
        675                 680                 685

Asn Pro Glu Ile Gln Tyr Thr Ser Asn Tyr Ala Lys Ser Asn Asn Val
            690                 695                 700

Glu Phe Ala Val Asn Pro Asp Gly Val Tyr Thr Glu Pro Arg Pro Ile
705                 710                 715                 720

Gly Thr Arg Tyr Leu Thr Arg Asn Leu
                725

<210> SEQ ID NO 111
<211> LENGTH: 729
<212> TYPE: PRT
<213> ORGANISM: Unknown
<220> FEATURE:
<223> OTHER INFORMATION: capsid protein of AAV serotype, clone F3VP1

<400> SEQUENCE: 111

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95
```

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Gly Ala Lys Thr Ala Pro Gly Lys Lys Arg
130                 135                 140

Pro Ile Gly Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Ala Ala Pro Ser
            180                 185                 190

Ser Val Gly Ser Gly Thr Met Ala Ala Gly Gly Ala Pro Met Ala
            195                 200                 205

Asp Asn Asn Glu Gly Ala Asp Gly Val Gly Asn Ala Ser Gly Asn Trp
210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Ser Ser Ser Gly Ala Thr Asn Asp Asn His Tyr Phe Gly Tyr
            260                 265                 270

Ser Thr Pro Trp Gly Tyr Phe Asp Phe Asn Arg Phe His Cys His Phe
            275                 280                 285

Ser Pro Arg Asp Trp Gln Arg Leu Ile Asn Asn Trp Gly Phe Arg
            290                 295                 300

Pro Lys Lys Leu Arg Phe Lys Leu Leu Asn Ile Gln Val Lys Glu Val
305                 310                 315                 320

Thr Thr Asn Asp Gly Val Thr Thr Ile Ala Asn Asn Leu Thr Ser Thr
                325                 330                 335

Val Gln Val Phe Ser Asp Ser Glu Tyr Gln Leu Pro Tyr Val Leu Gly
            340                 345                 350

Ser Ala His Gln Gly Cys Leu Pro Pro Phe Pro Ala Asp Val Phe Met
            355                 360                 365

Ile Pro Gln Tyr Gly Tyr Leu Thr Leu Asp Asn Gly Ser Gln Ser Val
370                 375                 380

Gly Arg Ser Ser Phe Tyr Cys Leu Glu Tyr Phe Pro Ser Gln Met Leu
385                 390                 395                 400

Arg Thr Gly Asn Asn Phe Glu Phe Ser Tyr Ser Phe Glu Asp Val Pro
                405                 410                 415

Phe His Ser Ser Tyr Ala His Ser Gln Ser Leu Asp Arg Leu Met Asn
            420                 425                 430

Pro Leu Ile Asp Gln Tyr Leu Tyr Tyr Leu Ala Arg Thr Gln Ser Thr
            435                 440                 445

Thr Gly Ser Thr Arg Glu Leu Gln Phe His Gln Ala Gly Pro Asn Thr
            450                 455                 460

Met Ala Glu Gln Ser Lys Asn Trp Leu Pro Gly Pro Cys Tyr Arg Gln
465                 470                 475                 480

Gln Arg Leu Ser Lys Asn Leu Asp Phe Asn Asn Ser Asn Phe Ala
                485                 490                 495

Trp Thr Ala Ala Thr Lys Tyr His Leu Asn Gly Arg Asn Ser Leu Thr
            500                 505                 510
```

Asn Pro Gly Ile Pro Met Ala Thr Asn Lys Asp Asp Glu Asp Gln Phe
            515                 520                 525

Phe Pro Ile Asn Gly Val Leu Val Phe Gly Lys Thr Gly Ala Ala Asn
        530                 535                 540

Lys Thr Thr Leu Glu Asn Val Leu Met Thr Ser Glu Glu Ile Lys
545                 550                 555                 560

Thr Thr Asn Pro Val Ala Thr Glu Glu Tyr Gly Val Val Ser Ser Asn
                565                 570                 575

Leu Gln Ser Ser Thr Ala Gly Pro Gln Ser Gln Thr Ile Asn Ser Gln
            580                 585                 590

Gly Ala Leu Pro Gly Met Val Trp Gln Asn Arg Asp Val Tyr Leu Gln
            595                 600                 605

Gly Pro Ile Trp Ala Lys Ile Pro His Thr Asp Gly Asn Phe His Pro
        610                 615                 620

Ser Pro Leu Met Gly Gly Phe Gly Leu Lys His Pro Pro Gln Ile
625                 630                 635                 640

Leu Ile Lys Asn Thr Pro Val Pro Ala Asn Pro Pro Glu Val Phe Thr
                645                 650                 655

Pro Ala Lys Phe Ala Ser Phe Ile Thr Gln Tyr Ser Thr Gly Gln Val
            660                 665                 670

Ser Val Glu Ile Glu Trp Glu Leu Gln Lys Glu Asn Ser Lys Arg Trp
        675                 680                 685

Asn Pro Glu Ile Gln Tyr Thr Ser Asn Tyr Ala Lys Ser Asn Asn Val
            690                 695                 700

Glu Phe Ala Val Asn Pro Asp Gly Val Tyr Thr Glu Pro Arg Pro Ile
705                 710                 715                 720

Gly Thr Arg Tyr Leu Thr Arg Asn Leu
                725

<210> SEQ ID NO 112
<211> LENGTH: 735
<212> TYPE: PRT
<213> ORGANISM: Unknown
<220> FEATURE:
<223> OTHER INFORMATION: capsid protein of AAV serotype, clone 42.6B

<400> SEQUENCE: 112

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

```
Pro Val Glu Pro Ser Pro Gln Arg Ser Pro Asp Ser Thr Gly Ile
145                 150                 155                 160

Gly Lys Thr Gly Gln Gln Pro Ala Lys Lys Arg Leu Asn Phe Gly Gln
            165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
            195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
                260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
        290                 295                 300

Asn Asn Trp Gly Phe Arg Pro Arg Lys Leu Arg Phe Lys Leu Phe Asn
305                 310                 315                 320

Ile Gln Val Lys Glu Val Thr Thr Asp Asp Gly Val Thr Thr Ile Ala
                325                 330                 335

Asn Asn Leu Thr Ser Thr Ile Gln Val Phe Ser Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
            370                 375                 380

Asn Gly Ser Gln Ser Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Glu Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ala Arg Thr Gln Ser Thr Thr Gly Ser Thr Arg Glu Leu Gln Phe His
    450                 455                 460

Gln Ala Gly Pro Asn Thr Met Ala Glu Gln Ser Lys Asn Trp Leu Pro
465                 470                 475                 480

Gly Pro Cys Tyr Arg Gln Gln Arg Leu Ser Lys Asn Ile Asp Ser Asn
            485                 490                 495

Asn Asn Ser Asn Phe Ala Trp Thr Gly Ala Thr Lys Tyr His Leu Asn
            500                 505                 510

Gly Arg Asn Ser Leu Thr Asn Pro Gly Val Ala Met Ala Thr Asn Lys
            515                 520                 525

Asp Asp Glu Asp Gln Phe Phe Pro Ile Asn Gly Val Leu Val Phe Gly
    530                 535                 540

Lys Thr Gly Ala Ala Asn Lys Thr Thr Leu Glu Asn Val Leu Met Thr
545                 550                 555                 560
```

```
Ser Glu Glu Glu Ile Lys Thr Thr Asn Pro Val Ala Thr Glu Tyr
                565                 570                 575

Gly Val Val Ser Ser Asn Leu Gln Ser Ser Thr Ala Gly Pro Gln Thr
            580                 585                 590

Gln Thr Val Asn Ser Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly Asn Phe His Pro Ser Pro Leu Met Asp Gly Phe Gly Leu Lys
625                 630                 635                 640

His Pro Pro Pro Gln Ile Leu Ile Lys Asn Thr Pro Val Pro Ala Asn
                645                 650                 655

Pro Pro Glu Val Phe Thr Pro Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Ala Lys Ser Asn Asn Val Glu Phe Ala Val Asn Asn Glu Gly Val Tyr
705                 710                 715                 720

Thr Glu Pro Arg Pro Ile Gly Thr Arg Tyr Leu Thr Arg Asn Leu
                725                 730                 735

<210> SEQ ID NO 113
<211> LENGTH: 685
<212> TYPE: PRT
<213> ORGANISM: Unknown
<220> FEATURE:
<223> OTHER INFORMATION: capsid protein of AAV serotype, clone 42.12

<400> SEQUENCE: 113

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190
```

```
Pro Ala Gly Pro Ser Gly Leu Gly Ser Gly Thr Met Ala Gly Gly
            195                 200                 205

Gly Ala Pro Met Ala Asp Asn Asn Glu Gly Ala Asp Gly Val Gly Ser
        210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
        370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Thr Asn Pro Leu Ile Asp Gln Tyr Leu Tyr Tyr Leu
        435                 440                 445

Ala Arg Thr Gln Ser Thr Thr Gly Ser Thr Arg Gly Leu Gln Phe His
        450                 455                 460

Gln Ala Gly Pro Asn Thr Met Ala Glu Gln Ser Lys Asn Trp Leu Pro
465                 470                 475                 480

Gly Pro Cys Tyr Arg Gln Gln Arg Leu Ser Lys Asn Ile Asp Ser Asn
                485                 490                 495

Asn Asn Ser Asn Phe Ala Trp Thr Gly Ala Thr Lys Tyr His Leu Asn
            500                 505                 510

Gly Arg Asn Ser Leu Thr Asn Pro Gly Val Ala Met Ala Thr Asn Lys
        515                 520                 525

Asp Asp Glu Asp Gln Phe Phe Pro Ile Asn Gly Val Leu Val Phe Gly
        530                 535                 540

Lys Thr Gly Ala Ala Asn Lys Thr Thr Leu Glu Asn Val Leu Met Thr
545                 550                 555                 560

Ser Glu Glu Glu Ile Lys Thr Thr Asn Pro Val Ala Thr Glu Glu Tyr
                565                 570                 575

Gly Val Val Ser Ser Asn Leu Gln Ser Ser Thr Ala Gly Pro Gln Thr
            580                 585                 590

Gln Thr Val Asn Ser Gln Gly Ala Leu Pro Gly Met Val Trp Gln Asn
        595                 600                 605
```

```
Arg Asp Val Tyr Leu Gln Gly Pro Ile Trp Ala Lys Ile Pro His Thr
    610                 615                 620
Asp Gly Asn Phe His Pro Ser Pro Leu Met Gly Gly Phe Gly Leu Lys
625                 630                 635                 640
His Pro Pro Pro Gln Ile Leu Ile Lys Tyr Thr Ser Asn Tyr Tyr Lys
                645                 650                 655
Ser Thr Asn Val Asp Phe Ala Val Asn Thr Glu Gly Thr Tyr Ser Glu
                660                 665                 670
Pro Arg Pro Ile Gly Thr Arg Tyr Leu Thr Arg Asn Leu
                675                 680                 685

<210> SEQ ID NO 114
<211> LENGTH: 724
<212> TYPE: PRT
<213> ORGANISM: Unknown
<220> FEATURE:
<223> OTHER INFORMATION: capsid protein of AAV serotype, clone AAV5CAP

<400> SEQUENCE: 114

Met Ser Phe Val Asp His Pro Pro Asp Trp Leu Glu Glu Val Gly Glu
1               5                   10                  15
Gly Leu Arg Glu Phe Leu Gly Leu Glu Ala Gly Pro Pro Lys Pro Lys
            20                  25                  30
Pro Asn Gln Gln His Gln Asp Gln Ala Arg Gly Leu Val Leu Pro Gly
        35                  40                  45
Tyr Asn Tyr Leu Gly Pro Gly Asn Gly Leu Asp Arg Gly Glu Pro Val
    50                  55                  60
Asn Arg Ala Asp Glu Val Ala Arg Glu His Asp Ile Ser Tyr Asn Glu
65                  70                  75                  80
Gln Leu Glu Ala Gly Asp Asn Pro Tyr Leu Lys Tyr Asn His Ala Asp
                85                  90                  95
Ala Glu Phe Gln Glu Lys Leu Ala Asp Asp Thr Ser Phe Gly Gly Asn
            100                 105                 110
Leu Gly Lys Ala Val Phe Gln Ala Lys Lys Arg Val Leu Glu Pro Phe
        115                 120                 125
Gly Leu Val Glu Glu Gly Ala Lys Thr Ala Pro Thr Gly Lys Arg Ile
    130                 135                 140
Asp Asp His Phe Pro Lys Arg Lys Lys Ala Arg Thr Glu Glu Asp Ser
145                 150                 155                 160
Lys Pro Ser Thr Ser Ser Asp Ala Glu Ala Gly Pro Ser Gly Ser Gln
                165                 170                 175
Gln Leu Gln Ile Pro Ala Gln Pro Ala Ser Ser Leu Gly Ala Asp Thr
            180                 185                 190
Met Ser Ala Gly Gly Gly Gly Pro Leu Gly Asp Asn Asn Gln Gly Ala
        195                 200                 205
Asp Gly Val Gly Asn Ala Ser Gly Asp Trp His Cys Asp Ser Thr Trp
    210                 215                 220
Met Gly Asp Arg Val Val Thr Lys Ser Thr Arg Thr Trp Val Leu Pro
225                 230                 235                 240
Ser Tyr Asn Asn His Gln Tyr Arg Glu Ile Lys Ser Gly Ser Val Asp
                245                 250                 255
Gly Ser Asn Ala Asn Ala Tyr Phe Gly Tyr Ser Thr Pro Trp Gly Tyr
            260                 265                 270
Phe Asp Phe Asn Arg Phe His Ser His Trp Ser Pro Arg Asp Trp Gln
        275                 280                 285
```

```
Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
690                 695                 700
```

```
Ser Thr Gly Glu Tyr Arg Thr Thr Arg Pro Ile Gly Thr Arg Tyr Leu
705                 710                 715                 720

Thr Arg Pro Leu

<210> SEQ ID NO 115
<211> LENGTH: 9
<212> TYPE: DNA
<213> ORGANISM: Artificial Sequence
<220> FEATURE:
<223> OTHER INFORMATION: DraIII restriction enzyme site

<400> SEQUENCE: 115 caccacgtc                                                             9

<210> SEQ ID NO 116
<211> LENGTH: 28
<212> TYPE: DNA
<213> ORGANISM: Unknown
<220> FEATURE:
<223> OTHER INFORMATION: AV2cas

<400> SEQUENCE: 116
cgcagagacc aaagttcaac tgaaacga                                         28

<210> SEQ ID NO 117
<211> LENGTH: 255
<212> TYPE: DNA
<213> ORGANISM: Unknown
<220> FEATURE:
<223> OTHER INFORMATION: adeno-associated virus serotype 10

<400> SEQUENCE: 117
ggtaattcct ccggaaattg gcattgcgat tccacatggc tgggcgacag agtcatcacc      60
accagcaccc gaacctgggt cctgcccacc tacaacaacc acatctacaa gcaaatctcc    120
agcgagacag gagccaccaa cgacaaccac tacttcggct acagcacccc ctggggtat     180 tttgacttta acagattcca ctgccacttt tcaccacgtg actggcagcg actcatcaac    240
aacaactggg gattc                                                     255

<210> SEQ ID NO 118
<211> LENGTH: 258
<212> TYPE: DNA
<213> ORGANISM: Unknown
<220> FEATURE:
<223> OTHER INFORMATION: adeno-associated virus serotype 11

<400> SEQUENCE: 118
ggtaattcct ccggaaattg gcattgcgat tccacatggc tgggcgacag agtcatcacc      60
accagcaccc gaacctgggc cctgccaacc tacaacaacc acctctacaa acaaatctcc    120
agcgcttcaa cggggggccag caacgacaac cactactttg ctacagcac ccctggggg      180 tattttgact ttaacagatt ccactgccac ttctcaccac gtgactggca gcgactcatc    240
aacaacaact ggggattc                                                  258

<210> SEQ ID NO 119
<211> LENGTH: 255
<212> TYPE: DNA
<213> ORGANISM: Unknown
<220> FEATURE:
<223> OTHER INFORMATION: adeno-associated virus serotype 12
```

```
<400> SEQUENCE: 119
ggtaattcct ccggaaattg gcattgcgat tccacatggc tgggcgaccg agtcattacc      60
accagcaccc ggacttgggc cctgcccacc tacaacaacc acctctacaa gcaaatctcc     120
agccaatcgg gtgccaccaa cgacaaccac tacttcggct acagcacccc ttggggtat     180 tttgatttca acagattcca ctgccatttc tcaccacgtg actggcagcg actcatcaac     240
aacaactggg gattc                                                      255

<210> SEQ ID NO 120
<211> LENGTH: 2205
<212> TYPE: DNA
<213> ORGANISM: Unknown
<220> FEATURE:
<223> OTHER INFORMATION: adeno-associated virus serotype, clone A3.1vp1

<400> SEQUENCE: 120
atggctgccg atggttatct tccagattgg ctcgaggaca ctctctctga aggaatcaga      60
cagtggtgga agctcaaacc tggcccacca ccgccgaaac ctaaccaaca acaccgggac     120
gacagtaggg gtcttgtgct tcctgggtac aagtacctcg gacccttcaa cggactcgac     180
aaaggagagc cggtcaacga ggcagacgcc gcggccctcg agcacgacaa agcctacgac     240
caccagctca gcaaggggga caacccgtac ctcaaataca accacgcgga cgctgaattt     300
caggagcgtc ttcaagaaga tacgtctttc ggggcaacc tcgggcgagc agtcttccag     360
gccaaaaaga gggtactcga gcctcttggt ctggttgagg aagctgttaa cggctcct      420 ggaaaaaaga gacctataga gcagtctcct gcagaaccgg actcttcctc gggcatcggc     480
aaatcaggcc agcagcccgc taagaaaaga ctcaattttg gtcagactgg cgacacagag     540
tcagtcccag accctcaacc aatcggagaa ccccccgcag ccccctctgg tgtgggatct     600
aatacaatgg cttcaggcgg tgggcacca atggcagaca taacgaagg cgccgacgga     660 gtgggtaatt cctcgggaaa ttggcattgc gattccacat ggatgggcga cagagttatc     720
accaccagca caagaacctg ggccctcccc acctacaata tcacctcta caagcaaatc     780 tccagcgaat cgggagccac caacgacaac cactacttcg gctacagcac ccctggggg     840 tattttgact ttaacagatt ccactgtcac ttctcaccac gtgactggca gcgactcatc     900
aacaacaact ggggatttag acccaagaaa ctcaatttca gctcttcaa catccaagtc     960 aaggaggtca cgcagaatga tggaaccacg accatcgcca taaccttac agcacggtg    1020 caggtcttca cagactctga gtaccagctg cccctacgtcc tcggttcggc tcaccagggc    1080
tgccttccgc cgttcccagc agacgtcttc atgattcctc agtacggcta cttgactctg    1140
aacaatggca gccaagcgt aggacgttct tcattctact gtctagagta ttttccctct    1200
cagatgctga ggacgggaaa caacttcacc ttcagctaca cttttgaaga cgtgcctttc    1260
cacagcagct acgcgcacag ccagagtctg gatcggctga tgaatcctct cattgaccag    1320
tacctgtatt acctgagcaa aactcagggt acaagtggaa caacgcagca atcgagactg    1380
cagttcagcc aagctgggcc tagctccatg gctcagcagg ccaaaaactg gctaccggga    1440
cccagctacc gacagcagcg aatgtctaag acggctaatg caacaacaa cagtgaattt    1500 gcttggactg cagccaccaa atattacctg aatggaagaa attctctggt caatcccggg    1560
cccccaatgg ccagtcacaa ggacgatgag gaaaagtatt tccccatgca cggaaatctc    1620
atctttggaa acaaggcac aggaactacc aatgtggaca ttgaatcagt gcttattaca    1680
gacgaagaag aaatcagaac aactaatcct gtggctacag aacaatacgg acaggttgcc    1740
```

```
accaaccatc agagtcagaa caccacagct tcctatggaa gtgtggacag ccagggaatc    1800
ttacctggaa tggtgtggca ggaccgcgat gtctatcttc aaggtcccat ttgggccaaa    1860
actcctcaca cggacggaca ctttcatcct tctccgctca tgggaggctt tggactgaaa    1920
caccctcctc cccagatcct gatcaaaaac acacctgtgc cagcgaatcc cgcgaccact    1980
ttcactcctg gaaagtttgc ttcgttcatt acccagtatt ccaccggaca ggtcagcgtg    2040
gaaatagagt gggagctgca gaaagaaaac agcaaacgct ggaacccaga aattcagtac    2100
acctccaact acaacaagtc ggtgaatgtg gagtttaccg tggacgcaaa cggtgtttat    2160
tctgaacccc gccctattgg cactcgttac cttacccgga acttg                    2205
```

The invention claimed is:

1. A recombinant adeno-associated virus (AAV) comprising an AAVrh.8 capsid comprising vp1, vp2 and vp3 proteins, wherein at least one vp1 has the sequence of amino acids 1 to 736 of SEQ ID NO:97 or a sequence at least 95% identical to SEQ ID NO: 97, said AAV having packaged in the capsid a nucleic acid molecule comprising at least one AAV inverted terminal repeat (ITR), and a non-AAV nucleic acid sequence encoding a gene product operably linked to sequences which direct expression of the product in a host cell.

2. The recombinant AAV according to claim 1, wherein the amino acid sequence is at least 99% identical to amino acids 1 to 736 of SEQ ID NO: 97.

3. The recombinant AAV according to claim 1, wherein the AAV ITR is from AAV2.

4. The recombinant AAV according to claim 1, wherein the vp1 protein has an amino acid sequence at least 97% identical to amino acids 1 to 736 of SEQ ID NO: 97.

5. A recombinant adeno-associated virus (AAV) comprising an AAVrh.8 capsid comprising vp1, vp2 and vp3 proteins, wherein at least one vp2 has the amino acid sequence of 138 to 736 of SEQ ID NO: 97 or a sequence at least 95% identical to amino acids 138 to 736 of SEQ ID NO: 97, said AAV having packaged in the capsid a nucleic acid molecule comprising at least one AAV inverted terminal repeat (ITR) and a non-AAV nucleic acid sequence encoding a gene product operably linked to sequences which direct expression thereof in a host cell.

6. A recombinant adeno-associated virus (AAV) comprising an AAVrh.8 capsid comprising vp1, vp2 and vp3 proteins, wherein at least one vp3 has the amino acid sequence of 203 to 736 of SEQ ID NO: 97 or a sequence at least 95% identical to amino acids 203 to 736 of SEQ ID NO: 97, said AAV having packaged in the capsid a nucleic acid molecule comprising at least one AAV inverted terminal repeat (ITR) and a non-AAV nucleic acid sequence encoding a gene product operably linked to sequences which direct expression of the product in a host cell.

7. The recombinant AAV according to claim wherein the AAV ITR is from AAV2.

8. The recombinant AAV according to claim 6, wherein at least one vp1 protein has an amino acid sequence of about amino acids 1 to 736 of SEQ ID NO: 97.

9. The recombinant AAV according to claim 6, wherein at least one vp2 protein has an amino acid sequence of about amino acids 138 to 736 of SEQ ID NO: 97.

10. The recombinant AAV according to claim 6, wherein at least one vp1 protein has an amino acid sequence at least 97% identical to amino acids 1 to 736 of SEQ ID NO: 97.

11. The recombinant AAV according to claim 6, wherein at least one vp1 protein has an amino acid sequence at least 99% identical to amino acids 1 to 736 of SEQ ID NO: 97.

12. The recombinant AAV according to claim 6, wherein the non-AAV nucleic acid sequence encodes Factor VIII.

13. The recombinant AAV according to claim 6, wherein the non-AAV nucleic acid sequence encodes Factor IX.

14. The recombinant AAV according to claim 6, wherein the non-AAV nucleic acid sequence encodes a low density lipoprotein (LDL) receptor.

15. The recombinant AAV according to claim 6, wherein the non-AAV nucleic acid sequence encodes a high density lipoprotein (HDL) receptor.

16. The recombinant AAV according to claim 6, wherein the non-AAV nucleic acid sequence encodes a very low density lipoprotein (VLDL) receptor.

17. The recombinant AAV according to claim 6, wherein the non-AAV nucleic acid sequence encodes a scavenger receptor.

18. The recombinant AAV according to claim 6, wherein the non-AAV nucleic acid sequence encodes VEGF.

19. The recombinant AAV according to claim 6, wherein the non-AAV nucleic acid sequence encodes GUSB.

20. The recombinant AAV according to claim 6, wherein the non-AAV nucleic acid sequence encodes alpha-1 antitrypsin (A1AT).

21. The recombinant AAV according to claim 6, wherein the non-AAV nucleic acid sequence encodes erythropoietin.

22. The recombinant AAV according to claim 6, wherein the non-AAV nucleic acid sequence encodes ornithine transcarbamylase (OTC).

23. The recombinant AAV according to claim 6, wherein the non-AAV nucleic acid sequence encodes hepatocyte growth factor.

24. The recombinant AAV according to claim 6, wherein the non-AAV nucleic acid sequence encodes glucose-6-phosphatase.

25. The recombinant AAV according to claim 6, wherein the non-AAV nucleic acid sequence encodes nerve growth factor.

26. The recombinant AAV according to claim 6, wherein the non-AAV nucleic acid sequence encodes interleukin-10.

27. The recombinant AAV according to claim 6, wherein the non-AAV nucleic acid sequence encodes an immunoglobulin.

28. The recombinant AAV according to claim 17, wherein the immunoglobulin is selected from immunoglobulins IgG, IgM, IgA, IgD and IgE, chimeric immunoglobulins, human antibodies, humanized antibodies, single chain antibodies, and engineered immunoglobulins.

29. The recombinant AAV according to claim 6, wherein the non-AAV nucleic acid sequence encodes a T cell receptor, a chimeric T cell receptor, a single chain T cell receptor, a class I or class II MHC molecule, or an engineered MHC molecule.

30. A composition comprising a pharmaceutically compatible carrier and at least the recombinant AAV according to claim 6.

31. A composition comprising a pharmaceutically compatible carrier and at least the recombinant AAV according to claim 1.

* * * * *